(12) United States Patent
Knudsen

(10) Patent No.: US 8,445,198 B2
(45) Date of Patent: May 21, 2013

(54) METHODS, KITS AND DEVICES FOR IDENTIFYING BIOMARKERS OF TREATMENT RESPONSE AND USE THEREOF TO PREDICT TREATMENT EFFICACY

(75) Inventor: Steen Knudsen, Birkroed (DK)

(73) Assignee: Medical Prognosis Institute, Hørsholm (DK)

( * ) Notice: Subject to any disclaimer, the term of this patent is extended or adjusted under 35 U.S.C. 154(b) by 659 days.

(21) Appl. No.: 12/151,949

(22) Filed: May 9, 2008

(65) Prior Publication Data

US 2009/0023149 A1    Jan. 22, 2009

Related U.S. Application Data

(63) Continuation-in-part of application No. PCT/IB2006/004048, filed on Dec. 1, 2006.

(30) Foreign Application Priority Data

| Dec. 1, 2005 | (DK) | ................................. | 2005 01696 |
| May 11, 2007 | (DK) | ................................. | 2007 00714 |
| Jul. 11, 2007 | (DK) | ................................. | 2007 01023 |

(51) Int. Cl.
*C12Q 1/68* (2006.01)
(52) U.S. Cl.
USPC ......................................................... 435/6.1
(58) Field of Classification Search ..................... 435/6.1
See application file for complete search history.

(56) References Cited

U.S. PATENT DOCUMENTS

| 6,911,306 | B1 * | 6/2005 | Vertino ......................... 435/6.14 |
| 7,709,616 | B2 * | 5/2010 | Bentwich et al. ............. 536/23.1 |
| 2002/0164663 | A1 | 11/2002 | Fuqua et al. |
| 2003/0073083 | A1 | 4/2003 | Tamayo et al. |
| 2004/0018525 | A1 * | 1/2004 | Wirtz et al. ........................ 435/6 |
| 2004/0072722 | A1 | 4/2004 | Kornblith et al. |
| 2005/0176669 | A1 | 8/2005 | Al-Murrani |
| 2005/0260586 | A1 | 11/2005 | Demuth et al. |
| 2005/0260646 | A1 | 11/2005 | Baker et al. |
| 2006/0105360 | A1 * | 5/2006 | Croce et al. ........................ 435/6 |
| 2008/0306006 | A1 * | 12/2008 | Croce et al. ...................... 514/12 |
| 2009/0221435 | A1 * | 9/2009 | Baskerville et al. ............... 506/9 |

FOREIGN PATENT DOCUMENTS

| EP | 1550731 | 7/2005 |
| JP | 2001-17171 | 1/2001 |
| JP | 2002-531006 A | 9/2002 |
| WO | WO 03/082078 | 10/2003 |
| WO | WO 2005/014856 | 2/2005 |
| WO | WO-2005/047534 A2 | 5/2005 |
| WO | WO 2005/066371 | 7/2005 |
| WO | WO 2005/087948 | 9/2005 |
| WO | WO 2005/094863 | 10/2005 |
| WO | WO 2005/100606 | 10/2005 |
| WO | WO2008112283 A2 * | 9/2008 |

OTHER PUBLICATIONS

Bild et al. Nature 2006 439:353-7.*
Dahlén et al., "Activation of the *GLI* Oncogene Through Fusion with the β-Actin Gene (*ACTB*) in a Group of Distinctive Pericytic Neoplasms," *American Journal of Pathology* 164:1645-1653 (2004).
Fournier et al., "Gene Expression Signature in Organized and Growth-Arrested Mammary Acini Predicts Good Outcome in Breast Cancer," *Cancer Research* 66:7095-7102 (2006).
Kornmann et al., "Thymidylate Synthase and Dihydropyrimidine Dehydrogenase mRNA Expression Levels: Predictors for Survival in Colorectal Cancer Patients Receiving Adjuvant 5-Fluorouracil," *Clinical Cancer Research* 9:4116-4124 (2003).
van't Veer et al., "Gene Expression Profiling Predicts Clinical Outcome of Breast Cancer," *Nature* 415:530-536 (2002).
Communication from the European Patent Office regarding EP 06 848 658.2-2402, mailed Sep. 22, 2008.
Transmittal of International Search Report and Written Opinion of PCT/EP2008/003789, mailed Jan. 9, 2009.
International Search Report and Written Opinion for PCT/IB2006/004048, mailed May 14, 2008.
Chinese Patent Office Action (CN 200680052220.2), dated Mar. 21, 2012.
Japanese Patent Office Action (JP 2008-542865), dated Apr. 18, 2012.
Liu et al., "Roles of USF, Ikaros and Sp proteins in the transcriptional regulation of the human reduced folate carrier B promoter," *Biochem.* 383:249-257 (2004).
Office Action for Japanese Patent Application No. 2008-542865 dated Dec. 3, 2012.
Office Action for Chinese Patent Application No. 200680052220.2 issued Feb. 5, 2013.
Genbank Accession No. AY889152.1 dated Mar. 29, 2005.

* cited by examiner

*Primary Examiner* — Brian Whiteman
(74) *Attorney, Agent, or Firm* — Kristina Bieker-Brady; Clark & Elbing LLP

(57) ABSTRACT

The present invention features methods, kits, and devices for predicting the sensitivity of a patient to a compound or medical treatment. The invention also features methods for identifying gene biomarkers whose expression correlates to treatment sensitivity or resistance within a patient population or subpopulation.

84 Claims, 11 Drawing Sheets

Months after diagnosis

SEQUENCE LISTING

<160> NUMBER OF SEQ ID NOS: 3336

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tcctgtactt gtcctcagct tgggc                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gccccactgg acaacactga ttcct                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgcctgctcc tgtacttgtc ctcag                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
aaatgtttcc ttgtgcctgc tcctg                                          25

<210> SEQ ID NO 5

<400> SEQUENCE: 5

000

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aagcctatac gtttctgtgg agtaa                                          25

<210> SEQ ID NO 7
<211> LENGTH: 25
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 7
acttgtcctc agcttgggct tcttc                                            25

<210> SEQ ID NO 8

<400> SEQUENCE: 8

000

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tggaccccac tggctgagaa tctgg                                            25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ttggacatct ctagtgtagc tgcca                                            25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cacccagctg gtcctgtgga tggga                                            25

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15
```

000

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tcctccatca cctgaaacac tggac                                           25

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tccttgtgcc tgctcctgta cttgt                                           25

<210> SEQ ID NO 25

```
<400> SEQUENCE: 25

000

<210> SEQ ID NO 26
<400> SEQUENCE: 26

000

<210> SEQ ID NO 27
<400> SEQUENCE: 27

000

<210> SEQ ID NO 28
<400> SEQUENCE: 28

000

<210> SEQ ID NO 29
<400> SEQUENCE: 29

000

<210> SEQ ID NO 30
<400> SEQUENCE: 30

000

<210> SEQ ID NO 31
<400> SEQUENCE: 31

000

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tgcctgctcc tgtacttgtc ctcag                                           25

<210> SEQ ID NO 33
<400> SEQUENCE: 33

000

<210> SEQ ID NO 34
<400> SEQUENCE: 34

000

<210> SEQ ID NO 35
<400> SEQUENCE: 35

000
```

```
<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
tgcctgctcc tgtacttgtc ctcag                                          25

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
```

```
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000
```

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

```
<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
<400> SEQUENCE: 102
000

<210> SEQ ID NO 103
<400> SEQUENCE: 103
```

000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
000

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

```
<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
```

```
<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000
```

-continued

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

```
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
```

000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

-continued

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184
<400> SEQUENCE: 184
000

<210> SEQ ID NO 185
<400> SEQUENCE: 185
000

<210> SEQ ID NO 186
<400> SEQUENCE: 186
000

<210> SEQ ID NO 187
<400> SEQUENCE: 187
000

<210> SEQ ID NO 188
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191
<400> SEQUENCE: 191
000

<210> SEQ ID NO 192
<400> SEQUENCE: 192
000

<210> SEQ ID NO 193
<400> SEQUENCE: 193
000

<210> SEQ ID NO 194
<400> SEQUENCE: 194
000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
<400> SEQUENCE: 200
000

<210> SEQ ID NO 201
<400> SEQUENCE: 201
000

<210> SEQ ID NO 202
<400> SEQUENCE: 202
000

<210> SEQ ID NO 203
<400> SEQUENCE: 203
000

<210> SEQ ID NO 204
<400> SEQUENCE: 204
000

<210> SEQ ID NO 205
<400> SEQUENCE: 205
000

<210> SEQ ID NO 206

```
<400> SEQUENCE: 206
000

<210> SEQ ID NO 207
<400> SEQUENCE: 207
000

<210> SEQ ID NO 208
<400> SEQUENCE: 208
000

<210> SEQ ID NO 209
<400> SEQUENCE: 209
000

<210> SEQ ID NO 210
<400> SEQUENCE: 210
000

<210> SEQ ID NO 211
<400> SEQUENCE: 211
000

<210> SEQ ID NO 212
<400> SEQUENCE: 212
000

<210> SEQ ID NO 213
<400> SEQUENCE: 213
000

<210> SEQ ID NO 214
<400> SEQUENCE: 214
000

<210> SEQ ID NO 215
<400> SEQUENCE: 215
000

<210> SEQ ID NO 216
<400> SEQUENCE: 216
000

<210> SEQ ID NO 217
<400> SEQUENCE: 217
000
```

```
<210> SEQ ID NO 218
<400> SEQUENCE: 218
000

<210> SEQ ID NO 219
<400> SEQUENCE: 219
000

<210> SEQ ID NO 220
<400> SEQUENCE: 220
000

<210> SEQ ID NO 221
<400> SEQUENCE: 221
000

<210> SEQ ID NO 222
<400> SEQUENCE: 222
000

<210> SEQ ID NO 223
<400> SEQUENCE: 223
000

<210> SEQ ID NO 224
<400> SEQUENCE: 224
000

<210> SEQ ID NO 225
<400> SEQUENCE: 225
000

<210> SEQ ID NO 226
<400> SEQUENCE: 226
000

<210> SEQ ID NO 227
<400> SEQUENCE: 227
000

<210> SEQ ID NO 228
<400> SEQUENCE: 228
000

<210> SEQ ID NO 229
```

```
<400> SEQUENCE: 229

000

<210> SEQ ID NO 230
<400> SEQUENCE: 230

000

<210> SEQ ID NO 231
<400> SEQUENCE: 231

000

<210> SEQ ID NO 232
<400> SEQUENCE: 232

000

<210> SEQ ID NO 233
<400> SEQUENCE: 233

000

<210> SEQ ID NO 234
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
atatatggac ctagcttgag gcaat                                            25

<210> SEQ ID NO 235
<400> SEQUENCE: 235

000

<210> SEQ ID NO 236
<400> SEQUENCE: 236

000

<210> SEQ ID NO 237
<400> SEQUENCE: 237

000

<210> SEQ ID NO 238
<400> SEQUENCE: 238

000

<210> SEQ ID NO 239
<400> SEQUENCE: 239

000
```

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

```
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
```

000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
000

<210> SEQ ID NO 267
<400> SEQUENCE: 267
000

<210> SEQ ID NO 268
<400> SEQUENCE: 268
000

<210> SEQ ID NO 269
<400> SEQUENCE: 269
000

<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

```
<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
```

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

-continued

<400> SEQUENCE: 308

000

<210> SEQ ID NO 309
<400> SEQUENCE: 309

000

<210> SEQ ID NO 310
<400> SEQUENCE: 310

000

<210> SEQ ID NO 311
<400> SEQUENCE: 311

000

<210> SEQ ID NO 312
<400> SEQUENCE: 312

000

<210> SEQ ID NO 313
<400> SEQUENCE: 313

000

<210> SEQ ID NO 314
<400> SEQUENCE: 314

000

<210> SEQ ID NO 315
<400> SEQUENCE: 315

000

<210> SEQ ID NO 316
<400> SEQUENCE: 316

000

<210> SEQ ID NO 317
<400> SEQUENCE: 317

000

<210> SEQ ID NO 318
<400> SEQUENCE: 318

000

<210> SEQ ID NO 319
<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

```
<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
```

000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412
<400> SEQUENCE: 412

000

<210> SEQ ID NO 413
<400> SEQUENCE: 413

000

<210> SEQ ID NO 414
<400> SEQUENCE: 414

000

<210> SEQ ID NO 415
<400> SEQUENCE: 415

000

<210> SEQ ID NO 416
<400> SEQUENCE: 416

000

<210> SEQ ID NO 417
<400> SEQUENCE: 417

000

<210> SEQ ID NO 418
<400> SEQUENCE: 418

000

<210> SEQ ID NO 419
<400> SEQUENCE: 419

000

<210> SEQ ID NO 420
<400> SEQUENCE: 420

000

<210> SEQ ID NO 421
<400> SEQUENCE: 421

000

<210> SEQ ID NO 422
<400> SEQUENCE: 422

000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<400> SEQUENCE: 426
000

<210> SEQ ID NO 427
<400> SEQUENCE: 427
000

<210> SEQ ID NO 428
<400> SEQUENCE: 428
000

<210> SEQ ID NO 429
<400> SEQUENCE: 429
000

<210> SEQ ID NO 430
<400> SEQUENCE: 430
000

<210> SEQ ID NO 431
<400> SEQUENCE: 431
000

<210> SEQ ID NO 432
<400> SEQUENCE: 432
000

<210> SEQ ID NO 433
<400> SEQUENCE: 433
000

```
<210> SEQ ID NO 434
<400> SEQUENCE: 434
000

<210> SEQ ID NO 435
<400> SEQUENCE: 435
000

<210> SEQ ID NO 436
<400> SEQUENCE: 436
000

<210> SEQ ID NO 437
<400> SEQUENCE: 437
000

<210> SEQ ID NO 438
<400> SEQUENCE: 438
000

<210> SEQ ID NO 439
<400> SEQUENCE: 439
000

<210> SEQ ID NO 440
<400> SEQUENCE: 440
000

<210> SEQ ID NO 441
<400> SEQUENCE: 441
000

<210> SEQ ID NO 442
<400> SEQUENCE: 442
000

<210> SEQ ID NO 443
<400> SEQUENCE: 443
000

<210> SEQ ID NO 444
<400> SEQUENCE: 444
000

<210> SEQ ID NO 445
<400> SEQUENCE: 445
```

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

```
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497
<400> SEQUENCE: 497
000

<210> SEQ ID NO 498
<400> SEQUENCE: 498
000

<210> SEQ ID NO 499
<400> SEQUENCE: 499
000

<210> SEQ ID NO 500
<400> SEQUENCE: 500
000

<210> SEQ ID NO 501
<400> SEQUENCE: 501
000

<210> SEQ ID NO 502
<400> SEQUENCE: 502
```

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

```
<210> SEQ ID NO 514
<400> SEQUENCE: 514
000

<210> SEQ ID NO 515
<400> SEQUENCE: 515
000

<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519
<400> SEQUENCE: 519
000

<210> SEQ ID NO 520
<400> SEQUENCE: 520
000

<210> SEQ ID NO 521
<400> SEQUENCE: 521
000

<210> SEQ ID NO 522
<400> SEQUENCE: 522
000

<210> SEQ ID NO 523
<400> SEQUENCE: 523
000

<210> SEQ ID NO 524
<400> SEQUENCE: 524
000

<210> SEQ ID NO 525
<400> SEQUENCE: 525
```

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

-continued

```
<400> SEQUENCE: 548
000

<210> SEQ ID NO 549
<400> SEQUENCE: 549
000

<210> SEQ ID NO 550
<400> SEQUENCE: 550
000

<210> SEQ ID NO 551
<400> SEQUENCE: 551
000

<210> SEQ ID NO 552
<400> SEQUENCE: 552
000

<210> SEQ ID NO 553
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
000

<210> SEQ ID NO 557
<400> SEQUENCE: 557
000

<210> SEQ ID NO 558
<400> SEQUENCE: 558
000

<210> SEQ ID NO 559
<400> SEQUENCE: 559
000
```

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

```
<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582
```

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

-continued

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629
<400> SEQUENCE: 629

000

<210> SEQ ID NO 630
<400> SEQUENCE: 630

000

<210> SEQ ID NO 631
<400> SEQUENCE: 631

000

<210> SEQ ID NO 632
<400> SEQUENCE: 632

000

<210> SEQ ID NO 633
<400> SEQUENCE: 633

000

<210> SEQ ID NO 634
<400> SEQUENCE: 634

000

<210> SEQ ID NO 635
<400> SEQUENCE: 635

000

<210> SEQ ID NO 636
<400> SEQUENCE: 636

000

<210> SEQ ID NO 637
<400> SEQUENCE: 637

000

<210> SEQ ID NO 638
<400> SEQUENCE: 638

000

<210> SEQ ID NO 639
<400> SEQUENCE: 639

000

-continued

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

-continued

<210> SEQ ID NO 674
<400> SEQUENCE: 674
000

<210> SEQ ID NO 675
<400> SEQUENCE: 675
000

<210> SEQ ID NO 676
<400> SEQUENCE: 676
000

<210> SEQ ID NO 677
<400> SEQUENCE: 677
000

<210> SEQ ID NO 678
<400> SEQUENCE: 678
000

<210> SEQ ID NO 679
<400> SEQUENCE: 679
000

<210> SEQ ID NO 680
<400> SEQUENCE: 680
000

<210> SEQ ID NO 681
<400> SEQUENCE: 681
000

<210> SEQ ID NO 682
<400> SEQUENCE: 682
000

<210> SEQ ID NO 683
<400> SEQUENCE: 683
000

<210> SEQ ID NO 684
<400> SEQUENCE: 684
000

<210> SEQ ID NO 685
<400> SEQUENCE: 685

000

<210> SEQ ID NO 686
<400> SEQUENCE: 686
000

<210> SEQ ID NO 687
<400> SEQUENCE: 687
000

<210> SEQ ID NO 688
<400> SEQUENCE: 688
000

<210> SEQ ID NO 689
<400> SEQUENCE: 689
000

<210> SEQ ID NO 690
<400> SEQUENCE: 690
000

<210> SEQ ID NO 691
<400> SEQUENCE: 691
000

<210> SEQ ID NO 692
<400> SEQUENCE: 692
000

<210> SEQ ID NO 693
<400> SEQUENCE: 693
000

<210> SEQ ID NO 694
<400> SEQUENCE: 694
000

<210> SEQ ID NO 695
<400> SEQUENCE: 695
000

<210> SEQ ID NO 696
<400> SEQUENCE: 696
000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

```
<400> SEQUENCE: 708
000

<210> SEQ ID NO 709
<400> SEQUENCE: 709
000

<210> SEQ ID NO 710
<400> SEQUENCE: 710
000

<210> SEQ ID NO 711
<400> SEQUENCE: 711
000

<210> SEQ ID NO 712
<400> SEQUENCE: 712
000

<210> SEQ ID NO 713
<400> SEQUENCE: 713
000

<210> SEQ ID NO 714
<400> SEQUENCE: 714
000

<210> SEQ ID NO 715
<400> SEQUENCE: 715
000

<210> SEQ ID NO 716
<400> SEQUENCE: 716
000

<210> SEQ ID NO 717
<400> SEQUENCE: 717
000

<210> SEQ ID NO 718
<400> SEQUENCE: 718
000

<210> SEQ ID NO 719
<400> SEQUENCE: 719
000
```

-continued

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

```
<400> SEQUENCE: 731

000

<210> SEQ ID NO 732
<400> SEQUENCE: 732

000

<210> SEQ ID NO 733
<400> SEQUENCE: 733

000

<210> SEQ ID NO 734
<400> SEQUENCE: 734

000

<210> SEQ ID NO 735
<400> SEQUENCE: 735

000

<210> SEQ ID NO 736
<400> SEQUENCE: 736

000

<210> SEQ ID NO 737
<400> SEQUENCE: 737

000

<210> SEQ ID NO 738
<400> SEQUENCE: 738

000

<210> SEQ ID NO 739
<400> SEQUENCE: 739

000

<210> SEQ ID NO 740
<400> SEQUENCE: 740

000

<210> SEQ ID NO 741
<400> SEQUENCE: 741

000

<210> SEQ ID NO 742
<400> SEQUENCE: 742
```

000

<210> SEQ ID NO 743
<400> SEQUENCE: 743
000

<210> SEQ ID NO 744
<400> SEQUENCE: 744
000

<210> SEQ ID NO 745
<400> SEQUENCE: 745
000

<210> SEQ ID NO 746
<400> SEQUENCE: 746
000

<210> SEQ ID NO 747
<400> SEQUENCE: 747
000

<210> SEQ ID NO 748
<400> SEQUENCE: 748
000

<210> SEQ ID NO 749
<400> SEQUENCE: 749
000

<210> SEQ ID NO 750
<400> SEQUENCE: 750
000

<210> SEQ ID NO 751
<400> SEQUENCE: 751
000

<210> SEQ ID NO 752
<400> SEQUENCE: 752
000

<210> SEQ ID NO 753
<400> SEQUENCE: 753
000

```
<210> SEQ ID NO 754
<400> SEQUENCE: 754
000

<210> SEQ ID NO 755
<400> SEQUENCE: 755
000

<210> SEQ ID NO 756
<400> SEQUENCE: 756
000

<210> SEQ ID NO 757
<400> SEQUENCE: 757
000

<210> SEQ ID NO 758
<400> SEQUENCE: 758
000

<210> SEQ ID NO 759
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
```

000

<210> SEQ ID NO 766
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 766
tggaccccac tggctgagaa tctgg          25

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

-continued

<210> SEQ ID NO 799
<400> SEQUENCE: 799
000

<210> SEQ ID NO 800
<400> SEQUENCE: 800
000

<210> SEQ ID NO 801
<400> SEQUENCE: 801
000

<210> SEQ ID NO 802
<400> SEQUENCE: 802
000

<210> SEQ ID NO 803
<400> SEQUENCE: 803
000

<210> SEQ ID NO 804
<400> SEQUENCE: 804
000

<210> SEQ ID NO 805
<400> SEQUENCE: 805
000

<210> SEQ ID NO 806
<400> SEQUENCE: 806
000

<210> SEQ ID NO 807
<400> SEQUENCE: 807
000

<210> SEQ ID NO 808
<400> SEQUENCE: 808
000

<210> SEQ ID NO 809
<400> SEQUENCE: 809
000

<210> SEQ ID NO 810

```
<400> SEQUENCE: 810
000

<210> SEQ ID NO 811
<400> SEQUENCE: 811
000

<210> SEQ ID NO 812
<400> SEQUENCE: 812
000

<210> SEQ ID NO 813
<400> SEQUENCE: 813
000

<210> SEQ ID NO 814
<400> SEQUENCE: 814
000

<210> SEQ ID NO 815
<400> SEQUENCE: 815
000

<210> SEQ ID NO 816
<400> SEQUENCE: 816
000

<210> SEQ ID NO 817
<400> SEQUENCE: 817
000

<210> SEQ ID NO 818
<400> SEQUENCE: 818
000

<210> SEQ ID NO 819
<400> SEQUENCE: 819
000

<210> SEQ ID NO 820
<400> SEQUENCE: 820
000

<210> SEQ ID NO 821
<400> SEQUENCE: 821
000
```

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845
<400> SEQUENCE: 845
000

<210> SEQ ID NO 846
<400> SEQUENCE: 846
000

<210> SEQ ID NO 847
<400> SEQUENCE: 847
000

<210> SEQ ID NO 848
<400> SEQUENCE: 848
000

<210> SEQ ID NO 849
<400> SEQUENCE: 849
000

<210> SEQ ID NO 850
<400> SEQUENCE: 850
000

<210> SEQ ID NO 851
<400> SEQUENCE: 851
000

<210> SEQ ID NO 852
<400> SEQUENCE: 852
000

<210> SEQ ID NO 853
<400> SEQUENCE: 853
000

<210> SEQ ID NO 854
<400> SEQUENCE: 854
000

<210> SEQ ID NO 855
<400> SEQUENCE: 855
000

```
<210> SEQ ID NO 856
<400> SEQUENCE: 856
000

<210> SEQ ID NO 857
<400> SEQUENCE: 857
000

<210> SEQ ID NO 858
<400> SEQUENCE: 858
000

<210> SEQ ID NO 859
<400> SEQUENCE: 859
000

<210> SEQ ID NO 860
<400> SEQUENCE: 860
000

<210> SEQ ID NO 861
<400> SEQUENCE: 861
000

<210> SEQ ID NO 862
<400> SEQUENCE: 862
000

<210> SEQ ID NO 863
<400> SEQUENCE: 863
000

<210> SEQ ID NO 864
<400> SEQUENCE: 864
000

<210> SEQ ID NO 865
<400> SEQUENCE: 865
000

<210> SEQ ID NO 866
<400> SEQUENCE: 866
000

<210> SEQ ID NO 867
<400> SEQUENCE: 867
```

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879
<400> SEQUENCE: 879
000

<210> SEQ ID NO 880
<400> SEQUENCE: 880
000

<210> SEQ ID NO 881
<400> SEQUENCE: 881
000

<210> SEQ ID NO 882
<400> SEQUENCE: 882
000

<210> SEQ ID NO 883
<400> SEQUENCE: 883
000

<210> SEQ ID NO 884
<400> SEQUENCE: 884
000

<210> SEQ ID NO 885
<400> SEQUENCE: 885
000

<210> SEQ ID NO 886
<400> SEQUENCE: 886
000

<210> SEQ ID NO 887
<400> SEQUENCE: 887
000

<210> SEQ ID NO 888
<400> SEQUENCE: 888
000

<210> SEQ ID NO 889
<400> SEQUENCE: 889
000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

-continued

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

-continued

```
<400> SEQUENCE: 913
000

<210> SEQ ID NO 914
<400> SEQUENCE: 914
000

<210> SEQ ID NO 915
<400> SEQUENCE: 915
000

<210> SEQ ID NO 916
<400> SEQUENCE: 916
000

<210> SEQ ID NO 917
<400> SEQUENCE: 917
000

<210> SEQ ID NO 918
<400> SEQUENCE: 918
000

<210> SEQ ID NO 919
<400> SEQUENCE: 919
000

<210> SEQ ID NO 920
<400> SEQUENCE: 920
000

<210> SEQ ID NO 921
<400> SEQUENCE: 921
000

<210> SEQ ID NO 922
<400> SEQUENCE: 922
000

<210> SEQ ID NO 923
<400> SEQUENCE: 923
000

<210> SEQ ID NO 924
<400> SEQUENCE: 924
```

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

-continued

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

-continued

<210> SEQ ID NO 959
<400> SEQUENCE: 959
000

<210> SEQ ID NO 960
<400> SEQUENCE: 960
000

<210> SEQ ID NO 961
<400> SEQUENCE: 961
000

<210> SEQ ID NO 962
<400> SEQUENCE: 962
000

<210> SEQ ID NO 963
<400> SEQUENCE: 963
000

<210> SEQ ID NO 964
<400> SEQUENCE: 964
000

<210> SEQ ID NO 965
<400> SEQUENCE: 965
000

<210> SEQ ID NO 966
<400> SEQUENCE: 966
000

<210> SEQ ID NO 967
<400> SEQUENCE: 967
000

<210> SEQ ID NO 968
<400> SEQUENCE: 968
000

<210> SEQ ID NO 969
<400> SEQUENCE: 969
000

<210> SEQ ID NO 970

```
<400> SEQUENCE: 970
000

<210> SEQ ID NO 971
<400> SEQUENCE: 971
000

<210> SEQ ID NO 972
<400> SEQUENCE: 972
000

<210> SEQ ID NO 973
<400> SEQUENCE: 973
000

<210> SEQ ID NO 974
<400> SEQUENCE: 974
000

<210> SEQ ID NO 975
<400> SEQUENCE: 975
000

<210> SEQ ID NO 976
<400> SEQUENCE: 976
000

<210> SEQ ID NO 977
<400> SEQUENCE: 977
000

<210> SEQ ID NO 978
<400> SEQUENCE: 978
000

<210> SEQ ID NO 979
<400> SEQUENCE: 979
000

<210> SEQ ID NO 980
<400> SEQUENCE: 980
000

<210> SEQ ID NO 981
<400> SEQUENCE: 981
000
```

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

```
<400> SEQUENCE: 993
000

<210> SEQ ID NO 994
<400> SEQUENCE: 994
000

<210> SEQ ID NO 995
<400> SEQUENCE: 995
000

<210> SEQ ID NO 996
<400> SEQUENCE: 996
000

<210> SEQ ID NO 997
<400> SEQUENCE: 997
000

<210> SEQ ID NO 998
<400> SEQUENCE: 998
000

<210> SEQ ID NO 999
<400> SEQUENCE: 999
000

<210> SEQ ID NO 1000
<400> SEQUENCE: 1000
000

<210> SEQ ID NO 1001
<400> SEQUENCE: 1001
000

<210> SEQ ID NO 1002
<400> SEQUENCE: 1002
000

<210> SEQ ID NO 1003
<400> SEQUENCE: 1003
000

<210> SEQ ID NO 1004
<400> SEQUENCE: 1004
```

000

<210> SEQ ID NO 1005
<400> SEQUENCE: 1005
000

<210> SEQ ID NO 1006
<400> SEQUENCE: 1006
000

<210> SEQ ID NO 1007
<400> SEQUENCE: 1007
000

<210> SEQ ID NO 1008
<400> SEQUENCE: 1008
000

<210> SEQ ID NO 1009
<400> SEQUENCE: 1009
000

<210> SEQ ID NO 1010
<400> SEQUENCE: 1010
000

<210> SEQ ID NO 1011
<400> SEQUENCE: 1011
000

<210> SEQ ID NO 1012
<400> SEQUENCE: 1012
000

<210> SEQ ID NO 1013
<400> SEQUENCE: 1013
000

<210> SEQ ID NO 1014
<400> SEQUENCE: 1014
000

<210> SEQ ID NO 1015
<400> SEQUENCE: 1015
000

-continued

```
<210> SEQ ID NO 1016
<400> SEQUENCE: 1016
000

<210> SEQ ID NO 1017
<400> SEQUENCE: 1017
000

<210> SEQ ID NO 1018
<400> SEQUENCE: 1018
000

<210> SEQ ID NO 1019
<400> SEQUENCE: 1019
000

<210> SEQ ID NO 1020
<400> SEQUENCE: 1020
000

<210> SEQ ID NO 1021
<400> SEQUENCE: 1021
000

<210> SEQ ID NO 1022
<400> SEQUENCE: 1022
000

<210> SEQ ID NO 1023
<400> SEQUENCE: 1023
000

<210> SEQ ID NO 1024
<400> SEQUENCE: 1024
000

<210> SEQ ID NO 1025
<400> SEQUENCE: 1025
000

<210> SEQ ID NO 1026
<400> SEQUENCE: 1026
000

<210> SEQ ID NO 1027
<400> SEQUENCE: 1027
```

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

-continued

<210> SEQ ID NO 1039
<400> SEQUENCE: 1039
000

<210> SEQ ID NO 1040
<400> SEQUENCE: 1040
000

<210> SEQ ID NO 1041
<400> SEQUENCE: 1041
000

<210> SEQ ID NO 1042
<400> SEQUENCE: 1042
000

<210> SEQ ID NO 1043
<400> SEQUENCE: 1043
000

<210> SEQ ID NO 1044
<400> SEQUENCE: 1044
000

<210> SEQ ID NO 1045
<400> SEQUENCE: 1045
000

<210> SEQ ID NO 1046
<400> SEQUENCE: 1046
000

<210> SEQ ID NO 1047
<400> SEQUENCE: 1047
000

<210> SEQ ID NO 1048
<400> SEQUENCE: 1048
000

<210> SEQ ID NO 1049
<400> SEQUENCE: 1049
000

<210> SEQ ID NO 1050

```
<400> SEQUENCE: 1050
000

<210> SEQ ID NO 1051
<400> SEQUENCE: 1051
000

<210> SEQ ID NO 1052
<400> SEQUENCE: 1052
000

<210> SEQ ID NO 1053
<400> SEQUENCE: 1053
000

<210> SEQ ID NO 1054
<400> SEQUENCE: 1054
000

<210> SEQ ID NO 1055
<400> SEQUENCE: 1055
000

<210> SEQ ID NO 1056
<400> SEQUENCE: 1056
000

<210> SEQ ID NO 1057
<400> SEQUENCE: 1057
000

<210> SEQ ID NO 1058
<400> SEQUENCE: 1058
000

<210> SEQ ID NO 1059
<400> SEQUENCE: 1059
000

<210> SEQ ID NO 1060
<400> SEQUENCE: 1060
000

<210> SEQ ID NO 1061
<400> SEQUENCE: 1061
000
```

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

-continued

000

<210> SEQ ID NO 1085
<400> SEQUENCE: 1085
000

<210> SEQ ID NO 1086
<400> SEQUENCE: 1086
000

<210> SEQ ID NO 1087
<400> SEQUENCE: 1087
000

<210> SEQ ID NO 1088
<400> SEQUENCE: 1088
000

<210> SEQ ID NO 1089
<400> SEQUENCE: 1089
000

<210> SEQ ID NO 1090
<400> SEQUENCE: 1090
000

<210> SEQ ID NO 1091
<400> SEQUENCE: 1091
000

<210> SEQ ID NO 1092
<400> SEQUENCE: 1092
000

<210> SEQ ID NO 1093
<400> SEQUENCE: 1093
000

<210> SEQ ID NO 1094
<400> SEQUENCE: 1094
000

<210> SEQ ID NO 1095
<400> SEQUENCE: 1095
000

-continued

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108
<400> SEQUENCE: 1108
000

<210> SEQ ID NO 1109
<400> SEQUENCE: 1109
000

<210> SEQ ID NO 1110
<400> SEQUENCE: 1110
000

<210> SEQ ID NO 1111
<400> SEQUENCE: 1111
000

<210> SEQ ID NO 1112
<400> SEQUENCE: 1112
000

<210> SEQ ID NO 1113
<400> SEQUENCE: 1113
000

<210> SEQ ID NO 1114
<400> SEQUENCE: 1114
000

<210> SEQ ID NO 1115
<400> SEQUENCE: 1115
000

<210> SEQ ID NO 1116
<400> SEQUENCE: 1116
000

<210> SEQ ID NO 1117
<400> SEQUENCE: 1117
000

<210> SEQ ID NO 1118
<400> SEQUENCE: 1118
000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129

<400> SEQUENCE: 1129

000

<210> SEQ ID NO 1130

<400> SEQUENCE: 1130

000

<210> SEQ ID NO 1131

<400> SEQUENCE: 1131

000

<210> SEQ ID NO 1132

<400> SEQUENCE: 1132

000

<210> SEQ ID NO 1133

<400> SEQUENCE: 1133

000

<210> SEQ ID NO 1134

<400> SEQUENCE: 1134

000

<210> SEQ ID NO 1135

<400> SEQUENCE: 1135

000

<210> SEQ ID NO 1136

<400> SEQUENCE: 1136

000

<210> SEQ ID NO 1137

<400> SEQUENCE: 1137

000

<210> SEQ ID NO 1138

<400> SEQUENCE: 1138

000

<210> SEQ ID NO 1139

<400> SEQUENCE: 1139

000

<210> SEQ ID NO 1140

<400> SEQUENCE: 1140

000

<210> SEQ ID NO 1141

<400> SEQUENCE: 1141

000

```
<210> SEQ ID NO 1142
<400> SEQUENCE: 1142
000

<210> SEQ ID NO 1143
<400> SEQUENCE: 1143
000

<210> SEQ ID NO 1144
<400> SEQUENCE: 1144
000

<210> SEQ ID NO 1145
<400> SEQUENCE: 1145
000

<210> SEQ ID NO 1146
<400> SEQUENCE: 1146
000

<210> SEQ ID NO 1147
<400> SEQUENCE: 1147
000

<210> SEQ ID NO 1148
<400> SEQUENCE: 1148
000

<210> SEQ ID NO 1149
<400> SEQUENCE: 1149
000

<210> SEQ ID NO 1150
<400> SEQUENCE: 1150
000

<210> SEQ ID NO 1151
<400> SEQUENCE: 1151
000

<210> SEQ ID NO 1152
<400> SEQUENCE: 1152
000

<210> SEQ ID NO 1153
```

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

-continued

<210> SEQ ID NO 1176
<400> SEQUENCE: 1176
000

<210> SEQ ID NO 1177
<400> SEQUENCE: 1177
000

<210> SEQ ID NO 1178
<400> SEQUENCE: 1178
000

<210> SEQ ID NO 1179
<400> SEQUENCE: 1179
000

<210> SEQ ID NO 1180
<400> SEQUENCE: 1180
000

<210> SEQ ID NO 1181
<400> SEQUENCE: 1181
000

<210> SEQ ID NO 1182
<400> SEQUENCE: 1182
000

<210> SEQ ID NO 1183
<400> SEQUENCE: 1183
000

<210> SEQ ID NO 1184
<400> SEQUENCE: 1184
000

<210> SEQ ID NO 1185
<400> SEQUENCE: 1185
000

<210> SEQ ID NO 1186
<400> SEQUENCE: 1186
000

<210> SEQ ID NO 1187
<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203

<400> SEQUENCE: 1203

000

<210> SEQ ID NO 1204

<400> SEQUENCE: 1204

000

<210> SEQ ID NO 1205

<400> SEQUENCE: 1205

000

<210> SEQ ID NO 1206

<400> SEQUENCE: 1206

000

<210> SEQ ID NO 1207

<400> SEQUENCE: 1207

000

<210> SEQ ID NO 1208

<400> SEQUENCE: 1208

000

<210> SEQ ID NO 1209

<400> SEQUENCE: 1209

000

<210> SEQ ID NO 1210

<400> SEQUENCE: 1210

000

<210> SEQ ID NO 1211

<400> SEQUENCE: 1211

000

<210> SEQ ID NO 1212

<400> SEQUENCE: 1212

000

<210> SEQ ID NO 1213

<400> SEQUENCE: 1213

000

<210> SEQ ID NO 1214

<400> SEQUENCE: 1214

000

<210> SEQ ID NO 1215

<400> SEQUENCE: 1215

000

<210> SEQ ID NO 1216

<400> SEQUENCE: 1216

000

<210> SEQ ID NO 1217

<400> SEQUENCE: 1217

000

<210> SEQ ID NO 1218

<400> SEQUENCE: 1218

000

<210> SEQ ID NO 1219

<400> SEQUENCE: 1219

000

<210> SEQ ID NO 1220

<400> SEQUENCE: 1220

000

<210> SEQ ID NO 1221

<400> SEQUENCE: 1221

000

-continued

```
<210> SEQ ID NO 1222
<400> SEQUENCE: 1222
000

<210> SEQ ID NO 1223
<400> SEQUENCE: 1223
000

<210> SEQ ID NO 1224
<400> SEQUENCE: 1224
000

<210> SEQ ID NO 1225
<400> SEQUENCE: 1225
000

<210> SEQ ID NO 1226
<400> SEQUENCE: 1226
000

<210> SEQ ID NO 1227
<400> SEQUENCE: 1227
000

<210> SEQ ID NO 1228
<400> SEQUENCE: 1228
000

<210> SEQ ID NO 1229
<400> SEQUENCE: 1229
000

<210> SEQ ID NO 1230
<400> SEQUENCE: 1230
000

<210> SEQ ID NO 1231
<400> SEQUENCE: 1231
000

<210> SEQ ID NO 1232
<400> SEQUENCE: 1232
000

<210> SEQ ID NO 1233
```

<400> SEQUENCE: 1233

000

<210> SEQ ID NO 1234

<400> SEQUENCE: 1234

000

<210> SEQ ID NO 1235

<400> SEQUENCE: 1235

000

<210> SEQ ID NO 1236

<400> SEQUENCE: 1236

000

<210> SEQ ID NO 1237

<400> SEQUENCE: 1237

000

<210> SEQ ID NO 1238

<400> SEQUENCE: 1238

000

<210> SEQ ID NO 1239

<400> SEQUENCE: 1239

000

<210> SEQ ID NO 1240

<400> SEQUENCE: 1240

000

<210> SEQ ID NO 1241

<400> SEQUENCE: 1241

000

<210> SEQ ID NO 1242

<400> SEQUENCE: 1242

000

<210> SEQ ID NO 1243

<400> SEQUENCE: 1243

000

<210> SEQ ID NO 1244

<400> SEQUENCE: 1244

000

<210> SEQ ID NO 1245
<400> SEQUENCE: 1245
000

<210> SEQ ID NO 1246
<400> SEQUENCE: 1246
000

<210> SEQ ID NO 1247
<400> SEQUENCE: 1247
000

<210> SEQ ID NO 1248
<400> SEQUENCE: 1248
000

<210> SEQ ID NO 1249
<400> SEQUENCE: 1249
000

<210> SEQ ID NO 1250
<400> SEQUENCE: 1250
000

<210> SEQ ID NO 1251
<400> SEQUENCE: 1251
000

<210> SEQ ID NO 1252
<400> SEQUENCE: 1252
000

<210> SEQ ID NO 1253
<400> SEQUENCE: 1253
000

<210> SEQ ID NO 1254
<400> SEQUENCE: 1254
000

<210> SEQ ID NO 1255
<400> SEQUENCE: 1255
000

<210> SEQ ID NO 1256

<400> SEQUENCE: 1256

000

<210> SEQ ID NO 1257

<400> SEQUENCE: 1257

000

<210> SEQ ID NO 1258

<400> SEQUENCE: 1258

000

<210> SEQ ID NO 1259

<400> SEQUENCE: 1259

000

<210> SEQ ID NO 1260

<400> SEQUENCE: 1260

000

<210> SEQ ID NO 1261

<400> SEQUENCE: 1261

000

<210> SEQ ID NO 1262

<400> SEQUENCE: 1262

000

<210> SEQ ID NO 1263

<400> SEQUENCE: 1263

000

<210> SEQ ID NO 1264

<400> SEQUENCE: 1264

000

<210> SEQ ID NO 1265

<400> SEQUENCE: 1265

000

<210> SEQ ID NO 1266

<400> SEQUENCE: 1266

000

<210> SEQ ID NO 1267

<400> SEQUENCE: 1267

000

<210> SEQ ID NO 1268
<400> SEQUENCE: 1268
000

<210> SEQ ID NO 1269
<400> SEQUENCE: 1269
000

<210> SEQ ID NO 1270
<400> SEQUENCE: 1270
000

<210> SEQ ID NO 1271
<400> SEQUENCE: 1271
000

<210> SEQ ID NO 1272
<400> SEQUENCE: 1272
000

<210> SEQ ID NO 1273
<400> SEQUENCE: 1273
000

<210> SEQ ID NO 1274
<400> SEQUENCE: 1274
000

<210> SEQ ID NO 1275
<400> SEQUENCE: 1275
000

<210> SEQ ID NO 1276
<400> SEQUENCE: 1276
000

<210> SEQ ID NO 1277
<400> SEQUENCE: 1277
000

<210> SEQ ID NO 1278
<400> SEQUENCE: 1278
000

-continued

<210> SEQ ID NO 1279
<400> SEQUENCE: 1279
000

<210> SEQ ID NO 1280
<400> SEQUENCE: 1280
000

<210> SEQ ID NO 1281
<400> SEQUENCE: 1281
000

<210> SEQ ID NO 1282
<400> SEQUENCE: 1282
000

<210> SEQ ID NO 1283
<400> SEQUENCE: 1283
000

<210> SEQ ID NO 1284
<400> SEQUENCE: 1284
000

<210> SEQ ID NO 1285
<400> SEQUENCE: 1285
000

<210> SEQ ID NO 1286
<400> SEQUENCE: 1286
000

<210> SEQ ID NO 1287
<400> SEQUENCE: 1287
000

<210> SEQ ID NO 1288
<400> SEQUENCE: 1288
000

<210> SEQ ID NO 1289
<400> SEQUENCE: 1289
000

<210> SEQ ID NO 1290

<400> SEQUENCE: 1290

000

<210> SEQ ID NO 1291

<400> SEQUENCE: 1291

000

<210> SEQ ID NO 1292

<400> SEQUENCE: 1292

000

<210> SEQ ID NO 1293

<400> SEQUENCE: 1293

000

<210> SEQ ID NO 1294

<400> SEQUENCE: 1294

000

<210> SEQ ID NO 1295

<400> SEQUENCE: 1295

000

<210> SEQ ID NO 1296

<400> SEQUENCE: 1296

000

<210> SEQ ID NO 1297

<400> SEQUENCE: 1297

000

<210> SEQ ID NO 1298

<400> SEQUENCE: 1298

000

<210> SEQ ID NO 1299

<400> SEQUENCE: 1299

000

<210> SEQ ID NO 1300

<400> SEQUENCE: 1300

000

<210> SEQ ID NO 1301

<400> SEQUENCE: 1301

000

-continued

<210> SEQ ID NO 1302

<400> SEQUENCE: 1302

000

<210> SEQ ID NO 1303

<400> SEQUENCE: 1303

000

<210> SEQ ID NO 1304

<400> SEQUENCE: 1304

000

<210> SEQ ID NO 1305

<400> SEQUENCE: 1305

000

<210> SEQ ID NO 1306

<400> SEQUENCE: 1306

000

<210> SEQ ID NO 1307

<400> SEQUENCE: 1307

000

<210> SEQ ID NO 1308

<400> SEQUENCE: 1308

000

<210> SEQ ID NO 1309

<400> SEQUENCE: 1309

000

<210> SEQ ID NO 1310

<400> SEQUENCE: 1310

000

<210> SEQ ID NO 1311

<400> SEQUENCE: 1311

000

<210> SEQ ID NO 1312

<400> SEQUENCE: 1312

000

<210> SEQ ID NO 1313

<400> SEQUENCE: 1313

000

<210> SEQ ID NO 1314

<400> SEQUENCE: 1314

000

<210> SEQ ID NO 1315

<400> SEQUENCE: 1315

000

<210> SEQ ID NO 1316

<400> SEQUENCE: 1316

000

<210> SEQ ID NO 1317

<400> SEQUENCE: 1317

000

<210> SEQ ID NO 1318

<400> SEQUENCE: 1318

000

<210> SEQ ID NO 1319

<400> SEQUENCE: 1319

000

<210> SEQ ID NO 1320

<400> SEQUENCE: 1320

000

<210> SEQ ID NO 1321

<400> SEQUENCE: 1321

000

<210> SEQ ID NO 1322

<400> SEQUENCE: 1322

000

<210> SEQ ID NO 1323

<400> SEQUENCE: 1323

000

<210> SEQ ID NO 1324

<400> SEQUENCE: 1324

000

<210> SEQ ID NO 1325

<400> SEQUENCE: 1325

000

<210> SEQ ID NO 1326

<400> SEQUENCE: 1326

000

<210> SEQ ID NO 1327

<400> SEQUENCE: 1327

000

<210> SEQ ID NO 1328

<400> SEQUENCE: 1328

000

<210> SEQ ID NO 1329

<400> SEQUENCE: 1329

000

<210> SEQ ID NO 1330

<400> SEQUENCE: 1330

000

<210> SEQ ID NO 1331

<400> SEQUENCE: 1331

000

<210> SEQ ID NO 1332

<400> SEQUENCE: 1332

000

<210> SEQ ID NO 1333

<400> SEQUENCE: 1333

000

<210> SEQ ID NO 1334

<400> SEQUENCE: 1334

000

<210> SEQ ID NO 1335

<400> SEQUENCE: 1335

000

-continued

<210> SEQ ID NO 1336

<400> SEQUENCE: 1336

000

<210> SEQ ID NO 1337

<400> SEQUENCE: 1337

000

<210> SEQ ID NO 1338

<400> SEQUENCE: 1338

000

<210> SEQ ID NO 1339

<400> SEQUENCE: 1339

000

<210> SEQ ID NO 1340

<400> SEQUENCE: 1340

000

<210> SEQ ID NO 1341

<400> SEQUENCE: 1341

000

<210> SEQ ID NO 1342

<400> SEQUENCE: 1342

000

<210> SEQ ID NO 1343

<400> SEQUENCE: 1343

000

<210> SEQ ID NO 1344

<400> SEQUENCE: 1344

000

<210> SEQ ID NO 1345

<400> SEQUENCE: 1345

000

<210> SEQ ID NO 1346

<400> SEQUENCE: 1346

000

<210> SEQ ID NO 1347

<400> SEQUENCE: 1347

000

<210> SEQ ID NO 1348

<400> SEQUENCE: 1348

000

<210> SEQ ID NO 1349

<400> SEQUENCE: 1349

000

<210> SEQ ID NO 1350

<400> SEQUENCE: 1350

000

<210> SEQ ID NO 1351

<400> SEQUENCE: 1351

000

<210> SEQ ID NO 1352

<400> SEQUENCE: 1352

000

<210> SEQ ID NO 1353

<400> SEQUENCE: 1353

000

<210> SEQ ID NO 1354

<400> SEQUENCE: 1354

000

<210> SEQ ID NO 1355

<400> SEQUENCE: 1355

000

<210> SEQ ID NO 1356

<400> SEQUENCE: 1356

000

<210> SEQ ID NO 1357

<400> SEQUENCE: 1357

000

<210> SEQ ID NO 1358

<400> SEQUENCE: 1358

000

-continued

<210> SEQ ID NO 1359
<400> SEQUENCE: 1359
000

<210> SEQ ID NO 1360
<400> SEQUENCE: 1360
000

<210> SEQ ID NO 1361
<400> SEQUENCE: 1361
000

<210> SEQ ID NO 1362
<400> SEQUENCE: 1362
000

<210> SEQ ID NO 1363
<400> SEQUENCE: 1363
000

<210> SEQ ID NO 1364
<400> SEQUENCE: 1364
000

<210> SEQ ID NO 1365
<400> SEQUENCE: 1365
000

<210> SEQ ID NO 1366
<400> SEQUENCE: 1366
000

<210> SEQ ID NO 1367
<400> SEQUENCE: 1367
000

<210> SEQ ID NO 1368
<400> SEQUENCE: 1368
000

<210> SEQ ID NO 1369
<400> SEQUENCE: 1369
000

<210> SEQ ID NO 1370

<400> SEQUENCE: 1370

000

<210> SEQ ID NO 1371

<400> SEQUENCE: 1371

000

<210> SEQ ID NO 1372

<400> SEQUENCE: 1372

000

<210> SEQ ID NO 1373

<400> SEQUENCE: 1373

000

<210> SEQ ID NO 1374

<400> SEQUENCE: 1374

000

<210> SEQ ID NO 1375

<400> SEQUENCE: 1375

000

<210> SEQ ID NO 1376

<400> SEQUENCE: 1376

000

<210> SEQ ID NO 1377

<400> SEQUENCE: 1377

000

<210> SEQ ID NO 1378

<400> SEQUENCE: 1378

000

<210> SEQ ID NO 1379

<400> SEQUENCE: 1379

000

<210> SEQ ID NO 1380

<400> SEQUENCE: 1380

000

<210> SEQ ID NO 1381

<400> SEQUENCE: 1381

000

<210> SEQ ID NO 1382

<400> SEQUENCE: 1382

000

<210> SEQ ID NO 1383

<400> SEQUENCE: 1383

000

<210> SEQ ID NO 1384

<400> SEQUENCE: 1384

000

<210> SEQ ID NO 1385

<400> SEQUENCE: 1385

000

<210> SEQ ID NO 1386

<400> SEQUENCE: 1386

000

<210> SEQ ID NO 1387

<400> SEQUENCE: 1387

000

<210> SEQ ID NO 1388

<400> SEQUENCE: 1388

000

<210> SEQ ID NO 1389

<400> SEQUENCE: 1389

000

<210> SEQ ID NO 1390

<400> SEQUENCE: 1390

000

<210> SEQ ID NO 1391

<400> SEQUENCE: 1391

000

<210> SEQ ID NO 1392

<400> SEQUENCE: 1392

000

<210> SEQ ID NO 1393

<400> SEQUENCE: 1393

000

<210> SEQ ID NO 1394

<400> SEQUENCE: 1394

000

<210> SEQ ID NO 1395

<400> SEQUENCE: 1395

000

<210> SEQ ID NO 1396

<400> SEQUENCE: 1396

000

<210> SEQ ID NO 1397

<400> SEQUENCE: 1397

000

<210> SEQ ID NO 1398

<400> SEQUENCE: 1398

000

<210> SEQ ID NO 1399

<400> SEQUENCE: 1399

000

<210> SEQ ID NO 1400

<400> SEQUENCE: 1400

000

<210> SEQ ID NO 1401

<400> SEQUENCE: 1401

000

<210> SEQ ID NO 1402

<400> SEQUENCE: 1402

000

<210> SEQ ID NO 1403

<400> SEQUENCE: 1403

000

<210> SEQ ID NO 1404

<400> SEQUENCE: 1404

000

<210> SEQ ID NO 1405
<400> SEQUENCE: 1405
000

<210> SEQ ID NO 1406
<400> SEQUENCE: 1406
000

<210> SEQ ID NO 1407
<400> SEQUENCE: 1407
000

<210> SEQ ID NO 1408
<400> SEQUENCE: 1408
000

<210> SEQ ID NO 1409
<400> SEQUENCE: 1409
000

<210> SEQ ID NO 1410
<400> SEQUENCE: 1410
000

<210> SEQ ID NO 1411
<400> SEQUENCE: 1411
000

<210> SEQ ID NO 1412
<400> SEQUENCE: 1412
000

<210> SEQ ID NO 1413
<400> SEQUENCE: 1413
000

<210> SEQ ID NO 1414
<400> SEQUENCE: 1414
000

<210> SEQ ID NO 1415
<400> SEQUENCE: 1415
000

-continued

<210> SEQ ID NO 1416

<400> SEQUENCE: 1416

000

<210> SEQ ID NO 1417

<400> SEQUENCE: 1417

000

<210> SEQ ID NO 1418

<400> SEQUENCE: 1418

000

<210> SEQ ID NO 1419

<400> SEQUENCE: 1419

000

<210> SEQ ID NO 1420

<400> SEQUENCE: 1420

000

<210> SEQ ID NO 1421

<400> SEQUENCE: 1421

000

<210> SEQ ID NO 1422

<400> SEQUENCE: 1422

000

<210> SEQ ID NO 1423

<400> SEQUENCE: 1423

000

<210> SEQ ID NO 1424

<400> SEQUENCE: 1424

000

<210> SEQ ID NO 1425

<400> SEQUENCE: 1425

000

<210> SEQ ID NO 1426

<400> SEQUENCE: 1426

000

<210> SEQ ID NO 1427

<400> SEQUENCE: 1427

000

<210> SEQ ID NO 1428

<400> SEQUENCE: 1428

000

<210> SEQ ID NO 1429

<400> SEQUENCE: 1429

000

<210> SEQ ID NO 1430

<400> SEQUENCE: 1430

000

<210> SEQ ID NO 1431

<400> SEQUENCE: 1431

000

<210> SEQ ID NO 1432

<400> SEQUENCE: 1432

000

<210> SEQ ID NO 1433

<400> SEQUENCE: 1433

000

<210> SEQ ID NO 1434

<400> SEQUENCE: 1434

000

<210> SEQ ID NO 1435

<400> SEQUENCE: 1435

000

<210> SEQ ID NO 1436

<400> SEQUENCE: 1436

000

<210> SEQ ID NO 1437

<400> SEQUENCE: 1437

000

<210> SEQ ID NO 1438

<400> SEQUENCE: 1438

000

<210> SEQ ID NO 1439

<400> SEQUENCE: 1439

000

<210> SEQ ID NO 1440

<400> SEQUENCE: 1440

000

<210> SEQ ID NO 1441

<400> SEQUENCE: 1441

000

<210> SEQ ID NO 1442

<400> SEQUENCE: 1442

000

<210> SEQ ID NO 1443

<400> SEQUENCE: 1443

000

<210> SEQ ID NO 1444

<400> SEQUENCE: 1444

000

<210> SEQ ID NO 1445

<400> SEQUENCE: 1445

000

<210> SEQ ID NO 1446

<400> SEQUENCE: 1446

000

<210> SEQ ID NO 1447

<400> SEQUENCE: 1447

000

<210> SEQ ID NO 1448

<400> SEQUENCE: 1448

000

<210> SEQ ID NO 1449

<400> SEQUENCE: 1449

000

<210> SEQ ID NO 1450

```
<400> SEQUENCE: 1450
000

<210> SEQ ID NO 1451
<400> SEQUENCE: 1451
000

<210> SEQ ID NO 1452
<400> SEQUENCE: 1452
000

<210> SEQ ID NO 1453
<400> SEQUENCE: 1453
000

<210> SEQ ID NO 1454
<400> SEQUENCE: 1454
000

<210> SEQ ID NO 1455
<400> SEQUENCE: 1455
000

<210> SEQ ID NO 1456
<400> SEQUENCE: 1456
000

<210> SEQ ID NO 1457
<400> SEQUENCE: 1457
000

<210> SEQ ID NO 1458
<400> SEQUENCE: 1458
000

<210> SEQ ID NO 1459
<400> SEQUENCE: 1459
000

<210> SEQ ID NO 1460
<400> SEQUENCE: 1460
000

<210> SEQ ID NO 1461
<400> SEQUENCE: 1461
000
```

-continued

<210> SEQ ID NO 1462

<400> SEQUENCE: 1462

000

<210> SEQ ID NO 1463

<400> SEQUENCE: 1463

000

<210> SEQ ID NO 1464

<400> SEQUENCE: 1464

000

<210> SEQ ID NO 1465

<400> SEQUENCE: 1465

000

<210> SEQ ID NO 1466

<400> SEQUENCE: 1466

000

<210> SEQ ID NO 1467

<400> SEQUENCE: 1467

000

<210> SEQ ID NO 1468

<400> SEQUENCE: 1468

000

<210> SEQ ID NO 1469

<400> SEQUENCE: 1469

000

<210> SEQ ID NO 1470

<400> SEQUENCE: 1470

000

<210> SEQ ID NO 1471

<400> SEQUENCE: 1471

000

<210> SEQ ID NO 1472

<400> SEQUENCE: 1472

000

<210> SEQ ID NO 1473

<400> SEQUENCE: 1473

000

<210> SEQ ID NO 1474

<400> SEQUENCE: 1474

000

<210> SEQ ID NO 1475

<400> SEQUENCE: 1475

000

<210> SEQ ID NO 1476

<400> SEQUENCE: 1476

000

<210> SEQ ID NO 1477

<400> SEQUENCE: 1477

000

<210> SEQ ID NO 1478

<400> SEQUENCE: 1478

000

<210> SEQ ID NO 1479

<400> SEQUENCE: 1479

000

<210> SEQ ID NO 1480

<400> SEQUENCE: 1480

000

<210> SEQ ID NO 1481

<400> SEQUENCE: 1481

000

<210> SEQ ID NO 1482

<400> SEQUENCE: 1482

000

<210> SEQ ID NO 1483

<400> SEQUENCE: 1483

000

<210> SEQ ID NO 1484

<400> SEQUENCE: 1484

000

<210> SEQ ID NO 1485

<400> SEQUENCE: 1485

000

<210> SEQ ID NO 1486

<400> SEQUENCE: 1486

000

<210> SEQ ID NO 1487

<400> SEQUENCE: 1487

000

<210> SEQ ID NO 1488

<400> SEQUENCE: 1488

000

<210> SEQ ID NO 1489

<400> SEQUENCE: 1489

000

<210> SEQ ID NO 1490

<400> SEQUENCE: 1490

000

<210> SEQ ID NO 1491

<400> SEQUENCE: 1491

000

<210> SEQ ID NO 1492

<400> SEQUENCE: 1492

000

<210> SEQ ID NO 1493

<400> SEQUENCE: 1493

000

<210> SEQ ID NO 1494

<400> SEQUENCE: 1494

000

<210> SEQ ID NO 1495

<400> SEQUENCE: 1495

000

-continued

<210> SEQ ID NO 1496

<400> SEQUENCE: 1496

000

<210> SEQ ID NO 1497

<400> SEQUENCE: 1497

000

<210> SEQ ID NO 1498

<400> SEQUENCE: 1498

000

<210> SEQ ID NO 1499

<400> SEQUENCE: 1499

000

<210> SEQ ID NO 1500

<400> SEQUENCE: 1500

000

<210> SEQ ID NO 1501

<400> SEQUENCE: 1501

000

<210> SEQ ID NO 1502

<400> SEQUENCE: 1502

000

<210> SEQ ID NO 1503

<400> SEQUENCE: 1503

000

<210> SEQ ID NO 1504

<400> SEQUENCE: 1504

000

<210> SEQ ID NO 1505

<400> SEQUENCE: 1505

000

<210> SEQ ID NO 1506

<400> SEQUENCE: 1506

000

<210> SEQ ID NO 1507

<400> SEQUENCE: 1507

000

<210> SEQ ID NO 1508

<400> SEQUENCE: 1508

000

<210> SEQ ID NO 1509

<400> SEQUENCE: 1509

000

<210> SEQ ID NO 1510

<400> SEQUENCE: 1510

000

<210> SEQ ID NO 1511

<400> SEQUENCE: 1511

000

<210> SEQ ID NO 1512

<400> SEQUENCE: 1512

000

<210> SEQ ID NO 1513

<400> SEQUENCE: 1513

000

<210> SEQ ID NO 1514

<400> SEQUENCE: 1514

000

<210> SEQ ID NO 1515

<400> SEQUENCE: 1515

000

<210> SEQ ID NO 1516

<400> SEQUENCE: 1516

000

<210> SEQ ID NO 1517

<400> SEQUENCE: 1517

000

<210> SEQ ID NO 1518

<400> SEQUENCE: 1518

000

-continued

<210> SEQ ID NO 1519
<400> SEQUENCE: 1519
000

<210> SEQ ID NO 1520
<400> SEQUENCE: 1520
000

<210> SEQ ID NO 1521
<400> SEQUENCE: 1521
000

<210> SEQ ID NO 1522
<400> SEQUENCE: 1522
000

<210> SEQ ID NO 1523
<400> SEQUENCE: 1523
000

<210> SEQ ID NO 1524
<400> SEQUENCE: 1524
000

<210> SEQ ID NO 1525
<400> SEQUENCE: 1525
000

<210> SEQ ID NO 1526
<400> SEQUENCE: 1526
000

<210> SEQ ID NO 1527
<400> SEQUENCE: 1527
000

<210> SEQ ID NO 1528
<400> SEQUENCE: 1528
000

<210> SEQ ID NO 1529
<400> SEQUENCE: 1529
000

<210> SEQ ID NO 1530

```
<400> SEQUENCE: 1530
000

<210> SEQ ID NO 1531
<400> SEQUENCE: 1531
000

<210> SEQ ID NO 1532
<400> SEQUENCE: 1532
000

<210> SEQ ID NO 1533
<400> SEQUENCE: 1533
000

<210> SEQ ID NO 1534
<400> SEQUENCE: 1534
000

<210> SEQ ID NO 1535
<400> SEQUENCE: 1535
000

<210> SEQ ID NO 1536
<400> SEQUENCE: 1536
000

<210> SEQ ID NO 1537
<400> SEQUENCE: 1537
000

<210> SEQ ID NO 1538
<400> SEQUENCE: 1538
000

<210> SEQ ID NO 1539
<400> SEQUENCE: 1539
000

<210> SEQ ID NO 1540
<400> SEQUENCE: 1540
000

<210> SEQ ID NO 1541
<400> SEQUENCE: 1541
000
```

<210> SEQ ID NO 1542

<400> SEQUENCE: 1542

000

<210> SEQ ID NO 1543

<400> SEQUENCE: 1543

000

<210> SEQ ID NO 1544

<400> SEQUENCE: 1544

000

<210> SEQ ID NO 1545

<400> SEQUENCE: 1545

000

<210> SEQ ID NO 1546

<400> SEQUENCE: 1546

000

<210> SEQ ID NO 1547

<400> SEQUENCE: 1547

000

<210> SEQ ID NO 1548

<400> SEQUENCE: 1548

000

<210> SEQ ID NO 1549

<400> SEQUENCE: 1549

000

<210> SEQ ID NO 1550

<400> SEQUENCE: 1550

000

<210> SEQ ID NO 1551

<400> SEQUENCE: 1551

000

<210> SEQ ID NO 1552

<400> SEQUENCE: 1552

000

<210> SEQ ID NO 1553

<400> SEQUENCE: 1553

000

<210> SEQ ID NO 1554

<400> SEQUENCE: 1554

000

<210> SEQ ID NO 1555

<400> SEQUENCE: 1555

000

<210> SEQ ID NO 1556

<400> SEQUENCE: 1556

000

<210> SEQ ID NO 1557

<400> SEQUENCE: 1557

000

<210> SEQ ID NO 1558

<400> SEQUENCE: 1558

000

<210> SEQ ID NO 1559

<400> SEQUENCE: 1559

000

<210> SEQ ID NO 1560

<400> SEQUENCE: 1560

000

<210> SEQ ID NO 1561

<400> SEQUENCE: 1561

000

<210> SEQ ID NO 1562

<400> SEQUENCE: 1562

000

<210> SEQ ID NO 1563

<400> SEQUENCE: 1563

000

<210> SEQ ID NO 1564

<400> SEQUENCE: 1564

000

<210> SEQ ID NO 1565

<400> SEQUENCE: 1565

000

<210> SEQ ID NO 1566

<400> SEQUENCE: 1566

000

<210> SEQ ID NO 1567

<400> SEQUENCE: 1567

000

<210> SEQ ID NO 1568

<400> SEQUENCE: 1568

000

<210> SEQ ID NO 1569

<400> SEQUENCE: 1569

000

<210> SEQ ID NO 1570

<400> SEQUENCE: 1570

000

<210> SEQ ID NO 1571

<400> SEQUENCE: 1571

000

<210> SEQ ID NO 1572

<400> SEQUENCE: 1572

000

<210> SEQ ID NO 1573

<400> SEQUENCE: 1573

000

<210> SEQ ID NO 1574

<400> SEQUENCE: 1574

000

<210> SEQ ID NO 1575

<400> SEQUENCE: 1575

000

-continued

<210> SEQ ID NO 1576
<400> SEQUENCE: 1576
000

<210> SEQ ID NO 1577
<400> SEQUENCE: 1577
000

<210> SEQ ID NO 1578
<400> SEQUENCE: 1578
000

<210> SEQ ID NO 1579
<400> SEQUENCE: 1579
000

<210> SEQ ID NO 1580
<400> SEQUENCE: 1580
000

<210> SEQ ID NO 1581
<400> SEQUENCE: 1581
000

<210> SEQ ID NO 1582
<400> SEQUENCE: 1582
000

<210> SEQ ID NO 1583
<400> SEQUENCE: 1583
000

<210> SEQ ID NO 1584
<400> SEQUENCE: 1584
000

<210> SEQ ID NO 1585
<400> SEQUENCE: 1585
000

<210> SEQ ID NO 1586
<400> SEQUENCE: 1586
000

<210> SEQ ID NO 1587
<400> SEQUENCE: 1587

000

<210> SEQ ID NO 1588

<400> SEQUENCE: 1588

000

<210> SEQ ID NO 1589

<400> SEQUENCE: 1589

000

<210> SEQ ID NO 1590

<400> SEQUENCE: 1590

000

<210> SEQ ID NO 1591

<400> SEQUENCE: 1591

000

<210> SEQ ID NO 1592

<400> SEQUENCE: 1592

000

<210> SEQ ID NO 1593

<400> SEQUENCE: 1593

000

<210> SEQ ID NO 1594

<400> SEQUENCE: 1594

000

<210> SEQ ID NO 1595

<400> SEQUENCE: 1595

000

<210> SEQ ID NO 1596

<400> SEQUENCE: 1596

000

<210> SEQ ID NO 1597

<400> SEQUENCE: 1597

000

<210> SEQ ID NO 1598

<400> SEQUENCE: 1598

000

-continued

<210> SEQ ID NO 1599
<400> SEQUENCE: 1599
000

<210> SEQ ID NO 1600
<400> SEQUENCE: 1600
000

<210> SEQ ID NO 1601
<400> SEQUENCE: 1601
000

<210> SEQ ID NO 1602
<400> SEQUENCE: 1602
000

<210> SEQ ID NO 1603
<400> SEQUENCE: 1603
000

<210> SEQ ID NO 1604
<400> SEQUENCE: 1604
000

<210> SEQ ID NO 1605
<400> SEQUENCE: 1605
000

<210> SEQ ID NO 1606
<400> SEQUENCE: 1606
000

<210> SEQ ID NO 1607
<400> SEQUENCE: 1607
000

<210> SEQ ID NO 1608
<400> SEQUENCE: 1608
000

<210> SEQ ID NO 1609
<400> SEQUENCE: 1609
000

<210> SEQ ID NO 1610

<400> SEQUENCE: 1610

000

<210> SEQ ID NO 1611

<400> SEQUENCE: 1611

000

<210> SEQ ID NO 1612

<400> SEQUENCE: 1612

000

<210> SEQ ID NO 1613

<400> SEQUENCE: 1613

000

<210> SEQ ID NO 1614

<400> SEQUENCE: 1614

000

<210> SEQ ID NO 1615

<400> SEQUENCE: 1615

000

<210> SEQ ID NO 1616

<400> SEQUENCE: 1616

000

<210> SEQ ID NO 1617

<400> SEQUENCE: 1617

000

<210> SEQ ID NO 1618

<400> SEQUENCE: 1618

000

<210> SEQ ID NO 1619

<400> SEQUENCE: 1619

000

<210> SEQ ID NO 1620

<400> SEQUENCE: 1620

000

<210> SEQ ID NO 1621

<400> SEQUENCE: 1621

000

<210> SEQ ID NO 1622

<400> SEQUENCE: 1622

000

<210> SEQ ID NO 1623

<400> SEQUENCE: 1623

000

<210> SEQ ID NO 1624

<400> SEQUENCE: 1624

000

<210> SEQ ID NO 1625

<400> SEQUENCE: 1625

000

<210> SEQ ID NO 1626

<400> SEQUENCE: 1626

000

<210> SEQ ID NO 1627

<400> SEQUENCE: 1627

000

<210> SEQ ID NO 1628

<400> SEQUENCE: 1628

000

<210> SEQ ID NO 1629

<400> SEQUENCE: 1629

000

<210> SEQ ID NO 1630

<400> SEQUENCE: 1630

000

<210> SEQ ID NO 1631

<400> SEQUENCE: 1631

000

<210> SEQ ID NO 1632

<400> SEQUENCE: 1632

000

<210> SEQ ID NO 1633

<400> SEQUENCE: 1633

000

<210> SEQ ID NO 1634

<400> SEQUENCE: 1634

000

<210> SEQ ID NO 1635

<400> SEQUENCE: 1635

000

<210> SEQ ID NO 1636

<400> SEQUENCE: 1636

000

<210> SEQ ID NO 1637

<400> SEQUENCE: 1637

000

<210> SEQ ID NO 1638

<400> SEQUENCE: 1638

000

<210> SEQ ID NO 1639

<400> SEQUENCE: 1639

000

<210> SEQ ID NO 1640

<400> SEQUENCE: 1640

000

<210> SEQ ID NO 1641

<400> SEQUENCE: 1641

000

<210> SEQ ID NO 1642

<400> SEQUENCE: 1642

000

<210> SEQ ID NO 1643

<400> SEQUENCE: 1643

000

<210> SEQ ID NO 1644

<400> SEQUENCE: 1644

000

<210> SEQ ID NO 1645

<400> SEQUENCE: 1645

000

<210> SEQ ID NO 1646

<400> SEQUENCE: 1646

000

<210> SEQ ID NO 1647

<400> SEQUENCE: 1647

000

<210> SEQ ID NO 1648

<400> SEQUENCE: 1648

000

<210> SEQ ID NO 1649

<400> SEQUENCE: 1649

000

<210> SEQ ID NO 1650

<400> SEQUENCE: 1650

000

<210> SEQ ID NO 1651

<400> SEQUENCE: 1651

000

<210> SEQ ID NO 1652

<400> SEQUENCE: 1652

000

<210> SEQ ID NO 1653

<400> SEQUENCE: 1653

000

<210> SEQ ID NO 1654

<400> SEQUENCE: 1654

000

<210> SEQ ID NO 1655

<400> SEQUENCE: 1655

000

<210> SEQ ID NO 1656

<400> SEQUENCE: 1656

000

<210> SEQ ID NO 1657

<400> SEQUENCE: 1657

000

<210> SEQ ID NO 1658

<400> SEQUENCE: 1658

000

<210> SEQ ID NO 1659

<400> SEQUENCE: 1659

000

<210> SEQ ID NO 1660

<400> SEQUENCE: 1660

000

<210> SEQ ID NO 1661

<400> SEQUENCE: 1661

000

<210> SEQ ID NO 1662

<400> SEQUENCE: 1662

000

<210> SEQ ID NO 1663

<400> SEQUENCE: 1663

000

<210> SEQ ID NO 1664

<400> SEQUENCE: 1664

000

<210> SEQ ID NO 1665

<400> SEQUENCE: 1665

000

<210> SEQ ID NO 1666

<400> SEQUENCE: 1666

000

<210> SEQ ID NO 1667

<400> SEQUENCE: 1667

000

<210> SEQ ID NO 1668

<400> SEQUENCE: 1668

000

<210> SEQ ID NO 1669

<400> SEQUENCE: 1669

000

<210> SEQ ID NO 1670

<400> SEQUENCE: 1670

000

<210> SEQ ID NO 1671

<400> SEQUENCE: 1671

000

<210> SEQ ID NO 1672

<400> SEQUENCE: 1672

000

<210> SEQ ID NO 1673

<400> SEQUENCE: 1673

000

<210> SEQ ID NO 1674

<400> SEQUENCE: 1674

000

<210> SEQ ID NO 1675

<400> SEQUENCE: 1675

000

<210> SEQ ID NO 1676

<400> SEQUENCE: 1676

000

<210> SEQ ID NO 1677

<400> SEQUENCE: 1677

000

<210> SEQ ID NO 1678

<400> SEQUENCE: 1678

000

<210> SEQ ID NO 1679

<400> SEQUENCE: 1679

000

<210> SEQ ID NO 1680

<400> SEQUENCE: 1680

000

<210> SEQ ID NO 1681

<400> SEQUENCE: 1681

000

<210> SEQ ID NO 1682

<400> SEQUENCE: 1682

000

<210> SEQ ID NO 1683

<400> SEQUENCE: 1683

000

<210> SEQ ID NO 1684

<400> SEQUENCE: 1684

000

<210> SEQ ID NO 1685

<400> SEQUENCE: 1685

000

<210> SEQ ID NO 1686

<400> SEQUENCE: 1686

000

<210> SEQ ID NO 1687

<400> SEQUENCE: 1687

000

<210> SEQ ID NO 1688

<400> SEQUENCE: 1688

000

<210> SEQ ID NO 1689

<400> SEQUENCE: 1689

000

<210> SEQ ID NO 1690

```
<400> SEQUENCE: 1690

000

<210> SEQ ID NO 1691

<400> SEQUENCE: 1691

000

<210> SEQ ID NO 1692

<400> SEQUENCE: 1692

000

<210> SEQ ID NO 1693

<400> SEQUENCE: 1693

000

<210> SEQ ID NO 1694

<400> SEQUENCE: 1694

000

<210> SEQ ID NO 1695

<400> SEQUENCE: 1695

000

<210> SEQ ID NO 1696

<400> SEQUENCE: 1696

000

<210> SEQ ID NO 1697

<400> SEQUENCE: 1697

000

<210> SEQ ID NO 1698

<400> SEQUENCE: 1698

000

<210> SEQ ID NO 1699

<400> SEQUENCE: 1699

000

<210> SEQ ID NO 1700

<400> SEQUENCE: 1700

000

<210> SEQ ID NO 1701

<400> SEQUENCE: 1701

000
```

<210> SEQ ID NO 1702

<400> SEQUENCE: 1702

000

<210> SEQ ID NO 1703

<400> SEQUENCE: 1703

000

<210> SEQ ID NO 1704

<400> SEQUENCE: 1704

000

<210> SEQ ID NO 1705

<400> SEQUENCE: 1705

000

<210> SEQ ID NO 1706

<400> SEQUENCE: 1706

000

<210> SEQ ID NO 1707

<400> SEQUENCE: 1707

000

<210> SEQ ID NO 1708

<400> SEQUENCE: 1708

000

<210> SEQ ID NO 1709

<400> SEQUENCE: 1709

000

<210> SEQ ID NO 1710

<400> SEQUENCE: 1710

000

<210> SEQ ID NO 1711

<400> SEQUENCE: 1711

000

<210> SEQ ID NO 1712

<400> SEQUENCE: 1712

000

<210> SEQ ID NO 1713

<400> SEQUENCE: 1713

000

<210> SEQ ID NO 1714

<400> SEQUENCE: 1714

000

<210> SEQ ID NO 1715

<400> SEQUENCE: 1715

000

<210> SEQ ID NO 1716

<400> SEQUENCE: 1716

000

<210> SEQ ID NO 1717

<400> SEQUENCE: 1717

000

<210> SEQ ID NO 1718

<400> SEQUENCE: 1718

000

<210> SEQ ID NO 1719

<400> SEQUENCE: 1719

000

<210> SEQ ID NO 1720

<400> SEQUENCE: 1720

000

<210> SEQ ID NO 1721

<400> SEQUENCE: 1721

000

<210> SEQ ID NO 1722

<400> SEQUENCE: 1722

000

<210> SEQ ID NO 1723

<400> SEQUENCE: 1723

000

<210> SEQ ID NO 1724

<400> SEQUENCE: 1724

000

<210> SEQ ID NO 1725
<400> SEQUENCE: 1725
000

<210> SEQ ID NO 1726
<400> SEQUENCE: 1726
000

<210> SEQ ID NO 1727
<400> SEQUENCE: 1727
000

<210> SEQ ID NO 1728
<400> SEQUENCE: 1728
000

<210> SEQ ID NO 1729
<400> SEQUENCE: 1729
000

<210> SEQ ID NO 1730
<400> SEQUENCE: 1730
000

<210> SEQ ID NO 1731
<400> SEQUENCE: 1731
000

<210> SEQ ID NO 1732
<400> SEQUENCE: 1732
000

<210> SEQ ID NO 1733
<400> SEQUENCE: 1733
000

<210> SEQ ID NO 1734
<400> SEQUENCE: 1734
000

<210> SEQ ID NO 1735
<400> SEQUENCE: 1735
000

<210> SEQ ID NO 1736

<400> SEQUENCE: 1736

000

<210> SEQ ID NO 1737

<400> SEQUENCE: 1737

000

<210> SEQ ID NO 1738

<400> SEQUENCE: 1738

000

<210> SEQ ID NO 1739

<400> SEQUENCE: 1739

000

<210> SEQ ID NO 1740

<400> SEQUENCE: 1740

000

<210> SEQ ID NO 1741

<400> SEQUENCE: 1741

000

<210> SEQ ID NO 1742

<400> SEQUENCE: 1742

000

<210> SEQ ID NO 1743

<400> SEQUENCE: 1743

000

<210> SEQ ID NO 1744

<400> SEQUENCE: 1744

000

<210> SEQ ID NO 1745

<400> SEQUENCE: 1745

000

<210> SEQ ID NO 1746

<400> SEQUENCE: 1746

000

<210> SEQ ID NO 1747

<400> SEQUENCE: 1747

000

<210> SEQ ID NO 1748

<400> SEQUENCE: 1748

000

<210> SEQ ID NO 1749

<400> SEQUENCE: 1749

000

<210> SEQ ID NO 1750

<400> SEQUENCE: 1750

000

<210> SEQ ID NO 1751

<400> SEQUENCE: 1751

000

<210> SEQ ID NO 1752

<400> SEQUENCE: 1752

000

<210> SEQ ID NO 1753

<400> SEQUENCE: 1753

000

<210> SEQ ID NO 1754

<400> SEQUENCE: 1754

000

<210> SEQ ID NO 1755

<400> SEQUENCE: 1755

000

<210> SEQ ID NO 1756

<400> SEQUENCE: 1756

000

<210> SEQ ID NO 1757

<400> SEQUENCE: 1757

000

<210> SEQ ID NO 1758

<400> SEQUENCE: 1758

000

<210> SEQ ID NO 1759

<400> SEQUENCE: 1759

000

<210> SEQ ID NO 1760

<400> SEQUENCE: 1760

000

<210> SEQ ID NO 1761

<400> SEQUENCE: 1761

000

<210> SEQ ID NO 1762

<400> SEQUENCE: 1762

000

<210> SEQ ID NO 1763

<400> SEQUENCE: 1763

000

<210> SEQ ID NO 1764

<400> SEQUENCE: 1764

000

<210> SEQ ID NO 1765

<400> SEQUENCE: 1765

000

<210> SEQ ID NO 1766

<400> SEQUENCE: 1766

000

<210> SEQ ID NO 1767

<400> SEQUENCE: 1767

000

<210> SEQ ID NO 1768

<400> SEQUENCE: 1768

000

<210> SEQ ID NO 1769

<400> SEQUENCE: 1769

000

<210> SEQ ID NO 1770

-continued

```
<400> SEQUENCE: 1770
000

<210> SEQ ID NO 1771
<400> SEQUENCE: 1771
000

<210> SEQ ID NO 1772
<400> SEQUENCE: 1772
000

<210> SEQ ID NO 1773
<400> SEQUENCE: 1773
000

<210> SEQ ID NO 1774
<400> SEQUENCE: 1774
000

<210> SEQ ID NO 1775
<400> SEQUENCE: 1775
000

<210> SEQ ID NO 1776
<400> SEQUENCE: 1776
000

<210> SEQ ID NO 1777
<400> SEQUENCE: 1777
000

<210> SEQ ID NO 1778
<400> SEQUENCE: 1778
000

<210> SEQ ID NO 1779
<400> SEQUENCE: 1779
000

<210> SEQ ID NO 1780
<400> SEQUENCE: 1780
000

<210> SEQ ID NO 1781
<400> SEQUENCE: 1781
000
```

-continued

<210> SEQ ID NO 1782

<400> SEQUENCE: 1782

000

<210> SEQ ID NO 1783

<400> SEQUENCE: 1783

000

<210> SEQ ID NO 1784

<400> SEQUENCE: 1784

000

<210> SEQ ID NO 1785

<400> SEQUENCE: 1785

000

<210> SEQ ID NO 1786

<400> SEQUENCE: 1786

000

<210> SEQ ID NO 1787

<400> SEQUENCE: 1787

000

<210> SEQ ID NO 1788

<400> SEQUENCE: 1788

000

<210> SEQ ID NO 1789

<400> SEQUENCE: 1789

000

<210> SEQ ID NO 1790

<400> SEQUENCE: 1790

000

<210> SEQ ID NO 1791

<400> SEQUENCE: 1791

000

<210> SEQ ID NO 1792

<400> SEQUENCE: 1792

000

<210> SEQ ID NO 1793

```
<400> SEQUENCE: 1793
000

<210> SEQ ID NO 1794
<400> SEQUENCE: 1794
000

<210> SEQ ID NO 1795
<400> SEQUENCE: 1795
000

<210> SEQ ID NO 1796
<400> SEQUENCE: 1796
000

<210> SEQ ID NO 1797
<400> SEQUENCE: 1797
000

<210> SEQ ID NO 1798
<400> SEQUENCE: 1798
000

<210> SEQ ID NO 1799
<400> SEQUENCE: 1799
000

<210> SEQ ID NO 1800
<400> SEQUENCE: 1800
000

<210> SEQ ID NO 1801
<400> SEQUENCE: 1801
000

<210> SEQ ID NO 1802
<400> SEQUENCE: 1802
000

<210> SEQ ID NO 1803
<400> SEQUENCE: 1803
000

<210> SEQ ID NO 1804
<400> SEQUENCE: 1804
```

000

<210> SEQ ID NO 1805

<400> SEQUENCE: 1805

000

<210> SEQ ID NO 1806

<400> SEQUENCE: 1806

000

<210> SEQ ID NO 1807

<400> SEQUENCE: 1807

000

<210> SEQ ID NO 1808

<400> SEQUENCE: 1808

000

<210> SEQ ID NO 1809

<400> SEQUENCE: 1809

000

<210> SEQ ID NO 1810

<400> SEQUENCE: 1810

000

<210> SEQ ID NO 1811

<400> SEQUENCE: 1811

000

<210> SEQ ID NO 1812

<400> SEQUENCE: 1812

000

<210> SEQ ID NO 1813

<400> SEQUENCE: 1813

000

<210> SEQ ID NO 1814

<400> SEQUENCE: 1814

000

<210> SEQ ID NO 1815

<400> SEQUENCE: 1815

000

-continued

<210> SEQ ID NO 1816

<400> SEQUENCE: 1816

000

<210> SEQ ID NO 1817

<400> SEQUENCE: 1817

000

<210> SEQ ID NO 1818

<400> SEQUENCE: 1818

000

<210> SEQ ID NO 1819

<400> SEQUENCE: 1819

000

<210> SEQ ID NO 1820

<400> SEQUENCE: 1820

000

<210> SEQ ID NO 1821

<400> SEQUENCE: 1821

000

<210> SEQ ID NO 1822

<400> SEQUENCE: 1822

000

<210> SEQ ID NO 1823

<400> SEQUENCE: 1823

000

<210> SEQ ID NO 1824

<400> SEQUENCE: 1824

000

<210> SEQ ID NO 1825

<400> SEQUENCE: 1825

000

<210> SEQ ID NO 1826

<400> SEQUENCE: 1826

000

<210> SEQ ID NO 1827

<400> SEQUENCE: 1827

000

<210> SEQ ID NO 1828

<400> SEQUENCE: 1828

000

<210> SEQ ID NO 1829

<400> SEQUENCE: 1829

000

<210> SEQ ID NO 1830

<400> SEQUENCE: 1830

000

<210> SEQ ID NO 1831

<400> SEQUENCE: 1831

000

<210> SEQ ID NO 1832

<400> SEQUENCE: 1832

000

<210> SEQ ID NO 1833

<400> SEQUENCE: 1833

000

<210> SEQ ID NO 1834

<400> SEQUENCE: 1834

000

<210> SEQ ID NO 1835

<400> SEQUENCE: 1835

000

<210> SEQ ID NO 1836

<400> SEQUENCE: 1836

000

<210> SEQ ID NO 1837

<400> SEQUENCE: 1837

000

<210> SEQ ID NO 1838

<400> SEQUENCE: 1838

000

<210> SEQ ID NO 1839

<400> SEQUENCE: 1839

000

<210> SEQ ID NO 1840

<400> SEQUENCE: 1840

000

<210> SEQ ID NO 1841

<400> SEQUENCE: 1841

000

<210> SEQ ID NO 1842

<400> SEQUENCE: 1842

000

<210> SEQ ID NO 1843

<400> SEQUENCE: 1843

000

<210> SEQ ID NO 1844

<400> SEQUENCE: 1844

000

<210> SEQ ID NO 1845

<400> SEQUENCE: 1845

000

<210> SEQ ID NO 1846

<400> SEQUENCE: 1846

000

<210> SEQ ID NO 1847

<400> SEQUENCE: 1847

000

<210> SEQ ID NO 1848

<400> SEQUENCE: 1848

000

<210> SEQ ID NO 1849

<400> SEQUENCE: 1849

000

<210> SEQ ID NO 1850

<400> SEQUENCE: 1850

000

<210> SEQ ID NO 1851

<400> SEQUENCE: 1851

000

<210> SEQ ID NO 1852

<400> SEQUENCE: 1852

000

<210> SEQ ID NO 1853

<400> SEQUENCE: 1853

000

<210> SEQ ID NO 1854

<400> SEQUENCE: 1854

000

<210> SEQ ID NO 1855

<400> SEQUENCE: 1855

000

<210> SEQ ID NO 1856

<400> SEQUENCE: 1856

000

<210> SEQ ID NO 1857

<400> SEQUENCE: 1857

000

<210> SEQ ID NO 1858

<400> SEQUENCE: 1858

000

<210> SEQ ID NO 1859

<400> SEQUENCE: 1859

000

<210> SEQ ID NO 1860

<400> SEQUENCE: 1860

000

<210> SEQ ID NO 1861

<400> SEQUENCE: 1861

000

<210> SEQ ID NO 1862

<400> SEQUENCE: 1862

000

<210> SEQ ID NO 1863

<400> SEQUENCE: 1863

000

<210> SEQ ID NO 1864

<400> SEQUENCE: 1864

000

<210> SEQ ID NO 1865

<400> SEQUENCE: 1865

000

<210> SEQ ID NO 1866

<400> SEQUENCE: 1866

000

<210> SEQ ID NO 1867

<400> SEQUENCE: 1867

000

<210> SEQ ID NO 1868

<400> SEQUENCE: 1868

000

<210> SEQ ID NO 1869

<400> SEQUENCE: 1869

000

<210> SEQ ID NO 1870

<400> SEQUENCE: 1870

000

<210> SEQ ID NO 1871

<400> SEQUENCE: 1871

000

<210> SEQ ID NO 1872

<400> SEQUENCE: 1872

000

<210> SEQ ID NO 1873

<400> SEQUENCE: 1873

000

<210> SEQ ID NO 1874

<400> SEQUENCE: 1874

000

<210> SEQ ID NO 1875

<400> SEQUENCE: 1875

000

<210> SEQ ID NO 1876

<400> SEQUENCE: 1876

000

<210> SEQ ID NO 1877

<400> SEQUENCE: 1877

000

<210> SEQ ID NO 1878

<400> SEQUENCE: 1878

000

<210> SEQ ID NO 1879

<400> SEQUENCE: 1879

000

<210> SEQ ID NO 1880

<400> SEQUENCE: 1880

000

<210> SEQ ID NO 1881

<400> SEQUENCE: 1881

000

<210> SEQ ID NO 1882

<400> SEQUENCE: 1882

000

<210> SEQ ID NO 1883

<400> SEQUENCE: 1883

000

<210> SEQ ID NO 1884

<400> SEQUENCE: 1884

000

<210> SEQ ID NO 1885

<400> SEQUENCE: 1885

000

<210> SEQ ID NO 1886

<400> SEQUENCE: 1886

000

<210> SEQ ID NO 1887

<400> SEQUENCE: 1887

000

<210> SEQ ID NO 1888

<400> SEQUENCE: 1888

000

<210> SEQ ID NO 1889

<400> SEQUENCE: 1889

000

<210> SEQ ID NO 1890

<400> SEQUENCE: 1890

000

<210> SEQ ID NO 1891

<400> SEQUENCE: 1891

000

<210> SEQ ID NO 1892

<400> SEQUENCE: 1892

000

<210> SEQ ID NO 1893

<400> SEQUENCE: 1893

000

<210> SEQ ID NO 1894

<400> SEQUENCE: 1894

000

<210> SEQ ID NO 1895

<400> SEQUENCE: 1895

000

-continued

<210> SEQ ID NO 1896
<400> SEQUENCE: 1896
000

<210> SEQ ID NO 1897
<400> SEQUENCE: 1897
000

<210> SEQ ID NO 1898
<400> SEQUENCE: 1898
000

<210> SEQ ID NO 1899
<400> SEQUENCE: 1899
000

<210> SEQ ID NO 1900
<400> SEQUENCE: 1900
000

<210> SEQ ID NO 1901
<400> SEQUENCE: 1901
000

<210> SEQ ID NO 1902
<400> SEQUENCE: 1902
000

<210> SEQ ID NO 1903
<400> SEQUENCE: 1903
000

<210> SEQ ID NO 1904
<400> SEQUENCE: 1904
000

<210> SEQ ID NO 1905
<400> SEQUENCE: 1905
000

<210> SEQ ID NO 1906
<400> SEQUENCE: 1906
000

<210> SEQ ID NO 1907
<400> SEQUENCE: 1907

000

<210> SEQ ID NO 1908

<400> SEQUENCE: 1908

000

<210> SEQ ID NO 1909

<400> SEQUENCE: 1909

000

<210> SEQ ID NO 1910

<400> SEQUENCE: 1910

000

<210> SEQ ID NO 1911

<400> SEQUENCE: 1911

000

<210> SEQ ID NO 1912

<400> SEQUENCE: 1912

000

<210> SEQ ID NO 1913

<400> SEQUENCE: 1913

000

<210> SEQ ID NO 1914

<400> SEQUENCE: 1914

000

<210> SEQ ID NO 1915

<400> SEQUENCE: 1915

000

<210> SEQ ID NO 1916

<400> SEQUENCE: 1916

000

<210> SEQ ID NO 1917

<400> SEQUENCE: 1917

000

<210> SEQ ID NO 1918

<400> SEQUENCE: 1918

000

<210> SEQ ID NO 1919

<400> SEQUENCE: 1919

000

<210> SEQ ID NO 1920

<400> SEQUENCE: 1920

000

<210> SEQ ID NO 1921

<400> SEQUENCE: 1921

000

<210> SEQ ID NO 1922

<400> SEQUENCE: 1922

000

<210> SEQ ID NO 1923

<400> SEQUENCE: 1923

000

<210> SEQ ID NO 1924

<400> SEQUENCE: 1924

000

<210> SEQ ID NO 1925

<400> SEQUENCE: 1925

000

<210> SEQ ID NO 1926

<400> SEQUENCE: 1926

000

<210> SEQ ID NO 1927

<400> SEQUENCE: 1927

000

<210> SEQ ID NO 1928

<400> SEQUENCE: 1928

000

<210> SEQ ID NO 1929

<400> SEQUENCE: 1929

000

<210> SEQ ID NO 1930

```
<400> SEQUENCE: 1930
000

<210> SEQ ID NO 1931
<400> SEQUENCE: 1931
000

<210> SEQ ID NO 1932
<400> SEQUENCE: 1932
000

<210> SEQ ID NO 1933
<400> SEQUENCE: 1933
000

<210> SEQ ID NO 1934
<400> SEQUENCE: 1934
000

<210> SEQ ID NO 1935
<400> SEQUENCE: 1935
000

<210> SEQ ID NO 1936
<400> SEQUENCE: 1936
000

<210> SEQ ID NO 1937
<400> SEQUENCE: 1937
000

<210> SEQ ID NO 1938
<400> SEQUENCE: 1938
000

<210> SEQ ID NO 1939
<400> SEQUENCE: 1939
000

<210> SEQ ID NO 1940
<400> SEQUENCE: 1940
000

<210> SEQ ID NO 1941
<400> SEQUENCE: 1941
000
```

<210> SEQ ID NO 1942

<400> SEQUENCE: 1942

000

<210> SEQ ID NO 1943

<400> SEQUENCE: 1943

000

<210> SEQ ID NO 1944

<400> SEQUENCE: 1944

000

<210> SEQ ID NO 1945

<400> SEQUENCE: 1945

000

<210> SEQ ID NO 1946

<400> SEQUENCE: 1946

000

<210> SEQ ID NO 1947

<400> SEQUENCE: 1947

000

<210> SEQ ID NO 1948

<400> SEQUENCE: 1948

000

<210> SEQ ID NO 1949

<400> SEQUENCE: 1949

000

<210> SEQ ID NO 1950

<400> SEQUENCE: 1950

000

<210> SEQ ID NO 1951

<400> SEQUENCE: 1951

000

<210> SEQ ID NO 1952

<400> SEQUENCE: 1952

000

<210> SEQ ID NO 1953

<400> SEQUENCE: 1953

000

<210> SEQ ID NO 1954

<400> SEQUENCE: 1954

000

<210> SEQ ID NO 1955

<400> SEQUENCE: 1955

000

<210> SEQ ID NO 1956

<400> SEQUENCE: 1956

000

<210> SEQ ID NO 1957

<400> SEQUENCE: 1957

000

<210> SEQ ID NO 1958

<400> SEQUENCE: 1958

000

<210> SEQ ID NO 1959

<400> SEQUENCE: 1959

000

<210> SEQ ID NO 1960

<400> SEQUENCE: 1960

000

<210> SEQ ID NO 1961

<400> SEQUENCE: 1961

000

<210> SEQ ID NO 1962

<400> SEQUENCE: 1962

000

<210> SEQ ID NO 1963

<400> SEQUENCE: 1963

000

<210> SEQ ID NO 1964

<400> SEQUENCE: 1964

000

<210> SEQ ID NO 1965
<400> SEQUENCE: 1965
000

<210> SEQ ID NO 1966
<400> SEQUENCE: 1966
000

<210> SEQ ID NO 1967
<400> SEQUENCE: 1967
000

<210> SEQ ID NO 1968
<400> SEQUENCE: 1968
000

<210> SEQ ID NO 1969
<400> SEQUENCE: 1969
000

<210> SEQ ID NO 1970
<400> SEQUENCE: 1970
000

<210> SEQ ID NO 1971
<400> SEQUENCE: 1971
000

<210> SEQ ID NO 1972
<400> SEQUENCE: 1972
000

<210> SEQ ID NO 1973
<400> SEQUENCE: 1973
000

<210> SEQ ID NO 1974
<400> SEQUENCE: 1974
000

<210> SEQ ID NO 1975
<400> SEQUENCE: 1975
000

<210> SEQ ID NO 1976

<400> SEQUENCE: 1976

000

<210> SEQ ID NO 1977

<400> SEQUENCE: 1977

000

<210> SEQ ID NO 1978

<400> SEQUENCE: 1978

000

<210> SEQ ID NO 1979

<400> SEQUENCE: 1979

000

<210> SEQ ID NO 1980

<400> SEQUENCE: 1980

000

<210> SEQ ID NO 1981

<400> SEQUENCE: 1981

000

<210> SEQ ID NO 1982

<400> SEQUENCE: 1982

000

<210> SEQ ID NO 1983

<400> SEQUENCE: 1983

000

<210> SEQ ID NO 1984

<400> SEQUENCE: 1984

000

<210> SEQ ID NO 1985

<400> SEQUENCE: 1985

000

<210> SEQ ID NO 1986

<400> SEQUENCE: 1986

000

<210> SEQ ID NO 1987

<400> SEQUENCE: 1987

000

<210> SEQ ID NO 1988

<400> SEQUENCE: 1988

000

<210> SEQ ID NO 1989

<400> SEQUENCE: 1989

000

<210> SEQ ID NO 1990

<400> SEQUENCE: 1990

000

<210> SEQ ID NO 1991

<400> SEQUENCE: 1991

000

<210> SEQ ID NO 1992

<400> SEQUENCE: 1992

000

<210> SEQ ID NO 1993

<400> SEQUENCE: 1993

000

<210> SEQ ID NO 1994

<400> SEQUENCE: 1994

000

<210> SEQ ID NO 1995

<400> SEQUENCE: 1995

000

<210> SEQ ID NO 1996

<400> SEQUENCE: 1996

000

<210> SEQ ID NO 1997

<400> SEQUENCE: 1997

000

<210> SEQ ID NO 1998

<400> SEQUENCE: 1998

000

```
<210> SEQ ID NO 1999
<400> SEQUENCE: 1999
000

<210> SEQ ID NO 2000
<400> SEQUENCE: 2000
000

<210> SEQ ID NO 2001
<400> SEQUENCE: 2001
000

<210> SEQ ID NO 2002
<400> SEQUENCE: 2002
000

<210> SEQ ID NO 2003
<400> SEQUENCE: 2003
000

<210> SEQ ID NO 2004
<400> SEQUENCE: 2004
000

<210> SEQ ID NO 2005
<400> SEQUENCE: 2005
000

<210> SEQ ID NO 2006
<400> SEQUENCE: 2006
000

<210> SEQ ID NO 2007
<400> SEQUENCE: 2007
000

<210> SEQ ID NO 2008
<400> SEQUENCE: 2008
000

<210> SEQ ID NO 2009
<400> SEQUENCE: 2009
000

<210> SEQ ID NO 2010
```

```
<400> SEQUENCE: 2010
000

<210> SEQ ID NO 2011
<400> SEQUENCE: 2011
000

<210> SEQ ID NO 2012
<400> SEQUENCE: 2012
000

<210> SEQ ID NO 2013
<400> SEQUENCE: 2013
000

<210> SEQ ID NO 2014
<400> SEQUENCE: 2014
000

<210> SEQ ID NO 2015
<400> SEQUENCE: 2015
000

<210> SEQ ID NO 2016
<400> SEQUENCE: 2016
000

<210> SEQ ID NO 2017
<400> SEQUENCE: 2017
000

<210> SEQ ID NO 2018
<400> SEQUENCE: 2018
000

<210> SEQ ID NO 2019
<400> SEQUENCE: 2019
000

<210> SEQ ID NO 2020
<400> SEQUENCE: 2020
000

<210> SEQ ID NO 2021
<400> SEQUENCE: 2021
000
```

-continued

<210> SEQ ID NO 2022
<400> SEQUENCE: 2022
000

<210> SEQ ID NO 2023
<400> SEQUENCE: 2023
000

<210> SEQ ID NO 2024
<400> SEQUENCE: 2024
000

<210> SEQ ID NO 2025
<400> SEQUENCE: 2025
000

<210> SEQ ID NO 2026
<400> SEQUENCE: 2026
000

<210> SEQ ID NO 2027
<400> SEQUENCE: 2027
000

<210> SEQ ID NO 2028
<400> SEQUENCE: 2028
000

<210> SEQ ID NO 2029
<400> SEQUENCE: 2029
000

<210> SEQ ID NO 2030
<400> SEQUENCE: 2030
000

<210> SEQ ID NO 2031
<400> SEQUENCE: 2031
000

<210> SEQ ID NO 2032
<400> SEQUENCE: 2032
000

<210> SEQ ID NO 2033

<400> SEQUENCE: 2033

000

<210> SEQ ID NO 2034

<400> SEQUENCE: 2034

000

<210> SEQ ID NO 2035

<400> SEQUENCE: 2035

000

<210> SEQ ID NO 2036

<400> SEQUENCE: 2036

000

<210> SEQ ID NO 2037

<400> SEQUENCE: 2037

000

<210> SEQ ID NO 2038

<400> SEQUENCE: 2038

000

<210> SEQ ID NO 2039

<400> SEQUENCE: 2039

000

<210> SEQ ID NO 2040

<400> SEQUENCE: 2040

000

<210> SEQ ID NO 2041

<400> SEQUENCE: 2041

000

<210> SEQ ID NO 2042

<400> SEQUENCE: 2042

000

<210> SEQ ID NO 2043

<400> SEQUENCE: 2043

000

<210> SEQ ID NO 2044

<400> SEQUENCE: 2044

000

<210> SEQ ID NO 2045

<400> SEQUENCE: 2045

000

<210> SEQ ID NO 2046

<400> SEQUENCE: 2046

000

<210> SEQ ID NO 2047

<400> SEQUENCE: 2047

000

<210> SEQ ID NO 2048

<400> SEQUENCE: 2048

000

<210> SEQ ID NO 2049

<400> SEQUENCE: 2049

000

<210> SEQ ID NO 2050

<400> SEQUENCE: 2050

000

<210> SEQ ID NO 2051

<400> SEQUENCE: 2051

000

<210> SEQ ID NO 2052

<400> SEQUENCE: 2052

000

<210> SEQ ID NO 2053

<400> SEQUENCE: 2053

000

<210> SEQ ID NO 2054

<400> SEQUENCE: 2054

000

<210> SEQ ID NO 2055

<400> SEQUENCE: 2055

000

-continued

<210> SEQ ID NO 2056
<400> SEQUENCE: 2056
000

<210> SEQ ID NO 2057
<400> SEQUENCE: 2057
000

<210> SEQ ID NO 2058
<400> SEQUENCE: 2058
000

<210> SEQ ID NO 2059
<400> SEQUENCE: 2059
000

<210> SEQ ID NO 2060
<400> SEQUENCE: 2060
000

<210> SEQ ID NO 2061
<400> SEQUENCE: 2061
000

<210> SEQ ID NO 2062
<400> SEQUENCE: 2062
000

<210> SEQ ID NO 2063
<400> SEQUENCE: 2063
000

<210> SEQ ID NO 2064
<400> SEQUENCE: 2064
000

<210> SEQ ID NO 2065
<400> SEQUENCE: 2065
000

<210> SEQ ID NO 2066
<400> SEQUENCE: 2066
000

<210> SEQ ID NO 2067
<400> SEQUENCE: 2067

000

<210> SEQ ID NO 2068

<400> SEQUENCE: 2068

000

<210> SEQ ID NO 2069

<400> SEQUENCE: 2069

000

<210> SEQ ID NO 2070

<400> SEQUENCE: 2070

000

<210> SEQ ID NO 2071

<400> SEQUENCE: 2071

000

<210> SEQ ID NO 2072

<400> SEQUENCE: 2072

000

<210> SEQ ID NO 2073

<400> SEQUENCE: 2073

000

<210> SEQ ID NO 2074

<400> SEQUENCE: 2074

000

<210> SEQ ID NO 2075

<400> SEQUENCE: 2075

000

<210> SEQ ID NO 2076

<400> SEQUENCE: 2076

000

<210> SEQ ID NO 2077

<400> SEQUENCE: 2077

000

<210> SEQ ID NO 2078

<400> SEQUENCE: 2078

000

<210> SEQ ID NO 2079

<400> SEQUENCE: 2079

000

<210> SEQ ID NO 2080

<400> SEQUENCE: 2080

000

<210> SEQ ID NO 2081

<400> SEQUENCE: 2081

000

<210> SEQ ID NO 2082

<400> SEQUENCE: 2082

000

<210> SEQ ID NO 2083

<400> SEQUENCE: 2083

000

<210> SEQ ID NO 2084

<400> SEQUENCE: 2084

000

<210> SEQ ID NO 2085

<400> SEQUENCE: 2085

000

<210> SEQ ID NO 2086

<400> SEQUENCE: 2086

000

<210> SEQ ID NO 2087

<400> SEQUENCE: 2087

000

<210> SEQ ID NO 2088

<400> SEQUENCE: 2088

000

<210> SEQ ID NO 2089

<400> SEQUENCE: 2089

000

<210> SEQ ID NO 2090

```
<400> SEQUENCE: 2090
000

<210> SEQ ID NO 2091
<400> SEQUENCE: 2091
000

<210> SEQ ID NO 2092
<400> SEQUENCE: 2092
000

<210> SEQ ID NO 2093
<400> SEQUENCE: 2093
000

<210> SEQ ID NO 2094
<400> SEQUENCE: 2094
000

<210> SEQ ID NO 2095
<400> SEQUENCE: 2095
000

<210> SEQ ID NO 2096
<400> SEQUENCE: 2096
000

<210> SEQ ID NO 2097
<400> SEQUENCE: 2097
000

<210> SEQ ID NO 2098
<400> SEQUENCE: 2098
000

<210> SEQ ID NO 2099
<400> SEQUENCE: 2099
000

<210> SEQ ID NO 2100
<400> SEQUENCE: 2100
000

<210> SEQ ID NO 2101
<400> SEQUENCE: 2101
000
```

```
<210> SEQ ID NO 2102
<400> SEQUENCE: 2102
000

<210> SEQ ID NO 2103
<400> SEQUENCE: 2103
000

<210> SEQ ID NO 2104
<400> SEQUENCE: 2104
000

<210> SEQ ID NO 2105
<400> SEQUENCE: 2105
000

<210> SEQ ID NO 2106
<400> SEQUENCE: 2106
000

<210> SEQ ID NO 2107
<400> SEQUENCE: 2107
000

<210> SEQ ID NO 2108
<400> SEQUENCE: 2108
000

<210> SEQ ID NO 2109
<400> SEQUENCE: 2109
000

<210> SEQ ID NO 2110
<400> SEQUENCE: 2110
000

<210> SEQ ID NO 2111
<400> SEQUENCE: 2111
000

<210> SEQ ID NO 2112
<400> SEQUENCE: 2112
000

<210> SEQ ID NO 2113
```

<400> SEQUENCE: 2113

000

<210> SEQ ID NO 2114

<400> SEQUENCE: 2114

000

<210> SEQ ID NO 2115

<400> SEQUENCE: 2115

000

<210> SEQ ID NO 2116

<400> SEQUENCE: 2116

000

<210> SEQ ID NO 2117

<400> SEQUENCE: 2117

000

<210> SEQ ID NO 2118

<400> SEQUENCE: 2118

000

<210> SEQ ID NO 2119

<400> SEQUENCE: 2119

000

<210> SEQ ID NO 2120

<400> SEQUENCE: 2120

000

<210> SEQ ID NO 2121

<400> SEQUENCE: 2121

000

<210> SEQ ID NO 2122

<400> SEQUENCE: 2122

000

<210> SEQ ID NO 2123

<400> SEQUENCE: 2123

000

<210> SEQ ID NO 2124

<400> SEQUENCE: 2124

000

<210> SEQ ID NO 2125

<400> SEQUENCE: 2125

000

<210> SEQ ID NO 2126

<400> SEQUENCE: 2126

000

<210> SEQ ID NO 2127

<400> SEQUENCE: 2127

000

<210> SEQ ID NO 2128

<400> SEQUENCE: 2128

000

<210> SEQ ID NO 2129

<400> SEQUENCE: 2129

000

<210> SEQ ID NO 2130

<400> SEQUENCE: 2130

000

<210> SEQ ID NO 2131

<400> SEQUENCE: 2131

000

<210> SEQ ID NO 2132

<400> SEQUENCE: 2132

000

<210> SEQ ID NO 2133

<400> SEQUENCE: 2133

000

<210> SEQ ID NO 2134

<400> SEQUENCE: 2134

000

<210> SEQ ID NO 2135

<400> SEQUENCE: 2135

000

<210> SEQ ID NO 2136

<400> SEQUENCE: 2136

000

<210> SEQ ID NO 2137

<400> SEQUENCE: 2137

000

<210> SEQ ID NO 2138

<400> SEQUENCE: 2138

000

<210> SEQ ID NO 2139

<400> SEQUENCE: 2139

000

<210> SEQ ID NO 2140

<400> SEQUENCE: 2140

000

<210> SEQ ID NO 2141

<400> SEQUENCE: 2141

000

<210> SEQ ID NO 2142

<400> SEQUENCE: 2142

000

<210> SEQ ID NO 2143

<400> SEQUENCE: 2143

000

<210> SEQ ID NO 2144

<400> SEQUENCE: 2144

000

<210> SEQ ID NO 2145

<400> SEQUENCE: 2145

000

<210> SEQ ID NO 2146

<400> SEQUENCE: 2146

000

<210> SEQ ID NO 2147

<400> SEQUENCE: 2147

000

<210> SEQ ID NO 2148

<400> SEQUENCE: 2148

000

<210> SEQ ID NO 2149

<400> SEQUENCE: 2149

000

<210> SEQ ID NO 2150

<400> SEQUENCE: 2150

000

<210> SEQ ID NO 2151

<400> SEQUENCE: 2151

000

<210> SEQ ID NO 2152

<400> SEQUENCE: 2152

000

<210> SEQ ID NO 2153

<400> SEQUENCE: 2153

000

<210> SEQ ID NO 2154

<400> SEQUENCE: 2154

000

<210> SEQ ID NO 2155

<400> SEQUENCE: 2155

000

<210> SEQ ID NO 2156

<400> SEQUENCE: 2156

000

<210> SEQ ID NO 2157

<400> SEQUENCE: 2157

000

<210> SEQ ID NO 2158

<400> SEQUENCE: 2158

000

<210> SEQ ID NO 2159
<400> SEQUENCE: 2159
000

<210> SEQ ID NO 2160
<400> SEQUENCE: 2160
000

<210> SEQ ID NO 2161
<400> SEQUENCE: 2161
000

<210> SEQ ID NO 2162
<400> SEQUENCE: 2162
000

<210> SEQ ID NO 2163
<400> SEQUENCE: 2163
000

<210> SEQ ID NO 2164
<400> SEQUENCE: 2164
000

<210> SEQ ID NO 2165
<400> SEQUENCE: 2165
000

<210> SEQ ID NO 2166
<400> SEQUENCE: 2166
000

<210> SEQ ID NO 2167
<400> SEQUENCE: 2167
000

<210> SEQ ID NO 2168
<400> SEQUENCE: 2168
000

<210> SEQ ID NO 2169
<400> SEQUENCE: 2169
000

<210> SEQ ID NO 2170

-continued

<400> SEQUENCE: 2170

000

<210> SEQ ID NO 2171

<400> SEQUENCE: 2171

000

<210> SEQ ID NO 2172

<400> SEQUENCE: 2172

000

<210> SEQ ID NO 2173

<400> SEQUENCE: 2173

000

<210> SEQ ID NO 2174

<400> SEQUENCE: 2174

000

<210> SEQ ID NO 2175

<400> SEQUENCE: 2175

000

<210> SEQ ID NO 2176

<400> SEQUENCE: 2176

000

<210> SEQ ID NO 2177

<400> SEQUENCE: 2177

000

<210> SEQ ID NO 2178

<400> SEQUENCE: 2178

000

<210> SEQ ID NO 2179

<400> SEQUENCE: 2179

000

<210> SEQ ID NO 2180

<400> SEQUENCE: 2180

000

<210> SEQ ID NO 2181

<400> SEQUENCE: 2181

000

<210> SEQ ID NO 2182

<400> SEQUENCE: 2182

000

<210> SEQ ID NO 2183

<400> SEQUENCE: 2183

000

<210> SEQ ID NO 2184

<400> SEQUENCE: 2184

000

<210> SEQ ID NO 2185

<400> SEQUENCE: 2185

000

<210> SEQ ID NO 2186

<400> SEQUENCE: 2186

000

<210> SEQ ID NO 2187

<400> SEQUENCE: 2187

000

<210> SEQ ID NO 2188

<400> SEQUENCE: 2188

000

<210> SEQ ID NO 2189

<400> SEQUENCE: 2189

000

<210> SEQ ID NO 2190

<400> SEQUENCE: 2190

000

<210> SEQ ID NO 2191

<400> SEQUENCE: 2191

000

<210> SEQ ID NO 2192

<400> SEQUENCE: 2192

000

<210> SEQ ID NO 2193

-continued

<400> SEQUENCE: 2193

000

<210> SEQ ID NO 2194

<400> SEQUENCE: 2194

000

<210> SEQ ID NO 2195

<400> SEQUENCE: 2195

000

<210> SEQ ID NO 2196

<400> SEQUENCE: 2196

000

<210> SEQ ID NO 2197

<400> SEQUENCE: 2197

000

<210> SEQ ID NO 2198

<400> SEQUENCE: 2198

000

<210> SEQ ID NO 2199

<400> SEQUENCE: 2199

000

<210> SEQ ID NO 2200

<400> SEQUENCE: 2200

000

<210> SEQ ID NO 2201

<400> SEQUENCE: 2201

000

<210> SEQ ID NO 2202

<400> SEQUENCE: 2202

000

<210> SEQ ID NO 2203

<400> SEQUENCE: 2203

000

<210> SEQ ID NO 2204

<400> SEQUENCE: 2204

000

<210> SEQ ID NO 2205

<400> SEQUENCE: 2205

000

<210> SEQ ID NO 2206

<400> SEQUENCE: 2206

000

<210> SEQ ID NO 2207

<400> SEQUENCE: 2207

000

<210> SEQ ID NO 2208

<400> SEQUENCE: 2208

000

<210> SEQ ID NO 2209

<400> SEQUENCE: 2209

000

<210> SEQ ID NO 2210

<400> SEQUENCE: 2210

000

<210> SEQ ID NO 2211

<400> SEQUENCE: 2211

000

<210> SEQ ID NO 2212

<400> SEQUENCE: 2212

000

<210> SEQ ID NO 2213

<400> SEQUENCE: 2213

000

<210> SEQ ID NO 2214

<400> SEQUENCE: 2214

000

<210> SEQ ID NO 2215

<400> SEQUENCE: 2215

000

-continued

<210> SEQ ID NO 2216

<400> SEQUENCE: 2216

000

<210> SEQ ID NO 2217

<400> SEQUENCE: 2217

000

<210> SEQ ID NO 2218

<400> SEQUENCE: 2218

000

<210> SEQ ID NO 2219

<400> SEQUENCE: 2219

000

<210> SEQ ID NO 2220

<400> SEQUENCE: 2220

000

<210> SEQ ID NO 2221

<400> SEQUENCE: 2221

000

<210> SEQ ID NO 2222

<400> SEQUENCE: 2222

000

<210> SEQ ID NO 2223

<400> SEQUENCE: 2223

000

<210> SEQ ID NO 2224

<400> SEQUENCE: 2224

000

<210> SEQ ID NO 2225

<400> SEQUENCE: 2225

000

<210> SEQ ID NO 2226

<400> SEQUENCE: 2226

000

<210> SEQ ID NO 2227

<400> SEQUENCE: 2227

000

<210> SEQ ID NO 2228

<400> SEQUENCE: 2228

000

<210> SEQ ID NO 2229

<400> SEQUENCE: 2229

000

<210> SEQ ID NO 2230

<400> SEQUENCE: 2230

000

<210> SEQ ID NO 2231

<400> SEQUENCE: 2231

000

<210> SEQ ID NO 2232

<400> SEQUENCE: 2232

000

<210> SEQ ID NO 2233

<400> SEQUENCE: 2233

000

<210> SEQ ID NO 2234

<400> SEQUENCE: 2234

000

<210> SEQ ID NO 2235

<400> SEQUENCE: 2235

000

<210> SEQ ID NO 2236

<400> SEQUENCE: 2236

000

<210> SEQ ID NO 2237

<400> SEQUENCE: 2237

000

<210> SEQ ID NO 2238

<400> SEQUENCE: 2238

000

<210> SEQ ID NO 2239
<400> SEQUENCE: 2239
000

<210> SEQ ID NO 2240
<400> SEQUENCE: 2240
000

<210> SEQ ID NO 2241
<400> SEQUENCE: 2241
000

<210> SEQ ID NO 2242
<400> SEQUENCE: 2242
000

<210> SEQ ID NO 2243
<400> SEQUENCE: 2243
000

<210> SEQ ID NO 2244
<400> SEQUENCE: 2244
000

<210> SEQ ID NO 2245
<400> SEQUENCE: 2245
000

<210> SEQ ID NO 2246
<400> SEQUENCE: 2246
000

<210> SEQ ID NO 2247
<400> SEQUENCE: 2247
000

<210> SEQ ID NO 2248
<400> SEQUENCE: 2248
000

<210> SEQ ID NO 2249
<400> SEQUENCE: 2249
000

<210> SEQ ID NO 2250

```
<400> SEQUENCE: 2250
000

<210> SEQ ID NO 2251
<400> SEQUENCE: 2251
000

<210> SEQ ID NO 2252
<400> SEQUENCE: 2252
000

<210> SEQ ID NO 2253
<400> SEQUENCE: 2253
000

<210> SEQ ID NO 2254
<400> SEQUENCE: 2254
000

<210> SEQ ID NO 2255
<400> SEQUENCE: 2255
000

<210> SEQ ID NO 2256
<400> SEQUENCE: 2256
000

<210> SEQ ID NO 2257
<400> SEQUENCE: 2257
000

<210> SEQ ID NO 2258
<400> SEQUENCE: 2258
000

<210> SEQ ID NO 2259
<400> SEQUENCE: 2259
000

<210> SEQ ID NO 2260
<400> SEQUENCE: 2260
000

<210> SEQ ID NO 2261
<400> SEQUENCE: 2261
000
```

<210> SEQ ID NO 2262

<400> SEQUENCE: 2262

000

<210> SEQ ID NO 2263

<400> SEQUENCE: 2263

000

<210> SEQ ID NO 2264

<400> SEQUENCE: 2264

000

<210> SEQ ID NO 2265

<400> SEQUENCE: 2265

000

<210> SEQ ID NO 2266

<400> SEQUENCE: 2266

000

<210> SEQ ID NO 2267

<400> SEQUENCE: 2267

000

<210> SEQ ID NO 2268

<400> SEQUENCE: 2268

000

<210> SEQ ID NO 2269

<400> SEQUENCE: 2269

000

<210> SEQ ID NO 2270

<400> SEQUENCE: 2270

000

<210> SEQ ID NO 2271

<400> SEQUENCE: 2271

000

<210> SEQ ID NO 2272

<400> SEQUENCE: 2272

000

<210> SEQ ID NO 2273

<210> SEQ ID NO 2273

<400> SEQUENCE: 2273

000

<210> SEQ ID NO 2274

<400> SEQUENCE: 2274

000

<210> SEQ ID NO 2275

<400> SEQUENCE: 2275

000

<210> SEQ ID NO 2276

<400> SEQUENCE: 2276

000

<210> SEQ ID NO 2277

<400> SEQUENCE: 2277

000

<210> SEQ ID NO 2278

<400> SEQUENCE: 2278

000

<210> SEQ ID NO 2279

<400> SEQUENCE: 2279

000

<210> SEQ ID NO 2280

<400> SEQUENCE: 2280

000

<210> SEQ ID NO 2281
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2281
gagggctgga gaggttgggt gcgcttgtgc gtttcacttt                                40

<210> SEQ ID NO 2282
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2282
gccctgaagc tccggactac agctcccagg cctctccaag                                40

<210> SEQ ID NO 2283
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2283
tgttggccta gttctgtgtg aagactagt gattttgttg                              40

<210> SEQ ID NO 2284
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2284
gtatttacct agttgtaatg tgggttgcca tggtgttttg                             40

<210> SEQ ID NO 2285
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2285
aacgagtaaa aggcgtacat gggagcgcgg ggcggcagag                             40

<210> SEQ ID NO 2286
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2286
ttatgacgaa tcatacaggg acatccagtt tttcagtatc                             40

<210> SEQ ID NO 2287
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2287
ggccaccaca gacaccaaca agttcagtcc gtttctgcag                             40

<210> SEQ ID NO 2288
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2288
tattagctga gggagggctg gaggcggctg cattccgact                             40

<210> SEQ ID NO 2289

-continued

<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2289
cgcatgtcct ggccctcgtc cttccatggc actggcaccg                             40

<210> SEQ ID NO 2290
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2290
gatctaaagg tccctggttc gatcccgggt ttcggcacca                             40

<210> SEQ ID NO 2291
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2291
tatttattac aaggtccttc ttccccgtaa aactttgtcc                             40

<210> SEQ ID NO 2292
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2292
aacgatacta aactgttttt gcgatgtgtt cctaatatgc                             40

<210> SEQ ID NO 2293
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2293
ttaatgctaa tcgtgatagg ggttttttgcc tccaactgac                            40

<210> SEQ ID NO 2294
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2294
gatctcatgc agtcattctc caaaagaaag cactttctgt                             40

<210> SEQ ID NO 2295
<211> LENGTH: 40
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 2295
accatcgacc gttgattgta ccctatggct aaccatcatc                                40

<210> SEQ ID NO 2296
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2296
atacaattaa ggcacgcggt gaatgccaag aatggggctg                                40

<210> SEQ ID NO 2297
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2297
gaaagatgct aaactatttt tgcgatgtgt tcctaatatg                                40

<210> SEQ ID NO 2298
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2298
ctggagataa tgattctgca tttctaatta actcccaggt                                40

<210> SEQ ID NO 2299
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2299
gtctcacaca gaaatcgcac ccgtcacctt ggcctactta                                40

<210> SEQ ID NO 2300
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2300
cccataaagt agaaagcact actaacagca ctggagggtg                                40

<210> SEQ ID NO 2301
<211> LENGTH: 40
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 2301
gagtgtcagt ttgtcaaata ccccaagtgc ggcacatgct                            40

<210> SEQ ID NO 2302
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2302
tcctcctcct cctttcgtt ccggctccct ggctggctcc                             40

<210> SEQ ID NO 2303
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2303
ctgtttcata cttgaggaga aattatcctt ggtgtgttcg                            40

<210> SEQ ID NO 2304
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2304
cacctggctc tgagaactga attccatagg ctgtgagctc                            40

<210> SEQ ID NO 2305
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2305
tctagcgaca gagtggttca attccacctt tcgggcgcca                            40

<210> SEQ ID NO 2306
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2306
aacattcatt gctgtcggtg ggttgaactg tgtggacaag                            40

<210> SEQ ID NO 2307

<400> SEQUENCE: 2307

000

-continued

<210> SEQ ID NO 2308
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2308
gactatggaa gccagtgtgt ggaaatgctt ctgctagatt                                40

<210> SEQ ID NO 2309
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2309
cctgttgcca caaacccgta gatccgaact tgtggtatta                                40

<210> SEQ ID NO 2310
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2310
agctggtgtt gtgaatcagg ccgttgccaa tcagagaacg                                40

<210> SEQ ID NO 2311
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2311
ttctaccaca gggtagaacc acggacagga taccggggca                                40

<210> SEQ ID NO 2312
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2312
tgagaactga attccatggg ttgtgtcagt gtcagacctc                                40

<210> SEQ ID NO 2313
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2313
attaaaaatg attggtacgt ctgtgggtag agtactgcat                                40

<210> SEQ ID NO 2314
<211> LENGTH: 40

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2314
cacctggcac tgagaactga attccatagg ctgtgagctc                            40

<210> SEQ ID NO 2315
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2315
attagagact cgttaagaga aggtgagaag ggctcagtaa                            40

<210> SEQ ID NO 2316
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2316
gtgtgtatac ttatgtgtgt gtatgtgtga gtgtgaatat                            40

<210> SEQ ID NO 2317
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2317
aattgtgaca actgagtggg aggtttgtgt gatgattatc                            40

<210> SEQ ID NO 2318
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2318
agtaaggaag caatcagcaa gtatactgcc ctagaagtgc                            40

<210> SEQ ID NO 2319
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2319
tgaggcctgt tgccacaaac ccgtagatcc gaacttgtgg                            40

<210> SEQ ID NO 2320
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 2320
gatgtttggg aaacaatggg agtgagagaa tgggagagct                              40

<210> SEQ ID NO 2321
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2321
gccctggcgg aacgctgaga agacagtcga acttgactat                              40

<210> SEQ ID NO 2322

<400> SEQUENCE: 2322

000

<210> SEQ ID NO 2323
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2323
gtcatgctgc caccagcagg cagagaagaa gcagaagaac                              40

<210> SEQ ID NO 2324
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2324
aaaaatccca gcggccacct ttcctccctg ccccattggg                              40

<210> SEQ ID NO 2325
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2325
atggtagagc gctcgctttg cttgcgagag gtagcgggat                              40

<210> SEQ ID NO 2326
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2326
caaacatcat gtgacgtctg tggagcggcg gcggcggcgg                              40
```

<210> SEQ ID NO 2327
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2327
gctgccccct cccttagcaa cgtggccccg gcgttccaaa                                40

<210> SEQ ID NO 2328
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2328
ggcctcatgc tgccaagggc tggcaagaag tccctgcttg                                40

<210> SEQ ID NO 2329
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2329
ggaagtggag caaatggatg gaaagcaatt tttggaagat                                40

<210> SEQ ID NO 2330
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2330
caataaatgt gcctataaag gcgccggctc cggggcgcgg                                40

<210> SEQ ID NO 2331
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2331
aacaactttg tgctggtgcc ggggaagttt gtgtctccta                                40

<210> SEQ ID NO 2332
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2332
tccggatgga gcgtgggttc gaatcccact tctgacacca                                40

<210> SEQ ID NO 2333

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2333
ctatattgga ccgcagcgct gagagctttt gtgtttaatg                           40

<210> SEQ ID NO 2334

<400> SEQUENCE: 2334

000

<210> SEQ ID NO 2335

<400> SEQUENCE: 2335

000

<210> SEQ ID NO 2336
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2336
aggccaaggt gacgggtgcg atttctgtgt gagacaattc                           40

<210> SEQ ID NO 2337
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2337
ggagccctgt ctgcaaagag tggtgcgtgt gcgtgtgtga                           40

<210> SEQ ID NO 2338

<400> SEQUENCE: 2338

000

<210> SEQ ID NO 2339

<400> SEQUENCE: 2339

000

<210> SEQ ID NO 2340

<400> SEQUENCE: 2340

000

<210> SEQ ID NO 2341
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 2341
ggccgcagca acctcggttc gtatccgagt cacggcacca                            40

<210> SEQ ID NO 2342
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2342
acgcgaaagg tccccggttc gaaaccgggc ggaaacacca                            40

<210> SEQ ID NO 2343

<400> SEQUENCE: 2343

000

<210> SEQ ID NO 2344
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2344
aaaatggcgg cgggaaaagc gagcggcgag agcgaggagg                            40

<210> SEQ ID NO 2345

<400> SEQUENCE: 2345

000

<210> SEQ ID NO 2346
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2346
tgtgtgttgc gggggtgggg gccggtgaaa gtgatttgat                            40

<210> SEQ ID NO 2347
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2347
cgaaacattc gcggtgcact tcttttcag tatcctattc                             40

<210> SEQ ID NO 2348
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2348
ttccgtggtt cctgaagaga tggtagacta tggaacgtag                                40

<210> SEQ ID NO 2349

<400> SEQUENCE: 2349

000

<210> SEQ ID NO 2350
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2350
ccaggtcttg gagtaggtca ttgggtggat cctctatttc                                40

<210> SEQ ID NO 2351

<400> SEQUENCE: 2351

000

<210> SEQ ID NO 2352

<400> SEQUENCE: 2352

000

<210> SEQ ID NO 2353
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2353
aagctcccaa attagctttt taaatagaag ctgagagtta                                40

<210> SEQ ID NO 2354
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2354
taaacataga ggaaatttca cgttttcagt gtcaaatgct                                40

<210> SEQ ID NO 2355
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2355
gacgaatgtt gctcggtgaa cccctttcg gtatcaaatt                                 40

<210> SEQ ID NO 2356

-continued

<400> SEQUENCE: 2356

000

<210> SEQ ID NO 2357
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2357
gtggtacttg aagataggtt atccgtgttg ccttcgcttt                              40

<210> SEQ ID NO 2358
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2358
gtgacgaaac aaacatggtg cacttctttt tcggtatcaa                              40

<210> SEQ ID NO 2359
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2359
cagagtgcct tcttttggag cgttactgtt tgagaaaaac                              40

<210> SEQ ID NO 2360
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2360
gtgtttattt gaatctcaca tcgctcataa gaatacacgc                              40

<210> SEQ ID NO 2361
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2361
ccagtataca atccgttttt cagtttagct tgagatcaga                              40

<210> SEQ ID NO 2362
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2362
ggtacttgaa gagaagttgt tcgtggtgga ttcgctttac   40

<210> SEQ ID NO 2363
<400> SEQUENCE: 2363

000

<210> SEQ ID NO 2364
<400> SEQUENCE: 2364

000

<210> SEQ ID NO 2365
<400> SEQUENCE: 2365

000

<210> SEQ ID NO 2366
<400> SEQUENCE: 2366

000

<210> SEQ ID NO 2367
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2367
atcacgcctc ctcactcctc tcctcccgtc ttctcctctc   40

<210> SEQ ID NO 2368
<400> SEQUENCE: 2368

000

<210> SEQ ID NO 2369
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2369
taagagctct tcacccttca ccaccttctc cacccagcat   40

<210> SEQ ID NO 2370
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2370
cctcagtaac agtctccagt cacggccacc gacgcctggc   40

<210> SEQ ID NO 2371
<400> SEQUENCE: 2371

<210> SEQ ID NO 2372

<400> SEQUENCE: 2372

000

<210> SEQ ID NO 2373

<400> SEQUENCE: 2373

000

<210> SEQ ID NO 2374

<400> SEQUENCE: 2374

000

<210> SEQ ID NO 2375

<400> SEQUENCE: 2375

000

<210> SEQ ID NO 2376

<400> SEQUENCE: 2376

000

<210> SEQ ID NO 2377
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2377
gttctatata aagtattgca cttgtcccgg cctgtggaag                         40

<210> SEQ ID NO 2378
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2378
tggccgattt tggcactagc acattttgc ttgtgtctct                          40

<210> SEQ ID NO 2379
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2379
attactagca gttaatgatt ggtttgttag ttaatggccc                         40

<210> SEQ ID NO 2380
<211> LENGTH: 40

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2380
ggaccggctg gccccatctg gaagactagt gattttgttg                                 40

<210> SEQ ID NO 2381
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2381
gtggctgtgc aaatccatgc aaaactgatt gtgataatgt                                 40

<210> SEQ ID NO 2382
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2382
gatcctagta gtgccaaagt gctcatagtg caggtagttt                                 40

<210> SEQ ID NO 2383
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2383
ttctgctgtg caaatccatg caaaactgac tgtggtagtg                                 40

<210> SEQ ID NO 2384
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2384
cactctagtg ctttatggct ttttattcct atgtgatagt                                 40

<210> SEQ ID NO 2385

<400> SEQUENCE: 2385

000

<210> SEQ ID NO 2386
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2386
```
acgctgccct gggcattgca cttgtctcgg tctgacagtg                                  40

<210> SEQ ID NO 2387

<400> SEQUENCE: 2387

000

<210> SEQ ID NO 2388
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2388
tgtagttgtg caaatctatg caaaactgat ggtggcctgc                                  40

<210> SEQ ID NO 2389
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2389
aggtacctga aaagatggtt gaccatagaa catgcgctat                                  40

<210> SEQ ID NO 2390
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2390
ccaaagtgct gttcgtgcag gtagtgtgat tacccaacct                                  40

<210> SEQ ID NO 2391
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2391
ccttggccat gtaaaagtgc ttacagtgca ggtagctttt                                  40

<210> SEQ ID NO 2392

<400> SEQUENCE: 2392

000

<210> SEQ ID NO 2393
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2393
taaggtgcat ctagtgcaga tagtgaagta gattagcatc                                  40

```
<210> SEQ ID NO 2394
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2394
taaagtgctt atagtgcagg tagtgtttag ttatctactg                            40

<210> SEQ ID NO 2395
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2395
gatggtttag tgaggccctc ggatcagccc gctgggtcag                            40

<210> SEQ ID NO 2396

<400> SEQUENCE: 2396

000

<210> SEQ ID NO 2397

<400> SEQUENCE: 2397

000

<210> SEQ ID NO 2398
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2398
tgaggttgct tcagtgaaca ttcaacgctg tcggtgagtt                            40

<210> SEQ ID NO 2399

<400> SEQUENCE: 2399

000

<210> SEQ ID NO 2400

<400> SEQUENCE: 2400

000

<210> SEQ ID NO 2401

<400> SEQUENCE: 2401

000

<210> SEQ ID NO 2402

<400> SEQUENCE: 2402
```

-continued

000

<210> SEQ ID NO 2403

<400> SEQUENCE: 2403

000

<210> SEQ ID NO 2404

<400> SEQUENCE: 2404

000

<210> SEQ ID NO 2405
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2405
caattagcca attgtgggta taattagctg catgtagaat                               40

<210> SEQ ID NO 2406

<400> SEQUENCE: 2406

000

<210> SEQ ID NO 2407
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2407
aattaatgac caaaatgtca gatgtgtcca cagctaatta                               40

<210> SEQ ID NO 2408
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2408
attccctgca tcactctcat gaaatggctg agaaagtgag                               40

<210> SEQ ID NO 2409
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2409
gagccggtct ctttacatct caaataccag gtatttaggt                               40

<210> SEQ ID NO 2410
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 2410
ccttacgtgg gccactggat ggctcctcca tgtcttggag                              40

<210> SEQ ID NO 2411

<400> SEQUENCE: 2411

000

<210> SEQ ID NO 2412
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2412
ctccgctctg agcaatcatg tgcagtgcca atatgggaaa                              40

<210> SEQ ID NO 2413
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2413
gctgtatatc tgaaaggtac agtactgtga taactgaaga                              40

<210> SEQ ID NO 2414
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2414
agtaccaaag tgctcatagt gcaggtagtt ttggcatgac                              40

<210> SEQ ID NO 2415

<400> SEQUENCE: 2415

000

<210> SEQ ID NO 2416
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2416
ggagatattg cacattacta agttgcatgt tgtcacggcc                              40

<210> SEQ ID NO 2417
<211> LENGTH: 40
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 2417
tccctcactt gaactgactg ccagagttca cagacagctg                                40

<210> SEQ ID NO 2418

<400> SEQUENCE: 2418

000

<210> SEQ ID NO 2419

<400> SEQUENCE: 2419

000

<210> SEQ ID NO 2420

<400> SEQUENCE: 2420

000

<210> SEQ ID NO 2421

<400> SEQUENCE: 2421

000

<210> SEQ ID NO 2422
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2422
ggatttggga gcttatcaga atctccaggg gtactttata                                40

<210> SEQ ID NO 2423

<400> SEQUENCE: 2423

000

<210> SEQ ID NO 2424

<400> SEQUENCE: 2424

000

<210> SEQ ID NO 2425
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2425
tgaggtagta agttgtattg ttgtggggta gggatattag                                40

<210> SEQ ID NO 2426

<400> SEQUENCE: 2426

000

<210> SEQ ID NO 2427
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2427
gtttctttct cacggtaact ggcagcctcg ttgtgggctg                         40

<210> SEQ ID NO 2428

<400> SEQUENCE: 2428

000

<210> SEQ ID NO 2429

<400> SEQUENCE: 2429

000

<210> SEQ ID NO 2430
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2430
tgtgacactt caaactcgta ccgtgagtaa taatgcgccg                         40

<210> SEQ ID NO 2431
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2431
cttggttttt gcaataatgc tagcagagta cacacaagaa                         40

<210> SEQ ID NO 2432

<400> SEQUENCE: 2432

000

<210> SEQ ID NO 2433
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2433
tgagaatctt gatgatgctg catcggcaat caacgactat                         40

<210> SEQ ID NO 2434
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 2434
tgtaattcca ttgagggttt ctggtgactc cagcttcgta                          40

<210> SEQ ID NO 2435

<400> SEQUENCE: 2435

000

<210> SEQ ID NO 2436
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2436
cattagggac acgtgtgagt gtgccaggct cattcctgag                          40

<210> SEQ ID NO 2437

<400> SEQUENCE: 2437

000

<210> SEQ ID NO 2438

<400> SEQUENCE: 2438

000

<210> SEQ ID NO 2439
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2439
tagttcatgg cgtccagcag cagcttctgg cagaccgggt                          40

<210> SEQ ID NO 2440

<400> SEQUENCE: 2440

000

<210> SEQ ID NO 2441
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2441
cgttacattc aacgggtatt tattgagcac ccactctgtg                          40

<210> SEQ ID NO 2442

<400> SEQUENCE: 2442
```

000

<210> SEQ ID NO 2443

<400> SEQUENCE: 2443

000

<210> SEQ ID NO 2444
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2444
ctcagtcgtg ccctagcagc gggaacagta ctgcagtgag                                40

<210> SEQ ID NO 2445
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2445
gttcaaaacg tgaggcgctg ctatacccccc tcgtggggaa                               40

<210> SEQ ID NO 2446
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2446
ggacaaggga ggagacacgc agaggtgaca gaaaggttag                                40

<210> SEQ ID NO 2447
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2447
caggctcaca cctccctccc ccaactctct ggaatgtata                                40

<210> SEQ ID NO 2448
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2448
ctccccatgg ccctgtctcc caacccttgt accagtgctg                                40

<210> SEQ ID NO 2449
<211> LENGTH: 40
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 2449
aaggtctttg gtcttggagg aaggtgtgct actggaagag                                   40

<210> SEQ ID NO 2450
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2450
ctcagccgtg ccctagcagc gggaacagtt ctgcagtgag                                   40

<210> SEQ ID NO 2451
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2451
tcacagtgaa ccggtctctt tccctactgt gtcacactcc                                   40

<210> SEQ ID NO 2452

<400> SEQUENCE: 2452

000

<210> SEQ ID NO 2453
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2453
gtcaggctca gtcccctccc gataaacccc taaataggga                                   40

<210> SEQ ID NO 2454

<400> SEQUENCE: 2454

000

<210> SEQ ID NO 2455

<400> SEQUENCE: 2455

000

<210> SEQ ID NO 2456

<400> SEQUENCE: 2456

000

<210> SEQ ID NO 2457

<400> SEQUENCE: 2457

000

```
<210> SEQ ID NO 2458
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2458
tcagggttta tgaagttatc aaagcccctt gatggaatta                              40

<210> SEQ ID NO 2459
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2459
cttggtgtgt tctcggtagc tatggaaatc ccagggtttc                              40

<210> SEQ ID NO 2460

<400> SEQUENCE: 2460

000

<210> SEQ ID NO 2461

<400> SEQUENCE: 2461

000

<210> SEQ ID NO 2462

<400> SEQUENCE: 2462

000

<210> SEQ ID NO 2463

<400> SEQUENCE: 2463

000

<210> SEQ ID NO 2464

<400> SEQUENCE: 2464

000

<210> SEQ ID NO 2465
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2465
ttccaggtgt ccaccaagga cgtgccgctg gcgctgatgg                              40

<210> SEQ ID NO 2466
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 2466
tgccaagggt ttgggggaac attcaacctg tcggtgagtt                            40

<210> SEQ ID NO 2467
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2467
ttaaagcagg agaggtgaga ggaagaatta atgtgtgctc                            40

<210> SEQ ID NO 2468
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2468
gggattaatg accagctggg ggagttgata gccctcagtg                            40

<210> SEQ ID NO 2469

<400> SEQUENCE: 2469

000

<210> SEQ ID NO 2470

<400> SEQUENCE: 2470

000

<210> SEQ ID NO 2471

<400> SEQUENCE: 2471

000

<210> SEQ ID NO 2472
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2472
cagttgcata gtcacaaaag tgatcattgg caggtgtggc                            40

<210> SEQ ID NO 2473

<400> SEQUENCE: 2473

000

<210> SEQ ID NO 2474
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 2474
ctgtgggatc tggttctgta gctgagagca catcgctaaa                          40

<210> SEQ ID NO 2475
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2475
tctagcagca cagaaatatt ggcacaggga agcgagtctg                          40

<210> SEQ ID NO 2476

<400> SEQUENCE: 2476

000

<210> SEQ ID NO 2477
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2477
ttacacagct cacgagtgcc tgctggggtg gaacctggtc                          40

<210> SEQ ID NO 2478

<400> SEQUENCE: 2478

000

<210> SEQ ID NO 2479

<400> SEQUENCE: 2479

000

<210> SEQ ID NO 2480

<400> SEQUENCE: 2480

000

<210> SEQ ID NO 2481

<400> SEQUENCE: 2481

000

<210> SEQ ID NO 2482

<400> SEQUENCE: 2482

000

<210> SEQ ID NO 2483
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 2483
gacgggacat tattactttt ggtacgcgct gtgacacttc                          40

<210> SEQ ID NO 2484
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2484
gttctgttgc taagacaaca ggatgctagc aggcatatgc                          40

<210> SEQ ID NO 2485
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2485
tctcaggctg tgaccctcta gagggaagcg ctttctgttg                          40

<210> SEQ ID NO 2486
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2486
tgaattattg cacaataaat tcatgccctg ttgtgtctta                          40

<210> SEQ ID NO 2487
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2487
gagcattaag atttcctatt ctttgaggca aatattgacc                          40

<210> SEQ ID NO 2488
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2488
gtgaaagaaa gtgcttcctt tcagagggtt actctttgag                          40

<210> SEQ ID NO 2489

<400> SEQUENCE: 2489

000
```

```
<210> SEQ ID NO 2490
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2490
cctgaaaggt ctggtgttaa gcaaatactc ggtgaccaga                           40

<210> SEQ ID NO 2491
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2491
gttcacagtg ggagaaatat gcttcgtatt actctttctc                           40

<210> SEQ ID NO 2492
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2492
cagctatgtg gactctagct gccaaaggcg cttctccttc                           40

<210> SEQ ID NO 2493

<400> SEQUENCE: 2493

000

<210> SEQ ID NO 2494

<400> SEQUENCE: 2494

000

<210> SEQ ID NO 2495

<400> SEQUENCE: 2495

000

<210> SEQ ID NO 2496
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2496
aacttggcta caaggctctt tccctctcta tgaaggacag                           40

<210> SEQ ID NO 2497
<211> LENGTH: 40
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 2497
agttggggag aactttatga ttattctcat gcatcatctt                              40

<210> SEQ ID NO 2498
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2498
gagtgtggat ctaatcttca gctgattaaa tgtccctcat                              40

<210> SEQ ID NO 2499

<400> SEQUENCE: 2499

000

<210> SEQ ID NO 2500
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2500
agcaaaagct attatttgcc cttgatgagc caatcagatg                              40

<210> SEQ ID NO 2501
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2501
gcgctgacaa atcttgcctg attctgtatg atccatgaga                              40

<210> SEQ ID NO 2502
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2502
taatgagaat tatgtttgca cattgaggca ggataaatcc                              40

<210> SEQ ID NO 2503
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2503
gacaaacatg caggaaaaat tatcccctgg ggattctaca                              40

```
<210> SEQ ID NO 2504
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2504
ttgtgggtca gctgcccagc tatcggctgg attagtgaat                           40

<210> SEQ ID NO 2505

<400> SEQUENCE: 2505

000

<210> SEQ ID NO 2506
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2506
actggaatta tgttttatct taagtccaca ctggatcctc                           40

<210> SEQ ID NO 2507
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2507
taaagtgagt tatggaggtt actctcctgt gagaggaaat                           40

<210> SEQ ID NO 2508
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2508
tacacctaag gcatgtactg tattaatgaa ccaataaaac                           40

<210> SEQ ID NO 2509
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2509
catgatgggg tggggtgaga tggggagcga agactattac                           40

<210> SEQ ID NO 2510
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 2510
gcccgggcat gcattttatc tagcaccatg tgtttcagct    40

<210> SEQ ID NO 2511

<400> SEQUENCE: 2511

000

<210> SEQ ID NO 2512
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2512
gtttaaacag ccagtgcaaa catttagatc tgagtcaaaa    40

<210> SEQ ID NO 2513

<400> SEQUENCE: 2513

000

<210> SEQ ID NO 2514
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2514
cagggattgt gggttcgagt cccacccggg gtaaagaaag    40

<210> SEQ ID NO 2515
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2515
gaactgtttg ctttggatgg gcttggtcct cattggctga    40

<210> SEQ ID NO 2516
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2516
aaataatgac tggccataag atcaagacaa gtgtccaaag    40

<210> SEQ ID NO 2517
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2517

<210> SEQ ID NO 2518
<211> LENGTH: 41
<212> TYPE: DNA
<213> ORGANISM: Artificial Sequence
<220> FEATURE:
<223> OTHER INFORMATION: Description of Artificial Sequence: Synthetic probe

<400> SEQUENCE: 2518
ctcacggcgt tgccatggag acaactccgg ggctggggct c            41

<210> SEQ ID NO 2519
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2519
tccgtcactt gaactggctg ccagcgttca cagacagctg              40

<210> SEQ ID NO 2520
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2520
gtacatctgg atgtagttgt gctgcagctg cttctggtag              40

<210> SEQ ID NO 2521
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2521
cggcaaaaac ctctgtcaga acaaaattag gtgatctatc              40

<210> SEQ ID NO 2522

<400> SEQUENCE: 2522

000

<210> SEQ ID NO 2523
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2523
cacaaaaagg cataagcaga catcttgccc tttggtttct              40

<210> SEQ ID NO 2524
<211> LENGTH: 40
<212> TYPE: DNA
<213> ORGANISM: Artificial Sequence caggtacatg ttgatcagca ggggctggga ggcgccgctc              40

```
<220> FEATURE:
<223> OTHER INFORMATION: Description of Artificial Sequence: Synthetic
      probe

<400> SEQUENCE: 2524
aggagatatg ccaagatata ttcacagctt tatatacaca                              40

<210> SEQ ID NO 2525
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2525
gctgctctgc tgaggggctg gactctgtcc agaagcacca                              40

<210> SEQ ID NO 2526
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2526
cattctctac aagcatatgg ccttgggaca ttaagatggc                              40

<210> SEQ ID NO 2527
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2527
aacatcaaga tctattgacc tgagaggtaa atattgaccg                              40

<210> SEQ ID NO 2528
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2528
aaatgttgtt atagtatccc acctaccctg atgtatcttt                              40

<210> SEQ ID NO 2529
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2529
gaacaggctt caaggttctt ggcaggaata ttccgtgtag                              40

<210> SEQ ID NO 2530
<211> LENGTH: 40
<212> TYPE: DNA
<213> ORGANISM: Artificial Sequence
<220> FEATURE:
<223> OTHER INFORMATION: Description of Artificial Sequence: Synthetic
```

```
                                probe

<400> SEQUENCE: 2530
atgccttgtg ctctgtgcta attcagaaga ataagcctgt                               40

<210> SEQ ID NO 2531
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2531
cttgtcgact agccagttat gaacagagga ggatgttctc                               40

<210> SEQ ID NO 2532
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2532
ggagatccct tcaaggtact tagtttaaa tgagtgctct                                40

<210> SEQ ID NO 2533

<400> SEQUENCE: 2533

000

<210> SEQ ID NO 2534
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2534
ttgtgcactg cacaaccta gtggcgccat tcaattatag                                40

<210> SEQ ID NO 2535
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2535
ctctcttttt cctgcttgat ttgcctaatg gaagctgaca                               40

<210> SEQ ID NO 2536

<400> SEQUENCE: 2536

000

<210> SEQ ID NO 2537
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

<210> SEQ ID NO 2537

<400> SEQUENCE: 2537
agcacatccc atgatcacag taatgttctt tggagatgta          40

<210> SEQ ID NO 2538

<400> SEQUENCE: 2538

000

<210> SEQ ID NO 2539

<400> SEQUENCE: 2539

000

<210> SEQ ID NO 2540
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2540
accaacctgg aggactccat gctgttgagc tgttcacaag          40

<210> SEQ ID NO 2541

<400> SEQUENCE: 2541

000

<210> SEQ ID NO 2542

<400> SEQUENCE: 2542

000

<210> SEQ ID NO 2543

<400> SEQUENCE: 2543

000

<210> SEQ ID NO 2544
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2544
gcattaggga gaatagttga tggattacaa atctctgcat          40

<210> SEQ ID NO 2545

<400> SEQUENCE: 2545

000

<210> SEQ ID NO 2546

<400> SEQUENCE: 2546

000

<210> SEQ ID NO 2547
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2547
taagctatgg aatgtaaaga agtatgtatc tcaggccggg                              40

<210> SEQ ID NO 2548

<400> SEQUENCE: 2548

000

<210> SEQ ID NO 2549

<400> SEQUENCE: 2549

000

<210> SEQ ID NO 2550
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2550
tgctgctgtt aatgccatta ggatgactat ttatatcacc                              40

<210> SEQ ID NO 2551
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2551
cataagtcat tcctagaaat tgttcataat gcctgtaaca                              40

<210> SEQ ID NO 2552

<400> SEQUENCE: 2552

000

<210> SEQ ID NO 2553
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2553
aatcatagag gaaaatccac gttttcagta tcaaatgctg                              40

<210> SEQ ID NO 2554

<400> SEQUENCE: 2554

000

<210> SEQ ID NO 2555

<400> SEQUENCE: 2555

000

<210> SEQ ID NO 2556

<400> SEQUENCE: 2556

000

<210> SEQ ID NO 2557
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2557
cacgaagaag ttcagcaacc aggagaccag gtgggggccg                40

<210> SEQ ID NO 2558
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2558
tcgccccagt gttcagacta cctgttcagg acaatgccgt                40

<210> SEQ ID NO 2559

<400> SEQUENCE: 2559

000

<210> SEQ ID NO 2560
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2560
aattgagcaa acagtgcaat tttctgtaat tatgccagtg                40

<210> SEQ ID NO 2561
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2561
cctcacggtc cagttttccc aggaatccct tagatgctaa                40

<210> SEQ ID NO 2562
<211> LENGTH: 40
<212> TYPE: DNA
<213> ORGANISM: Artificial Sequence
<220> FEATURE:
<223> OTHER INFORMATION: Description of Artificial Sequence: Synthetic -continued probe

<400> SEQUENCE: 2562
gccaacccag tgttcagact acctgttcag gaggctctca        40

<210> SEQ ID NO 2563

<400> SEQUENCE: 2563

000

<210> SEQ ID NO 2564

<400> SEQUENCE: 2564

000

<210> SEQ ID NO 2565
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2565
ccctggctgg gatatcatca tatactgtaa gtttgcgatg        40

<210> SEQ ID NO 2566
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2566
tcaggctgtg acactctaga gggaagcgct ttctgttgtc        40

<210> SEQ ID NO 2567
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2567
gaaaagaaag tgcatccttt tagaggttta ctgtttgagg        40

<210> SEQ ID NO 2568
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2568
tgctacagtc aagatgcgaa tcattatttg ctgctctaga        40

<210> SEQ ID NO 2569

<400> SEQUENCE: 2569

000

```
<210> SEQ ID NO 2570
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2570
gtcagcagtg ccttagcagc acgtaaatat tggcgttaag                          40

<210> SEQ ID NO 2571
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2571
gaggtcacaa tcaacattca ttgttgtcgg tgggttgtga                          40

<210> SEQ ID NO 2572
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2572
gtcagaataa tgtcaaagtg cttacagtgc aggtagtgat                          40

<210> SEQ ID NO 2573

<400> SEQUENCE: 2573

000

<210> SEQ ID NO 2574
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2574
tgccaattcc ataggtcaca ggtatgttcg cctcaatgcc                          40

<210> SEQ ID NO 2575

<400> SEQUENCE: 2575

000

<210> SEQ ID NO 2576
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2576
catttcttta ggccaatatt ctgtatgact gtgctacttc                          40

<210> SEQ ID NO 2577
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2577
ggcatggagt tcaagcagca ttgtacaggg ctatcaaagc                            40

<210> SEQ ID NO 2578
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2578
gtctctaata ctgcctggta atgatgacgg cggagccctg                            40

<210> SEQ ID NO 2579
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2579
tatggatcaa gcagcattgt acagggctat gaaggcattg                            40

<210> SEQ ID NO 2580

<400> SEQUENCE: 2580

000

<210> SEQ ID NO 2581

<400> SEQUENCE: 2581

000

<210> SEQ ID NO 2582

<400> SEQUENCE: 2582

000

<210> SEQ ID NO 2583

<400> SEQUENCE: 2583

000

<210> SEQ ID NO 2584

<400> SEQUENCE: 2584

000

<210> SEQ ID NO 2585
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 2585
gtagcattca ggtcaagcaa cattgtacag ggctatgaaa                                40

<210> SEQ ID NO 2586
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2586
tctcaggctg tgtccctcta cagggaagcg ctttctgttg                                40

<210> SEQ ID NO 2587

<400> SEQUENCE: 2587

000

<210> SEQ ID NO 2588
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2588
gttccactct agcagcacgt aaatattggc gtagtgaaat                                40

<210> SEQ ID NO 2589
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2589
ttgttggaca ctctttccct gttgcactac tgtgggcctc                                40

<210> SEQ ID NO 2590

<400> SEQUENCE: 2590

000

<210> SEQ ID NO 2591
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2591
tgatataaat agtcatccta atggcattaa cagcagcact                                40

<210> SEQ ID NO 2592

<400> SEQUENCE: 2592

000

<210> SEQ ID NO 2593
```

```
<400> SEQUENCE: 2593

000

<210> SEQ ID NO 2594

<400> SEQUENCE: 2594

000

<210> SEQ ID NO 2595

<400> SEQUENCE: 2595

000

<210> SEQ ID NO 2596
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2596
tctcagcctg tgaccctcta gagggaagcg ctttctgttg                            40

<210> SEQ ID NO 2597

<400> SEQUENCE: 2597

000

<210> SEQ ID NO 2598
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2598
caatgtcagc agtgccttag cagcacgtaa atattggcgt                            40

<210> SEQ ID NO 2599

<400> SEQUENCE: 2599

000

<210> SEQ ID NO 2600

<400> SEQUENCE: 2600

000

<210> SEQ ID NO 2601

<400> SEQUENCE: 2601

000

<210> SEQ ID NO 2602

<400> SEQUENCE: 2602

000
```

<210> SEQ ID NO 2603

<400> SEQUENCE: 2603

000

<210> SEQ ID NO 2604

<400> SEQUENCE: 2604

000

<210> SEQ ID NO 2605

<400> SEQUENCE: 2605

000

<210> SEQ ID NO 2606

<400> SEQUENCE: 2606

000

<210> SEQ ID NO 2607
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2607
gtggtgcatt gtagttgcat tgcatgttct ggtggtaccc                              40

<210> SEQ ID NO 2608
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2608
tctgtatggt attgcacttg tcccggcctg ttgagtttgg                              40

<210> SEQ ID NO 2609
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2609
ccttagcaga gctgtggagt gtgacaatgg tgtttgtgtc                              40

<210> SEQ ID NO 2610

<400> SEQUENCE: 2610

000

<210> SEQ ID NO 2611

<400> SEQUENCE: 2611

000

<210> SEQ ID NO 2612

<400> SEQUENCE: 2612

000

<210> SEQ ID NO 2613

<400> SEQUENCE: 2613

000

<210> SEQ ID NO 2614

<400> SEQUENCE: 2614

000

<210> SEQ ID NO 2615

<400> SEQUENCE: 2615

000

<210> SEQ ID NO 2616
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2616
tacctcagaa gcctcactca accctctccc gctgagtctc                               40

<210> SEQ ID NO 2617

<400> SEQUENCE: 2617

000

<210> SEQ ID NO 2618

<400> SEQUENCE: 2618

000

<210> SEQ ID NO 2619

<400> SEQUENCE: 2619

000

<210> SEQ ID NO 2620

<400> SEQUENCE: 2620

000

<210> SEQ ID NO 2621

<400> SEQUENCE: 2621

000

<210> SEQ ID NO 2622

<400> SEQUENCE: 2622

000

<210> SEQ ID NO 2623

<400> SEQUENCE: 2623

000

<210> SEQ ID NO 2624

<400> SEQUENCE: 2624

000

<210> SEQ ID NO 2625
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2625
ctaatactgt ctggtaaaac cgtccatccg ctgcctgatc                          40

<210> SEQ ID NO 2626
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2626
aggctttgtg cgcgcattaa agctcgccgg accccccgacc                         40

<210> SEQ ID NO 2627

<400> SEQUENCE: 2627

000

<210> SEQ ID NO 2628
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2628
gtcctgtcta aaggaagaag tttgttctac tgtaaacagt                          40

<210> SEQ ID NO 2629

<400> SEQUENCE: 2629

000

<210> SEQ ID NO 2630

<400> SEQUENCE: 2630

000

<210> SEQ ID NO 2631

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2631
tggttcccgc ccctgtaac agcaactcca tgtggaagtg                              40

<210> SEQ ID NO 2632

<400> SEQUENCE: 2632

000

<210> SEQ ID NO 2633

<400> SEQUENCE: 2633

000

<210> SEQ ID NO 2634

<400> SEQUENCE: 2634

000

<210> SEQ ID NO 2635
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2635
ggacaattca acagtggtga gtcacttcgc cacttttcag                             40

<210> SEQ ID NO 2636

<400> SEQUENCE: 2636

000

<210> SEQ ID NO 2637

<400> SEQUENCE: 2637

000

<210> SEQ ID NO 2638

<400> SEQUENCE: 2638

000

<210> SEQ ID NO 2639

<400> SEQUENCE: 2639

000

<210> SEQ ID NO 2640

<400> SEQUENCE: 2640

000
```

<210> SEQ ID NO 2641

<400> SEQUENCE: 2641

000

<210> SEQ ID NO 2642
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2642
tgagccctcg gaggactcca tttgttttga tgatggattc                              40

<210> SEQ ID NO 2643
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2643
gcccaacaga acaacttgtt tctccagagc ctgaggttta                              40

<210> SEQ ID NO 2644
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2644
tcttctgaca atgaaggtag gcggacaacg aggagattgc                              40

<210> SEQ ID NO 2645
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2645
gaagacggac ttggttccgt ttgaccagcc agagcagggg                              40

<210> SEQ ID NO 2646
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2646
gtccggcgcg agtggagctg ttgtaaaatg gcggccgaag                              40

<210> SEQ ID NO 2647

<400> SEQUENCE: 2647

000

```
<210> SEQ ID NO 2648

<400> SEQUENCE: 2648

000

<210> SEQ ID NO 2649
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2649
attgtccaaa cgcaattctc gagtctatgg ctccggccga                                40

<210> SEQ ID NO 2650
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2650
ccgcccgccg ttccttttc ctatgcatat acttctttga                                 40

<210> SEQ ID NO 2651
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2651
caccgccggc cgatgggcgt cttaccagac atggttagac                                40

<210> SEQ ID NO 2652

<400> SEQUENCE: 2652

000

<210> SEQ ID NO 2653
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2653
tgtcctgacc cagctaaagc tgccagttga agaactgttg                                40

<210> SEQ ID NO 2654
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2654
cttaccctgg tgcgtggggc cgcagggcta acaccaaaaa                                40

<210> SEQ ID NO 2655
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2655
tcattggtcc agagggaga taggttcctg tgatttttcc                              40

<210> SEQ ID NO 2656
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2656
gtctgcacat tggttaggct gggctgggtt agaccctcgg                             40

<210> SEQ ID NO 2657
<400> SEQUENCE: 2657

000

<210> SEQ ID NO 2658
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2658
ttaaggcacg cggtgaatgc caagagcgga gcctacggct                             40

<210> SEQ ID NO 2659
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2659
agctggtgtt gtgaatcagg ccgacgagca gcgcatcctc                             40

<210> SEQ ID NO 2660
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2660
ctcagtctgc gggccccgag gagggttgtg ggccctttt                              40

<210> SEQ ID NO 2661
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2661
```

```
cgagaggcac tttgtacttc tgccaggaga ccatatgata                              40

<210> SEQ ID NO 2662
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2662
ttacccagcc gggccgccaa caccagatcc ttctccttct                              40

<210> SEQ ID NO 2663
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2663
ccgctttgtt cacagtggct aagttctgca cctgaagaga                              40

<210> SEQ ID NO 2664
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2664
gtatatgtgt gtgtgtgtgt gtgtgtgtgt gtgtgtgtgt                              40

<210> SEQ ID NO 2665

<400> SEQUENCE: 2665

000

<210> SEQ ID NO 2666

<400> SEQUENCE: 2666

000

<210> SEQ ID NO 2667

<400> SEQUENCE: 2667

000

<210> SEQ ID NO 2668

<400> SEQUENCE: 2668

000

<210> SEQ ID NO 2669

<400> SEQUENCE: 2669

000

<210> SEQ ID NO 2670
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2670
gtctgtcttc tgtatatacc ctgtagatcc gaatttgtgt                              40

<210> SEQ ID NO 2671
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2671
aatcacattg ccagggatta ccacgcaacc acgaccttgg                              40

<210> SEQ ID NO 2672
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2672
ctgtggtctc agaatcgggg ttttgagggc gagatgagtt                              40

<210> SEQ ID NO 2673

<400> SEQUENCE: 2673

000

<210> SEQ ID NO 2674
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2674
atctcagtag ccaatatttt tctctgctgg tatcaaatga                              40

<210> SEQ ID NO 2675

<400> SEQUENCE: 2675

000

<210> SEQ ID NO 2676
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2676
tgtacagcag gcacagacag gcagtcacat gacaacccag                              40

<210> SEQ ID NO 2677
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 2677
cttgtgtttt cacagcagcc acaggccta catccttcct                              40

<210> SEQ ID NO 2678
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2678
agaaggcgct ccctgctagc ccggctctgt tctaattata                             40

<210> SEQ ID NO 2679

<400> SEQUENCE: 2679

000

<210> SEQ ID NO 2680
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2680
tcctgtcaca aatcacattg ccagggattt ccaaccgacc                             40

<210> SEQ ID NO 2681
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2681
agttggtttg tgtacactgg ctcagttcag caggaacagg                             40

<210> SEQ ID NO 2682

<400> SEQUENCE: 2682

000

<210> SEQ ID NO 2683

<400> SEQUENCE: 2683

000

<210> SEQ ID NO 2684
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2684
```
ggttaagact ctaacaaacg agttgtgaat tgtagcaatg					40

<210> SEQ ID NO 2685

<400> SEQUENCE: 2685

000

<210> SEQ ID NO 2686
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2686
gggatactca aaatgggggc gctttccttt ttgtctgtac					40

<210> SEQ ID NO 2687

<400> SEQUENCE: 2687

000

<210> SEQ ID NO 2688

<400> SEQUENCE: 2688

000

<210> SEQ ID NO 2689

<400> SEQUENCE: 2689

000

<210> SEQ ID NO 2690
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2690
actttctgct ctctggtgaa agtgccgcca tcttttgagt					40

<210> SEQ ID NO 2691

<400> SEQUENCE: 2691

000

<210> SEQ ID NO 2692
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2692
agcagcttag aatctactgc cctaaatgcc ccttctggca					40

<210> SEQ ID NO 2693

<400> SEQUENCE: 2693

```
<210> SEQ ID NO 2694
<400> SEQUENCE: 2694

000

<210> SEQ ID NO 2695
<400> SEQUENCE: 2695

000

<210> SEQ ID NO 2696
<400> SEQUENCE: 2696

000

<210> SEQ ID NO 2697
<400> SEQUENCE: 2697

000

<210> SEQ ID NO 2698
<400> SEQUENCE: 2698

000

<210> SEQ ID NO 2699
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2699
caaaggtcac aattaacatt cattgttgtc ggtgggttgt                          40

<210> SEQ ID NO 2700
<400> SEQUENCE: 2700

000

<210> SEQ ID NO 2701
<400> SEQUENCE: 2701

000

<210> SEQ ID NO 2702
<400> SEQUENCE: 2702

000

<210> SEQ ID NO 2703
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 2703
tgggaacctt gttaaaatgc agattctgat tctcaggtct                    40

<210> SEQ ID NO 2704

<400> SEQUENCE: 2704

000

<210> SEQ ID NO 2705

<400> SEQUENCE: 2705

000

<210> SEQ ID NO 2706

<400> SEQUENCE: 2706

000

<210> SEQ ID NO 2707

<400> SEQUENCE: 2707

000

<210> SEQ ID NO 2708

<400> SEQUENCE: 2708

000

<210> SEQ ID NO 2709

<400> SEQUENCE: 2709

000

<210> SEQ ID NO 2710

<400> SEQUENCE: 2710

000

<210> SEQ ID NO 2711
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2711
ttaaggcacg cggtgaatgc caagagaggc gcctccgccg                    40

<210> SEQ ID NO 2712
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2712
tcagaggact ccaaggaaca ttcaacgctg tcggtgagtt                    40

```
<210> SEQ ID NO 2713
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2713
cttcctccct gggcatctct agcacagggg atccccaaac                          40

<210> SEQ ID NO 2714
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2714
ctatgacaga aggtactctg tgggagggag gagataatag                          40

<210> SEQ ID NO 2715
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2715
ggtgggatta cccggctgcc gctgtcgcct ggatggtctc                          40

<210> SEQ ID NO 2716

<400> SEQUENCE: 2716

000

<210> SEQ ID NO 2717

<400> SEQUENCE: 2717

000

<210> SEQ ID NO 2718
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2718
ctgatggctg cactcaacat tcattgctgt cggtgggttt                          40

<210> SEQ ID NO 2719
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2719
ttatcataaa ataatcacag ccctcaggtg ctgtgaggca                          40
```

```
<210> SEQ ID NO 2720
<400> SEQUENCE: 2720
000

<210> SEQ ID NO 2721
<400> SEQUENCE: 2721
000

<210> SEQ ID NO 2722
<400> SEQUENCE: 2722
000

<210> SEQ ID NO 2723
<400> SEQUENCE: 2723
000

<210> SEQ ID NO 2724
<400> SEQUENCE: 2724
000

<210> SEQ ID NO 2725
<400> SEQUENCE: 2725
000

<210> SEQ ID NO 2726
<400> SEQUENCE: 2726
000

<210> SEQ ID NO 2727
<400> SEQUENCE: 2727
000

<210> SEQ ID NO 2728
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2728
caatcggtta gcgcgttcgg ctgttaaccg aaaggttggt                            40

<210> SEQ ID NO 2729
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2729
tttaaaaggt cacaatcaac attcattgct gtcggtgggt                            40
```

<210> SEQ ID NO 2730

<400> SEQUENCE: 2730

000

<210> SEQ ID NO 2731
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2731
tctgttgaat ataaattgga attgcacttt agcaatggtg                            40

<210> SEQ ID NO 2732

<400> SEQUENCE: 2732

000

<210> SEQ ID NO 2733

<400> SEQUENCE: 2733

000

<210> SEQ ID NO 2734

<400> SEQUENCE: 2734

000

<210> SEQ ID NO 2735
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2735
ctgggattat gctaaacaga gcaatttcct agccctcacg                            40

<210> SEQ ID NO 2736

<400> SEQUENCE: 2736

000

<210> SEQ ID NO 2737

<400> SEQUENCE: 2737

000

<210> SEQ ID NO 2738

<400> SEQUENCE: 2738

000

<210> SEQ ID NO 2739

<400> SEQUENCE: 2739

000

<210> SEQ ID NO 2740

<400> SEQUENCE: 2740

000

<210> SEQ ID NO 2741

<400> SEQUENCE: 2741

000

<210> SEQ ID NO 2742

<400> SEQUENCE: 2742

000

<210> SEQ ID NO 2743

<400> SEQUENCE: 2743

000

<210> SEQ ID NO 2744

<400> SEQUENCE: 2744

000

<210> SEQ ID NO 2745

<400> SEQUENCE: 2745

000

<210> SEQ ID NO 2746

<400> SEQUENCE: 2746

000

<210> SEQ ID NO 2747

<400> SEQUENCE: 2747

000

<210> SEQ ID NO 2748

<400> SEQUENCE: 2748

000

<210> SEQ ID NO 2749

<400> SEQUENCE: 2749

000

<210> SEQ ID NO 2750
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2750
gagtgtttct tggcagtgt cttagctggt tgttgtgagc                              40

<210> SEQ ID NO 2751
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2751
ctagctccgt tcgtgatccg ggagcctggt gccagcgaga                             40

<210> SEQ ID NO 2752
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2752
gaagatcggt tgtcatctgg tctggtcagc ccggccccga                             40

<210> SEQ ID NO 2753
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2753
tgttaagtgg aaaagcctcc aggaacgtgg cagaaaaagg                             40

<210> SEQ ID NO 2754
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2754
gcaacggcct gattcacaac accagctgcc ccaccacacc                             40

<210> SEQ ID NO 2755

<400> SEQUENCE: 2755

000

<210> SEQ ID NO 2756

<400> SEQUENCE: 2756

000

<210> SEQ ID NO 2757
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2757
gacctgattc ccatctttgt atttggcgac cacccgactg      40

<210> SEQ ID NO 2758

<400> SEQUENCE: 2758

000

<210> SEQ ID NO 2759

<400> SEQUENCE: 2759

000

<210> SEQ ID NO 2760
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2760
tctgtattta atttggctca gccgggaaga ttttggctc      40

<210> SEQ ID NO 2761
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2761
ttgcagagcc taagacacag gcccagagag gcagtgatcg      40

<210> SEQ ID NO 2762

<400> SEQUENCE: 2762

000

<210> SEQ ID NO 2763
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2763
tgtggtcacg tttctccctc tctgctggcc cccatctgtc      40

<210> SEQ ID NO 2764
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2764
cttctcctcc tgttcgccgc aggcgcccgt cccagtagtc      40

<210> SEQ ID NO 2765

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2765
aacaactttg tgctggtgcc ggggaagttt gtgtctccaa                             40

<210> SEQ ID NO 2766
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2766
aaaagtaaac aacaatttgc cgctgccagc ctcccattag                             40

<210> SEQ ID NO 2767
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2767
atactagatt aaatttcagc cccgggccaa tctgtcaaag                             40

<210> SEQ ID NO 2768
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2768
gaggtgtttg tgctccactc ggctcccttg gttacataac                             40

<210> SEQ ID NO 2769
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2769
atgtttaaca gtccaggttt tgtagaatat gtggtggacc                             40

<210> SEQ ID NO 2770
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2770
tcacatccct tgcatggtgg agggtgagct ttctgaaaac                             40

<210> SEQ ID NO 2771
<211> LENGTH: 40
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 2771
cttcttgtat aagcactgtg ctaaaattgc agacactagg                40

<210> SEQ ID NO 2772
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2772
tgagtatgat agaagtcagt gcactacaga actttgtctc                40

<210> SEQ ID NO 2773
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2773
ctgcgctctc ggaaatgact cgctccaatc ccgcttcgcg                40

<210> SEQ ID NO 2774
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2774
cagtgcaatg atattgtcaa agcatctggg accagccttg                40

<210> SEQ ID NO 2775
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2775
agtaaacaat gtcggctttc cgcctcctcc cctgccatcc                40

<210> SEQ ID NO 2776

<400> SEQUENCE: 2776

000

<210> SEQ ID NO 2777
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2777
gcatctactg cagtgaaggc acttgtagca ttatggtgac                40

<210> SEQ ID NO 2778
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2778
ctcaggggct tcgccactga ttgtccaaac gcaattcttg                              40

<210> SEQ ID NO 2779
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2779
gaaagtgcat acagcccctg gccctctctg cccttccgtc                              40

<210> SEQ ID NO 2780

<400> SEQUENCE: 2780

000

<210> SEQ ID NO 2781
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2781
ttggcgtcct tgtctctctc tcccctgccc agtggcctcc                              40

<210> SEQ ID NO 2782

<400> SEQUENCE: 2782

000

<210> SEQ ID NO 2783
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2783
caacggaatc ccaaaagcag ctgttgtctc cagagcattc                              40

<210> SEQ ID NO 2784
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2784
ttttgttcgt tcggctcgcg tgaggcaggg gcggcctctc                              40

```
<210> SEQ ID NO 2785
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2785
cggacagcgc gccggcacct tggctctaga ctgcttactg                             40

<210> SEQ ID NO 2786

<400> SEQUENCE: 2786

000

<210> SEQ ID NO 2787

<400> SEQUENCE: 2787

000

<210> SEQ ID NO 2788

<400> SEQUENCE: 2788

000

<210> SEQ ID NO 2789

<400> SEQUENCE: 2789

000

<210> SEQ ID NO 2790

<400> SEQUENCE: 2790

000

<210> SEQ ID NO 2791

<400> SEQUENCE: 2791

000

<210> SEQ ID NO 2792

<400> SEQUENCE: 2792

000

<210> SEQ ID NO 2793
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2793
ggttctactc tcttacccct cccccacgtg gttgttgctg                             40

<210> SEQ ID NO 2794

<400> SEQUENCE: 2794
```

<210> SEQ ID NO 2795

<400> SEQUENCE: 2795

000

<210> SEQ ID NO 2796

<400> SEQUENCE: 2796

000

<210> SEQ ID NO 2797
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2797
caatcctggc tgcaggcata tttgcatatt ggatgctgtg    40

<210> SEQ ID NO 2798
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2798
tctcaggctg tcgtcctcta gagggaagca ctttctgttg    40

<210> SEQ ID NO 2799

<400> SEQUENCE: 2799

000

<210> SEQ ID NO 2800
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2800
tccttcattc caccggagtc tgtctcatac ccaaccagat    40

<210> SEQ ID NO 2801

<400> SEQUENCE: 2801

000

<210> SEQ ID NO 2802
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2802

-continued caaaagctcg gtctgaggcc cctcagtctt gcttcctaac          40

<210> SEQ ID NO 2803
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2803
tgtgatgagc tggcagtgta ttgttagctg gttgaatatg          40

<210> SEQ ID NO 2804
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2804
gctgatctgt ggcttaggta gtttcatgtt gttgggattg          40

<210> SEQ ID NO 2805

<400> SEQUENCE: 2805

000

<210> SEQ ID NO 2806

<400> SEQUENCE: 2806

000

<210> SEQ ID NO 2807

<400> SEQUENCE: 2807

000

<210> SEQ ID NO 2808

<400> SEQUENCE: 2808

000

<210> SEQ ID NO 2809

<400> SEQUENCE: 2809

000

<210> SEQ ID NO 2810

<400> SEQUENCE: 2810

000

<210> SEQ ID NO 2811

<400> SEQUENCE: 2811

000

<210> SEQ ID NO 2812

```
<400> SEQUENCE: 2812

000

<210> SEQ ID NO 2813

<400> SEQUENCE: 2813

000

<210> SEQ ID NO 2814
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2814
tgtctgtggt accctactct ggagagtgac aatcatgtat                            40

<210> SEQ ID NO 2815

<400> SEQUENCE: 2815

000

<210> SEQ ID NO 2816

<400> SEQUENCE: 2816

000

<210> SEQ ID NO 2817

<400> SEQUENCE: 2817

000

<210> SEQ ID NO 2818

<400> SEQUENCE: 2818

000

<210> SEQ ID NO 2819
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2819
agtttcttta attaatgaag tttttgggtc tgctccactt                            40

<210> SEQ ID NO 2820

<400> SEQUENCE: 2820

000

<210> SEQ ID NO 2821

<400> SEQUENCE: 2821

000
```

<210> SEQ ID NO 2822

<400> SEQUENCE: 2822

000

<210> SEQ ID NO 2823

<400> SEQUENCE: 2823

000

<210> SEQ ID NO 2824

<400> SEQUENCE: 2824

000

<210> SEQ ID NO 2825

<400> SEQUENCE: 2825

000

<210> SEQ ID NO 2826

<400> SEQUENCE: 2826

000

<210> SEQ ID NO 2827
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2827
agtgattgtc tagcaccatt tgaaatcagt gttcttgggg                            40

<210> SEQ ID NO 2828

<400> SEQUENCE: 2828

000

<210> SEQ ID NO 2829

<400> SEQUENCE: 2829

000

<210> SEQ ID NO 2830

<400> SEQUENCE: 2830

000

<210> SEQ ID NO 2831

<400> SEQUENCE: 2831

000

<210> SEQ ID NO 2832

<400> SEQUENCE: 2832

<210> SEQ ID NO 2833

<400> SEQUENCE: 2833

000

<210> SEQ ID NO 2834

<400> SEQUENCE: 2834

000

<210> SEQ ID NO 2835
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2835
acctgatgct cacgtataag acgagcaaaa agcttgttgg                               40

<210> SEQ ID NO 2836

<400> SEQUENCE: 2836

000

<210> SEQ ID NO 2837

<400> SEQUENCE: 2837

000

<210> SEQ ID NO 2838

<400> SEQUENCE: 2838

000

<210> SEQ ID NO 2839

<400> SEQUENCE: 2839

000

<210> SEQ ID NO 2840

<400> SEQUENCE: 2840

000

<210> SEQ ID NO 2841

<400> SEQUENCE: 2841

000

<210> SEQ ID NO 2842

<400> SEQUENCE: 2842

000

<210> SEQ ID NO 2843

<400> SEQUENCE: 2843

000

<210> SEQ ID NO 2844

<400> SEQUENCE: 2844

000

<210> SEQ ID NO 2845
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2845
gtgcattgct gttgcattgc acgtgtgtga ggcgggtgca                              40

<210> SEQ ID NO 2846
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2846
cagaggggag gcccagagga gagggaagct tgggcaaagg                              40

<210> SEQ ID NO 2847
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2847
tcggatccgt ctgagcttgg ctggtcggaa gtctcatcat                              40

<210> SEQ ID NO 2848
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2848
tggagaccca ctgccccagg tgctgctggg ggttgtagtc                              40

<210> SEQ ID NO 2849

<400> SEQUENCE: 2849

000

<210> SEQ ID NO 2850
<211> LENGTH: 40
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 2850
ctgctccgct cagagccttt tcctctccac ttcctgttca                           40

<210> SEQ ID NO 2851

<400> SEQUENCE: 2851

000

<210> SEQ ID NO 2852
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2852
ctctgtggcc atttcggttt ttccagtccg atgcccctga                           40

<210> SEQ ID NO 2853

<400> SEQUENCE: 2853

000

<210> SEQ ID NO 2854

<400> SEQUENCE: 2854

000

<210> SEQ ID NO 2855
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2855
ggtgtttgtg ctccactcag ctcccttggt tacataacag                           40

<210> SEQ ID NO 2856

<400> SEQUENCE: 2856

000

<210> SEQ ID NO 2857

<400> SEQUENCE: 2857

000

<210> SEQ ID NO 2858

<400> SEQUENCE: 2858

000

<210> SEQ ID NO 2859

<400> SEQUENCE: 2859

000

<210> SEQ ID NO 2860
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2860
taaatgtgta atttctccct tgacggcccc cggccgctgg                40

<210> SEQ ID NO 2861
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2861
atgcaatgca cccgggcaag gattctgaga gggtgagccc                40

<210> SEQ ID NO 2862

<400> SEQUENCE: 2862

000

<210> SEQ ID NO 2863

<400> SEQUENCE: 2863

000

<210> SEQ ID NO 2864
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2864
caggtgggtg ctgaggccgc gttgttgctt gaagctagcc                40

<210> SEQ ID NO 2865
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2865
aggctgggaa ggcaaaggga cgttcaattg tcatcactgg                40

<210> SEQ ID NO 2866

<400> SEQUENCE: 2866

000

<210> SEQ ID NO 2867

<400> SEQUENCE: 2867

000

<210> SEQ ID NO 2868

<400> SEQUENCE: 2868

000

<210> SEQ ID NO 2869
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2869
caatcacaga tagcacccct caccttgagc ccattttcac                              40

<210> SEQ ID NO 2870

<400> SEQUENCE: 2870

000

<210> SEQ ID NO 2871
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2871
ctgactatgc ctccccgcat cccctagggc attggtgtaa                              40

<210> SEQ ID NO 2872

<400> SEQUENCE: 2872

000

<210> SEQ ID NO 2873

<400> SEQUENCE: 2873

000

<210> SEQ ID NO 2874

<400> SEQUENCE: 2874

000

<210> SEQ ID NO 2875

<400> SEQUENCE: 2875

000

<210> SEQ ID NO 2876

<400> SEQUENCE: 2876

000

<210> SEQ ID NO 2877
<211> LENGTH: 40
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 2877
tcggtttggt tcagctggta tgctttccag tatctcattc          40

<210> SEQ ID NO 2878
<400> SEQUENCE: 2878
000

<210> SEQ ID NO 2879
<400> SEQUENCE: 2879
000

<210> SEQ ID NO 2880
<400> SEQUENCE: 2880
000

<210> SEQ ID NO 2881
<400> SEQUENCE: 2881
000

<210> SEQ ID NO 2882
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2882
aaggtctgga ttgatcgtac tgctttctga aaggtaaaaa          40

<210> SEQ ID NO 2883
<400> SEQUENCE: 2883
000

<210> SEQ ID NO 2884
<400> SEQUENCE: 2884
000

<210> SEQ ID NO 2885
<400> SEQUENCE: 2885
000

<210> SEQ ID NO 2886
<400> SEQUENCE: 2886
000

<210> SEQ ID NO 2887
<400> SEQUENCE: 2887

000

<210> SEQ ID NO 2888
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2888
ggttttgtgt ttttgtaaac agcagaaggt attagtccat                             40

<210> SEQ ID NO 2889

<400> SEQUENCE: 2889

000

<210> SEQ ID NO 2890

<400> SEQUENCE: 2890

000

<210> SEQ ID NO 2891

<400> SEQUENCE: 2891

000

<210> SEQ ID NO 2892

<400> SEQUENCE: 2892

000

<210> SEQ ID NO 2893
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2893
gggggccgat acactgtacg agagtgagta gcaggtctca                             40

<210> SEQ ID NO 2894

<400> SEQUENCE: 2894

000

<210> SEQ ID NO 2895

<400> SEQUENCE: 2895

000

<210> SEQ ID NO 2896

<400> SEQUENCE: 2896

000

<210> SEQ ID NO 2897

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2897
tcagtttggt tcagctggta tgctttccag tatctcattc                          40

<210> SEQ ID NO 2898

<400> SEQUENCE: 2898

000

<210> SEQ ID NO 2899
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2899
cactttttcc tttgtggaaa tcctgggtga catcacctcc                          40

<210> SEQ ID NO 2900
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2900
gactgcagag caaaagacac gatgggtgtc tattgttttc                          40

<210> SEQ ID NO 2901
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2901
ttttcctgct tgatttgctt aatggaagct gacagtgaag                          40

<210> SEQ ID NO 2902

<400> SEQUENCE: 2902

000

<210> SEQ ID NO 2903

<400> SEQUENCE: 2903

000

<210> SEQ ID NO 2904

<400> SEQUENCE: 2904

000

<210> SEQ ID NO 2905
```

<400> SEQUENCE: 2905

000

<210> SEQ ID NO 2906
<400> SEQUENCE: 2906

000

<210> SEQ ID NO 2907
<400> SEQUENCE: 2907

000

<210> SEQ ID NO 2908
<400> SEQUENCE: 2908

000

<210> SEQ ID NO 2909
<400> SEQUENCE: 2909

000

<210> SEQ ID NO 2910
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2910
cattatgcaa atggtatgag aggaaaatta ggcaataagg                              40

<210> SEQ ID NO 2911
<400> SEQUENCE: 2911

000

<210> SEQ ID NO 2912
<400> SEQUENCE: 2912

000

<210> SEQ ID NO 2913
<400> SEQUENCE: 2913

000

<210> SEQ ID NO 2914
<400> SEQUENCE: 2914

000

<210> SEQ ID NO 2915
<400> SEQUENCE: 2915

000

-continued

<210> SEQ ID NO 2916

<400> SEQUENCE: 2916

000

<210> SEQ ID NO 2917

<400> SEQUENCE: 2917

000

<210> SEQ ID NO 2918
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2918
ttttgtctag caccatttga aatcggttat gatgtagggg                              40

<210> SEQ ID NO 2919
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2919
caagtggtta attgagccca caagtgacct actcaatcag                              40

<210> SEQ ID NO 2920

<400> SEQUENCE: 2920

000

<210> SEQ ID NO 2921
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2921
tgtctgcacc tgtcactagc agtgcaatgt taaaagggca                              40

<210> SEQ ID NO 2922

<400> SEQUENCE: 2922

000

<210> SEQ ID NO 2923

<400> SEQUENCE: 2923

000

<210> SEQ ID NO 2924
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2924
gatctcgtgc tgtgaccctc tagagggaag cactttctgt                              40

<210> SEQ ID NO 2925
<400> SEQUENCE: 2925

000

<210> SEQ ID NO 2926
<400> SEQUENCE: 2926

000

<210> SEQ ID NO 2927
<400> SEQUENCE: 2927

000

<210> SEQ ID NO 2928
<400> SEQUENCE: 2928

000

<210> SEQ ID NO 2929
<400> SEQUENCE: 2929

000

<210> SEQ ID NO 2930
<400> SEQUENCE: 2930

000

<210> SEQ ID NO 2931
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2931
tctttgtatc tagcaccatt tgaaatcagt gttttaggag                              40

<210> SEQ ID NO 2932
<400> SEQUENCE: 2932

000

<210> SEQ ID NO 2933
<400> SEQUENCE: 2933

000

<210> SEQ ID NO 2934
<211> LENGTH: 40

<212> TYPE: DNA
<213> ORGANISM: Artificial Sequence
<220> FEATURE:
<223> OTHER INFORMATION: Description of Artificial Sequence: Synthetic probe

<400> SEQUENCE: 2934
tgaggtagta gattgtatag ttttagggtc atacccatc                    40

<210> SEQ ID NO 2935
<400> SEQUENCE: 2935
000

<210> SEQ ID NO 2936
<400> SEQUENCE: 2936
000

<210> SEQ ID NO 2937
<400> SEQUENCE: 2937
000

<210> SEQ ID NO 2938
<400> SEQUENCE: 2938
000

<210> SEQ ID NO 2939
<400> SEQUENCE: 2939
000

<210> SEQ ID NO 2940
<400> SEQUENCE: 2940
000

<210> SEQ ID NO 2941
<400> SEQUENCE: 2941
000

<210> SEQ ID NO 2942
<400> SEQUENCE: 2942
000

<210> SEQ ID NO 2943
<400> SEQUENCE: 2943
000

<210> SEQ ID NO 2944
<400> SEQUENCE: 2944
000

<210> SEQ ID NO 2945
<400> SEQUENCE: 2945

000

<210> SEQ ID NO 2946
<400> SEQUENCE: 2946

000

<210> SEQ ID NO 2947
<400> SEQUENCE: 2947

000

<210> SEQ ID NO 2948
<400> SEQUENCE: 2948

000

<210> SEQ ID NO 2949
<400> SEQUENCE: 2949

000

<210> SEQ ID NO 2950
<400> SEQUENCE: 2950

000

<210> SEQ ID NO 2951
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2951
ttctttgtct atacatttcc tagatttcta tgcagttggg                              40

<210> SEQ ID NO 2952
<400> SEQUENCE: 2952

000

<210> SEQ ID NO 2953
<400> SEQUENCE: 2953

000

<210> SEQ ID NO 2954
<400> SEQUENCE: 2954

000

<210> SEQ ID NO 2955
<400> SEQUENCE: 2955

000

<210> SEQ ID NO 2956

<400> SEQUENCE: 2956

000

<210> SEQ ID NO 2957

<400> SEQUENCE: 2957

000

<210> SEQ ID NO 2958
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2958
gagggattac agattaactc ccacttctcc agactcagaa                              40

<210> SEQ ID NO 2959

<400> SEQUENCE: 2959

000

<210> SEQ ID NO 2960
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2960
cgaggaggag gtgactgctg tggatggtta tgagacagac                              40

<210> SEQ ID NO 2961
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2961
ctccagtgtg gtgtgcctgc cccttccgt cattgctgtg                               40

<210> SEQ ID NO 2962

<400> SEQUENCE: 2962

000

<210> SEQ ID NO 2963

<400> SEQUENCE: 2963

000

<210> SEQ ID NO 2964

<400> SEQUENCE: 2964

000

<210> SEQ ID NO 2965

<400> SEQUENCE: 2965

000

<210> SEQ ID NO 2966
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2966
ctggtcagtt gggagtctga gatgaagcac tgtagctcag          40

<210> SEQ ID NO 2967
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2967
aaagaaaaga aagtgcttcc tttcagaggg ttactctttg          40

<210> SEQ ID NO 2968

<400> SEQUENCE: 2968

000

<210> SEQ ID NO 2969

<400> SEQUENCE: 2969

000

<210> SEQ ID NO 2970

<400> SEQUENCE: 2970

000

<210> SEQ ID NO 2971

<400> SEQUENCE: 2971

000

<210> SEQ ID NO 2972

<400> SEQUENCE: 2972

000

<210> SEQ ID NO 2973

<400> SEQUENCE: 2973

000

-continued

<210> SEQ ID NO 2974

<400> SEQUENCE: 2974

000

<210> SEQ ID NO 2975

<400> SEQUENCE: 2975

000

<210> SEQ ID NO 2976

<400> SEQUENCE: 2976

000

<210> SEQ ID NO 2977

<400> SEQUENCE: 2977

000

<210> SEQ ID NO 2978

<400> SEQUENCE: 2978

000

<210> SEQ ID NO 2979

<400> SEQUENCE: 2979

000

<210> SEQ ID NO 2980

<400> SEQUENCE: 2980

000

<210> SEQ ID NO 2981

<400> SEQUENCE: 2981

000

<210> SEQ ID NO 2982

<400> SEQUENCE: 2982

000

<210> SEQ ID NO 2983

<400> SEQUENCE: 2983

000

<210> SEQ ID NO 2984

<400> SEQUENCE: 2984

000

<210> SEQ ID NO 2985

<400> SEQUENCE: 2985

<210> SEQ ID NO 2986

<400> SEQUENCE: 2986

000

<210> SEQ ID NO 2987

<400> SEQUENCE: 2987

000

<210> SEQ ID NO 2988

<400> SEQUENCE: 2988

000

<210> SEQ ID NO 2989
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 2989
gtgaacatca cagcaagtct gtgctgcttc ccgtccctac        40

<210> SEQ ID NO 2990

<400> SEQUENCE: 2990

000

<210> SEQ ID NO 2991

<400> SEQUENCE: 2991

000

<210> SEQ ID NO 2992

<400> SEQUENCE: 2992

000

<210> SEQ ID NO 2993

<400> SEQUENCE: 2993

000

<210> SEQ ID NO 2994

<400> SEQUENCE: 2994

000

<210> SEQ ID NO 2995

<400> SEQUENCE: 2995

000

```
<210> SEQ ID NO 2996

<400> SEQUENCE: 2996

000

<210> SEQ ID NO 2997

<400> SEQUENCE: 2997

000

<210> SEQ ID NO 2998

<400> SEQUENCE: 2998

000

<210> SEQ ID NO 2999

<400> SEQUENCE: 2999

000

<210> SEQ ID NO 3000

<400> SEQUENCE: 3000

000

<210> SEQ ID NO 3001

<400> SEQUENCE: 3001

000

<210> SEQ ID NO 3002

<400> SEQUENCE: 3002

000

<210> SEQ ID NO 3003

<400> SEQUENCE: 3003

000

<210> SEQ ID NO 3004

<400> SEQUENCE: 3004

000

<210> SEQ ID NO 3005

<400> SEQUENCE: 3005

000

<210> SEQ ID NO 3006

<400> SEQUENCE: 3006

000

<210> SEQ ID NO 3007

<400> SEQUENCE: 3007
```

```
<210> SEQ ID NO 3008
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3008
ggtgcactct aaattcctgt ccctgcggaa ggctgactaa                         40

<210> SEQ ID NO 3009

<400> SEQUENCE: 3009

000

<210> SEQ ID NO 3010

<400> SEQUENCE: 3010

000

<210> SEQ ID NO 3011

<400> SEQUENCE: 3011

000

<210> SEQ ID NO 3012

<400> SEQUENCE: 3012

000

<210> SEQ ID NO 3013

<400> SEQUENCE: 3013

000

<210> SEQ ID NO 3014

<400> SEQUENCE: 3014

000

<210> SEQ ID NO 3015

<400> SEQUENCE: 3015

000

<210> SEQ ID NO 3016

<400> SEQUENCE: 3016

000

<210> SEQ ID NO 3017

<400> SEQUENCE: 3017

000
```

<210> SEQ ID NO 3018

<400> SEQUENCE: 3018

000

<210> SEQ ID NO 3019

<400> SEQUENCE: 3019

000

<210> SEQ ID NO 3020
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3020
cacaggattt caggggagaa acggtggatt ttcacaagag                40

<210> SEQ ID NO 3021
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3021
gagatgaggt agctgccagg tgccatgggg gtataggtga                40

<210> SEQ ID NO 3022

<400> SEQUENCE: 3022

000

<210> SEQ ID NO 3023

<400> SEQUENCE: 3023

000

<210> SEQ ID NO 3024
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3024
gggatactca aaatgggggc gctttccttt ttgtctgtac                40

<210> SEQ ID NO 3025
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3025
gaaaaactta agattccctc tcggccctca tttttagctg                40

<210> SEQ ID NO 3026

<400> SEQUENCE: 3026

000

<210> SEQ ID NO 3027

<400> SEQUENCE: 3027

000

<210> SEQ ID NO 3028
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3028
gctcactggg caggagccct aatcggattc gacagctgag                            40

<210> SEQ ID NO 3029
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3029
cagatatttt ctcaggcaat cctcagccac agccttcttg                            40

<210> SEQ ID NO 3030
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3030
cggactaaca ctccgcgggt gtttccatgg agaccgaggc                            40

<210> SEQ ID NO 3031

<400> SEQUENCE: 3031

000

<210> SEQ ID NO 3032

<400> SEQUENCE: 3032

000

<210> SEQ ID NO 3033

<400> SEQUENCE: 3033

000

<210> SEQ ID NO 3034

<400> SEQUENCE: 3034

000

<210> SEQ ID NO 3035
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 3035
gttgtagcat gtggttgtat taatgaacgt tacaggagag                            40

<210> SEQ ID NO 3036

<400> SEQUENCE: 3036

000

<210> SEQ ID NO 3037
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 3037
tattatacat catttcccat caatcgacga actaaagcct                            40

<210> SEQ ID NO 3038

<400> SEQUENCE: 3038

000

<210> SEQ ID NO 3039

<400> SEQUENCE: 3039

000

<210> SEQ ID NO 3040

<400> SEQUENCE: 3040

000

<210> SEQ ID NO 3041

<400> SEQUENCE: 3041

000

<210> SEQ ID NO 3042

<400> SEQUENCE: 3042

000

<210> SEQ ID NO 3043

<400> SEQUENCE: 3043

000

<210> SEQ ID NO 3044

<400> SEQUENCE: 3044

-continued

000

<210> SEQ ID NO 3045
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3045
tgtacagcag gcacagacag gcagtcacat gacaacccag                                40

<210> SEQ ID NO 3046

<400> SEQUENCE: 3046

000

<210> SEQ ID NO 3047

<400> SEQUENCE: 3047

000

<210> SEQ ID NO 3048

<400> SEQUENCE: 3048

000

<210> SEQ ID NO 3049
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3049
aaggaaaatc aaacccacaa tgctgaacac aacaatgacc                                40

<210> SEQ ID NO 3050

<400> SEQUENCE: 3050

000

<210> SEQ ID NO 3051

<400> SEQUENCE: 3051

000

<210> SEQ ID NO 3052

<400> SEQUENCE: 3052

000

<210> SEQ ID NO 3053

<400> SEQUENCE: 3053

000

<210> SEQ ID NO 3054

<400> SEQUENCE: 3054

000

<210> SEQ ID NO 3055

<400> SEQUENCE: 3055

000

<210> SEQ ID NO 3056

<400> SEQUENCE: 3056

000

<210> SEQ ID NO 3057

<400> SEQUENCE: 3057

000

<210> SEQ ID NO 3058

<400> SEQUENCE: 3058

000

<210> SEQ ID NO 3059

<400> SEQUENCE: 3059

000

<210> SEQ ID NO 3060

<400> SEQUENCE: 3060

000

<210> SEQ ID NO 3061

<400> SEQUENCE: 3061

000

<210> SEQ ID NO 3062

<400> SEQUENCE: 3062

000

<210> SEQ ID NO 3063

<400> SEQUENCE: 3063

000

<210> SEQ ID NO 3064

<400> SEQUENCE: 3064

000

<210> SEQ ID NO 3065
<211> LENGTH: 40
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 3065 accagactt tcctagtccc tgagaccta acttgtgagg                                40

<210> SEQ ID NO 3066

<400> SEQUENCE: 3066

000

<210> SEQ ID NO 3067
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3067
tccctgagac cctaacttgt gatgtttacc gtttaaatcc                              40

<210> SEQ ID NO 3068

<400> SEQUENCE: 3068

000

<210> SEQ ID NO 3069

<400> SEQUENCE: 3069

000

<210> SEQ ID NO 3070

<400> SEQUENCE: 3070

000

<210> SEQ ID NO 3071

<400> SEQUENCE: 3071

000

<210> SEQ ID NO 3072

<400> SEQUENCE: 3072

000

<210> SEQ ID NO 3073

<400> SEQUENCE: 3073

000

<210> SEQ ID NO 3074

<400> SEQUENCE: 3074

000

<210> SEQ ID NO 3075

<400> SEQUENCE: 3075

000

<210> SEQ ID NO 3076
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3076
gccttcgccg cacacaagct cgtgtctgtg ggtccgtgtc        40

<210> SEQ ID NO 3077
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3077
cgagctctgg ctccgtgtct tcactcccgt gcttgtccga        40

<210> SEQ ID NO 3078

<400> SEQUENCE: 3078

000

<210> SEQ ID NO 3079

<400> SEQUENCE: 3079

000

<210> SEQ ID NO 3080

<400> SEQUENCE: 3080

000

<210> SEQ ID NO 3081

<400> SEQUENCE: 3081

000

<210> SEQ ID NO 3082

<400> SEQUENCE: 3082

000

<210> SEQ ID NO 3083

<400> SEQUENCE: 3083

000

<210> SEQ ID NO 3084

<400> SEQUENCE: 3084

000

<210> SEQ ID NO 3085

-continued

<400> SEQUENCE: 3085

000

<210> SEQ ID NO 3086

<400> SEQUENCE: 3086

000

<210> SEQ ID NO 3087

<400> SEQUENCE: 3087

000

<210> SEQ ID NO 3088

<400> SEQUENCE: 3088

000

<210> SEQ ID NO 3089

<400> SEQUENCE: 3089

000

<210> SEQ ID NO 3090

<400> SEQUENCE: 3090

000

<210> SEQ ID NO 3091

<400> SEQUENCE: 3091

000

<210> SEQ ID NO 3092

<400> SEQUENCE: 3092

000

<210> SEQ ID NO 3093

<400> SEQUENCE: 3093

000

<210> SEQ ID NO 3094

<400> SEQUENCE: 3094

000

<210> SEQ ID NO 3095

<400> SEQUENCE: 3095

000

<210> SEQ ID NO 3096

<400> SEQUENCE: 3096

```
<210> SEQ ID NO 3097
<400> SEQUENCE: 3097

000

<210> SEQ ID NO 3098
<400> SEQUENCE: 3098

000

<210> SEQ ID NO 3099
<400> SEQUENCE: 3099

000

<210> SEQ ID NO 3100
<400> SEQUENCE: 3100

000

<210> SEQ ID NO 3101
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3101
caaatggcgc atcaatgact atcgctctta caaagctctt                              40

<210> SEQ ID NO 3102
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3102
cagaacatgc aatgcaacta caatgcacca cagctgcccg                              40

<210> SEQ ID NO 3103
<400> SEQUENCE: 3103

000

<210> SEQ ID NO 3104
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3104
ttatcataaa ataatcacag ccctcaggtg ctgtgaggca                              40

<210> SEQ ID NO 3105
<400> SEQUENCE: 3105
```

000

<210> SEQ ID NO 3106

<400> SEQUENCE: 3106

000

<210> SEQ ID NO 3107

<400> SEQUENCE: 3107

000

<210> SEQ ID NO 3108
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3108
gctgacgtca cgggcagaat tgtcccattt agggatcccg                          40

<210> SEQ ID NO 3109
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3109
ctcaggccat taacctcagt tggtcactaa tccctaggaa                          40

<210> SEQ ID NO 3110
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3110
gaatcttgcc cttggatgca tactgtaatt tccattaaag                          40

<210> SEQ ID NO 3111

<400> SEQUENCE: 3111

000

<210> SEQ ID NO 3112

<400> SEQUENCE: 3112

000

<210> SEQ ID NO 3113
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3113
ctgatagtac acggggccaa aatagatgta tgcttctaag                          40

<210> SEQ ID NO 3114
<400> SEQUENCE: 3114

000

<210> SEQ ID NO 3115
<400> SEQUENCE: 3115

000

<210> SEQ ID NO 3116
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3116
tgaggccctc taggccgtga attaatgtgt cataactcac                          40

<210> SEQ ID NO 3117
<400> SEQUENCE: 3117

000

<210> SEQ ID NO 3118
<400> SEQUENCE: 3118

000

<210> SEQ ID NO 3119
<400> SEQUENCE: 3119

000

<210> SEQ ID NO 3120
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3120
ttggcctcct aagccaggga ttgtgggttc gagtcccacc                          40

<210> SEQ ID NO 3121
<400> SEQUENCE: 3121

000

<210> SEQ ID NO 3122
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<210> SEQ ID NO 3122

<400> SEQUENCE: 3122
tttttgctcc cagtcagtag gaagattgtt tcaaatctgt 40

<210> SEQ ID NO 3123

<400> SEQUENCE: 3123

000

<210> SEQ ID NO 3124

<400> SEQUENCE: 3124

000

<210> SEQ ID NO 3125

<400> SEQUENCE: 3125

000

<210> SEQ ID NO 3126

<400> SEQUENCE: 3126

000

<210> SEQ ID NO 3127
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3127
ctgactttca gttcctattt aaaatgtctg aattgggagc 40

<210> SEQ ID NO 3128

<400> SEQUENCE: 3128

000

<210> SEQ ID NO 3129
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3129
tagcacttag caggttgtat tatcattgtc cgtgtctatg 40

<210> SEQ ID NO 3130

<400> SEQUENCE: 3130

000

<210> SEQ ID NO 3131

<400> SEQUENCE: 3131

000

<210> SEQ ID NO 3132

<400> SEQUENCE: 3132

000

<210> SEQ ID NO 3133

<400> SEQUENCE: 3133

000

<210> SEQ ID NO 3134

<400> SEQUENCE: 3134

000

<210> SEQ ID NO 3135

<400> SEQUENCE: 3135

000

<210> SEQ ID NO 3136
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3136
ggagacactg taacaacatt ttactcctga ctgattacat                         40

<210> SEQ ID NO 3137

<400> SEQUENCE: 3137

000

<210> SEQ ID NO 3138

<400> SEQUENCE: 3138

000

<210> SEQ ID NO 3139

<400> SEQUENCE: 3139

000

<210> SEQ ID NO 3140

<400> SEQUENCE: 3140

000

<210> SEQ ID NO 3141

<400> SEQUENCE: 3141

000

<210> SEQ ID NO 3142

<400> SEQUENCE: 3142

```
<210> SEQ ID NO 3143
<400> SEQUENCE: 3143

000

<210> SEQ ID NO 3144
<400> SEQUENCE: 3144

000

<210> SEQ ID NO 3145
<400> SEQUENCE: 3145

000

<210> SEQ ID NO 3146
<400> SEQUENCE: 3146

000

<210> SEQ ID NO 3147
<400> SEQUENCE: 3147

000

<210> SEQ ID NO 3148
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3148
aaaaccaaat ggctggctac tcatgtactg ttgaatgtct                            40

<210> SEQ ID NO 3149
<400> SEQUENCE: 3149

000

<210> SEQ ID NO 3150
<400> SEQUENCE: 3150

000

<210> SEQ ID NO 3151
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3151
ctgtagatac tttctccctg agcccctcct gccccctgc                             40

<210> SEQ ID NO 3152
```

```
<400> SEQUENCE: 3152

000

<210> SEQ ID NO 3153
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3153
gtttatttga atgtgtgatg gggaggtcat caaaatgaac                              40

<210> SEQ ID NO 3154
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3154
ctccagttgg gggtggggag ttgggaacag tgtgaatggg                              40

<210> SEQ ID NO 3155

<400> SEQUENCE: 3155

000

<210> SEQ ID NO 3156

<400> SEQUENCE: 3156

000

<210> SEQ ID NO 3157

<400> SEQUENCE: 3157

000

<210> SEQ ID NO 3158

<400> SEQUENCE: 3158

000

<210> SEQ ID NO 3159

<400> SEQUENCE: 3159

000

<210> SEQ ID NO 3160

<400> SEQUENCE: 3160

000

<210> SEQ ID NO 3161

<400> SEQUENCE: 3161

000
```

```
<210> SEQ ID NO 3162
<400> SEQUENCE: 3162
000

<210> SEQ ID NO 3163
<400> SEQUENCE: 3163
000

<210> SEQ ID NO 3164
<400> SEQUENCE: 3164
000

<210> SEQ ID NO 3165
<400> SEQUENCE: 3165
000

<210> SEQ ID NO 3166
<400> SEQUENCE: 3166
000

<210> SEQ ID NO 3167
<400> SEQUENCE: 3167
000

<210> SEQ ID NO 3168
<400> SEQUENCE: 3168
000

<210> SEQ ID NO 3169
<400> SEQUENCE: 3169
000

<210> SEQ ID NO 3170
<400> SEQUENCE: 3170
000

<210> SEQ ID NO 3171
<400> SEQUENCE: 3171
000

<210> SEQ ID NO 3172
<400> SEQUENCE: 3172
000

<210> SEQ ID NO 3173
<400> SEQUENCE: 3173
```

000

<210> SEQ ID NO 3174

<400> SEQUENCE: 3174

000

<210> SEQ ID NO 3175

<400> SEQUENCE: 3175

000

<210> SEQ ID NO 3176

<400> SEQUENCE: 3176

000

<210> SEQ ID NO 3177

<400> SEQUENCE: 3177

000

<210> SEQ ID NO 3178

<400> SEQUENCE: 3178

000

<210> SEQ ID NO 3179

<400> SEQUENCE: 3179

000

<210> SEQ ID NO 3180

<400> SEQUENCE: 3180

000

<210> SEQ ID NO 3181

<400> SEQUENCE: 3181

000

<210> SEQ ID NO 3182

<400> SEQUENCE: 3182

000

<210> SEQ ID NO 3183

<400> SEQUENCE: 3183

000

<210> SEQ ID NO 3184

<400> SEQUENCE: 3184

000

<210> SEQ ID NO 3185

<400> SEQUENCE: 3185

000

<210> SEQ ID NO 3186

<400> SEQUENCE: 3186

000

<210> SEQ ID NO 3187

<400> SEQUENCE: 3187

000

<210> SEQ ID NO 3188

<400> SEQUENCE: 3188

000

<210> SEQ ID NO 3189

<400> SEQUENCE: 3189

000

<210> SEQ ID NO 3190

<400> SEQUENCE: 3190

000

<210> SEQ ID NO 3191

<400> SEQUENCE: 3191

000

<210> SEQ ID NO 3192

<400> SEQUENCE: 3192

000

<210> SEQ ID NO 3193

<400> SEQUENCE: 3193

000

<210> SEQ ID NO 3194

<400> SEQUENCE: 3194

000

<210> SEQ ID NO 3195

<400> SEQUENCE: 3195

000

<210> SEQ ID NO 3196

-continued

<400> SEQUENCE: 3196

000

<210> SEQ ID NO 3197

<400> SEQUENCE: 3197

000

<210> SEQ ID NO 3198

<400> SEQUENCE: 3198

000

<210> SEQ ID NO 3199

<400> SEQUENCE: 3199

000

<210> SEQ ID NO 3200

<400> SEQUENCE: 3200

000

<210> SEQ ID NO 3201

<400> SEQUENCE: 3201

000

<210> SEQ ID NO 3202

<400> SEQUENCE: 3202

000

<210> SEQ ID NO 3203

<400> SEQUENCE: 3203

000

<210> SEQ ID NO 3204

<400> SEQUENCE: 3204

000

<210> SEQ ID NO 3205

<400> SEQUENCE: 3205

000

<210> SEQ ID NO 3206

<400> SEQUENCE: 3206

000

<210> SEQ ID NO 3207

<400> SEQUENCE: 3207

000

```
<210> SEQ ID NO 3208
<400> SEQUENCE: 3208
000

<210> SEQ ID NO 3209
<400> SEQUENCE: 3209
000

<210> SEQ ID NO 3210
<400> SEQUENCE: 3210
000

<210> SEQ ID NO 3211
<400> SEQUENCE: 3211
000

<210> SEQ ID NO 3212
<400> SEQUENCE: 3212
000

<210> SEQ ID NO 3213
<400> SEQUENCE: 3213
000

<210> SEQ ID NO 3214
<400> SEQUENCE: 3214
000

<210> SEQ ID NO 3215
<400> SEQUENCE: 3215
000

<210> SEQ ID NO 3216
<400> SEQUENCE: 3216
000

<210> SEQ ID NO 3217
<400> SEQUENCE: 3217
000

<210> SEQ ID NO 3218
<400> SEQUENCE: 3218
000

<210> SEQ ID NO 3219
```

<400> SEQUENCE: 3219

000

<210> SEQ ID NO 3220

<400> SEQUENCE: 3220

000

<210> SEQ ID NO 3221

<400> SEQUENCE: 3221

000

<210> SEQ ID NO 3222

<400> SEQUENCE: 3222

000

<210> SEQ ID NO 3223

<400> SEQUENCE: 3223

000

<210> SEQ ID NO 3224

<400> SEQUENCE: 3224

000

<210> SEQ ID NO 3225

<400> SEQUENCE: 3225

000

<210> SEQ ID NO 3226

<400> SEQUENCE: 3226

000

<210> SEQ ID NO 3227

<400> SEQUENCE: 3227

000

<210> SEQ ID NO 3228

<400> SEQUENCE: 3228

000

<210> SEQ ID NO 3229

<400> SEQUENCE: 3229

000

<210> SEQ ID NO 3230

<400> SEQUENCE: 3230

000

<210> SEQ ID NO 3231
<400> SEQUENCE: 3231
000

<210> SEQ ID NO 3232
<400> SEQUENCE: 3232
000

<210> SEQ ID NO 3233
<400> SEQUENCE: 3233
000

<210> SEQ ID NO 3234
<400> SEQUENCE: 3234
000

<210> SEQ ID NO 3235
<400> SEQUENCE: 3235
000

<210> SEQ ID NO 3236
<400> SEQUENCE: 3236
000

<210> SEQ ID NO 3237
<400> SEQUENCE: 3237
000

<210> SEQ ID NO 3238
<400> SEQUENCE: 3238
000

<210> SEQ ID NO 3239
<400> SEQUENCE: 3239
000

<210> SEQ ID NO 3240
<400> SEQUENCE: 3240
000

<210> SEQ ID NO 3241
<400> SEQUENCE: 3241
000

-continued

<210> SEQ ID NO 3242

<400> SEQUENCE: 3242

000

<210> SEQ ID NO 3243

<400> SEQUENCE: 3243

000

<210> SEQ ID NO 3244

<400> SEQUENCE: 3244

000

<210> SEQ ID NO 3245

<400> SEQUENCE: 3245

000

<210> SEQ ID NO 3246

<400> SEQUENCE: 3246

000

<210> SEQ ID NO 3247

<400> SEQUENCE: 3247

000

<210> SEQ ID NO 3248

<400> SEQUENCE: 3248

000

<210> SEQ ID NO 3249

<400> SEQUENCE: 3249

000

<210> SEQ ID NO 3250

<400> SEQUENCE: 3250

000

<210> SEQ ID NO 3251

<400> SEQUENCE: 3251

000

<210> SEQ ID NO 3252

<400> SEQUENCE: 3252

000

<210> SEQ ID NO 3253

<400> SEQUENCE: 3253

000

<210> SEQ ID NO 3254
<400> SEQUENCE: 3254
000

<210> SEQ ID NO 3255
<400> SEQUENCE: 3255
000

<210> SEQ ID NO 3256
<400> SEQUENCE: 3256
000

<210> SEQ ID NO 3257
<400> SEQUENCE: 3257
000

<210> SEQ ID NO 3258
<400> SEQUENCE: 3258
000

<210> SEQ ID NO 3259
<400> SEQUENCE: 3259
000

<210> SEQ ID NO 3260
<400> SEQUENCE: 3260
000

<210> SEQ ID NO 3261
<400> SEQUENCE: 3261
000

<210> SEQ ID NO 3262
<400> SEQUENCE: 3262
000

<210> SEQ ID NO 3263
<400> SEQUENCE: 3263
000

<210> SEQ ID NO 3264
<400> SEQUENCE: 3264
000

<210> SEQ ID NO 3265

<400> SEQUENCE: 3265

000

<210> SEQ ID NO 3266

<400> SEQUENCE: 3266

000

<210> SEQ ID NO 3267

<400> SEQUENCE: 3267

000

<210> SEQ ID NO 3268

<400> SEQUENCE: 3268

000

<210> SEQ ID NO 3269

<400> SEQUENCE: 3269

000

<210> SEQ ID NO 3270

<400> SEQUENCE: 3270

000

<210> SEQ ID NO 3271

<400> SEQUENCE: 3271

000

<210> SEQ ID NO 3272

<400> SEQUENCE: 3272

000

<210> SEQ ID NO 3273

<400> SEQUENCE: 3273

000

<210> SEQ ID NO 3274

<400> SEQUENCE: 3274

000

<210> SEQ ID NO 3275
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3275
ggatttaatg agaaatattg agcccttttgg ttcaggaact          40

<210> SEQ ID NO 3276
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3276
gctctgttgt gataaattgg ctgtgtgctt catttggact          40

<210> SEQ ID NO 3277

<400> SEQUENCE: 3277

000

<210> SEQ ID NO 3278

<400> SEQUENCE: 3278

000

<210> SEQ ID NO 3279

<400> SEQUENCE: 3279

000

<210> SEQ ID NO 3280

<400> SEQUENCE: 3280

000

<210> SEQ ID NO 3281

<400> SEQUENCE: 3281

000

<210> SEQ ID NO 3282

<400> SEQUENCE: 3282

000

<210> SEQ ID NO 3283
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3283
gaaaagaaca tgcatccttt cagagggtta ctctttgaga          40

<210> SEQ ID NO 3284

<400> SEQUENCE: 3284

000

<210> SEQ ID NO 3285

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3285
gagcatcagt atgtagtgca atcagtcagg agaaaatgag                              40

<210> SEQ ID NO 3286
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3286
cctcttcaat ggatttggtc cccttcaacc agctgtagct                              40

<210> SEQ ID NO 3287

<400> SEQUENCE: 3287

000

<210> SEQ ID NO 3288

<400> SEQUENCE: 3288

000

<210> SEQ ID NO 3289

<400> SEQUENCE: 3289

000

<210> SEQ ID NO 3290

<400> SEQUENCE: 3290

000

<210> SEQ ID NO 3291

<400> SEQUENCE: 3291

000

<210> SEQ ID NO 3292

<400> SEQUENCE: 3292

000

<210> SEQ ID NO 3293

<400> SEQUENCE: 3293

000

<210> SEQ ID NO 3294

<400> SEQUENCE: 3294

000
```

-continued

<210> SEQ ID NO 3295
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3295
aaaatcagct ttaattaatt tgagtgccag ctctgtgtat                           40

<210> SEQ ID NO 3296

<400> SEQUENCE: 3296

000

<210> SEQ ID NO 3297

<400> SEQUENCE: 3297

000

<210> SEQ ID NO 3298

<400> SEQUENCE: 3298

000

<210> SEQ ID NO 3299

<400> SEQUENCE: 3299

000

<210> SEQ ID NO 3300

<400> SEQUENCE: 3300

000

<210> SEQ ID NO 3301

<400> SEQUENCE: 3301

000

<210> SEQ ID NO 3302

<400> SEQUENCE: 3302

000

<210> SEQ ID NO 3303

<400> SEQUENCE: 3303

000

<210> SEQ ID NO 3304
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3304
gatctggcct aaagaggtat agggcatggg aagatggagc      40

<210> SEQ ID NO 3305
<400> SEQUENCE: 3305
000

<210> SEQ ID NO 3306
<400> SEQUENCE: 3306
000

<210> SEQ ID NO 3307
<400> SEQUENCE: 3307
000

<210> SEQ ID NO 3308
<400> SEQUENCE: 3308
000

<210> SEQ ID NO 3309
<400> SEQUENCE: 3309
000

<210> SEQ ID NO 3310
<400> SEQUENCE: 3310
000

<210> SEQ ID NO 3311
<400> SEQUENCE: 3311
000

<210> SEQ ID NO 3312
<400> SEQUENCE: 3312
000

<210> SEQ ID NO 3313
<400> SEQUENCE: 3313
000

<210> SEQ ID NO 3314
<400> SEQUENCE: 3314
000

<210> SEQ ID NO 3315
<400> SEQUENCE: 3315
000

<210> SEQ ID NO 3316
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 3316
gaagaaacat ctcaaatcat gctgacagca ttttcactat                40

<210> SEQ ID NO 3317
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 3317
ttattgcttg aatgagtttc agggtattgg ccttcataaa                40

<210> SEQ ID NO 3318

<400> SEQUENCE: 3318

000

<210> SEQ ID NO 3319

<400> SEQUENCE: 3319

000

<210> SEQ ID NO 3320

<400> SEQUENCE: 3320

000

<210> SEQ ID NO 3321

<400> SEQUENCE: 3321

000

<210> SEQ ID NO 3322

<400> SEQUENCE: 3322

000

<210> SEQ ID NO 3323

<400> SEQUENCE: 3323

000

<210> SEQ ID NO 3324

<400> SEQUENCE: 3324

000

<210> SEQ ID NO 3325

<400> SEQUENCE: 3325

000

```
<210> SEQ ID NO 3326
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3326
ttcctctcag agcatgttgt catagaagta aatgaaaagg                              40

<210> SEQ ID NO 3327
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3327
ctctcctgca cataatgagg tctgatttac tgtgatcatt                              40

<210> SEQ ID NO 3328
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3328
attaatggta attatgtgcg taaatcccca tgctctcaat                              40

<210> SEQ ID NO 3329
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3329
gagccgttta aatttagcgc tttgggctgc ctggagcgag                              40

<210> SEQ ID NO 3330
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3330 gcagggatt tgaggggtgg ttgtgtgatt tgtacagctg                               40

<210> SEQ ID NO 3331
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3331
cttctcagag ttggagatga agaaagagaa aggtggccac                              40
```

-continued

```
<210> SEQ ID NO 3332
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3332
ccttggagta aagtagcagc acataatggt ttgtggattt                           40

<210> SEQ ID NO 3333
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3333
aatgctatgg aatgtaaaga agtatgtatt tttggtaggc                           40

<210> SEQ ID NO 3334

<400> SEQUENCE: 3334

000

<210> SEQ ID NO 3335
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3335
ccagctcggg cagccgtggc catcttactg ggcagcattg                           40

<210> SEQ ID NO 3336
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3336
aatgattgta gagggcggg gcatgaagag tgccgttctg                            40
```

METHODS, KITS AND DEVICES FOR IDENTIFYING BIOMARKERS OF TREATMENT RESPONSE AND USE THEREOF TO PREDICT TREATMENT EFFICACY

FIELD OF THE INVENTION

The invention features methods, kits, and devices for identifying biomarkers of patient sensitivity to medical treatments, e.g., sensitivity to chemotherapeutic agents, and predicting treatment efficacy using the biomarkers.

BACKGROUND OF THE INVENTION

DNA microarrays have been used to measure gene expression in tumor samples from patients and to facilitate diagnosis. Gene expression can reveal the presence of cancer in a patient, its type, stage, and origin, and whether genetic mutations are involved. Gene expression may even have a role in predicting the efficacy of chemotherapy. Over recent decades, the National Cancer Institute (NCI) has tested compounds, including chemotherapy agents, for their effect in limiting the growth of 60 human cancer cell lines. The NCI has also measured gene expression in these 60 cancer cell lines using DNA microarrays. Various studies have explored the relationship between gene expression and compound effect using the NCI datasets. Critical time is often lost due to a trial and error approach to finding an effective chemotherapy for patients with cancer. In addition, cancer cells often develop resistance to a previously effective therapy. In such situations, patient outcome could be greatly improved by early detection of such resistance.

There remains a need for proven methods and devices that predict the sensitivity or resistance of cancer patients to a medical treatment.

SUMMARY OF THE INVENTION

The invention features methods, kits, and devices for determining the sensitivity or resistance of a patient, e.g., a cancer patient, to a treatment, e.g., treatment with a compound, such as a chemotherapeutic agent, or radiation. In particular, the methods, kits, and devices can be used to determine the sensitivity or resistance of a cancer patient to any medical treatment, including, e.g., treatment with a compound, drug, or radiation. The methods, kits, and devices of the invention have been used to accurately determine treatment efficacy in cancer patients (e.g., patients with lung, lymphoma, and brain cancer) and can be used to determine treatment efficacy in patients diagnosed with any cancer.

Methods, kits, and devices for detecting the level of expression of biomarkers (e.g., genes and microRNAs) that indicate sensitivity or resistance to radiation therapy or the chemotherapy agents Vincristine, Cisplatin, Azaguanine, Etoposide, Adriamycin, Aclarubicin, Mitoxantrone, Mitomycin, Paclitaxel, Gemcitabine, Taxotere, Dexamethasone, Ara-C, Methylprednisolone, Methotrexate, Bleomycin, Methyl-GAG, Carboplatin, 5-FU (5-Fluorouracil), Rituximab, PXD101, (a histone deacetylase (HDAC) inhibitor), 5-Aza-2'-deoxycytidine (Decitabine), Melphalan, IL4-PE38 fusion protein, IL13-PE38QQR fusion protein (cintredekin besudotox), Valproic acid (VPA), All-trans retinoic acid (ATRA), Cytoxan, Topotecan (Hycamtin), Suberoylanilide hydroxamic acid (SAHA, vorinostat, Zolinza), Depsipeptide (FR901229), Bortezomib, Leukeran, Fludarabine, Vinblastine, Busulfan, Dacarbazine, Oxaliplatin, Hydroxyurea, Tegafur, Daunorubicin, Bleomycin, Estramustine, Chlorambucil, Mechlorethamine, Streptozocin, Carmustine, Lomustine, Mercaptopurine, Teniposide, Dactinomycin, Tretinoin, Sunitinib, SPC2996, Ifosfamide, Tamoxifen, Floxuridine, Irinotecan, and Satraplatin are also provided. The methods, kits, and devices can be used to predict the sensitivity or resistance of a subject (e.g., a cancer patient) diagnosed with a disease condition, e.g., cancer (e.g., cancers of the breast, prostate, lung and bronchus, colon and rectum, urinary bladder, skin, kidney, pancreas, oral cavity and pharynx, ovary, thyroid, parathyroid, stomach, brain, esophagus, liver and intrahepatic bile duct, cervix larynx, heart, testis, small and large intestine, anus, anal canal and anorectum, vulva, gallbladder, pleura, bones and joints, hypopharynx, eye and orbit, nose, nasal cavity and middle ear, nasopharynx, ureter, peritoneum, omentum and mesentery, or gastrointestines, as well as any form of cancer including, e.g., chronic myeloid leukemia, acute lymphocytic leukemia, non-Hodgkin's lymphoma, melanoma, carcinoma, basal cell carcinoma, malignant mesothelioma, neuroblastoma, multiple myeloma, leukemia, retinoblastoma, acute myeloid leukemia, chronic lymphocytic leukemia, Hodgkin's lymphoma, carcinoid tumors, acute tumor, or soft tissue sarcoma) to a treatment, e.g., treatment with a compound or drug, e.g., a chemotherapeutic agent, or radiation.

In a first aspect, the invention features a method of determining sensitivity of a cancer in a patient to a treatment for cancer by measuring the level of expression of at least one gene in a cell (e.g., a cancer cell) of the patient, in which the gene is selected from the group consisting of ACTB, ACTN4, ADA, ADAM9, ADAMTS1, ADD1, AF1Q, AIF1, AKAP1, AKAP13, AKR1C1, AKT1, ALDH2, ALDOC, ALG5, ALMS1, ALOX15B, AMIGO2, AMPD2, AMPD3, ANAPC5, ANP32A, ANP32B, ANXA1, AP1G2, APOBEC3B, APRT, ARHE, ARHGAP15, ARHGAP25, ARHGDIB, ARHGEF6, ARL7, ASAH1, ASPH, ATF3, ATIC, ATP2A2, ATP2A3, ATP5D, ATP5G2, ATP6V1B2, BC008967, BCAT1, BCHE, BCL11B, BDNF, BHLHB2, BIN2, BLMH, BMI1, BNIP3, BRDT, BRRN1, BTN3A3, C11orf2, C14orf139, C15orf25, C18orf10, C1orf24, C1orf29, C1orf38, C1QR1, C22orf18, C6orf32, CACNA1G, CACNB3, CALM1, CALML4, CALU, CAP350, CASP2, CASP6, CASP7, CAST, CBLB, CCNA2, CCNB1IP1, CCND3, CCR7, CCR9, CD1A, CD1C, CD1D, CD1E, CD2, CD28, CD3D, CD3E, CD3G, CD3Z, CD44, CD47, CD59, CD6, CD63, CD8A, CD8B1, CD99, CDC10, CDC14B, CDH11, CDH2, CDKL5, CDKN2A, CDW52, CECR1, CENPB, CENTB1, CENTG2, CEP1, CG018, CHRNA3, CHS1, CIAPIN1, CKAP4, CKIP-1, CNP, COL4A1, COL5A2, COL6A1, CORO1C, CRABP1, CRK, CRY1, CSDA, CTBP1, CTSC, CTSL, CUGBP2, CUTC, CXCL1, CXCR4, CXorf9, CYFIP2, CYLD, CYR61, DATF1, DAZAP1, DBN1, DBT, DCTN1, DDX18, DDX5, DGKA, DIAPH1, DKC1, DKFZP434J154, DKFZP564C186, DKFZP564G2022, DKFZp564J157, DKFZP564K0822, DNAJC10, DNAJC7, DNAPTP6, DOCK10, DOCK2, DPAGT1, DPEP2, DPYSL3, DSIPI, DUSP1, DXS9879E, EEF1B2, EFNB2, EHD2, EIF5A, ELK3, ENO2, EPAS1, EPB41L4B, ERCC2, ERG, ERP70, EVER1, EVI2A, EVL, EXT1, EZH2, F2R, FABP5, FAD104, FAM46A, FAU, FCGR2A, FCGR2C, FER1L3, FHL1, FHOD1, FKBP1A, FKBP9, FLJ10350, FLJ10539, FLJ10774, FLJ12270, FLJ13373, FLJ20859, FLJ21159, FLJ22457, FLJ35036, FLJ46603, FLNC, FLOT1, FMNL1, FNBP1, FOLH1, FOXF2, FSCN1, FTL, FYB, FYN, G0S2, G6PD, GALIG, GALNT6, GATA2, GATA3, GFPT1, GIMAP5, GIT2, GJA1, GLRB, GLTSCR2, GLUL, GMDS, GNAQ, GNB2, GNB5, GOT2, GPR65, GPRASP1, GPSM3, GRP58, GSTM2, GTF3A, GTSE1, GZMA, GZMB, H1F0, H1FX, H2AFX, H3F3A, HA-1, HEXB, HIC, HIST1H4C, HK1, HLA-A, HLA-B, HLA-DRA, HMGA1, HMGN2, HMMR, HNRPA1, HNRPD, HNRPM, HOXA9, HRMT1L1, HSA9761, HSPA5, HSU79274, HTATSF1, ICAM1, ICAM2, IER3, IFI16, IFI44, IFITM2, IFITM3, IFRG28, IGFBP2, IGSF4, IL13RA2, IL21R, IL2RG, IL4R, IL6, IL6R, IL6ST, IL8, IMPDH2, INPP5D, INSIG1, IQGAP1, IQGAP2, IRS2, ITGA5, ITM2A, JARID2, JUNB, K-ALPHA-1, KHDRBS1, KIAA0355, KIAA0802, KIAA0877, KIAA0922, KIAA1078, KIAA1128, KIAA1393, KIFC1, LAIR1, LAMB1, LAMB3, LAT, LBR, LCK, LCP1, LCP2, LEF1, LEPRE1, LGALS1, LGALS9, LHFPL2, LNK, LOC54103, LOC55831, LOC81558, LOC94105, LONP, LOX, LOXL2, LPHN2, LPXN, LRMP, LRP12, LRRC5, LRRN3, LST1, LTB, LUM, LY9, LY96, MAGEB2, MAL, MAP1B, MAP1LC3B, MAP4K1, MAPK1, MARCKS, MAZ, MCAM, MCL1, MCM5, MCM7, MDH2, MDN1, MEF2C, MFNG, MGC17330, MGC21654, MGC2744, MGC4083, MGC8721, MGC8902, MGLL, MLPH, MPHOSPH6, MPP1, MPZL1, MRP63, MRPS2, MT1E, MT1K, MUF1, MVP, MYB, MYL9, MYO1B, NAP1L1, NAP1L2, NARF, NASP, NCOR2, NDN, NDUFAB1, NDUFS6, NFKBIA, NID2, NIPA2, NME4, NME7, NNMT, NOL5A, NOL8, NOMO2, NOTCH1, NPC1, NQO1, NR1D2, NUDC, NUP210, NUP88, NVL, NXF1, OBFC1, OCRL, OGT, OXA1L, P2RX5, P4HA1, PACAP, PAF53, PAFAH1B3, PALM2-AKAP2, PAX6, PCBP2, PCCB, PFDN5, PFN1, PFN2, PGAM1, PHEMX, PHLDA1, PIM2, PITPNC1, PLACE, PLAGL1, PLAUR, PLCB1, PLEK2, PLEKHC1, PLOD2, PLSCR1, PNAS-4, PNMA2, POLR2F, PPAP2B, PRF1, PRG1, PRIM1, PRKCH, PRKCQ, PRKD2, PRNP, PRP19, PRPF8, PRSS23, PSCDBP, PSMB9, PSMC3, PSME2, PTGER4, PTGES2, PTOV1, PTP4A3, PTPN7, PTPNS1, PTRF, PURA, PWP1, PYGL, QKI, RAB3GAP, RAB7L1, RAB9P40, RAC2, RAFTLIN, RAG2, RAP1B, RASGRP2, RBPMS, RCN1, RFC3, RFC5, RGC32, RGS3, RHOH, RIMS3, RIOK3, RIPK2, RIS1, RNASE6, RNF144, RPL10, RPL10A, RPL12, RPL13A, RPL17, RPL18, RPL36A, RPLP0, RPLP2, RPS15, RPS19, RPS2, RPS4X, RPS4Y1, RRAS, RRAS2, RRBP1, RRM2, RUNX1, RUNX3, S100A4, SART3, SATB1, SCAP1, SCARB1, SCN3A, SEC31L2, SEC61G, SELL, SELPLG, SEMA4G, SEPT10, SEPT6, SERPINA1, SERPINB1, SERPINB6, SFRS5, SFRS6, SFRS7, SH2D1A, SH3GL3, SH3TC1, SHD1, SHMT2, SIAT1, SKB1, SKP2, SLA, SLC1A4, SLC20A1, SLC25A15, SLC25A5, SLC39A14, SLC39A6, SLC43A3, SLC4A2, SLC7A11, SLC7A6, SMAD3, SMOX, SNRPA, SNRPB, SOD2, SOX4, SP140, SPANXC, SPI1, SRF, SRM, SSA2, SSBP2, SSRP1, SSSCA1, STAG3, STAT1, STAT4, STAT5A, STC1, STC2, STOML2, T3JAM, TACC1, TACC3, TAF5, TAL1, TAP1, TARP, TBCA, TCF12, TCF4, TFDP2, TFPI, TIMM17A, TIMP1, TJP1, TK2, TM4SF1, TM4SF2, TM4SF8, TM6SF1, TMEM2, TMEM22, TMSB10, TMSNB, TNFAIP3, TNFAIP8, TNFRSF10B, TNFRSF1A, TNFRSF7, TNIK, TNPO1, TOB1, TOMM20, TOX, TPK1, TPM2, TRA@, TRA1, TRAM2, TRB@, TRD@, TRIM, TRIM14, TRIM22, TRIM28, TRIP13, TRPV2, TUBGCP3, TUSC3, TXN, TXNDC5, UBASH3A, UBE2A, UBE2L6, UBE2S, UCHL1, UCK2, UCP2, UFD1L, UGDH, ULK2, UMPS, UNG, USP34, USP4, VASP, VAV1, VLDLR, VWF, WASPIP, WBSCR20A, WBSCR20C, WHSC1, WNT5A, ZAP70, ZFP36L1, ZNF32, ZNF335, ZNF593, ZNFN1A1, and ZYX; in which change in the level of expression of the gene indicates the cell is sensitive or resistant to the treatment.

In an embodiment, the method further includes determining a patient's resistance or sensitivity to radiation therapy or the chemotherapy agents Vincristine, Cisplatin, Adriamycin, Etoposide, Azaguanine, Aclarubicin, Mitoxantrone, Paclitaxel, Mitomycin, Gemcitabine, Taxotere, Dexamethasone, Methylprednisolone, Ara-C, Methotrexate, Bleomycin, Methyl-GAG, Rituximab, PXD101 (a histone deacetylase (HDAC) inhibitor), 5-Aza-2'-deoxycytidine (Decitabine), Melphalan, IL4-PE38 fusion protein, IL13-PE38QQR fusion protein (cintredekin besudotox), Valproic acid (VPA), All-trans retinoic acid (ATRA), Cytoxan, Topotecan (Hycamtin), Suberoylanilide hydroxamic acid (SAHA, vorinostat, Zolinza), Depsipeptide (FR901229), Bortezomib, Leukeran, Fludarabine, Vinblastine, Busulfan, Dacarbazine, Oxaliplatin, Hydroxyurea, Tegafur, Daunorubicin, Bleomycin, Estramustine, Chlorambucil, Mechlorethamine, Streptozocin, Carmustine, Lomustine, Mercaptopurine, Teniposide, Dactinomycin, Tretinoin, Sunitinib, SPC2996, Ifosfamide, Tamoxifen, Floxuridine, Irinotecan, and Satraplatin by measuring the level of expression of one or more of the genes known to change (e.g., to increase or decrease) in a patient sensitive to treatment with these agents (e.g., a patient is determined to be sensitive, or likely to be sensitive, to the indicated treatment if the level of expression of one or more of the gene(s) increases or decreases relative to the level of expression of the gene(s) in a control sample (e.g., a cell or tissue) in which increased or decreased expression of the gene(s) indicates sensitivity to the treatment, and vice versa). Alternatively, a patient's resistance or sensitivity to radiation therapy or any of the chemotherapy agents listed above can be determined by measuring the level of expression of at least one microRNA in a cell (e.g., a cancer cell) known to change (e.g., the level of expression is increased or decreased) in a patient sensitive to a treatment with these agents, in which the microRNA is selected from the group consisting of ath-MIR180aNo2, Hcd102 left, Hcd111 left, Hcd115 left, Hcd120 left, Hcd142 right, Hcd145 left, Hcd148_HPR225 left, Hcd181 left, Hcd181 right, Hcd210_HPR205 right, Hcd213_HPR182 left, Hcd230 left, Hcd243 right, Hcd246 right, Hcd248 right, Hcd249 right, Hcd250 left, Hcd255 left, Hcd257 left, Hcd257 right, Hcd263 left, Hcd266 left, Hcd270 right, Hcd279 left, Hcd279 right, Hcd28_HPR39left, Hcd28_HPR39 right, Hcd282PO right, Hcd289 left, Hcd294 left, Hcd318 right, Hcd323 left, Hcd330 right, Hcd338 left, Hcd340 left, Hcd350 right, Hcd355_HPR190 left, Hcd361 right, Hcd366 left, Hcd373 right, Hcd383 left, Hcd383 right, Hcd384 left, Hcd397 left, Hcd404 left, Hcd412 left, Hcd413 right, Hcd415 right, Hcd417 right, Hcd421 right, Hcd425 left, Hcd438 right, Hcd434 right, Hcd438 left, Hcd440_HPR257 right, Hcd444 right, Hcd447 right, Hcd448 left, Hcd498 right, Hcd503 left, Hcd511 right, Hcd512 left, Hcd514 right, Hcd517 left, Hcd517 right, Hcd530 right, Hcd536_HPR104 right, Hcd542 left, Hcd544 left, Hcd547 left, Hcd559 right, Hcd562 right, Hcd569 right, Hcd570 right, Hcd578 right, Hcd581 right, Hcd586 left, Hcd586 right, Hcd587 right, Hcd605 left, Hcd605 left, Hcd605 right, Hcd608 right, Hcd627 left, Hcd631 left, Hcd631 right, Hcd634 left, Hcd642 right, Hcd649 right, Hcd654 left, Hcd658 right, Hcd669 right, Hcd674 left, Hcd678 right, Hcd683 left, Hcd684 right, Hcd689 right, Hcd690 right, Hcd691 right, Hcd693 right, Hcd697 right, Hcd704 left, Hcd704 left, Hcd712 right, Hcd716 right, Hcd731 left, Hcd738 left, Hcd739 right, Hcd739 right, Hcd749 right, Hcd753 left, Hcd754 left, Hcd755 left, Hcd760 left, Hcd763 right, Hcd768 left, Hcd768 right, Hcd770 left, Hcd773 left, Hcd777 left, Hcd778 right, Hcd781 left, Hcd781 right, Hcd782 left, Hcd783 left, Hcd788 left, Hcd794 right, Hcd796 left, Hcd799 left, Hcd807 right, Hcd812 left, Hcd817 left, Hcd817 right, Hcd829 right, Hcd852 right, Hcd861 right, Hcd863PO right, Hcd866 right, Hcd869 left, Hcd873 left, Hcd886 right, Hcd889 right, Hcd891 right, Hcd892 left, Hcd913 right, Hcd923 left, Hcd923 right, Hcd938 left, Hcd938 right, Hcd939 right, Hcd946 left, Hcd948 right, Hcd960 left, Hcd965 left, Hcd970 left, Hcd975 left, Hcd976 right, Hcd99 right, HPR100 right, HPR129 left, HPR154 left, HPR159 left, HPR163 left, HPR169 right, HPR172 right, HPR181 left, HPR187 left, HPR199 right, HPR206 left, HPR213 right, HPR214 right, HPR220 left, HPR220 right, HPR227 right, HPR232 right, HPR233 right, HPR244 right, HPR262 left, HPR264 right, HPR266 right, HPR271 right, HPR76 right, hsa_mir_490_Hcd20 right, HSHELA01, HSTRNL, HUMTRAB, HUMTRF, HUMTRN, HUMTRS, HUMTRV1A, let-7f-2-prec2, mir-001b-1-prec1, mir-001b-2-prec, mir-007-1-prec, mir-007-2-precNo2, mir-010a-precNo2, mir-015b-precNo2, mir-016a-chr13, mir-016b-chr3, mir-017-precNo1, mir-017-precNo2, mir-018-prec, mir-019a-prec, mir-019b-1-prec, mir-019b-2-prec, mir-020-prec, mir-022-prec, mir-023a-prec, mir-023b-prec, mir-024-2-prec, mir-025-prec, mir-027b-prec, mir-029c-prec, mir-032-precNo2, mir-033b-prec, mir-033-prec, mir-034-precNo1, mir-034-precNo2, mir-092-prec-13=092-1No2, mir-092-prec-X=092-2, mir-093-prec-7.1=093-1, mir-095-prec-4, mir-096-prec-7No1, mir-096-prec-7No2, mir-098-prec-X, mir-099b-prec-19No1, mir-100-1/2-prec, mir-100No1, mir-101-prec-9, mir-102-prec-1, mir-103-2-prec, mir-103-prec-5=103-1, mir-106aNo1, mir-106-prec-X, mir-107No1, mir-107-prec-10, mir-122a-prec, mir-123-precNo1, mir-123-precNo2, mir-124a-1-prec1, mir-124a-2-prec, mir-124a-3-prec, mir-125b-1, mir-125b-2-precNo2, mir-127-prec, mir-128b-precNo1, mir-128b-precNo2, mir-133a-1, mir-135-2-prec, mir-136-precNo2, mir-138-1-prec, mir-140No2, mir-142-prec, mir-143-prec, mir-144-precNo2, mir-145-prec, mir-146bNo1, mir-146-prec, mir-147-prec, mir-148aNo1, mir-148-prec, mir-149-prec, mir-150-prec, mir-153-1-prec1, mir-154-prec1No1, mir-155-prec, mir-15aNo1, mir-16-1No1, mir-16-2No1, mir-181a-precNo1, mir-181b-1No1, mir-181b-2No1, mir-181b-precNo1, mir-181b-precNo2, mir-181c-precNo1, mir-181dNo1, mir-188-prec, mir-18bNo2, mir-191-prec, mir-192No2, mir-193bNo2, mir-194-2No1, mir-195-prec, mir-196-2-precNo2, mir-197-prec, mir-198-prec, mir-199a-1-prec, mir-199a-2-prec, mir-199b-precNo1, mir-200a-prec, mir-200bNo1, mir-200bNo2, mir-202*, mir-202-prec, mir-204-precNo2, mir-205-prec, mir-208-prec, mir-20bNo1, mir-212-precNo1, mir-212-precNo2, mir-213-precNo1, mir-214-prec, mir-215-precNo2, mir-216-precNo1, mir-219-2No1, mir-219-prec, mir-223-prec, mir-29b-1No1, mir-29b-2=102prec7.1=7.2, mir-321No1, mir-321No2, mir-324No1, mir-324No2, mir-328No1, mir-342No1, mir-361No1, mir-367No1, mir-370No1, mir-371No1, miR-373*No1, mir-375, mir-376aNo1, mir-379No1, mir-380-5p, mir-382, mir-384, mir-409-3p, mir-423No1, mir-424No2, mir-429No1, mir-429No2, mir-4323p, mir-4325p, mir-449No1, mir-450-1, mir-450-2No1, mir-483No1, mir-484, mir-487No1, mir-495No1, mir-499No2, mir-501No2, mir-503No1, mir-509No1, mir-514-1No2, mir-515-15p, mir-515-23p, mir-516-33p, mir-516-43p, mir-518e/526c, mir-519a-1/52, mir-519a-2No2, mir-519b, mir-519c/52, mir-520c/52, mir-526a-2No1, mir-526a-2No2, MPR103 right, MPR121 left, MPR121 left, MPR130 left, MPR130 right, MPR133 right, MPR141 left, MPR151 left, MPR156 left, MPR162 left, MPR174 left, MPR174 right, MPR185 right, MPR197 right, MPR203 left, MPR207 right, MPR215 left, MPR216 left, MPR224 left, MPR224 right, MPR228 left, MPR234 right, MPR237 left, MPR243 left, MPR244 right, MPR249 left, MPR254 right, MPR74 left, MPR88 right, and MPR95 left.

In an embodiment, the method includes determining the expression of two of the listed genes or microRNAs, more preferably three, four, five, six, seven, eight, nine, or ten of the listed genes, and most preferably twenty, thirty, forty, fifty, sixty, seventy, eighty, ninety, or one hundred or more of the listed genes. In another embodiment, the change in the level of gene or microRNA expression (e.g., an increase or decrease) is determined relative to the level of gene or microRNA expression in a cell or tissue known to be sensitive to the treatment, such that a similar level of gene or microRNA expression exhibited by a cell or tissue of the patient indicates the patient is sensitive to the treatment. In another embodiment, the change in the level of gene or microRNA expression (e.g., an increase or decrease) is determined relative to the level of gene or microRNA expression in a cell or tissue known to be resistant to the treatment, such that a similar level of gene or microRNA expression exhibited by a cell or tissue of the patient indicates the patient is resistant to the treatment.

In a second aspect, the invention features a method of determining sensitivity of a cancer in a patient to a treatment for cancer by measuring the level of expression of at least one microRNA in a cell (e.g., a cancer cell) of the patient, in which the microRNA is selected from the group set forth in the first aspect of the invention. In an embodiment, the method further includes determining a patient's resistance or sensitivity to radiation therapy or any of the chemotherapy agents set forth in the first aspect of the invention by measuring the level of expression of one or more of the microRNAs known to change (e.g., to increase or decrease) in a patient sensitive to treatment with these agents (e.g., a patient is determined to be sensitive, or likely to be sensitive, to the indicated treatment if the level of expression of one or more of the microRNA(s) increases or decreases relative to the level of expression of the microRNA(s) in a control sample (e.g., a cell or tissue) in which increased or decreased expression of the microRNA(s) indicates sensitivity to the treatment, and vice versa). In an embodiment, the method includes determining the expression of two of the listed genes or microRNAs, more preferably three, four, five, six, seven, eight, nine, or ten of the listed genes, and most preferably twenty, thirty, forty, fifty, sixty, seventy, eighty, ninety, or one hundred or more of the listed genes. In another embodiment, the change in the level of microRNA expression (e.g., an increase or decrease) is determined relative to the level of microRNA expression in a cell or tissue known to be sensitive to the treatment, such that a similar level of microRNA expression exhibited by a cell or tissue of the patient indicates the patient is sensitive to the treatment. In another embodiment, the change in the level of microRNA expression (e.g., an increase or decrease) is determined relative to the level of microRNA expression in a cell or tissue known to be resistant to the treatment, such that a similar level of microRNA expression exhibited by a cell or tissue of the patient indicates the patient is resistant to the treatment.

In another embodiment, the invention features a method for determining the development of resistance by a patient (e.g., resistance of a cell, such as a cancer cell, in the patient) to a treatment to which the patient was previously sensitive. The method includes measuring the level of expression of one or more of the microRNAs set forth in the first aspect of the invention, such that the level of expression of a microRNA which is decreased in a cell or tissue known to be sensitive to the treatment indicates that the patient is resistant to or has a propensity to become resistant to the treatment. Alternatively, a decrease in the expression level of a microRNA which is increased in a cell or tissue known to be sensitive to the treatment indicates that the patient is resistant to or has a propensity to become resistant to the treatment.

In a third aspect, the invention features a kit that includes a single-stranded nucleic acid molecule (e.g., one or a plurality thereof; e.g., a deoxyribonucleic acid molecule or a ribonucleic acid molecule) that is substantially complementary to (e.g., that has at least 80%, 90%, 95% 97%, 99%, or 100% identical to the complement of) or that is substantially identical to (e.g., that has at least 80%, 90%, 95% 97%, 99%, or 100% identity to) at least 5 consecutive nucleotides (more preferably at least 10, 15, 20, 25, 30, 35, 40, 45, 50, 55, 60, 65, 70, 75, 80, 85, 90, 95, 100, 150, 200, 250, 300, or more consecutive nucleotides; the nucleic acid can also be 5-20, 25, 5-50, 50-100, or over 100 consecutive nucleotides long) of at least one of the genes (e.g., at least 2, 3, 4, 5, 6, 7, 8, 9, 10, 20, 30, 40, 50, 60, 70, 80, 90, 100, or more of the genes) set forth in the first aspect of the invention, such that the single-stranded nucleic acid molecule is sufficient for measuring the level of expression of the gene(s) by allowing specific hybridization between the single-stranded nucleic acid molecule and a nucleic acid molecule encoded by the gene, or a complement thereof. Alternatively, the kit includes one or more single-stranded nucleic acid molecules that are substantially complementary to or substantially identical to at least 5 consecutive nucleotides of at least one of the microRNAs set forth in the first aspect of the invention, such that the single-stranded nucleic acid molecule is sufficient for measuring the level of expression of the microRNA(s) by allowing specific hybridization between the single-stranded nucleic acid molecule and the microRNA, or a complement thereof. The kit further includes instructions for applying nucleic acid molecules collected from a sample from a cancer patient (e.g., from a cell of the patient), determining the level of expression of the gene(s) or microRNA(s) hybridized to the single-stranded nucleic acid, and determining the patient's sensitivity to a treatment for cancer when use of the kit indicates that the level of expression of the gene(s) or microRNA(s) changes (e.g., increases or decreases relative to a control sample (e.g., tissue or cell) known to be sensitive or resistant to the treatment, as is discussed above in connection with the first aspect of the invention). In an embodiment, the instructions further indicate that a change in the level of expression of the gene(s) or microRNA(s) relative to the expression of the gene(s) or microRNA(s) in a control sample (e.g., a cell or tissue known to be sensitive or resistant to the treatment) indicates a change in sensitivity of the patient to the treatment (e.g., a decrease in the level of expression of a gene or microRNA known to be expressed in cells sensitive to the treatment indicates that the patient is becoming resistant to the treatment or is likely to become resistant to the treatment, and vice versa).

In another embodiment, the kit can be utilized to determine a patient's resistance or sensitivity to radiation therapy or the chemotherapy agents Vincristine, Cisplatin, Adriamycin, Etoposide, Azaguanine, Aclarubicin, Mitoxantrone, Paclitaxel, Mitomycin, Gemcitabine, Taxotere, Dexamethasone, Methylprednisolone, Ara-C, Methotrexate, Bleomycin, Methyl-GAG, Rituximab, PXD101 (a histone deacetylase (HDAC) inhibitor), 5-Aza-2'-deoxycytidine (Decitabine), Melphalan, IL4-PE38 fusion protein, IL13-PE38QQR fusion protein (cintredekin besudotox), Valproic acid (VPA), All-trans retinoic acid (ATRA), Cytoxan, Topotecan (Hycamtin), Suberoylanilide hydroxamic acid (SAHA, vorinostat, Zolinza), Depsipeptide (FR901229), Bortezomib, Leukeran, Fludarabine, Vinblastine, Busulfan, Dacarbazine, Oxaliplatin, Hydroxyurea, Tegafur, Daunorubicin, Bleomycin, Estramustine, Chlorambucil, Mechlorethamine, Streptozocin, Carmustine, Lomustine, Mercaptopurine, Teniposide, Dactinomycin, Tretinoin, Sunitinib, SPC2996, Ifosfamide, Tamoxifen, Floxuridine, Irinotecan, and Satraplatin by measuring the level of expression of one or more of the genes or microRNAs set forth in the first aspect of the invention and known to change (e.g., to increase or decrease) in a patient sensitive to treatment with these agents (e.g., a patient is determined to be sensitive, or likely to be sensitive, to the indicated treatment if the level of expression of one or more of the gene(s) or microRNA(s) increases or decreases relative to the level of expression of the gene(s) or microRNA(s) in a control sample (e.g., a cell or tissue) in which increased or decreased expression of the gene(s) or microRNA(s) indicates sensitivity to the treatment, and vice versa).

In another embodiment, the nucleic acid molecules are characterized by their ability to specifically identify nucleic acid molecules complementary to the genes or microRNAs in a sample collected from a cancer patient.

In a fourth aspect, the invention features a kit that includes a single-stranded nucleic acid molecule (e.g., one or a plurality thereof; e.g., a deoxyribonucleic acid molecule or a ribonucleic acid molecule) that is substantially complementary to (e.g., that has at least 80%, 90%, 95% 97%, 99%, or 100% identical to the complement of) or that is substantially identical to (e.g., that has at least 80%, 90%, 95% 97%, 99%, or 100% identity to) at least 5 consecutive nucleotides (more preferably at least 10, 15, 20, 25, 30, 35, 40, 45, 50, 55, 60, 65, 70, 75, 80, 85, 90, 95, 100, 150, 200, 250, 300, or more consecutive nucleotides; the nucleic acid can also be 5-20, 25, 5-50, 50-100, or over 100 consecutive nucleotides long) of at least one of the microRNAs (e.g., at least 2, 3, 4, 5, 6, 7, 8, 9, 10, 20, 30, 40, 50, 60, 70, 80, 90, 100, or more of the microRNAs) set forth in the first aspect of the invention, such that the single-stranded nucleic acid molecule is sufficient for measuring the level of expression of the microRNA(s) by allowing specific hybridization between the single-stranded nucleic acid molecule and a microRNA, or a complement thereof. The kit further includes instructions for applying nucleic acid molecules collected from a sample from a cancer patient (e.g., from a cell of the patient), determining the level of expression of the microRNA(s) hybridized to the single-stranded nucleic acid, and determining the patient's sensitivity to a treatment for cancer when use of the kit indicates that the level of expression of microRNA(s) changes (e.g., increases or decreases relative to a control sample (e.g., tissue or cell) known to be sensitive or resistant to the treatment, as is discussed above in connection with the first aspect of the invention). In an embodiment, the instructions further indicate that a change in the level of expression of microRNA(s) relative to the expression of microRNA(s) in a control sample (e.g., a cell or tissue known to be sensitive or resistant to the treatment) indicates a change in sensitivity of the patient to the treatment (e.g., a decrease in the level of expression of a microRNA known to be expressed in cells sensitive to the treatment indicates that the patient is becoming resistant to the treatment or is likely to become resistant to the treatment, and vice versa).

In another embodiment, the kit can be utilized to determine a patient's resistance or sensitivity to radiation therapy or the chemotherapy agents Vincristine, Cisplatin, Adriamycin, Etoposide, Azaguanine, Aclarubicin, Mitoxantrone, Paclitaxel, Mitomycin, Gemcitabine, Taxotere, Dexamethasone, Methylprednisolone, Ara-C, Methotrexate, Bleomycin, Methyl-GAG, Rituximab, PXD101 (a histone deacetylase (HDAC) inhibitor), 5-Aza-2'-deoxycytidine (Decitabine), Melphalan, IL4-PE38 fusion protein, IL13-PE38QQR fusion protein (cintredekin besudotox), Valproic acid (VPA), All-trans retinoic acid (ATRA), Cytoxan, Topotecan (Hycamtin), Suberoylanilide hydroxamic acid (SAHA, vorinostat, Zolinza), Depsipeptide (FR901229), Bortezomib, Leukeran, Fludarabine, Vinblastine, Busulfan, Dacarbazine, Oxaliplatin, Hydroxyurea, Tegafur, Daunorubicin, Bleomycin, Estramustine, Chlorambucil, Mechlorethamine, Streptozocin, Carmustine, Lomustine, Mercaptopurine, Teniposide, Dactinomycin, Tretinoin, Sunitinib, SPC2996, Ifosfamide, Tamoxifen, Floxuridine, Irinotecan, and Satraplatin by measuring the level of expression of one or more of the microRNAs set forth in the first aspect of the invention and known to change (e.g., to increase or decrease) in a patient sensitive to treatment with these agents (e.g., a patient is determined to be sensitive, or likely to be sensitive, to the indicated treatment if the level of expression of one or more of the microRNA(s) increases or decreases relative to the level of expression of the microRNA(s) in a control sample (e.g., a cell or tissue) in which increased or decreased expression of the or microRNA(s) indicates sensitivity to the treatment, and vice versa).

In another embodiment, the nucleic acid molecules are characterized by their ability to specifically identify nucleic acid molecules complementary to the microRNAs in a sample collected from a cancer patient.

In a fifth aspect, the invention features a method of identifying biomarkers (e.g., genes and microRNAs) indicative of sensitivity of a cancer patient to a treatment for cancer by obtaining pluralities of measurements of the expression level of a gene or microRNA (e.g., by detection of the expression of a gene or microRNA using a single probe or by using multiple probes directed to a single gene or microRNA) in different cell types and measurements of the growth of those cell types in the presence of a treatment for cancer relative to the growth of the cell types in the absence of the treatment for cancer; correlating each plurality of measurements of the expression level of the gene or microRNA in cells with the growth of the cells to obtain a correlation coefficient; selecting the median correlation coefficient calculated for the gene or microRNA; and identifying the gene or microRNA as a biomarker for use in determining the sensitivity of a cancer patient to said treatment for cancer if said median correlation coefficient exceeds 0.3 (preferably the gene or microRNA is identified as a biomarker for a patient's sensitivity to a treatment if the correlation coefficient exceeds 0.4, 0.5, 0.6, 0.7, 0.8, 0.9, 0.95, or 0.99 or more). In an embodiment, the method is performed in the presence of a second treatment.

In a sixth aspect, the invention features a method of determining sensitivity of a patient (e.g., a cancer patient) to a treatment for cancer by obtaining a measurement of the level of expression of a gene or microRNA in a sample (e.g., a cell or tissue) from the patient; applying a model predictive of sensitivity to a treatment for cancer to the measurement, in which the model is developed using an algorithm selected from the group consisting of linear sums, nearest neighbor, nearest centroid, linear discriminant analysis, support vector machines, and neural networks; and determining whether or not the patient will be responsive to the treatment for cancer. In an embodiment, the measurement is obtained by measuring the level of expression of any of the genes or microRNAs set forth in the first aspect of the invention in a cell known to be sensitive or resistant to the treatment. In another embodiment, the method is performed in the presence of a second treatment. In another embodiment, the model combines the outcomes of linear sums, linear discriminant analysis, support vector machines, neural networks, k-nearest neighbors, and nearest centroids, or the model is cross-validated using a random sample of multiple measurements. In another embodiment, treatment, e.g., a compound, has previously failed to show efficacy in a patient. In several embodiments, the linear sum is compared to a sum of a reference population with known sensitivity; the sum of a reference population is the median of the sums derived from the population members' biomarker gene expression. In another embodiment, the model is derived from the components of a data set obtained by independent component analysis or is derived from the components of a data set obtained by principal component analysis. In another embodiment, the invention features a kit, apparatus, and software used to implement the method of the sixth aspect of the invention.

In several embodiments of all aspects of the invention, the level of expression of the gene(s) is determined by measuring the level of mRNA transcribed from the gene(s), by detecting the level of a protein product of the gene(s), or by detecting the level of the biological activity of a protein product of the gene(s). In further embodiments of all aspects of the invention, an increase or decrease in the expression level of the gene(s) or microRNA(s), relative to the expression level of the gene(s) or microRNA(s) in a cell or tissue sensitive to the treatment, indicates increased sensitivity of the cancer patient to the treatment. Alternatively, an increase or decrease in the expression level of the gene(s) or microRNA(s), relative to the expression level of the gene(s) or microRNA(s) in a cell or tissue resistant to the treatment, indicates increased resistance of the cancer patient to the treatment. In another embodiment of all aspects of the invention, the cell is a cancer cell. In another embodiment of all aspects of the invention, the expression level of the gene(s) is measured using a quantitative reverse transcription-polymerase chain reaction (qRT-PCR). In an embodiment of all aspects of the invention, the level of expression of two of the listed genes or microRNAs is measured, more preferably the level of expression of three, four, five, six, seven, eight, nine, or ten of the listed genes or microRNAs is measured, and most preferably twenty, thirty, forty, fifty, sixty, seventy, eighty, ninety, or one hundred or more of the listed genes or microRNAs is measured. In another embodiment of all aspects of the invention, the expression level of the gene(s) or microRNA(s) is determined using the kit of the third or fourth aspects of the invention.

In another embodiment of all aspects of the invention, the treatment is radiation therapy or a compound, such as a chemotherapy agent selected from the group consisting of Vincristine, Cisplatin, Adriamycin, Etoposide, Azaguanine, Aclarubicin, Mitoxantrone, Paclitaxel, Mitomycin, Gemcitabine, Taxotere, Dexamethasone, Methylprednisolone, Ara-C, Methotrexate, Bleomycin, Methyl-GAG, Rituximab, PXD101 (a histone deacetylase (HDAC) inhibitor), 5-Aza-2'-deoxycytidine (Decitabine), Melphalan, IL4-PE38 fusion protein, IL13-PE38QQR fusion protein (cintredekin besudotox), Valproic acid (VPA), All-trans retinoic acid (ATRA), Cytoxan, Topotecan (Hycamtin), Suberoylanilide hydroxamic acid (SAHA, vorinostat, Zolinza), Depsipeptide (FR901229), Bortezomib, Leukeran, Fludarabine, Vinblastine, Busulfan, Dacarbazine, Oxaliplatin, Hydroxyurea, Tegafur, Daunorubicin, Bleomycin, Estramustine, Chlorambucil, Mechlorethamine, Streptozocin, Carmustine, Lomustine, Mercaptopurine, Teniposide, Dactinomycin, Tretinoin, Sunitinib, SPC2996, Ifosfamide, Tamoxifen, Floxuridine, Irinotecan, and Satraplatin. In another embodiment of all aspects of the invention, the treatment has previously failed to show effect in a subject (e.g., a subject selected from a subpopulation determined to be sensitive to the treatment, a subject selected from a subpopulation predicted to die without treatment, a subject selected from a subpopulation predicted to have disease symptoms without treatment, a subject selected from a subpopulation predicted to be cured without treatment.

In another embodiment of all aspects of the invention, the treatment is, e.g., administration of a compound, a protein, an antibody, an oligonucleotide, a chemotherapeutic agent, or radiation to a patient. In an embodiment of all aspects of the invention, the treatment is, e.g., a chemotherapeutic agent, such as, e.g., Vincristine, Cisplatin, Azaguanine, Etoposide, Adriamycin, Aclarubicin, Mitoxantrone, Mitomycin, Paclitaxel, Gemcitabine, Taxotere, Dexamethasone, Ara-C, Methylprednisolone, Methotrexate, Bleomycin, Methyl-GAG, Carboplatin, 5-FU (5-Fluorouracil), a histone deacetylase (HDAC) inhibitor such as PXD101, 5-Aza-2'-deoxycytidine (Decitabine), alpha emitters such as astatine-211, bismuth-212, bismuth-213, lead-212, radium-223, actinium-225, and thorium-227, beta emitters such as tritium, strontium-90, cesium-137, carbon-11, nitrogen-13, oxygen-15, fluorine-18, iron-52, cobalt-55, cobalt-60, copper-61, copper-62, copper-64, zinc-62, zinc-63, arsenic-70, arsenic-71, arsenic-74, bromine-76, bromine-79, rubidium-82, yttrium-86, zirconium-89, indium-110, iodine-120, iodine-124, iodine-129, iodine-131, iodine-125, xenon-122, technetium-94m, technetium-94, technetium-99m, and technetium-99, gamma emitters such as cobalt-60, cesium-137, and technetium-99m, Alemtuzumab, Daclizumab, Rituximab (e.g., MABTHERA™), Trastuzumab (e.g., HERCEPTIN™), Gemtuzumab, Ibritumomab, Edrecolomab, Tositumomab, CeaVac, Epratuzumab, Mitumomab, Bevacizumab, Cetuximab, Edrecolomab, Lintuzumab, MDX-210, IGN-101, MDX-010, MAb, AME, ABX-EGF, EMD 72 000, Apolizumab, Labetuzumab, ior-t1, MDX-220, MRA, H-11 scFv, Oregovomab, huJ591 MAb, BZL, Visilizumab, TriGem, TriAb, R3, MT-201, G-250, unconjugated, ACA-125, Onyvax-105, CDP-860, BrevaRex MAb, AR54, IMC-1C11, GlioMAb-H, ING-1, Anti-LCG MAbs, MT-103, KSB-303, Therex, KW-2871, Anti-HMI.24, Anti-PTHrP, 2C4 antibody, SGN-30, TRAIL-RI MAb, CAT, Prostate cancer antibody, H22×Ki-4, ABX-MA1, Imuteran, Monopharm-C, Acivicin, Aclarubicin, Acodazole Hydrochloride, Acronine, Adozelesin, Adriamycin, Aldesleukin, Altretamine, Ambomycin, A. metantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Camptothecin, Caracemide, Carbetimer, Carboplatin, Carmustine, Carubicin Hydrochloride, Carzelesin, Cedefingol, Chlorambucil, Cirolemycin, Cisplatin, Cladribine, Combretestatin A-4, Crisnatol Mesylate, Cyclophosphamide, Cytarabine, Dacarbazine, DACA (N-[2-(Dimethyl-amino) ethyl]acridine-4-carboxamide), Dactinomycin, Daunorubicin Hydrochloride, Daunomycin, Decitabine, Dexormaplatin, Dezaguanine, Dezaguanine Mesylate, Diaziquone, Docetaxel, Dolasatins, Doxorubicin, Doxorubicin Hydrochloride, Droloxifene, Droloxifene Citrate, Dromostanolone Propionate, Duazomycin, Edatrexate, Eflornithine Hydrochloride, Ellipticine, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, 5-FdUMP, Fluorocitabine, Fosquidone, Fostriecin Sodium, Gemcitabine, Gemcitabine Hydrochloride, Gold Au 198, Homocamptothecin, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-I a, Interferon Gamma-I b, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Ormaplatin, Oxisuran, Paclitaxel, Pegaspargase, Peliomycin, Pentamustine, PeploycinSulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Rhizoxin, Rhizoxin D, Riboprine, Rogletimide, Safingol, Safingol Hydrochloride, Semustine, Simtrazene, Sparfosate Sodium, Sparsomycin, Spirogermanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Thymitaq, Tiazofurin, Tirapazamine, Tomudex, TOP53, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine, Vinblastine Sulfate, Vincristine, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, Zorubicin Hydrochloride, 2-Chlorodeoxyadenosine, 2' Deoxyformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, sulfur mustard, nitrogen mustard (mechlor ethamine), cyclophosphamide, melphalan, chlorambucil, ifosfamide, busulfan, N-methyl-Nnitrosourea (MNU), N, N'-Bis(2-chloroethyl)-N-nitrosourea (BCNU), N-(2-chloroethyl)-N' cyclohexyl-N-nitrosourea (CCNU), N-(2-chloroethyl)-N'-(trans-4-methylcyclohexyl-N-nitrosourea (MeCCNU), N-(2-chloroethyl)-N'-(diethyl)ethylphosphonate-N-nitrosourea (fotemustine), streptozotocin, diacarbazine (DTIC), mitozolomide, temozolomide, thiotepa, mitomycin C, AZQ, adozelesin, Cisplatin, Carboplatin, Ormaplatin, Oxaliplatin, C1-973, DWA 2114R, JM216, JM335, Bis(platinum), tomudex, azacitidine, cytarabine, gemcitabine, 6-Mercaptopurine, 6-Thioguanine, Hypoxanthine, teniposide 9-amino camptothecin, Topotecan, CPT-11, Doxorubicin, Daunomycin, Epirubicin, darubicin, mitoxantrone, losoxantrone, Dactinomycin (Actinomycin D), amsacrine, pyrazoloacridine, all-trans retinol, 14-hydroxy-retro-retinol, all-trans retinoic acid, N-(4-Hydroxyphenyl) retinamide, 13-cis retinoic acid, 3-Methyl TTNEB, 9-cis retinoic acid, fludarabine (2-F-ara-AMP), 2-chlorodeoxyadenosine (2-Cda), 20-pi-1,25 dihydroxyvitamin D3,5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, antidorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, argininedeaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2' deoxycoformycin (DCF), deslorelin, dexifosfamide, dexrazoxane, dexverapamil, diaziquone, didemnin B, didox, diethylnorspermine, dihydro-5-azacytidine, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epirubicin, epothilones (A, R=H, B, R=Me), epithilones, episteride, estramustine analogue, estrogen agonists, estrogen antagonists, etanidazole, etoposide, etoposide 4'-phosphate (etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, homoharringtonine (HHT), hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide, estrogen, and progesterone combinations, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maytansine, mannostatin A, marimastat, masoprocol, maspin, matrilysin inhibitors, matrix metalloproteinase inhibitors, menogaril, merbarone, meterelin, methioninase, metoclopramide, MIF inhibitor, ifepristone, miltefosine, mirimostim, mismatched double stranded RNA, mithracin, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A and myobacterium cell wall skeleton combinations, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone and pentazocine combinations, napavin, naphterpin, nartograstim, nedaplatin, nemorubicin, neridronic acid, neutral endopeptidase, nilutamide, nisamycin, nitric oxide modulators, nitroxide antioxidant, nitrullyn, 06-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, podophyllotoxin, porfimer sodium, porfiromycin, propyl bisacridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B 1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, or zinostatin stimalamer. In another embodiment of all aspects of the invention, a second treatment is utilized to determine gene expression in a sample from the patient.

In another embodiment of all aspects of the invention, the gene is selected from the group consisting of ABL1, ACTB, ACTN1, ACTN4, ACTR2, ADA, ADAM9, ADAMTS1, ADD1, ADORA2A, AF1Q, AIF1, AKAP1, AKAP13, AKR1B1, AKR1C1, AKT1, ALDH2, ALDH3A1, ALDOC, ALG5, ALMS1, ALOX15B, AMIGO2, AMPD2, AMPD3, ANAPC5, ANP32A, ANP32B, ANPEP, ANXA1, ANXA2, AP1G2, APOBEC3B, APRT, ARHE, ARHGAP15, ARHGAP25, ARHGDIB, ARHGEF6, ARL7, ASAH1, ASPH, ATF3, ATIC, ATOX1, ATP1B3, ATP2A2, ATP2A3, ATP5D, ATP5G2, ATP6V1B2, B2M, BASP1, BAX, BC008967, BCAT1, BCHE, BCL11B, BDNF, BHLHB2, BIN2, BLM, BLMH, BLVRA, BMI1, BNIP3, BRDT, BRRN1, BTN3A2, BTN3A3, C11orf2, C14orf139, C15orf25, C18orf10, C1orf24, C1orf29, C1orf38, C1QR1, C22orf18, C5orf13, C6orf32, CACNA1G, CACNB3, CALD1, CALM1, CALML4, CALU, CAP350, CAPG, CAPN2, CAPN3, CASP2, CASP6, CASP7, CAST, CBFB, CBLB, CBR1, CBX3, CCL2, CCL21, CCNA2, CCNB1IP1, CCND3, CCR7, CCR9, CCT5, CD151, CD1A, CD1B, CD1C, CD1D, CD1E, CD2, CD28, CD37, CD3D, CD3E, CD3G, CD3Z, CD44, CD47, CD53, CD59, CD6, CD63, CD81, CD8A, CD8B1, CD99, CDC10, CDCl$_4$B, CDH11, CDH2, CDKL5, CDKN2A, CDW52, CECR1, CENPB, CENTB1, CENTG2, CEP1, CG018, CHRNA3, CHS1, CIAPIN1, CKAP4, CKIP-1, CNN3, CNP, COL1A1, COL4A1, COL4A2, COL5A2, COL6A1, COL6A2, COPA, COPEB, CORO1A, CORO1C, COX7B, CPSF1, CRABP1, CREB3L1, CRIP2, CRK, CRY1, CSDA, CSPG2, CSRP1, CST3, CTBP1, CTGF, CTNNA1, CTSB, CTSC, CTSD, CTSL, CUGBP2, CUTC, CXCL1, CXCR4, CXorf9, CYFIP2, CYLD, CYR61, DATF1, DAZAP1, DBN1, DBT, DCTN1, DDOST, DDX18, DDX5, DGKA, DIAPH1, DIPA, DKC1, DKFZP434J154, DKFZP564C186, DKFZP564G2022, DKFZp564J157, DKFZP564K0822, DNAJC10, DNAPTP6, DOCK10, DOCK2, DPAGT1, DPEP2, DPYSL3, DSIPI, DUSP1, DUSP3, DXS9879E, DYRK2, E2F4, ECE1, ECM1, EEF1A1, EEF1B2, EEF1G, EFNB2, EHD2, EIF2S2, EIF3S2, EIF4B, EIF4G3, EIF5A, ELA2B, ELK3, EMP3, ENO2, EPAS1, EPB41L4B, ERCC2, ERG, ERP70, EVER1, EVI2A, EVL, EXT1, EZH2, F2R, FABP5, FAD104, FAM46A, FARSLA, FAT, FAU, FBL, FCGR2A, FCGR2C, FER1L3, FGFR1, FHL1, FHOD1, FKBP1A, FKBP9, FLII, FLJ10350, FLJ10539, FLJ10774, FLJ12270, FLJ13373, FLJ20859, FLJ21159, FLJ22457, FLJ35036, FLJ46603, FLNC, FLOT1, FMNL1, FN1, FNBP1, FOLH1, FOXF2, FSCN1, FSTL1, FTH1, FTL, FYB, FYN, GOS2, G6PD, GALIG, GALNT6, GAPD, GAS7, GATA2, GATA3, GFPT1, GIMP5, GIT2, GJA1, GLRB, GLTSCR2, GLUL, GMDS, GMFG, GNA15, GNAI2, GNAQ, GNB2, GNB5, GOT2, GPNMB, GPR65, GPRASP1, GPSM3, GRP58, GSTM2, GTF3A, GTSE1, GYPC, GZMA, GZMB, H1F0, H1FX, H2AFX, H3F3A, HA-1, HCLS1, HEM1, HEXB, HIC, HIST1H4C, HK1, HLA-A, HLA-B, HLA-DRA, HMGA1, HMGB2, HMGN2, HMMR, HNRPA1, HNRPD, HNRPM, HOXA9, HPRT1, HRMT1L1, HSA9761, HSPA5, HSU79274, HTATSF1, HU6800, ICAM1, ICAM2, IER3, IFI16, IFI44, IFITM2, IFITM3, IFRG28, IGFBP2, IGFBP3, IGSF4, IL13RA2, IL21R, IL2RG, IL4R, IL6, IL6R, IL6ST, IL8, IMPDH2, INPP5D, INSIG1 IQGAP1, IQGAP2, IRS2, ITGA3, ITGA5, ITGB2, ITK, ITM2A, JAK1, JARID2, JUNB, K-ALPHA-1, KHDRBS1, KIAA0220, KIAA0355, KIAA0802, KIAA0877, KIAA0922, KIAA1078, KIAA1128, KIAA1393, KIFC1, KPNB1, LAIR1, LAMB1, LAMB3, LAMR1, LAPTM5, LAT, LBR, LCK, LCP1, LCP2, LDHB, LEF1, LEPRE1, LGALS1, LGALS9, LHFPL2, LMNB1, LNK, LOC54103, LOC55831, LOC81558, LOC94105, LONP, LOX, LOXL2, LPHN2, LPXN, LRMP, LRP12, LRRC5, LRRN3, LST1, LTB, LUM, LY9, LY96, M6PRBP1, MAD2L1BP, MAGEB2, MAL, MAN1A1, MAP1B, MAP1LC3B, MAP4K1, MAPK1, MAPRE1, MARCKS, MAZ, MCAM, MCL1, MCM5, MCM1, MDH2, MDK, MDN1, MEF2C, MFNG, MGC17330, MGC21654, MGC2744, MGC4083, MGC8721, MGC8902, MGLL, MIA, MICA, MLPH, MME, MMP2, MPHOSPH6, MPP1, MPZL1, MRP63, MRPL12, MRPS2, MSN, MT1E, MT1K, MUF1, MVP, MYB, MYC, MYL6, MYL9, MYO1B, NAP1L1, NAP1L2, NARF, NARS, NASP, NBL1, NCL, NCOR2, NDN, NDUFAB1, NDUFS6, NFIL3, NFKBIA, NID2, NIPA2, NK4, NME4, NME7, NNMT, NOL5A, NOL8, NOMO2, NOTCH1, NPC1, NQO1, NR1D2, NUCB2, NUDC, NUP210, NUP88, NVL, NXF1, OBFC1, OCRL, OGT, OK/SW-cl.56, OPTN, OXA1L, P2RX5, P4HA1, PACAP, PAF53, PAFAH1B3, PALM2-AKAP2, PAX6, PBEF1, PCBP2, PCCB, PEA15, PFDN5, PFN1, PFN2, PGAM1, PGK1, PHEMX, PHLDA1, PIM2, PITPNC1, PKM2, PLACE, PLAGL1, PLAU, PLAUR, PLCB1, PLEK2, PLEKHC1, PLOD2, PLSCR1, PNAS-4, PNMA2, POLR2F, PON2, PPAP2B, PPIA, PPIF, PPP1R11, PPP2CB, PRF1, PRG1, PRIM1, PRKCA, PRKCB1, PRKCH, PRKCQ, PRKD2, PRNP, PRP19, PRPF8, PRPS1, PRSS11, PRSS23, PSCDBP, PSMB9, PSMC3, PSMC5, PSME2, PTGER4, PTGES2, PTMA, PTOV1, PTP4A3, PTPN7, PTPNS1, PTPRC, PTPRCAP, PTRF, PTS, PURA, PWP1, PYGL, QKI, RAB31, RAB3GAP, RAB7, RAB7L1, RAB9P40, RAC2, RAFTLIN, RAG2, RALY, RAP1B, RASGRP2, RBMX, RBPMS, RCN1, REA, RFC3, RFC5, RGC32, RGS3, RHOC, RHOH, RIMS3, RIOK3, RIPK2, RIS1, RNASE6, RNF144, RNPS1, RPL10, RPL10A, RPL11, RPL12, RPL13, RPL13A, RPL17, RPL18, RPL18A, RPL24, RPL3, RPL32, RPL36A, RPL39, RPL7, RPL9, RPLP0, RPLP2, RPS10, RPS11, RPS15, RPS15A, RPS19, RPS2, RPS23, RPS24, RPS25, RPS27, RPS28, RPS4X, RPS4Y1, RPS6, RPS7, RPS9, RRAS, RRAS2, RRBP1, RRM2, RUNX1, RUNX3, S100A13, S100A4, SART3, SATB1, SCAP1, SCARB1, SCARB2, SCN3A, SCTR, SEC31L2, SEC61G, SELL, SELPLG, SEMA4G, SEPT6, SEPT10, SEPW1, SERPINA1, SERPINB1, SERPINB6, SFRS3, SFRS5, SFRS6, SFRS7, SH2D1A, SH3GL3, SH3TC1, SHD1, SHFM1, SHMT2, SIAT1, SKB1, SKP2, SLA, SLC1A4, SLC20A1, SLC25A15, SLC25A5, SLC39A14, SLC39A6, SLC43A3, SLC4A2, SLC7A11, SLC7A6, SMA3, SMAD3, SMARCD3, SMOX, SMS, SND1, SNRPA, SNRPB, SNRPB2, SNRPE, SNRPF, SOD2, SOX4, SP140, SPANXC, SPARC, SPI1, SRF, SRM, SRRM1, SSA2, SSBP2, SSRP1, SSSCA1, STAG3, STAT1, STAT4, STAT5A, STC1, STC2, STMN1, STOML2, SUI1, T3JAM, TACC1, TACC3, TAF5, TAGLN, TALE TAP1, TARP, TBCA, TCF12, TCF4, TCF7, TFDP2, TFPI, TFRC, TGFB1, TIMM17A, TIMP1, TJP1, TK2, TM4SF1, TM4SF2, TM4SF8, TM6SF1, TMEM2, TMEM22, TMSB10, TMSNB, TNFAIP3, TNFAIP8, TNFRSF10B, TNFRSF1A, TNFRSF7, TNIK, TNPO1, TOB1, TOMM20, TOP2A, TOX, TPK1, TPM2, TRA@, TRA1, TRAM2, TRB@, TRD@, TRIM, TRIM14, TRIM22, TRIM28, TRIP13, TRPV2, TUBA3, TUBGCP3, TUFM, TUSC3, TXN, TXNDC5, UBASH3A, UBB, UBC, UBE2A, UBE2L6, UBE2S, UCHL1, UCK2, UCP2, UFD1L, UGCG, UGDH, UGT2B17, ULK2, UMPS, UNG, UROD, USP34, USP4, USP7, VASP, VAV1, VIM, VLDLR, VWF, WARS, WASPIP, WBSCR20A, WBSCR20C, WHSC1, WNT5A, XPO1, ZAP128, ZAP70, ZFP36L1, ZNF32, ZNF335, ZNF593, ZNFN1A1, or ZYX.

The nucleic acid sequence of each listed genes is publicly available through the GenBank or RefSeq database. The gene sequences are also included as part of the HG-U133A GeneChip from Affymetrix, Inc.

"Resistant" or "resistance" as used herein means that a cell, a tumor, a patient (e.g., a human), or a living organism is able to withstand treatment, e.g., with a compound, such as a chemotherapeutic agent, or radiation treatment, in that the treatment inhibits the growth of a cell, e.g., a cancer cell, in vitro or in a tumor, patient, or living organism by less than 10%, 20%, 30%, 40%, 50%, 60%, or 70% relative to the growth of a similar cell not exposed to the treatment. Resistance to treatment can be determined by a cell-based assay that measures the growth of treated cells as a function of the cells' absorbance of an incident light beam as used to perform the NCI60 assays described herein. In this example, greater absorbance indicates greater cell growth, and thus, resistance to the treatment. A reduction in growth indicates more resistance to a treatment. By "chemoresistant" or "chemoresistance" is meant resistance to a compound.

"Sensitive" or "sensitivity" as used herein means that a cell, a tumor, a patient (e.g., a human), or a living organism is responsive to treatment, e.g., with a compound, such as a chemotherapeutic agent, or radiation treatment, in that the treatment inhibits the growth of a cell, e.g., a cancer cell, in vitro or in a tumor, patient, or living organism by 70%, 80%, 90%, 95%, 99%, or 100%. Sensitivity to treatment may be determined by a cell-based assay that measures the growth of treated cells as a function of the cells' absorbance of an incident light beam as used to perform the NCI60 assays described herein. In this example, lesser absorbance indicates reduced cell growth, and thus, sensitivity to the treatment. A greater reduction in growth indicates more sensitivity to the treatment. By "chemosensitive" or "chemosensitivity" is meant sensitivity to a compound.

"Complement" of a nucleic acid sequence or a "complementary" nucleic acid sequence as used herein refers to an oligonucleotide which is in "antiparallel association" when it is aligned with the nucleic acid sequence such that the 5' end of one sequence is paired with the 3' end of the other. Nucleotides and other bases can have complements and may be present in complementary nucleic acids. Bases not commonly found in natural nucleic acids that can be included in the nucleic acids of the present invention include, for example, inosine and 7-deazaguanine.

"Complementarity" may not be perfect; stable duplexes of complementary nucleic acids can contain mismatched base pairs or unmatched bases. Skilled artisans can determine duplex stability empirically considering a number of variables including, for example, the length of the oligonucleotide, percent concentration of cytosine and guanine bases in the oligonucleotide, ionic strength, and incidence of mismatched base pairs. Typically, complementarity is determined by comparing contiguous nucleic acid sequences.

When complementary nucleic acid sequences form a stable duplex, they are said to be "hybridized" or to "hybridize" to each other or it is said that "hybridization" has occurred. Nucleic acids are referred to as being "complementary" if they contain nucleotides or nucleotide homologues that can form hydrogen bonds according to Watson-Crick base-pairing rules (e.g., G with C, A with T, or A with U) or other hydrogen bonding motifs such as, for example, diaminopurine with T, 5-methyl C with G, 2-thiothymidine with A, inosine with C, and pseudoisocytosine with G. Anti-sense RNA can be complementary to other oligonucleotides, e.g., mRNA.

"Biomarker" as used herein indicates a transcription product (e.g., RNA, such as an RNA primary transcript, mRNA, tRNA, rRNA, microRNA (miRNA), or complementary RNA or DNA (e.g., cDNA) strands thereof) or a translation product (e.g., a polypeptide or metabolite thereof) of a biomarker gene, as defined herein, whose level of expression indicates the sensitivity or resistance of a cell (e.g., a cancer cell), tissue, organism, or patient (e.g., a human) to a treatment (e.g., chemotherapy, radiation therapy, or surgery).

"Compound" as used herein means a chemical or biological substance, e.g., a drug, a protein, an antibody, or an oligonucleotide, which can be used to treat a disease or which has biological activity in vivo or in vitro. Compounds may or may not be approved by the U.S. Food and Drug Administration (FDA). Preferred compounds include, e.g., chemotherapy agents that can inhibit cancer growth. Preferred chemotherapy agents include, e.g., Vincristine, Cisplatin, Azaguanine, Etoposide, Adriamycin, Aclarubicin, Mitoxantrone, Mitomycin, Paclitaxel, Gemcitabine, Taxotere, Dexamethasone, Ara-C, Methylprednisolone, Methotrexate, Bleomycin, Methyl-GAG, Carboplatin, 5-FU (5-Fluorouracil), Rituximab (e.g., MABTHERA™), histone deacetylase (HDAC) inhibitors, and 5-Aza-2'-deoxycytidine (Decitabine). Exemplary radioactive chemotherapeutic agents include compounds containing alpha emitters such as astatine-211, bismuth-212, bismuth-213, lead-212, radium-223, actinium-225, and thorium-227, beta emitters such as tritium, strontium-90, cesium-137, carbon-11, nitrogen-13, oxygen-15, fluorine-18, iron-52, cobalt-55, cobalt-60, copper-61, copper-62, copper-64, zinc-62, zinc-63, arsenic-70, arsenic-71, arsenic-74, bromine-76, bromine-79, rubidium-82, yttrium-86, zirconium-89, indium-110, iodine-120, iodine-124, iodine-129, iodine-131, iodine-125, xenon-122, technetium-94m, technetium-94, technetium-99m, and technetium-99, and gamma emitters such as cobalt-60, cesium-137, and technetium-99m. Exemplary chemotherapeutic agents also include antibodies such as Alemtuzumab, Daclizumab, Rituximab (e.g., MABTHERA™), Trastuzumab (e.g., HERCEPTIN™), Gemtuzumab, Ibritumomab, Edrecolomab, Tositumomab, CeaVac, Epratuzumab, Mitumomab, Bevacizumab, Cetuximab, Edrecolomab, Lintuzumab, MDX-210, IGN-101, MDX-010, MAb, AME, ABX-EGF, EMD 72 000, Apolizumab, Labetuzumab, ior-t1, MDX-220, MRA, H-11 scFv, Oregovomab, huJ591 MAb, BZL, Visilizumab, TriGem, TriAb, R3, MT-201, G-250, ACA-125, Onyvax-105, CDP-860, BrevaRex MAb, AR54, IMC-1C11, GlioMAb-H, ING-1, Anti-LCG MAbs, MT-103, KSB-303, Therex, KW-2871, Anti-HMI.24, Anti-PTHrP, 2C4 antibody, SGN-30, TRAIL-RI MAb, CAT, Prostate cancer antibody, H22xKi-4, ABX-MA1, Imuteran, and Monopharm-C. Exemplary chemotherapeutic agents also include Acivicin; Aclarubicin; Acodazole Hydrochloride; Acronine; Adozelesin; Adriamycin; Aldesleukin; Altretamine; Ambomycin; A. methanotone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabine; Dacarbazine; DACA (N-[2-(Dimethyl-amino) ethyl]acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil;

5-FdUMP; Fluorocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'-Bis(2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis(platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other chemotherapeutic agents include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2' deoxycoformycin (DCF); deslorelin; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide, estrogen, and progesterone combinations; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin;

mitoxantrone; mofarotene; molgramostim; monoclonal antibody, human chorionic gonadotrophin; monophosphoryl lipid A and myobacterium cell wall skeleton combinations; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone and pentazocine combinations; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bisacridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

To "inhibit growth" as used herein means causing a reduction in cell growth in vivo or in vitro by, e.g., 10%, 20%, 30%, 40%, 50%, 60%, 70%, 80%, 90%, 95%, or 99% or more, as evident by a reduction in the size or number of cells exposed to a treatment (e.g., exposure to a compound), relative to the size or number of cells in the absence of the treatment. Growth inhibition can be the result of a treatment that induces apoptosis in a cell, induces necrosis in a cell, slows cell cycle progression, disrupts cellular metabolism, induces cell lysis, or induces some other mechanism that reduces the size or number of cells.

"Biomarker gene" as used herein means a gene in a cell (e.g., a cancer cell) the expression of which, as measured by, e.g., detecting the level of one or more biomarkers produced from the gene, correlates to sensitivity or resistance of the cell, tissue, organism, or patient (e.g., a human) to a treatment (e.g., chemotherapy, radiation therapy, or surgery).

"Microarray" as used herein means a device employed by any method that quantifies one or more subject oligonucleotides, e.g., DNA or RNA, or analogues thereof, at a time. One exemplary class of microarrays consists of DNA probes attached to a glass or quartz surface. Many microarrays, e.g., those made by Affymetrix, use several probes for determining the expression of a single gene. The DNA microarray can contain oligonucleotide probes that may be, e.g., full-length cDNAs complementary to an RNA or cDNA fragments that hybridize to part of an RNA. Exemplary RNAs include mRNA, miRNA, and miRNA precursors. Exemplary microarrays also include a "nucleic acid microarray" having a substrate-bound plurality of nucleic acids, hybridization to each of the plurality of bound nucleic acids being separately detectable. The substrate can be solid or porous, planar or non-planar, unitary or distributed. Exemplary nucleic acid microarrays include all of the devices so called in Schena (ed.), DNA Microarrays: A Practical Approach (Practical Approach Series), Oxford University Press (1999); Nature Genet. 21(1)(suppl.):1-60 (1999); and Schena (ed.), Microarray Biochip: Tools and Technology, Eaton Publishing Company/BioTechniques Books Division (2000). Additionally, exemplary nucleic acid microarrays can include a substrate-bound plurality of nucleic acids in which the plurality of nucleic acids is disposed on a plurality of beads, rather than on a unitary planar substrate, as is described, inter alia, in Brenner et al., *Proc. Natl. Acad. Sci. USA* 97(4):1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, and 5,405,783, herein incorporated by reference.

Exemplary microarrays can also include "peptide microarrays" or "protein microarrays" having a substrate-bound plurality of polypeptides, the binding of a oligonucleotide, a peptide, or a protein to the plurality of bound polypeptides being separately detectable. Alternatively, the peptide microarray, can have a plurality of binders, including, but not limited to, monoclonal antibodies, polyclonal antibodies, phage display binders, yeast 2 hybrid binders, aptamers, that can specifically detect the binding of specific oligonucleotides, peptides, or proteins. Examples of peptide arrays may be found in International Patent Publication Nos. WO 02/31463, WO 02/25288, WO 01/94946, WO 01/88162, WO 01/68671, WO 01/57259, WO 00/61806, WO 00/54046, WO 00/47774, WO 99/40434, WO 99/39210, and WO 97/42507, and in U.S. Pat. Nos. 6,268,210, 5,766,960, and 5,143,854, herein incorporated by reference.

"Gene expression" as used herein means the level of expression of a biomarker gene (e.g., the level of a transcription product, such as an mRNA, tRNA, or microRNA, or its complement (e.g., a cDNA complement of the transcription product), or a translation product, such as a polypeptide or metabolite thereof) in a cell, tissue, organism, or patient (e.g., a human). Gene expression can be measured by detecting the presence, quantity, or activity of a DNA, RNA, or polypeptide, or modifications thereof (e.g., splicing, phosphorylation, and acetylation) associated with a given gene.

"NCI60" as used herein means a panel of 60 cancer cell lines from lung, colon, breast, ovarian, leukemia, renal, melanoma, prostate, and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COLO205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR$_3$, OVAR_OVCAR$_4$, OVAR_OVCAR$_5$, OVAR_OVCAR$_8$, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

"Treatment" or "medical treatment" means administering to a patient (e.g., a human) or living organism or exposing to a cell or tumor a compound (e.g., a drug, a protein, an antibody, an oligonucleotide, a chemotherapeutic agent, and a radioactive agent) or some other form of medical intervention used to treat or prevent cancer or the symptoms of cancer (e.g., cryotherapy and radiation therapy). Radiation therapy includes the administration to a patient of radiation generated from sources such as particle accelerators and related medical devices that emit X-radiation, gamma radiation, or electron (Beta radiation) beams. A treatment may further include surgery, e.g., to remove a tumor from a patient or living organism.

Other features and advantages of the invention will be apparent from the following description, drawings, and claims.

DETAILED DESCRIPTION

Figure 1:
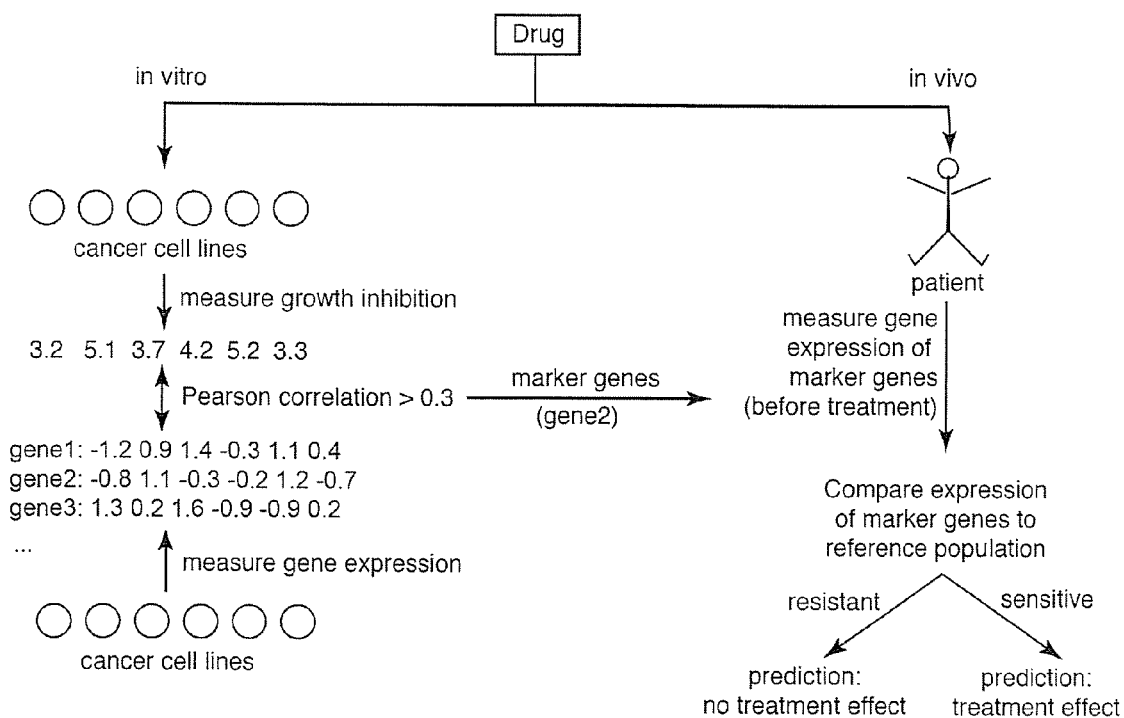
FIG. 1 depicts an illustration of the method of identifying biomarkers and predicting patient sensitivity to a medical treatment. The method has an in vitro component where the growth inhibition of a compound or medical treatment is measured on cell lines (6 of the 60 cell lines tested are shown). The gene expression is measured on the same cell lines without compound treatment. Those genes that have a correlation above a certain cutoff (e.g., a preffered cutoff of 0.3, in which a correlation coefficient equal to or greater than the cutoff of 0.3 is deemed statstcally significant by, e.g., cross-validation) to the growth inhibition are termed marker genes and the expression of those genes in vivo, e.g., may predict the sensitivity or resistance of a patient's cancer to a compound or other medical treatment. The in vivo component is applied to a patient to determine whether or not the treatment will be effective in treating disease in the patient. Here, the gene expression in cells of a sample of the suspected disease tissue (e.g., a tumor) in the patient is measured before or after treatment. The activity of the marker genes in the sample is compared to a reference population of patients known to be sensitive or resistant to the treatment. The expression of marker genes in the cells of the patient known to be expressed in the cells of reference patients sensitive to the treatment indicates that the patient to be treated is sensitive to the treatment and vice versa. Based on this comparison the patient is predicted to be sensitive or resistant to treatment with the compound.

The invention features methods for identifying biomarkers of treatment sensitivity, e.g., chemosensitivity to compounds, or resistance, devices that include the biomarkers, kits that include the devices, and methods for predicting treatment efficacy in a patient (e.g., a human diagnosed with cancer). The kits of the invention include microarrays having oligonucleotide probes that are biomarkers of sensitivity or resistance to treatment (e.g., treatment with a chemotherapeutic agent) that hybridize to nucleic acids derived from or obtained from a subject and instructions for using the device to predict the sensitivity or resistance of the subject to the treatment. The invention also features methods of using the microarrays to determine whether a subject, e.g., a cancer patient, will be sensitive or resistant to treatment with, e.g., a chemotherapy agent. Also featured are methods of identifying biomarkers of sensitivity or resistance to a medical treatment based on the correlation of gene or microRNA expression to treatment efficacy, e.g., the growth inhibition of cancer cells. Gene or microRNA biomarkers that identify subjects as sensitive or resistant to a treatment can also be identified within patient populations already thought to be sensitive or resistant to that treatment. Thus, the methods, devices, and kits of the invention can be used to identify patient subpopulations that are responsive to a treatment thought to be ineffective for treating disease (e.g., cancer) in the general population. More generally, cancer patient sensitivity to a compound or other medical treatment can be predicted using biomarker expression regardless of prior knowledge about patient responsiveness to treatment. The method according to the present invention can be implemented using software that is run on an apparatus (e.g., a computer) for measuring biomarker expression in connection with a microarray. The microarray (e.g., a DNA microarray), included in a kit for processing a tumor sample from a patient, and the apparatus for reading the microarray and turning the result into a chemosensitivity profile for the patient may be used to implement the methods of the invention.

Microarrays Containing Oligonucleotide Probes

The microarrays of the invention include one or more oligonucleotide probes that have nucleotide sequences that are substantially identical to or substantially complementary to, e.g., at least 5, 8, 12, 20, 30, 40, 60, 80, 100, 150, or 200 consecutive nucleotides (or nucleotide analogues) of the biomarker genes or biomarker gene products (e.g., transcription or translation gene products, such as microRNAs) listed below. The oligonucleotide probes may be, e.g., 5-20, 25, 5-50, 50-100, or over 100 nucleotides long. The oligonucleotide probes may be deoxyribonucleic acids (DNA) or ribonucleic acids (RNA). Consecutive nucleotides within the oligonucleotide probes (e.g., 5-20, 25, 5-50, 50-100, or over 100 consecutive nucleotides), which are used as biomarkers of chemosensitivity, may also appear as consecutive nucleotides in one or more of the genes described herein beginning at or near, e.g., the first, tenth, twentieth, thirtieth, fortieth, fiftieth, sixtieth, seventieth, eightieth, ninetieth, hundredth, hundred-fiftieth, two-hundredth, five-hundredth, or one-thousandth nucleotide of the genes or microRNAs listed in Tables 1-136 below. Column List_2006 of Tables 1-21 indicates the preferred biomarker genes for the compound lists. Column List_Preferred of Tables 1-21 indicates the most preferred biomarker genes. Column List_2005 of Tables 1-21 indicates additional biomarkers employed in Examples 1-8. Column Correlation of Tables 1-21 indicates the correlation coefficient of the biomarker gene expression to cancer cell growth inhibition. Tables 80-136 indicate microRNA biomarkers that can be used to determine a patient's (e.g., a human's) sensitivity to a treatment. The following combinations of biomarkers have been used to detect a patient's sensitivity to the indicated treatment:

a) One or more of the gene sequences SFRS3, CCT5, RPL39, SLC25A5, UBE2S, EEF1A1, RPLP2, RPL24, RPS23, RPL39, RPL18, NCL, RPL9, RPL10A, RPS10, EIF3S2, SHFM1, RPS28, REA, RPL36A, GAPD, HNRPA1, RPS11, HNRPA1, LDHB, RPL3, RPL11, MRPL12, RPL18A, COX7B, and RPS7, preferably gene sequences UBB, RPS4X, S100A4, NDUFS6, B2M, C14orf139, MAN1A1, SLC25A5, RPL10, RPL12, EIF5A, RPL36A, SUI1, BLMH, CTBP1, TBCA, MDH2, and DXS9879E, and most preferably gene sequences RPS4X, S100A4, NDUFS6, C14orf139, SLC25A5, RPL10, RPL12, EIF5A, RPL36A, BLMH, CTBP1, TBCA, MDH2, and DXS9879E, whose expression indicates chemosensitivity to Vincristine.

b) One or more of the gene sequences B2M, ARHGDIB, FTL, NCL, MSN, SNRPF, XPO1, LDHB, SNRPF, GAPD, PTPN7, ARHGDIB, RPS27, IFI16, C5orf13, and HCLS1, preferably gene sequences C1QR1, HCLS1, CD53, SLA, PTPN7, PTPRCAP, ZNFN1A1, CENTB1, PTPRC, 1E116, ARHGEF6, SEC31L2, CD3Z, GZMB, CD3D, MAP4K1, GPR65, PRF1, ARHGAP15, TM6SF1, and TCF4, and most preferably gene sequences C1QR1, SLA, PTPN7, ZNFN1A1, CENTB1, 1E116, ARHGEF6, SEC31L2, CD3Z, GZMB, CD3D, MAP4K1, GPR65, PRF1, ARHGAP15, TM6SF1, and TCF4, whose expression indicates chemosensitivity to Cisplatin.

c) One or more of the gene sequences PRPS1, DDOST, B2M, SPARC, LGALS1, CBFB, SNRPB2, MCAM, MCAM, EIF2S2, HPRT1, SRM, FKBP1A, GYPC, UROD, MSN, HNRPA1, SND1, COPA, MAPRE1, EIF3S2, ATP1B3, EMP3, ECM1, ATOX1, NARS, PGK1, OK/SW-c1.56, FN1, EEF1A1, GNAI2, PRPS1, RPL7, PSMB9, GPNMB, PPP1R11, MIA, RAB7, VIM, and SMS, preferably gene sequences MSN, SPARC, VIM, SRM, SCARB1, SIAT1, CUGBP2, GAS7, ICAM1, WASPIP, ITM2A, PALM2-AKAP2, ANPEP, PTPNS1, MPP1, LNK, FCGR2A, EMP3, RUNX3, EVI2A, BTN3A3, LCP2, BCHE, LY96, LCP1, 1E116, MCAM, MEF2C, SLC1A4, BTN3A2, FYN, FN1, C1orf38, CHS1, CAPN3, FCGR2C, TNIK, AMPD2, SEPT6, RAFTLIN, SLC43A3, RAC2, LPXN, CKIP-1, FLJ10539, FLJ35036, DOCK10, TRPV2, IFRG28, LEF1, and ADAMTS1, and most preferably gene sequences SRM, SCARB1, SIAT1, CUGBP2, ICAM1, WASPIP, ITM2A, PALM2-AKAP2, PTPNS1, MPP1, LNK, FCGR2A, RUNX3, EVI2A, BTN3A3, LCP2, BCHE, LY96, LCP1, IFI16, MCAM, MEF2C, SLC1A4, FYN, C1orf38, CHS1, FCGR2C, TNIK, AMPD2, SEPT6, RAFTLIN, SLC43A3, RAC2, LPXN, CKIP-1, FLJ10539, FLJ35036, DOCK10, TRPV2, IFRG28, LEF1, and ADAMTS1, whose expression indicates chemosensitivity to Azaguanine.

d) One or more of the gene sequences B2M, MYC, CD99, RPS24, PPIF, PBEF1, and ANP32B, preferably gene sequences CD99, INSIG1, LAPTM5, PRG1, MUF1, HCLS1, CD53, SLA, SSBP2, GNB5, MFNG, GMFG, PSMB9, EVI2A, PTPN7, PTGER4, CXorf9, PTPRCAP, ZNFN1A1, CENTB1, PTPRC, NAP1L1, HLA-DRA, IFI16, CORO1A, ARHGEF6, PSCDBP, SELPLG, LAT, SEC31L2, CD3Z, SH2D1A, GZMB, SCN3A, ITK, RAFTLIN, DOCK2, CD3D, RAC2, ZAP70, GPR65, PRF1, ARHGAP15, NOTCH1, and UBASH3A, and most preferably gene sequences CD99, INSIGE PRG1, MUF1, SLA, SSBP2, GNB5, MFNG, PSMB9, EVI2A, PTPN7, PTGER4, CXorf9, ZNFN1A1, CENTB1, NAP1L1, HLA-DRA, IFI16, ARHGEF6, PSCDBP, SELPLG, LAT, SEC31L2, CD3Z, SH2D1A, GZMB, SCN3A, RAFTLIN, DOCK2, CD3D, RAC2, ZAP70, GPR65, PRF1, ARHGAP15, NOTCH1, and UBASH3A, whose expression indicates chemosensitivity to Etoposide.

e) One or more of the gene sequences KIAA0220, B2M, TOP2A, CD99, SNRPE, RPS27, HNRPA1, CBX3, ANP32B, HNRPA1, DDX5, PPIA, SNRPF, and USP7, preferably gene sequences CD99, LAPTM5, ALDOC, HCLS1, CD53, SLA, SSBP2, IL2RG, GMFG, CXorf9, RHOH, PTPRCAP, ZNFN1A1, CENTB1, TCF7, CD1C, MAP4K1, CD1B, CD3G, PTPRC, CCR9, CORO1A, CXCR4, ARHGEF6, HEM1, SELPLG, LAT, SEC31L2, CD3Z, SH2D1A, CD1A, LAIR1, ITK, TRB@, CD3D, WBSCR20C, ZAP70, IFI44, GPR65, AIF1, ARHGAP15, NARF, and PACAP, and most preferably gene sequences CD99, ALDOC, SLA, SSBP2, IL2RG, CXorf9, RHOH, ZNFN1A1, CENTB1, CD1C, MAP4K1, CD3G, CCR9, CXCR4, ARHGEF6, SELPLG, LAT, SEC31L2, CD3Z, SH2D1A, CD1A, LAIR1, TRB@, CD3D, WBSCR20C, ZAP70, IFI44, GPR65, AIF1, ARHGAP15, NARF, and PACAP, whose expression indicates chemosensitivity to Adriamycin.

f) One or more of the gene sequences RPLP2, LAMR1, RPS25, EIF5A, TUFM, HNRPA1, RPS9, MYB, LAMR1, ANP32B, HNRPA1, HNRPA1, EIF4B, HMGB2, RPS15A, and RPS7, preferably gene sequences RPL12, RPL32, RPLP2, MYB, ZNFN1A1, SCAP1, STAT4, SP140, AMPD3, TNFAIP8, DDX18, TAF5, FBL, RPS2, PTPRC, DOCK2, GPR65, HOXA9, FLJ12270, and HNRPD, and most preferably gene sequences RPL12, RPLP2, MYB, ZNFN1A1, SCAP1, STAT4, SP140, AMPD3, TNFAIP8, DDX18, TAF5, RPS2, DOCK2, GPR65, HOXA9, FLJ12270, and HNRPD, whose expression indicates chemosensitivity to Aclarubicin.

g) One or more of the gene sequences ARHGEF6, B2M, TOP2A, TOP2A, ELA2B, PTMA, LMNB1, TNFRSF1A, NAP1L1, B2M, HNRPA1, RPL9, C5orf13, NCOR2, ANP32B, OK/SW-cl.56, TUBA3, HMGN2, PRPS1, DDX5, PRG1, PPIA, G6PD, PSMB9, SNRPF, and MAP1B, preferably gene sequences PGAM1, DPYSL3, INSIG1, GJA1, BNIP3, PRG1, G6PD, BASP1, PLOD2, LOXL2, SSBP2, C1orf29, TOX, STC1, TNFRSF1A, NCOR2, NAP1L1, LOC94105, COL6A2, ARHGEF6, GATA3, TFPI, LAT, CD3Z, AF1Q, MAP1B, PTPRC, PRKCA, TRIM22, CD3D, BCAT1, IFI44, CCL2, RAB31, CUTC, NAP1L2, NME7, FLJ21159, and COL5A2, and most preferably gene sequences PGAM1, DPYSL3, INSIG1, GJA1, BNIP3, PRG1, G6PD, PLOD2, LOXL2, SSBP2, C1orf29, TOX, STC1, TNFRSF1A, NCOR2, NAP1L1, LOC94105, ARHGEF6, GATA3, TFPI, LAT, CD3Z, AF1Q, MAP1B, TRIM22, CD3D, BCAT1, IFI44, CUTC, NAP1L2, NME7, FLJ21159, and COL5A2, whose expression indicates chemosensitivity to Mitoxantrone.

h) One or more of the gene sequences GAPD, GAPD, GAPD, TOP2A, SUI1, TOP2A, FTL, HNRPC, TNFRSF1A, SHC1, CCT7, P4HB, CTSL, DDX5, G6PD, and SNRPF, preferably gene sequences STC1, GPR65, DOCK10, COL5A2, FAM46A, and LOC54103, and most preferably gene sequences STC1, GPR65, DOCK10, COL5A2, FAM46A, and LOC54103, whose expression indicates chemosensitivity to Mitomycin.

i) One or more of the gene sequences RPS23, SFRS3, KIAA0114, RPL39, SFRS3, LOC51035, RPS6, EXOSC2, RPL35, IFRD2, SMN2, EEF1A1, RPS3, RPS18, and RPS7, preferably gene sequences RPL10, RPS4X, NUDC, RALY, DKC1, DKFZP564C186, PRP19, RAB9P40, HSA9761, GMDS, CEP1, IL13RA2, MAGEB2, HMGN2, ALMS1, GPR65, FLJ10774, NOL8, DAZAP1, SLC25A15, PAF53, DXS9879E, PITPNC1, SPANXC, and KIAA1393, and most preferably RPL10, RPS4X, NUDC, DKC1, DKFZP564C186, PRP19, RAB9P40, HSA9761, GMDS, CEP1, IL13RA2, MAGEB2, HMGN2, ALMS1, GPR65, FLJ10774, NOL8, DAZAP1, SLC25A15, PAF53, DXS9879E, PITPNC1, SPANXC, and KIAA1393, whose expression indicates chemosensitivity to Paclitaxel.

j) One or more of the gene sequences CSDA, LAMR1, and TUBA3, preferably gene sequences PFN1, PGAM1, K-ALPHA-1, CSDA, UCHL1, PWP1, PALM2-AKAP2, TNFRSF1A, ATP5G2, AF1Q, NME4, and FHOD1, and most preferably gene sequences PFN1, PGAM1, K-ALPHA-1, CSDA, UCHL1, PWP1, PALM2-AKAP2, TNFRSF1A, ATP5G2, AF1Q, NME4, and FHOD1, whose expression indicates chemosensitivity to Gemcitabine.

k) One or more of the gene sequences RPS23, SFRS3, KIAA0114, SFRS3, RPS6, DDX39, and RPS7, preferably gene sequences ANP32B, GTF3A, RRM2, TRIM14, SKP2, TRIP13, RFC3, CASP7, TXN, MCM5, PTGES2, OBFC1, EPB41L4B, and CALML4, and most preferably gene sequences ANP32B, GTF3A, RRM2, TRIM14, SKP2, TRIP13, RFC3, CASP7, TXN, MCM5, PTGES2, OBFC1, EPB41L4B, and CALML4, whose expression indicates chemosensitivity to Taxotere.

l) One or more of the gene sequences IL2RG, H1FX, RDBP, ZAP70, CXCR4, TM4SF2, ARHGDIB, CDA, CD3E, STMN1, GNA15, AXL, CCND3, SATB1, EIF5A, LCK, NKX2-5, LAPTM5, IQGAP2, FLII, EIF3S5, TRB, CD3D, HOXB2, GATA3, HMGB2, PSMB9, ATP5G2, CORO1A, ARHGDIB, DRAP1, PTPRCAP, RHOH, and ATP2A3, preferably gene sequences IFITM2, UBE2L6, LAPTM5, USP4, ITM2A, ITGB2, ANPEP, CD53, IL2RG, CD37, GPRASP1, PTPN7, CXorf9, RHOH, GIT2, ADORA2A, ZNFN1A1, GNA15, CEP1, TNFRSF7, MAP4K1, CCR7, CD3G, PTPRC, ATP2A3, UCP2, CORO1A, GATA3, CDKN2A, HEM1, TARP, LAIR1, SH2D1A, FLII, SEPT6, HA-1, CREB3L1, ERCC2, CD3D, LST1, A1F1, ADA, DATF1, ARHGAP15, PLAC8, CECR1, LOC81558, and EHD2, and most preferably gene sequences IFITM2, UBE2L6, USP4, ITM2A, IL2RG, GPRASP1, PTPN7, CXorf9, RHOH, GIT2, ZNFN1A1, CEP1, TNFRSF7, MAP4K1, CCR7, CD3G, ATP2A3, UCP2, GATA3, CDKN2A, TARP, LAIR1, SH2D1A, SEPT6, HA-1, ERCC2, CD3D, LST1, A1F1, ADA, DATF1, ARHGAP15, PLAC8, CECR1, LOC81558, and EHD2, whose expression indicates chemosensitivity to Dexamethasone.

m) One or more of the gene sequences TM4SF2, ARHGDIB, ADA, H2AFZ, NAP1L1, CCND3, FABP5, LAMR1, REA, MCM5, SNRPF, and USP7, preferably gene sequences ITM2A, RHOH, PRIM1, CENTB1, GNA15, NAP1L1, ATP5G2, GATA3, PRKCQ, SH2D1A, SEPT6, PTPRC, NME4, RPL13, CD3D, CD1E, ADA, and FHOD1, and most preferably gene sequences ITM2A, RHOH, PRIM1, CENTB1, NAP1L1, ATP5G2, GATA3, PRKCQ, SH2D1A, SEPT6, NME4, CD3D, CD1E, ADA, and FHOD1, whose expression indicates chemosensitivity to Ara-C.

n) One or more of the gene sequences LGALS9, CD7, IL2RG, PTPN7, ARHGEF6, CENTB1, SEPT6, SLA, LCP1, IFITM1, ZAP70, CXCR4, TM4SF2, ZNF91, ARHGDIB, TFDP2, ADA, CD99, CD3E, CD1C, STMN1, CD53, CD7, GNA15, CCND3, MAZ, SATB1, ZNF22, AES, AIF1, MYB, LCK, C5orf13, NKX2-5, ZNFN1A1, STAT5A, CHI3L2, LAPTM5, MAP4K1, DDX11, GPSM3, TRB, CD3D, CD3G, PRKCB1, CD1E, HCLS1, GATA3, TCF7, RHOG, CDW52, HMGB2, DGKA, ITGB2, PSMB9, IDH2, AES, MCM5, NUCB2, CORO1A, ARHGDIB, PTPRCAP, CD47, RHOH, LGALS9, and ATP2A3, preferably gene sequences CD99, SRRM1, ARHGDIB, LAPTM5, VWF, ITM2A, ITGB2, LGALS9, INPPSD, SATB1, CD53, TFDP2, SLA, IL2RG, MFNG, CD37, GMFG, SELL, CDW52, LRMP, ICAM2, RIMS3, PTPN7, ARHGAP25, LCK, CXorf9, RHOH, PTPRCAP, GIT2, ZNFN1A1, CENTB1, LCP2, SPI1, GNA15, GZMA, CEP1, BLM, CD8A, SCAP1, CD2, CD1C, TNFRSF7, VAV1, MAP4K1, CCR7, C6orf32, ALOX15B, BRDT, CD3G, PTPRC, LTB, ATP2A3, NVL, RASGRP2, LCP1, CORO1A, CXCR4, PRKD2, GATA3, TRA@, PRKCB1, HEM1, KIAA0922, TARP, SEC31L2, PRKCQ, SH2D1A, CHRNA3, CD1A, LST1, LAIR1, CACNA1G, TRB@, SEPT6, HA-1, DOCK2, CD3D, TRD@, T3JAM, ENBP1, CD6, AIF1, FOLH1, CD1E, LY9, UGT2B17, ADA, CDKL5, TRIM, EVL, DATF1, RGC32, PRKCH, ARHGAP15, NOTCH1, BIN2, SEMA4G, DPEP2, CECR1, BCL11B, STAG3, GALNT6, UBASH3A, PHEMX, FLJ13373, LEF1, IL21R, MGC17330, AKAP13, ZNF335, and GIMAP5, and most preferably gene sequences CD99, ARHGDIB, VWF, ITM2A, LGALS9, INPP5D, SATB1, TFDP2, SLA, IL2RG, MFNG, SELL, CDW52, LRMP, ICAM2, RIMS3, PTPN7, ARHGAP25, LCK, CXorf9, RHOH, GIT2, ZNEN1A1, CENTB1, LCP2, SPI1, GZMA, CEP1, CD8A, SCAP1, CD2, CD1C, TNFRSF7, VAV1, MAP4K1, CCR7, C6orf32, ALOX15B, BRDT, CD3G, LTB, ATP2A3, NVL, RASGRP2, LCP1, CXCR4, PRKD2, GATA3, TRA@, KIAA0922, TARP, SEC31L2, PRKCQ, SH2D1A, CHRNA3, CD1A, LST1, LAIR1, CACNA1G, TRB@, SEPT6, HA-1, DOCK2, CD3D, TRD@, T3JAM, ENBP1, CD6, AIF1, FOLH1, CD1E, LY9, ADA, CDKL5, TRIM, EVL, DATF1, RGC32, PRKCH, ARHGAP15, NOTCH1, BIN2, SEMA4G, DPEP2, CECR1, BCL11B, STAG3, GALNT6, UBASH3A, PHEMX, FLJ13373, LEF1, IL21R, MGC17330, AKAP13, ZNF335, and GIMAP5, whose expression indicates chemosensitivity to Methylprednisolone.

o) One or more of the gene sequences RPLP2, RPL4, HMGA1, RPL27, IMPDH2, LAMR1, PTMA, ATPSB, NPM1, NCL, RPS25, RPL9, TRAP1, RPL21, LAMR1, REA, HNRPA1, LDHB, RPS2, NME1, PAICS, EEF1B2, RPS15A, RPL19, RPL6, ATP5G2, SNRPF, SNRPG, and RPS7, preferably gene sequences PRPF8, RPL18, RNPS1, RPL32, EEF1G, GOT2, RPL13A, PTMA, RPS15, RPLP2, CSDA, KHDRBS1, SNRPA, IMPDH2, RPS19, NUP88, ATPSD, PCBP2, ZNF593, HSU79274, PRIM1, PFDN5, OXA1L, H3F3A, ATIC, RPL13, CIAPIN1 FBL, RPS2, PCCB, RBMX, SHMT2, RPLP0, HNRPA1, STOML2, RPS9, SKB1, GLTSCR2, CCNB1IP1, MRPS2, FLJ20859, and FLJ12270, and most preferably gene sequences PRPF8, RPL18, GOT2, RPL13A, RPS15, RPLP2, CSDA, KHDRBS1, SNRPA, IMPDH2, RPS19, NUP88, ATP5D, PCBP2, ZNF593, HSU79274, PRIM1, PFDN5, OXA1L, H3F3A, ATIC, CIAPIN1, RPS2, PCCB, SHMT2, RPLP0, HNRPA1, STOML2, SKB1, GLTSCR2, CCNBHP1, MRPS2, FLJ20859, and FLJ12270, whose expression indicates chemosensitivity to Methotrexate.

p) One or more of the gene sequences ACTB, COL5A1, MT1E, CSDA, COL4A2, MMP2, COL1A1, TNFRSF1A, CFHL1, TGFBI, FSCN1, NNMT, PLAUR, CSPG2, NFIL3, C5orf13, NCOR2, TUBB4, MYLK, TUBA3, PLAU, COL4A2, COL6A2, COL6A3, IFITM2, PSMB9, CSDA, and COL1A1, preferably gene sequences MSN, PFN1, HK1, ACTR2, MCL1, ZYX, RAP1B, GNB2, EPAS1, PGAM1, CKAP4, DUSP1, MYL9, K-ALPHA-1, LGALS1, CSDA, AKR1B1, IFITM2, ITGA5, VIM, DPYSL3, JUNB, ITGA3, NFKBIA, LAMB1, FHL1, INSIG1, TIMP1, GJA1, PSME2, PRG1, EXT1, DKFZP434J154, OPTN, M6PRBP1, MVP, VASP, ARL7, NNMT, TAP1, COL1A1, BASP1, PLOD2, ATF3, PALM2-AKAP2, IL8, ANPEP, LOXL2, TGFB1, IL4R, DGKA, STC2, SEC61G, NFIL3, RGS3, NK4, F2R, TPM2, PSMB9, LOX, STC1, CSPG2, PTGER4, IL6, SMAD3, PLAU, WNT5A, BDNF, TNFRSF1A, FLNC, DKFZP564K0822, FLOT1, PTRF, HLA-B, COL6A2, MGC4083, TNFRSF10B, PLAGL1, PNMA2, TFPI, LAT, GZMB, CYR61, PLAUR, FSCN1, ERP70, AF1Q, UBC, FGFR1, HIC, BAX, COL4A2, COL6A1, IFITM3, MAP1B, FLJ46603, RAFTLIN, RRAS, FTL, KIAA0877, MT1E, CDC10, DOCK2, TRIM22, RIS1, BCAT1, PRF1, DBN1, MT1K, TMSB10, RAB31, FLJ10350, C1orf24, NME7, TMEM22, TPK1, COL5A2, ELK3, CYLD, ADAMTS1, EHD2, and ACTB, and most preferably gene sequences PFN1, HK1, MCL1, ZYX, RAP1B, GNB2, EPAS1, PGAM1, CKAP4, DUSP1, MYL9, K-ALPHA-1, LGALS1, CSDA, IFITM2, ITGA5, DPYSL3, JUNB, NFKBIA, LAMB1, FHL1, INSIG1, TIMP1, GJA1, PSME2, PRG1, EXT1, DKFZP434J154, MVP, VASP, ARL7, NNMT, TAP1, PLOD2, ATF3, PALM2-AKAP2, IL8, LOXL2, IL4R, DGKA, STC2, SEC61G, RGS3, F2R, TPM2, PSMB9, LOX, STC1, PTGER4, IL6, SMAD3, WNT5A, BDNF, TNFRSF1A, FLNC, DKFZP564K0822, FLOT1, PTRF, HLA-B, MGC4083, TNFRSF10B, PLAGL1, PNMA2, TFPI, LAT, GZMB, CYR61, PLAUR, FSCN1, ERP70, AF1Q, HIC, COL6A1, IFITM3, MAP1B, FLJ46603, RAFTLIN, RRAS, FTL, KIAA0877, MT1E, CDC10, DOCK2, TRIM22, RIS1, BCAT1, PRF1, DBN1, MT1K, TMSB10, FLJ10350, C1orf24, NME7, TMEM22, TPK1, COL5A2, ELK3, CYLD, ADAMTS1, EHD2, and ACTB, whose expression indicates chemosensitivity to Bleomycin.

q) One or more of the gene sequences NOS2A, MUC1, TFF3, GP1BB, IGLL1, BATF, MYB, PTPRS, NEFL, AIP, CEL, DGKA, RUNX1, ACTR1A, and CLCNKA, preferably gene sequences PTMA, SSRP1, NUDC, CTSC, AP1G2, PSME2, LBR, EFNB2, SERPINA1, SSSCA1, EZH2, MYB, PRIM1, H2AFX, HMGA1, HMMR, TK2, WHSC1, DIAPH1, LAMB3, DPAGT1, UCK2, SERPINB1, MDN1, BRRN1, G0S2, RAC2, MGC21654, GTSE1, TACC3, PLEK2, PLAC8, HNRPD, and PNAS-4, and most preferably gene sequences SSRP1, NUDC, CTSC, AP1G2, PSME2, LBR, EFNB2, SERPINA1, SSSCA1, EZH2, MYB, PRIM1, H2AFX, HMGA1, HMMR, TK2, WHSC1, DIAPH1, LAMB3, DPAGT1, UCK2, SERPINB1, MDN1, BRRN1, G0S2, RAC2, MGC21654, GTSE1, TACC3, PLEK2, PLAC8, HNRPD, and PNAS-4, whose expression indicates chemosensitivity to Methyl-GAG.

r) One or more of the gene sequences MSN, ITGA5, VIM, TNFAIP3, CSPG2, WNT5A, FOXF2, LOC94105, IFI16, LRRN3, FGFR1, DOCK10, LEPRE1, COL5A2, and ADAMTS1, and most preferably gene sequences ITGA5, TNFAIP3, WNT5A, FOXF2, LOC94105, IFI16, LRRN3, DOCK10, LEPRE1, COL5A2, and ADAMTS1, whose expression indicates chemosensitivity to carboplatin.

s) One or more of the gene sequences RPL18, RPL10A, RNPS1, ANAPC5, EEF1B2, RPL13A, RPS15, AKAP1, NDUFAB1, APRT, ZNF593, MRP63, IL6R, RPL13, SART3, RPS6, UCK2, RPL3, RPL17, RPS2, PCCB, TOMM20, SHMT2, RPLP0, GTF3A, STOML2, DKFZp564J157, MRPS2, ALG5, and CALML4, and most preferably gene sequences RPL18, RPL10A, ANAPC5, EEF1B2, RPL13A, RPS15, AKAP1, NDUFAB1, APRT, ZNF593, MRP63, IL6R, SART3, UCK2, RPL17, RPS2, PCCB, TOMM20, SHMT2, RPLP0, GTF3A, STOML2, DKFZp564J157, MRPS2, ALG5, and CALML4, whose expression indicates chemosensitivity to 5-FU (5-Fluorouracil).

t) One or more of the gene sequences ITK, KIFC1, VLDLR, RUNX1, PAFAH1B3, H1FX, RNF144, TMSNB, CRY1, MAZ, SLA, SRF, UMPS, CD3Z, PRKCQ, HNRPM, ZAP70, ADD1, RFC5, TM4SF2, PFN2, BMI1, TUBGCP3, ATP6V1B2, RALY, PSMC5, CD1D, ADA, CD99, CD2, CNP, ERG, MYL6, CD3E, CD1A, CD1B, STMN1, PSMC3, RPS4Y1, AKT1, TAL1, GNA15, UBE2A, TCF12, UBE2S, CCND3, PAX6, MDK, CAPG, RAG2, ACTN1, GSTM2, SATB1, NASP, IGFBP2, CDH2, CRABP1, DBN1, CTNNA1, AKR1C1, CACNB3, FARSLA, CASP2, CASP2, E2F4, LCP2, CASP6, MYB, SFRS6, GLRB, NDN, CPSF1, GNAQ, TUSC3, GNAQ, JARID2, OCRL, FHL1, EZH2, SMOX, SLC4A2, UFD1L, SEPW1, ZNF32, HTATSF1, SHD1, PTOV1, NXF1, FYB, TRIM28, BC008967, TRB@, TFRC, H1F0, CD3D, CD3G, CENPB, ALDH2, ANXA1, H2AFX, CD1E, DDX5, ABL1, CCNA2, ENO2, SNRPB, GATA3, RRM2, GLUL, TCF7, FGFR1, SOX4, MAL, NUCB2, SMA3, FAT, UNG, ARHGDIB, RUNX1, MPHOSPH6, DCTN1, SH3GL3, VIM, PLEKHC1, CD47, POLR2F, RHOH, ADD1, and ATP2A3, preferably gene sequences ITK, KIFC1, VLDLR, RUNX1, PAFAH1B3, H1FX, RNF144, TMSNB, CRY1, MAZ, SLA, SRF, UMPS, CD3Z, PRKCQ, HNRPM, ZAP70, ADD1, RFC5, TM4SF2, PFN2, BMI1, TUBGCP3, ATP6V1B2, RALY, PSMC5, CD1D, ADA, CD99, CD2, CNP, ERG, MYL6, CD3E, CD1A, CD1B, STMN1, PSMC3, RPS4Y1, AKT1, TAL1, GNA15, UBE2A, TCF12, UBE2S, CCND3, PAX6, MDK, CAPG, RAG2, ACTN1, GSTM2, SATB1, NASP, IGFBP2, CDH2, CRABP1, DBN1, CTNNA1, AKR1C1, CACNB3, FARSLA, CASP2, CASP2, E2F4, LCP2, CASP6, MYB, SFRS6, GLRB, NDN, CPSF1, GNAQ, TUSC3, GNAQ, JARID2, OCRL, FHL1, EZH2, SMOX, SLC4A2, UFD1L, SEPW1, ZNF32, HTATSF1, SHD1, PTOV1, NXF1, FYB, TRIM28, BC008967, TRB@, TFRC, H1F0, CD3D, CD3G, CENPB, ALDH2, ANXA1, H2AFX, CD1E, DDX5, ABL1, CCNA2, ENO2, SNRPB, GATA3, RRM2, GLUL, TCF7, FGFR1, SOX4, MAL, NUCB2, SMA3, FAT, UNG, ARHGDIB, RUNX1, MPHOSPH6, DCTN1, SH3GL3, VIM, PLEKHC1, CD47, POLR2F, RHOH, ADD1, and ATP2A3, and most preferably gene sequences KIFC1, VLDLR, RUNX1, PAFAH1B3, H1FX, RNF144, TMSNB, CRY1, MAZ, SLA, SRF, UMPS, CD3Z, PRKCQ, HNRPM, ZAP70, ADD1, RFC5, TM4SF2, PFN2, BMI1, TUBGCP3, ATP6V1B2, CD1D, ADA, CD99, CD2, CNP, ERG, CD3E, CD1A, PSMC3, RPS4Y1, AKT1, TALE UBE2A, TCF12, UBE2S, CCND3, PAX6, RAG2, GSTM2, SATB1, NASP, IGFBP2, CDH2, CRABP1, DBN1, AKR1C1, CACNB3, CASP2, CASP2, LCP2, CASP6, MYB, SFRS6, GLRB, NDN, GNAQ, TUSC3, GNAQ, JARID2, OCRL, FHL1, EZH2, SMOX, SLC4A2, UFD1L, ZNF32, HTATSF1, SHD1, PTOV1, NXF1, FYB, TRIM28, BC008967, TRB@, H1F0, CD3D, CD3G, CENPB, ALDH2, ANXA1, H2AFX, CD1E, DDX5, CCNA2, ENO2, SNRPB, GATA3, RRM2, GLUL, SOX4, MAL, UNG, ARHGDIB, RUNX1, MPHOSPH6, DCTN1, SH3GL3, PLEKHC1, CD47, POLR2F, RHOH, and ADD1, whose expression indicates chemosensitivity to Rituximab (e.g., MABTHERA™).

u) One or more of the gene sequences CCL21, ANXA2, SCARB2, MAD2L1BP, CAST, PTS, NBL1, ANXA2, CD151, TRAM2, HLA-A, CRIP2, UGCG, PRSS11, MME, CBR1, LGALS1, DUSP3, PFN2, MICA, FTH1, RHOC, ZAP128, PON2, COL5A2, CST3, MCAM, IGFBP3, MMP2, GALIG, CTSD, ALDH3A1, CSRP1, S100A4, CALD1, CTGF, CAPG, HLA-A, ACTN1, TAGLN, FSTL1, SCTR, BLVRA, COPEB, DIPA, SMARCD3, FN1, CTSL, CD63, DUSP1, CKAP4, MVP, PEA15, S100A13, and ECE1, preferably gene sequences TRA1, ACTN4, WARS, CALM1, CD63, CD81, FKBP1A, CALU, IQGAP1, CTSB, MGC8721, STAT1, TACC1, TM4SF8, CD59, CKAP4, DUSP1, RCN1, MGC8902, LGALS1, BHLHB2, RRBP1, PKM2, PRNP, PPP2CB, CNN3, ANXA2, IER3, JAK1, MARCKS, LUM, FER1L3, SLC20A1, EIF4G3, HEXB, EXT1, TJP1, CTSL, SLC39A6, RIOK3, CRK, NNMT, COL1A1, TRAM2, ADAM9, DNAJC7, PLSCR1, PRSS23, PLOD2, NPC1, TOB1, GFPT1, IL8, DYRK2, PYGL, LOXL2, KIAA0355, UGDH, NFIL3, PURA, ULK2, CENTG2, NID2, CAP350, CXCL1, BTN3A3, IL6, WNT5A, FOXF2, LPHN2, CDH11, P4HA1, GRP58, ACTN1, CAPN2, DSIPI, MAP1LC3B, GALIG, IGSF4, IRK, ATP2A2, OGT, TNFRSF10B, KIAA1128, TM4SF1, RBPMS, RIPK2, CBLB, NR1D2, BTN3A2, SLC7A11, MPZL1, IGFBP3, SSA2, FN1, NQO1, ASPH, ASAH1, MGLL, SERPINB6, HSPA5, ZFP36L1, COL4A2, COL4A1, CD44, SLC39A14, NIPA2, FKBP9, IL6ST, DKFZP564G2022, PPAP2B, MAP1B, MAPK1, MYO1B, CAST, RRAS2, QKI, LHFPL2, 38970, ARHE, KIAA1078, FTL, KIAA0877, PLCB1, KIAA0802, KPNB1, RAB3GAP, SERPINB1, TIMM17A, SOD2, HLA-A, NOMO2, L0055831, PHLDA1, TMEM2, MLPH, FAD104, LRRC5, RAB7L1, FLJ35036, DOCK10, LRP12, TXNDC5, CDC14B, HRMT1L1, CORO1C, DNAJC10, TNPO1, LONP, AMIGO2, DNAPTP6, and ADAMTS1, and most preferably gene sequences TRA1, ACTN4, CALM1, CD63, FKBP1A, CALU, IQGAP1, MGC8721, STAT1, TACC1, TM4SF8, CD59, CKAP4, DUSP1, RCN1, MGC8902, LGALS1, BHLHB2, RRBP1, PRNP, IER3, MARCKS, LUM, FER1L3, SLC20A1, HEXB, EXT1, TJP1, CTSL, SLC39A6, RIOK3, CRK, NNMT, TRAM2, ADAM9, DNAJC7, PLSCR1, PRSS23, PLOD2, NPC1, TOB1, GFPT1, IL8, PYGL, LOXL2, KIAA0355, UGDH, PURA, ULK2, CENTG2, NID2, CAP350, CXCL1, BTN3A3, IL6, WNT5A, FOXF2, LPHN2, CDH11, P4HA1, GRP58, DSIPI, MAP1LC3B, GALIG, IGSF4, IRK, ATP2A2, OGT, TNFRSF10B, KIAA1128, TM4SF1, RBPMS, RIPK2, CBLB, NR1D2, SLC7A11, MPZL1, SSA2, NQO1, ASPH, ASAH1, MGLL, SERPINB6, HSPA5, ZFP36L1, COL4A1, CD44, SLC39A14, NIPA2, FKBP9, IL6ST, DKFZP564G2022, PPAP2B, MAP1B, MAPK1, MYO1B, CAST, RRAS2, QKI, LHFPL2, 38970, ARHE, KIAA1078, FTL, KIAA0877, PLCB1, KIAA0802, RAB3GAP, SERPINBE TIMM17A, SOD2, HLA-A, NOMO2, L0055831, PHLDA1, TMEM2, MLPH, FAD104, LRRC5, RAB7L1, FLJ35036, DOCK10, LRP12, TXNDC5, CDC14B, HRMT1L1, CORO1C, DNAJC10, TNPO1, LONP, AMIGO2, DNAPTP6, and ADAMTS1, whose expression indicates sensitivity to radiation therapy.

v) One or more of the gene sequences FAU, NOL5A, ANP32A, ARHGDIB, LBR, FABP5, ITM2A, SFRS5, IQGAP2, SLC7A6, SLA, IL2RG, MFNG, GPSM3, PIM2, EVER1, LRMP, ICAM2, RIMS3, FMNL1, MYB, PTPN7, LCK, CXorf9, RHOH, ZNFN1A1, CENTB1, LCP2, DBT, CEP1, IL6R, VAV1, MAP4K1, CD28, PTP4A3, CD3G, LTB, USP34, NVL, CD8B1, SFRS6, LCP1, CXCR4, PSCDBP, SELPLG, CD3Z, PRKCQ, CD1A, GATA2, P2RX5, LAIR1, C1orf38, SH2D1A, TRB@, SEPT6, HA-1, DOCK2, WBSCR20C, CD3D, RNASE6, SFRS7, WBSCR20A, NUP210, CD6, HNRPA1, AIF1, CYFIP2, GLTSCR2, Cllorf2, ARHGAP15, BIN2, SH3TC1, STAG3, TM6SF1, C15orf25, FLJ22457, PACAP, and MGC2744, whose expression indicates sensitivity to an HDAC inhibitor.

w) One or more of the gene sequences CD99, SNRPA, CUGBP2, STAT5A, SLA, IL2RG, GTSE1, MYB, PTPN7, CXorf9, RHOH, ZNFN1A1, CENTB1, LCP2, HIST1H4C, CCR7, APOBEC3B, MCM7, LCP1, SELPLG, CD3Z, PRKCQ, GZMB, SCN3A, LAIR1, SH2D1A, SEPT6, CG018, CD3D, C18orf10, PRF1, AIF1, MCM5, LPXN, C22orf18, ARHGAP15, and LEF1, whose expression indicates sensitivity to 5-Aza-2'-deoxycytidine (Decitabine).

Probes that may be employed on microarrays of the invention include oligonucleotide probes having sequences complementary to any of the biomarker gene or microRNA sequences described above. Additionally, probes employed on microarrays of the invention may also include proteins, peptides, or antibodies that selectively bind any of the oligonucleotide probe sequences or their complementary sequences. Exemplary probes are listed in Tables 22-44, wherein for each treatment listed, the biomarkers indicative of treatment sensitivity, the correlation of biomarker expression to growth inhibition, and the sequence of an exemplary probe (Tables 22-44) to detect biomarker (Tables 1-21) expression are shown.

Identification of Biomarker Genes

The gene expression measurements of the NCI60 cancer cell lines were obtained from the National Cancer Institute and the Massachusetts Institute of Technology (MIT). Each dataset was normalized so that sample expression measured by different chips could be compared. The preferred method of normalization is the logit transformation, which is performed for each gene y on each chip:

$$\text{logit}(y)=\log [(y-\text{background})/(\text{saturation}-y)],$$

where background is calculated as the minimum intensity measured on the chip minus 0.1% of the signal intensity range: min-0.001*(max-min), and saturation is calculated as the maximum intensity measured on the chip plus 0.1% of the signal intensity range: max+0.001*(max−min). The resulting logit transformed data is then z-transformed to mean zero and standard deviation 1.

Next, gene expression is correlated to cancer cell growth inhibition. Growth inhibition data (GI50) of the NCI60 cell lines in the presence of any one of thousands of tested compounds was obtained from the NCI. The correlation between the logit-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given compound may be correlated to the patient's gene expression. Since a plurality of measurements may be available for a single gene, the most accurate determination of correlation coefficient was found to be the median of the correlation coefficients calculated for all probes measuring expression of the same gene.

The median correlation coefficient of gene expression measured on a probe to growth inhibition or patient sensitivity is calculated for all genes, and genes that have a median correlation above 0.3, 0.4, 0.5, 0.6, 0.7, 0.8, 0.9, 0.95, or 0.99 are retained as biomarker genes. Preferably, the correlation coefficient of biomarker genes will exceed 0.3. This is repeated for all the compounds to be tested. The result is a list of marker genes that correlates to sensitivity for each compound tested.

Predicting Patient Sensitivity or Resistance to Medical Treatment

For a given compound, the biomarker whose expression has been shown to correlate to chemosensitivity can be used to classify a patient, e.g., a cancer patient, as sensitive to a medical treatment, e.g., administration of a chemotherapeutic agent or radiation. Using a tumor sample or a blood sample (e.g., in case of leukemia or lymphoma) from a patient, expression of the biomarker in the cells of the patient in the presence of the treatment agent is determined (using, for example, an RNA extraction kit, a DNA microarray and a DNA microarray scanner). The biomarker expression measurements are then logit transformed as described above. The sum of the expression measurements of the biomarkers is then compared to the median of the sums derived from a training set population of patients having the same tumor. If the sum of biomarker expression in the patient is closest to the median of the sums of expression in the surviving members of the training set, the patient is predicted to be sensitive to the compound or other medical treatment. If the sum of expression in the patient is closest to the median of the sums of expression in the non-surviving members of the training set, the patient is predicted to be resistant to the compound.

Machine learning techniques such as Neural Networks, Support Vector Machines, K Nearest Neighbor, and Nearest Centroids may also be employed to develop models that discriminate patients sensitive to treatment from those resistant to treatment using biomarker expression as model variables which assign each patient a classification as resistant or sensitive. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; and V. Tresp et al., "Neural Network Modeling of Physiological Processes", in Hanson S. J. et al. (Eds.), Computational Learning Theory and Natural Learning Systems 2, MIT Press, 1994, hereby incorporated by reference.

Other variables can be used to determine relative biomarker expression between a patient (e.g., a cancer patient) and a normal subject (e.g., a control subject), including but not limited to, measurement of biomarker DNA copy number and the identification of biomarker genetic mutations.

A more compact microarray can be designed using only the oligonucleotide probes having measurements yielding the median correlation coefficients with cancer cell growth inhibition. Thus, in this embodiment, only one probe needs to be used to measure expression of each biomarker. Biomarkers include polypeptides and metabolites thereof. A skilled artisan can use employ assays that measure changes in polypeptide biomarker expression (e.g., Western blot, immunofluorescent staining, and flow cytometry) to determine a patient's sensitivity to a treatment (e.g., chemotherapy, radiation therapy, or surgery).

Identifying a Subpopulation of Patients Sensitive to a Treatment for Cancer

The invention can also be used to identify a subpopulation of patients, e.g., cancer patients, that are sensitive to a compound or other medical treatment previously thought to be ineffective for the treatment of cancer. To this end, genes or microRNAs whose expression correlates to sensitivity to a compound or other treatment can be identified so that patients sensitive to a compound or other treatment may be identified. To identify such biomarkers, gene or microRNA expression within cell lines can be correlated to the growth of those cell lines in the presence of the same compound or other treatment. Preferably, genes or microRNAs whose expression correlates to cell growth with a correlation coefficient exceeding 0.3 may be considered possible biomarkers.

Alternatively, genes or microRNAs can be identified as biomarkers according to their ability to discriminate patients known to be sensitive to a treatment from those known to be resistant. The significance of the differences in gene or microRNA expression between the sensitive and resistant patients may be measured using, e.g., t-tests. Alternatively, naïve Bayesian classifiers may be used to identify gene biomarkers that discriminate sensitive and resistant patient subpopulations given the gene expressions of the sensitive and resistant subpopulations within a treated patient population.

The patient subpopulations considered can be further divided into patients predicted to survive without treatment, patients predicted to die without treatment, and patients predicted to have symptoms without treatment. The above methodology may be similarly applied to any of these further defined patient subpopulations to identify biomarkers able to predict a subject's sensitivity to compounds or other treatments for the treatment of cancer.

Patients with elevated expression of biomarkers correlated to sensitivity to a compound or other medical treatment would be predicted to be sensitive to that compound or other medical treatment.

The invention is particularly useful for recovering compounds or other treatments that failed in clinical trials by identifying sensitive patient subpopulations using the gene or microRNA expression methodology disclosed herein to identify biomarkers that can be used to predict clinical outcome.

Kit, Apparatus, and Software for Clinical Use

This invention can also be used to predict patients who are resistant or sensitive to a particular treatment by using a kit that includes a kit for RNA extraction from tumors (e.g., Trizol from Invitrogen Inc.), a kit for RNA amplification (e.g., MessageAmp from Ambion Inc.), a microarray for measuring biomarker expression (e.g., HG-U133A GeneChip from Affymetrix Inc.), a microarray hybridization station and scanner (e.g., GeneChip System 3000Dx from Affymetrix Inc.), and software for analyzing the expression of marker genes as described in herein (e.g., implemented in R from R-Project or S-Plus from Insightful Corp.).

Methodology of the In Vitro Cancer Growth Inhibition Screen

The human tumor cell lines of the cancer screening panel are grown in RPMI 1640 medium containing 5% fetal bovine serum and 2 mM L-glutamine. Cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air, and 100% relative humidity for 24 hrs prior to addition of experimental compounds.

After 24 hrs, two plates of each cell line are fixed in situ with TCA, to represent a measurement of the cell population for each cell line at the time of compound addition (Tz). Experimental compounds are solubilized in dimethyl sulfoxide at 400-fold the desired final maximum test concentration and stored frozen prior to use. At the time of compound addition, an aliquot of frozen concentrate is thawed and diluted to twice the desired final maximum test concentration with complete medium containing 50 μg/mL Gentamicin. Additional four, 10-fold or ½ log serial dilutions are made to provide a total of five compound concentrations plus control. Aliquots of 100 μL of these different compound dilutions are added to the appropriate microtiter wells already containing 100 μL of medium, resulting in the required final compound concentrations.

Following compound addition, the plates are incubated for an additional 48 hrs at 37° C., 5% $CO_2$, 95% air, and 100% relative humidity. For adherent cells, the assay is terminated by the addition of cold TCA. Cells are fixed in situ by the gentle addition of 50 μL of cold 50% (w/v) TCA (final concentration, 10% TCA) and incubated for 60 min at 4° C. The supernatant is discarded, and the plates are washed five times with tap water and air-dried. Sulforhodamine B (SRB) solution (100 μL) at 0.4% (w/v) in 1% acetic acid is added to each well, and plates are incubated for 10 min at room temperature. After staining, unbound dye is removed by washing five times with 1% acetic acid and the plates are air-dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μL of 80% TCA (final concentration, 16% TCA). Using the seven absorbance measurements [time zero, (Tz), control growth, (C), and test growth in the presence of compound at the five concentration levels (Ti)], the percentage growth is calculated at each of the compound concentrations levels. Percentage growth inhibition is calculated as:

$$[(Ti-Tz)/(C-Tz)]\times 100 \text{ for concentrations for which } Ti >/= Tz$$

$$[(Ti-Tz)/Tz]\times 100 \text{ for concentrations for which } Ti < Tz$$

Three dose response parameters are calculated for each experimental agent. Growth inhibition of 50% (GI50) is calculated from $[(Ti-Tz)/(C-Tz)]\times 100=50$, which is the compound concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from $[(Ti-Tz)/Tz]\times 100=-50$. Values are calculated for each of these three parameters if the level of activity is reached; however, if the effect is not reached or is exceeded, the value for that parameter is expressed as greater or less than the maximum or minimum concentration tested.

RNA Extraction and Gene Expression Measurement

Cell/tissue samples are snap frozen in liquid nitrogen until processing. RNA is extracted using e.g., Trizol Reagent (Invitrogen) following manufacturers instructions. RNA is amplified using e.g., MessageAmp kit (Ambion) following manufacturers instructions. Amplified RNA is quantified using e.g., HG-U133A GeneChip (Affymetrix) and compatible apparatus e.g., GCS3000Dx (Affymetrix), using manufacturers instructions.

The resulting gene expression measurements are further processed as described in this document. The procedures described can be implemented using R software available from R-Project and supplemented with packages available from Bioconductor.

For many drugs 10-30 biomarkers are sufficient to give an adequate response, thus, given the relatively small number of biomarkers required, procedures, such as quantitative reverse transcriptase polymerase chain reaction (qRT-PCR), can be performed to measure, with greater precision, the amount of biomarker genes expressed in a sample. This will provide an alternative to or a complement to microarrays so that a single companion test, typically more quantitative than microarrays alone, employing biomarkers of the invention can be used to predict sensitivity to a new drug. qRT-PCR can be performed alone or in combination with a microarray described herein. Procedures for performing qRT-PCR are described in, e.g., U.S. Pat. No. 7,101,663 and U.S. Patent Application Nos. 2006/0177837 and 2006/0088856. The methods of the invention are readily applicable to newly discovered drugs as well as drugs described herein.

The following examples are provided so that those of ordinary skill in the art can see how to use the methods and kits of the invention. The examples are not intended to limit the scope of what the inventor regards as their invention.

EXAMPLES

Example 1

Identification of Gene Biomarkers for Chemosensitivity to Common Chemotherapy Drugs DNA chip measurements of the 60 cancer cell lines of the NCI60 data set were downloaded from the Broad Institute (Cambridge, Mass.) and logit normalized. Growth inhibition data of thousands of compounds against the same cell lines were downloaded from the National Cancer Institute. Compounds where the difference concentration to achieve 50% in growth inhibition (GI50) was less than 1 log were deemed uninformative and rejected. Each gene's expression in each cell line was correlated to its growth (−log(GI50)) in those cell lines in the presence of a given compound. The median Pearson correlation coefficient was used when multiple expression measurements were available for a given gene, and genes having a median correlation coefficient greater than 0.3 were identified as biomarkers for a given compound.

Example 2

Prediction of Treatment Sensitivity for Brain Cancer Patients

DNA chip measurements of gene expression in tumors from 60 brain cancer patients were downloaded from the Broad Institute. All data files were logit normalized. For each of the common chemotherapy drugs Cisplatin, Vincristine, Adriamycine, Etoposide, Aclarubicine, Mitoxantrone and Azaguanine, the gene expression for the marker genes was summed. The sum was normalized by dividing by the standard deviation of all patients and compared to the median of the sums of patients who survived and the median of the sums of patients who died:

$$NormalizedSum(compound) = \frac{sum(marker\ genes\ for\ compound)}{sd(sums\ of\ all\ patients)}$$

$$Sensitivity(compound) = \left[\frac{NormalizedSum(compound) - }{median(NormalizedSumdeadpatients(compound))}\right]^2 - \left[\frac{NormalizedSum(compound) - }{median(NormalizedSumsurvivingpatients(compound))}\right]^2$$

Figure 2:
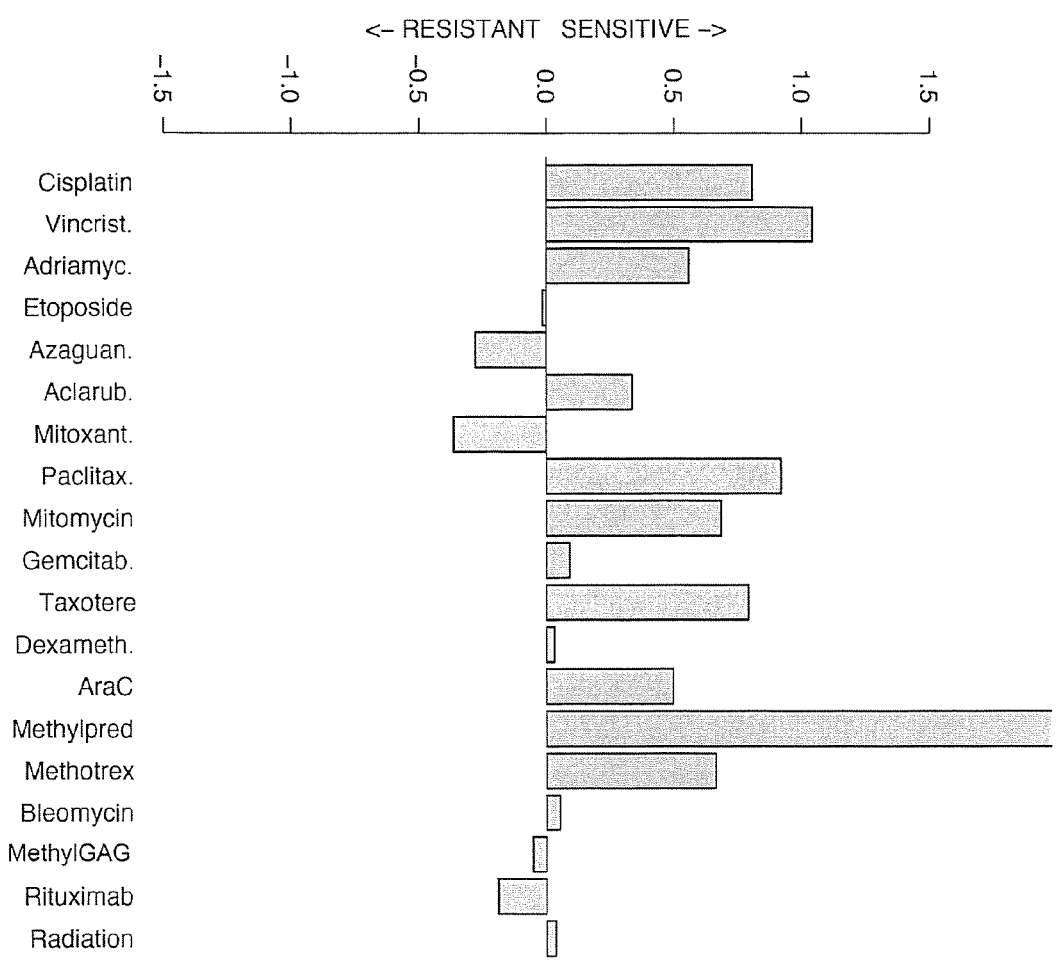
FIG. 2 depicts the treatment sensitivity predictions for a 5-year-old American boy with a brain tumor. The subject had surgery to remove the tumor and, based on the analysis of gene expression in cells from a sample of the tumor, the subject was predicted to be chemosensitive to ten chemotherapy drugs. The subject received Vincristine and Cisplatin and survived.
Figure 3:
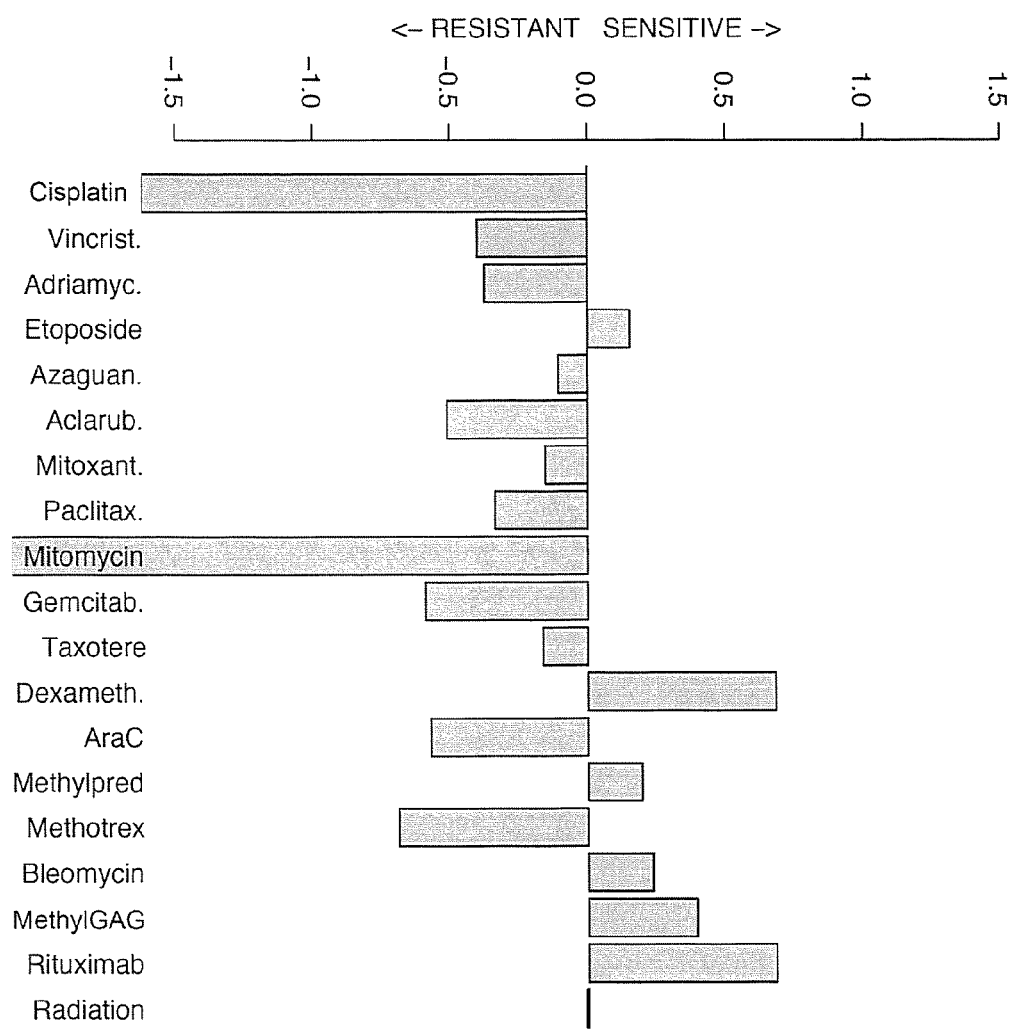
FIG. 3 depicts the treatment sensitivity predictions for a 7-month-old American girl with a brain tumor. The subject had surgery to remove the tumor, and based on the analysis of gene expression in cells from a sample of the tumor, the subject was predicted to be chemoresistant to twelve chemotheraphydrugs. The subject received Vincristine and Cisplatin, but passed away 9 months later.
Figure 4:
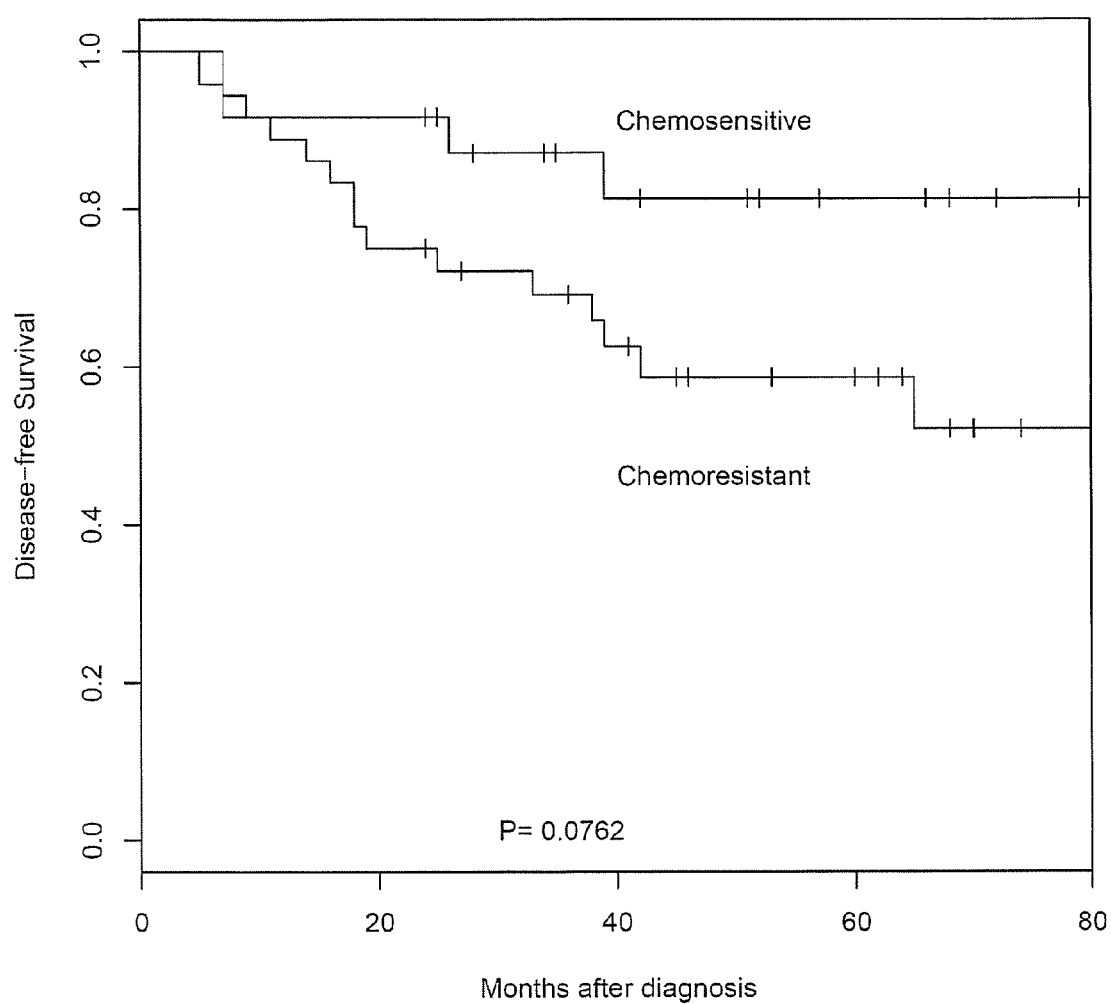
FIG. 4 depicts the survival rate of 60 brain cancer patients divided into a group predicted to be chemosensitive to Cisplatin and a group predicted to be chemoresistant to Cisplatin. All patients received Cisplatin after surgery.

FIGS. 2 and 3 show the resulting treatment sensitivity predictions for two of the 60 patients. All patients received Cisplatin and the prediction of survival amongst the 60 patients based on their Cisplatin chemosensitivity yielded the Kaplan-Meier survival curve shown in FIG. 4. The expression of the 16 Cisplatin biomarker genes was first reduced to 5 components (dimensions) using Independent Component Analysis (fastICA). Five different classification methods were trained on the five components from the 60 patients: K Nearest Neighbor with K=1, K Nearest Neighbor with K=3, Nearest Centroid, Support Vector Machine, and Neural Network. Chemosensitivity or sensitivity to radiation treatment was predicted by combining the classifications of the five methods wherein each classification method was assigned a single vote: unanimous chemosensitive/treatment sensitive prediction resulted in a prediction of chemosensitive/treatment sensitive. All other predictions resulted in a prediction of chemoresistant/treatment resistant. The performance of the combined classifier was validated using leave-one-out cross validation and the survival of the two predicted groups shown in FIG. 4. The survival rate of the patients predicted to be chemosensitive was higher than the patients predicted to be chemoresistant.

Example 3

Prediction of Chemosensitivity for Lymphoma (DLBCL) Patients

Figure 5:
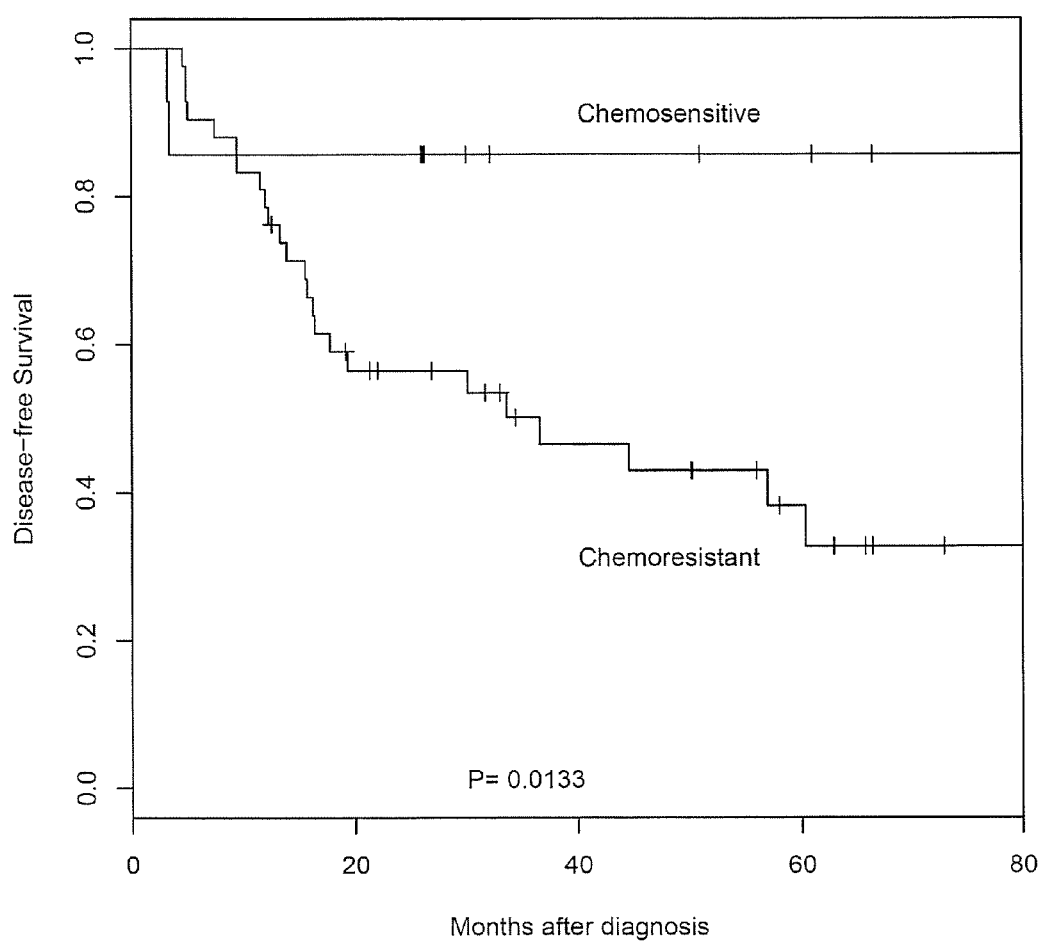
FIG. 5 depicts the survival rate of 56 lymphoma patients divided into a group predicted to be chemosensitive to Vincristine and Adriamycin and a group predicted to be chemoresistant. All patients received Vincristine and Adriamycin.

DNA chip measurements of gene expression in the tumors from 56 DLBCL (diffuse large B-cell lymphoma) patients were downloaded from the Broad Institute. All data files were logit normalized. All patients received Vincristine and Adriamycine and the prediction of survival amongst the 56 patients based on their Vincristine and Adriamycine chemosensitivity yielded the Kaplan-Meier survival curve shown in FIG. 5. The expression of the 33 Vincristine genes and 16 Adriamycine genes was first reduced to 3 components (dimensions) using Independent Component Analysis (fastICA). Five different classification methods were trained on the independent components from the 56 patients: K Nearest Neighbor with K=1, K Nearest Neighbor with K=3, Nearest Centroid, Support Vector Machine, and Neural Network. Chemosensitivity was predicted by combining the classifications of the five methods wherein each classification method was assigned a single vote: unanimous chemosensitive prediction resulted in a prediction of chemosensitive. All other predictions resulted in a prediction of chemoresistant. The performance of the combined classifier was validated using leave-one-out cross validation and the survival of the two predicted groups is shown in FIG. 5. The survival rate of the patients predicted to be chemosensitive was higher than the patients predicted to be chemoresistant.

Example 4

Prediction of Chemosensitivity for Lung Cancer Patients

Figure 6:
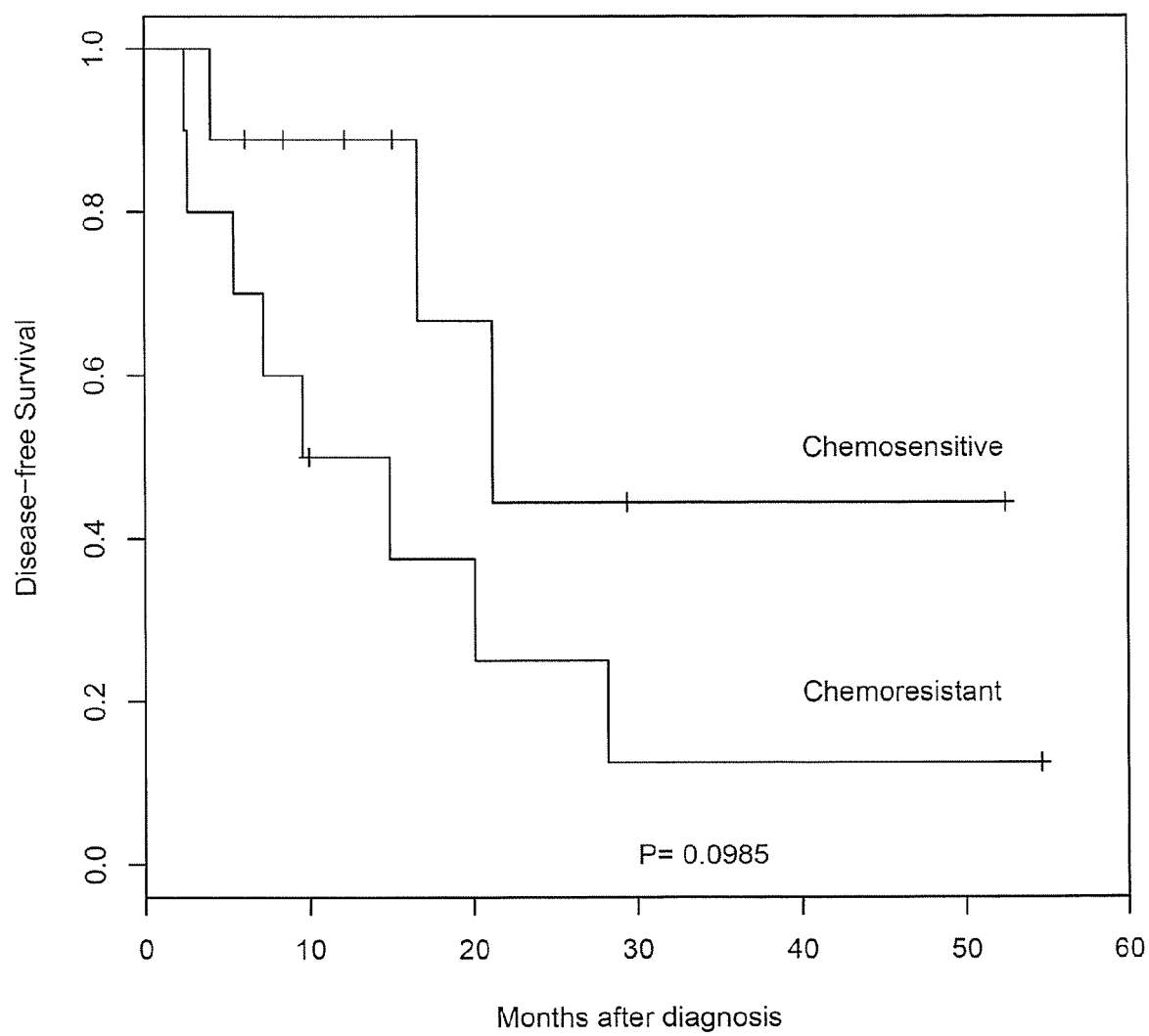
FIG. 6 depicts the survial rate of 19 lung cancer patients divided into a group predicted to be chemosensitive to Cisplatin and a group predicted to be chemoresistant. All patients received Cisplatin.

DNA chip measurements of gene expression in the tumors from 86 lung cancer (adenocarcinoma) patients was downloaded from the University of Michigan, Ann Arbor. Of the 86 patients, 19 had Stage III of the disease and received adjuvant chemotherapy. Raw data was logit normalized. Instead of the combined classifier described for the brain cancer and lymphoma examples above, the sum of biomarker gene expression was calculated for each patient and used to discriminate chemosensitive and chemoresistant patients. For each patient, the gene expression of the 16 marker genes for Cisplatin sensitivity (all Stage III patients received Cisplatin after surgery) was summed. If the sum was closer to the median of the sums of the surviving patients, the patient was predicted to be sensitive to Cisplatin. If the sum was closest to the median of the sums of the non-surviving patients, the patient was predicted to be resistant to Cisplatin. The survival rates of the two predicted groups are shown in FIG. 6. The survival rate of the patients predicted to be chemosensitive was higher than the patients predicted to be chemoresistant.

Example 5

Prediction of Rituximab Sensitivity for Lymphoma (DLBCL) Patients

The method is not limited to cytotoxic chemicals. It is also applicable to predicting the efficacy of protein therapeutics, such as monoclonal antibodies, approved for treating cancer. For example, the monoclonal antibody Rituximab (e.g., MABTHERA™ and RITUXAN™) was examined. Data for cytotoxicity of Rituximab in cell lines in vitro were obtained from published reports (Ghetie et al., *Blood* 97(5):1392-1398, 2001). This cytotoxicity in each cell line was correlated to the expression of genes in these cell lines (downloaded from the NCBI Gene Expression Omnibus database using accession numbers GSE2350, GSE1880, GDS181). The identified marker genes were used to predict the sensitivity of DLBCL to Rituximab in a small set of 14 patients treated with Rituximab and CHOP (R-CHOP) (downloaded from NCBI Gene Expression Omnibus under accession number GSE4475). Conversion between different chip types was performed using matching tables available through Affymetrix.

Figure 7:
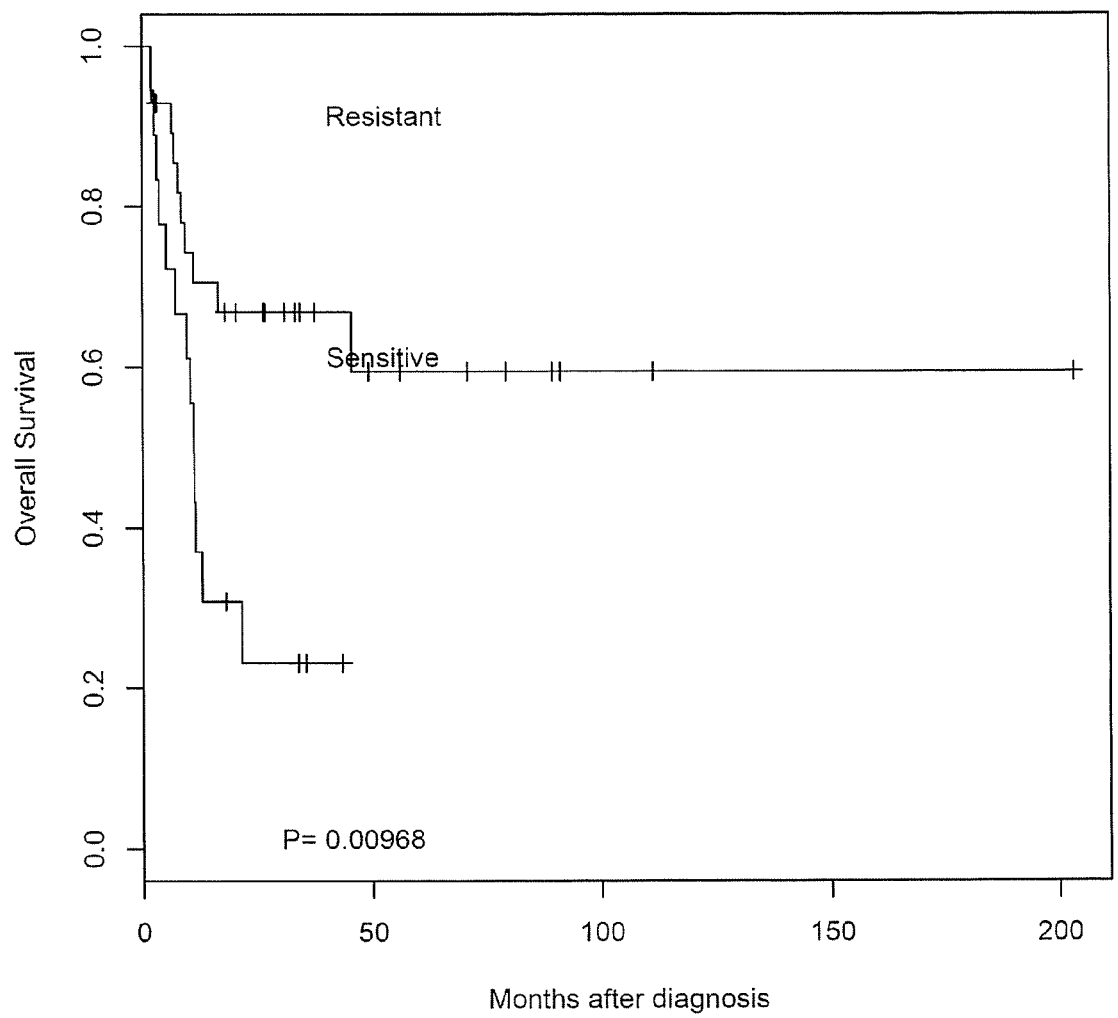
FIG. 7 depicts the survival rate of 14 diffuse large-B-cell lymphoma (DLBCL) patients divided into a group predicted to be chemosensitive to the drug combination R-CHOP and a group predicted to be chemoresistant. All patients were treated with R-CHOP.

The survival of patients predicted to be sensitive to be R-CHOP is compared to the survival of patients predicted to be resistant to R-CHOP in FIG. 7. The survival rate of the patients predicted to be chemosensitive was higher than the patients predicted to be chemoresistant.

Figure 8:
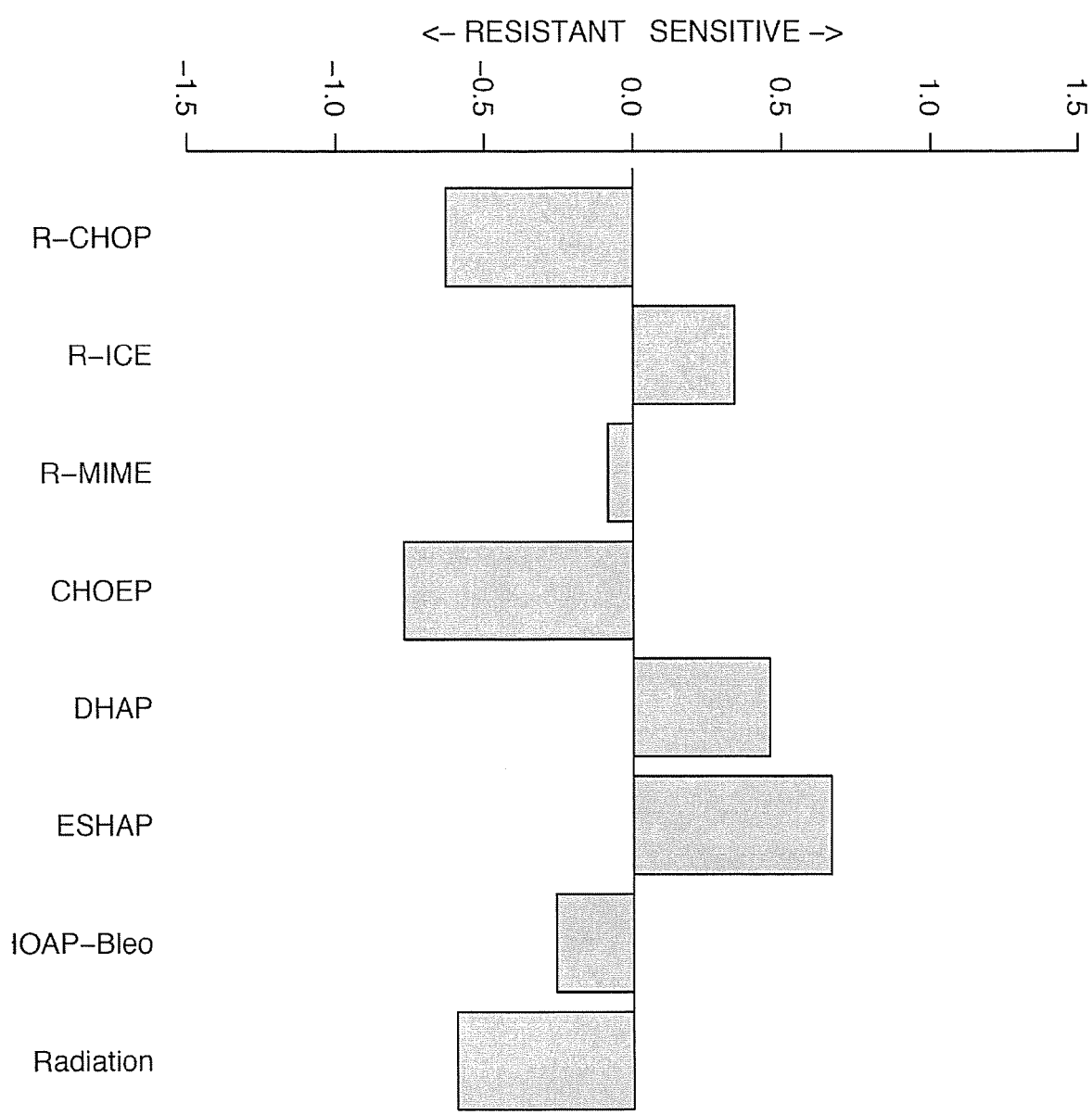
FIG. 8 depicts the predictions of sensitivity or resistance to treatment of a patient diagnosed with DLBCL. Various drug combinations and radiation therapy are considered. The drug combinations (indicated by abbreviations) are those commonly used to treat DLBCL.

To predict the sensitivity toward combination therapies, such as those used to treat Diffuse Large B-cell Lymphoma (DLBCL), patient sensitivity to a particular combination therapy is predicted by combining the marker genes for the individual compounds used in the combination. An example of this is shown in FIG. 8, where the predicted sensitivities of one patient towards a number of combination therapies used against DLBCL (identified by their acronyms) are shown: R-CHOP contains Rituximab (e.g., MABTHERA™), Vincristine, Doxorubicin (Adriamycin), Cyclophosphamide, and Prednisolone; R-ICE contains Rituximab, Ifosfamide, Carboplatin, and Etoposide; R-MIME contains Rituximab, Mitoguazone, Ifosfamide, Methotrexate, and Etoposide; CHOEP contains Cyclophosphamide, Doxorubicin, Etoposide, Vincristine and Prednisone; DHAP contains Dexamethasone, Cytarabine (Ara C), and Cisplatin; ESHAP contains Etoposide, Methylprednisolone (Solumedrol), Cytarabine (Ara-C) and Cisplatin; and HOAP-Bleo contains Doxorubicin, Vincristine, Ara C, Prednisone, and Bleomycin.

Example 6

Prediction of Radiosensitivity for Brain Tumor (Medulloblastoma) Patients

Figure 9:
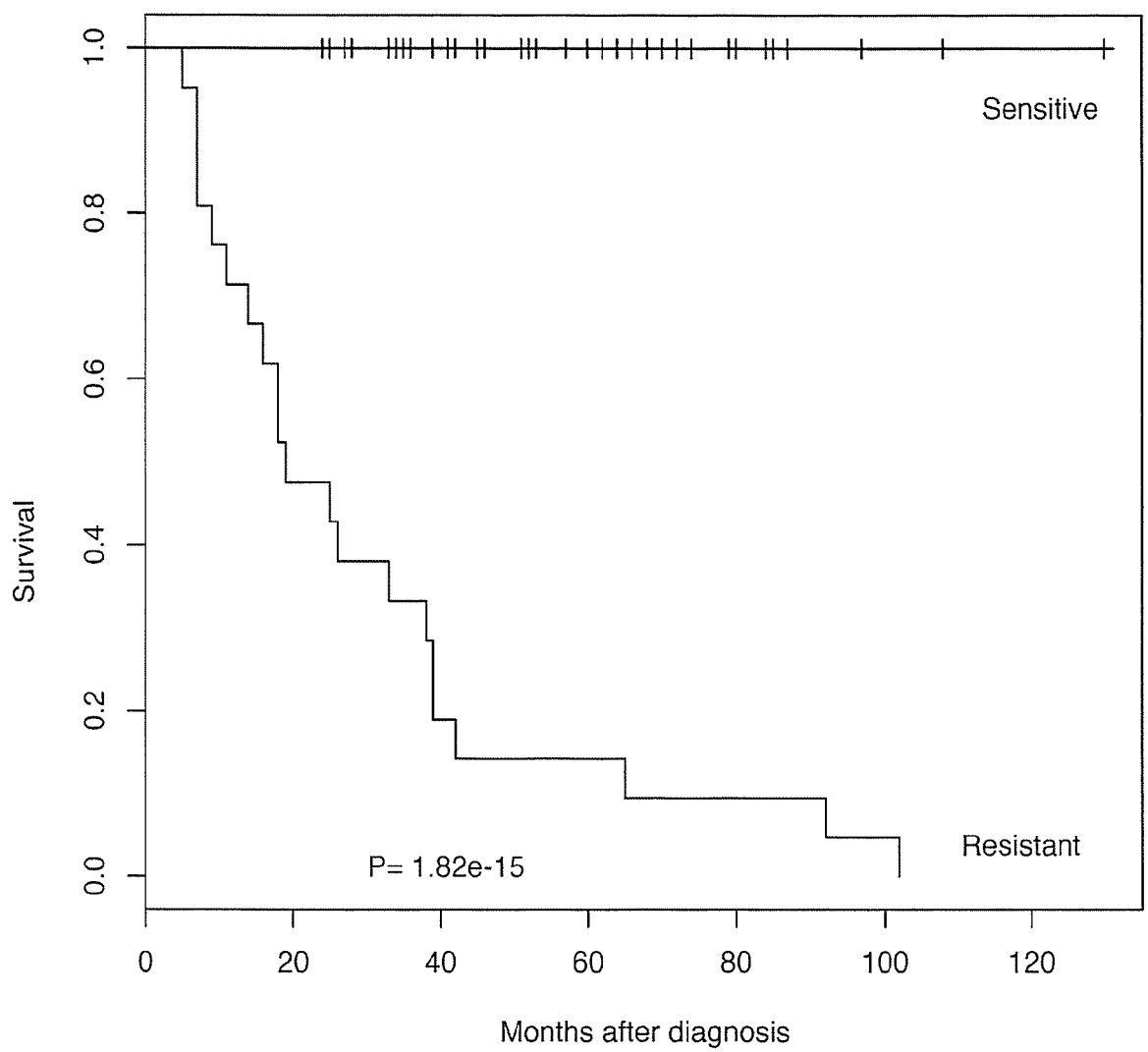
FIG. 9 depicts the survival rate of 60 brain cancer patients divided into a group predicted to be sensitive to radiation treatment and a group predicted to be resistant. All patients were treated with radiation.

The method of identifying biomarkers can also be applied to other forms of treatment such as radiation therapy. For example, sensitivity to radiation therapy was predicted for brain tumor patients. Radiation therapy in the form of craniospinal irradiation yielding 2,400-3,600 centiGray (cGy) with a tumor dose of 5,300-7,200 cGy was administered to the brain tumor patients using a medical device that emits beams of radiation. Sensitivity of the 60 cancer cell lines used in the NCI60 dataset to radiation treatment was obtained from published reports. This sensitivity was correlated to the expression of genes in the cell lines as described above to identify marker genes. DNA microarray measurements of gene expression in brain tumors obtained from patients subsequently treated with radiation therapy were obtained from the Broad Institute. The identified gene biomarkers were used to classify the patients as sensitive or resistant to radiation therapy. The survival of the patients in the two predicted categories is shown in FIG. 9. The survival rate of the patients predicted to be sensitive to radiation therapy was higher than the patients predicted to be resistant to radiation therapy.

Example 7

Drug Rescue

Every member of a population may not be equally responsive to a particular treatment. For example, new compounds often fail in late clinical trials because of lack of efficacy in the population tested. While such compounds may not be effective in the overall population, there may be subpopulations sensitive to those failed compounds due to various reasons, including inherent differences in gene expression. The method as described herein can be used to rescue failed compounds by identifying a patient subpopulation sensitive to a compound using their gene expression as an indicator. Subsequent clinical trials restricted to a sensitive patient subpopulation may demonstrate efficacy of a previously failed compound within that particular patient subpopulation, advancing the compound towards approval for use in that subpopulation.

To this end, in vitro measurements of the inhibitory effects of a compound on various cancer cell lines are compared to the gene expression of cells. The growth of the cancer cell samples can be correlated to gene expression measurements as described above. This will identify marker genes that can be used to predict patient sensitivity to the failed compound. Once biomarkers are identified, the expression of biomarker genes in cells obtained from patients can be measured according to the procedure detailed above. The patients are predicted to be responsive or non-responsive to compound treatment according to their gene biomarker expression profile. Clinical effect must then be demonstrated in the group of patients that are predicted to be sensitive to the failed compound.

The method may be further refined if patients responsive to the compound treatment are further subdivided into those predicted to survive without the compound and those predicted to die or suffer a relapse without the compound. Clinical efficacy in the subpopulation that is predicted to die or suffer relapse can be further demonstrated. Briefly, the gene expression at the time of diagnosis of patients who later die from their disease is compared to gene expression at the time of diagnosis of patients who are still alive after a period of time (e.g., 5 years). Genes differentially expressed between the two groups are identified as prospective biomarkers and a model is built using those gene biomarkers to predict treatment efficacy.

Examples of compounds that have failed in clinical trials include Gefinitib (e.g., Iressa, AstraZeneca) in refractory, advanced non-small-cell lung cancer (NSCLC), Bevacizumab (e.g., Avastin, Genentech) in first-line treatment for advanced pancreatic cancer, Bevacizumab (e.g., Avastin, Genentech) in relapsed metastatic breast cancer patients, and Erlotinib (e.g., Tarceva, Genentech) in metastatic non-small cell lung cancer (NSCLC). The method of the invention may be applied to these compounds, among others, so that sensitive patient subpopulations responsive to those compounds may be identified.

Example 8

Median of the Correlations Versus Correlation of the Median

Figure 10:
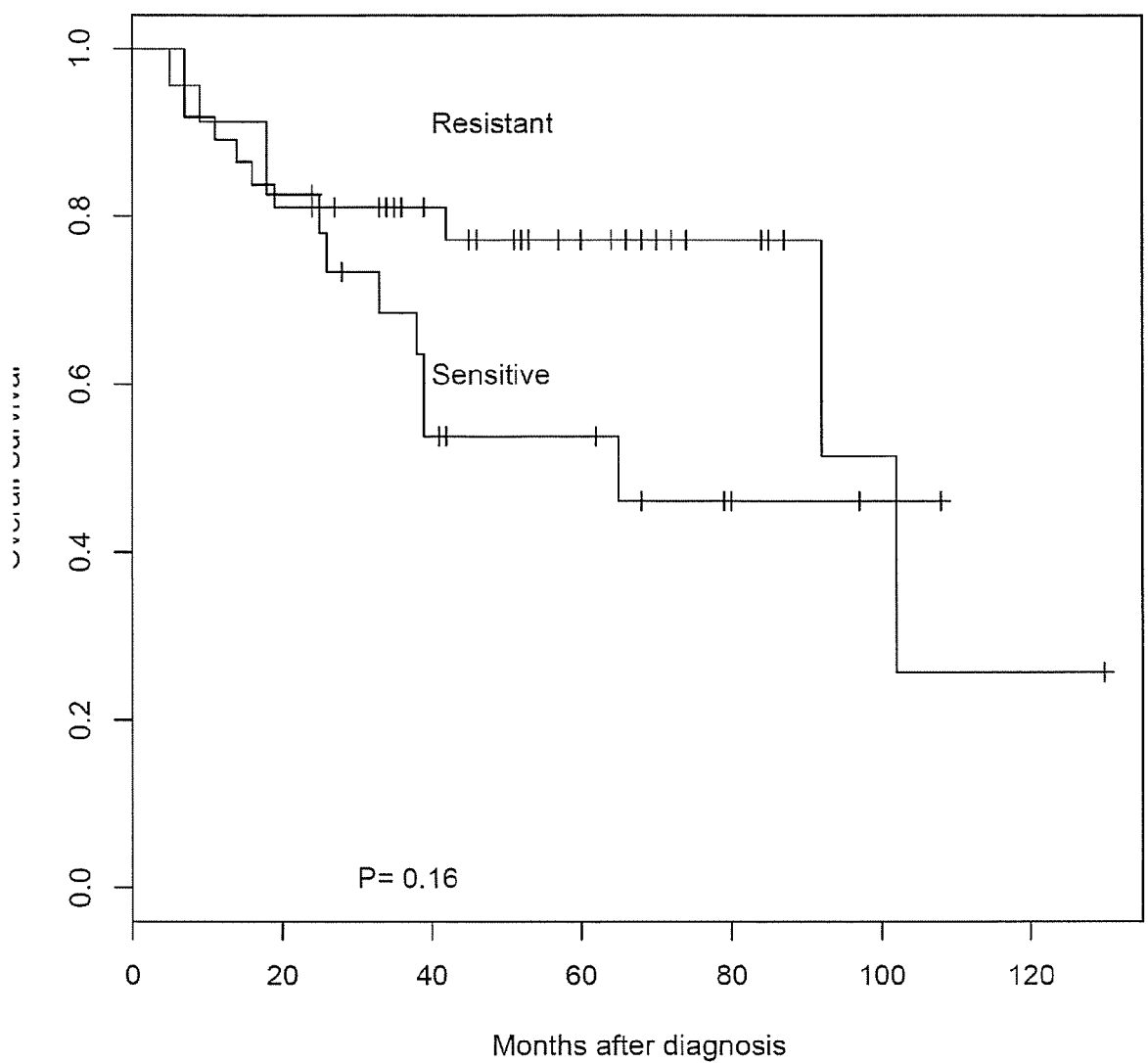
FIG. 10 depicts the survival rate of 60 brain cancer patients divided into a group predicted to be sensitive to radiation treatment and a group predicted to be resistant. All patients were treated with radiation. Gene biomarkers used in predicting radiation sensitivity or resistance were obtained using the correlation of the median gene expression measurement to cancer cell growth as opposed to the median of the correlations as employed in FIG. 9.

The median of the correlations of the individual probe measurements to cancer cell growth as employed by the invention was compared to the correlation of the median probe measurements: this will determine at which step of the method a median calculation should be performed. In the former, several correlations are calculated for each gene since multiple probes measure a given gene's expression, but only the median of the correlation coefficients is finally retained to identify biomarkers. In the latter, only one correlation is calculated for each gene because only the median gene expression measurement is considered for each gene. FIG. 10 shows the results of using the correlation of the median expression measurements to identify biomarker genes of radiation sensitivity predicting the survival of 60 brain cancer patients. The difference in survival between the group predicted to be radiation sensitive and the group predicted to be radiation resistant in FIG. 10 is much smaller than the difference depicted in FIG. 9 which employed a median correlation coefficient suggesting that the invention's median of the correlations employed in FIG. 9 outperforms the correlation of the median depicted in FIG. 10.

If we look at individual marker genes like OMD, the median of the correlation to measured radiosensitivity of cell lines in vitro is 0.32. The correlation of the median, however, is 0.39. Adjusting the cutoff from 0.3 to 0.4 to compensate for the difference does not improve on FIG. 10, however.

We have also compared median correlation to weighted voting as proposed by Staunton et al., *PNAS* 98(19):10787-10792, 2001). Weighted voting produced a poor result similar to that of FIG. 10, with a P-value of 0.11.

Example 9

Other Methods of Identifying Biomarkers

The examples shown above all rely on the availability of measurements of inhibition by a compound or treatment of the growth of cell lines in vitro. Such measurements may not always be available or practical. In that case an alternative method of identifying biomarkers can be employed. If the target(s) of the compound is/are known, it is possible to build a model based on the gene expression of the known target(s). One example is the drug sunitinib (SU11248), for which eight targets are known. Sunitinib inhibits at least eight receptor protein-tyrosine kinases including vascular endothelial growth factor receptors 1-3 (VEGFR1-VEGFR3), platelet-derived growth factor receptors (PDGFRA and PDGFRB), stem cell factor receptor (Kit), Flt-3, and colony-stimulating factor-1 receptor (CSF-1R). U.S. Patent Application Publication 2006/0040292 mentions prediction of response measuring just two targets, PDGFRA and KIT. Using the sum of the gene expression of four targets it is possible to predict with more reliability the response to sunitinib. As an example, the predicted sunitinib sensitivity of cell lines HT29, U118, 786, and H226 is 0.24, 2.3, 0.14 and 0.60, respectively, based on the sum of the four targets PDGFRB, KDR, KIT and FLT3. This correlates well with the measured response in mouse xenografts of these cells (correlation coefficient 0.86) as well as with the measured anti-angiogenetic effect measured in mouse xenografts (Potapova et al. Contribution of individual targets to the antitumor efficacy of the multitargeted receptor tyrosine kinase inhibitor SU11248 (*Mol. Cancer. Ther.* 5(5): 1280-9, 2006). This is better than a model based only on two targets PDGFRA and KIT (correlaton coefficient 0.56).

Figure 11:
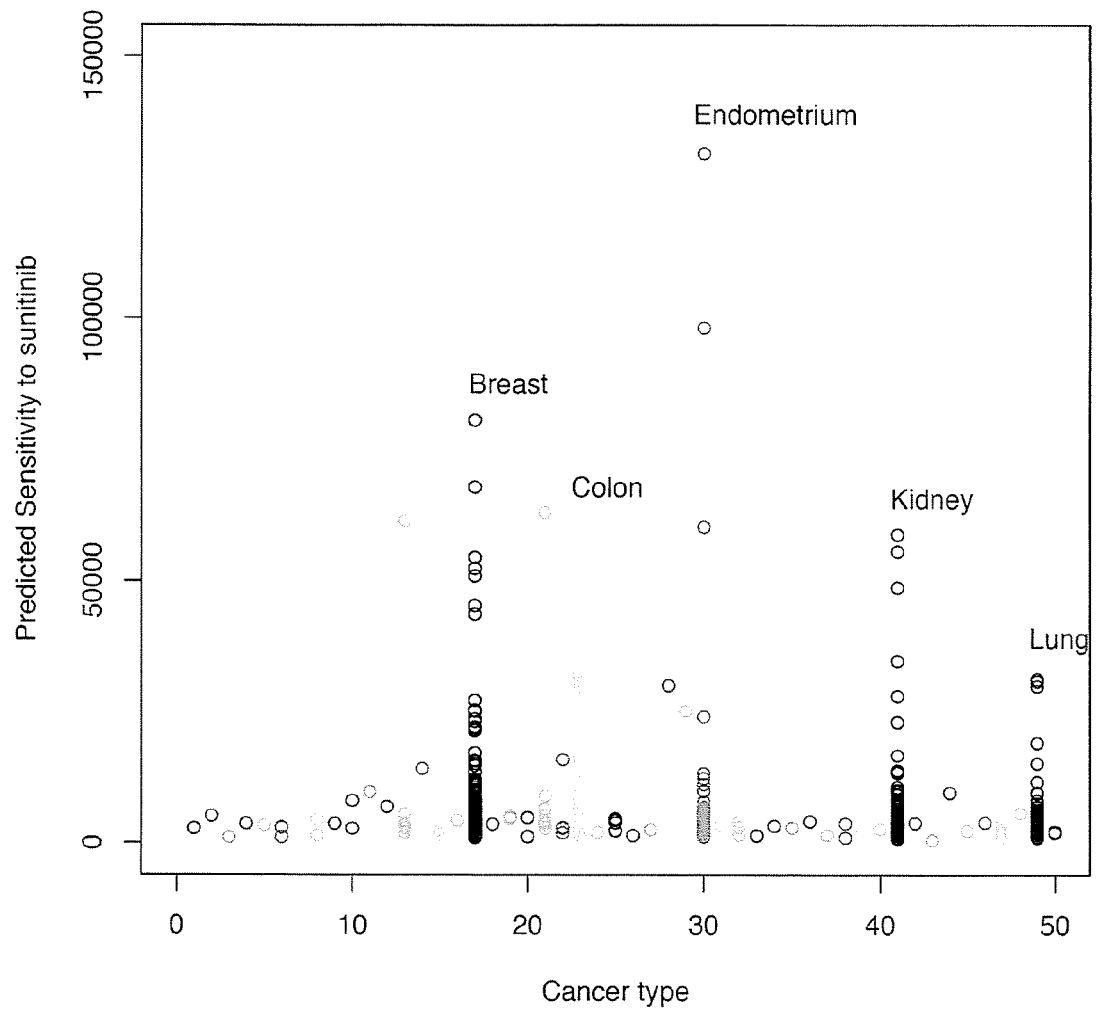
FIG. 11 depicts the predicted sensitivity of cancer patients to sunitinib. The cancer patients are grouped according to cancer type or origin and cancer types with predicted high sensitivity are labeled.

This four-gene predictor of sunitinib response can be applied to a large number of tumor samples from patients with different tumors from which gene expression analysis has been performed in order to get an idea of the range of sensitivities within each cancer type as well as which cancer types are most susceptible to treatment with sunitinib. FIG. 11 shows just a small fraction of the cancer samples available. The comparison is based on normalizing the samples in such a way (e.g., logit normalization) that different cancer types become comparable. Sunitinib is currently approved by the FDA for renal cancer and gastrointestinal cancer. Both kidney and colon show a good response in this plot.

Any other drug response response predictor based on gene expression can be tested in the same manner as shown in FIG. 11.

The approach of identifying biomarkers based on known targets can also be applied to RNA antagonists such as SPC2996 targeted against Bcl-2. A response predictor can be built based on measuring the gene expression of Bcl-2 in samples from cancer patients. The same approach can be used for the targets of all mRNA antagonists or inhibitors.

Example 10

Identifying Candidate Drugs for a Known Target

The methods of the invention described herein can also be used for identifying candidate drugs to a known target. Basically, the method of identifying biomarkers is run backwards in order to identify candidate drugs. If one starts with a known target, the expression of its corresponding gene is determined in the NCI 60 cell lines and correlated to the measured growth inhibition of all the thousands of drugs tested in the NCI 60 cell lines. This provides a list, ranked by correlation coefficient, of candidate drugs for the target. It is even possible to test new drugs and compare their correlation coefficient to the target gene expression to the correlation coefficients of the already tested drugs.

Example 11

Using microRNAs as Biomarkers of Drug Response

In recent years it has become clear that microRNAs (miRNA) play an important role in regulating the translation of mRNAs. As such, microRNAs may contain important information relevant for the prediction of drug sensitivity. This information may be complementary to the information contained in mRNA expression. Shown below is the correlation between predicted and measured chemosensitivity of the NCI 60 cell lines. The prediction is based either on mRNA measurements with DNA microarrays as described herein or predictions based on measurements of microRNA concentration (ArrayExpress accession number E-MEXP-1029) using a microRNA specific microarray (ArrayExpress accession number A-MEXP-620). Whenever more than one probe is used to determine the concentration of a given microRNA, the median correlation procedure is used for calculating correlation between microRNA concentration and $-\log(GI50)$.

|  | miRNA | mRNA | Combined |
|---|---|---|---|
| cisplatin | 0.16 | 0.02 | 0.21 |
| PXD101 | 0.44 | 0.31 | 0.50 |
| vincristine | 0.06 | 0.11 | 0.26 |
| etoposide | 0.32 | 0.41 | 0.44 |
| adriamycine | 0.24 | 0.22 | 0.28 |

As the above table shows, the correlation (determined using leave-one-out cross-validation) is highest when using a combination (linear sum) of microRNA and mRNA predictions. These results suggest that a more accurate drug response predictor can be built using a combination of microRNA and mRNA. It is possible to measure both in the same experiment, as long as one takes into consideration that microRNAs in general do not have a polyA tail as mRNA does. Only slight modifications to the amplification and labeling methods used for mRNA may be needed to incorporate microRNAs into the analysis. Commercial kits for microRNA extraction, amplification, and labeling are available from suppliers (e.g., Ambion Inc.).

Tables 22A-76A list the microRNA probes that are useful for detection of sensitivity to individual drugs, as determined by their median correlation to −log(GI50) for the indicated drug.

Other Embodiments

All publications and patent applications mentioned in this specification are herein incorporated by reference to the same extent as if each independent publication or patent application was specifically and individually indicated to be incorporated by reference. While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

Legend:
List_2006: biomarkers identified in 2006 using the new U133A chip measurements
List_2005: biomarkers listed in 2005 patent filing
HU6800: biomarkers obtained with old HU6800 chip measurements
List_Prior: matching biomakrers in prior art
List_Preferr: Prederred list of biomarkers
Correlation: The correlation of the biomarker to sensitivity to the compound

TABLE 1

Vincristine biomarkers

| | List_2006 | List_2005 | List_Prior | List_Preferr | Correlation |
|---|---|---|---|---|---|
| [1,] | UBB | | UBB | | 0.39 |
| [2,] | RPS4X | | | RPS4X | 0.34 |
| [3,] | S100A4 | | | S100A4 | 0.32 |
| [4,] | NDUFS6 | | | NDUFS6 | 0.31 |
| [5,] | B2M | | B2M | | 0.35 |
| [6,] | C14orf139 | | | C14orf139 | 0.3 |
| [7,] | MAN1A1 | | MAN1A1 | | 0.33 |
| [8,] | SLC25A5 | SLC25A5 | | SLC25A5 | 0.32 |
| [9,] | RPL10 | | | RPL10 | 0.38 |
| [10,] | RPL12 | | | RPL12 | 0.31 |
| [11,] | EIF5A | | | EIF5A | 0.31 |
| [12,] | RPL36A | RPL36A | | RPL36A | 0.3 |
| [13,] | SUI1 | | SUI1 | | 0.33 |
| [14,] | BLMH | | | BLMH | 0.32 |
| [15,] | CTBP1 | | | CTBP1 | 0.32 |
| [16,] | TBCA | | | TBCA | 0.3 |
| [17,] | MDH2 | | | MDH2 | 0.34 |
| [18,] | DXS9879E | | | DXS9879E | 0.35 |
| [19,] | | SFRS3 | | | |
| [20,] | | CCT5 | | | |
| [21,] | | RPL39 | | | |

TABLE 1-continued

Vincristine biomarkers

| | List_2006 | List_2005 | List_Prior | List_Preferr | Correlation |
|---|---|---|---|---|---|
| [22,] | | UBE2S | | | |
| [23,] | | EEF1A1 | | | |
| [24,] | | COX7B | | | |
| [25,] | | RPLP2 | | | |
| [26,] | | RPL24 | | | |
| [27,] | | RPS23 | | | |
| [28,] | | RPL18 | | | |
| [29,] | | NCL | | | |
| [30,] | | RPL9 | | | |
| [31,] | | RPL10A | | | |
| [32,] | | RPS10 | | | |
| [33,] | | EIF3S2 | | | |
| [34,] | | SHFM1 | | | |
| [35,] | | RPS28 | | | |
| [36,] | | REA | | | |
| [37,] | | GAPD | | | |
| [38,] | | HNRPA1 | | | |
| [39,] | | RPS11 | | | |
| [40,] | | LDHB | | | |
| [41,] | | RPL3 | | | |
| [42,] | | RPL11 | | | |
| [43,] | | MRPL12 | | | |
| [44,] | | RPL18A | | | |
| [45,] | | RPS7 | | | |

TABLE 2

Cisplatin biomarkers

| | List_2006 | List_2005 | List_Prior | List_Preferr | Correlation |
|---|---|---|---|---|---|
| [1,] | C1QR1 | | | C1QR1 | 0.3 |
| [2,] | HCLS1 | HCLS1 | HCLS1 | | 0.33 |
| [3,] | CD53 | | CD53 | | 0.35 |
| [4,] | SLA | | | SLA | 0.37 |
| [5,] | PTPN7 | PTPN7 | | PTPN7 | 0.31 |
| [6,] | PTPRCAP | | PTPRCAP | | 0.32 |
| [7,] | ZNFN1A1 | | | ZNFN1A1 | 0.33 |
| [8,] | CENTB1 | | | CENTB1 | 0.37 |
| [9,] | PTPRC | | PTPRC | | 0.36 |
| [10,] | IFI16 | IFI16 | | IFI16 | 0.31 |
| [11,] | ARHGEF6 | | | ARHGEF6 | 0.35 |
| [12,] | SEC31L2 | | | SEC31L2 | 0.32 |
| [13,] | CD3Z | | | CD3Z | 0.32 |
| [14,] | GZMB | | | GZMB | 0.3 |
| [15,] | CD3D | | | CD3D | 0.34 |
| [16,] | MAP4K1 | | | MAP4K1 | 0.32 |
| [17,] | GPR65 | | | GPR65 | 0.39 |
| [18,] | PRF1 | | | PRF1 | 0.31 |
| [19,] | ARHGAP15 | | | ARHGAP15 | 0.35 |
| [20,] | TM6SF1 | | | TM6SF1 | 0.41 |
| [21,] | TCF4 | | | TCF4 | 0.4 |
| [22,] | | GAPD | | | |
| [23,] | | ARHGDIB | | | |
| [24,] | | RPS27 | | | |
| [25,] | | C5orf13 | | | |
| [26,] | | LDHB | | | |
| [27,] | | SNRPF | | | |
| [28,] | | B2M | | | |
| [29,] | | FTL | | | |
| [30,] | | NCL | | | |
| [31,] | | MSN | | | |
| [32,] | | XPO1 | | | |

TABLE 3

Azaguanine biomarkers

| | List_2006 | List_2005 | List_Prior | List_Preferr | Correlation |
|---|---|---|---|---|---|
| [1,] | MSN | MSN | MSN | | 0.36 |
| [2,] | SPARC | SPARC | SPARC | | 0.48 |

TABLE 3-continued

Azaguanine biomarkers

| | List_2006 | List_2005 | List_Prior | List_Preferr | Correlation |
|---|---|---|---|---|---|
| [3,] | VIM | VIM | VIM | | 0.47 |
| [4,] | SRM | SRM | | SRM | 0.32 |
| [5,] | SCARB1 | | | SCARB1 | 0.4 |
| [6,] | SIAT1 | | | SIAT1 | 0.31 |
| [7,] | CUGBP2 | | | CUGBP2 | 0.37 |
| [8,] | GAS7 | | GAS7 | | 0.34 |
| [9,] | ICAM1 | | | ICAM1 | 0.43 |
| [10,] | WASPIP | | | WASPIP | 0.44 |
| [11,] | ITM2A | | | ITM2A | 0.31 |
| [12,] | PALM2-AKAP2 | | | PALM2-AKAP2 | 0.31 |
| [13,] | ANPEP | | ANPEP | | 0.33 |
| [14,] | PTPNS1 | | | PTPNS1 | 0.39 |
| [15,] | MPP1 | | | MPP1 | 0.32 |
| [16,] | LNK | | | LNK | 0.43 |
| [17,] | FCGR2A | | | FCGR2A | 0.3 |
| [18,] | EMP3 | EMP3 | EMP3 | | 0.33 |
| [19,] | RUNX3 | | | RUNX3 | 0.43 |
| [20,] | EVI2A | | | EVI2A | 0.4 |
| [21,] | BTN3A3 | | | BTN3A3 | 0.4 |
| [22,] | LCP2 | | | LCP2 | 0.34 |
| [23,] | BCHE | | | BCHE | 0.35 |
| [24,] | LY96 | | | LY96 | 0.47 |
| [25,] | LCP1 | | | LCP1 | 0.42 |
| [26,] | IFI16 | | | IFI16 | 0.33 |
| [27,] | MCAM | MCAM | | MCAM | 0.37 |
| [28,] | MEF2C | | | MEF2C | 0.41 |
| [29,] | SLC1A4 | | | SLC1A4 | 0.49 |
| [30,] | BTN3A2 | | BTN3A2 | | 0.43 |
| [31,] | FYN | | | FYN | 0.31 |
| [32,] | FN1 | FN1 | FN1 | | 0.33 |
| [33,] | C1orf38 | | | C1orf38 | 0.37 |
| [34,] | CHS1 | | | CHS1 | 0.33 |
| [35,] | CAPN3 | | CAPN3 | | 0.5 |
| [36,] | FCGR2C | | | FCGR2C | 0.34 |
| [37,] | TNIK | | | TNIK | 0.35 |
| [38,] | AMPD2 | | | AMPD2 | 0.3 |
| [39,] | SEPT6 | | | SEPT6 | 0.41 |
| [40,] | RAFTLIN | | | RAFTLIN | 0.39 |
| [41,] | SLC43A3 | | | SLC43A3 | 0.52 |
| [42,] | RAC2 | | | RAC2 | 0.33 |
| [43,] | LPXN | | | LPXN | 0.54 |
| [44,] | CKIP-1 | | | CKIP-1 | 0.33 |
| [45,] | FLJ10539 | | | FLJ10539 | 0.33 |
| [46,] | FLJ35036 | | | FLJ35036 | 0.36 |
| [47,] | DOCK10 | | | DOCK10 | 0.3 |
| [48,] | TRPV2 | | | TRPV2 | 0.31 |
| [49,] | IFRG28 | | | IFRG28 | 0.3 |
| [50,] | LEF1 | | | LEF1 | 0.31 |
| [51,] | ADAMTS1 | | | ADAMTS1 | 0.36 |
| [52,] | | PRPS1 | | | |
| [53,] | | DDOST | | | |
| [54,] | | B2M | | | |
| [55,] | | LGALS1 | | | |
| [56,] | | CBFB | | | |
| [57,] | | SNRPB2 | | | |
| [58,] | | EIF2S2 | | | |
| [59,] | | HPRT1 | | | |
| [60,] | | FKBP1A | | | |
| [61,] | | GYPC | | | |
| [62,] | | UROD | | | |
| [63,] | | HNRPA1 | | | |
| [64,] | | SND1 | | | |
| [65,] | | COPA | | | |
| [66,] | | MAPRE1 | | | |
| [67,] | | EIF3S2 | | | |
| [68,] | | ATP1B3 | | | |
| [69,] | | ECM1 | | | |
| [70,] | | ATOX1 | | | |
| [71,] | | NARS | | | |
| [72,] | | PGK1 | | | |
| [73,] | | OK/SW-cl.56 | | | |
| [74,] | | EEF1A1 | | | |
| [75,] | | GNAI2 | | | |
| [76,] | | RPL7 | | | |
| [77,] | | PSMB9 | | | |
| [78,] | | GPNMB | | | |

TABLE 3-continued

Azaguanine biomarkers

| | List_2006 | List_2005 | List_Prior | List_Preferr | Correlation |
|---|---|---|---|---|---|
| [79,] | | PPP1R11 | | | |
| [80,] | | MIA | | | |
| [81,] | | RAB7 | | | |
| [82,] | | SMS | | | |

TABLE 4

Etoposide biomarkers

| | List_2006 | List_2005 | List_Prior | List_Preferr | Correlation |
|---|---|---|---|---|---|
| [1,] | CD99 | CD99 | | CD99 | 0.3 |
| [2,] | INSIG1 | | | INSIG1 | 0.35 |
| [3,] | LAPTM5 | LAPTM5 | | | 0.32 |
| [4,] | PRG1 | | | PRG1 | 0.34 |
| [5,] | MUF1 | | | MUF1 | 0.35 |
| [6,] | HCLS1 | HCLS1 | | | 0.33 |
| [7,] | CD53 | CD53 | | | 0.32 |
| [8,] | SLA | | | SLA | 0.37 |
| [9,] | SSBP2 | | | SSBP2 | 0.37 |
| [10,] | GNB5 | | | GNB5 | 0.35 |
| [11,] | MFNG | | | MFNG | 0.33 |
| [12,] | GMFG | GMFG | | | 0.32 |
| [13,] | PSMB9 | | | PSMB9 | 0.31 |
| [14,] | EVI2A | | | EVI2A | 0.41 |
| [15,] | PTPN7 | | | PTPN7 | 0.3 |
| [16,] | PTGER4 | | | PTGER4 | 0.3 |
| [17,] | CXorf9 | | | CXorf9 | 0.3 |
| [18,] | PTPRCAP | PTPRCAP | | | 0.3 |
| [19,] | ZNFN1A1 | | | ZNFN1A1 | 0.35 |
| [20,] | CENTB1 | | | CENTB1 | 0.3 |
| [21,] | PTPRC | PTPRC | | | 0.31 |
| [22,] | NAP1L1 | | | NAP1L1 | 0.31 |
| [23,] | HLA-DRA | | | HLA-DRA | 0.34 |
| [24,] | IFI16 | | | IFI16 | 0.38 |
| [25,] | CORO1A | CORO1A | | | 0.3 |
| [26,] | ARHGEF6 | | | ARHGEF6 | 0.33 |
| [27,] | PSCDBP | | | PSCDBP | 0.4 |
| [28,] | SELPLG | | | SELPLG | 0.35 |
| [29,] | LAT | | | LAT | 0.3 |
| [30,] | SEC31L2 | | | SEC31L2 | 0.42 |
| [31,] | CD3Z | | | CD3Z | 0.36 |
| [32,] | SH2D1A | | | SH2D1A | 0.33 |
| [33,] | GZMB | | | GZMB | 0.34 |
| [34,] | SCN3A | | | SCN3A | 0.3 |
| [35,] | ITK | ITK | | | 0.35 |
| [36,] | RAFTLIN | | | RAFTLIN | 0.39 |
| [37,] | DOCK2 | | | DOCK2 | 0.33 |
| [38,] | CD3D | | | CD3D | 0.31 |
| [39,] | RAC2 | | | RAC2 | 0.34 |
| [40,] | ZAP70 | | | ZAP70 | 0.35 |
| [41,] | GPR65 | | | GPR65 | 0.35 |
| [42,] | PRF1 | | | PRF1 | 0.32 |
| [43,] | ARHGAP15 | | | ARHGAP15 | 0.32 |
| [44,] | NOTCH1 | | | NOTCH1 | 0.31 |
| [45,] | UBASH3A | | | UBASH3A | 0.32 |
| [46,] | | B2M | | | |
| [47,] | | MYC | | | |
| [48,] | | RPS24 | | | |
| [49,] | | PPIF | | | |
| [50,] | | PBEF1 | | | |
| [51,] | | ANP32B | | | |

TABLE 5

Adriamycin biomarkers

| | List_2006 | List_2005 | List_Prior | List_Preferr | Correlation |
|---|---|---|---|---|---|
| [1,] | CD99 | CD99 | | CD99 | 0.41 |
| [2,] | LAPTM5 | LAPTM5 | | | 0.39 |
| [3,] | ALDOC | | | ALDOC | 0.31 |
| [4,] | HCLS1 | HCLS1 | | | 0.32 |
| [5,] | CD53 | CD53 | | | 0.31 |
| [6,] | SLA | | | SLA | 0.35 |
| [7,] | SSBP2 | | | SSBP2 | 0.34 |
| [8,] | IL2RG | | | IL2RG | 0.38 |
| [9,] | GMFG | GMFG | | | 0.32 |
| [10,] | CXorf9 | | | CXorf9 | 0.32 |
| [11,] | RHOH | | | RHOH | 0.31 |
| [12,] | PTPRCAP | PTPRCAP | | | 0.32 |
| [13,] | ZNFN1A1 | | | ZNFN1A1 | 0.43 |
| [14,] | CENTB1 | | | CENTB1 | 0.36 |
| [15,] | TCF7 | TCF7 | | | 0.32 |
| [16,] | CD1C | | | CD1C | 0.3 |
| [17,] | MAP4K1 | | | MAP4K1 | 0.35 |
| [18,] | CD1B | CD1B | | | 0.39 |
| [19,] | CD3G | | | CD3G | 0.31 |
| [20,] | PTPRC | PTPRC | | | 0.38 |
| [21,] | CCR9 | | | CCR9 | 0.34 |
| [22,] | CORO1A | CORO1A | | | 0.38 |
| [23,] | CXCR4 | | | CXCR4 | 0.3 |
| [24,] | ARHGEF6 | | | ARHGEF6 | 0.31 |
| [25,] | HEM1 | HEM1 | | | 0.32 |
| [26,] | SELPLG | | | SELPLG | 0.31 |
| [27,] | LAT | | | LAT | 0.31 |
| [28,] | SEC31L2 | | | SEC31L2 | 0.33 |
| [29,] | CD3Z | | | CD3Z | 0.37 |
| [30,] | SH2D1A | | | SH2D1A | 0.37 |
| [31,] | CD1A | | | CD1A | 0.4 |
| [32,] | LAIR1 | | | LAIR1 | 0.39 |
| [33,] | ITK | ITK | | | 0.3 |
| [34,] | TRB@ | | | TRB@ | 0.34 |
| [35,] | CD3D | | | CD3D | 0.33 |
| [36,] | WBSCR20C | | | WBSCR20C | 0.34 |
| [37,] | ZAP70 | | | ZAP70 | 0.33 |
| [38,] | IFI44 | | | IFI44 | 0.32 |
| [39,] | GPR65 | | | GPR65 | 0.31 |
| [40,] | AIF1 | | | AIF1 | 0.3 |
| [41,] | ARHGAP15 | | | ARHGAP15 | 0.37 |
| [42,] | NARF | | | NARF | 0.3 |
| [43,] | PACAP | | | PACAP | 0.32 |
| [44,] | | KIAA0220 | | | |
| [45,] | | B2M | | | |
| [46,] | | TOP2A | | | |
| [47,] | | SNRPE | | | |
| [48,] | | RPS27 | | | |
| [49,] | | HNRPA1 | | | |
| [50,] | | CBX3 | | | |
| [51,] | | ANP32B | | | |
| [52,] | | DDX5 | | | |
| [53,] | | PPIA | | | |
| [54,] | | SNRPF | | | |
| [55,] | | USP7 | | | |

TABLE 6

Aclarubicin biomarkers

| | List_2006 | List_2005 | List_Prior | List_Preferr | Correlation |
|---|---|---|---|---|---|
| [1,] | RPL12 | | | RPL12 | 0.3 |
| [2,] | RPL32 | RPL32 | | | 0.37 |
| [3,] | RPLP2 | RPLP2 | | RPLP2 | 0.37 |
| [4,] | MYB | MYB | | MYB | 0.31 |
| [5,] | ZNFN1A1 | | | ZNFN1A1 | 0.34 |
| [6,] | SCAP1 | | | SCAP1 | 0.33 |
| [7,] | STAT4 | | | STAT4 | 0.31 |
| [8,] | SP140 | | | SP140 | 0.4 |
| [9,] | AMPD3 | | | AMPD3 | 0.3 |
| [10,] | TNFAIP8 | | | TNFAIP8 | 0.4 |
| [11,] | DDX18 | | | DDX18 | 0.31 |
| [12,] | TAF5 | | | TAF5 | 0.3 |
| [13,] | FBL | | FBL | | 0.41 |
| [14,] | RPS2 | | | RPS2 | 0.34 |
| [15,] | PTPRC | | PTPRC | | 0.37 |
| [16,] | DOCK2 | | | DOCK2 | 0.32 |
| [17,] | GPR65 | | | GPR65 | 0.35 |
| [18,] | HOXA9 | | | HOXA9 | 0.33 |
| [19,] | FLJ12270 | | | FLJ12270 | 0.31 |
| [20,] | HNRPD | | | HNRPD | 0.4 |
| [21,] | | LAMR1 | | | |
| [22,] | | RPS25 | | | |
| [23,] | | EIF5A | | | |
| [24,] | | TUFM | | | |
| [25,] | | HNRPA1 | | | |
| [26,] | | RPS9 | | | |
| [27,] | | ANP32B | | | |
| [28,] | | EIF4B | | | |
| [29,] | | HMGB2 | | | |
| [30,] | | RPS15A | | | |
| [31,] | | RPS7 | | | |

TABLE 7

Mitoxantrone biomarkers

| | List_2006 | List_2005 | List_Prior | List_Preferr | Correlation |
|---|---|---|---|---|---|
| [1,] | PGAM1 | | | PGAM1 | 0.32 |
| [2,] | DPYSL3 | | | DPYSL3 | 0.36 |
| [3,] | INSIG1 | | | INSIG1 | 0.32 |
| [4,] | GJA1 | | | GJA1 | 0.31 |
| [5,] | BNIP3 | | | BNIP3 | 0.31 |
| [6,] | PRG1 | PRG1 | | PRG1 | 0.39 |
| [7,] | G6PD | G6PD | | G6PD | 0.34 |
| [8,] | BASP1 | | BASP1 | | 0.31 |
| [9,] | PLOD2 | | | PLOD2 | 0.34 |
| [10,] | LOXL2 | | | LOXL2 | 0.31 |
| [11,] | SSBP2 | | | SSBP2 | 0.36 |
| [12,] | C1orf29 | | | C1orf29 | 0.35 |
| [13,] | TOX | | | TOX | 0.35 |
| [14,] | STC1 | | | STC1 | 0.39 |
| [15,] | TNFRSF1A | TNFRSF1A | | TNFRSF1A | 0.34 |
| [16,] | NCOR2 | NCOR2 | | NCOR2 | 0.3 |
| [17,] | NAP1L1 | NAP1L1 | | NAP1L1 | 0.32 |
| [18,] | LOC94105 | | | LOC94105 | 0.34 |
| [19,] | COL6A2 | | COL6A2 | | 0.3 |
| [20,] | ARHGEF6 | ARHGEF6 | | ARHGEF6 | 0.34 |
| [21,] | GATA3 | | | GATA3 | 0.35 |
| [22,] | TFPI | | | TFPI | 0.31 |
| [23,] | LAT | | | LAT | 0.31 |
| [24,] | CD3Z | | | CD3Z | 0.37 |
| [25,] | AF1Q | | | AF1Q | 0.33 |
| [26,] | MAP1B | MAP1B | | MAP1B | 0.34 |
| [27,] | PTPRC | | PTPRC | | 0.31 |
| [28,] | PRKCA | | PRKCA | | 0.35 |
| [29,] | TRIM22 | | | TRIM22 | 0.3 |
| [30,] | CD3D | | | CD3D | 0.31 |
| [31,] | BCAT1 | | | BCAT1 | 0.32 |
| [32,] | IFI44 | | | IFI44 | 0.33 |
| [33,] | CCL2 | CCL2 | | CCL2 | 0.37 |
| [34,] | RAB31 | RAB31 | | RAB31 | 0.31 |
| [35,] | CUTC | | | CUTC | 0.33 |
| [36,] | NAP1L2 | | | NAP1L2 | 0.33 |
| [37,] | NME7 | | | NME7 | 0.35 |
| [38,] | FLJ21159 | | | FLJ21159 | 0.33 |
| [39,] | COL5A2 | | | COL5A2 | 0.38 |
| [40,] | | B2M | | | |
| [41,] | | OK/SW-cl.56 | | | |
| [42,] | | TOP2A | | | |
| [43,] | | ELA2B | | | |
| [44,] | | PTMA | | | |
| [45,] | | LMNB1 | | | |
| [46,] | | HNRPA1 | | | |
| [47,] | | RPL9 | | | |
| [48,] | | C5orf13 | | | |
| [49,] | | ANP32B | | | |
| [50,] | | TUBA3 | | | |
| [51,] | | HMGN2 | | | |
| [52,] | | PRPS1 | | | |
| [53,] | | DDX5 | | | |
| [54,] | | PPIA | | | |
| [55,] | | PSMB9 | | | |
| [56,] | | SNRPF | | | |

TABLE 8

Mitomycin biomarkers

| | List_2006 | HU6800 | List_Prior | List_Preferr | Correlation |
|---|---|---|---|---|---|
| [1,] | STC1 | | | STC1 | 0.34 |
| [2,] | GPR65 | | | GPR65 | 0.32 |
| [3,] | DOCK10 | | | DOCK10 | 0.35 |
| [4,] | COL5A2 | | | COL5A2 | 0.33 |
| [5,] | FAM46A | | | FAM46A | 0.36 |
| [6,] | LOC54103 | | | LOC54103 | 0.39 |

TABLE 9

Paclitaxel (Taxol) biomarkers

| | List_2006 | HU6800 | List_Prior | List_Preferr | Correlation |
|---|---|---|---|---|---|
| [1,] | RPL10 | | | RPL10 | 0.31 |
| [2,] | RPS4X | | | RPS4X | 0.31 |
| [3,] | NUDC | | | NUDC | 0.3 |
| [4,] | RALY | | RALY | | 0.31 |
| [5,] | DKC1 | | | DKC1 | 0.3 |
| [6,] | DKFZP564C186 | | | DKFZP564C186 | 0.32 |
| [7,] | PRP19 | | | PRP19 | 0.31 |
| [8,] | RAB9P40 | | | RAB9P40 | 0.33 |
| [9,] | HSA9761 | | | HSA9761 | 0.37 |
| [10,] | GMDS | | | GMDS | 0.3 |

TABLE 9-continued

Paclitaxel (Taxol) biomarkers

| | List_2006 | HU6800 | List_Prior | List_Preferr | Correlation |
|---|---|---|---|---|---|
| [11,] | CEP1 | | | CEP1 | 0.3 |
| [12,] | IL13RA2 | | | IL13RA2 | 0.34 |
| [13,] | MAGEB2 | | | MAGEB2 | 0.41 |
| [14,] | HMGN2 | | | HMGN2 | 0.35 |
| [15,] | ALMS1 | | | ALMS1 | 0.3 |
| [16,] | GPR65 | | | GPR65 | 0.31 |
| [17,] | FLJ10774 | | | FLJ10774 | 0.31 |
| [18,] | NOL8 | | | NOL8 | 0.31 |
| [19,] | DAZAP1 | | | DAZAP1 | 0.32 |
| [20,] | SLC25A15 | | | SLC25A15 | 0.31 |
| [21,] | PAF53 | | | PAF53 | 0.36 |
| [22,] | DXS9879E | | | DXS9879E | 0.31 |
| [23,] | PITPNC1 | | | PITPNC1 | 0.33 |
| [24,] | SPANXC | | | SPANXC | 0.3 |
| [25,] | KIAA1393 | | | KIAA1393 | 0.33 |

TABLE 10

Gemcitabine (Gemzar) biomarkers

| | List_2006 | HU6800 | List_Prior | List_Preferr | Correlation |
|---|---|---|---|---|---|
| [1,] | PFN1 | | | PFN1 | 0.37 |
| [2,] | PGAM1 | | | PGAM1 | 0.35 |
| [3,] | K-ALPHA-1 | | | K-ALPHA-1 | 0.34 |
| [4,] | CSDA | | | CSDA | 0.31 |
| [5,] | UCHL1 | | | UCHL1 | 0.36 |
| [6,] | PWP1 | | | PWP1 | 0.37 |
| [7,] | PALM2-AKAP2 | | | PALM2-AKAP2 | 0.31 |
| [8,] | TNFRSF1A | | | TNFRSF1A | 0.31 |
| [9,] | ATP5G2 | | | ATP5G2 | 0.36 |
| [10,] | AF1Q | | | AF1Q | 0.31 |
| [11,] | NME4 | | | NME4 | 0.31 |
| [12,] | FHOD1 | | | FHOD1 | 0.32 |

TABLE 11

Taxotere (docetaxel) biomarkers

| | List_2006 | List_2005 | List_Prior | List_Preferr | Correlation |
|---|---|---|---|---|---|
| [1,] | ANP32B | | | ANP32B | 0.45 |
| [2,] | GTF3A | | | GTF3A | 0.31 |
| [3,] | RRM2 | | | RRM2 | 0.31 |
| [4,] | TRIM14 | | | TRIM14 | 0.31 |
| [5,] | SKP2 | | | SKP2 | 0.33 |
| [6,] | TRIP13 | | | TRIP13 | 0.36 |
| [7,] | RFC3 | | | RFC3 | 0.45 |
| [8,] | CASP7 | | | CASP7 | 0.32 |
| [9,] | TXN | | | TXN | 0.36 |
| [10,] | MCM5 | | | MCM5 | 0.34 |
| [11,] | PTGES2 | | | PTGES2 | 0.39 |
| [12,] | OBFC1 | | | OBFC1 | 0.37 |
| [13,] | EPB41L4B | | | EPB41L4B | 0.32 |
| [14,] | CALML4 | | | CALML4 | 0.31 |

TABLE 12

Dexamethasone biomarkers

| | List_2006 | HU6800 | List_Prior | List_Preferr | Correlation |
|---|---|---|---|---|---|
| [1,] | IFITM2 | | | IFITM2 | 0.38 |
| [2,] | UBE2L6 | | | UBE2L6 | 0.32 |
| [3,] | LAPTM5 | LAPTM5 | LAPTM5 | | 0.36 |
| [4,] | USP4 | | | USP4 | 0.33 |
| [5,] | ITM2A | | | ITM2A | 0.38 |

TABLE 12-continued

Dexamethasone biomarkers

| | List_2006 | HU6800 | List_Prior | List_Preferr | Correlation |
|---|---|---|---|---|---|
| [6,] | ITGB2 | | | ITGB2 | 0.42 |
| [7,] | ANPEP | | | ANPEP | 0.31 |
| [8,] | CD53 | | | CD53 | 0.34 |
| [9,] | IL2RG | IL2RG | | IL2RG | 0.36 |
| [10,] | CD37 | | | CD37 | 0.34 |
| [11,] | GPRASP1 | | | GPRASP1 | 0.36 |
| [12,] | PTPN7 | | | PTPN7 | 0.31 |
| [13,] | CXorf9 | | | CXorf9 | 0.36 |
| [14,] | RHOH | RHOH | | RHOH | 0.33 |
| [15,] | GIT2 | | | GIT2 | 0.31 |
| [16,] | ADORA2A | | | ADORA2A | 0.31 |
| [17,] | ZNFN1A1 | | | ZNFN1A1 | 0.35 |
| [18,] | GNA15 | GNA15 | GNA15 | | 0.33 |
| [19,] | CEP1 | | | CEP1 | 0.31 |
| [20,] | TNFRSF7 | | | TNFRSF7 | 0.46 |
| [21,] | MAP4K1 | | | MAP4K1 | 0.3 |
| [22,] | CCR7 | | | CCR7 | 0.33 |
| [23,] | CD3G | | | CD3G | 0.35 |
| [24,] | PTPRC | | PTPRC | | 0.41 |
| [25,] | ATP2A3 | ATP2A3 | | ATP2A3 | 0.4 |
| [26,] | UCP2 | | | UCP2 | 0.3 |
| [27,] | CORO1A | CORO1A | CORO1A | | 0.39 |
| [28,] | GATA3 | GATA3 | | GATA3 | 0.37 |
| [29,] | CDKN2A | | | CDKN2A | 0.32 |
| [30,] | HEM1 | | HEM1 | | 0.3 |
| [31,] | TARP | | | TARP | 0.3 |
| [32,] | LAIR1 | | | LAIR1 | 0.34 |
| [33,] | SH2D1A | | | SH2D1A | 0.34 |
| [34,] | FLII | FLII | FLII | | 0.33 |
| [35,] | SEPT6 | | | SEPT6 | 0.34 |
| [36,] | HA-1 | | | HA-1 | 0.34 |
| [37,] | CREB3L1 | | | CREB3L1 | 0.31 |
| [38,] | ERCC2 | | | ERCC2 | 0.65 |
| [39,] | CD3D | CD3D | | CD3D | 0.32 |
| [40,] | LST1 | | | LST1 | 0.39 |
| [41,] | AIF1 | | | AIF1 | 0.35 |
| [42,] | ADA | | | ADA | 0.33 |
| [43,] | DATF1 | | | DATF1 | 0.41 |
| [44,] | ARHGAP15 | | | ARHGAP15 | 0.3 |
| [45,] | PLAC8 | | | PLAC8 | 0.31 |
| [46,] | CECR1 | | | CECR1 | 0.31 |
| [47,] | LOC81558 | | | LOC81558 | 0.33 |
| [48,] | EHD2 | | | EHD2 | 0.37 |

TABLE 13

Ara-C (Cytarabine hydrochloride) biomarkers

| | List_2006 | HU6800 | List_Prior | List_Preferr | Correlation |
|---|---|---|---|---|---|
| [1,] | ITM2A | | | ITM2A | 0.32 |
| [2,] | RHOH | | | RHOH | 0.31 |
| [3,] | PRIM1 | | | PRIM1 | 0.3 |
| [4,] | CENTB1 | | | CENTB1 | 0.31 |
| [5,] | GNA15 | | GNA15 | | 0.32 |
| [6,] | NAP1L1 | NAP1L1 | | NAP1L1 | 0.31 |
| [7,] | ATP5G2 | | | ATP5G2 | 0.31 |
| [8,] | GATA3 | | | GATA3 | 0.33 |
| [9,] | PRKCQ | | | PRKCQ | 0.32 |
| [10,] | SH2D1A | | | SH2D1A | 0.3 |
| [11,] | SEPT6 | | | SEPT6 | 0.42 |
| [12,] | PTPRC | | PTPRC | | 0.35 |
| [13,] | NME4 | | | NME4 | 0.33 |
| [14,] | RPL13 | | RPL13 | | 0.3 |
| [15,] | CD3D | | | CD3D | 0.31 |
| [16,] | CD1E | | | CD1E | 0.32 |
| [17,] | ADA | ADA | | ADA | 0.34 |
| [18,] | FHOD1 | | | FHOD1 | 0.31 |

TABLE 14

Methylprednisolone biomarkers

| | List_2006 | HU6800 | List_Prior | List_Preferr | Correlation |
|---|---|---|---|---|---|
| [1,] | CD99 | CD99 | | CD99 | 0.31 |
| [2,] | SRRM1 | | SRRM1 | | 0.31 |
| [3,] | ARHGDIB | ARHGDIB | | ARHGDIB | 0.31 |
| [4,] | LAPTM5 | LAPTM5 | LAPTM5 | | 0.37 |
| [5,] | VWF | | | VWF | 0.45 |
| [6,] | ITM2A | | | ITM2A | 0.35 |
| [7,] | ITGB2 | ITGB2 | ITGB2 | | 0.43 |
| [8,] | LGALS9 | LGALS9 | | LGALS9 | 0.43 |
| [9,] | INPP5D | | | INPP5D | 0.34 |
| [10,] | SATB1 | SATB1 | | SATB1 | 0.32 |
| [11,] | CD53 | CD53 | CD53 | | 0.33 |
| [12,] | TFDP2 | TFDP2 | | TFDP2 | 0.4 |
| [13,] | SLA | SLA | | SLA | 0.31 |
| [14,] | IL2RG | IL2RG | | IL2RG | 0.3 |
| [15,] | MFNG | | | MFNG | 0.3 |
| [16,] | CD37 | | CD37 | | 0.37 |
| [17,] | GMFG | | GMFG | | 0.4 |
| [18,] | SELL | | | SELL | 0.33 |
| [19,] | CDW52 | CDW52 | | CDW52 | 0.33 |
| [20,] | LRMP | | | LRMP | 0.32 |
| [21,] | ICAM2 | | | ICAM2 | 0.38 |
| [22,] | RIMS3 | | | RIMS3 | 0.36 |
| [23,] | PTPN7 | PTPN7 | | PTPN7 | 0.39 |
| [24,] | ARHGAP25 | | | ARHGAP25 | 0.37 |
| [25,] | LCK | LCK | | LCK | 0.3 |
| [26,] | CXorf9 | | | CXorf9 | 0.3 |
| [27,] | RHOH | RHOH | | RHOH | 0.51 |
| [28,] | PTPRCAP | PTPRCAP | PTPRCAP | | 0.5 |
| [29,] | GIT2 | | | GIT2 | 0.33 |
| [30,] | ZNFN1A1 | ZNFN1A1 | | ZNFN1A1 | 0.53 |
| [31,] | CENTB1 | CENTB1 | | CENTB1 | 0.36 |
| [32,] | LCP2 | | | LCP2 | 0.34 |
| [33,] | SPI1 | | | SPI1 | 0.3 |
| [34,] | GNA15 | GNA15 | GNA15 | | 0.39 |
| [35,] | GZMA | | | GZMA | 0.31 |
| [36,] | CEP1 | | | CEP1 | 0.37 |
| [37,] | BLM | | BLM | | 0.33 |
| [38,] | CD8A | | | CD8A | 0.38 |
| [39,] | SCAP1 | | | SCAP1 | 0.32 |
| [40,] | CD2 | | | CD2 | 0.48 |
| [41,] | CD1C | CD1C | | CD1C | 0.37 |
| [42,] | TNFRSF7 | | | TNFRSF7 | 0.31 |
| [43,] | VAV1 | | | VAV1 | 0.41 |
| [44,] | MAP4K1 | MAP4K1 | | MAP4K1 | 0.36 |
| [45,] | CCR7 | | | CCR7 | 0.37 |
| [46,] | C6orf32 | | | C6orf32 | 0.38 |
| [47,] | ALOX15B | | | ALOX15B | 0.43 |
| [48,] | BRDT | | | BRDT | 0.33 |
| [49,] | CD3G | CD3G | | CD3G | 0.51 |
| [50,] | PTPRC | | PTPRC | | 0.37 |
| [51,] | LTB | | | LTB | 0.32 |
| [52,] | ATP2A3 | ATP2A3 | | ATP2A3 | 0.3 |
| [53,] | NVL | | | NVL | 0.31 |
| [54,] | RASGRP2 | | | RASGRP2 | 0.35 |
| [55,] | LCP1 | LCP1 | | LCP1 | 0.34 |
| [56,] | CORO1A | CORO1A | CORO1A | | 0.41 |
| [57,] | CXCR4 | CXCR4 | | CXCR4 | 0.3 |
| [58,] | PRKD2 | | | PRKD2 | 0.33 |
| [59,] | GATA3 | GATA3 | | GATA3 | 0.39 |
| [60,] | TRA@ | | | TRA@ | 0.4 |
| [61,] | PRKCB1 | PRKCB1 | | PRKCB1 | 0.35 |
| [62,] | HEM1 | | HEM1 | | 0.32 |
| [63,] | KIAA0922 | | | KIAA0922 | 0.36 |
| [64,] | TARP | | | TARP | 0.49 |
| [65,] | SEC31L2 | | | SEC31L2 | 0.32 |
| [66,] | PRKCQ | | | PRKCQ | 0.37 |
| [67,] | SH2D1A | | | SH2D1A | 0.33 |
| [68,] | CHRNA3 | | | CHRNA3 | 0.5 |
| [69,] | CD1A | | | CD1A | 0.44 |
| [70,] | LST1 | | | LST1 | 0.36 |
| [71,] | LAIR1 | | | LAIR1 | 0.47 |
| [72,] | CACNA1G | | | CACNA1G | 0.33 |
| [73,] | TRB@ | TRB@ | | TRB@ | 0.31 |
| [74,] | SEPT6 | SEPT6 | | SEPT6 | 0.33 |
| [75,] | HA-1 | | | HA-1 | 0.42 |
| [76,] | DOCK2 | | | DOCK2 | 0.32 |
| [77,] | CD3D | CD3D | | CD3D | 0.41 |
| [78,] | TRD@ | | | TRD@ | 0.38 |
| [79,] | T3JAM | | | T3JAM | 0.37 |
| [80,] | FNBP1 | | | FNBP1 | 0.37 |
| [81,] | CD6 | | | CD6 | 0.4 |
| [82,] | AIF1 | AIF1 | | AIF1 | 0.31 |
| [83,] | FOLH1 | | | FOLH1 | 0.45 |
| [84,] | CD1E | | | CD1E | 0.58 |
| [85,] | LY9 | | | LY9 | 0.39 |
| [86,] | UGT2B17 | | UGT2B17 | | 0.47 |
| [87,] | ADA | ADA | | ADA | 0.39 |
| [88,] | CDKL5 | | | CDKL5 | 0.44 |
| [89,] | TRIM | | | TRIM | 0.38 |
| [90,] | EVL | | | EVL | 0.39 |
| [91,] | DATF1 | | | DATF1 | 0.31 |
| [92,] | RGC32 | | | RGC32 | 0.51 |
| [93,] | PRKCH | | | PRKCH | 0.3 |
| [94,] | ARHGAP15 | | | ARHGAP15 | 0.34 |
| [95,] | NOTCH1 | | | NOTCH1 | 0.36 |
| [96,] | BIN2 | | | BIN2 | 0.31 |
| [97,] | SEMA4G | | | SEMA4G | 0.35 |
| [98,] | DPEP2 | | | DPEP2 | 0.33 |
| [99,] | CECR1 | | | CECR1 | 0.36 |
| [100,] | BCL11B | | | BCL11B | 0.33 |
| [101,] | STAG3 | | | STAG3 | 0.41 |
| [102,] | GALNT6 | | | GALNT6 | 0.32 |
| [103,] | UBASH3A | | | UBASH3A | 0.3 |
| [104,] | PHEMX | | | PHEMX | 0.38 |
| [105,] | FLJ13373 | | | FLJ13373 | 0.34 |
| [106,] | LEF1 | | | LEF1 | 0.49 |
| [107,] | IL21R | | | IL21R | 0.42 |
| [108,] | MGC17330 | | | MGC17330 | 0.33 |
| [109,] | AKAP13 | | | AKAP13 | 0.53 |
| [110,] | ZNF335 | | | ZNF335 | 0.3 |
| [111,] | GIMAP5 | | | GIMAP5 | 0.34 |

TABLE 15

Methotrexate biomarkers

| | List_2006 | HU6800 | List_Prior | List_Preferr | Correlation |
|---|---|---|---|---|---|
| [1,] | PRPF8 | | | PRPF8 | 0.34 |
| [2,] | RPL18 | | | RPL18 | 0.34 |
| [3,] | RNPS1 | | RNPS1 | | 0.36 |

TABLE 15-continued

Methotrexate biomarkers

| | List_2006 | HU6800 | List_Prior | List_Preferr | Correlation |
|---|---|---|---|---|---|
| [4,] | RPL32 | | | RPL32 | 0.39 |
| [5,] | EEF1G | | | EEF1G | 0.34 |
| [6,] | GOT2 | | | GOT2 | 0.31 |
| [7,] | RPL13A | | | RPL13A | 0.31 |
| [8,] | PTMA | PTMA | PTMA | | 0.41 |
| [9,] | RPS15 | | | RPS15 | 0.39 |
| [10,] | RPLP2 | RPLP2 | | RPLP2 | 0.32 |
| [11,] | CSDA | | | CSDA | 0.39 |
| [12,] | KHDRBS1 | | | KHDRBS1 | 0.32 |
| [13,] | SNRPA | | | SNRPA | 0.31 |
| [14,] | IMPDH2 | IMPDH2 | | IMPDH2 | 0.39 |
| [15,] | RPS19 | | | RPS19 | 0.47 |
| [16,] | NUP88 | | | NUP88 | 0.36 |
| [17,] | ATP5D | | | ATP5D | 0.33 |
| [18,] | PCBP2 | | | PCBP2 | 0.32 |
| [19,] | ZNF593 | | | ZNF593 | 0.4 |
| [20,] | HSU79274 | | | HSU79274 | 0.32 |
| [21,] | PRIM1 | | | PRIM1 | 0.3 |
| [22,] | PFDN5 | | | PFDN5 | 0.33 |
| [23,] | OXA1L | | | OXA1L | 0.37 |
| [24,] | H3F3A | | | H3F3A | 0.42 |
| [25,] | ATIC | | | ATIC | 0.31 |
| [26,] | RPL13 | | | RPL13 | 0.36 |
| [27,] | CIAPIN1 | | | CIAPIN1 | 0.34 |
| [28,] | FBL | | | FBL | 0.33 |
| [29,] | RPS2 | RPS2 | | RPS2 | 0.32 |
| [30,] | PCCB | | | PCCB | 0.36 |
| [31,] | RBMX | | RBMX | | 0.33 |
| [32,] | SHMT2 | | | SHMT2 | 0.34 |
| [33,] | RPLP0 | | | RPLP0 | 0.35 |
| [34,] | HNRPA1 | HNRPA1 | | HNRPA1 | 0.35 |
| [35,] | STOML2 | | | STOML2 | 0.32 |
| [36,] | RPS9 | | RPS9 | | 0.36 |
| [37,] | SKB1 | | | SKB1 | 0.33 |
| [38,] | GLTSCR2 | | | GLTSCR2 | 0.37 |
| [39,] | CCNB1IP1 | | | CCNB1IP1 | 0.3 |
| [40,] | MRPS2 | | | MRPS2 | 0.33 |
| [41,] | FLJ20859 | | | FLJ20859 | 0.34 |
| [42,] | FLJ12270 | | | FLJ12270 | 0.3 |

TABLE 16

Bleomycin biomarkers

| | List_2006 | HU6800 | List_Prior | List_Preferr | Correlation |
|---|---|---|---|---|---|
| [1,] | MSN | | MSN | | 0.3 |
| [2,] | PFN1 | | PFN1 | | 0.45 |
| [3,] | HK1 | | | HK1 | 0.33 |
| [4,] | ACTR2 | | ACTR2 | | 0.31 |
| [5,] | MCL1 | | | MCL1 | 0.31 |
| [6,] | ZYX | | | ZYX | 0.32 |
| [7,] | RAP1B | | | RAP1B | 0.34 |
| [8,] | GNB2 | | | GNB2 | 0.32 |
| [9,] | EPAS1 | | | EPAS1 | 0.31 |
| [10,] | PGAM1 | | | PGAM1 | 0.42 |
| [11,] | CKAP4 | | | CKAP4 | 0.31 |
| [12,] | DUSP1 | | | DUSP1 | 0.4 |
| [13,] | MYL9 | | | MYL9 | 0.4 |
| [14,] | K-ALPHA-1 | | | K-ALPHA-1 | 0.37 |
| [15,] | LGALS1 | | | LGALS1 | 0.38 |
| [16,] | CSDA | CSDA | | CSDA | 0.3 |
| [17,] | AKR1B1 | | AKR1B1 | | 0.32 |
| [18,] | IFITM2 | IFITM2 | | IFITM2 | 0.36 |
| [19,] | ITGA5 | | | ITGA5 | 0.43 |
| [20,] | VIM | | VIM | | 0.39 |
| [21,] | DPYSL3 | | | DPYSL3 | 0.44 |
| [22,] | JUNB | | | JUNB | 0.32 |
| [23,] | ITGA3 | | ITGA3 | | 0.38 |
| [24,] | NFKBIA | | | NFKBIA | 0.32 |
| [25,] | LAMB1 | | | LAMB1 | 0.37 |
| [26,] | FHL1 | | | FHL1 | 0.31 |
| [27,] | INSIG1 | | | INSIG1 | 0.31 |
| [28,] | TIMP1 | | | TIMP1 | 0.48 |
| [29,] | GJA1 | | | GJA1 | 0.54 |
| [30,] | PSME2 | | | PSME2 | 0.34 |
| [31,] | PRG1 | | | PRG1 | 0.46 |
| [32,] | EXT1 | | | EXT1 | 0.35 |
| [33,] | DKFZP434J154 | | | DKFZP434J154 | 0.31 |
| [34,] | OPTN | | OPTN | | 0.31 |
| [35,] | M6PRBP1 | | M6PRBP1 | | 0.52 |
| [36,] | MVP | | | MVP | 0.34 |
| [37,] | VASP | | | VASP | 0.31 |
| [38,] | ARL7 | | | ARL7 | 0.39 |
| [39,] | NNMT | NNMT | | NNMT | 0.34 |
| [40,] | TAP1 | | | TAP1 | 0.3 |
| [41,] | COL1A1 | COL1A1 | COL1A1 | | 0.33 |
| [42,] | BASP1 | | BASP1 | | 0.35 |
| [43,] | PLOD2 | | | PLOD2 | 0.37 |
| [44,] | ATF3 | | | ATF3 | 0.42 |
| [45,] | PALM2-AKAP2 | | | PALM2-AKAP2 | 0.33 |
| [46,] | IL8 | | | IL8 | 0.34 |
| [47,] | ANPEP | | ANPEP | | 0.35 |

TABLE 16-continued

Bleomycin biomarkers

| | List_2006 | HU6800 | List_Prior | List_Preferr | Correlation |
|---|---|---|---|---|---|
| [48,] | LOXL2 | | | LOXL2 | 0.32 |
| [49,] | TGFB1 | | TGFB1 | | 0.31 |
| [50,] | IL4R | | | IL4R | 0.31 |
| [51,] | DGKA | | | DGKA | 0.32 |
| [52,] | STC2 | | | STC2 | 0.31 |
| [53,] | SEC61G | | | SEC61G | 0.41 |
| [54,] | NFIL3 | NFIL3 | NFIL3 | | 0.47 |
| [55,] | RGS3 | | | RGS3 | 0.37 |
| [56,] | NK4 | | NK4 | | 0.34 |
| [57,] | F2R | | | F2R | 0.34 |
| [58,] | TPM2 | | | TPM2 | 0.35 |
| [59,] | PSMB9 | PSMB9 | | PSMB9 | 0.34 |
| [60,] | LOX | | | LOX | 0.37 |
| [61,] | STC1 | | | STC1 | 0.35 |
| [62,] | CSPG2 | CSPG2 | CSPG2 | | 0.35 |
| [63,] | PTGER4 | | | PTGER4 | 0.31 |
| [64,] | IL6 | | | IL6 | 0.34 |
| [65,] | SMAD3 | | | SMAD3 | 0.38 |
| [66,] | PLAU | PLAU | PLAU | | 0.35 |
| [67,] | WNT5A | | | WNT5A | 0.44 |
| [68,] | BDNF | | | BDNF | 0.34 |
| [69,] | TNFRSF1A | TNFRSF1A | | TNFRSF1A | 0.46 |
| [70,] | FLNC | | | FLNC | 0.34 |
| [71,] | DKFZP564K0822 | | | DKFZP564K0822 | 0.34 |
| [72,] | FLOT1 | | | FLOT1 | 0.38 |
| [73,] | PTRF | | | PTRF | 0.39 |
| [74,] | HLA-B | | | HLA-B | 0.36 |
| [75,] | COL6A2 | COL6A2 | COL6A2 | | 0.32 |
| [76,] | MGC4083 | | | MGC4083 | 0.32 |
| [77,] | TNFRSF10B | | | TNFRSF10B | 0.34 |
| [78,] | PLAGL1 | | | PLAGL1 | 0.31 |
| [79,] | PNMA2 | | | PNMA2 | 0.38 |
| [80,] | TFPI | | | TFPI | 0.38 |
| [81,] | LAT | | | LAT | 0.46 |
| [82,] | GZMB | | | GZMB | 0.51 |
| [83,] | CYR61 | | | CYR61 | 0.37 |
| [84,] | PLAUR | PLAUR | | PLAUR | 0.35 |
| [85,] | FSCN1 | FSCN1 | | FSCN1 | 0.32 |
| [86,] | ERP70 | | | ERP70 | 0.32 |
| [87,] | AF1Q | | | AF1Q | 0.3 |
| [88,] | UBC | | UBC | | 0.37 |
| [89,] | FGFR1 | | FGFR1 | | 0.33 |
| [90,] | HIC | | | HIC | 0.33 |
| [91,] | BAX | | BAX | | 0.35 |
| [92,] | COL4A2 | COL4A2 | COL4A2 | | 0.32 |
| [93,] | COL6A1 | | | COL6A1 | 0.32 |
| [94,] | IFITM3 | | | IFITM3 | 0.3 |
| [95,] | MAP1B | | | MAP1B | 0.38 |
| [96,] | FLJ46603 | | | FLJ46603 | 0.37 |
| [97,] | RAFTLIN | | | RAFTLIN | 0.34 |
| [98,] | RRAS | | | RRAS | 0.31 |
| [99,] | FTL | | | FTL | 0.3 |
| [100,] | KIAA0877 | | | KIAA0877 | 0.31 |
| [101,] | MT1E | MT1E | | MT1E | 0.31 |
| [102,] | CDC10 | | | CDC10 | 0.51 |
| [103,] | DOCK2 | | | DOCK2 | 0.32 |
| [104,] | TRIM22 | | | TRIM22 | 0.36 |
| [105,] | RIS1 | | | RIS1 | 0.37 |
| [106,] | BCAT1 | | | BCAT1 | 0.42 |
| [107,] | PRF1 | | | PRF1 | 0.34 |
| [108,] | DBN1 | | | DBN1 | 0.36 |
| [109,] | MT1K | | | MT1K | 0.3 |
| [110,] | TMSB10 | | | TMSB10 | 0.42 |
| [111,] | RAB31 | | RAB31 | | 0.45 |
| [112,] | FLJ10350 | | | FLJ10350 | 0.4 |
| [113,] | C1orf24 | | | C1orf24 | 0.34 |
| [114,] | NME7 | | | NME7 | 0.46 |
| [115,] | TMEM22 | | | TMEM22 | 0.3 |
| [116,] | TPK1 | | | TPK1 | 0.37 |
| [117,] | COL5A2 | | | COL5A2 | 0.34 |
| [118,] | ELK3 | | | ELK3 | 0.38 |
| [119,] | CYLD | | | CYLD | 0.4 |
| [120,] | ADAMTS1 | | | ADAMTS1 | 0.31 |
| [121,] | EHD2 | | | EHD2 | 0.41 |
| [122,] | ACTB | ACTB | | ACTB | 0.33 |

TABLE 17

Methyl-GAG (Methyl glyoxal bis(amidinohydrazone) dihydrochloride)

| | List_2006 | HU6800 | List_Prior | List_Preferr | Correlation |
|---|---|---|---|---|---|
| [1,] | PTMA | | PTMA | | 0.32 |
| [2,] | SSRP1 | | | SSRP1 | 0.37 |
| [3,] | NUDC | | | NUDC | 0.35 |
| [4,] | CTSC | | | CTSC | 0.35 |
| [5,] | AP1G2 | | | AP1G2 | 0.33 |
| [6,] | PSME2 | | | PSME2 | 0.3 |
| [7,] | LBR | | | LBR | 0.38 |
| [8,] | EFNB2 | | | EFNB2 | 0.31 |
| [9,] | SERPINA1 | | | SERPINA1 | 0.34 |
| [10,] | SSSCA1 | | | SSSCA1 | 0.32 |
| [11,] | EZH2 | | | EZH2 | 0.36 |
| [12,] | MYB | MYB | | MYB | 0.33 |
| [13,] | PRIM1 | | | PRIM1 | 0.39 |
| [14,] | H2AFX | | | H2AFX | 0.33 |
| [15,] | HMGA1 | | | HMGA1 | 0.35 |
| [16,] | HMMR | | | HMMR | 0.33 |
| [17,] | TK2 | | | TK2 | 0.42 |
| [18,] | WHSC1 | | | WHSC1 | 0.35 |
| [19,] | DIAPH1 | | | DIAPH1 | 0.34 |
| [20,] | LAMB3 | | | LAMB3 | 0.31 |
| [21,] | DPAGT1 | | | DPAGT1 | 0.42 |
| [22,] | UCK2 | | | UCK2 | 0.31 |
| [23,] | SERPINB1 | | | SERPINB1 | 0.31 |
| [24,] | MDN1 | | | MDN1 | 0.35 |
| [25,] | BRRN1 | | | BRRN1 | 0.33 |
| [26,] | G0S2 | | | G0S2 | 0.43 |
| [27,] | RAC2 | | | RAC2 | 0.35 |
| [28,] | MGC21654 | | | MGC21654 | 0.36 |
| [29,] | GTSE1 | | | GTSE1 | 0.35 |
| [30,] | TACC3 | | | TACC3 | 0.31 |
| [31,] | PLEK2 | | | PLEK2 | 0.32 |
| [32,] | PLAC8 | | | PLAC8 | 0.31 |
| [33,] | HNRPD | | | HNRPD | 0.35 |
| [34,] | PNAS-4 | | | PNAS-4 | 0.3 |

TABLE 18

Carboplatin biomarkers

| | List_2006 | HU6800 | List_Prior | List_Preferr | Correlation |
|---|---|---|---|---|---|
| [1,] | MSN | | MSN | | 0.31 |
| [2,] | ITGA5 | | | ITGA5 | 0.43 |
| [3,] | VIM | | VIM | | 0.34 |
| [4,] | TNFAIP3 | | | TNFAIP3 | 0.4 |
| [5,] | CSPG2 | | CSPG2 | | 0.35 |
| [6,] | WNT5A | | | WNT5A | 0.34 |
| [7,] | FOXF2 | | | FOXF2 | 0.36 |
| [8,] | LOC94105 | | | LOC94105 | 0.32 |
| [9,] | IFI16 | | | IFI16 | 0.38 |
| [10,] | LRRN3 | | | LRRN3 | 0.33 |
| [11,] | FGFR1 | | FGFR1 | | 0.37 |
| [12,] | DOCK10 | | | DOCK10 | 0.4 |
| [13,] | LEPRE1 | | | LEPRE1 | 0.32 |
| [14,] | COL5A2 | | | COL5A2 | 0.3 |
| [15,] | ADAMTS1 | | | ADAMTS1 | 0.34 |

TABLE 19

5-FU (5-Fluorouracil) biomarkers

| | List_2006 | HU6800 | List_Prior | List_Preferr | Correlation |
|---|---|---|---|---|---|
| [1,] | RPL18 | | | RPL18 | 0.39 |
| [2,] | RPL10A | | | RPL10A | 0.36 |
| [3,] | RNPS1 | | RNPS1 | | 0.3 |
| [4,] | ANAPC5 | | | ANAPC5 | 0.5 |
| [5,] | EEF1B2 | | | EEF1B2 | 0.4 |
| [6,] | RPL13A | | | RPL13A | 0.38 |
| [7,] | RPS15 | | | RPS15 | 0.34 |
| [8,] | AKAP1 | | | AKAP1 | 0.37 |
| [9,] | NDUFAB1 | | | NDUFAB1 | 0.3 |
| [10,] | APRT | | | APRT | 0.32 |
| [11,] | ZNF593 | | | ZNF593 | 0.37 |
| [12,] | MRP63 | | | MRP63 | 0.31 |
| [13,] | IL6R | | | IL6R | 0.31 |
| [14,] | RPL13 | | RPL13 | | 0.31 |
| [15,] | SART3 | | | SART3 | 0.35 |
| [16,] | RPS6 | | RPS6 | | 0.49 |
| [17,] | UCK2 | | | UCK2 | 0.38 |
| [18,] | RPL3 | | RPL3 | | 0.32 |
| [19,] | RPL17 | | | RPL17 | 0.34 |
| [20,] | RPS2 | | | RPS2 | 0.32 |
| [21,] | PCCB | | | PCCB | 0.31 |
| [22,] | TOMM20 | | | TOMM20 | 0.39 |
| [23,] | SHMT2 | | | SHMT2 | 0.36 |
| [24,] | RPLP0 | | | RPLP0 | 0.3 |
| [25,] | GTF3A | | | GTF3A | 0.5 |
| [26,] | STOML2 | | | STOML2 | 0.4 |
| [27,] | DKFZp564J157 | | | DKFZp564J157 | 0.38 |
| [28,] | MRPS2 | | | MRPS2 | 0.34 |
| [29,] | ALG5 | | | ALG5 | 0.37 |
| [30,] | CALML4 | | | CALML4 | 0.3 |

TABLE 20

Rituximab (e.g., Mabthera) biomarkers

| | List_2006 | List_Prior | List_Preferr | Correlation |
|---|---|---|---|---|
| [1,] | ITK | ITK | | 0.36 |
| [2,] | KIFC1 | | KIFC1 | 0.36 |
| [3,] | VLDLR | | VLDLR | 0.39 |
| [4,] | RUNX1 | | RUNX1 | 0.32 |
| [5,] | PAFAH1B3 | | PAFAH1B3 | 0.32 |
| [6,] | H1FX | | H1FX | 0.43 |
| [7,] | RNF144 | | RNF144 | 0.38 |
| [8,] | TMSNB | | TMSNB | 0.47 |
| [9,] | CRY1 | | CRY1 | 0.37 |
| [10,] | MAZ | | MAZ | 0.33 |
| [11,] | SLA | | SLA | 0.35 |
| [12,] | SRF | | SRF | 0.37 |
| [13,] | UMPS | | UMPS | 0.41 |
| [14,] | CD3Z | | CD3Z | 0.33 |
| [15,] | PRKCQ | | PRKCQ | 0.31 |
| [16,] | HNRPM | | HNRPM | 0.45 |
| [17,] | ZAP70 | | ZAP70 | 0.38 |
| [18,] | ADD1 | | ADD1 | 0.31 |
| [19,] | RFC5 | | RFC5 | 0.35 |
| [20,] | TM4SF2 | | TM4SF2 | 0.33 |
| [21,] | PFN2 | | PFN2 | 0.3 |
| [22,] | BMI1 | | BMI1 | 0.31 |
| [23,] | TUBGCP3 | | TUBGCP3 | 0.33 |
| [24,] | ATP6V1B2 | | ATP6V1B2 | 0.42 |
| [25,] | RALY | RALY | | 0.31 |
| [26,] | PSMC5 | PSMC5 | | 0.36 |
| [27,] | CD1D | | CD1D | 0.32 |
| [28,] | ADA | | ADA | 0.34 |
| [29,] | CD99 | | CD99 | 0.33 |
| [30,] | CD2 | | CD2 | 0.43 |
| [31,] | CNP | | CNP | 0.48 |
| [32,] | ERG | | ERG | 0.47 |
| [33,] | MYL6 | MYL6 | | 0.41 |
| [34,] | CD3E | | CD3E | 0.36 |
| [35,] | CD1A | | CD1A | 0.46 |
| [36,] | CD1B | CD1B | | 0.47 |
| [37,] | STMN1 | STMN1 | | 0.32 |
| [38,] | PSMC3 | | PSMC3 | 0.38 |
| [39,] | RPS4Y1 | | RPS4Y1 | 0.36 |
| [40,] | AKT1 | | AKT1 | 0.38 |
| [41,] | TAL1 | | TAL1 | 0.37 |
| [42,] | GNA15 | GNA15 | | 0.37 |
| [43,] | UBE2A | | UBE2A | 0.35 |
| [44,] | TCF12 | | TCF12 | 0.35 |
| [45,] | UBE2S | | UBE2S | 0.52 |
| [46,] | CCND3 | | CCND3 | 0.38 |
| [47,] | PAX6 | | PAX6 | 0.35 |
| [48,] | MDK | MDK | | 0.3 |
| [49,] | CAPG | CAPG | | 0.36 |
| [50,] | RAG2 | | RAG2 | 0.39 |
| [51,] | ACTN1 | ACTN1 | | 0.37 |
| [52,] | GSTM2 | | GSTM2 | 0.47 |
| [53,] | SATB1 | | SATB1 | 0.36 |
| [54,] | NASP | | NASP | 0.3 |
| [55,] | IGFBP2 | | IGFBP2 | 0.46 |
| [56,] | CDH2 | | CDH2 | 0.49 |
| [57,] | CRABP1 | | CRABP1 | 0.36 |
| [58,] | DBN1 | | DBN1 | 0.49 |
| [59,] | CTNNA1 | CTNNA1 | | 0.53 |
| [60,] | AKR1C1 | | AKR1C1 | 0.32 |
| [61,] | CACNB3 | | CACNB3 | 0.37 |
| [62,] | FARSLA | FARSLA | | 0.35 |
| [63,] | CASP2 | | CASP2 | 0.42 |
| [64,] | CASP2 | | CASP2 | 0.31 |
| [65,] | E2F4 | E2F4 | | 0.36 |
| [66,] | LCP2 | | LCP2 | 0.35 |
| [67,] | CASP6 | | CASP6 | 0.32 |
| [68,] | MYB | | MYB | 0.3 |
| [69,] | SFRS6 | | SFRS6 | 0.44 |
| [70,] | GLRB | | GLRB | 0.34 |
| [71,] | NDN | | NDN | 0.39 |
| [72,] | CPSF1 | CPSF1 | | 0.33 |
| [73,] | GNAQ | | GNAQ | 0.44 |
| [74,] | TUSC3 | | TUSC3 | 0.41 |
| [75,] | GNAQ | | GNAQ | 0.54 |
| [76,] | JARID2 | | JARID2 | 0.44 |
| [77,] | OCRL | | OCRL | 0.5 |
| [78,] | FHL1 | | FHL1 | 0.36 |
| [79,] | EZH2 | | EZH2 | 0.4 |
| [80,] | SMOX | | SMOX | 0.35 |
| [81,] | SLC4A2 | | SLC4A2 | 0.35 |
| [82,] | UFD1L | | UFD1L | 0.3 |
| [83,] | SEPW1 | SEPW1 | | 0.31 |
| [84,] | ZNF32 | | ZNF32 | 0.35 |
| [85,] | HTATSF1 | | HTATSF1 | 0.35 |
| [86,] | SHD1 | | SHD1 | 0.43 |
| [87,] | PTOV1 | | PTOV1 | 0.42 |
| [88,] | NXF1 | | NXF1 | 0.46 |
| [89,] | FYB | | FYB | 0.47 |
| [90,] | TRIM28 | | TRIM28 | 0.38 |
| [91,] | BC008967 | | BC008967 | 0.4 |
| [92,] | TRB@ | | TRB@ | 0.3 |
| [93,] | TFRC | TFRC | | 0.31 |
| [94,] | H1F0 | | H1F0 | 0.36 |
| [95,] | CD3D | | CD3D | 0.32 |
| [96,] | CD3G | | CD3G | 0.4 |
| [97,] | CENPB | | CENPB | 0.36 |
| [98,] | ALDH2 | | ALDH2 | 0.33 |
| [99,] | ANXA1 | | ANXA1 | 0.35 |
| [100,] | H2AFX | | H2AFX | 0.51 |
| [101,] | CD1E | | CD1E | 0.33 |
| [102,] | DDX5 | | DDX5 | 0.39 |
| [103,] | ABL1 | ABL1 | | 0.3 |
| [104,] | CCNA2 | | CCNA2 | 0.3 |
| [105,] | ENO2 | | ENO2 | 0.35 |
| [106,] | SNRPB | | SNRPB | 0.38 |
| [107,] | GATA3 | | GATA3 | 0.36 |
| [108,] | RRM2 | | RRM2 | 0.48 |
| [109,] | GLUL | | GLUL | 0.4 |
| [110,] | TCF7 | TCF7 | | 0.39 |
| [111,] | FGFR1 | FGFR1 | | 0.33 |
| [112,] | SOX4 | | SOX4 | 0.3 |
| [113,] | MAL | | MAL | 0.3 |
| [114,] | NUCB2 | NUCB2 | | 0.38 |
| [115,] | SMA3 | | SMA3 | 0.31 |
| [116,] | FAT | FAT | | 0.52 |
| [117,] | UNG | | UNG | 0.31 |
| [118,] | ARHGDIB | | ARHGDIB | 0.36 |
| [119,] | RUNX1 | | RUNX1 | 0.38 |
| [120,] | MPHOSPH6 | | MPHOSPH6 | 0.5 |
| [121,] | DCTN1 | | DCTN1 | 0.34 |
| [122,] | SH3GL3 | | SH3GL3 | 0.38 |
| [123,] | VIM | | VIM | 0.41 |
| [124,] | PLEKHC1 | | PLEKHC1 | 0.3 |
| [125,] | CD47 | | CD47 | 0.32 |
| [126,] | POLR2F | | POLR2F | 0.37 |
| [127,] | RHOH | | RHOH | 0.43 |
| [128,] | ADD1 | | ADD1 | 0.46 |
| [129,] | ATP2A3 | | ATP2A3 | 0.38 |

TABLE 21

Radiation sensitivity biomarkers

| | List_2006 | HU6800 | List_Prior | List_Preferr | Correlation |
|---|---|---|---|---|---|
| [1,] | TRA1 | | | TRA1 | 0.36 |
| [2,] | ACTN4 | | | ACTN4 | 0.36 |

TABLE 21-continued

Radiation sensitivity biomarkers

| List_2006 | HU6800 | List_Prior | List_Preferr | Correlation |
|---|---|---|---|---|
| [3,] WARS | | WARS | | 0.39 |
| [4,] CALM1 | | | CALM1 | 0.32 |
| [5,] CD63 | CD63 | | CD63 | 0.32 |
| [6,] CD81 | | CD81 | | 0.43 |
| [7,] FKBP1A | | | FKBP1A | 0.38 |
| [8,] CALU | | | CALU | 0.47 |
| [9,] IQGAP1 | | | IQGAP1 | 0.37 |
| [10,] CTSB | | CTSB | | 0.33 |
| [11,] MGC8721 | | | MGC8721 | 0.35 |
| [12,] STAT1 | | | STAT1 | 0.37 |
| [13,] TACC1 | | | TACC1 | 0.41 |
| [14,] TM4SF8 | | | TM4SF8 | 0.33 |
| [15,] CD59 | | | CD59 | 0.31 |
| [16,] CKAP4 | CKAP4 | | CKAP4 | 0.45 |
| [17,] DUSP1 | DUSP1 | | DUSP1 | 0.38 |
| [18,] RCN1 | | | RCN1 | 0.31 |
| [19,] MGC8902 | | | MGC8902 | 0.35 |
| [20,] LGALS1 | LGALS1 | | LGALS1 | 0.33 |
| [21,] BHLHB2 | | | BHLHB2 | 0.3 |
| [22,] RRBP1 | | | RRBP1 | 0.31 |
| [23,] PKM2 | | PKM2 | | 0.33 |
| [24,] PRNP | | | PRNP | 0.42 |
| [25,] PPP2CB | | PPP2CB | | 0.31 |
| [26,] CNN3 | | CNN3 | | 0.36 |
| [27,] ANXA2 | ANXA2 | ANXA2 | | 0.32 |
| [28,] IER3 | | | IER3 | 0.34 |
| [29,] JAK1 | | JAK1 | | 0.33 |
| [30,] MARCKS | | | MARCKS | 0.43 |
| [31,] LUM | | | LUM | 0.48 |
| [32,] FER1L3 | | | FER1L3 | 0.47 |
| [33,] SLC20A1 | | | SLC20A1 | 0.41 |
| [34,] EIF4G3 | | EIF4G3 | | 0.36 |
| [35,] HEXB | | | HEXB | 0.46 |
| [36,] EXT1 | | | EXT1 | 0.47 |
| [37,] TJP1 | | | TJP1 | 0.32 |
| [38,] CTSL | CTSL | | CTSL | 0.38 |
| [39,] SLC39A6 | | | SLC39A6 | 0.36 |
| [40,] RIOK3 | | | RIOK3 | 0.38 |
| [41,] CRK | | | CRK | 0.37 |
| [42,] NNMT | | | NNMT | 0.37 |
| [43,] COL1A1 | | COL1A1 | | 0.35 |
| [44,] TRAM2 | TRAM2 | | TRAM2 | 0.35 |
| [45,] ADAM9 | | | ADAM9 | 0.52 |
| [46,] DNAJC7 | | | DNAJC7 | 0.38 |
| [47,] PLSCR1 | | | PLSCR1 | 0.35 |
| [48,] PRSS23 | | | PRSS23 | 0.3 |
| [49,] PLOD2 | | | PLOD2 | 0.36 |
| [50,] NPC1 | | | NPC1 | 0.39 |
| [51,] TOB1 | | | TOB1 | 0.37 |
| [52,] GFPT1 | | | GFPT1 | 0.47 |
| [53,] IL8 | | | IL8 | 0.36 |
| [54,] DYRK2 | | DYRK2 | | 0.3 |
| [55,] PYGL | | | PYGL | 0.46 |
| [56,] LOXL2 | | | LOXL2 | 0.49 |
| [57,] KIAA0355 | | | KIAA0355 | 0.36 |
| [58,] UGDH | | | UGDH | 0.49 |
| [59,] NFIL3 | | NFIL3 | | 0.53 |
| [60,] PURA | | | PURA | 0.32 |
| [61,] ULK2 | | | ULK2 | 0.37 |
| [62,] CENTG2 | | | CENTG2 | 0.35 |
| [63,] NID2 | | | NID2 | 0.42 |
| [64,] CAP350 | | | CAP350 | 0.31 |
| [65,] CXCL1 | | | CXCL1 | 0.36 |
| [66,] BTN3A3 | | | BTN3A3 | 0.35 |
| [67,] IL6 | | | IL6 | 0.32 |
| [68,] WNT5A | | | WNT5A | 0.3 |
| [69,] FOXF2 | | | FOXF2 | 0.44 |
| [70,] LPHN2 | | | LPHN2 | 0.34 |
| [71,] CDH11 | | | CDH11 | 0.39 |
| [72,] P4HA1 | | | P4HA1 | 0.33 |
| [73,] GRP58 | | | GRP58 | 0.44 |
| [74,] ACTN1 | ACTN1 | ACTN1 | | 0.41 |
| [75,] CAPN2 | | CAPN2 | | 0.54 |
| [76,] DSIPI | | | DSIPI | 0.44 |
| [77,] MAP1LC3B | | | MAP1LC3B | 0.5 |
| [78,] GALIG | GALIG | | GALIG | 0.36 |

TABLE 21-continued

Radiation sensitivity biomarkers

| List_2006 | HU6800 | List_Prior | List_Preferr | Correlation |
|---|---|---|---|---|
| [79,] IGSF4 | | | IGSF4 | 0.4 |
| [80,] IRS2 | | | IRS2 | 0.35 |
| [81,] ATP2A2 | | | ATP2A2 | 0.35 |
| [82,] OGT | | | OGT | 0.3 |
| [83,] TNFRSF10B | | | TNFRSF10B | 0.31 |
| [84,] KIAA1128 | | | KIAA1128 | 0.35 |
| [85,] TM4SF1 | | | TM4SF1 | 0.35 |
| [86,] RBPMS | | | RBPMS | 0.43 |
| [87,] RIPK2 | | | RIPK2 | 0.42 |
| [88,] CBLB | | | CBLB | 0.46 |
| [89,] NR1D2 | | | NR1D2 | 0.47 |
| [90,] BTN3A2 | | BTN3A2 | | 0.38 |
| [91,] SLC7A11 | | | SLC7A11 | 0.4 |
| [92,] MPZL1 | | | MPZL1 | 0.3 |
| [93,] IGFBP3 | IGFBP3 | IGFBP3 | | 0.31 |
| [94,] SSA2 | | | SSA2 | 0.36 |
| [95,] FN1 | FN1 | FN1 | | 0.32 |
| [96,] NQO1 | | | NQO1 | 0.4 |
| [97,] ASPH | | | ASPH | 0.36 |
| [98,] ASAH1 | | | ASAH1 | 0.33 |
| [99,] MGLL | | | MGLL | 0.35 |
| [100,] SERPINB6 | | | SERPINB6 | 0.51 |
| [101,] HSPA5 | | | HSPA5 | 0.33 |
| [102,] ZFP36L1 | | | ZFP36L1 | 0.39 |
| [103,] COL4A2 | | COL4A2 | | 0.3 |
| [104,] COL4A1 | | | COL4A1 | 0.3 |
| [105,] CD44 | | | CD44 | 0.35 |
| [106,] SLC39A14 | | | SLC39A14 | 0.38 |
| [107,] NIPA2 | | | NIPA2 | 0.36 |
| [108,] FKBP9 | | | FKBP9 | 0.48 |
| [109,] IL6ST | | | IL6ST | 0.4 |
| [110,] DKFZP564G2022 | | | DKFZP564G2022 | 0.39 |
| [111,] PPAP2B | | | PPAP2B | 0.33 |
| [112,] MAP1B | | | MAP1B | 0.3 |
| [113,] MAPK1 | | | MAPK1 | 0.3 |
| [114,] MYO1B | | | MYO1B | 0.38 |
| [115,] CAST | CAST | | CAST | 0.31 |
| [116,] RRAS2 | | | RRAS2 | 0.52 |
| [117,] QKI | | | QKI | 0.31 |
| [118,] LHFPL2 | | | LHFPL2 | 0.36 |
| [119,] SEPT10 | | | SEPT10 | 0.38 |
| [120,] ARHE | | | ARHE | 0.5 |
| [121,] KIAA1078 | | | KIAA1078 | 0.34 |
| [122,] FTL | | | FTL | 0.38 |
| [123,] KIAA0877 | | | KIAA0877 | 0.41 |
| [124,] PLCB1 | | | PLCB1 | 0.3 |
| [125,] KIAA0802 | | | KIAA0802 | 0.32 |
| [126,] KPNB1 | | KPNB1 | | 0.37 |
| [127,] RAB3GAP | | | RAB3GAP | 0.43 |
| [128,] SERPINB1 | | | SERPINB1 | 0.46 |
| [129,] TIMM17A | | | TIMM17A | 0.38 |
| [130,] SOD2 | | | SOD2 | 0.35 |
| [131,] HLA-A | HLA-A | | HLA-A | 0.33 |
| [132,] NOMO2 | | | NOMO2 | 0.43 |
| [133,] LOC55831 | | | LOC55831 | 0.32 |
| [134,] PHLDA1 | | | PHLDA1 | 0.32 |
| [135,] TMEM2 | | | TMEM2 | 0.47 |
| [136,] MLPH | | | MLPH | 0.35 |
| [137,] FAD104 | | | FAD104 | 0.34 |
| [138,] LRRC5 | | | LRRC5 | 0.42 |
| [139,] RAB7L1 | | | RAB7L1 | 0.41 |
| [140,] FLJ35036 | | | FLJ35036 | 0.36 |
| [141,] DOCK10 | | | DOCK10 | 0.41 |
| [142,] LRP12 | | | LRP12 | 0.36 |
| [143,] TXNDC5 | | | TXNDC5 | 0.4 |
| [144,] CDC14B | | | CDC14B | 0.39 |
| [145,] HRMT1L1 | | | HRMT1L1 | 0.38 |
| [146,] CORO1C | | | CORO1C | 0.38 |
| [147,] DNAJC10 | | | DNAJC10 | 0.31 |
| [148,] TNPO1 | | | TNPO1 | 0.33 |
| [149,] LONP | | | LONP | 0.32 |
| [150,] AMIGO2 | | | AMIGO2 | 0.38 |
| [151,] DNAPTP6 | | | DNAPTP6 | 0.31 |
| [152,] ADAMTS1 | | | ADAMTS1 | 0.37 |
| [153,] | CCL21 | | | |
| [154,] | SCARB2 | | | |

TABLE 21-continued

Radiation sensitivity biomarkers

| | List_2006 | HU6800 | List_Prior | List_Preferr | Correlation |
|---|---|---|---|---|---|
| [155,] | | MAD2L1BP | | | |
| [156,] | | PTS | | | |
| [157,] | | NBL1 | | | |
| [158,] | | CD151 | | | |
| [159,] | | CRIP2 | | | |
| [160,] | | UGCG | | | |
| [161,] | | PRSS11 | | | |
| [162,] | | MME | | | |
| [163,] | | CBR1 | | | |
| [164,] | | DUSP3 | | | |
| [165,] | | PFN2 | | | |
| [166,] | | MICA | | | |
| [167,] | | FTH1 | | | |
| [168,] | | RHOC | | | |
| [169,] | | ZAP128 | | | |
| [170,] | | PON2 | | | |
| [171,] | | COL5A2 | | | |
| [172,] | | CST3 | | | |
| [173,] | | MCAM | | | |
| [174,] | | MMP2 | | | |
| [175,] | | CTSD | | | |
| [176,] | | ALDH3A1 | | | |
| [177,] | | CSRP1 | | | |
| [178,] | | S100A4 | | | |
| [179,] | | CALD1 | | | |
| [180,] | | CTGF | | | |
| [181,] | | CAPG | | | |
| [182,] | | TAGLN | | | |
| [183,] | | FSTL1 | | | |
| [184,] | | SCTR | | | |
| [185,] | | BLVRA | | | |
| [186,] | | COPEB | | | |
| [187,] | | DIPA | | | |
| [188,] | | SMARCD3 | | | |
| [189,] | | MVP | | | |
| [190,] | | PEA15 | | | |
| [191,] | | S100A13 | | | |
| [192,] | | ECE1 | | | |

TABLE 22

Vincristine biomarkers.

| SEQ ID NO | Gene | Correlation | Medianprobe |
|---|---|---|---|
| 1 | SLC25A5 | 0.32 | TCCTGTACTTGTCCTCAGCTTGGGC |
| 2 | RPL10 | 0.38 | GCCCCACTGGACAACACTGATTCCT |
| 3 | RPL12 | 0.31 | TGCCTGCTCCTGTACTTGTCCTCAG |
| 4 | RPS4X | 0.39 | AAATGTTTCCTTGTGCCTGCTCCTG |
| 5 | EIF5A | 0.31 | TCCTGTACTTGTCCTCAGCTTGGGC |
| 6 | BLMH | 0.32 | AAGCCTATACGTTTCTGTGGAGTAA |
| 7 | TBCA | 0.3 | ACTTGTCCTCAGCTTGGGCTTCTTC |
| 1 | MDH2 | 0.34 | TCCTGTACTTGTCCTCAGCTTGGGC |
| 9 | S100A4 | 0.32 | TGGACCCCACTGGCTGAGAATCTGG |
| 10 | C14orf139 | 0.3 | TTGGACATCTCTAGTGTAGCTGCCA |

TABLE 23

Cisplatin biomarkers.

| SEQ ID NO | Gene | Correlation | Medianprobe |
|---|---|---|---|
| 11 | C1QR1 | 0.3 | CACCCAGCTGGTCCTGTGGATGGGA |
| 3 | SLA | 0.37 | TGCCTGCTCCTGTACTTGTCCTCAG |
| 7 | PTPN7 | 0.31 | ACTTGTCCTCAGCTTGGGCTTCTTC |
| 11 | ZNFN1A1 | 0.33 | CACCCAGCTGGTCCTGTGGATGGGA |
| 10 | CENTB1 | 0.37 | TTGGACATCTCTAGTGTAGCTGCCA |
| 16 | IFI16 | 0.31 | TCCTCCATCACCTGAAACACTGGAC |
| 3 | ARHGEF6 | 0.35 | TGCCTGCTCCTGTACTTGTCCTCAG |
| 6 | SEC31L2 | 0.32 | AAGCCTATACGTTTCTGTGGAGTAA |
| 10 | CD3Z | 0.32 | TTGGACATCTCTAGTGTAGCTGCCA |
| 16 | GZMB | 0.3 | TCCTCCATCACCTGAAACACTGGAC |
| 16 | CD3D | 0.34 | TCCTCCATCACCTGAAACACTGGAC |
| 11 | MAP4K1 | 0.32 | CACCCAGCTGGTCCTGTGGATGGGA |
| 11 | GPR65 | 0.39 | CACCCAGCTGGTCCTGTGGATGGGA |

TABLE 23-continued

Cisplatin biomarkers.

| SEQ ID NO | Gene | Correlation | Medianprobe |
|---|---|---|---|
| 24 | PRF1 | 0.31 | TCCTTGTGCCTGCTCCTGTACTTGT |
| 11 | ARHGAP15 | 0.35 | CACCCAGCTGGTCCTGTGGATGGGA |
| 3 | TM6SF1 | 0.41 | TGCCTGCTCCTGTACTTGTCCTCAG |
| 4 | TCF4 | 0.4 | AAATGTTTCCTTGTGCCTGCTCCTG |

TABLE 24

Etoposide biomarkers.

| SEQ ID NO | Gene | Correlation | Medianprobe |
|---|---|---|---|
| 6 | CD99 | 0.3 | AAGCCTATACGTTTCTGTGGAGTAA |
| 24 | INSIG1 | 0.35 | TCCTTGTGCCTGCTCCTGTACTTGT |
| 2 | PRG1 | 0.34 | GCCCCACTGGACAACACTGATTCCT |
| 6 | MUF1 | 0.35 | AAGCCTATACGTTTCTGTGGAGTAA |
| 11 | SLA | 0.37 | CACCCAGCTGGTCCTGTGGATGGGA |
| 9 | SSBP2 | 0.37 | TGGACCCCACTGGCTGAGAATCTGG |
| 24 | GNB5 | 0.35 | TCCTTGTGCCTGCTCCTGTACTTGT |
| 2 | MFNG | 0.33 | GCCCCACTGGACAACACTGATTCCT |
| 6 | PSMB9 | 0.31 | AAGCCTATACGTTTCTGTGGAGTAA |
| 16 | EVI2A | 0.41 | TCCTCCATCACCTGAAACACTGGAC |
| 6 | PTPN7 | 0.3 | AAGCCTATACGTTTCTGTGGAGTAA |
| 3 | PTGER4 | 0.3 | TGCCTGCTCCTGTACTTGTCCTCAG |
| 2 | CXorf9 | 0.3 | GCCCCACTGGACAACACTGATTCCT |
| 7 | ZNFN1A1 | 0.35 | ACTTGTCCTCAGCTTGGGCTTCTTC |
| 9 | CENTB1 | 0.3 | TGGACCCCACTGGCTGAGAATCTGG |
| 16 | NAP1L1 | 0.31 | TCCTCCATCACCTGAAACACTGGAC |
| 3 | HLA-DRA | 0.34 | TGCCTGCTCCTGTACTTGTCCTCAG |
| 11 | IFI16 | 0.38 | CACCCAGCTGGTCCTGTGGATGGGA |
| 9 | ARHGEF6 | 0.33 | TGGACCCCACTGGCTGAGAATCTGG |
| 6 | PSCDBP | 0.4 | AAGCCTATACGTTTCTGTGGAGTAA |
| 10 | SELPLG | 0.35 | TTGGACATCTCTAGTGTAGCTGCCA |
| 4 | SEC31L2 | 0.42 | AAATGTTTCCTTGTGCCTGCTCCTG |
| 3 | CD3Z | 0.36 | TGCCTGCTCCTGTACTTGTCCTCAG |
| 11 | SH2D1A | 0.33 | CACCCAGCTGGTCCTGTGGATGGGA |
| 9 | GZMB | 0.34 | TGGACCCCACTGGCTGAGAATCTGG |
| 2 | SCN3A | 0.3 | GCCCCACTGGACAACACTGATTCCT |
| 16 | RAFTLIN | 0.39 | TCCTCCATCACCTGAAACACTGGAC |
| 3 | DOCK2 | 0.33 | TGCCTGCTCCTGTACTTGTCCTCAG |

TABLE 24-continued

Etoposide biomarkers.

| SEQ ID NO | Gene | Correlation | Medianprobe |
|---|---|---|---|
| 7 | CD3D | 0.31 | ACTTGTCCTCAGCTTGGGCTTCTTC |
| 16 | ZAP70 | 0.35 | TCCTCCATCACCTGAAACACTGGAC |
| 9 | GPR65 | 0.35 | TGGACCCCACTGGCTGAGAATCTGG |
| 9 | PRF1 | 0.32 | TGGACCCCACTGGCTGAGAATCTGG |
| 7 | ARHGAP15 | 0.32 | ACTTGTCCTCAGCTTGGGCTTCTTC |
| 3 | NOTCH1 | 0.31 | TGCCTGCTCCTGTACTTGTCCTCAG |
| 7 | UBASH3A | 0.32 | ACTTGTCCTCAGCTTGGGCTTCTTC |

TABLE 25

Azaguanine biomarkers.

| SEQ ID NO | Gene | Correlation | Medianprobe |
|---|---|---|---|
| 3 | SRM | 0.32 | TGCCTGCTCCTGTACTTGTCCTCAG |
| 10 | SCARB1 | 0.4 | TTGGACATCTCTAGTGTAGCTGCCA |
| 4 | SIAT1 | 0.31 | AAATGTTTCCTTGTGCCTGCTCCTG |
| 9 | CUGBP2 | 0.37 | TGGACCCCACTGGCTGAGAATCTGG |
| 1 | WASPIP | 0.44 | TCCTGTACTTGTCCTCAGCTTGGGC |
| 6 | ITM2A | 0.31 | AAGCCTATACGTTTCTGTGGAGTAA |
| 7 | PALM2-AKAP2 | 0.31 | ACTTGTCCTCAGCTTGGGCTTCTTC |
| 10 | LNK | 0.43 | TTGGACATCTCTAGTGTAGCTGCCA |
| 3 | FCGR2A | 0.3 | TGCCTGCTCCTGTACTTGTCCTCAG |
| 1 | RUNX3 | 0.43 | TCCTGTACTTGTCCTCAGCTTGGGC |
| 4 | EVI2A | 0.4 | AAATGTTTCCTTGTGCCTGCTCCTG |
| 7 | BTN3A3 | 0.4 | ACTTGTCCTCAGCTTGGGCTTCTTC |
| 24 | LCP2 | 0.34 | TCCTTGTGCCTGCTCCTGTACTTGT |
| 16 | BCHE | 0.35 | TCCTCCATCACCTGAAACACTGGAC |
| 3 | LY96 | 0.47 | TGCCTGCTCCTGTACTTGTCCTCAG |
| 7 | LCP1 | 0.42 | ACTTGTCCTCAGCTTGGGCTTCTTC |
| 11 | IFI16 | 0.33 | CACCCAGCTGGTCCTGTGGATGGGA |
| 10 | MCAM | 0.37 | TTGGACATCTCTAGTGTAGCTGCCA |
| 11 | MEF2C | 0.41 | CACCCAGCTGGTCCTGTGGATGGGA |
| 1 | FYN | 0.31 | TCCTGTACTTGTCCTCAGCTTGGGC |
| 6 | C1orf38 | 0.37 | AAGCCTATACGTTTCTGTGGAGTAA |
| 3 | FCGR2C | 0.34 | TGCCTGCTCCTGTACTTGTCCTCAG |
| 6 | TNIK | 0.35 | AAGCCTATACGTTTCTGTGGAGTAA |
| 1 | AMPD2 | 0.3 | TCCTGTACTTGTCCTCAGCTTGGGC |

TABLE 25-continued

Azaguanine biomarkers.

| SEQ ID NO | Gene | Correlation | Medianprobe |
|---|---|---|---|
| 4 | SEPT6 | 0.41 | AAATGTTTCCTTGTGCCTGCTCCTG |
| 24 | RAFTLIN | 0.39 | TCCTTGTGCCTGCTCCTGTACTTGT |
| 11 | SLC43A3 | 0.52 | CACCCAGCTGGTCCTGTGGATGGGA |
| 6 | LPXN | 0.54 | AAGCCTATACGTTTCTGTGGAGTAA |
| 1 | CKIP-1 | 0.33 | TCCTGTACTTGTCCTCAGCTTGGGC |
| 24 | FLJ10539 | 0.33 | TCCTTGTGCCTGCTCCTGTACTTGT |
| 6 | FLJ35036 | 0.36 | AAGCCTATACGTTTCTGTGGAGTAA |
| 2 | DOCK10 | 0.3 | GCCCCACTGGACAACACTGATTCCT |
| 7 | TRPV2 | 0.31 | ACTTGTCCTCAGCTTGGGCTTCTTC |
| 24 | IFRG28 | 0.3 | TCCTTGTGCCTGCTCCTGTACTTGT |
| 7 | LEF1 | 0.31 | ACTTGTCCTCAGCTTGGGCTTCTTC |
| 9 | ADAMTS1 | 0.36 | TGGACCCCACTGGCTGAGAATCTGG |

TABLE 26

Carboplatin biomarkers.

| SEQ ID NO | Gene | Correlation | Medianprobe |
|---|---|---|---|
| 4 | ITGA5 | 0.43 | AAATGTTTCCTTGTGCCTGCTCCTG |
| 3 | TNFAIP3 | 0.4 | TGCCTGCTCCTGTACTTGTCCTCAG |
| 16 | WNT5A | 0.34 | TCCTCCATCACCTGAAACACTGGAC |
| 3 | FOXF2 | 0.36 | TGCCTGCTCCTGTACTTGTCCTCAG |
| 4 | LOC94105 | 0.32 | AAATGTTTCCTTGTGCCTGCTCCTG |
| 16 | IFI16 | 0.38 | TCCTCCATCACCTGAAACACTGGAC |
| 10 | LRRN3 | 0.33 | TTGGACATCTCTAGTGTAGCTGCCA |
| 1 | DOCK10 | 0.4 | TCCTGTACTTGTCCTCAGCTTGGGC |
| 2 | LEPRE1 | 0.32 | GCCCCACTGGACAACACTCATTCCT |
| 9 | ADAMTS1 | 0.34 | TGGACCCCACTGGCTGAGAATCTGG |

TABLE 27

Adriamycin biomarkers.

| SEQ ID NO | Gene | Correlation | Medianprobe |
|---|---|---|---|
| 6 | CD99 | 0.41 | AAGCCTATACGTTTCTGTGGAGTAA |
| 24 | ALDOC | 0.31 | TCCTTGTGCCTGCTCCTGTACTTGT |
| 3 | SLA | 0.35 | TGCCTGCTCCTGTACTTGTCCTCAG |
| 16 | SSBP2 | 0.34 | TCCTCCATCACCTGAAACACTGGAC |
| 24 | IL2RG | 0.38 | TCCTTGTGCCTGCTCCTGTACTTGT |

TABLE 27-continued

Adriamycin biomarkers.

| SEQ ID NO | Gene | Correlation | Medianprobe |
|---|---|---|---|
| 9 | CXorf9 | 0.32 | TGGACCCCACTGGCTGAGAATCTGG |
| 7 | RHOH | 0.31 | ACTTGTCCTCAGCTTGGGCTTCTTC |
| 10 | ZNFN1A1 | 0.43 | TTGGACATCTCTAGTGTAGCTGCCA |
| 6 | CENTB1 | 0.36 | AAGCCTATACGTTTCTGTGGAGTAA |
| 16 | MAP4K1 | 0.35 | TCCTCCATCACCTGAAACACTGGAC |
| 4 | CD3G | 0.31 | AAATGTTTCCTTGTGCCTGCTCCTG |
| 11 | CCR9 | 0.34 | CACCCAGCTGGTCCTGTGGATGGGA |
| 24 | CXCR4 | 0.3 | TCCTTGTGCCTGCTCCTGTACTTGT |
| 16 | ARHGEF6 | 0.31 | TCCTCCATCACCTGAAACACTGGAC |
| 9 | SELPLG | 0.31 | TGGACCCCACTGGCTGAGAATCTGG |
| 3 | SEC31L2 | 0.33 | TGCCTGCTCCTGTACTTGTCCTCAG |
| 7 | CD3Z | 0.37 | ACTTGTCCTCAGCTTGGGCTTCTTC |
| 10 | SH2D1A | 0.37 | TTGGACATCTCTAGTGTAGCTGCCA |
| 6 | CD1A | 0.4 | AAGCCTATACGTTTCTGTGGAGTAA |
| 6 | LAIR1 | 0.39 | AAGCCTATACGTTTCTGTGGAGTAA |
| 16 | TRB@ | 0.34 | TCCTCCATCACCTGAAACACTGGAC |
| 24 | CD3D | 0.33 | TCCTTGTGCCTGCTCCTGTACTTGT |
| 7 | WBSCR20C | 0.34 | ACTTGTCCTCAGCTTGGGCTTCTTC |
| 1 | ZAP70 | 0.33 | TCCTGTACTTGTCCTCAGCTTGGGC |
| 3 | IFI44 | 0.32 | TGCCTGCTCCTGTACTTGTCCTCAG |
| 6 | GPR65 | 0.31 | AAGCCTATACGTTTCTGTGGAGTAA |
| 11 | AIF1 | 0.3 | CACCCAGCTGGTCCTGTGGATGGGA |
| 1 | ARHGAP15 | 0.37 | TCCTGTACTTGTCCTCAGCTTGGGC |
| 16 | NARF | 0.3 | TCCTCCATCACCTGAAACACTGGAC |
| 11 | PACAP | 0.32 | CACCCAGCTGGTCCTGTGGATGGGA |

TABLE 28

Aclarubicin biomarkers.

| SEQ ID NO | Gene | Correlation | Medianprobe |
|---|---|---|---|
| 4 | RPL12 | 0.3 | AAATGTTTCCTTGTGCCTGCTCCTG |
| 10 | RPLP2 | 0.37 | TTGGACATCTCTAGTGTAGCTGCCA |
| 24 | MYB | 0.31 | TCCTTGTGCCTGCTCCTGTACTTGT |
| 4 | ZNFN1A1 | 0.34 | AAATGTTTCCTTGTGCCTGCTCCTG |
| 3 | SCAP1 | 0.33 | TGCCTGCTCCTGTACTTGTCCTCAG |
| 4 | STAT4 | 0.31 | AAATGTTTCCTTGTGCCTGCTCCTG |

TABLE 28-continued

Aclarubicin biomarkers.

| SEQ ID NO | Gene | Correlation | Medianprobe |
|---|---|---|---|
| 6 | SP140 | 0.4 | AAGCCTATACGTTTCTGTGGAGTAA |
| 3 | AMPD3 | 0.3 | TGCCTGCTCCTGTACTTGTCCTCAG |
| 6 | TNFAIP8 | 0.4 | AAGCCTATACGTTTCTGTGGAGTAA |
| 24 | DDX18 | 0.31 | TCCTTGTGCCTGCTCCTGTACTTGT |
| 24 | TAF5 | 0.3 | TCCTTGTGCCTGCTCCTGTACTTGT |
| 11 | RPS2 | 0.34 | CACCCAGCTGGTCCTGTGGATGGGA |
| 6 | DOCK2 | 0.32 | AAGCCTATACGTTTCTGTGGAGTAA |
| 6 | GPR65 | 0.35 | AAGCCTATACGTTTCTGTGGAGTAA |
| 24 | HOXA9 | 0.33 | TCCTTGTGCCTGCTCCTGTACTTGT |
| 4 | FLJ12270 | 0.31 | AAATGTTTCCTTGTGCCTGCTCCTG |
| 7 | HNRPD | 0.4 | ACTTGTCCTCAGCTTGGGCTTCTTC |

TABLE 29

Mitoxantrone biomarkers.

| SEQ ID NO | Gene | Correlation | Medianprobe |
|---|---|---|---|
| 3 | PGAM1 | 0.32 | TGCCTGCTCCTGTACTTGTCCTCAG |
| 4 | DPYSL3 | 0.36 | AAATGTTTCCTTGTGCCTGCTCCTG |
| 24 | INSIG1 | 0.32 | TCCTTGTGCCTGCTCCTGTACTTGT |
| 10 | GJA1 | 0.31 | TTGGACATCTCTAGTGTAGCTGCCA |
| 10 | BNIP3 | 0.31 | TTGGACATCTCTAGTGTAGCTGCCA |
| 2 | PRG1 | 0.39 | GCCCCACTGGACAACACTGATTCCT |
| 3 | G6PD | 0.34 | TGCCTGCTCCTGTACTTGTCCTCAG |
| 2 | PLOD2 | 0.34 | GCCCCACTGGACAACACTGATTCCT |
| 24 | LOXL2 | 0.31 | TCCTTGTGCCTGCTCCTGTACTTGT |
| 16 | SSBP2 | 0.36 | TCCTCCATCACCTGAAACACTGGAC |
| 24 | C1orf29 | 0.35 | TCCTTGTGCCTGCTCCTGTACTTGT |
| 24 | TOX | 0.35 | TCCTTGTGCCTGCTCCTGTACTTGT |
| 1 | STC1 | 0.39 | TCCTGTACTTGTCCTCAGCTTGGGC |
| 4 | TNFRSF1A | 0.34 | AAATGTTTCCTTGTGCCTGCTCCTG |
| 16 | NCOR2 | 0.3 | TCCTCCATCACCTGAAACACTGGAC |
| 24 | NAP1L1 | 0.32 | TCCTTGTGCCTGCTCCTGTACTTGT |
| 6 | LOC94105 | 0.34 | AAGCCTATACGTTTCTGTGGAGTAA |
| 16 | ARHGEF6 | 0.34 | TCCTCCATCACCTGAAACACTGGAC |
| 24 | GATA3 | 0.35 | TCCTTGTGCCTGCTCCTGTACTTGT |
| 1 | TFPI | 0.31 | TCCTGTACTTGTCCTCAGCTTGGGC |
| 6 | CD3Z | 0.37 | AAGCCTATACGTTTCTGTGGAGTAA |

TABLE 29-continued

Mitoxantrone biomarkers.

| SEQ ID NO | Gene | Correlation | Medianprobe |
|---|---|---|---|
| 2 | AF1Q | 0.33 | GCCCCACTGGACAACACTGATTCCT |
| 3 | MAP1B | 0.34 | TGCCTGCTCCTGTACTTGTCCTCAG |
| 24 | CD3D | 0.31 | TCCTTGTGCCTGCTCCTGTACTTGT |
| 1 | BCAT1 | 0.32 | TCCTGTACTTGTCCTCAGCTTGGGC |
| 9 | IFI44 | 0.33 | TGGACCCCACTGGCTGAGAATCTGG |
| 4 | CUTC | 0.33 | AAATGTTTCCTTGTGCCTGCTCCTG |
| 6 | NAP1L2 | 0.33 | AAGCCTATACGTTTCTGTGGAGTAA |
| 4 | NME7 | 0.35 | AAATGTTTCCTTGTGCCTGCTCCTG |
| 1 | FLJ21159 | 0.33 | TCCTGTACTTGTCCTCAGCTTGGGC |

TABLE 30

Mitomycin biomarkers.

| SEQ ID NO | Gene | Correlation | Medianprobe |
|---|---|---|---|
| 3 | STC1 | 0.34 | TGCCTGCTCCTGTACTTGTCCTCAG |
| 2 | GPR65 | 0.32 | GCCCCACTGGACAACACTGATTCCT |
| 7 | DOCK10 | 0.35 | ACTTGTCCTCAGCTTGGGCTTCTTC |
| 24 | FAM46A | 0.36 | TCCTTGTGCCTGCTCCTGTACTTGT |
| 7 | LOC54103 | 0.39 | ACTTGTCCTCAGCTTGGGCTTCTTC |

TABLE 31

Paclitaxel (Taxol) biomarkers.

| SEQ ID NO | Gene | Correlation | Medianprobe |
|---|---|---|---|
| 16 | RPL10 | 0.31 | TCCTCCATCACCTGAAACACTGGAC |
| 16 | RPS4X | 0.31 | TCCTCCATCACCTGAAACACTGGAC |
| 24 | DKC1 | 0.3 | TCCTTGTGCCTGCTCCTGTACTTGT |
| 7 | DKFZP564C186 | 0.32 | ACTTGTCCTCAGCTTGGGGTTCTTC |
| 3 | PRP19 | 0.31 | TGCCTGCTCCTGTACTTGTCCTCAG |
| 2 | PAB9P40 | 0.33 | GCCCCACTGGACAACACTGATTCCT |
| 4 | HSA9761 | 0.37 | AAATGTTTCCTTGTGCCTGCTCCTG |
| 4 | GMDS | 0.3 | AAATGTTTCCTTGTGCCTGCTCCTG |
| 4 | CEP1 | 0.3 | AAATGTTTCCTTGTGCCTGCTCCTG |
| 4 | IL13RA2 | 0.34 | AAATGTTTCCTTGTGCCTGCTCCTG |
| 7 | MAGEB2 | 0.41 | ACTTGTCCTCAGCTTGGGCTTCTTC |
| 11 | HMGN2 | 0.35 | CACCCAGCTGGTCCTGTGGATGGGA |

TABLE 31-continued

Paclitaxel (Taxol) biomarkers.

| SEQ ID NO | Gene | Correlation | Medianprobe |
|---|---|---|---|
| 16 | ALMS1 | 0.3 | TCCTCCATCACCTGAAACACTGGAC |
| 3 | GPR65 | 0.31 | TGCCTGCTCCTGTACTTGTCCTCAG |
| 9 | FLJ10774 | 0.31 | TGGACCCCACTGGCTGAGAATCTGG |
| 3 | NOL8 | 0.31 | TGCCTGCTCCTGTACTTGTCCTCAG |
| 3 | DAZAP1 | 0.32 | TGCCTGCTCCTGTACTTGTCCTCAG |
| 10 | SLC25A15 | 0.31 | TTGGACATCTCTAGTGTAGCTGCCA |
| 16 | PAF53 | 0.36 | TCCTCCATCACCTGAAACACTGGAC |
| 16 | PITPNC1 | 0.33 | TCCTCCATCACCTGAAACACTGGAC |
| 9 | SPANXC | 0.3 | TGGACCCCACTGGCTGAGAATCTGG |
| 11 | KIAA1393 | 0.33 | CACCCAGCTGGTCCTGTGGATGGGA |

TABLE 32

Gemcitabine (Gemzar) biomarkers.

| SEQ ID NO | Gene | Correlation | Medianprobe |
|---|---|---|---|
| 11 | UBE2L6 | 0.38 | CACCCAGCTGGTCCTGTGGATGGGA |
| 11 | TAP1 | 0.33 | CACCCAGCTGGTCCTGTGGATGGGA |
| 1 | F2R | 0.3 | TCCTGTACTTGTCCTCAGCTTGGGC |
| 3 | PSMB9 | 0.31 | TGCCTGCTCCTGTACTTGTCCTCAG |
| 6 | IL7R | 0.31 | AAGCCTATACGTTTCTGTGGAGTAA |
| 6 | TNFAIP8 | 0.33 | AAGCCTATACGTTTCTGTGGAGTAA |
| 9 | HLA-C | 0.33 | TGGACCCCACTGGCTGAGAATCTGG |
| 9 | IFI44 | 0.31 | TGGACCCCACTGGCTGAGAATCTGG |

TABLE 33

Taxotere (docetaxel) biomarkers.

| SEQ ID NO | Gene | Correlation | Medianprobe |
|---|---|---|---|
| 2 | ANP32B | 0.45 | GCCCCACTGGACAACACTGATTCCT |
| 10 | GTF3A | 0.31 | TTGGACATCTCTAGTGTAGCTGCCA |
| 7 | TRIM14 | 0.31 | ACTTGTCCTCAGCTTGGGCTTCTTC |
| 2 | SKP2 | 0.33 | GCCCCACTGGACAACACTGATTCCT |
| 1 | TRIP13 | 0.36 | TCCTGTACTTGTCCTCAGCTTGGGC |
| 2 | RFC3 | 0.45 | GCCCCACTGGACAACACTGATTCCT |
| 3 | CASP7 | 0.32 | TGCCTGCTCCTGTACTTGTCCTCAG |
| 6 | TXN | 0.36 | AAGCCTATACGTTTCTGTGGAGTAA |
| 4 | MCM5 | 0.34 | AAATGTTTCCTTGTGCCTGCTCCTG |

TABLE 33-continued

Taxotere (docetaxel) biomarkers.

| SEQ ID NO | Gene | Correlation | Medianprobe |
|---|---|---|---|
| 4 | PTGES2 | 0.39 | AAATGTTTCCTTGTGCCTGCTCCTG |
| 9 | OBFC1 | 0.37 | TGGACCCCACTGGCTGAGAATCTGG |
| 2 | EPB41L4B | 0.32 | GCCCCACTGGACAACACTGATTCCT |
| 16 | CALML4 | 0.31 | TCCTCCATCACCTGAAACACTGGAC |

TABLE 34

Dexamethasone biomarkers.

| SEQ ID NO | Gene | Correlation | Medianprobe |
|---|---|---|---|
| 234 | IFITM2 | 0.38 | ATATATGGACCTAGCTTGAGGCAAT |
| 6 | UBE2L6 | 0.32 | AAGCCTATACGTTTCTGTGGAGTAA |
| 11 | ITM2A | 0.38 | CACCCAGCTGGTCCTGTGGATGGGA |
| 16 | IL2RG | 0.36 | TCCTCCATCACCTGAAACACTGGAC |
| 1 | GPRASP1 | 0.36 | TCCTGTACTTGTCCTCAGCTTGGGC |
| 24 | PTPN7 | 0.31 | TCCTTGTGCCTGCTCCTGTACTTGT |
| 2 | CXorf9 | 0.36 | GCCCCACTGGACAACACTGATTCCT |
| 3 | RHOH | 0.33 | TGCCTGCTCCTGTACTTGTCCTCAG |
| 7 | GIT2 | 0.31 | ACTTGTCCTCAGCTTGGGCTTCTTC |
| 24 | ZNFN1A1 | 0.35 | TCCTTGTGCCTGCTCCTGTACTTGT |
| 11 | CEP1 | 0.31 | CACCCAGCTGGTCCTGTGGATGGGA |
| 6 | MAP4K1 | 0.3 | AAGCCTATACGTTTCTGTGGAGTAA |
| 4 | CCR7 | 0.33 | AAATGTTTCCTTGTGCCTGCTCCTG |
| 11 | CD3G | 0.35 | CACCCAGCTGGTCCTGTGGATGGGA |
| 6 | UCP2 | 0.3 | AAGCCTATACGTTTCTGTGGAGTAA |
| 9 | GATA3 | 0.37 | TGGACCCCACTGGCTGAGAATCTGG |
| 1 | CDKN2A | 0.32 | TCCTGTACTTGTCCTCAGCTTGGGC |
| 2 | TARP | 0.3 | GCCCCACTGGACAACACTGATTCCT |
| 10 | LAIR1 | 0.34 | TTGGACATCTCTAGTGTAGCTGCCA |
| 24 | SH2D1A | 0.34 | TCCTTGTGCCTGCTCCTGTACTTGT |
| 3 | SEPT6 | 0.34 | TGCCTGCTCCTGTACTTGTCCTCAG |
| 24 | HA-1 | 0.34 | TCCTTGTGCCTGCTCCTGTACTTGT |
| 16 | CD3D | 0.32 | TCCTCCATCACCTGAAACACTGGAC |
| 11 | LST1 | 0.39 | CACCCAGCTGGTCCTGTGGATGGGA |
| 6 | AIF1 | 0.35 | AAGCCTATACGTTTCTGTGGAGTAA |
| 3 | ADA | 0.33 | TGCCTGCTCCTGTACTTGTCCTCAG |
| 11 | DATF1 | 0.41 | CACCCAGCTGGTCCTGTGGATGGGA |

TABLE 34-continued

Dexamethasone biomarkers.

| SEQ ID NO | Gene | Correlation | Medianprobe |
|---|---|---|---|
| 1 | ARHGAP15 | 0.3 | TCCTGTACTTGTCCTCAGCTTGGGC |
| 11 | PLAC8 | 0.31 | CACCCAGCTGGTCCTGTGGATGGGA |
| 2 | CECR1 | 0.31 | GCCCCACTGGACAACACTGATTCCT |
| 9 | LOC81558 | 0.33 | TGGACCCCACTGGCTGAGAATCTGG |
| 7 | EHD2 | 0.37 | ACTTGTCCTCAGCTTGGGCTTCTTC |

TABLE 35

Ara-C (Cytarabine hydrochloride) biomarkers.

| SEQ ID NO | Gene | Correlation | Medianprobe |
|---|---|---|---|
| 9 | ITM2A | 0.32 | TGGACCCCACTGGCTGAGAATCTGG |
| 4 | RHOH | 0.31 | AAATGTTTCCTTGTGCCTGCTCCTG |
| 16 | PRIM1 | 0.3 | TCCTCCATCACCTGAAACACTGGAC |
| 24 | CENTB1 | 0.31 | TCCTTGTGCCTGCTCCTGTACTTGT |
| 2 | NAP1L1 | 0.31 | GCCCCACTGGACAACACTGATTCCT |
| 16 | ATP5G2 | 0.31 | TCCTCCATCACCTGAAACACTGGAC |
| 4 | GATA3 | 0.33 | AAATGTTTCCTTGTGCCTGCTCCTG |
| 6 | PRKCQ | 0.32 | AAGCCTATACGTTTCTGTGGAGTAA |
| 2 | SH2D1A | 0.3 | GCCCCACTGGACAACACTGATTCCT |
| 7 | SEPT6 | 0.42 | ACTTGTCCTCAGCTTGGGCTTCTTC |
| 7 | NME4 | 0.33 | ACTTGTCCTCAGCTTGGGCTTCTTC |
| 6 | CD3D | 0.31 | AAGCCTATACGTTTCTGTGGAGTAA |
| 9 | CD1E | 0.32 | TGGACCCCACTGGCTGAGAATCTGG |
| 2 | ADA | 0.34 | GCCCCACTGGACAACACTGATTCCT |
| 11 | FHOD1 | 0.31 | CACCCAGCTGGTCCTGTGGATGGGA |

TABLE 36

Methylprednisolone biomarkers.

| SEQ ID NO | Gene | Correlation | Medianprobe |
|---|---|---|---|
| 2 | CD99 | 0.31 | GCCCCACTGGACAACACTGATTCCT |
| 3 | ARHGDIB | 0.31 | TGCCTGCTCCTGTACTTGTCCTCAG |
| 2 | ITM2A | 0.35 | GCCCCACTGGACAACACTGATTCCT |
| 16 | LGALS9 | 0.43 | TCCTCCATCACCTGAAACACTGGAC |
| 9 | INPP5D | 0.34 | TGGACCCCACTGGCTGAGAATCTGG |
| 24 | SATB1 | 0.32 | TCCTTGTGCCTGCTCCTGTACTTGT |
| 4 | TFDP2 | 0.4 | AAATGTTTCCTTGTGCCTGCTCCTG |
| 9 | SLA | 0.31 | TGGACCCCACTGGCTGAGAATCTGG |
| 3 | IL2RG | 0.3 | TGCCTGCTCCTGTACTTGTCCTCAG |
| 3 | MFNG | 0.3 | TGCCTGCTCCTGTACTTGTCCTCAG |
| 4 | SELL | 0.33 | AAATGTTTCCTTGTGCCTGCTCCTG |
| 16 | CDW52 | 0.33 | TCCTCCATCACCTGAAACACTGGAC |
| 1 | LRMP | 0.32 | TCCTGTACTTGTCCTCAGCTTGGGC |
| 11 | ICAM2 | 0.38 | CACCCAGCTGGTCCTGTGGATGGGA |
| 3 | RIMS3 | 0.36 | TGCCTGCTCCTGTACTTGTCCTCAG |
| 9 | PTPN7 | 0.39 | TGGACCCCACTGGCTGAGAATCTGG |
| 1 | ARHGAP25 | 0.37 | TCCTGTACTTGTCCTCAGCTTGGGC |
| 16 | LCK | 0.3 | TCCTCCATCACCTGAAACACTGGAC |
| 10 | CXorf9 | 0.3 | TTGGACATCTCTAGTGTAGCTGCCA |
| 6 | RHOH | 0.51 | AAGCCTATACGTTTCTGTGGAGTAA |
| 7 | GIT2 | 0.33 | ACTTGTCCTCAGCTTGGGCTTCTTC |
| 24 | ZNFN1A1 | 0.53 | TCCTTGTGCCTGCTCCTGTACTTGT |
| 16 | CENTB1 | 0.36 | TCCTCCATCACCTGAAACACTGGAC |
| 1 | LCP2 | 0.34 | TCCTGTACTTGTCCTCAGCTTGGGC |
| 1 | SPI1 | 0.3 | TCCTGTACTTGTCCTCAGCTTGGGC |
| 6 | GZMA | 0.31 | AAGCCTATACGTTTCTGTGGAGTAA |
| 6 | CEP1 | 0.37 | AAGCCTATACGTTTCTGTGGAGTAA |
| 9 | CD8A | 0.38 | TGGACCCCACTGGCTGAGAATCTGG |
| 16 | SCAP1 | 0.32 | TCCTCCATCACCTGAAACACTGGAC |
| 2 | CD2 | 0.48 | GCCCCACTGGACAACACTGATTCCT |
| 7 | VAV1 | 0.41 | ACTTGTCCTCAGCTTGGGCTTCTTC |
| 1 | MAP4K1 | 0.36 | TCCTGTACTTGTCCTCAGCTTGGGC |
| 7 | CCR7 | 0.37 | ACTTGTCCTCAGCTTGGGCTTCTTC |
| 24 | C6orf32 | 0.38 | TCCTTGTGCCTGCTCCTGTACTTGT |
| 3 | ALOX15B | 0.43 | TGCCTGCTCCTGTACTTGTCCTCAG |
| 6 | BRDT | 0.33 | AAGCCTATACGTTTCTGTGGAGTAA |
| 6 | CD3G | 0.51 | AAGCCTATACGTTTCTGTGGAGTAA |
| 7 | LTB | 0.32 | ACTTGTCCTCAGCTTGGGCTTCTTC |
| 10 | NVL | 0.31 | TTGGACATCTCTAGTGTAGCTGCCA |
| 3 | RASGRP2 | 0.35 | TGCCTGCTCCTGTACTTGTCCTCAG |
| 4 | LCP1 | 0.34 | AAATGTTTCCTTGTGCCTGCTCCTG |
| 6 | CXCR4 | 0.3 | AAGCCTATACGTTTCTGTGGAGTAA |
| 11 | PRKD2 | 0.33 | CACCCAGCTGGTCCTGTGGATGGGA |
| 1 | GATA3 | 0.39 | TCCTGTACTTGTCCTCAGCTTGGGC |

TABLE 36-continued

Methylprednisolone biomarkers.

| SEQ ID NO | Gene | Correlation | Medianprobe |
|---|---|---|---|
| 2 | KIAA0922 | 0.36 | GCCCCACTGGACAACACTGATTCCT |
| 16 | TARP | 0.49 | TCCTCCATCACCTGAAACACTGGAC |
| 7 | SEC31L2 | 0.32 | ACTTGTCCTCAGCTTGGGCTTCTTC |
| 10 | PRKCQ | 0.37 | TTGGACATCTCTAGTGTAGCTGCCA |
| 6 | SH2D1A | 0.33 | AAGCCTATACGTTTCTGTGGAGTAA |
| 6 | CHRNA3 | 0.5 | AAGCCTATACGTTTCTGTGGAGTAA |
| 6 | CD1A | 0.44 | AAGCCTATACGTTTCTGTGGAGTAA |
| 11 | LST1 | 0.36 | CACCCAGCTGGTCCTGTGGATGGGA |
| 11 | LAIR1 | 0.47 | CACCCAGCTGGTCCTGTGGATGGGA |
| 2 | CACNA1G | 0.33 | GCCCCACTGGACAACACTGATTCCT |
| 7 | TRB@ | 0.31 | ACTTGTCCTCAGCTTGGGCTTCTTC |
| 24 | SEPT6 | 0.33 | TCCTTGTGCCTGCTCCTGTACTTGT |
| 11 | HA-1 | 0.42 | CACCCAGCTGGTCCTGTGGATGGGA |
| 1 | DOCK2 | 0.32 | TCCTGTACTTGTCCTCAGCTTGGGC |
| 1 | CD3D | 0.41 | TCCTGTACTTGTCCTCAGCTTGGGC |
| 3 | TRD@ | 0.38 | TGCCTGCTCCTGTACTTGTCCTCAG |
| 3 | T3JAM | 0.37 | TGCCTGCTCCTGTACTTGTCCTCAG |
| 1 | FNBP1 | 0.37 | TCCTGTACTTGTCCTCAGCTTGGGC |
| 11 | CD6 | 0.4 | CACCCAGCTGGTCCTGTGGATGGGA |
| 3 | AIF1 | 0.31 | TGCCTGCTCCTGTACTTGTCCTCAG |
| 1 | FOLH1 | 0.45 | TCCTGTACTTGTCCTCAGCTTGGGC |
| 11 | CD1E | 0.58 | CACCCAGCTGGTCCTGTGGATGGGA |
| 24 | LY9 | 0.39 | TCCTTGTGCCTGCTCCTGTACTTGT |
| 4 | ADA | 0.39 | AAATGTTTCCTTGTGCCTGCTCCTG |
| 2 | CDKL5 | 0.44 | GCCCCACTGGACAACACTGATTCCT |
| 6 | TRIM | 0.38 | AAGCCTATACGTTTCTGTGGAGTAA |
| 7 | DATF1 | 0.31 | ACTTGTCCTCAGCTTGGGCTTCTTC |
| 24 | RGC32 | 0.51 | TCCTTGTGCCTGCTCCTGTACTTGT |
| 11 | ARHGAP15 | 0.34 | CACCCAGCTGGTCCTGTGGATGGGA |
| 24 | NOTCH1 | 0.36 | TCCTTGTGCCTGCTCCTGTACTTGT |
| 4 | BIN2 | 0.31 | AAATGTTTCCTTGTGCCTGCTCCTG |
| 6 | SEMA4G | 0.35 | AAGCCTATACGTTTCTGTGGAGTAA |
| 11 | DPEP2 | 0.33 | CACCCAGCTGGTCCTGTGGATGGGA |
| 1 | CECR1 | 0.36 | TCCTGTACTTGTCCTCAGCTTGGGC |
| 3 | BCL11B | 0.33 | TGCCTGCTCCTGTACTTGTCCTCAG |
| 10 | STAG3 | 0.41 | TTGGACATCTCTAGTGTAGCTGCCA |
| 3 | GALNT6 | 0.32 | TGCCTGCTCCTGTACTTGTCCTCAG |
| 4 | UBASH3A | 0.3 | AAATGTTTCCTTGTGCCTGCTCCTG |
| 16 | PHEMX | 0.38 | TCCTCCATCACCTGAAACACTGGAC |
| 24 | FLJ13373 | 0.34 | TCCTTGTGCCTGCTCCTGTACTTGT |
| 16 | LEF1 | 0.49 | TCCTCCATCACCTGAAACACTGGAC |
| 10 | IL21R | 0.42 | TTGGACATCTCTAGTGTAGCTGCCA |
| 24 | MGC17330 | 0.33 | TCCTTGTGCCTGCTCCTGTACTTGT |
| 24 | AKAP13 | 0.53 | TCCTTGTGCCTGCTCCTGTACTTGT |
| 4 | GIMAP5 | 0.34 | AAATGTTTCCTTGTGCCTGCTCCTG |

TABLE 37

Methotrexate biomarkers.

| SEQ ID NO | Gene | Correlation | Medianprobe |
|---|---|---|---|
| 16 | PRPF8 | 0.34 | TCCTCCATCACCTGAAACACTGGAC |
| 6 | RPL18 | 0.34 | AAGCCTATACGTTTCTGTGGAGTAA |
| 11 | GOT2 | 0.31 | CACCCAGCTGGTCCTGTGGATGGGA |
| 1 | RPL13A | 0.31 | TCCTGTACTTGTCCTCAGCTTGGGC |
| 11 | RPS15 | 0.39 | CACCCAGCTGGTCCTGTGGATGGGA |
| 2 | RPLP2 | 0.32 | GCCCCACTGGACAACACTGATTCCT |
| 2 | CSDA | 0.39 | GCCCCACTGGACAACACTGATTCCT |
| 16 | KHDRBS1 | 0.32 | TCCTCCATCACCTGAAACACTGGAC |
| 1 | SNRPA | 0.31 | TCCTGTACTTGTCCTCAGCTTGGGC |
| 4 | IMPDH2 | 0.39 | AAATGTTTCCTTGTGCCTGCTCCTG |
| 4 | RPS19 | 0.47 | AAATGTTTCCTTGTGCCTGCTCCTG |
| 11 | NUP88 | 0.36 | CACCCAGCTGGTCCTGTGGATGGGA |
| 3 | ATP5D | 0.33 | TGCCTGCTCCTGTACTTGTCCTCAG |
| 4 | PCBP2 | 0.32 | AAATGTTTCCTTGTGCCTGCTCCTG |
| 4 | ZNF593 | 0.4 | AAATGTTTCCTTGTGCCTGCTCCTG |
| 9 | HSU79274 | 0.32 | TGGACCCCACTGGCTGAGAATCGG |
| 11 | PRIM1 | 0.3 | CACCCAGCTGGTCCTGTGGATGGGA |
| 16 | PFDN5 | 0.33 | TCCTCCATCACCTGAAACACTGGAC |
| 11 | OXA1L | 0.37 | CACCCAGCTGGTCCTGTGGATGGGA |
| 7 | ATIC | 0.31 | ACTTGTCCTCAGCTTGGGCTTCTTC |
| 7 | CIAPIN1 | 0.34 | ACTTGTCCTCAGCTTGGGCTTCTTC |
| 11 | RPS2 | 0.32 | CACCCAGCTGGTCCTGTGGATGGGA |
| 2 | PCCB | 0.36 | GCCCCACTGGACAACACTGATTCCT |

TABLE 37-continued

Methotrexate biomarkers.

| SEQ ID NO | Gene | Correlation | Medianprobe |
|---|---|---|---|
| 7 | SHMT2 | 0.34 | ACTTGTCCTCAGCTTGGGCTTCTTC |
| 6 | RPLP0 | 0.35 | AAGCCTATACGTTTCTGTGGAGTAA |
| 9 | HNRPA1 | 0.35 | TGGACCCCACTGGCTGAGAATCTGG |
| 3 | STOML2 | 0.32 | TGCCTGCTCCTGTACTTGTCCTCAG |
| 7 | SKB1 | 0.33 | ACTTGTCCTCAGCTTGGGCTTCTTC |
| 6 | GLTSCR2 | 0.37 | AAGCCTATACGTTTCTGTGGAGTAA |
| 24 | CCNB1IP1 | 0.3 | TCCTTGTGCCTGCTCCTGTACTTGT |
| 10 | MRPS2 | 0.33 | TTGGACATCTCTAGTGTAGCTGCCA |
| 3 | FLJ20859 | 0.34 | TGCCTGCTCCTGTACTTGTCCTCAG |
| 7 | FLJ12270 | 0.3 | ACTTGTCCTCAGCTTGGGCTTCTTC |

TABLE 38

Bleomycin biomarkers.

| SEQ ID NO | Gene | Correlation | Medianprobe |
|---|---|---|---|
| 2 | PFN1 | 0.45 | GCCCCACTGGACAACACTGATTCCT |
| 10 | HK1 | 0.33 | TTGGACATCTCTAGTGTAGCTGCCA |
| 9 | MCL1 | 0.31 | TGGACCCCACTGGCTGAGAATCTGG |
| 9 | ZYX | 0.32 | TGGACCCCACTGGCTGAGAATCTGG |
| 7 | RAP1B | 0.34 | ACTTGTCCTCAGCTTGGGCTTCTTC |
| 11 | GNB2 | 0.32 | CACCCAGCTGGTCCTGTGGATGGGA |
| 7 | EPAS1 | 0.31 | ACTTGTCCTCAGCTTGGGCTTCTTC |
| 3 | PGAM1 | 0.42 | TGCCTGCTCCTGTACTTGTCCTCAG |
| 7 | CKAP4 | 0.31 | ACTTGTCCTCAGCTTGGGCTTCTTC |
| 4 | DUSP1 | 0.4 | AAATGTTTCCTTGTGCCTGCTCCTG |
| 10 | MYL9 | 0.4 | TTGGACATCTCTAGTGTAGCTGCCA |
| 10 | K-ALPHA-1 | 0.37 | TTGGACATCTCTAGTGTAGCTGCCA |
| 24 | CSDA | 0.3 | TCCTTGTGCCTGCTCCTGTACTTGT |
| 10 | IFITM2 | 0.36 | TTGGACATCTCTAGTGTAGCTGCCA |
| 2 | ITGA5 | 0.43 | GCCCCACTGGACAACACTGATTCCT |
| 9 | DPYSL3 | 0.44 | TGGACCCCACTGGCTGAGAATCTGG |
| 1 | JUNB | 0.32 | TCCTGTACTTGTCCTCAGCTTGGGC |
| 16 | NFKBIA | 0.32 | TCCTCCATCACCTGAAACACTGGAC |
| 4 | LAMB1 | 0.37 | AAATGTTTCCTTGTGCCTGCTCCTG |
| 9 | FHL1 | 0.31 | TGGACCCCACTGGCTGAGAATCTGG |
| 9 | INSIG1 | 0.31 | TGGACCCCACTGGCTGAGAATCTGG |
| 9 | TIMP1 | 0.48 | TGGACCCCACTGGCTGAGAATCTGG |
| 6 | GJA1 | 0.54 | AAGCCTATACGTTTCTGTGGAGTAA |
| 24 | PRG1 | 0.46 | TCCTTGTGCCTGCTCCTGTACTTGT |
| 24 | EXT1 | 0.35 | TCCTTGTGCCTGCTCCTGTACTTGT |
| 24 | DKFZP434J154 | 0.31 | GCCCCACTGGACAACACTGATTCCT |
| 11 | MVP | 0.34 | CACCCAGCTGGTCCTGTGGATGGGA |
| 16 | VASP | 0.31 | TCCTCCATCACCTGAAACACTGGAC |
| 9 | ARL7 | 0.39 | TGGACCCCACTGGCTGAGAATCTGG |
| 1 | NNMT | 0.34 | TCCTGTACTTGTCCTCAGCTTGGGC |
| 1 | TAP1 | 0.3 | TCCTGTACTTGTCCTCAGCTTGGGC |
| 2 | PLOD2 | 0.37 | GCCCCACTGGACAACACTGATTCCT |
| 11 | ATF3 | 0.42 | CACCCAGCTGGTCCTGTGGATGGGA |
| 9 | PALM2-AKAP2 | 0.33 | TGGACCCCACTGGCTGAGAATCTGG |
| 2 | IL8 | 0.34 | GCCCCACTGGACAACACTGATTCCT |
| 2 | LOXL2 | 0.32 | GCCCCACTGGACAACACTGATTCCT |
| 7 | IL4R | 0.31 | ACTTGTCCTCAGCTTGGGCTTCTTC |
| 2 | DGKA | 0.32 | GCCCCACTGGACAACACTGATTCCT |
| 11 | SEC61G | 0.41 | CACCCAGCTGGTCCTGTGGATGGGA |
| 9 | RGS3 | 0.37 | TGGACCCCACTGGCTGAGAATCTGG |
| 11 | F2R | 0.34 | CACCCAGCTGGTCCTGTGGATGGGA |
| 11 | TPM2 | 0.35 | CACCCAGCTGGTCCTGTGGATGGGA |
| 11 | PSMB9 | 0.34 | CACCCAGCTGGTCCTGTGGATGGGA |
| 1 | LOX | 0.37 | TCCTGTACTTGTCCTCAGCTTGGGC |
| 16 | STC1 | 0.35 | TCCTCCATCACCTGAAACACTGGAC |
| 11 | PTGER4 | 0.31 | CACCCAGCTGGTCCTGTGGATGGGA |
| 10 | SMAD3 | 0.38 | TTGGACATCTCTAGTGTAGCTGCCA |
| 9 | WNT5A | 0.44 | TGGACCCCAGTGGCTGAGAATCTGG |
| 16 | BDNF | 0.34 | TCCTCCATCACCTGAAACACTGGAC |
| 16 | TNFRSF1A | 0.46 | TCCTCCATCACCTGAAACACTGGAC |
| 7 | FLNC | 0.34 | ACTTGTCCTCAGCTTGGGCTTCTTC |
| 10 | DKFZP564K0822 | 0.34 | TTGGACATCTCTAGTGTAGCTGCCA |
| 10 | FLOT1 | 0.38 | TTGGACATCTCTAGTGTAGCTGCCA |
| 9 | PTRF | 0.39 | TGGACCCCACTGGCTGAGAATCTGG |
| 10 | HLA-B | 0.36 | TTGGACATCTCTAGTGTAGCTGCCA |
| 2 | MGC4083 | 0.32 | GCCCCACTGGACAACACTGATTCCT |
| 3 | TNFRSF10B | 0.34 | TGCCTGCTCCTGTACTTGTCCTCAG |
| 3 | PLAGL1 | 0.31 | TGCCTGCTCCTGTACTTGTCCTCAG |
| 2 | PNMA2 | 0.38 | GCCCCACTGGACAACACTGATTCCT |

TABLE 38-continued

Bleomycin biomarkers.

| SEQ ID NO | Gene | Correlation | Medianprobe |
|---|---|---|---|
| 1 | TFPI | 0.38 | TCCTGTACTTGTCCTCAGCTTGGGC |
| 16 | GZMB | 0.51 | TCCTCCATCACCTGAAACACTGGAC |
| 6 | PLAUR | 0.35 | AAGCCTATACGTTTCTGTGGAGTAA |
| 7 | FSCN1 | 0.32 | ACTTGTCCTCAGCTTGGGCTTCTTC |
| 7 | ERP70 | 0.32 | ACTTGTCCTCAGCTTGGGCTTCTTC |
| 10 | AF1Q | 0.3 | TTGGACATCTCTAGTGTAGCTGCCA |
| 3 | HIC | 0.33 | TGCCTGCTCCTGTACTTGTCCTCAG |
| 6 | COL6A1 | 0.32 | AAGCCTATACGTTTCTGTGGAGTAA |
| 2 | IFITM3 | 0.3 | GCCCCACTGGACAACACTGATTCCT |
| 11 | MAP1B | 0.38 | CACCCAGCTGGTCCTGTGGATGGGA |
| 16 | FLJ46603 | 0.37 | TCCTCCATCACCTGAAACACTGGAC |
| 9 | RAFTLIN | 0.34 | TGGACCCCACTGGCTGAGAATCTGG |
| 1 | RRAS | 0.31 | TCCTGTACTTGTCCTCAGCTTGGGC |
| 11 | FTL | 0.3 | CACCCAGCTGGTCCTGTGGATGGGA |
| 11 | KIAA0877 | 0.31 | CACCCAGCTGGTCCTGTGGATGGGA |
| 24 | MT1E | 0.31 | TCCTTGTGCCTGCTCCTGTACTTGT |
| 4 | CDC10 | 0.51 | AAATGTTTCCTTGTGCCTGCTCCTG |
| 6 | DOCK2 | 0.32 | AAGCCTATACGTTTCTGTGGAGTAA |
| 7 | RIS1 | 0.37 | ACTTGTCCTCAGCTTGGGCTTCTTC |
| 10 | BCAT1 | 0.42 | TTGGACATCTCTAGTGTAGCTGCCA |
| 16 | PRF1 | 0.34 | TCCTCCATCACCTGAAACACTGGAC |
| 2 | DBN1 | 0.36 | GCCCCACTGGACAACACTGATTCCT |
| 3 | MT1K | 0.3 | TGCCTGCTCCTGTACTTGTCCTCAG |
| 2 | TMSB10 | 0.42 | GCCCCACTGGACAACACTGATTCCT |
| 4 | FLJ10350 | 0.4 | AAATGTTTCCTTGTGCCTGCTCCTG |
| 3 | C1orf24 | 0.34 | TGCCTGCTCCTGTACTTGTCCTCAG |
| 1 | NME7 | 0.46 | TCCTGTACTTGTCCTCAGCTTGGGC |
| 3 | TMEM22 | 0.3 | TGCCTGCTCCTGTACTTGTCCTCAG |
| 16 | TPK1 | 0.37 | TCCTCCATCACCTGAAACACTGGAC |
| 3 | ELK3 | 0.38 | TGCCTGCTCCTGTACTTGTCCTCAG |
| 24 | CYLD | 0.4 | TCCTTGTGCCTGCTCCTGTACTTGT |
| 6 | ADAMTS1 | 0.31 | AAGCCTATACGTTTCTGTGGAGTAA |
| 16 | EHD2 | 0.41 | TCCTCCATCACCTGAAACACTGGAC |
| 24 | ACTB | 0.33 | TCCTTGTGCCTGCTCCTGTACTTGT |

TABLE 39

Methyl-GAG (methyl glyoxal bis amidinohydrazone dihydrochloride) biomarkers.

| SEQ ID NO | Gene | Correlation | Medianprobe |
|---|---|---|---|
| 3 | SSRP1 | 0.37 | TGCCTGCTCCTGTACTTGTCCTCAG |
| 11 | CTSC | 0.35 | CACCCAGCTGGTCCTGTGGATGGGA |
| 7 | LBR | 0.38 | ACTTGTCCTCAGCTTGGGCTTCTTC |
| 4 | EFNB2 | 0.31 | AAATGTTTCCTTGTGCCTGCTCCTG |
| 24 | SERPINA1 | 0.34 | TCCTTGTGCCTGCTCCTGTACTTGT |
| 1 | SSSCA1 | 0.32 | TCCTGTACTTGTCCTCAGCTTGGGC |
| 10 | EZH2 | 0.36 | TTGGACATCTCTAGTGTAGCTGCCA |
| 2 | MYB | 0.33 | GCCCCACTGGACAACACTGATTCCT |
| 16 | PRIM1 | 0.39 | TCCTCCATCACCTGAAACACTGGAC |
| 24 | H2AFX | 0.33 | TCCTTGTGCCTGCTCCTGTACTTGT |
| 10 | HMGA1 | 0.35 | TTGGACATCTCTAGTGTAGCTGCCA |
| 24 | HMMR | 0.33 | TCCTTGTGCCTGCTCCTGTACTTGT |
| 11 | TK2 | 0.42 | CACCCAGCTGGTCCTGTGGATGGGA |
| 4 | WHSC1 | 0.35 | AAATGTTTCCTTGTGCCTGCTCCTG |
| 2 | DIAPH1 | 0.34 | GCCCCACTGGACAACACTGATTCCT |
| 2 | LAMB3 | 0.31 | GCCCCACTGGACAACACTGATTCCT |
| 3 | DPAGT1 | 0.42 | TGCCTGCTCCTGTACTTGTCCTCAG |
| 2 | UCK2 | 0.31 | GCCCCACTGGACAACACTGATTCCT |
| 24 | SERPINB1 | 0.31 | TCCTTGTGCCTGCTCCTGTACTTGT |
| 3 | MDN1 | 0.35 | TGCCTGCTCCTGTACTTGTCCTCAG |
| 11 | G0S2 | 0.43 | CACCCAGCTGGTCCTGTGGATGGGA |
| 9 | MGC21654 | 0.36 | TGGACCCCACTGGCTGAGAATCTGG |
| 7 | GTSE1 | 0.35 | ACTTGTCCTCAGCTTGGGCTTCTTC |
| 16 | TACC3 | 0.31 | TCCTCCATCACCTGAAACACTGGAC |
| 11 | PLAC8 | 0.31 | CACCCAGCTGGTCCTGTGGATGGGA |
| 10 | HNRPD | 0.35 | TTGGACATCTCTAGTGTAGCTGCCA |
| 10 | PNAS-4 | 0.3 | TTGGACATCTCTAGTGTAGCTGCCA |

TABLE 40

HDAC inhibitors biomarkers.

| SEQ ID NO | Gene | Correlation | Medianprobe |
|---|---|---|---|
| 10 | FAU | 0.33 | TTGGACATCTCTAGTGTAGCTGCCA |
| 9 | NOL5A | 0.33 | TGGACCCCACTGGCTGAGAATCTGG |
| 11 | ANP32A | 0.32 | CACCCAGCTGGTCCTGTGGATGGGA |
| 7 | ARHGDIB | 0.3 | ACTTGTCCTCAGCTTGGGCTTCTTC |

TABLE 40-continued

HDAC inhibitors biomarkers.

| SEQ ID NO | Gene | Correlation | Medianprobe |
|---|---|---|---|
| 7 | LBR | 0.31 | ACTTGTCCTCAGCTTGGGCTTCTTC |
| 16 | FABP5 | 0.33 | TCCTCCATCACCTGAAACACTGGAC |
| 10 | ITM2A | 0.32 | TTGGACATCTCTAGTGTAGCTGCCA |
| 16 | SFRS5 | 0.34 | TCCTCCATCACCTGAAACACTGGAC |
| 11 | IQGAP2 | 0.4 | CACCCAGCTGGTCCTGTGGATGGGA |
| 6 | SLC7A6 | 0.35 | AAGCCTATACGTTTCTGTGGAGTAA |
| 3 | SLA | 0.31 | TGCCTGCTCCTGTACTTGTCCTCAG |
| 16 | IL2RG | 0.31 | TCCTCCATCACCTGAAACACTGGAC |
| 1 | MFNG | 0.39 | TCCTGTACTTGTCCTCAGCTTGGGC |
| 10 | GPSM3 | 0.32 | TTGGACATCTCTAGTGTAGCTGCCA |
| 10 | PIM2 | 0.3 | TTGGACATCTCTAGTGTAGCTGCCA |
| 2 | EVER1 | 0.35 | GCCCCACTGGACAACACTGATTCCT |
| 3 | LRMP | 0.35 | TGCCTGCTCCTGTACTTGTCCTCAG |
| 1 | ICAM2 | 0.44 | TCCTGTACTTGTCCTCAGCTTGGGC |
| 9 | RIMS3 | 0.43 | TGGACCCCACTGGCTGAGAATCTGG |
| 10 | FMNL1 | 0.35 | TTGGACATCTCTAGTGTAGCTGCCA |
| 3 | MYB | 0.37 | TGCCTGCTCCTGTACTTGTCCTCAG |
| 24 | PTPN7 | 0.36 | TCCTTGTGCCTGCTCCTGTACTTGT |
| 11 | LCK | 0.48 | CACCCAGCTGGTCCTGTGGATGGGA |
| 7 | CXorf9 | 0.3 | ACTTGTCCTCAGCTTGGGCTTCTTC |
| 24 | RHOH | 0.31 | TCCTTGTGCCTGCTCCTGTACTTGT |
| 4 | ZNFN1A1 | 0.33 | AAATGTTTCCTTGTGCCTGCTCCTG |
| 11 | CENTB1 | 0.45 | CACCCAGCTGGTCCTGTGGATGGGA |
| 3 | LCP2 | 0.31 | TGCCTGCTCCTGTACTTGTCCTCAG |
| 1 | DBT | 0.32 | TCCTGTACTTGTCCTCAGCTTGGGC |
| 10 | CEP1 | 0.31 | TTGGACATCTCTAGTGTAGCTGCCA |
| 9 | IL6R | 0.31 | TGGACCCCACTGGCTGAGAATCTGG |
| 24 | VAV1 | 0.32 | TCCTTGTGCCTGCTCCTGTACTTGT |
| 6 | MAP4K1 | 0.3 | AAGCCTATACGTTTCTGTGGAGTAA |
| 24 | CD28 | 0.36 | TCCTTGTGCCTGCTCCTGTACTTGT |
| 10 | PTP4A3 | 0.3 | TTGGACATCTCTAGTGTAGCTGCCA |
| 11 | CD3G | 0.33 | CACCCAGCTGGTCCTGTGGATGGGA |
| 1 | LTB | 0.4 | TCCTGTACTTGTCCTCAGCTTGGGC |
| 2 | USP34 | 0.44 | GCCCCACTGGACAACACTGATTCCT |
| 24 | NVL | 0.41 | TCCTTGTGCCTGCTCCTGTACTTGT |
| 7 | CD8B1 | 0.33 | ACTTGTCCTCAGCTTGGGCTTCTTC |
| 2 | SFRS6 | 0.31 | GCCCCACTGGACAACACTGATTCCT |
| 1 | LCP1 | 0.34 | TCCTGTACTTGTCCTCAGCTTGGGC |
| 3 | CXCR4 | 0.36 | TGCCTGCTCCTGTACTTGTCCTCAG |
| 9 | PSCDBP | 0.33 | TGGACCCCACTGGCTGAGAATCTGG |
| 10 | SELPLG | 0.33 | TTGGACATCTCTAGTGTAGCTGCCA |
| 24 | CD3Z | 0.3 | TCCTTGTGCCTGCTCCTGTACTTGT |
| 10 | PRKCQ | 0.33 | TTGGACATCTCTAGTGTAGCTGCCA |
| 2 | CD1A | 0.34 | GCCCCACTGGACAACACTGATTCCT |
| 10 | GATA2 | 0.31 | TTGGACATCTCTAGTGTAGCTGCCA |
| 3 | P2RX5 | 0.32 | TGCCTGCTCCTGTACTTGTCCTCAG |
| 9 | LAIR1 | 0.35 | TGGACCCCACTGGCTGAGAATCTGG |
| 2 | C1orf38 | 0.4 | GCCCCACTGGACAACACTGATTCCT |
| 24 | SH2D1A | 0.44 | TCCTTGTGCCTGCTCCTGTACTTGT |
| 11 | TRB@ | 0.33 | CACCCAGCTGGTCCTGTGGATGGGA |
| 2 | SEPT6 | 0.34 | GCCCCACTGGACAACACTGATTCCT |
| 6 | HA-1 | 0.32 | AAGCCTATACGTTTCTGTGGAGTAA |
| 24 | DOCK2 | 0.3 | TCCTTGTGCCTGCTCCTGTACTTGT |
| 3 | WBSCR20C | 0.31 | TGCCTGCTCCTGTACTTGTCCTCAG |
| 7 | CD3D | 0.3 | ACTTGTCCTCAGCTTGGGCTTCTTC |
| 2 | RNASE6 | 0.31 | GCCCCACTGGACAACACTGATTCCT |
| 4 | SFRS7 | 0.32 | AAATGTTTCCTTGTGCCTGCTCCTG |
| 6 | WBSCR20A | 0.3 | AAGCCTATACGTTTCTGTGGAGTAA |
| 10 | NUP210 | 0.31 | TTGGACATCTCTAGTGTAGCTGCCA |
| 24 | CD6 | 0.34 | TCCTTGTGCCTGCTCCTGTACTTGT |
| 2 | HNRPA1 | 0.3 | GCCCCACTGGACAACACTGATTCCT |
| 6 | AIF1 | 0.34 | AAGCCTATACGTTTCTGTGGAGTAA |
| 9 | CYFIP2 | 0.38 | TGGACCCCACTGGCTGAGAATCTGG |
| 24 | GLTSCR2 | 0.38 | TCCTTGTGCCTGCTCCTGTACTTGT |
| 6 | C11orf2 | 0.31 | AAGCCTATACGTTTCTGTGGAGTAA |
| 9 | ARHGAP15 | 0.33 | TGGACCCCACTGGCTGAGAATCTGG |
| 10 | BIN2 | 0.35 | TTGGACATCTCTAGTGTAGCTGCCA |
| 7 | SH3TC1 | 0.35 | ACTTGTCCTCAGCTTGGGCTTCTTC |
| 4 | STAG3 | 0.32 | AAATGTTTCCTTGTGCCTGCTCCTG |
| 7 | TM6SF1 | 0.34 | ACTTGTCCTCAGCTTGGGCTTCTTC |
| 16 | C15orf25 | 0.33 | TCCTCCATCACCTGAAACACTGGAC |
| 4 | FLJ22457 | 0.36 | AAATGTTTCCTTGTGCCTGCTCCTG |
| 3 | PACAP | 0.34 | TGCCTGCTCCTGTACTTGTCCTCAG |
| 2 | MGC2744 | 0.31 | GCCCCACTGGACAACACTGATTCCT |

TABLE 41

5-Fluorouracil biomarkers.

| SEQ ID NO | Gene | Correlation | Medianprobe |
|---|---|---|---|
| 4 | RPL18 | 0.38 | AAATGTTTCCTTGTGCCTGCTCCTG |
| 9 | RPL10A | 0.39 | TGGACCCCACTGGCTGAGAATCTGG |
| 7 | ANAPC5 | 0.37 | ACTTGTCCTCAGCTTGGGCTTCTTC |
| 1 | EEF1B2 | 0.3 | TCCTGTACTTGTCCTCAGCTTGGGC |
| 3 | RPL13A | 0.5 | TGCCTGCTCCTGTACTTGTCCTCAG |
| 7 | RPS15 | 0.4 | ACTTGTCCTCAGCTTGGGCTTCTTC |
| 2 | NDUFAB1 | 0.38 | GCCCCACTGGACAACACTGATTCCT |
| 4 | APRT | 0.32 | AAATGTTTCCTTGTGCCTGCTCCTG |
| 16 | ZNF593 | 0.34 | TCCTCCATCACCTGAAACACTGGAC |
| 4 | MRP63 | 0.32 | AAATGTTTCCTTGTGCCTGCTCCTG |
| 9 | IL6R | 0.41 | TGGACCCCACTGGCTGAGAATCTGG |
| 16 | SART3 | 0.37 | TCCTCCATCACCTGAAACACTGGAC |
| 2 | UCK2 | 0.32 | GCCCCACTGGACAACACTGATTCCT |
| 6 | RPL17 | 0.31 | AAGCCTATACGTTTCTGTGGAGTAA |
| 11 | RPS2 | 0.35 | CACCCAGCTGGTCCTGTGGATGGGA |
| 24 | PCCB | 0.38 | TCCTTGTGCCTGCTCCTGTACTTGT |
| 9 | TOMM20 | 0.32 | TGGACCCCACTGGCTGAGAATCTGG |
| 10 | SHMT2 | 0.32 | TTGGACATCTCTAGTGTAGCTGCCA |
| 24 | RPLP0 | 0.31 | TCCTTGTGCCTGCTCCTGTACTTGT |
| 11 | GTF3A | 0.32 | CACCCAGCTGGTCCTGTGGATGGGA |
| 9 | STOML2 | 0.33 | TGGACCCCACTGGCTGAGAATCTGG |
| 4 | DKFZp564J157 | 0.4 | AAATGTTTCCTTGTGCCTGCTCCTG |
| 1 | MRPS2 | 0.32 | TCCTGTACTTGTCCTCAGCTTGGGC |
| 10 | ALG5 | 0.3 | TTGGACATCTCTAGTGTAGCTGCCA |
| 11 | CALML4 | 0.33 | CACCCAGCTGGTCCTGTGGATGGGA |

TABLE 42

Radiation sensitivity biomarkers.

| SEQ ID NO | Gene | Correlation | Medianprobe |
|---|---|---|---|
| 9626 | TRA1 | 0.36 | TGGACCCCACTGGCTGAGAATCTGG |
| 7 | ACTN4 | 0.36 | ACTTGTCCTCAGCTTGGGCTTCTTC |
| 16 | CALM1 | 0.32 | TCCTCCATCACCTGAAACACTGGAC |
| 1 | CD63 | 0.32 | TCCTGTACTTGTCCTCAGCTTGGGC |
| 9 | FKBP1A | 0.38 | TGGACCCCACTGGCTGAGAATCTGG |
| 7 | CALU | 0.47 | ACTTGTCCTCAGCTTGGGCTTCTTC |
| 6 | IQGAP1 | 0.37 | TTGGACATCTCTAGTGTAGCTGCCA |
| 16 | MGC8721 | 0.35 | AAATGTTTCCTTGTGCCTGCTCCTG |
| 24 | STAT1 | 0.37 | TGGACCCCACTGGCTGAGAATCTGG |
| 1 | TACC1 | 0.41 | ACTTGTCCTCAGCTTGGGCTTCTTC |
| 6 | TM4SF8 | 0.33 | AAGCCTATACGTTTCTGTGGAGTAA |
| 16 | CD59 | 0.31 | TCCTCCATCACCTGAAACACTGGAC |
| 24 | CKAP4 | 0.45 | TCCTTGTGCCTGCTCCTGTACTTGT |
| 1 | DUSP1 | 0.38 | TCCTGTACTTGTCCTCAGCTTGGGC |
| 3 | RCN1 | 0.31 | TGCCTGCTCCTGTACTTGTCCTCAG |
| 3 | MGC8902 | 0.35 | TGCCTGCTCCTGTACTTGTCCTCAG |
| 7 | RRBP1 | 0.31 | ACTTGTCCTCAGCTTGGGCTTCTTC |
| 10 | PRNP | 0.42 | TTGGACATCTCTAGTGTAGCTGCCA |
| 2 | IER3 | 0.34 | GCCCCACTGGACAACACTGATTCCT |
| 2 | MARCKS | 0.43 | GCCCCACTGGACAACACTGATTCCT |
| 3 | FER1L3 | 0.47 | TGCCTGCTCCTGTACTTGTCCTCAG |
| 7 | SLC20A1 | 0.41 | ACTTGTCCTCAGCTTGGGCTTCTTC |
| 4 | HEXB | 0.46 | AAATGTTTCCTTGTGCCTGCTCCTG |
| 11 | EXT1 | 0.47 | CACCCAGCTGGTCCTGTGGATGGGA |
| 4 | TJP1 | 0.32 | AAATGTTTCCTTGTGCCTGCTCCTG |
| 1 | CTSL | 0.38 | TCCTGTACTTGTCCTCAGCTTGGGC |
| 1 | SLC39A6 | 0.36 | TCCTGTACTTGTCCTCAGCTTGGGC |
| 16 | RIOK3 | 0.38 | TCCTCCATCACCTGAAACACTGGAC |
| 3 | CRK | 0.37 | TGCCTGCTCCTGTACTTGTCCTCAG |
| 3 | NNMT | 0.37 | TGCCTGCTCCTGTACTTGTCCTCAG |
| 10 | TRAM2 | 0.35 | TTGGACATCTCTAGTGTAGCTGCCA |
| 1 | ADAM9 | 0.52 | TCCTGTACTTGTCCTCAGCTTGGGC |
| 9 | PLSCR1 | 0.35 | TGGACCCCACTGGCTGAGAATCTGG |
| 3 | PRSS23 | 0.3 | TGCCTGCTCCTGTACTTGTCCTCAG |
| 3 | PLOD2 | 0.36 | TGCCTGCTCCTGTACTTGTCCTCAG |
| 3 | NPC1 | 0.39 | TGCCTGCTCCTGTACTTGTCCTCAG |
| 11 | TOB1 | 0.37 | CACCCAGCTGGTCCTGTGGATGGGA |
| 11 | GFPT1 | 0.47 | CACCCAGCTGGTCCTGTGGATGGGA |
| 4 | IL8 | 0.36 | AAATGTTTCCTTGTGCCTGCTCCTG |
| 16 | PYGL | 0.46 | TCCTCCATCACCTGAAACACTGGAC |
| 10 | LOXL2 | 0.49 | TTGGACATCTCTAGTGTAGCTGCCA |
| 24 | KIAA0355 | 0.36 | TCCTTGTGCCTGCTCCTGTACTTGT |
| 10 | UGDH | 0.49 | TTGGACATCTCTAGTGTAGCTGCCA |
| 3 | PURA | 0.32 | TGCCTGCTCCTGTACTTGTCCTCAG |

TABLE 42-continued

Radiation sensitivity biomarkers.

| SEQ ID NO | Gene | Correlation | Medianprobe |
|---|---|---|---|
| 6 | ULK2 | 0.37 | AAGCCTATACGTTTCTGTGGAGTAA |
| 2 | CENTG2 | 0.35 | GCCCCACTGGACAACACTGATTCCT |
| 2 | CAP350 | 0.31 | GCCCCACTGGACAACACTGATTCCT |
| 1 | CXCL1 | 0.36 | TCCTGTACTTGTCCTCAGCTTGGGC |
| 6 | BTN3A3 | 0.35 | AAGCCTATACGTTTCTGTGGAGTAA |
| 6 | WNT5A | 0.3 | AAGCCTATACGTTTCTGTGGAGTAA |
| 4 | FOXF2 | 0.44 | AAATGTTTCCTTGTGCCTGCTCCTG |
| 2 | LPHN2 | 0.34 | GCCCCACTGGACAACACTGATTCCT |
| 9 | CDH11 | 0.39 | TGGACCCCACTGGCTGAGAATCTGG |
| 16 | P4HA1 | 0.33 | TCCTCCATCACCTGAAACACTGGAC |
| 11 | GRP58 | 0.44 | CACCCAGCTGGTCCTGTGGATGGGA |
| 9 | DSIPI | 0.44 | TGGACCCCACTGGCTGAGAATCTGG |
| 6 | MAP1LC3B | 0.5 | AAGCCTATACGTTTCTGTGGAGTAA |
| 4 | GALIG | 0.36 | AAATGTTTCCTTGTGCCTGCTCCTG |
| 16 | IGSF4 | 0.4 | TCCTCCATCACCTGAAACACTGGAC |
| 9 | IRS2 | 0.35 | TGGACCCCACTGGCTGAGAATCTGG |
| 11 | ATP2A2 | 0.35 | CACCCAGCTGGTCCTGTGGATGGGA |
| 1 | OGT | 0.3 | TCCTGTACTTGTCCTCAGCTTGGGC |
| 6 | TNFRSF10B | 0.31 | AAGCCTATACGTTTCTGTGGAGTAA |
| 11 | KIAA1128 | 0.35 | CACCCAGCTGGTCCTGTGGATGGGA |
| 11 | TM4SF1 | 0.35 | CACCCAGCTGGTCCTGTGGATGGGA |
| 3 | RIPK2 | 0.42 | TGCCTGCTCCTGTACTTGTCCTCAG |
| 10 | NR1D2 | 0.47 | TTGGACATCTCTAGTGTAGCTGCCA |
| 10 | SSA2 | 0.36 | TTGGACATCTCTAGTGTAGCTGCCA |
| 6 | NQO1 | 0.4 | AAGCCTATACGTTTCTGTGGAGTAA |
| 3 | ASPH | 0.36 | TGCCTGCTCCTGTACTTGTCCTCAG |
| 7 | ASAH1 | 0.33 | ACTTGTCCTCAGCTTGGGCTTCTTC |
| 9 | MGLL | 0.35 | TGGACCCCACTGGCTGAGAATCTGG |
| 6 | SERPINB6 | 0.51 | AAGCCTATACGTTTCTGTGGAGTAA |
| 24 | HSPA5 | 0.33 | TCCTTGTGCCTGCTCCTGTACTTGT |
| 24 | ZFP36L1 | 0.39 | TCCTTGTGCCTGCTCCTGTACTTGT |
| 7 | COL4A1 | 0.3 | ACTTGTCCTCAGCTTGGGCTTCTTC |
| 7 | NIPA2 | 0.36 | ACTTGTCCTCAGCTTGGGCTTCTTC |
| 4 | FKBP9 | 0.48 | AAATGTTTCCTTGTGCCTGCTCCTG |
| 2 | IL6ST | 0.4 | GCCCCACTGGACAACACTGATTCCT |
| 10 | DKFZP564G2022 | 0.39 | TTGGACATCTCTAGTGTAGCTGCCA |
| 9 | PPAP2B | 0.33 | TGGACCCCACTGGCTGAGAATCTGG |
| 11 | MAP1B | 0.3 | CACCCAGCTGGTCCTGTGGATGGGA |
| 9 | MAPK1 | 0.3 | TGGACCCCACTGGCTGAGAATCTGG |
| 7 | MYO1B | 0.38 | ACTTGTCCTCAGCTTGGGCTTCTTC |
| 3 | CAST | 0.31 | TGCCTGCTCCTGTACTTGTCCTCAG |
| 4 | RRAS2 | 0.52 | AAATGTTTCCTTGTGCCTGCTCCTG |
| 7 | QKI | 0.31 | ACTTGTCCTCAGCTTGGGCTTCTTC |
| 24 | LHFPL2 | 0.36 | TCCTTGTGCCTGCTCCTGTACTTGT |
| 2 | SEPT10 | 0.38 | GCCCCACTGGACAACACTGATTCCT |
| 6 | ARHE | 0.5 | AAGCCTATACGTTTCTGTGGAGTAA |
| 6 | KIAA1078 | 0.34 | AAGCCTATACGTTTCTGTGGAGTAA |
| 1 | FTL | 0.38 | TCCTGTACTTGTCCTCAGCTTGGGC |
| 4 | KIAA0877 | 0.41 | AAATGTTTCCTTGTGCCTGCTCCTG |
| 6 | PLCB1 | 0.3 | AAGCCTATACGTTTCTGTGGAGTAA |
| 3 | KIAA0802 | 0.32 | TGCCTGCTCCTGTACTTGTCCTCAG |
| 3 | RAB3GAP | 0.43 | TGCCTGCTCCTGTACTTGTCCTCAG |
| 3 | SERPINB1 | 0.46 | TGCCTGCTCCTGTACTTGTCCTCAG |
| 4 | TIMM17A | 0.38 | AAATGTTTCCTTGTGCCTGCTCCTG |
| 10 | SOD2 | 0.35 | TTGGACATCTCTAGTGTAGCTGCCA |
| 10 | HLA-A | 0.33 | TTGGACATCTCTAGTGTAGCTGCCA |
| 11 | NOMO2 | 0.43 | CACCCAGCTGGTCCTGTGGATGGGA |
| 1 | LOC55831 | 0.32 | TCCTGTACTTGTCCTCAGCTTGGGC |
| 11 | PHLDA1 | 0.32 | CACCCAGCTGGTCCTGTGGATGGGA |
| 9 | TMEM2 | 0.47 | TGGACCCCACTGGCTGAGAATCTGG |
| 7 | MLPH | 0.35 | ACTTGTCCTCAGCTTGGGCTTCTTC |
| 7 | FAD104 | 0.34 | ACTTGTCCTCAGCTTGGGCTTCTTC |
| 11 | LRRC5 | 0.42 | CACCCAGCTGGTCCTGTGGATGGGA |
| 10 | RAB7L1 | 0.41 | TTGGACATCTCTAGTGTAGCTGCCA |
| 1 | FLJ35036 | 0.36 | TCCTGTACTTGTCCTCAGCTTGGGC |
| 16 | DOCK10 | 0.41 | TCCTCCATCACCTGAAACACTGGAC |
| 6 | LRP12 | 0.36 | AAGCCTATACGTTTCTGTGGAGTAA |
| 7 | TXNDC5 | 0.4 | ACTTGTCCTCAGCTTGGGCTTCTTC |
| 3 | CDC14B | 0.39 | TGCCTGCTCCTGTACTTGTCCTCAG |
| 11 | HRMT1L1 | 0.38 | CACCCAGCTGGTCCTGTGGATGGGA |
| 10 | DNAJC10 | 0.31 | TTGGACATCTCTAGTGTAGCTGCCA |
| 2 | TNPO1 | 0.33 | GCCCCACTGGACAACACTGATTCCT |
| 4 | LONP | 0.32 | AAATGTTTCCTTGTGCCTGCTCCTG |
| 6 | AMIGO2 | 0.38 | AAGCCTATACGTTTCTGTGGAGTAA |

TABLE 42-continued

Radiation sensitivity biomarkers.

| SEQ ID NO | Gene | Correlation | Medianprobe |
|---|---|---|---|
| 3 | DNAPTP6 | 0.31 | TGCCTGCTCCTGTACTTGTCCTCAG |
| 10 | ADAMTS1 | 0.37 | TTGGACATCTCTAGTGTAGCTGCCA |

TABLE 43

Rituximab (e.g., Mabthera) biomarkers.

| SEQ ID NO | Gene | Correlation | Medianprobe |
|---|---|---|---|
| 16 | PSMB2 | 0.89 | TCCTCCATCACCTGAAACACTGGAC |
| 6 | BAT1 | 0.88 | AAGCCTATACGTTTCTGTGGAGTAA |
| 24 | ASCC3L1 | 0.89 | TCCTTGTGCCTGCTCCTGTACTTGT |
| 4 | SET | 0.94 | AAATGTTTCCTTGTGCCTGCTCCTG |
| 24 | YWHAZ | 0.83 | TCCTTGTGCCTGCTCCTGTACTTGT |
| 9 | GLUL | 0.8 | TGGACCCCACTGGCTGAGAATCTGG |
| 24 | LDHA | 0.8 | TCCTTGTGCCTGCTCCTGTACTTGT |
| 4 | HMGB1 | 0.84 | AAATGTTTCCTTGTGCCTGCTCCTG |
| 4 | SFRS2 | 0.87 | AAATGTTTCCTTGTGCCTGCTCCTG |
| 1 | DPYSL2 | 0.82 | TCCTGTACTTGTCCTCAGCTTGGGC |
| 11 | MGC8721 | 0.82 | CACCCAGCTGGTCCTGTGGATGGGA |
| 3 | NOL5A | 0.86 | TGCCTGCTCCTGTACTTGTCCTCAG |
| 4 | SFRS10 | 0.88 | AAATGTTTCCTTGTGCCTGCTCCTG |
| 1 | SF3B1 | 0.82 | TCCTGTACTTGTCCTCAGCTTGGGC |
| 3 | K-ALPHA-1 | 0.86 | TGCCTGCTCCTGTACTTGTCCTCAG |
| 9 | TXNRD1 | 0.86 | TGGACCCCACTGGCTGAGAATCTGG |
| 11 | ARHGDIB | 0.83 | CACCCAGCTGGTCCTGTGGATGGGA |
| 10 | ZFP36L2 | 0.92 | TTGGACATCTCTAGTGTAGCTGCCA |
| 9 | DHX15 | 0.81 | TGGACCCCACTGGCTGAGAATCTGG |
| 11 | SOX4 | 0.85 | CACCCAGCTGGTCCTGTGGATGGGA |
| 766 | GRSF1 | 0.81 | TGGACCCCACTGGCTGAGAATCTGG |
| 2 | MCM3 | 0.85 | GCCCCACTGGACAACACTGATTCCT |
| 16 | IFITM1 | 0.82 | TCCTCCATCACCTGAAACACTGGAC |
| 16 | RPA2 | 0.86 | TCCTCCATCACCTGAAACACTGGAC |
| 7 | LBR | 0.87 | ACTTGTCCTCAGCTTGGGCTTCTTC |
| 6 | CKS1B | 0.85 | AAGCCTATACGTTTCTGTGGAGTAA |
| 9 | NASP | 0.82 | TGGACCCCACTGGCTGAGAATCTGG |
| 16 | HNRPDL | 0.81 | TCCTCCATCACCTGAAACACTGGAC |
| 3 | CUGBP2 | 0.81 | TGCCTGCTCCTGTACTTGTCCTCAG |
| 24 | PTBP1 | 0.87 | TCCTTGTGCCTGCTCCTGTACTTGT |
| 10 | ARL7 | 0.83 | TTGGACATCTCTAGTGTAGCTGCCA |
| 7 | CTCF | 0.83 | ACTTGTCCTCAGCTTGGGCTTCTTC |
| 24 | HMGCR | 0.86 | TCCTTGTGCCTGCTCCTGTACTTGT |
| 4 | ITM2A | 0.88 | AAATGTTTCCTTGTGCCTGCTCCTG |
| 24 | SFRS3 | 0.93 | TCCTTGTGCCTGCTCCTGTACTTGT |
| 24 | SRPK2 | 0.82 | TCCTTGTGCCTGCTCCTGTACTTGT |
| 11 | JARID2 | 0.92 | CACCCAGCTGGTCCTGTGGATGGGA |
| 1 | M96 | 0.84 | TCCTGTACTTGTCCTCAGCTTGGGC |
| 16 | MAD2L1 | 0.87 | TCCTCCATCACCTGAAACACTGGAC |
| 7 | SATB1 | 0.81 | ACTTGTCCTCAGCTTGGGCTTCTTC |
| 7 | TMPO | 0.9 | ACTTGTCCTCAGCTTGGGCTTCTTC |
| 7 | SIVA | 0.84 | ACTTGTCCTCAGCTTGGGCTTCTTC |
| 16 | SEMA4D | 0.9 | TCCTCCATCACCTGAAACACTGGAC |
| 24 | TFDP2 | 0.87 | TCCTTGTGCCTGCTCCTGTACTTGT |
| 6 | SKP2 | 0.86 | AAGCCTATACGTTTCTGTGGAGTAA |
| 2 | SH3YL1 | 0.88 | GCCCCACTGGACAACACTGATTCCT |
| 16 | RFC4 | 0.87 | TCCTCCATCACCTGAAACACTGGAC |
| 6 | PCBP2 | 0.83 | AAGCCTATACGTTTCTGTGGAGTAA |
| 2 | IL2RG | 0.84 | GCCCCACTGGACAACACTGATTCCT |
| 1 | CDC45L | 0.89 | TCCTGTACTTGTCCTCAGCTTGGGC |
| 10 | GTSE1 | 0.83 | TTGGACATCTCTAGTGTAGCTGCCA |
| 6 | KIF11 | 0.85 | AAGCCTATACGTTTCTGTGGAGTAA |
| 10 | FEN1 | 0.88 | TTGGACATCTCTAGTGTAGCTGCCA |
| 9 | MYB | 0.9 | TGGACCCCACTGGCTGAGAATCTGG |
| 16 | LCK | 0.87 | TCCTCCATCACCTGAAACACTGGAC |
| 2 | CENPA | 0.84 | GCCCCACTGGACAACACTGATTCCT |
| 2 | CCNE2 | 0.84 | GCCCCACTGGACAACACTGATTCCT |
| 10 | H2AFX | 0.88 | TTGGACATCTCTAGTGTAGCTGCCA |
| 16 | SNRPG | 0.84 | TCCTCCATCACCTGAAACACTGGAC |
| 24 | CD3G | 0.94 | TCCTTGTGCCTGCTCCTGTACTTGT |
| 7 | STK6 | 0.9 | ACTTGTCCTCAGCTTGGGGTTCTTC |
| 3 | PTP4A2 | 0.81 | TGCCTGCTCCTGTACTTGTCCTCAG |
| 4 | FDFT1 | 0.91 | AAATGTTTCCTTGTGCCTGCTCCTG |
| 4 | HSPA8 | 0.84 | AAATGTTTCCTTGTGCCTGCTCCTG |
| 24 | HNRPR | 0.94 | TCCTTGTGCCTGCTCCTGTACTTGT |
| 4 | MCM7 | 0.92 | AAATGTTTCCTTGTGCCTGCTCCTG |

TABLE 43-continued

Rituximab (e.g., Mabthera) biomarkers.

| SEQ ID NO | Gene | Correlation | Medianprobe |
|---|---|---|---|
| 9 | SFRS6 | 0.85 | TGGACCCCACTGGCTGAGAATCTGG |
| 11 | PAK2 | 0.8 | CACCCAGCTGGTCCTGTGGATGGGA |
| 1 | LCP1 | 0.85 | TCCTGTACTTGTCCTCAGCTTGGGC |
| 7 | STAT3 | 0.81 | ACTTGTCCTCAGCTTGGGCTTCTTC |
| 24 | OK/SW-cl.56 | 0.8 | TCCTTGTGCCTGCTCCTGTACTTGT |
| 9 | WHSC1 | 0.81 | TGGACCCCACTGGCTGAGAATCTGG |
| 6 | DIAPH1 | 0.88 | AAGCCTATACGTTTCTGTGGAGTAA |
| 1 | KIF2C | 0.88 | TCCTGTACTTGTCCTCAGCTTGGGC |
| 11 | HDGFRP3 | 0.89 | CACCCAGCTGGTCCTGTGGATGGGA |
| 10 | PNMA2 | 0.93 | TTGGACATCTCTAGTGTAGCTGCCA |
| 1 | GATA3 | 0.93 | TCCTGTACTTGTCCTCAGCTTGGGC |
| 4 | BUB1 | 0.88 | AAATGTTTCCTTGTGCCTGCTCCTG |
| 11 | TPX2 | 0.8 | CACCCAGCTGGTCCTGTGGATGGGA |
| 24 | SH2D1A | 0.86 | TCCTTGTGCCTGCTCCTGTACTTGT |
| 16 | TNFAIP8 | 0.9 | TCCTCCATCACCTGAAACACTGGAC |
| 4 | CSE1L | 0.83 | AAATGTTTCCTTGTGCCTGCTCCTG |
| 1 | MCAM | 0.8 | TCCTGTACTTGTCCTCAGCTTGGGC |
| 2 | AF1Q | 0.83 | GCCCCACTGGACAACACTGATTCCT |
| 11 | CD47 | 0.86 | CACCCAGCTGGTCCTGTGGATGGGA |
| 6 | SFRS1 | 0.85 | AAGCCTATACGTTTCTGTGGAGTAA |
| 1 | FYB | 0.92 | TCCTGTACTTGTCCTCAGCTTGGGC |
| 7 | TRB@ | 0.84 | ACTTGTCCTCAGCTTGGGCTTCTTC |
| 2 | CXCR4 | 0.94 | GCCCCACTGGACAACACTGATTCCT |
| 16 | H3F3B | 0.84 | TCCTCCATCACCTGAAACACTGGAC |
| 7 | MKI67 | 0.83 | ACTTGTCCTCAGCTTGGGCTTCTTC |
| 24 | MAC30 | 0.82 | TCCTTGTGCCTGCTCCTGTACTTGT |
| 6 | ARID5B | 0.88 | AAGCCTATACGTTTCTGTGGAGTAA |
| 6 | LOC339287 | 0.81 | AAGCCTATACGTTTCTGTGGAGTAA |
| 24 | CD3D | 0.82 | TCCTTGTGCCTGCTCCTGTACTTGT |
| 6 | ZAP70 | 0.87 | AAGCCTATACGTTTCTGTGGAGTAA |
| 16 | LAPTM4B | 0.83 | TCCTCCATCACCTGAAACACTGGAC |
| 24 | SFRS7 | 0.87 | TCCTTGTGCCTGCTCCTGTACTTGT |
| 6 | HNRPA1 | 0.9 | AAGCCTATACGTTTCTGTGGAGTAA |
| 6 | HSPCA | 0.88 | AAGCCTATACGTTTCTGTGGAGTAA |
| 24 | AIF1 | 0.82 | TCCTTGTGCCTGCTCCTGTACTTGT |
| 6 | GTF3A | 0.87 | AAGCCTATACGTTTCTGTGGAGTAA |
| 10 | MCM5 | 0.91 | TTGGACATCTCTAGTGTAGCTGCCA |
| 6 | GTL3 | 0.85 | AAGCCTATACGTTTCTGTGGAGTAA |
| 3 | ZNF22 | 0.89 | TGCCTGCTCCTGTACTTGTCCTCAG |
| 2 | FLJ22794 | 0.83 | GCCCCACTGGACAACACTGATTCCT |
| 7 | LZTFL1 | 0.89 | ACTTGTCCTCAGCTTGGGCTTCTTC |
| 16 | e(y)2 | 0.87 | TCCTCCATCACCTGAAACACTGGAC |
| 16 | FLJ20152 | 0.92 | TCCTCCATCACCTGAAACACTGGAC |
| 7 | C10orf3 | 0.86 | ACTTGTCCTCAGCTTGGGCTTCTTC |
| 4 | NRN1 | 0.86 | AAATGTTTCCTTGTGCCTGCTCCTG |
| 2 | FLJ10858 | 0.81 | GCCCCACTGGACAACACTGATTCCT |
| 2 | BCL11B | 0.89 | GCCCCACTGGACAACACTGATTCCT |
| 6 | ASPM | 0.91 | AAGCCTATACGTTTCTGTGGAGTAA |
| 10 | LEF1 | 0.9 | TTGGACATCTCTAGTGTAGCTGCCA |
| 7 | LOC146909 | 0.83 | ACTTGTCCTCAGCTTGGGCTTCTTC |

TABLE 44

5-Aza-2'-deoxycytidine (decitabine) biomarkers.

| SEQ ID NO | Gene | Correlation | Medianprobe |
|---|---|---|---|
| 10 | CD99 | 0.31 | TTGGACATCTCTAGTGTAGCTGCCA |
| 1 | SNRPA | 0.32 | TCCTGTACTTGTCCTCAGCTTGGGC |
| 1 | CUGBP2 | 0.32 | TCCTGTACTTGTCCTCAGCTTGGGC |
| 2 | STAT5A | 0.32 | GCCCCACTGGACAACACTGATTCCT |
| 10 | SLA | 0.38 | TTGGACATCTCTAGTGTAGCTGCCA |
| 9 | IL2RG | 0.33 | TGGACCCCACTGGCTGAGAATCTGG |
| 7 | GTSE1 | 0.32 | ACTTGTCCTCAGCTTGGGCTTCTTC |
| 9 | MYB | 0.36 | TGGACCCCACTGGCTGAGAATCTGG |
| 1 | PTPN7 | 0.33 | TCCTGTACTTGTCCTCAGCTTGGGC |
| 1 | CXorf9 | 0.42 | TCCTGTACTTGTCCTCAGCTTGGGC |
| 4 | RHOH | 0.38 | AAATGTTTCCTTGTGCCTGCTCCTG |
| 6 | ZNFN1A1 | 0.33 | AAGCCTATACGTTTCTGTGGAGTAA |
| 11 | CENTB1 | 0.35 | CACCCAGCTGGTCCTGTGGATGGGA |
| 4 | LCP2 | 0.3 | AAATGTTTCCTTGTGCCTGCTCCTG |
| 9 | HIST1H4C | 0.33 | TGGACCCCACTGGCTGAGAATCTGG |
| 3 | CCR7 | 0.37 | TGCCTGCTCCTGTACTTGTCCTCAG |
| 24 | APOBEC3B | 0.31 | TCCTTGTGCCTGCTCCTGTACTTGT |
| 9 | MCM7 | 0.31 | TGGACCCCACTGGCTGAGAATCTGG |
| 6 | LCP1 | 0.31 | AAGCCTATACGTTTCTGTGGAGTAA |

TABLE 44-continued

5-Aza-2'-deoxycytidine (decitabine) biomarkers.

| SEQ ID NO | Gene | Correlation | Medianprobe |
|---|---|---|---|
| 9 | SELPLG | 0.4 | TGGACCCCACTGGCTGAGAATCTGG |
| 1 | CD3Z | 0.35 | TCCTGTACTTGTCCTCAGCTTGGGC |
| 3 | PRKCQ | 0.39 | TGCCTGCTCCTGTACTTGTCCTCAG |
| 2 | GZMB | 0.32 | GCCCCACTGGACAACACTGATTCCT |
| 6 | SCN3A | 0.4 | AAGCCTATACGTTTCTGTGGAGTAA |
| 3 | LAIR1 | 0.35 | TGCCTGCTCCTGTACTTGTCCTCAG |
| 2 | SH2D1A | 0.35 | GCCCCACTGGACAACACTGATTCCT |
| 7 | SEPT6 | 0.35 | ACTTGTCCTCAGCTTGGGCTTCTTC |
| 7 | CG018 | 0.32 | ACTTGTCCTCAGCTTGGGCTTCTTC |
| 9 | CD3D | 0.31 | TGGACCCCACTGGCTGAGAATCTGG |
| 24 | C18orf10 | 0.33 | TCCTTGTGCCTGCTCCTGTACTTGT |
| 16 | PRF1 | 0.31 | TCCTCCATCACCTGAAACACTGGAC |
| 10 | AIF1 | 0.31 | TTGGACATCTCTAGTGTAGCTGCCA |
| 7 | MCM5 | 0.31 | ACTTGTCCTCAGCTTGGGCTTCTTC |
| 16 | LPXN | 0.35 | TCCTCCATCACCTGAAACACTGGAC |
| 4 | C22orf18 | 0.33 | AAATGTTTCCTTGTGCCTGCTCCTG |
| 4 | ARHGAP15 | 0.31 | AAATGTTTCCTTGTGCCTGCTCCTG |
| 2 | LEF1 | 0.43 | GCCCCACTGGACAACACTGATTCCT |

TABLE 45

Idarubicin biomarkers.

| SEQ ID NO | Gene | Correlation | Medianprobe |
|---|---|---|---|
| 9 | SLC9A3R1 | 0.31 | TGGACCCCACTGGCTGAGAATCTGG |
| 9 | RPS19 | 0.32 | TGGACCCCACTGGCTGAGAATCTGG |
| 1 | ITM2A | 0.34 | TCCTGTACTTGTCCTCAGCTTGGGC |
| 6 | SSBP2 | 0.31 | AAGCCTATACGTTTCTGTGGAGTAA |
| 1 | CXorf9 | 0.31 | TCCTGTACTTGTCCTCAGCTTGGGC |
| 16 | RHOH | 0.32 | TCCTCCATCACCTGAAACACTGGAC |
| 4 | ZNFN1A1 | 0.36 | AAATGTTTCCTTGTGCCTGCTCCTG |
| 11 | FXYD2 | 0.35 | CACCCAGCTGGTCCTGTGGATGGGA |
| 9 | CCR9 | 0.39 | TGGACCCCACTGGCTGAGAATCTGG |
| 10 | NAP1L1 | 0.3 | TTGGACATCTCTAGTGTAGCTGCCA |
| 4 | CXCR4 | 0.31 | AAATGTTTCCTTGTGCCTGCTCCTG |
| 1 | SH2D1A | 0.3 | TCCTGTACTTGTCCTCAGCTTGGGC |
| 6 | CD1A | 0.3 | AAGCCTATACGTTTCTGTGGAGTAA |

TABLE 45-continued

Idarubicin biomarkers.

| SEQ ID NO | Gene | Correlation | Medianprobe |
|---|---|---|---|
| 4 | TRB@ | 0.32 | AAATGTTTCCTTGTGCCTGCTCCTG |
| 2 | SEPT6 | 0.32 | GCCCCACTGGACAACACTGATTCCT |
| 3 | RPS2 | 0.33 | TGCCTGCTCCTGTACTTGTCCTCAG |
| 3 | DOCK2 | 0.32 | TGCCTGCTCCTGTACTTGTCCTCAG |
| 7 | CD3D | 0.31 | ACTTGTCCTCAGCTTGGGCTTCTTC |
| 2 | CD6 | 0.3 | GCCCCACTGGACAACACTGATTCCT |
| 7 | ZAP70 | 0.34 | ACTTGTCCTCAGCTTGGGCTTCTTC |
| 3 | AIF1 | 0.3 | TGCCTGCTCCTGTACTTGTCCTCAG |
| 3 | CD1E | 0.32 | TGCCTGCTCCTGTACTTGTCCTCAG |
| 10 | CYFIP2 | 0.3 | TTGGACATCTCTAGTGTAGCTGCCA |
| 1 | ADA | 0.41 | TCCTGTACTTGTCCTCAGCTTGGGC |
| 24 | TRIM | 0.31 | TCCTTGTGCCTGCTCCTGTACTTGT |
| 3 | GLTSCR2 | 0.32 | TGCCTGCTCCTGTACTTGTCCTCAG |
| 2 | FLJ10858 | 0.35 | GCCCCACTGGACAACACTGATTCCT |
| 1 | BCL11B | 0.34 | TCCTGTACTTGTCCTCAGCTTGGGC |
| 3 | GIMAP6 | 0.36 | TGCCTGCTCCTGTACTTGTCCTCAG |
| 10 | STAG3 | 0.34 | TTGGACATCTCTAGTGTAGCTGCCA |
| 7 | UBASH3A | 0.39 | ACTTGTCCTCAGCTTGGGCTTCTTC |

TABLE 46

Melphalan biomarkers.

| SEQ ID NO | Gene | Correlation | Medianprobe |
|---|---|---|---|
| 9 | CD99 | 0.31 | TGGACCCCACTGGCTGAGAATCTGG |
| 3 | HLA-DPB1 | 0.32 | TGCCTGCTCCTGTACTTGTCCTCAG |
| 3 | ARHGDIB | 0.35 | TGCCTGCTCCTGTACTTGTCCTCAG |
| 11 | IFITM1 | 0.33 | CACCCAGCTGGTCCTGTGGATGGGA |
| 24 | UBE2L6 | 0.32 | TCCTTGTGCCTGCTCCTGTACTTGT |
| 24 | ITM2A | 0.37 | TCCTTGTGCCTGCTCCTGTACTTGT |
| 4 | SERPINA1 | 0.31 | AAATGTTTCCTTGTGCCTGCTCCTG |
| 4 | STAT5A | 0.38 | AAATGTTTCCTTGTGCCTGCTCCTG |
| 24 | INPP5D | 0.37 | TCCTTGTGCCTGCTCCTGTACTTGT |
| 3 | DGKA | 0.3 | TGCCTGCTCCTGTACTTGTCCTCAG |
| 3 | SATB1 | 0.34 | TGCCTGCTCCTGTACTTGTCCTCAG |
| 4 | SEMA4D | 0.37 | AAATGTTTCCTTGTGCCTGCTCCTG |
| 11 | TFDP2 | 0.31 | CACCCAGCTGGTCCTGTGGATGGGA |
| 16 | SLA | 0.49 | TCCTCCATCACCTGAAACACTGGAC |

TABLE 46-continued

Melphalan biomarkers.

| SEQ ID NO | Gene | Correlation | Medianprobe |
|---|---|---|---|
| 11 | IL2RG | 0.42 | CACCCAGCTGGTCCTGTGGATGGGA |
| 24 | CD48 | 0.33 | TCCTTGTGCCTGCTCCTGTACTTGT |
| 7 | MFNG | 0.48 | ACTTGTCCTCAGCTTGGGCTTCTTC |
| 11 | ALOX5AP | 0.3 | CACCCAGCTGGTCCTGTGGATGGGA |
| 6 | GPSM3 | 0.31 | AAGCCTATACGTTTCTGTGGAGTAA |
| 2 | PSMB9 | 0.34 | GCCCCACTGGACAACACTGATTCCT |
| 9 | KIAA0711 | 0.37 | TGGACCCCACTGGCTGAGAATCTGG |
| 4 | SELL | 0.32 | AAATGTTTCCTTGTGCCTGCTCCTG |
| 3 | ADA | 0.31 | TGCCTGCTCCTGTACTTGTCCTCAG |
| 10 | EDG1 | 0.49 | TTGGACATCTCTAGTGTAGCTGCCA |
| 11 | RIMS3 | 0.3 | CACCCAGCTGGTCCTGTGGATGGGA |
| 6 | FMNL1 | 0.33 | AAGCCTATACGTTTCTGTGGAGTAA |
| 2 | MYB | 0.3 | GCCCCACTGGACAACACTGATTCCT |
| 4 | PTPN7 | 0.34 | AAATGTTTCCTTGTGCCTGCTCCTG |
| 4 | LCK | 0.31 | AAATGTTTCCTTGTGCCTGCTCCTG |
| 11 | CXorf9 | 0.55 | CACCCAGCTGGTCCTGTGGATGGGA |
| 9 | RHOH | 0.35 | TGGACCCCACTGGCTGAGAATCTGG |
| 7 | ZNFN1A1 | 0.31 | ACTTGTCCTCAGCTTGGGCTTCTTC |
| 3 | CENTB1 | 0.32 | TGCCTGCTCCTGTACTTGTCCTCAG |
| 24 | LCP2 | 0.32 | TCCTTGTGCCTGCTCCTGTACTTGT |
| 11 | FXYD2 | 0.55 | CACCCAGCTGGTCCTGTGGATGGGA |
| 6 | CD1D | 0.44 | AAGCCTATACGTTTCTGTGGAGTAA |
| 3 | BATF | 0.32 | TGCCTGCTCCTGTACTTGTCCTCAG |
| 16 | STAT4 | 0.33 | TCCTCCATCACCTGAAACACTGGAC |
| 16 | VAV1 | 0.31 | TCCTCCATCACCTGAAACACTGGAC |
| 11 | MAP4K1 | 0.39 | CACCCAGCTGGTCCTGTGGATGGGA |
| 1 | CCR7 | 0.44 | TCCTGTACTTGTCCTCAGCTTGGGC |
| 1 | PDE4C | 0.32 | TCCTGTACTTGTCCTCAGCTTGGGC |
| 6 | CD3G | 0.32 | AAGCCTATACGTTTCTGTGGAGTAA |
| 10 | CCR9 | 0.36 | TTGGACATCTCTAGTGTAGGTGCCA |
| 1 | SP110 | 0.34 | TCCTGTACTTGTCCTCAGCTTGGGC |
| 4 | LCP1 | 0.35 | AAATGTTTCCTTGTGCCTGCTCCTG |
| 2 | IFI16 | 0.32 | GCCCCACTGGACAACACTGATTCCT |
| 7 | CXCR4 | 0.36 | ACTTGTCCTCAGCTTGGGCTTCTTC |
| 6 | ARHGEF6 | 0.47 | AAGCCTATACGTTTCTGTGGAGTAA |
| 10 | GATA3 | 0.55 | TTGGACATCTCTAGTGTAGCTGCCA |
| 10 | SELPLG | 0.47 | TTGGACATCTCTAGTGTAGCTGCCA |
| 9 | SEG31L2 | 0.36 | TGGACCCCACTGGCTGAGAATCTGG |
| 10 | CD3Z | 0.5 | TTGGACATCTCTAGTGTAGCTGCCA |
| 2 | PRKCQ | 0.56 | GCCGCACTGGACAACACTGATTCCT |
| 16 | SH2D1A | 0.33 | TCCTCCATCACCTGAAACACTGGAC |
| 3 | GZMB | 0.39 | TGCCTGCTCCTGTACTTGTCCTCAG |
| 3 | CD1A | 0.55 | TGCCTGCTCCTGTACTTGTCCTCAG |
| 11 | SCN3A | 0.64 | CACCCAGCTGGTCCTGTGGATGGGA |
| 11 | LAIR1 | 0.32 | CACCCAGCTGGTCCTGTGGATGGGA |
| 10 | FYB | 0.49 | TTGGACATCTCTAGTGTAGCTGCCA |
| 10 | TRB@ | 0.37 | TTGGACATCTCTAGTGTAGCTGCCA |
| 2 | SEPT6 | 0.32 | GCCCCACTGGACAACACTGATTCCT |
| 2 | HA-1 | 0.48 | GCCCCACTGGACAACACTGATTCCT |
| 10 | DOCK2 | 0.33 | TTGGACATCTCTAGTGTAGCTGCCA |
| 4 | CG018 | 0.37 | AAATGTTTCCTTGTGCCTGCTCCTG |
| 16 | CD3D | 0.32 | TCCTCCATCACCTGAAACACTGGAC |
| 3 | T3JAM | 0.41 | TGCCTGCTCCTGTACTTGTCCTCAG |
| 1 | FNBP1 | 0.36 | TCCTGTACTTGTCCTCAGCTTGGGC |
| 6 | CD6 | 0.36 | AAGCCTATACGTTTCTGTGGAGTAA |
| 9 | ZAP70 | 0.36 | TGGACCCCACTGGCTGAGAATCTGG |
| 7 | LST1 | 0.31 | ACTTGTCCTCAGCTTGGGCTTCTTC |
| 10 | GPR65 | 0.42 | TTGGACATCTCTAGTGTAGCTGCCA |
| 2 | PRF1 | 0.41 | GCCCCACTGGACAACACTGATTCCT |
| 2 | AIF1 | 0.32 | GCCCCACTGGACAACACTGATTCCT |
| 16 | FLJ20331 | 0.42 | TCCTCCATCACCTGAAACACTGGAC |
| 11 | RAG2 | 0.31 | CACCCAGCTGGTCCTGTGGATGGGA |
| 1 | WDR45 | 0.37 | TCCTGTACTTGTCCTCAGCTTGGGC |
| 1 | CD1E | 0.31 | TCCTGTACTTGTCCTCAGCTTGGGC |
| 16 | CYFIP2 | 0.4 | TCCTCCATCACCTGAAACACTGGAC |
| 11 | TARP | 0.36 | CACCCAGCTGGTCCTGTGGATGGGA |
| 7 | TRIM | 0.31 | ACTTGTCCTCAGCTTGGGCTTCTTC |
| 10 | RPL10L | 0.3 | TTGGACATCTCTAGTGTAGCTGCCA |
| 11 | GLTSCR2 | 0.46 | CACCCAGCTGGTCCTGTGGATGGGA |
| 6 | GIMAP5 | 0.32 | AAGCCTATACGTTTCTGTGGAGTAA |
| 3 | ARHGAP15 | 0.36 | TGCCTGCTCCTGTACTTGTCCTCAG |
| 2 | NOTCH1 | 0.34 | GCCCCACTGGACAACACTGATTCCT |
| 9 | BIN2 | 0.36 | TGGACCCCACTGGCTGAGAATCTGG |
| 24 | C13orf18 | 0.34 | TCCTTGTGCCTGCTCCTGTACTTGT |

TABLE 46-continued

Melphalan biomarkers.

| SEQ ID NO | Gene | Correlation | Medianprobe |
|---|---|---|---|
| 1 | CECR1 | 0.32 | TCCTGTACTTGTCCTCAGCTTGGGC |
| 24 | BCL11B | 0.32 | TCCTTGTGCCTGCTCCTGTACTTGT |
| 24 | GIMAP6 | 0.3 | TCCTTGTGCCTGCTCCTGTACTTGT |
| 10 | STAG3 | 0.58 | TTGGACATCTCTAGTGTAGCTGCCA |
| 1 | TM6SF1 | 0.31 | TCCTGTACTTGTCCTCAGCTTGGGC |
| 2 | HSD17B7 | 0.32 | GCCCCACTGGACAACACTGATTCCT |
| 7 | UBASH3A | 0.3 | ACTTGTCCTCAGCTTGGGCTTCTTC |
| 16 | MGC5566 | 0.45 | TCCTCCATCACCTGAAACACTGGAC |
| 6 | FLJ22457 | 0.39 | AAGCCTATACGTTTCTGTGGAGTAA |
| 3 | TPK1 | 0.33 | TGCCTGCTCCTGTACTTGTCCTCAG |
| 4 | PHF11 | 0.3 | AAATGTTTCCTTGTGCCTGCTCCTG |
| 24 | DKFZP434B0335 | 0.4 | TCCTTGTGCCTGCTCCTGTACTTGT |

TABLE 47

IL4-PR38 fusion protein biomarkers.

| SEQ ID NO | Gene | Correlation | Medianprobe |
|---|---|---|---|
| 16 | MCL1 | 0.3 | TCCTGCATCACCTGAAACACTGGAC |
| 11 | DDX23 | 0.35 | CACCCAGCTGGTCCTGTGGATGGGA |
| 3 | JUNB | 0.31 | TGCCTGCTCCTGTACTTGTCCTCAG |
| 11 | ZFP36 | 0.33 | CACCCAGCTGGTCCTGTGGATGGGA |
| 7 | IFITM1 | 0.32 | ACTTGTCCTCAGCTTGGGCTTCTTC |
| 9 | CKS1B | 0.3 | TGGACCCCACTGGCTGAGAATCTGG |
| 2 | SERPINA1 | 0.31 | GCCCCACTGGACAACACTGATTCCT |
| 7 | IL4R | 0.3 | ACTTGTCCTCAGCTTGGGCTTCTTC |
| 7 | CLDN3 | 0.31 | ACTTGTCCTCAGCTTGGGCTTCTTC |
| 4 | ARL4A | 0.33 | AAATGTTTCCTTGTGCCTGCTCCTG |
| 24 | HMMR | 0.31 | TCCTTGTGCCTGCTCCTGTACTTGT |
| 24 | FLJ12671 | 0.42 | TCCTTGTGCCTGCTCCTGTACTTGT |
| 2 | ANKHD1 | 0.42 | GCCCCACTGGACAACACTGATTCCT |
| 7 | KIF2C | 0.37 | ACTTGTCCTCAGCTTGGGCTTCTTC |
| 11 | RPA3 | 0.34 | CACCCAGCTGGTCCTGTGGATGGGA |
| 3 | MCCC2 | 0.34 | TGCCTGCTCCTGTACTTGTCCTCAG |
| 24 | CDH17 | 0.32 | TCCTTGTGCCTGCTCCTGTACTTGT |
| 10 | LSM5 | 0.33 | TTGGACATCTCTAGTGTAGCTGCCA |
| 2 | PRF1 | 0.32 | GCCCCACTGGACAACACTGATTCCT |

TABLE 47-continued

IL4-PR38 fusion protein biomarkers.

| SEQ ID NO | Gene | Correlation | Medianprobe |
|---|---|---|---|
| 16 | ROD1 | 0.34 | TCCTCCATCACCTGAAACACTGGAC |
| 16 | FLJ12666 | 0.37 | TCCTCCATCACCTGAAACACTGGAC |
| 10 | SUV420H1 | 0.31 | TTGGACATCTCTAGTGTAGCTGCCA |
| 16 | MUC13 | 0.36 | TCCTCCATCACCTGAAACACTGGAC |
| 2 | C13orf18 | 0.35 | GCCCCACTGGACAACACTGATTCCT |
| 3 | CDCA8 | 0.35 | TGCCTGCTCCTGTACTTGTCCTCAG |

TABLE 48

Valproic acid (VPA) biomarkers.

| SEQ ID NO | Gene | Correlation | Medianprobe |
|---|---|---|---|
| 4 | STOM | 0.32 | AAATGTTTCCTTGTGCCTGCTCCTG |
| 9 | TNFAIP3 | 0.32 | TGGACCCCACTGGCTGAGAATCTGG |
| 2 | ASNS | 0.31 | GCCCCACTGGACAACACTGATTCCT |
| 3 | GARS | 0.37 | TGCCTGCTCCTGTACTTGTCCTCAG |
| 6 | CXCR4 | 0.32 | AAGCCTATACGTTTCTGTGGAGTAA |
| 9 | EGLN3 | 0.31 | TGGACCCCACTGGCTGAGAATCTGG |
| 1 | LBH | 0.35 | TCCTGTACTTGTCCTCAGCTTGGGC |
| 3 | GDF15 | 0.3 | TGCCTGCTCCTGTACTTGTCCTCAG |

TABLE 49

All-trans retinoic acid (ATRA) biomarkers.

| SEQ ID NO | Gene | Correlation | Medianprobe |
|---|---|---|---|
| 6 | PPIB | 0.31 | AAGCCTATACGTTTCTGTGGAGTAA |
| 6 | ZFP36L2 | 0.48 | AAGCCTATACGTTTCTGTGGAGTAA |
| 7 | IFI30 | 0.46 | ACTTGTCCTCAGCTTGGGCTTCTTC |
| 16 | USP7 | 0.35 | TCCTCCATCACCTGAAACACTGGAC |
| 16 | SRM | 0.43 | TCCTCCATCACCTGAAACACTGGAC |
| 3 | SH3BP5 | 0.32 | TGCCTGCTCCTGTACTTGTCCTCAG |
| 10 | ALDOC | 0.41 | TTGGACATCTCTAGTGTAGCTGCCA |
| 7 | FADS2 | 0.33 | ACTTGTCCTCAGCTTGGGCTTCTTC |
| 10 | GUSB | 0.38 | TTGGACATCTCTAGTGTAGCTGCCA |
| 1 | PSCD1 | 0.48 | TCCTGTACTTGTCCTCAGCTTGGGC |
| 1 | IQGAP2 | 0.34 | TCCTGTACTTGTCCTCAGCTTGGGC |
| 2 | STS | 0.34 | GCCCCACTGGACAACACTGATTCCT |
| 9 | MFNG | 0.36 | TGGACCCCACTGGCTGAGAATCTGG |

TABLE 49-continued

All-trans retinoic acid (ATRA) biomarkers.

| SEQ ID NO | Gene | Correlation | Medianprobe |
|---|---|---|---|
| 7 | FLI1 | 0.33 | ACTTGTCCTCAGCTTGGGCTTCTTC |
| 9 | PIM2 | 0.35 | TGGACCCCACTGGCTGAGAATCTGG |
| 1 | INPP4A | 0.54 | TCCTGTACTTGTCCTCAGCTTGGGC |
| 2 | LRMP | 0.51 | GCCCCACTGGACAACACTGATTCCT |
| 4 | ICAM2 | 0.3 | AAATGTTTCCTTGTGCCTGCTCCTG |
| 11 | EVI2A | 0.33 | CACCCAGCTGGTCCTGTGGATGGGA |
| 4 | MAL | 0.46 | AAATGTTTCCTTGTGCCTGCTCCTG |
| 10 | BTN3A3 | 0.43 | TTGGACATCTCTAGTGTAGCTGCCA |
| 10 | PTPN7 | 0.4 | TTGGACATCTCTAGTGTAGCTGCCA |
| 10 | IL10RA | 0.42 | TTGGACATCTCTAGTGTAGCTGCCA |
| 6 | SPI1 | 0.41 | AAGCCTATACGTTTCTGTGGAGTAA |
| 3 | TRAF1 | 0.3 | TGCCTGCTCCTGTACTTGTCCTCAG |
| 24 | ITGB7 | 0.33 | TCCTTGTGCCTGCTCCTGTACTTGT |
| 9 | ARHGAP6 | 0.32 | TGGACCCCACTGGCTGAGAATCTGG |
| 2 | MAP4K1 | 0.52 | GCCCCACTGGACAACACTGATTCCT |
| 6 | CD28 | 0.34 | AAGCCTATACGTTTCTGTGGAGTAA |
| 16 | PTP4A3 | 0.3 | TCCTCCATCACCTGAAACACTGGAC |
| 7 | LTB | 0.32 | ACTTGTCCTCAGCTTGGGCTTCTTC |
| 3 | C1orf38 | 0.4 | TGCCTGCTCCTGTACTTGTCCTCAG |
| 16 | WBSCR22 | 0.53 | TCCTCCATCACCTGAAACACTGGAC |
| 16 | CD8B1 | 0.35 | TCCTCCATCACCTGAAACACTGGAC |
| 7 | LCP1 | 0.35 | ACTTGTCCTCAGCTTGGGCTTCTTC |
| 16 | FLJ13052 | 0.31 | TCCTCCATCACCTGAAACACTGGAC |
| 10 | MEF2C | 0.71 | TTGGACATCTCTAGTGTAGCTGCCA |
| 4 | PSCDBP | 0.41 | AAATGTTTCCTTGTGCCTGCTCCTG |
| 9 | IL16 | 0.51 | TGGACCCCACTGGCTGAGAATCTGG |
| 3 | SELPLG | 0.53 | TGCCTGCTCCTGTACTTGTCCTCAG |
| 4 | MAGEA9 | 0.6 | AAATGTTTCCTTGTGCCTGCTCCTG |
| 16 | LAIR1 | 0.43 | TCCTCCATCACCTGAAACACTGGAC |
| 16 | TNFRSF25 | 0.53 | TCCTCCATCACCTGAAACACTGGAC |
| 7 | EVI2B | 0.42 | ACTTGTCCTCAGCTTGGGCTTCTTC |
| 24 | IGJ | 0.37 | TCCTTGTGCCTGCTCCTGTACTTGT |
| 4 | PDCD4 | 0.47 | AAATGTTTCCTTGTGCCTGCTCCTG |
| 11 | RASA4 | 0.52 | CACCCAGCTGGTCCTGTGGATGGGA |
| 6 | HA-1 | 0.73 | AAGCCTATACGTTTCTGTGGAGTAA |
| 1 | PLCL2 | 0.47 | TCCTGTACTTGTCCTCAGCTTGGGC |
| 6 | RNASE6 | 0.31 | AAGCCTATACGTTTCTGTGGAGTAA |
| 10 | WBSCR20C | 0.35 | TTGGACATCTCTAGTGTAGCTGCCA |
| 6 | NUP210 | 0.36 | AAGCCTATACGTTTCTGTGGAGTAA |
| 7 | RPL10L | 0.39 | ACTTGTCCTCAGCTTGGGCTTCTTC |
| 9 | C11orf2 | 0.33 | TGGACCCCACTGGCTGAGAATCTGG |
| 3 | CABC1 | 0.32 | TGCCTGCTCCTGTACTTGTCCTCAG |
| 1 | ARHGEF3 | 0.37 | TCCTGTACTTGTCCTCAGCTTGGGC |
| 3 | TAPBPL | 0.42 | TGCCTGCTCCTGTACTTGTCCTCAG |
| 4 | CHST12 | 0.35 | AAATGTTTCCTTGTGCCTGCTCCTG |
| 3 | FKBP11 | 0.54 | TGCCTGCTCCTGTACTTGTCCTCAG |
| 10 | FLJ35036 | 0.42 | TTGGACATCTCTAGTGTAGCTGCCA |
| 11 | MYLIP | 0.38 | CACCCAGCTGGTCCTGTGGATGGGA |
| 7 | TXNDC5 | 0.31 | ACTTGTCCTCAGCTTGGGCTTGTTC |
| 16 | PACAP | 0.3 | TCCTCCATCACCTGAAACACTGGAC |
| 1 | TOSO | 0.34 | TCCTGTACTTGTCCTCAGCTTGGGC |
| 9 | PNAS-4 | 0.37 | TGGACCCCACTGGCTGAGAATCTGG |
| 6 | IL21R | 0.57 | AAGCCTATACGTTTCTGTGGAGTAA |
| 24 | TCF4 | 0.64 | TCCTTGTGCCTGCTCCTGTACTTGT |

TABLE 50

Cytoxan biomarkers.

| SEQ ID NO | Gene | Correlation | Medianprobe |
|---|---|---|---|
| 6 | C6orf29 | 0.31 | AAGCCTATACGTTTCTGTGGAGTAA |
| 4 | TRIM31 | 0.31 | AAATGTTTCCTTGTGCCTGCTCCTG |
| 2 | CD69 | 0.37 | GCCCCACTGGACAACACTGATTCCT |
| 7 | LRRN3 | 0.31 | ACTTGTCCTCAGCTTGGGCTTCTTC |
| 16 | GPR35 | 0.41 | TCCTCCATCACCTGAAACACTGGAC |
| 10 | CDW52 | 0.48 | TTGGACATCTCTAGTGTAGCTGCCA |

TABLE 51

Topotecan (Hycamtin) biomarkers.

| SEQ ID NO | Gene | Correlation | Medianprobe |
|---|---|---|---|
| 6 | K-ALPHA-1 | 0.32 | AAGCCTATACGTTTCTGTGGAGTAA |
| 6 | CSDA | 0.32 | AAGCCTATACGTTTCTGTGGAGTAA |
| 10 | UCHL1 | 0.32 | TTGGACATCTCTAGTGTAGCTGCCA |

TABLE 51-continued

Topotecan (Hycamtin) biomarkers.

| SEQ ID NO | Gene | Correlation | Medianprobe |
|---|---|---|---|
| 16 | NAP1L1 | 0.3 | TCCTCCATCACCTGAAACACTGGAC |
| 1 | ATP5G2 | 0.3 | TCCTGTACTTGTCCTCAGCTTGGGC |
| 6 | HDGFRP3 | 0.3 | AAGCCTATACGTTTCTGTGGAGTAA |
| 2 | IFI44 | 0.3 | GCCCCACTGGACAACACTGATTCCT |

TABLE 52

Suberoylanilide hydroxamic acid (SAHA, vorinostat, Zolinza) biomarkers.

| SEQ ID NO | Gene | Correlation | Medianprobe |
|---|---|---|---|
| 24 | NOL5A | 0.35 | TCCTTGTGCCTGCTCCTGTACTTGT |
| 3 | STOM | 0.35 | TGCCTGCTCCTGTACTTGTCCTCAG |
| 4 | SIAT1 | 0.36 | AAATGTTTCCTTGTGCCTGCTCCTG |
| 2 | CUGBP2 | 0.39 | GCCCCACTGGACAACACTGATTCCT |
| 9 | GUSB | 0.33 | TGGACCCCACTGGCTGAGAATCTGG |
| 24 | ITM2A | 0.34 | TCCTTGTGCCTGCTCCTGTACTTGT |
| 7 | JARID2 | 0.32 | ACTTGTCCTCAGCTTGGGCTTCTTC |
| 11 | RUNX3 | 0.32 | CACCCAGCTGGTCCTGTGGATGGGA |
| 3 | ICAM2 | 0.35 | TGCCTGCTCCTGTACTTGTCCTCAG |
| 6 | PTPN7 | 0.37 | AAGCCTATACGTTTCTGTGGAGTAA |
| 10 | VAV1 | 0.35 | TTGGACATCTCTAGTGTAGCTGCCA |
| 6 | PTP4A3 | 0.42 | AAGCCTATACGTTTCTGTGGAGTAA |
| 7 | MCAM | 0.35 | ACTTGTCCTCAGCTTGGGCTTCTTC |
| 7 | MEF2C | 0.32 | ACTTGTCCTCAGCTTGGGCTTCTTC |
| 3 | IDH3B | 0.3 | TGCCTGCTCCTGTACTTGTCCTCAG |
| 16 | RFP | 0.31 | TCCTCCATCACCTGAAACACTGGAC |
| 1 | SEPT6 | 0.31 | TCCTGTACTTGTCCTCAGCTTGGGC |
| 2 | SLC43A3 | 0.34 | GCCCCACTGGACAACACTGATTCCT |
| 9 | WBSCR20C | 0.46 | TGGACCCCACTGGCTGAGAATCTGG |
| 1 | SHMT2 | 0.34 | TCCTGTACTTGTCCTCAGCTTGGGC |
| 1 | GLTSCR2 | 0.31 | TCCTGTACTTGTCCTCAGCTTGGGC |
| 1 | CABC1 | 0.33 | TCCTGTACTTGTCCTCAGCTTGGGC |
| 7 | FLJ20859 | 0.42 | ACTTGTCCTCAGCTTGGGCTTCTTC |
| 1 | FLJ20010 | 0.51 | TCCTGTACTTGTCCTCAGCTTGGGC |
| 24 | MGC10993 | 0.33 | TCCTTGTGCCTGCTCCTGTACTTGT |
| 16 | FKBP11 | 0.31 | TCCTCCATCACCTGAAACACTGGAC |

TABLE 53

Depsipeptide (FR901228) biomarkers.

| SEQ ID NO | Gene | Correlation | Medianprobe |
|---|---|---|---|
| 4 | ZFP36L2 | 0.32 | AAATGTTTCCTTGTGCCTGCTCCTG |
| 3 | TRIB2 | 0.35 | TGCCTGCTCCTGTACTTGTCCTCAG |
| 7 | LCP2 | 0.37 | ACTTGTCCTCAGCTTGGGCTTCTTC |
| 3 | C6orf32 | 0.35 | TGCCTGCTCCTGTACTTGTCCTCAG |
| 11 | IL16 | 0.34 | CACCCAGCTGGTCCTGTGGATGGGA |
| 6 | CACNA1G | 0.31 | AAGCCTATACGTTTCTGTGGAGTAA |
| 2 | SPDEF | 0.31 | GCCCCACTGGACAACACTGATTCCT |
| 16 | HAB1 | 0.39 | TCCTCCATCACCTGAAACACTGGAC |
| 9 | TOSO | 0.31 | TGGACCCCACTGGCTGAGAATCTGG |
| 6 | ARHGAP25 | 0.33 | AAGCCTATACGTTTCTGTGGAGTAA |

TABLE 54

Bortezomib biomarkers.

| SEQ ID NO | Gene | Correlation | Medianprobe |
|---|---|---|---|
| 4 | PLEKHB2 | 0.32 | AAATGTTTCCTTGTGCCTGCTCCTG |
| 9 | ARPC1B | 0.32 | TGGACCCCACTGGCTGAGAATCTGG |
| 24 | MX1 | 0.39 | TCCTTGTGCCTGCTCCTGTACTTGT |
| 6 | CUGBP2 | 0.37 | AAGCCTATACGTTTCTGTGGAGTAA |
| 6 | IFI16 | 0.33 | AAGCCTATACGTTTCTGTGGAGTAA |
| 4 | TNFRSF14 | 0.3 | AAATGTTTCCTTGTGCCTGCTCCTG |
| 9 | SP110 | 0.39 | TGGACCCCACTGGCTGAGAATCTGG |
| 9 | ELF1 | 0.33 | TGGACCCCACTGGCTGAGAATCTGG |
| 1 | LPXN | 0.33 | TCCTGTACTTGTCCTCAGCTTGGGC |
| 1 | IFRG28 | 0.31 | TCCTGTACTTGTCCTCAGCTTGGGC |
| 2 | LEF1 | 0.33 | GCCCCACTGGACAACACTGATTCCT |
| 1 | PYCARD | 0.31 | TCCTGTACTTGTCCTCAGCTTGGGC |

TABLE 55

Leukeran biomarkers.

| SEQ ID NO | Gene | Correlation | Medianprobe |
|---|---|---|---|
| 2 | SSRP1 | 0.31 | GCCCCACTGGACAACACTGATTCCT |
| 4 | ALDOC | 0.36 | AAATGTTTCCTTGTGCCTGCTCCTG |
| 3 | C1QR1 | 0.31 | TGCCTGCTCCTGTACTTGTCCTCAG |
| 1 | TTF1 | 0.31 | TCCTGTACTTGTCCTCAGCTTGGGC |
| 2 | PRIM1 | 0.31 | GCCCCACTGGACAACACTGATTCCT |

TABLE 55-continued

Leukeran biomarkers.

| SEQ ID NO | Gene | Correlation | Medianprobe |
|---|---|---|---|
| 16 | USP34 | 0.38 | TCCTCCATCACCTGAAACACTGGAC |
| 1 | TK2 | 0.33 | TCCTGTACTTGTCCTCAGCTTGGGC |
| 3 | GOLGIN-67 | 0.31 | TGCCTGCTCCTGTACTTGTCCTCAG |
| 7 | NPD014 | 0.35 | ACTTGTCCTCAGCTTGGGCTTCTTC |
| 16 | KIAA0220 | 0.31 | TCCTCCATCACCTGAAACACTGGAC |
| 10 | SLC43A3 | 0.3 | TTGGACATCTCTAGTGTAGCTGCCA |
| 11 | WBSCR20C | 0.3 | CACCCAGCTGGTCCTGTGGATGGGA |
| 3 | ICAM2 | 0.3 | TGCCTGCTCCTGTACTTGTCCTCAG |
| 9 | TEX10 | 0.32 | TGGACCCCACTGGCTGAGAATCTGG |
| 7 | CHD7 | 0.3 | ACTTGTCCTCAGCTTGGGCTTCTTC |
| 10 | SAMSN1 | 0.34 | TTGGACATCTCTAGTGTAGCTGCCA |
| 7 | TPRT | 0.35 | ACTTGTCCTCAGCTTGGGCTTCTTC |

TABLE 56

Fludarabine biomarkers.

| SEQ ID NO | Gene | Correlation | Medianprobe |
|---|---|---|---|
| 7 | HLA-E | 0.3 | ACTTGTCCTCAGCTTGGGCTTCTTC |
| 3 | BAT3 | 0.34 | TGCCTGCTCCTGTACTTGTCCTCAG |
| 9 | ENO2 | 0.37 | TGGACCCCACTGGCTGAGAATCTGG |
| 1 | UBE2L6 | 0.3 | TCCTGTACTTGTCCTCAGCTTGGGC |
| 3 | CUGBP2 | 0.35 | TGCCTGCTCCTGTACTTGTCCTCAG |
| 2 | ITM2A | 0.32 | GCCCCACTGGACAACACTGATTCCT |
| 2 | PALM2-AKAP2 | 0.41 | GCCCCACTGGACAACACTGATTCCT |
| 2 | JARID2 | 0.33 | GCCCCACTGGACAACACTGATTCCT |
| 9 | DGKA | 0.33 | TGGACCCCACTGGCTGAGAATCTGG |
| 6 | SLC7A6 | 0.4 | AAGCCTATACGTTTCTGTGGAGTAA |
| 4 | TFDP2 | 0.35 | AAATGTTTCCTTGTGCCTGCTCCTG |
| 3 | ADA | 0.41 | TGCCTGCTCCTGTACTTGTCCTCAG |
| 3 | EDG1 | 0.33 | TGCCTGCTCCTGTACTTGTCCTCAG |
| 6 | ICAM2 | 0.46 | AAGCCTATACGTTTCTGTGGAGTAA |
| 16 | PTPN7 | 0.33 | TCCTCCATCACCTGAAACACTGGAC |
| 6 | CXorf9 | 0.35 | AAGCCTATACGTTTCTGTGGAGTAA |
| 11 | RHOH | 0.31 | CACCCAGCTGGTCCTGTGGATGGGA |
| 4 | MX2 | 0.32 | AAATGTTTCCTTGTGCCTGCTCCTG |
| 16 | ZNFN1A1 | 0.31 | TCCTCCATCACCTGAAACACTGGAC |

TABLE 56-continued

Fludarabine biomarkers.

| SEQ ID NO | Gene | Correlation | Medianprobe |
|---|---|---|---|
| 9 | COCH | 0.33 | TGGACCCCACTGGCTGAGAATCTGG |
| 9 | LCP2 | 0.34 | TGGACCCCACTGGCTGAGAATCTGG |
| 16 | CLGN | 0.31 | TCCTCCATCACCTGAAACACTGGAC |
| 2 | BNC1 | 0.38 | GCCCCACTGGACAACACTGATTCCT |
| 1 | FLNC | 0.3 | TCCTGTACTTGTCCTCAGCTTGGGC |
| 3 | HLA-DRB3 | 0.32 | TGCCTGCTCCTGTACTTGTCCTCAG |
| 9 | UCP2 | 0.34 | TGGACCCCACTGGCTGAGAATCTGG |
| 2 | HLA-DRB1 | 0.3 | GCCCCACTGGACAACACTGATTCCT |
| 24 | GATA3 | 0.37 | TCCTTGTGCCTGCTCCTGTACTTGT |
| 4 | PRKCQ | 0.39 | AAATGTTTCCTTGTGCCTGCTCCTG |
| 7 | SH2D1A | 0.37 | ACTTGTCCTCAGCTTGGGCTTCTTC |
| 7 | NFATC3 | 0.33 | ACTTGTCCTCAGCTTGGGCTTCTTC |
| 4 | TRB@ | 0.35 | AAATGTTTCCTTGTGCCTGCTCCTG |
| 16 | FNBP1 | 0.34 | TCCTCCATCACCTGAAACACTGGAC |
| 7 | SEPT6 | 0.33 | ACTTGTCCTCAGCTTGGGCTTCTTC |
| 6 | NME4 | 0.32 | AAGCCTATACGTTTCTGTGGAGTAA |
| 24 | DKFZP434C171 | 0.3 | TCCTTGTGCCTGCTCCTGTACTTGT |
| 1 | ZC3HAV1 | 0.32 | TCCTGTACTTGTCCTCAGCTTGGGC |
| 4 | SLC43A3 | 0.37 | AAATGTTTCCTTGTGCCTGCTCCTG |
| 4 | CD3D | 0.31 | AAATGTTTCCTTGTGCCTGCTCCTG |
| 16 | AIF1 | 0.35 | TCCTCCATCACCTGAAACACTGGAC |
| 16 | SPTAN1 | 0.34 | TCCTCCATCACCTGAAACACTGGAC |
| 24 | CD1E | 0.31 | TCCTTGTGCCTGCTCCTGTACTTGT |
| 6 | TRIM | 0.31 | AAGCCTATACGTTTCTGTGGAGTAA |
| 24 | DATF1 | 0.31 | TCCTTGTGCCTGCTCCTGTACTTGT |
| 1 | FHOD1 | 0.37 | TCCTGTACTTGTCCTCAGCTTGGGC |
| 11 | ARHGAP15 | 0.3 | CACCCAGCTGGTCCTGTGGATGGGA |
| 6 | STAG3 | 0.34 | AAGCCTATACGTTTCTGTGGAGTAA |
| 1 | SAP130 | 0.31 | TCCTGTACTTGTCCTCAGCTTGGGC |
| 7 | CYLD | 0.3 | ACTTGTCCTCAGCTTGGGCTTCTTC |

TABLE 57

Vinblastine biomarkers.

| SEQ ID NO | Gene | Correlation | Medianprobe |
|---|---|---|---|
| 7 | CD99 | 0.33 | ACTTGTCCTCAGCTTGGGCTTCTTC |

TABLE 58

Busulfan biomarkers.

| SEQ ID NO | Gene | Correlation | Medianprobe |
|---|---|---|---|
| 16 | RPLP2 | 0.37 | TCCTCCATCACCTGAAACACTGGAC |
| 7 | BTG1 | 0.36 | ACTTGTCCTCAGCTTGGGCTTCTTC |
| 3 | CSDA | 0.31 | TGCCTGCTCCTGTACTTGTCCTCAG |
| 6 | ARHGDIB | 0.38 | AAGCCTATACGTTTCTGTGGAGTAA |
| 16 | INSIG1 | 0.41 | TCCTCCATCACCTGAAACACTGGAC |
| 10 | ALDOC | 0.36 | TTGGACATCTCTAGTGTAGCTGCCA |
| 16 | WASPIP | 0.31 | TCCTCCATCACCTGAAACACTGGAC |
| 1 | C1QR1 | 0.46 | TCCTGTACTTGTCCTCAGCTTGGGC |
| 9 | EDEM1 | 0.36 | TGGACCCCACTGGCTGAGAATCTGG |
| 24 | SLA | 0.35 | TCCTTGTGCCTGCTCCTGTACTTGT |
| 24 | MFNG | 0.4 | TCCTTGTGCCTGCTCCTGTACTTGT |
| 2 | GPSM3 | 0.75 | GCCCCACTGGACAACACTGATTCCT |
| 7 | ADA | 0.53 | ACTTGTCCTCAGCTTGGGCTTCTTC |
| 1 | LRMP | 0.31 | TCCTGTACTTGTCCTCAGCTTGGGC |
| 16 | EVI2A | 0.52 | TCCTCCATCACCTGAAACACTGGAC |
| 7 | FMNL1 | 0.45 | ACTTGTCCTCAGCTTGGGCTTCTTC |
| 7 | PTPN7 | 0.3 | ACTTGTCCTCAGCTTGGGCTTCTTC |
| 7 | RHOH | 0.39 | ACTTGTCCTCAGCTTGGGCTTCTTC |
| 6 | ZNFN1A1 | 0.36 | AAGCCTATACGTTTCTGTGGAGTAA |
| 10 | CENTB1 | 0.33 | TTGGACATCTCTAGTGTAGCTGCCA |
| 9 | MAP4K1 | 0.31 | TGGACCCCACTGGCTGAGAATCTGG |
| 1 | CD28 | 0.51 | TCCTGTACTTGTCCTCAGCTTGGGC |
| 24 | SP110 | 0.38 | TCCTTGTGCCTGCTCCTGTACTTGT |
| 3 | NAP1L1 | 0.31 | TGCCTGCTCCTGTACTTGTCCTCAG |
| 16 | IFI16 | 0.35 | TCCTCCATCACCTGAAACACTGGAC |
| 4 | ARHGEF6 | 0.42 | AAATGTTTCCTTGTGCCTGCTCCTG |
| 1 | SELPLG | 0.45 | TCCTGTACTTGTCCTCAGCTTGGGC |
| 11 | CD3Z | 0.35 | CACCCAGCTGGTCCTGTGGATGGGA |
| 11 | SH2D1A | 0.38 | CACCCAGCTGGTCCTGTGGATGGGA |
| 3 | LAIR1 | 0.34 | TGCCTGCTCCTGTACTTGTCCTCAG |
| 2 | RAFTLIN | 0.36 | GCCCCACTGGACAACACTGATTCCT |
| 7 | HA-1 | 0.61 | ACTTGTCCTCAGCTTGGGCTTCTTC |
| 3 | DOCK2 | 0.4 | TGCCTGCTCCTGTACTTGTCCTCAG |
| 2 | CD3D | 0.31 | GCCCCACTGGACAACACTGATTCCT |
| 7 | T3JAM | 0.35 | ACTTGTCCTCAGCTTGGGCTTCTTC |
| 9 | ZAP70 | 0.36 | TGGACCCCACTGGCTGAGAATCTGG |
| 16 | GPR65 | 0.32 | TCCTCCATCACCTGAAACACTGGAC |
| 11 | CYFIP2 | 0.58 | CACCCAGCTGGTCCTGTGGATGGGA |
| 10 | LPXN | 0.34 | TTGGACATCTCTAGTGTAGCTGCCA |
| 1 | RPL10L | 0.41 | TCCTGTACTTGTCCTCAGCTTGGGC |
| 4 | GLTSCR2 | 0.33 | AAATGTTTCCTTGTGCCTGCTCCTG |
| 11 | ARHGAP15 | 0.47 | CACCCAGCTGGTCCTGTGGATGGGA |
| 3 | BCL11B | 0.31 | TGCCTGCTCCTGTACTTGTCCTCAG |
| 6 | TM6SF1 | 0.39 | AAGCCTATACGTTTCTGTGGAGTAA |
| 7 | PACAP | 0.33 | ACTTGTCCTCAGCTTGGGCTTCTTC |
| 9 | TCF4 | 0.32 | TGGACCCCACTGGCTGAGAATCTGG |

TABLE 59

Dacarbazine biomarkers.

| SEQ ID NO | Gene | Correlation | Medianprobe |
|---|---|---|---|
| 24 | ARHGDIB | 0.31 | TCCTTGTGCCTGCTCCTGTACTTGT |
| 16 | ITM2A | 0.4 | TCCTCCATCACCTGAAACACTGGAC |
| 11 | SSBP2 | 0.33 | CACCCAGCTGGTCCTGTGGATGGGA |
| 2 | PIM2 | 0.39 | GCCCCACTGGACAACACTGATTCCT |
| 2 | SELL | 0.31 | GCCCCACTGGACAACACTGATTCCT |
| 1 | ICAM2 | 0.43 | TCCTGTACTTGTCCTCAGCTTGGGC |
| 6 | EVI2A | 0.32 | AAGCCTATACGTTTCTGTGGAGTAA |
| 10 | MAL | 0.32 | TTGGACATCTCTAGTGTAGCTGCCA |
| 7 | PTPN7 | 0.34 | ACTTGTCCTCAGCTTGGGCTTCTTC |
| 24 | ZNFN1A1 | 0.32 | TCCTTGTGCCTGCTCCTGTACTTGT |
| 2 | LCP2 | 0.3 | GCCCCACTGGACAACACTGATTCCT |
| 9 | ARHGAP6 | 0.33 | TGGACCCCACTGGCTGAGAATCTGG |
| 7 | CD28 | 0.33 | ACTTGTCCTCAGCTTGGGCTTCTTC |
| 16 | CD8B1 | 0.32 | TCCTCCATCACCTGAAACACTGGAC |
| 24 | LCP1 | 0.34 | TCCTTGTGCCTGCTCCTGTACTTGT |
| 3 | NPD014 | 0.31 | TGCCTGCTCCTGTACTTGTCCTCAG |
| 6 | CD69 | 0.32 | AAGCCTATACGTTTCTGTGGAGTAA |
| 6 | NFATC3 | 0.32 | AAGCCTATACGTTTCTGTGGAGTAA |
| 4 | TRB@ | 0.32 | AAATGTTTCCTTGTGCCTGCTCCTG |
| 6 | IGJ | 0.33 | AAGCCTATACGTTTCTGTGGAGTAA |
| 10 | SLC43A3 | 0.3 | TTGGACATCTCTAGTGTAGCTGCCA |
| 16 | DOCK2 | 0.36 | TCCTCCATCACCTGAAACACTGGAC |
| 9 | FHOD1 | 0.33 | TGGACCCCACTGGCTGAGAATCTGG |
| 6 | PACAP | 0.31 | AAGCCTATACGTTTCTGTGGAGTAA |

TABLE 60

Oxaliplatin biomarkers.

| SEQ ID NO | Gene | Correlation | Medianprobe |
|---|---|---|---|
| 10 | RPL18 | 0.38 | TTGGACATCTCTAGTGTAGCTGCCA |
| 4 | RPL10A | 0.32 | AAATGTTTCCTTGTGCCTGCTCCTG |
| 9 | RPS3A | 0.34 | TGGACCCCACTGGCTGAGAATCTGG |
| 11 | EEF1B2 | 0.39 | CACCCAGCTGGTCCTGTGGATGGGA |
| 6 | GOT2 | 0.32 | AAGCCTATACGTTTCTGTGGAGTAA |
| 4 | RPL13A | 0.33 | AAATGTTTCCTTGTGCCTGCTCCTG |
| 2 | RPS15 | 0.41 | GCCCCACTGGACAACACTGATTCCT |
| 3 | NOL5A | 0.37 | TGCCTGCTCCTGTACTTGTCCTCAG |
| 3 | RPLP2 | 0.36 | TGCCTGCTCCTGTACTTGTCCTCAG |
| 9 | SLC9A3R1 | 0.43 | TGGACCCCACTGGCTGAGAATCTGG |
| 2 | E1F3S3 | 0.43 | GCCCCACTGGACAACACTGATTCCT |
| 3 | MTHFD2 | 0.33 | TGCCTGCTCCTGTACTTGTCCTCAG |
| 7 | IMPDH2 | 0.34 | ACTTGTCCTCAGCTTGGGCTTCTTC |
| 3 | ALDOC | 0.44 | TGCCTGCTCCTGTACTTGTCCTCAG |
| 11 | FABP5 | 0.33 | CACCCAGCTGGTCCTGTGGATGGGA |
| 24 | ITM2A | 0.35 | TCCTTGTGCCTGCTCCTGTACTTGT |
| 7 | PCK2 | 0.36 | ACTTGTCCTCAGCTTGGGCTTCTTC |
| 2 | MFNG | 0.33 | GCCCCACTGGACAACACTGATTCCT |
| 9 | GCH1 | 0.37 | TGGACCCCACTGGCTGAGAATCTGG |
| 11 | PIM2 | 0.39 | CACCCAGCTGGTCCTGTGGATGGGA |
| 24 | ADA | 0.32 | TCCTTGTGCCTGCTCCTGTACTTGT |
| 16 | ICAM2 | 0.31 | TCCTCCATCACCTGAAACACTGGAC |
| 10 | TTF1 | 0.47 | TTGGACATCTCTAGTGTAGCTGCCA |
| 3 | MYB | 0.36 | TGCCTGCTCCTGTACTTGTCCTCAG |
| 11 | PTPN7 | 0.37 | CACCCAGCTGGTCCTGTGGATGGGA |
| 16 | RHOH | 0.42 | TCCTCCATCACCTGAAACACTGGAC |
| 7 | ZNFN1A1 | 0.39 | ACTTGTCCTCAGCTTGGGCTTCTTC |
| 24 | PRIM1 | 0.36 | TCCTTGTGCCTGCTCCTGTACTTGT |
| 16 | FHIT | 0.48 | TCCTCCATCACCTGAAACACTGGAC |
| 9 | ASS | 0.45 | TGGACCCCACTGGCTGAGAATCTGG |
| 3 | SYK | 0.31 | TGCCTGCTCCTGTACTTGTCCTCAG |
| 10 | OXA1L | 0.32 | TTGGACATCTCTAGTGTAGCTGCCA |
| 3 | LCP1 | 0.31 | TGCCTGCTCCTGTACTTGTCCTCAG |
| 6 | DDX18 | 0.32 | AAGCCTATACGTTTCTGTGGAGTAA |
| 4 | NOLA2 | 0.35 | AAATGTTTCCTTGTGCCTGCTCCTG |
| 16 | KIAA0922 | 0.41 | TCCTCCATCACCTGAAACACTGGAC |
| 24 | PRKCQ | 0.34 | TCCTTGTGCCTGCTCCTGTACTTGT |
| 1 | NFATC3 | 0.32 | TCCTGTACTTGTCCTCAGCTTGGGC |
| 16 | ANAPC5 | 0.34 | TCCTCCATCACCTGAAACACTGGAC |
| 9 | TRB@ | 0.4 | TGGACCCCACTGGCTGAGAATCTGG |
| 24 | CXCR4 | 0.32 | TCCTTGTGCCTGCTCCTGTACTTGT |
| 1 | FNBP4 | 0.3 | TCCTGTACTTGTCCTCAGCTTGGGC |
| 10 | SEPT6 | 0.53 | TTGGACATCTCTAGTGTAGCTGCCA |
| 16 | RPS2 | 0.35 | TCCTCCATCACCTGAAACACTGGAC |
| 7 | MDN1 | 0.41 | ACTTGTCCTCAGCTTGGGCTTCTTC |
| 6 | PCCB | 0.32 | AAGCCTATACGTTTCTGTGGAGTAA |
| 9 | RASA4 | 0.33 | TGGACCCCACTGGCTGAGAATCTGG |
| 11 | WBSCR20C | 0.31 | CACCCAGCTGGTCCTGTGGATGGGA |
| 10 | SFRS7 | 0.32 | TTGGACATCTCTAGTGTAGCTGCCA |
| 3 | WBSCR20A | 0.3 | TGCCTGCTCCTGTACTTGTCCTCAG |
| 9 | NUP210 | 0.43 | TGGACCCCACTGGCTGAGAATCTGG |
| 24 | SHMT2 | 0.36 | TCCTTGTGCCTGCTCCTGTACTTGT |
| 10 | RPLP0 | 0.33 | TTGGACATCTCTAGTGTAGCTGCCA |
| 11 | MAP4K1 | 0.31 | CACCCAGCTGGTCCTGTGGATGGGA |
| 16 | HNRPA1 | 0.37 | TCCTCCATCACCTGAAACACTGGAC |
| 2 | CYFIP2 | 0.3 | GCCCCACTGGACAACACTGATTCCT |
| 16 | RPL10L | 0.32 | TCGTCCATCACCTGAAACACTGGAC |
| 9 | GLTSCR2 | 0.39 | TGGACCCCACTGGCTGAGAATCTGG |
| 1 | MRPL16 | 0.38 | TCCTGTACTTGTCCTCAGCTTGGGC |
| 2 | MRPS2 | 0.34 | GCCCCACTGGACAACACTGATTCCT |
| 6 | FLJ12270 | 0.31 | AAGCCTATACGTTTCTGTGGAGTAA |
| 10 | CDK5RAP3 | 0.32 | TTGGACATCTCTAGTGTAGCTGCCA |
| 1 | ARHGAP15 | 0.32 | TCCTGTACTTGTCCTCAGCTTGGGC |
| 24 | CUTC | 0.33 | TCCTTGTGCCTGCTCCTGTACTTGT |
| 7 | FKBP11 | 0.32 | ACTTGTCCTCAGCTTGGGCTTCTTC |
| 6 | ADPGK | 0.41 | AAGCCTATACGTTTCTGTGGAGTAA |
| 2 | FLJ22457 | 0.32 | GCCCCACTGGACAACACTGATTCCT |
| 24 | PUS3 | 0.31 | TCCTTGTGCCTGCTCCTGTACTTGT |
| 3 | PACAP | 0.36 | TGCCTGCTCCTGTACTTGTCCTCAG |
| 1 | CALML4 | 0.31 | TCCTGTACTTGTCCTCAGCTTGGGC |

TABLE 61

Hydroxyurea biomarkers.

| SEQ ID NO | Gene | Correlation | Medianprobe |
|---|---|---|---|
| 16 | CSDA | 0.31 | TCCTCCATCACCTGAAACACTGGAC |
| 6 | INSIG1 | 0.38 | AAGCCTATACGTTTCTGTGGAGTAA |
| 11 | UBE2L6 | 0.33 | CACCCAGCTGGTCCTGTGGATGGGA |
| 2 | PRG1 | 0.36 | GCCCCACTGGACAACACTGATTCCT |
| 7 | ITM2A | 0.3 | ACTTGTCCTCAGCTTGGGCTTCTTC |
| 11 | DGKA | 0.31 | CACCCAGCTGGTCCTGTGGATGGGA |
| 11 | SLA | 0.47 | CACCCAGCTGGTCCTGTGGATGGGA |
| 9 | PCBP2 | 0.51 | TGGACCCCACTGGCTGAGAATCTGG |
| 7 | IL2RG | 0.42 | ACTTGTCCTCAGCTTGGGCTTCTTC |
| 6 | ALOX5AP | 0.31 | AAGCCTATACGTTTCTGTGGAGTAA |
| 2 | PSMB9 | 0.33 | GCCCCACTGGACAACACTGATTCCT |
| 10 | LRMP | 0.36 | TTGGACATCTCTAGTGTAGCTGCCA |
| 9 | ICAM2 | 0.31 | TGGACCCCACTGGCTGAGAATCTGG |
| 16 | PTPN7 | 0.36 | TCCTCCATCACCTGAAACACTGGAC |
| 24 | CXorf9 | 0.38 | TCCTTGTGCCTGCTCCTGTACTTGT |
| 3 | RHOH | 0.41 | TGCCTGCTCCTGTACTTGTCCTCAG |
| 4 | ZNFN1A1 | 0.31 | AAATGTTTCCTTGTGCCTGCTCCTG |
| 10 | CENTB1 | 0.36 | TTGGACATCTCTAGTGTAGCTGCCA |
| 11 | LCP2 | 0.37 | CACCCAGCTGGTCCTGTGGATGGGA |
| 2 | STAT4 | 0.32 | GCCCCACTGGACAACACTGATTCCT |
| 24 | CCR7 | 0.31 | TCCTTGTGCCTGCTCCTGTACTTGT |
| 4 | CD3G | 0.33 | AAATGTTTCCTTGTGCCTGCTCCTG |
| 1 | SP110 | 0.32 | TCCTGTACTTGTCCTCAGCTTGGGC |
| 16 | TNFAIP8 | 0.31 | TCCTCCATCACCTGAAACACTGGAC |
| 9 | IFI16 | 0.4 | TGGACCCCACTGGCTGAGAATCTGG |
| 7 | CXCR4 | 0.37 | ACTTGTCCTCAGCTTGGGCTTCTTC |
| 10 | ARHGEF6 | 0.37 | TTGGACATCTCTAGTGTAGCTGCCA |
| 16 | SELPLG | 0.3 | TCCTCCATCACCTGAAACACTGGAC |
| 16 | CD3Z | 0.38 | TCCTCCATCACCTGAAACACTGGAC |
| 3 | PRKCQ | 0.3 | TGCCTGCTCCTGTACTTGTCCTCAG |
| 24 | SH2D1A | 0.3 | TCCTTGTGCCTGCTCCTGTACTTGT |
| 10 | CD1A | 0.31 | TTGGACATCTCTAGTGTAGCTGCCA |
| 9 | NFATC3 | 0.33 | TGGACCCCACTGGCTGAGAATCTGG |
| 16 | LAIR1 | 0.34 | TCCTCCATCACCTGAAACACTGGAC |
| 11 | TRB@ | 0.3 | CACCCAGCTGGTCCTGTGGATGGGA |
| 11 | SEPT6 | 0.34 | CAGCCAGCTGGTCCTGTGGATGGGA |
| 24 | RAFTLIN | 0.3 | TCCTTGTGCCTGCTCCTGTACTTGT |
| 9 | DOCK2 | 0.32 | TGGACCCCACTGGCTGAGAATCTGG |
| 3 | CD3D | 0.37 | TGCCTGCTCCTGTACTTGTCCTCAG |
| 6 | CD6 | 0.42 | AAGCCTATACGTTTCTGTGGAGTAA |
| 3 | AIF1 | 0.4 | TGCCTGCTCCTGTACTTGTCCTCAG |
| 2 | CD1E | 0.41 | GCCCCACTGGACAACACTGATTCCT |
| 1 | CYFIP2 | 0.35 | TCCTGTACTTGTCCTCAGCTTGGGC |
| 4 | TARP | 0.38 | AAATGTTTCCTTGTGCCTGCTCCTG |
| 6 | ADA | 0.33 | AAGCCTATACGTTTCTGTGGAGTAA |
| 9 | ARHGAP15 | 0.32 | TGGACCCCACTGGCTGAGAATCTGG |
| 2 | GIMAP6 | 0.34 | GCCCCACTGGACAACACTGATTCCT |
| 7 | STAG3 | 0.31 | ACTTGTCCTCAGCTTGGGCTTCTTC |
| 6 | FLJ22457 | 0.31 | AAGCCTATACGTTTCTGTGGAGTAA |
| 6 | PACAP | 0.35 | AAGCCTATACGTTTCTGTGGAGTAA |
| 1 | TCF4 | 0.4 | TCCTGTACTTGTCCTCAGCTTGGGC |

TABLE 62

Tegafur biomarkers.

| SEQ ID NO | Gene | Correlation | Medianprobe |
|---|---|---|---|
| 2 | RPL11 | 0.31 | GCCCCACTGGACAACACTGATTCCT |
| 3 | RPL17 | 0.38 | TGCCTGCTCCTGTACTTGTCCTCAG |
| 11 | ANAPC5 | 0.34 | CACCCAGCTGGTCCTGTGGATGGGA |
| 1 | RPL13A | 0.34 | TCCTGTACTTGTCCTCAGCTTGGGC |
| 16 | STOM | 0.37 | TCCTCCATCACCTGAAACACTGGAC |
| 2 | TUFM | 0.38 | GCCCCACTGGACAACACTGATTCCT |
| 1 | SCARB1 | 0.35 | TCCTGTACTTGTCCTCAGCTTGGGC |
| 11 | FABP5 | 0.33 | CACCCAGCTGGTCCTGTGGATGGGA |
| 24 | KIAA0711 | 0.35 | TCCTTGTGCCTGCTCCTGTACTTGT |
| 16 | ILGR | 0.33 | TCCTCCATCACCTGAAACACTGGAC |
| 4 | WBSCR22 | 0.3 | AAATGTTTCCTTGTGCCTGCTCCTG |
| 3 | UCK2 | 0.4 | TGCCTGCTCCTGTACTTGTCCTCAG |
| 6 | GZMB | 0.3 | AAGCCTATACGTTTCTGTGGAGTAA |
| 11 | C1orf38 | 0.32 | CACCCAGCTGGTCCTGTGGATGGGA |
| 1 | PCBP2 | 0.31 | TCCTGTACTTGTCCTCAGCTTGGGC |
| 3 | GPR65 | 0.44 | TGCCTGCTCCTGTACTTGTCCTCAG |
| 24 | GLTSCR2 | 0.38 | TCCTTGTGCCTGCTCCTGTACTTGT |
| 9 | FKBP11 | 0.38 | TGGACCCCACTGGCTGAGAATCTGG |

TABLE 63

Daunorubicin biomarkers.

| SEQ ID NO | Gene | Correlation | Medianprobe |
|---|---|---|---|
| 3 | ALDOC | 0.41 | TGCCTGCTCCTGTACTTGTCCTCAG |
| 2 | ITM2A | 0.32 | GCCCCACTGGACAACACTGATTCCT |
| 24 | SLA | 0.41 | TCCTTGTGCCTGCTCCTGTACTTGT |
| 24 | SSBP2 | 0.31 | TCCTTGTGCCTGCTCCTGTACTTGT |
| 9 | IL2RG | 0.31 | TGGACCCCACTGGCTGAGAATCTGG |
| 10 | MFNG | 0.47 | TTGGACATCTCTAGTGTAGCTGCCA |
| 16 | SELL | 0.33 | TCCTCCATCACCTGAAACACTGGAC |
| 4 | STC1 | 0.31 | AAATGTTTCCTTGTGCCTGCTCCTG |
| 6 | LRMP | 0.33 | AAGCCTATACGTTTCTGTGGAGTAA |
| 2 | MYB | 0.41 | GCCCCACTGGACAACACTGATTCCT |
| 4 | PTPN7 | 0.31 | AAATGTTTCCTTGTGCCTGCTCCTG |
| 9 | CXorf9 | 0.38 | TGGACCCCACTGGCTGAGAATCTGG |
| 4 | RHOH | 0.32 | AAATGTTTCCTTGTGCCTGCTCCTG |
| 11 | ZNFN1A1 | 0.36 | CACCCAGCTGGTCCTGTGGATGGGA |
| 9 | CENTB1 | 0.37 | TGGACCCCACTGGCTGAGAATCTGG |
| 9 | MAP4K1 | 0.32 | TGGACCCCACTGGCTGAGAATCTGG |
| 1 | CCR7 | 0.3 | TCCTGTACTTGTCCTCAGCTTGGGC |
| 4 | CD3G | 0.33 | AAATGTTTCCTTGTGCCTGCTCCTG |
| 9 | CCR9 | 0.33 | TGGACCCCACTGGCTGAGAATCTGG |
| 11 | CBFA2T3 | 0.31 | CACCCAGCTGGTCCTGTGGATGGGA |
| 4 | CXGR4 | 0.41 | AAATGTTTCCTTGTGCCTGCTCCTG |
| 1 | ARHGEF6 | 0.4 | TCCTGTACTTGTCCTCAGCTTGGGC |
| 24 | SELPLG | 0.45 | TCCTTGTGCCTGCTCCTGTACTTGT |
| 1 | SEC31L2 | 0.38 | TCCTGTACTTGTCCTCAGCTTGGGC |
| 11 | CD3Z | 0.33 | CACCCAGCTGGTCCTGTGGATGGGA |
| 1 | SH2D1A | 0.33 | TCCTGTACTTGTCCTCAGCTTGGGC |
| 9 | CD1A | 0.35 | TGGACCCCACTGGCTGAGAATCTGG |
| 11 | SCN3A | 0.33 | CACCCAGCTGGTCCTGTGGATGGGA |
| 3 | LAIR1 | 0.33 | TGCCTGCTCCTGTACTTGTCCTCAG |
| 4 | TRB@ | 0.3 | AAATGTTTCCTTGTGCCTGCTCCTG |
| 6 | DOCK2 | 0.35 | AAGCCTATACGTTTCTGTGGAGTAA |
| 11 | WBSCR20C | 0.38 | CACCCAGCTGGTCCTGTGGATGGGA |
| 3 | CD3D | 0.32 | TGCCTGCTCCTGTACTTGTCCTCAG |
| 11 | T3JAM | 0.34 | CACCCAGCTGGTCCTGTGGATGGGA |
| 7 | CD6 | 0.33 | ACTTGTCCTCAGCTTGGGCTTCTTC |
| 3 | ZAP70 | 0.32 | TGCCTGCTCCTGTACTTGTCCTCAG |
| 1 | GPR65 | 0.33 | TCCTGTACTTGTCCTCAGCTTGGGC |
| 2 | AIF1 | 0.3 | GCCCCACTGGACAACACTGATTCCT |
| 16 | WDR45 | 0.3 | TCCTCCATCACCTGAAACACTGGAC |
| 24 | CD1E | 0.3 | TCCTTGTGCCTGCTCCTGTACTTGT |
| 6 | CYFIP2 | 0.39 | AAGCCTATACGTTTCTGTGGAGTAA |
| 10 | TARP | 0.38 | TTGGACATCTCTAGTGTAGCTGCCA |
| 1 | TRIM | 0.34 | TCCTGTACTTGTCCTCAGCTTGGGC |
| 7 | ARHGAP15 | 0.37 | ACTTGTCCTCAGCTTGGGCTTCTTC |
| 6 | NOTCH1 | 0.39 | AAGCCTATACGTTTCTGTGGAGTAA |
| 6 | STAG3 | 0.35 | AAGCCTATACGTTTCTGTGGAGTAA |
| 3 | UBASH3A | 0.31 | TGCCTGCTCCTGTACTTGTCCTCAG |
| 3 | MGC5566 | 0.33 | TGCCTGCTCCTGTACTTGTCCTCAG |
| 24 | PACAP | 0.33 | TCCTTGTGCCTGCTCCTGTACTTGT |

TABLE 64

Bleomycin biomarkers.

| SEQ ID NO | Gene | Correlation | Medianprobe |
|---|---|---|---|
| 11 | PFN1 | 0.32 | CACCCAGCTGGTCCTGTGGATGGGA |
| 7 | CALU | 0.32 | ACTTGTCCTCAGCTTGGGCTTCTTC |
| 11 | ZYX | 0.34 | CACCCAGCTGGTCCTGTGGATGGGA |
| 2 | PSMD2 | 0.36 | GCCCCACTGGACAACACTGATTCCT |
| 1 | RAP1B | 0.32 | TCCTGTACTTGTCCTCAGCTTGGGC |
| 1 | EPAS1 | 0.35 | TCCTGTACTTGTCCTCAGCTTGGGC |
| 2 | PGAM1 | 0.36 | GCCCCACTGGACAACACTGATTCCT |
| 3 | STAT1 | 0.38 | TGCCTGCTCCTGTACTTGTCCTCAG |
| 2 | CKAP4 | 0.38 | GCCCCACTGGACAACACTGATTCCT |
| 1 | DUSP1 | 0.32 | TCCTGTACTTGTCCTCAGCTTGGGC |
| 16 | RCN1 | 0.32 | TCCTCCATCACCTGAAACACTGGAC |
| 9 | UCHL1 | 0.44 | TGGACCCCACTGGCTGAGAATCTGG |
| 4 | ITGA5 | 0.33 | AAATGTTTCCTTGTGCCTGCTCCTG |
| 3 | NFKBIA | 0.32 | TGCCTGCTCCTGTACTTGTCCTCAG |
| 2 | LAMB1 | 0.4 | GCCCCACTGGACAACACTGATTCCT |
| 10 | TGFBI | 0.37 | TTGGACATCTCTAGTGTAGCTGCCA |
| 2 | FHL1 | 0.31 | GCCCCACTGGACAACACTGATTCCT |
| 16 | GJA1 | 0.32 | TCCTCCATCACCTGAAACACTGGAC |
| 11 | PRG1 | 0.33 | CACCCAGCTGGTCCTGTGGATGGGA |
| 11 | EXT1 | 0.35 | CACCCAGCTGGTCCTGTGGATGGGA |

TABLE 64-continued

Bleomycin biomarkers.

| SEQ ID NO | Gene | Correlation | Medianprobe |
|---|---|---|---|
| 1 | MVP | 0.32 | TCCTGTACTTGTCCTCAGCTTGGGC |
| 9 | NNMT | 0.38 | TGGACCCCACTGGCTGAGAATCTGG |
| 16 | TAP1 | 0.37 | TCCTCCATCACCTGAAACACTGGAC |
| 9 | CRIM1 | 0.41 | TGGACCCCACTGGCTGAGAATCTGG |
| 2 | PLOD2 | 0.36 | GCCCCACTGGACAACACTGATTCCT |
| 1 | RPS19 | 0.34 | TCCTGTACTTGTCCTCAGCTTGGGC |
| 2 | AXL | 0.43 | GCCCCACTGGACAACACTGATTCCT |
| 16 | PALM2-AKAP2 | 0.42 | TCCTCCATCACCTGAAACACTGGAC |
| 1 | IL8 | 0.32 | TCCTGTACTTGTCCTCAGCTTGGGC |
| 3 | LOXL2 | 0.3 | TGCCTGCTCCTGTACTTGTCCTCAG |
| 11 | PAPSS2 | 0.31 | CACCCAGCTGGTCCTGTGGATGGGA |
| 24 | CAV1 | 0.31 | TCCTTGTGCCTGCTCCTGTACTTGT |
| 7 | F2R | 0.32 | ACTTGTCCTCAGCTTGGGCTTCTTC |
| 11 | PSMB9 | 0.38 | CACCCAGCTGGTCCTGTGGATGGGA |
| 9 | LOX | 0.36 | TGGACCCCACTGGCTGAGAATCTGG |
| 1 | C1orf29 | 0.36 | TCCTGTACTTGTCCTCAGCTTGGGC |
| 10 | STC1 | 0.32 | TTGGACATCTCTAGTGTAGCTGCCA |
| 24 | LIF | 0.34 | TCCTTGTGCCTGCTCCTGTACTTGT |
| 2 | KCNJ8 | 0.46 | GCCCCACTGGACAACACTGATTCCT |
| 3 | SMAD3 | 0.32 | TGCCTGCTCCTGTACTTGTCCTCAG |
| 4 | HPCAL1 | 0.45 | AAATGTTTCCTTGTGCCTGCTCCTG |
| 24 | WNT5A | 0.34 | TCCTTGTGCCTGCTCCTGTACTTGT |
| 3 | BDNF | 0.33 | TGCCTGCTCCTGTACTTGTCCTCAG |
| 1 | TNFRSF1A | 0.38 | TCCTGTACTTGTCCTCAGCTTGGGC |
| 11 | NCOR2 | 0.45 | CACCCAGCTGGTCCTGTGGATGGGA |
| 10 | FLNC | 0.44 | TTGGACATCTCTAGTGTAGCTGCCA |
| 4 | HMGA2 | 0.41 | AAATGTTTCCTTGTGCCTGCTCCTG |
| 6 | HLA-B | 0.42 | AAGCCTATACGTTTCTGTGGAGTAA |
| 4 | FLOT1 | 0.3 | AAATGTTTCCTTGTGCCTGCTCCTG |
| 11 | PTRF | 0.36 | CACCCAGCTGGTCCTGTGGATGGGA |
| 24 | IFI16 | 0.32 | TCCTTGTGCCTGCTCCTGTACTTGT |
| 16 | MGC4083 | 0.34 | TCCTCCATCACCTGAAACACTGGAC |
| 7 | TNFRSF10B | 0.4 | ACTTGTCCTCAGCTTGGGCTTCTTC |
| 1 | PNMA2 | 0.38 | TCCTGTACTTGTCCTCAGCTTGGGC |
| 24 | TFPI | 0.32 | TCCTTGTGCCTGCTCCTGTACTTGT |
| 3 | CLECSF2 | 0.33 | TGCCTGCTCCTGTACTTGTCCTCAG |
| 2 | SP110 | 0.34 | GCCCCACTGGACAACACTGATTCCT |
| 7 | PLAUR | 0.35 | ACTTGTCCTCAGCTTGGGCTTCTTC |
| 24 | ASPH | 0.42 | TCCTTGTGCCTGCTCCTGTACTTGT |
| 3 | FSCN1 | 0.38 | TGCCTGCTCCTGTACTTGTCCTCAG |
| 16 | HIC | 0.46 | TCCTCCATCACCTGAAACACTGGAC |
| 9 | HLA-C | 0.34 | TGGACCCCACTGGCTGAGAATCTGG |
| 16 | COL6A1 | 0.34 | TCCTCCATCACCTGAAACACTGGAC |
| 4 | IL6ST | 0.45 | AAATGTTTCCTTGTGCCTGCTCCTG |
| 2 | IFITM3 | 0.36 | GCCCCACTGGACAACACTGATTCCT |
| 16 | MAP1B | 0.31 | TCCTCCATCACCTGAAACACTGGAC |
| 7 | FLJ46603 | 0.3 | ACTTGTCCTCAGCTTGGGCTTCTTC |
| 2 | RAFTLIN | 0.32 | GCCCCACTGGACAACACTGATTCCT |
| 11 | FTL | 0.37 | CACCCAGCTGGTCCTGTGGATGGGA |
| 16 | KIAA0877 | 0.43 | TCCTCCATCACCTGAAACACTGGAC |
| 9 | MT1E | 0.41 | TGGACCCCACTGGCTGAGAATCTGG |
| 3 | CDC10 | 0.32 | TGCCTGCTCCTGTACTTGTCCTCAG |
| 4 | ZNF258 | 0.31 | AAATGTTTCCTTGTGCCTGCTCCTG |
| 10 | BCAT1 | 0.39 | TTGGACATCTCTAGTGTAGCTGCCA |
| 4 | IFI44 | 0.36 | AAATGTTTCCTTGTGCCTGCTCCTG |
| 2 | SOD2 | 0.36 | GCCCCACTGGACAACACTGATTCCT |
| 16 | TMSB10 | 0.33 | TCCTCCATCACCTGAAACACTGGAC |
| 10 | FLJ10350 | 0.3 | TTGGACATCTCTAGTGTAGCTGCCA |
| 11 | C1orf24 | 0.34 | CACCCAGCTGGTCCTGTGGATGGGA |
| 4 | EFHD2 | 0.36 | AAATGTTTCCTTGTGCCTGCTCCTG |
| 6 | RPS27L | 0.33 | AAGCCTATACGTTTCTGTGGAGTAA |
| 11 | TNFRSF12A | 0.43 | CACCCAGCTGGTCCTGTGGATGGGA |
| 10 | FAD104 | 0.38 | TTGGACATCTCTAGTGTAGCTGCCA |
| 7 | RAB7L1 | 0.58 | ACTTGTCCTCAGCTTGGGCTTCTTC |
| 10 | NME7 | 0.36 | TTGGACATCTCTAGTGTAGCTGCCA |
| 10 | TMEM22 | 0.34 | TTGGACATCTCTAGTGTAGCTGCCA |
| 2 | TPK1 | 0.31 | GCCCCACTGGACAACACTGATTCCT |
| 9 | ELK3 | 0.36 | TGGACCCCACTGGCTGAGAATCTGG |
| 6 | CYLD | 0.3 | AAGCCTATACGTTTCTGTGGAGTAA |
| 7 | AMIGO2 | 0.31 | ACTTGTCCTCAGCTTGGGCTTCTTC |
| 7 | ADAMTS1 | 0.43 | ACTTGTCCTCAGCTTGGGCTTCTTC |
| 7 | ACTB | 0.36 | ACTTGTCCTCAGCTTGGGCTTCTTC |

TABLE 65

Estramustine biomarkers.

| SEQ ID NO | Gene | Correlation | Medianprobe |
|---|---|---|---|
| 7 | HSPCB | 0.31 | ACTTGTCCTCAGCTTGGGCTTCTTC |
| 3 | LDHA | 0.42 | TGCCTGCTCCTGTACTTGTCCTCAG |
| 1 | TM4SF7 | 0.32 | TCCTGTACTTGTCCTCAGCTTGGGC |

TABLE 66

Chlorambucil biomarkers.

| SEQ ID NO | Gene | Correlation | Medianprobe |
|---|---|---|---|
| 9 | CSDA | 0.33 | TGGACCCCACTGGCTGAGAATCTGG |
| 24 | INSIG1 | 0.32 | TCCTTGTGCCTGCTCCTGTACTTGT |
| 9 | UBE2L6 | 0.39 | TGGACCCCACTGGCTGAGAATCTGG |
| 24 | PRG1 | 0.37 | TCCTTGTGCCTGCTCCTGTACTTGT |
| 2 | ITM2A | 0.3 | GCCCCACTGGACAACACTGATTCCT |
| 24 | DGKA | 0.38 | TCCTTGTGCCTGCTCCTGTACTTGT |
| 4 | TFDP2 | 0.32 | AAATGTTTCCTTGTGCCTGCTCCTG |
| 16 | SLA | 0.32 | TCCTCCATCACCTGAAACACTGGAC |
| 6 | IL2RG | 0.44 | AAGCCTATACGTTTCTGTGGAGTAA |
| 2 | ALOX5AP | 0.45 | GCCCCACTGGACAACACTGATTCCT |
| 10 | GPSM3 | 0.34 | TTGGACATCTCTAGTGTAGCTGCCA |
| 7 | PSMB9 | 0.36 | ACTTGTCCTCAGCTTGGGCTTCTTC |
| 3 | SELL | 0.42 | TGCCTGCTCCTGTACTTGTCCTCAG |
| 7 | ADA | 0.35 | ACTTGTCCTCAGCTTGGGCTTCTTC |
| 4 | EDG1 | 0.33 | AAATGTTTCCTTGTGCCTGCTCCTG |
| 16 | FMNL1 | 0.3 | TCCTCCATCACCTGAAACACTGGAC |
| 24 | PTPN7 | 0.5 | TCCTTGTGCCTGCTCCTGTACTTGT |
| 9 | CXorf9 | 0.41 | TGGACCCCACTGGCTGAGAATCTGG |
| 10 | RHOH | 0.35 | TTGGACATCTCTAGTGTAGCTGCCA |
| 24 | ZNFN1A1 | 0.32 | TCCTTGTGCCTGCTCCTGTACTTGT |
| 1 | CENTB1 | 0.47 | TCCTGTACTTGTCCTCAGCTTGGGC |
| 16 | LCP2 | 0.37 | TCCTCCATCACCTGAAACACTGGAC |
| 6 | CD1D | 0.36 | AAGCCTATACGTTTCTGTGGAGTAA |
| 4 | STAT4 | 0.31 | AAATGTTTCCTTGTGCCTGCTCCTG |
| 4 | VAV1 | 0.35 | AAATGTTTCCTTGTGCCTGCTCCTG |
| 10 | MAP4K1 | 0.36 | TTGGACATCTCTAGTGTAGCTGCCA |
| 1 | CCR7 | 0.31 | TCCTGTACTTGTCCTCAGCTTGGGC |
| 2 | PDE4C | 0.42 | GCCCCACTGGACAACACTGATTCCT |
| 6 | CD3G | 0.41 | AAGCCTATACGTTTCTGTGGAGTAA |

TABLE 66-continued

Chlorambucil biomarkers.

| SEQ ID NO | Gene | Correlation | Medianprobe |
|---|---|---|---|
| 6 | CCR9 | 0.43 | AAGCCTATACGTTTCTGTGGAGTAA |
| 10 | SP110 | 0.43 | TTGGACATCTCTAGTGTAGCTGCCA |
| 10 | TNFAIP8 | 0.48 | TTGGACATCTCTAGTGTAGCTGCCA |
| 4 | LCP1 | 0.31 | AAATGTTTCCTTGTGCCTGCTCCTG |
| 16 | IFI16 | 0.5 | TCCTCCATCACCTGAAACACTGGAC |
| 7 | CXCR4 | 0.37 | ACTTGTCCTCAGCTTGGGCTTCTTC |
| 7 | ARHGEF6 | 0.37 | ACTTGTCCTCAGCTTGGGCTTCTTC |
| 10 | SELPLG | 0.43 | TTGGACATCTCTAGTGTAGCTGCCA |
| 9 | SEC31L2 | 0.32 | TGGACCCCACTGGCTGAGAATCTGG |
| 6 | CD3Z | 0.3 | AAGCCTATACGTTTCTGTGGAGTAA |
| 2 | PRKCQ | 0.31 | GGCCCACTGGACAACACTGATTCCT |
| 7 | SH2D1A | 0.47 | ACTTGTCCTCAGCTTGGGCTTCTTC |
| 9 | GZMB | 0.48 | TGGACCCCACTGGCTGAGAATCTGG |
| 6 | CD1A | 0.3 | AAGCCTATACGTTTCTGTGGAGTAA |
| 10 | LAIR1 | 0.32 | TTGGACATCTCTAGTGTAGCTGCCA |
| 10 | AF1Q | 0.41 | TTGGACATCTCTAGTGTAGCTGCCA |
| 16 | TRB@ | 0.35 | TCCTCCATCACCTGAAACACTGGAC |
| 9 | SEPT6 | 0.35 | TGGACCCCACTGGCTGAGAATCTGG |
| 6 | DOCK2 | 0.39 | AAGCCTATACGTTTCTGTGGAGTAA |
| 10 | RPS19 | 0.41 | TTGGACATCTCTAGTGTAGCTGCCA |
| 10 | CD3D | 0.4 | TTGGACATCTCTAGTGTAGCTGCCA |
| 9 | T3JAM | 0.32 | TGGACCCCACTGGCTGAGAATCTGG |
| 2 | FNBP1 | 0.31 | GCCCCACTGGACAACACTGATTCCT |
| 9 | CD6 | 0.33 | TGGACCCCACTGGCTGAGAATCTGG |
| 11 | ZAP70 | 0.52 | CACCCAGCTGGTCCTGTGGATGGGA |
| 4 | LST1 | 0.34 | AAATGTTTCCTTGTGCCTGCTCCTG |
| 6 | BCAT1 | 0.35 | AAGCCTATACGTTTCTGTGGAGTAA |
| 6 | PRF1 | 0.4 | AAGCCTATACGTTTCTGTGGAGTAA |
| 10 | AIF1 | 0.3 | TTGGACATCTCTAGTGTAGCTGCCA |
| 9 | RAG2 | 0.38 | TGGACCCCACTGGCTGAGAATCTGG |
| 7 | CD1E | 0.35 | ACTTGTCCTCAGCTTGGGCTTCTTC |
| 10 | CYFIP2 | 0.38 | TTGGACATCTCTAGTGTAGCTGCCA |
| 9 | TARP | 0.3 | TGGACCCCACTGGCTGAGAATCTGG |
| 11 | TRIM | 0.36 | CACCCAGCTGGTCCTGTGGATGGGA |
| 16 | GLTSCR2 | 0.37 | TCCTCCATCACCTGAAACACTGGAC |
| 7 | GIMAP5 | 0.3 | ACTTGTCCTCAGCTTGGGCTTCTTC |
| 6 | ARHGAP15 | 0.32 | AAGCCTATACGTTTCTGTGGAGTAA |

TABLE 66-continued

Chlorambucil biomarkers.

| SEQ ID NO | Gene | Correlation | Medianprobe |
|---|---|---|---|
| 11 | NOTCH1 | 0.31 | CACCCAGCTGGTCCTGTGGATGGGA |
| 24 | BCL11B | 0.3 | TCCTTGTGCCTGCTCCTGTACTTGT |
| 10 | GIMAP6 | 0.34 | TTGGACATCTCTAGTGTAGCTGCCA |
| 1 | STAG3 | 0.4 | TCCTGTACTTGTCCTCAGCTTGGGC |
| 10 | TM6SF1 | 0.39 | TTGGACATCTCTAGTGTAGCTGCCA |
| 1 | UBASH3A | 0.37 | TCCTGTACTTGTCCTCAGCTTGGGC |
| 11 | MGC5566 | 0.36 | CACCCAGCTGGTCCTGTGGATGGGA |
| 16 | FLJ22457 | 0.31 | TCCTCCATCACCTGAAACACTGGAC |
| 4 | TPK1 | 0.33 | AAATGTTTCCTTGTGCCTGCTCCTG |

TABLE 67

Mechlorethamine biomarkers.

| SEQ ID NO | Gene | Correlation | Medianprobe |
|---|---|---|---|
| 2 | PRG1 | 0.37 | GCCCCACTGGACAACACTGATTCCT |
| 7 | SLC2A3 | 0.35 | ACTTGTCCTCAGCTTGGGCTTCTTC |
| 7 | RPS19 | 0.32 | ACTTGTCCTCAGCTTGGGCTTCTTC |
| 3 | PSMB10 | 0.34 | TGCCTGCTCCTGTACTTGTCCTCAG |
| 3 | ITM2A | 0.33 | TGCCTGCTCCTGTACTTGTCCTCAG |
| 3 | DGKA | 0.37 | TGCCTGCTCCTGTACTTGTCCTCAG |
| 16 | SEMA4D | 0.34 | TCCTCCATCACCTGAAACACTGGAC |
| 3 | SLA | 0.33 | TGCCTGCTCCTGTACTTGTCCTCAG |
| 9 | IL2RG | 0.3 | TGGACCCCACTGGCTGAGAATCTGG |
| 6 | MFNG | 0.42 | AAGCCTATACGTTTCTGTGGAGTAA |
| 6 | ALOX5AP | 0.31 | AAGCCTATACGTTTCTGTGGAGTAA |
| 6 | GPSM3 | 0.34 | AAGCCTATACGTTTCTGTGGAGTAA |
| 7 | PSMB9 | 0.36 | ACTTGTCCTCAGCTTGGGCTTCTTC |
| 11 | SELL | 0.34 | CACCCAGCTGGTCCTGTGGATGGGA |
| 4 | ADA | 0.35 | AAATGTTTCCTTGTGCCTGCTCCTG |
| 11 | FMNL1 | 0.4 | CACCCAGCTGGTCCTGTGGATGGGA |
| 9 | MYB | 0.34 | TGGACCCCACTGGCTGAGAATCTGG |
| 6 | PTPN7 | 0.43 | AAGCCTATACGTTTCTGTGGAGTAA |
| 3 | CXorf9 | 0.32 | TGCCTGCTCCTGTACTTGTCCTCAG |
| 10 | RHOH | 0.33 | TTGGACATCTCTAGTGTAGCTGCCA |
| 16 | ZNFN1A1 | 0.31 | TCCTCCATCACCTGAAACACTGGAC |
| 16 | CENTB1 | 0.43 | TCCTCCATCACCTGAAACACTGGAC |

TABLE 67-continued

Mechlorethamine biomarkers.

| SEQ ID NO | Gene | Correlation | Medianprobe |
|---|---|---|---|
| 10 | FXYD2 | 0.35 | TTGGACATCTCTAGTGTAGCTGCCA |
| 10 | CD1D | 0.4 | TTGGACATCTCTAGTGTAGCTGCCA |
| 10 | STAT4 | 0.44 | TTGGACATCTCTAGTGTAGCTGCCA |
| 2 | MAP4K1 | 0.34 | GCCCCACTGGACAACACTGATTCCT |
| 9 | CCR7 | 0.39 | TGGACCCCACTGGCTGAGAATCTGG |
| 24 | PDE4C | 0.33 | TCCTTGTGCCTGCTCCTGTACTTGT |
| 2 | CD3G | 0.4 | GCCCCACTGGACAACACTGATTCCT |
| 9 | CCR9 | 0.34 | TGGACCCCACTGGCTGAGAATCTGG |
| 4 | SP110 | 0.31 | AAATGTTTCCTTGTGCCTGCTCCTG |
| 1 | TK2 | 0.33 | TCCTGTACTTGTCCTCAGCTTGGGC |
| 2 | TNFAIP8 | 0.34 | GCCCCACTGGACAACACTGATTCCT |
| 1 | NAP1L1 | 0.35 | TCCTGTACTTGTCCTCAGCTTGGGC |
| 1 | SELPLG | 0.35 | TCCTGTACTTGTCCTCAGCTTGGGC |
| 3 | SEC31L2 | 0.38 | TGCCTGCTCCTGTACTTGTCCTCAG |
| 10 | CD3Z | 0.44 | TTGGACATCTCTAGTGTAGCTGCCA |
| 1 | PRKCQ | 0.37 | TCCTGTACTTGTCCTCAGCTTGGGC |
| 2 | SH2D1A | 0.41 | GCCCCACTGGACAACACTGATTCCT |
| 9 | GZMB | 0.43 | TGGACCCCACTGGCTGAGAATCTGG |
| 9 | CD1A | 0.39 | TGGACCCCACTGGCTGAGAATCTGG |
| 9 | LAIR1 | 0.35 | TGGACCCCACTGGCTGAGAATCTGG |
| 10 | TRB@ | 0.33 | TTGGACATCTCTAGTGTAGCTGCCA |
| 11 | SEPT6 | 0.3 | CACCCAGCTGGTCCTGTGGATGGGA |
| 9 | DOCK2 | 0.34 | TGGACCCCACTGGCTGAGAATCTGG |
| 9 | CG018 | 0.33 | TGGACCCCACTGGCTGAGAATCTGG |
| 1 | WBSCR20C | 0.34 | TCCTGTACTTGTCCTCAGCTTGGGC |
| 7 | CD3D | 0.33 | ACTTGTCCTCAGCTTGGGCTTCTTC |
| 6 | CD6 | 0.32 | AAGCCTATACGTTTCTGTGGAGTAA |
| 10 | LST1 | 0.33 | TTGGACATCTCTAGTGTAGCTGCCA |
| 6 | GPR65 | 0.42 | AAGCCTATACGTTTCTGTGGAGTAA |
| 11 | PRF1 | 0.34 | CACCCAGCTGGTCCTGTGGATGGGA |
| 1 | ALMS1 | 0.41 | TCCTGTACTTGTCCTCAGCTTGGGC |
| 2 | AIF1 | 0.31 | GCCCCACTGGACAACACTGATTCCT |
| 11 | CD1E | 0.31 | CACCCAGCTGGTCCTGTGGATGGGA |
| 2 | CYFIP2 | 0.33 | GCCCCACTGGACAACACTGATTCCT |
| 4 | TARP | 0.31 | AAATGTTTCCTTGTGCCTGCTCCTG |
| 6 | GLTSCR2 | 0.31 | AAGCCTATACGTTTCTGTGGAGTAA |
| 9 | FLJ12270 | 0.34 | TGGACCCCACTGGCTGAGAATCTGG |

TABLE 67-continued

Mechlorethamine biomarkers.

| SEQ ID NO | Gene | Correlation | Medianprobe |
|---|---|---|---|
| 2 | ARHGAP15 | 0.33 | GCCCCACTGGACAACACTGATTCCT |
| 2 | NAP1L2 | 0.32 | GCCCCACTGGACAACACTGATTCCT |
| 24 | CECR1 | 0.34 | TCCTTGTGCCTGCTCCTGTACTTGT |
| 1 | GIMAP6 | 0.35 | TCCTGTACTTGTCCTCAGCTTGGGC |
| 11 | STAG3 | 0.33 | CACCCAGCTGGTCCTGTGGATGGGA |
| 11 | TM6SF1 | 0.3 | CACCCAGCTGGTCCTGTGGATGGGA |
| 10 | C15orf25 | 0.36 | TTGGACATCTCTAGTGTAGCTGCCA |
| 1 | MGC5566 | 0.32 | TCCTGTACTTGTCCTCAGCTTGGGC |
| 4 | FLJ22457 | 0.34 | AAATGTTTCCTTGTGCCTGCTCCTG |
| 11 | ET | 0.32 | CACCCAGCTGGTCCTGTGGATGGGA |
| 11 | TPK1 | 0.34 | CACCCAGCTGGTCCTGTGGATGGGA |
| 10 | PHF11 | 0.36 | TTGGACATCTCTAGTGTAGCTGCCA |

TABLE 68

Streptozocin biomarkers.

| SEQ ID NO | Gene | Correlation | Medianprobe |
|---|---|---|---|
| 3 | PGK1 | 0.32 | TGCCTGCTCCTGTACTTGTCCTCAG |
| 9 | SCD | 0.31 | TGGACCCCACTGGCTGAGAATCTGG |
| 3 | INSIG1 | 0.3 | TGCCTGCTCCTGTACTTGTCCTCAG |
| 16 | IGBP1 | 0.39 | TCCTCCATCACCTGAAACACTGGAC |
| 16 | TNFAIP3 | 0.31 | TCCTCCATCACCTGAAACACTGGAC |
| 11 | TNFSF10 | 0.31 | CACCCAGCTGGTCCTGTGGATGGGA |
| 3 | ABCA1 | 0.34 | TGCCTGCTCCTGTACTTGTCCTCAG |
| 9 | AGA | 0.31 | TGGACCCCACTGGCTGAGAATCTGG |
| 11 | ABCA8 | 0.31 | CACCCAGCTGGTCCTGTGGATGGGA |
| 3 | DBC1 | 0.31 | TGCCTGCTCCTGTACTTGTCCTCAG |
| 7 | PTGER2 | 0.32 | ACTTGTCCTCAGCTTGGGCTTCTTC |
| 16 | UGT1A3 | 0.32 | TCCTCCATCACCTGAAACACTGGAC |
| 11 | C10orf10 | 0.3 | CACCCAGCTGGTCCTGTGGATGGGA |
| 9 | TM4SF13 | 0.34 | TGGACCCCACTGGCTGAGAATCTGG |
| 24 | CGI-90 | 0.31 | TCCTTGTGCCTGCTCCTGTACTTGT |
| 6 | LXN | 0.31 | AAGCCTATACGTTTCTGTGGAGTAA |
| 10 | DNAJC12 | 0.35 | TTGGACATCTCTAGTGTAGCTGCCA |
| 11 | HIPK2 | 0.31 | CACCCAGCTGGTCCTGTGGATGGGA |
| 7 | C9orf95 | 0.36 | ACTTGTCCTCAGCTTGGGCTTCTTC |

TABLE 69

Carmustine biomarkers.

| SEQ ID NO | Gene | Correlation | Medianprobe |
|---|---|---|---|
| 3 | RPLP2 | 0.34 | TGCCTGCTCCTGTACTTGTCCTCAG |
| 7 | CD99 | 0.31 | ACTTGTCCTCAGCTTGGGCTTCTTC |
| 16 | IFITM1 | 0.36 | TCCTCCATCACCTGAAACACTGGAC |
| 16 | INSIG1 | 0.31 | TCCTCCATCACCTGAAACACTGGAC |
| 3 | ALDOC | 0.4 | TGCCTGCTCCTGTACTTGTCCTCAG |
| 24 | ITM2A | 0.33 | TCCTTGTGCCTGCTCCTGTACTTGT |
| 10 | SERPINA1 | 0.39 | TTGGACATCTCTAGTGTAGCTGCCA |
| 6 | C1QR1 | 0.35 | AAGCCTATACGTTTCTGTGGAGTAA |
| 10 | STAT5A | 0.39 | TTGGACATCTCTAGTGTAGCTGCCA |
| 24 | INPP5D | 0.44 | TCCTTGTGCCTGCTCCTGTACTTGT |
| 4 | SATB1 | 0.36 | AAATGTTTCCTTGTGCCTGCTCCTG |
| 4 | VPS16 | 0.31 | AAATGTTTCCTTGTGCCTGCTCCTG |
| 1 | SLA | 0.37 | TCCTGTACTTGTCCTCAGCTTGGGC |
| 16 | IL2RG | 0.45 | TCCTCCATCACCTGAAACACTGGAC |
| 16 | MFNG | 0.33 | TCCTCCATCACCTGAAACACTGGAC |
| 6 | SELL | 0.38 | AAGCCTATACGTTTCTGTGGAGTAA |
| 2 | LRMP | 0.41 | GCCCCACTGGACAACACTGATTCCT |
| 16 | ICAM2 | 0.54 | TCCTCCATCACCTGAAACACTGGAC |
| 7 | MYB | 0.31 | ACTTGTCCTCAGCTTGGGCTTCTTC |
| 3 | PTPN7 | 0.3 | TGCCTGCTCCTGTACTTGTCCTCAG |
| 10 | ARHGAP25 | 0.42 | TTGGACATCTCTAGTGTAGCTGCCA |
| 9 | LCK | 0.41 | TGGACCCCACTGGCTGAGAATCTGG |
| 9 | CXorf9 | 0.35 | TGGACCCCACTGGCTGAGAATCTGG |
| 4 | RHOH | 0.41 | AAATGTTTCCTTGTGCCTGCTCCTG |
| 3 | ZNFN1A1 | 0.37 | TGCCTGCTCCTGTACTTGTCCTCAG |
| 7 | CENTB1 | 0.59 | ACTTGTCCTCAGCTTGGGCTTCTTC |
| 24 | ADD2 | 0.34 | TCCTTGTGCCTGCTCCTGTACTTGT |
| 10 | LCP2 | 0.33 | TTGGACATCTCTAGTGTAGCTGCCA |
| 3 | SFI1 | 0.39 | TGCCTGCTCCTGTACTTGTCCTCAG |
| 7 | DBT | 0.42 | ACTTGTCCTCAGCTTGGGCTTCTTC |
| 11 | GZMA | 0.34 | CACCCAGCTGGTCCTGTGGATGGGA |
| 9 | CD2 | 0.36 | TGGACCCCACTGGCTGAGAATCTGG |
| 7 | BATF | 0.38 | ACTTGTCCTCAGCTTGGGCTTCTTC |
| 1 | HIST1H4C | 0.31 | TCCTGTACTTGTCCTCAGCTTGGGC |
| 16 | ARHGAP6 | 0.4 | TCCTCCATCACCTGAAACACTGGAC |
| 9 | VAV1 | 0.42 | TGGACCCCACTGGCTGAGAATCTGG |
| 24 | MAP4K1 | 0.31 | TCCTTGTGCCTGCTCCTGTACTTGT |

TABLE 69-continued

Carmustine biomarkers.

| SEQ ID NO | Gene | Correlation | Medianprobe |
|---|---|---|---|
| 24 | CCR7 | 0.31 | TCCTTGTGCCTGCTCCTGTACTTGT |
| 16 | PDE4C | 0.57 | TCCTCCATCACCTGAAACACTGGAC |
| 6 | CD3G | 0.44 | AAGCCTATACGTTTCTGTGGAGTAA |
| 4 | CCR9 | 0.37 | AAATGTTTCCTTGTGCCTGCTCCTG |
| 1 | SP140 | 0.48 | TCCTGTACTTGTCCTCAGCTTGGGC |
| 9 | TK2 | 0.31 | TGGACCCCACTGGCTGAGAATCTGG |
| 16 | LCP1 | 0.38 | TCCTCCATCACCTGAAACACTGGAC |
| 2 | IFI16 | 0.34 | GCCCCACTGGACAACACTGATTCCT |
| 2 | CXCR4 | 0.42 | GCCCCACTGGACAACACTGATTCCT |
| 4 | ARHGEF6 | 0.45 | AAATGTTTCCTTGTGCCTGCTCCTG |
| 1 | PSCDBP | 0.42 | TCCTGTACTTGTCCTCAGCTTGGGC |
| 9 | SELPLG | 0.52 | TGGACCCCACTGGCTGAGAATCTGG |
| 1 | SEC31L2 | 0.42 | TCCTGTACTTGTCCTCAGCTTGGGC |
| 16 | CD3Z | 0.34 | TCCTCCATCACCTGAAACACTGGAC |
| 24 | PRKCQ | 0.46 | TCCTTGTGCCTGCTCCTGTACTTGT |
| 3 | SH2D1A | 0.46 | TGCCTGCTCCTGTACTTGTCCTCAG |
| 10 | GZMB | 0.55 | TTGGACATCTCTAGTGTAGCTGCCA |
| 24 | CD1A | 0.34 | TCCTTGTGCCTGCTCCTGTACTTGT |
| 10 | GATA2 | 0.41 | TTGGACATCTCTAGTGTAGCTGCCA |
| 16 | LY9 | 0.54 | TCCTCCATCACCTGAAACACTGGAC |
| 10 | LAIR1 | 0.3 | TTGGACATGTCTAGTGTAGCTGCCA |
| 16 | TRB@ | 0.33 | TCCTCCATCACCTGAAACACTGGAC |
| 7 | SEPT6 | 0.32 | ACTTGTCCTCAGCTTGGGCTTCTTC |
| 16 | HA-1 | 0.32 | TCCTCCATCACCTGAAACACTGGAC |
| 1 | SLC43A3 | 0.32 | TCCTGTACTTGTCCTCAGCTTGGGC |
| 16 | DOCK2 | 0.31 | TCCTCCATCACCTGAAACACTGGAC |
| 7 | CG018 | 0.42 | ACTTGTCCTCAGCTTGGGCTTCTTC |
| 3 | MLC1 | 0.33 | TGCCTGCTCCTGTACTTGTCCTCAG |
| 1 | CD3D | 0.35 | TCCTGTACTTGTCCTCAGCTTGGGC |
| 11 | T3JAM | 0.34 | CACCCAGCTGGTCCTGTGGATGGGA |
| 1 | CD6 | 0.43 | TCCTGTACTTGTCCTCAGCTTGGGC |
| 2 | ZAP70 | 0.43 | GCCCCACTGGACAACACTGATTCCT |
| 1 | DOK2 | 0.3 | TCCTGTACTTGTCCTCAGCTTGGGC |
| 1 | LST1 | 0.36 | TCCTGTACTTGTCCTCAGCTTGGGC |
| 1 | GPR65 | 0.31 | TCCTGTACTTGTCCTCAGCTTGGGC |
| 24 | PRF1 | 0.32 | TCCTTGTGCCTGCTCCTGTACTTGT |
| 10 | ALMS1 | 0.38 | TTGGACATCTCTAGTGTAGCTGCCA |
| 24 | AIF1 | 0.31 | TCCTTGTGCCTGCTCCTGTACTTGT |
| 2 | PRDX2 | 0.48 | GCCCCACTGGACAACACTGATTCCT |
| 4 | FLJ12151 | 0.36 | AAATGTTTCCTTGTGCCTGCTCCTG |
| 3 | FBXW12 | 0.37 | TGCCTGCTCCTGTACTTGTCCTCAG |
| 6 | CD1E | 0.34 | AAGCCTATACGTTTCTGTGGAGTAA |
| 24 | CYFIP2 | 0.3 | TCCTTGTGCCTGCTCCTGTACTTGT |
| 1 | TARP | 0.33 | TCCTGTACTTGTCCTCAGCTTGGGC |
| 11 | TRIM | 0.38 | CACCCAGCTGGTCCTGTGGATGGGA |
| 4 | RPL10L | 0.43 | AAATGTTTCCTTGTGCCTGCTCCTG |
| 11 | GLTSCR2 | 0.43 | CACCCAGCTGGTCCTGTGGATGGGA |
| 24 | CKIP-1 | 0.33 | TCCTTGTGCCTGCTCCTGTACTTGT |
| 24 | NRN1 | 0.3 | TCCTTGTGCCTGCTCCTGTACTTGT |
| 16 | ARHGAP15 | 0.4 | TCCTCCATCACCTGAAACACTGGAC |
| 3 | NOTCH1 | 0.32 | TGCCTGCTCCTGTACTTGTCCTCAG |
| 11 | PSCD4 | 0.4 | CACCCAGCTGGTCCTGTGGATGGGA |
| 6 | C13orf18 | 0.31 | AAGCCTATACGTTTCTGTGGAGTAA |
| 7 | BCL11B | 0.35 | ACTTGTCCTCAGCTTGGGCTTCTTC |
| 7 | GIMAP6 | 0.33 | ACTTGTCCTCAGCTTGGGCTTCTTC |
| 1 | STAG3 | 0.31 | TCCTGTACTTGTCCTCAGCTTGGGC |
| 1 | NARF | 0.34 | TCCTGTACTTGTCCTCAGCTTGGGC |
| 16 | TM6SF1 | 0.48 | TCCTCCATCACCTGAAACACTGGAC |
| 1 | C15orf25 | 0.32 | TCCTGTACTTGTCCTCAGCTTGGGC |
| 2 | FLJ11795 | 0.35 | GCCCCACTGGACAACACTGATTCCT |
| 2 | SAMSN1 | 0.37 | GCCCCACTGGACAACACTGATTCCT |
| 1 | UBASH3A | 0.4 | TCCTGTACTTGTCCTCAGCTTGGGC |
| 3 | PACAP | 0.31 | TGCCTGCTCCTGTACTTGTCCTCAG |
| 11 | LEF1 | 0.3 | CACCCAGCTGGTCCTGTGGATGGGA |
| 6 | IL21R | 0.34 | AAGCCTATACGTTTCTGTGGAGTAA |
| 2 | TCF4 | 0.41 | GCCCCACTGGACAACACTGATTCCT |
| 1 | DKFZP434B0335 | 0.33 | TCCTGTACTTGTCCTCAGCTTGGGC |

TABLE 70

Lomustine biomarkers.

| SEQ ID NO | Gene | Correlation | Medianprobe |
|---|---|---|---|
| 1 | RPS15 | 0.43 | TCCTGTACTTGTCCTCAGCTTGGGC |
| 9 | INSIG1 | 0.31 | TGGACCCCACTGGCTGAGAATCTGG |

TABLE 70-continued

Lomustine biomarkers.

| SEQ ID NO | Gene | Correlation | Medianprobe |
|---|---|---|---|
| 3 | ALDOC | 0.39 | TGCCTGCTCCTGTACTTGTCCTCAG |
| 16 | ITM2A | 0.32 | TCCTCCATCACCTGAAACACTGGAC |
| 3 | C1QR1 | 0.33 | TGCCTGCTCCTGTACTTGTCCTCAG |
| 3 | STAT5A | 0.37 | TGCCTGCTCCTGTACTTGTCCTCAG |
| 1 | INPP5D | 0.32 | TCCTGTACTTGTCCTCAGCTTGGGC |
| 3 | VPS16 | 0.32 | TGCCTGCTCCTGTACTTGTCCTCAG |
| 3 | SLA | 0.32 | TGCCTGCTCCTGTACTTGTCCTCAG |
| 7 | USP20 | 0.41 | ACTTGTCCTCAGCTTGGGCTTCTTC |
| 1 | IL2RG | 0.31 | TCCTGTACTTGTCCTCAGCTTGGGC |
| 7 | MFNG | 0.4 | ACTTGTCCTCAGCTTGGGCTTCTTC |
| 2 | LRMP | 0.43 | GCCCCACTGGACAACACTGATTCCT |
| 7 | EVI2A | 0.35 | ACTTGTCCTCAGCTTGGGCTTCTTC |
| 24 | PTPN7 | 0.35 | TCCTTGTGCCTGCTCCTGTACTTGT |
| 1 | ARHGAP25 | 0.39 | TCCTGTACTTGTCCTCAGCTTGGGC |
| 6 | RHOH | 0.31 | AAGCCTATACGTTTCTGTGGAGTAA |
| 1 | ZNFN1A1 | 0.31 | TCCTGTACTTGTCCTCAGCTTGGGC |
| 1 | CENTB1 | 0.35 | TCCTGTACTTGTCCTCAGCTTGGGC |
| 9 | LCP2 | 0.41 | TGGACCCCACTGGCTGAGAATCTGG |
| 3 | SPI1 | 0.35 | TGCCTGCTCCTGTACTTGTCCTCAG |
| 10 | ARHGAP6 | 0.33 | TTGGACATCTCTAGTGTAGCTGCCA |
| 11 | MAP4K1 | 0.34 | CACCCAGCTGGTCCTGTGGATGGGA |
| 16 | CCR7 | 0.35 | TCCTCCATCACCTGAAACACTGGAC |
| 2 | LY96 | 0.35 | GCCCCACTGGACAACACTGATTCCT |
| 7 | C6orf32 | 0.32 | ACTTGTCCTCAGCTTGGGCTTCTTC |
| 4 | MAGEA1 | 0.31 | AAATGTTTCCTTGTGCCTGCTCCTG |
| 10 | SP140 | 0.35 | TTGGACATCTCTAGTGTAGCTGCCA |
| 16 | LCP1 | 0.36 | TCCTCCATCACCTGAAACACTGGAC |
| 3 | IFI16 | 0.39 | TGCCTGCTCCTGTACTTGTCCTCAG |
| 16 | ARHGEF6 | 0.33 | TCCTCCATCACCTGAAACACTGGAC |
| 6 | PSCDBP | 0.43 | AAGCCTATACGTTTCTGTGGAGTAA |
| 7 | SELPLG | 0.3 | ACTTGTCCTCAGCTTGGGCTTCTTC |
| 6 | CD3Z | 0.35 | AAGCCTATACGTTTCTGTGGAGTAA |
| 2 | PRKCQ | 0.4 | TCCTTGTGCCTGCTCCTGTACTTGT |
| 6 | GZMB | 0.31 | AAGCCTATACGTTTCTGTGGAGTAA |
| 9 | LAIR1 | 0.38 | TGGACCCCACTGGCTGAGAATCTGG |
| 1 | SH2D1A | 0.36 | TCCTGTACTTGTCCTCAGCTTGGGC |
| 10 | TRB@ | 0.39 | TTGGACATCTCTAGTGTAGCTGCCA |
| 3 | RFP | 0.35 | TGCCTGCTCCTGTACTTGTCCTCAG |
| 16 | SEPT6 | 0.41 | TCCTCCATCACCTGAAACACTGGAC |
| 1 | HA-1 | 0.43 | TCCTGTACTTGTCCTCAGCTTGGGC |
| 7 | SLC43A3 | 0.4 | ACTTGTCCTCAGCTTGGGCTTCTTC |
| 24 | CD3D | 0.32 | TCCTTGTGCCTGCTCCTGTACTTGT |
| 9 | T3JAM | 0.3 | TGGACCCCACTGGCTGAGAATCTGG |
| 2 | GPR65 | 0.34 | GCCCCACTGGACAACACTGATTCCT |
| 3 | PRF1 | 0.36 | TGCCTGCTCCTGTACTTGTCCTCAG |
| 9 | AIF1 | 0.33 | TGGACCCCACTGGCTGAGAATCTGG |
| 4 | LPXN | 0.38 | AAATGTTTCCTTGTGCCTGCTCCTG |
| 9 | RPL10L | 0.3 | TGGACCCCACTGGCTGAGAATCTGG |
| 11 | SITPEC | 0.36 | CACCCAGCTGGTCCTGTGGATGGGA |
| 9 | ARHGAP15 | 0.33 | TGGACCCCACTGGCTGAGAATCTGG |
| 1 | C13orf18 | 0.32 | TCCTGTACTTGTCCTCAGCTTGGGC |
| 9 | NARF | 0.35 | TGGACCCCACTGGCTGAGAATCTGG |
| 24 | TM6SF1 | 0.34 | TCCTTGTGCCTGCTCCTGTACTTGT |
| 6 | PACAP | 0.31 | AAGCCTATACGTTTCTGTGGAGTAA |
| 24 | TCF4 | 0.33 | TCCTTGTGCCTGCTCCTGTACTTGT |

TABLE 71

Mercaptopurine biomarkers.

| SEQ ID NO | Gene | Correlation | Medianprobe |
|---|---|---|---|
| 2 | SSRP1 | 0.31 | GCCCCACTGGACAACACTGATTCCT |
| 4 | ALDOC | 0.36 | AAATGTTTCCTTGTGCCTGCTCCTG |
| 3 | C1QR1 | 0.31 | TGCCTGCTCCTGTACTTGTCCTCAG |
| 1 | TTF1 | 0.31 | TCCTGTACTTGTCCTCAGCTTGGGC |
| 2 | PRIM1 | 0.31 | GCCCCACTGGACAACACTGATTCCT |
| 16 | USP34 | 0.38 | TCCTCCATCACCTGAAACACTGGAC |
| 1 | TK2 | 0.33 | TCCTGTACTTGTCCTCAGCTTGGGC |
| 3 | GOLGIN-67 | 0.31 | TGCCTGCTCCTGTACTTGTCCTCAG |
| 7 | N2D014 | 0.35 | ACTTGTCCTCAGCTTGGGCTTCTTC |
| 16 | KIAA0220 | 0.31 | TCCTCCATCACCTGAAACACTGGAC |
| 10 | SLC43A3 | 0.3 | TTGGACATCTCTAGTGTAGCTGCCA |
| 11 | WBSCR20C | 0.3 | CACCCAGCTGGTCCTGTGGATGGGA |
| 3 | ICAM2 | 0.3 | TGCCTGCTCCTGTACTTGTCCTCAG |

TABLE 71-continued

Mercaptopurine biomarkers.

| SEQ ID NO | Gene | Correlation | Medianprobe |
|---|---|---|---|
| 9 | TEX10 | 0.32 | TGGACCCCACTGGCTGAGAATCTGG |
| 7 | CHD7 | 0.3 | ACTTGTCCTCAGCTTGGGCTTCTTC |
| 10 | SAMSN1 | 0.34 | TTGGACATCTCTAGTGTAGCTGCCA |
| 7 | TPRT | 0.35 | ACTTGTCCTCAGCTTGGGCTTCTTC |

TABLE 72

Teniposide biomarkers.

| SEQ ID NO | Gene | Correlation | Medianprobe |
|---|---|---|---|
| 3 | CD99 | 0.35 | TGCCTGCTCCTGTACTTGTCCTCAG |
| 6 | INSIG1 | 0.35 | AAGCCTATACGTTTCTGTGGAGTAA |
| 3 | PRG1 | 0.36 | TGCCTGCTCCTGTACTTGTCCTCAG |
| 7 | ALDOC | 0.3 | ACTTGTCCTCAGCTTGGGCTTCTTC |
| 6 | ITM2A | 0.33 | AAGCCTATACGTTTCTGTGGAGTAA |
| 2 | SLA | 0.43 | GCCCCACTGGACAACACTGATTCCT |
| 24 | SSBP2 | 0.31 | TCCTTGTGCCTGCTCCTGTACTTGT |
| 4 | IL2RG | 0.37 | AAATGTTTCCTTGTGCCTGCTCCTG |
| 10 | MFNG | 0.32 | TTGGACATCTCTAGTGTAGCTGCCA |
| 16 | ALOX5AP | 0.32 | TCCTCCATCACCTGAAACACTGGAC |
| 16 | C1orf29 | 0.3 | TCCTCCATCACCTGAAACACTGGAC |
| 11 | SELL | 0.33 | CACCCAGCTGGTCCTGTGGATGGGA |
| 9 | STC1 | 0.47 | TGGACCCCACTGGCTGAGAATCTGG |
| 16 | LRMP | 0.33 | TCCTCCATCACCTGAAACACTGGAC |
| 3 | MYB | 0.33 | TGCCTGCTCCTGTACTTGTCCTCAG |
| 6 | PTPN7 | 0.34 | AAGCCTATACGTTTCTGTGGAGTAA |
| 10 | CXorf9 | 0.42 | TTGGACATCTCTAGTGTAGCTGCCA |
| 6 | RHOH | 0.31 | AAGCCTATACGTTTCTGTGGAGTAA |
| 11 | ZNFN1A1 | 0.34 | CACCCAGCTGGTCCTGTGGATGGGA |
| 9 | CENTB1 | 0.37 | TGGACCCCACTGGCTGAGAATCTGG |
| 3 | ADD2 | 0.31 | TGCCTGCTCCTGTACTTGTCCTCAG |
| 7 | CD1D | 0.37 | ACTTGTCCTCAGCTTGGGCTTCTTC |
| 1 | BATF | 0.32 | TCCTGTACTTGTCCTCAGCTTGGGC |
| 2 | MAP4K1 | 0.3 | GCCCCACTGGACAACACTGATTCCT |
| 1 | CCR7 | 0.48 | TCCTGTACTTGTCCTCAGCTTGGGC |
| 9 | PDE4C | 0.33 | TGGACCCCACTGGCTGAGAATCTGG |
| 10 | CD3G | 0.33 | TTGGACATCTCTAGTGTAGCTGCCA |
| 7 | CCR9 | 0.36 | ACTTGTCCTCAGCTTGGGCTTCTTC |
| 4 | SP110 | 0.34 | AAATGTTTCCTTGTGCCTGCTCCTG |

TABLE 72-continued

Teniposide biomarkers.

| SEQ ID NO | Gene | Correlation | Medianprobe |
|---|---|---|---|
| 7 | TNFAIP8 | 0.31 | ACTTGTCCTCAGCTTGGGCTTCTTC |
| 6 | NAP1L1 | 0.32 | AAGCCTATACGTTTCTGTGGAGTAA |
| 7 | CXCR4 | 0.31 | ACTTGTCCTCAGCTTGGGCTTCTTC |
| 1 | ARHGEF6 | 0.31 | TCCTGTACTTGTCCTCAGCTTGGGC |
| 1 | GATA3 | 0.36 | TCCTGTACTTGTCCTCAGCTTGGGC |
| 6 | SELPLG | 0.38 | AAGCCTATACGTTTCTGTGGAGTAA |
| 9 | SEC31L2 | 0.46 | TGGACCCCACTGGCTGAGAATCTGG |
| 2 | CD3Z | 0.35 | GCCCCACTGGACAACACTGATTCCT |
| 4 | SH2D1A | 0.45 | AAATGTTTCCTTGTGCCTGCTCCTG |
| 24 | GZMB | 0.35 | TCCTTGTGCCTGCTCCTGTACTTGT |
| 2 | CD1A | 0.45 | GCCCCACTGGACAACACTGATTCCT |
| 24 | SCN3A | 0.31 | TCCTTGTGCCTGCTCCTGTACTTGT |
| 24 | LAIR1 | 0.31 | TCCTTGTGCCTGCTCCTGTACTTGT |
| 16 | AF1Q | 0.3 | TCCTCCATCACCTGAAACACTGGAC |
| 6 | TRB@ | 0.32 | AAGCCTATACGTTTCTGTGGAGTAA |
| 1 | DOCK2 | 0.33 | TCCTGTACTTGTCCTCAGCTTGGGC |
| 16 | MLC1 | 0.31 | TCCTCCATCACCTGAAACACTGGAC |
| 9 | CD3D | 0.31 | TGGACCCCACTGGCTGAGAATCTGG |
| 7 | T3JAM | 0.31 | ACTTGTCCTCAGCTTGGGCTTCTTC |
| 3 | CD6 | 0.38 | TGCCTGCTCCTGTACTTGTCCTCAG |
| 16 | ZAP70 | 0.34 | TCCTCCATCACCTGAAACACTGGAC |
| 24 | IFI44 | 0.37 | TCCTTGTGCCTGCTCCTGTACTTGT |
| 1 | GPR65 | 0.34 | TCCTGTACTTGTCCTCAGCTTGGGC |
| 16 | PRF1 | 0.34 | TCCTCCATCACCTGAAACACTGGAC |
| 7 | AIF1 | 0.33 | ACTTGTCCTCAGCTTGGGCTTCTTC |
| 2 | WDR45 | 0.41 | GCCCCACTGGACAACACTGATTCCT |
| 6 | CD1E | 0.31 | AAGCCTATACGTTTCTGTGGAGTAA |
| 9 | CYFIP2 | 0.32 | TGGACCCCACTGGCTGAGAATCTGG |
| 11 | TARP | 0.42 | CACCCAGCTGGTCCTGTGGATGGGA |
| 9 | TRIM | 0.33 | TGGACCCCACTGGCTGAGAATCTGG |
| 6 | ARHGAP15 | 0.38 | AAGCCTATACGTTTCTGTGGAGTAA |
| 3 | NOTCH1 | 0.32 | TGCCTGCTCCTGTACTTGTCCTCAG |
| 2 | STAG3 | 0.32 | GCCCCACTGGACAACACTGATTCCT |
| 6 | NARF | 0.31 | AAGCCTATACGTTTCTGTGGAGTAA |
| 2 | TM6SF1 | 0.33 | GCCCCACTGGACAACACTGATTCCT |
| 1 | UBASH3A | 0.33 | TCCTGTACTTGTCCTCAGCTTGGGC |
| 7 | MGC5566 | 0.31 | AGTTGTCCTCAGCTTGGGCTTCTTC |

TABLE 73

Dactinomycin biomarkers.

| SEQ ID NO | Gene | Correlation | Medianprobe |
|---|---|---|---|
| 2 | ALDOC | 0.37 | GCCCCACTGGACAACACTGATTCCT |
| 9 | C1QR1 | 0.36 | TGGACCCCACTGGCTGAGAATCTGG |
| 1 | SLA | 0.31 | TCCTGTACTTGTCCTCAGCTTGGGC |
| 6 | WBSCR20A | 0.31 | AAGCCTATACGTTTCTGTGGAGTAA |
| 7 | MFNG | 0.3 | ACTTGTCCTCAGCTTGGGCTTCTTC |
| 2 | SELL | 0.3 | GCCCCACTGGACAACACTGATTCCT |
| 10 | MYB | 0.36 | TTGGACATCTCTAGTGTAGCTGCCA |
| 24 | RHOH | 0.32 | TCCTTGTGCCTGCTCCTGTACTTGT |
| 4 | ZNFN1A1 | 0.3 | AAATGTTTCCTTGTGCCTGCTCCTG |
| 11 | LCP2 | 0.3 | CACCCAGCTGGTCCTGTGGATGGGA |
| 6 | MAP4K1 | 0.34 | AAGCCTATACGTTTCTGTGGAGTAA |
| 24 | CBFA2T3 | 0.35 | TCCTTGTGCCTGCTCCTGTACTTGT |
| 2 | LCP1 | 0.32 | GCCCCACTGGACAACACTGATTCCT |
| 7 | SELPLG | 0.33 | ACTTGTCCTCAGCTTGGGCTTCTTC |
| 2 | CD3Z | 0.35 | GCCCCACTGGACAACACTGATTCCT |
| 9 | LAIR1 | 0.33 | TGGACCCCACTGGCTGAGAATCTGG |
| 6 | WBSCR20C | 0.3 | AAGCCTATACGTTTCTGTGGAGTAA |
| 11 | CD3D | 0.35 | CACCCAGCTGGTCCTGTGGATGGGA |
| 4 | GPR65 | 0.32 | AAATGTTTCCTTGTGCCTGCTCCTG |
| 16 | ARHGAP15 | 0.32 | TCCTCCATCACCTGAAACACTGGAC |
| 24 | FLJ10178 | 0.36 | TCCTTGTGCCTGCTCCTGTACTTGT |
| 16 | NARF | 0.35 | TCCTCCATCACCTGAAACACTGGAC |
| 1 | PUS3 | 0.32 | TCCTGTACTTGTCCTCAGCTTGGGC |

TABLE 74

Tretinoin biomarkers.

| SEQ ID NO | Gene | Correlation | Medianprobe |
|---|---|---|---|
| 6 | PPIB | 0.31 | AAGCCTATACGTTTCTGTGGAGTAA |
| 6 | ZFP36L2 | 0.48 | AAGCCTATACGTTTCTGTGGAGTAA |
| 7 | IFI30 | 0.46 | ACTTGTCCTCAGCTTGGGCTTCTTC |
| 16 | USP7 | 0.35 | TCCTCCATCACCTGAAACACTGGAC |
| 16 | SRM | 0.43 | TCCTCCATCACCTGAAACACTGGAC |
| 3 | SH3BP5 | 0.32 | TGCCTGCTCCTGTACTTGTCCTCAG |
| 10 | ALDOC | 0.41 | TTGGACATCTCTAGTGTAGCTGCCA |
| 7 | FADS2 | 0.33 | ACTTGTCCTCAGCTTGGGCTTCTTC |
| 10 | GUSB | 0.38 | TTGGACATCTCTAGTGTAGCTGCCA |
| 1 | PSCD1 | 0.48 | TCCTGTACTTGTCCTCAGCTTGGGC |
| 1 | IQGAP2 | 0.34 | TCCTGTACTTGTCCTCAGCTTGGGC |
| 2 | STS | 0.34 | GCCCCACTGGACAACACTGATTCCT |
| 9 | MFNG | 0.36 | TGGACCCCACTGGCTGAGAATCTGG |
| 7 | FLI1 | 0.33 | ACTTGTCCTCAGCTTGGGCTTCTTC |
| 9 | PIM2 | 0.35 | TGGACCCCACTGGCTGAGAATCTGG |
| 1 | INPP4A | 0.54 | TCCTGTACTTGTCCTCAGCTTGGGC |
| 2 | LRMP | 0.51 | GCCCCACTGGACAACACTGATTCCT |
| 4 | ICAM2 | 0.3 | AAATGTTTCCTTGTGCCTGCTCCTG |
| 11 | EVI2A | 0.33 | CACCCAGCTGGTCCTGTGGATGGGA |
| 4 | MAL | 0.46 | AAATGTTTCCTTGTGCCTGCTCCTG |
| 10 | BTN3A3 | 0.43 | TTGGACATCTCTAGTGTAGCTGCCA |
| 10 | PTPN7 | 0.4 | TTGGACATCTCTAGTGTAGCTGCCA |
| 10 | IL10RA | 0.42 | TTGGACATCTCTAGTGTAGCTGCCA |
| 6 | SPI1 | 0.41 | AAGCCTATACGTTTCTGTGGAGTAA |
| 3 | TRAF1 | 0.3 | TGCCTGCTCCTGTACTTGTCCTCAG |
| 24 | ITGB7 | 0.33 | TCCTTGTGCCTGCTCCTGTACTTGT |
| 9 | ARHGAP6 | 0.32 | TGGACCCCACTGGCTGAGAATCTGG |
| 2 | MAP4K1 | 0.52 | GCCCCACTGGACAACACTGATTCCT |
| 6 | CD28 | 0.34 | AAGCCTATACGTTTCTGTGGAGTAA |
| 16 | PTP4A3 | 0.3 | TCCTCCATCACCTGAAACACTGGAC |
| 7 | LTB | 0.32 | ACTTGTCCTCAGCTTGGGCTTCTTC |
| 3 | C1orf38 | 0.4 | TGCCTGCTCCTGTACTTGTCCTCAG |
| 16 | WBSCR22 | 0.53 | TCCTCCATCACCTGAAACACTGGAC |
| 16 | CD8B1 | 0.35 | TCCTCCATCACCTGAAACACTGGAC |
| 7 | LCP1 | 0.35 | ACTTGTCCTCAGCTTGGGCTTCTTC |
| 16 | FLJ13052 | 0.31 | TCCTCCATCACCTGAAACACTGGAC |
| 10 | MEF2C | 0.71 | TTGGACATCTCTAGTGTAGCTGCCA |
| 4 | PSCDBP | 0.41 | AAATGTTTCCTTGTGCCTGCTCCTG |
| 9 | IL16 | 0.51 | TGGACCCCACTGGCTGAGAATCTGG |
| 3 | SELPLG | 0.53 | TGCCTGCTCCTGTACTTGTCCTCAG |
| 4 | MAGEA9 | 0.6 | AAATGTTTCCTTGTGCCTGCTCCTG |
| 16 | LAIR1 | 0.43 | TCCTCCATCACCTGAAACACTGGAC |
| 16 | TNFRSF25 | 0.53 | TCCTCCATCACCTGAAACACTGGAC |
| 7 | EVI2B | 0.42 | ACTTGTCCTCAGCTTGGGCTTCTTC |
| 24 | IGJ | 0.37 | TCCTTGTGCCTGCTCCTGTACTTGT |
| 4 | PDCD4 | 0.47 | AAATGTTTCCTTGTGCCTGCTCCTG |

TABLE 74-continued

Tretinoin biomarkers.

| SEQ ID NO | Gene | Correlation | Medianprobe |
|---|---|---|---|
| 11 | RASA4 | 0.52 | CACCCAGCTGGTCCTGTGGATGGGA |
| 6 | HA-1 | 0.73 | AAGCCTATACGTTTCTGTGGAGTAA |
| 1 | PLCL2 | 0.47 | TCCTGTACTTGTCCTCAGCTTGGGC |
| 6 | RNASE6 | 0.31 | AAGCCTATACGTTTCTGTGGAGTAA |
| 10 | WBSCR20C | 0.35 | TTGGACATCTCTAGTGTAGCTGCCA |
| 6 | NUP210 | 0.36 | AAGCCTATACGTTTCTGTGGAGTAA |
| 7 | RPL10L | 0.39 | ACTTGTCCTCAGCTTGGGCTTCTTC |
| 9 | C11orf2 | 0.33 | TGGACCCCACTGGCTGAGAATCTGG |
| 3 | CABC1 | 0.32 | TGCCTGCTCCTGTACTTGTCCTCAG |
| 1 | ARHGEF3 | 0.37 | TCCTGTACTTGTCCTCAGCTTGGGC |
| 3 | TAPBPL | 0.42 | TGCCTGCTCCTGTACTTGTCCTCAG |
| 4 | CHST12 | 0.35 | AAATGTTTCCTTGTGCCTGCTCCTG |
| 3 | FKBP11 | 0.54 | TGCCTGCTCCTGTACTTGTCCTCAG |
| 10 | FLJ35036 | 0.42 | TTGGACATCTCTAGTGTAGCTGCCA |
| 11 | MYLIP | 0.38 | CACCCAGCTGGTCCTGTGGATGGGA |
| 7 | TXNDC5 | 0.31 | ACTTGTCCTCAGCTTGGGCTTCTTC |
| 16 | PACAP | 0.3 | TCCTCCATCACCTGAAACACTGGAC |
| 1 | TOSO | 0.34 | TCCTGTACTTGTCCTCAGCTTGGGC |
| 9 | PNAS-4 | 0.37 | TGGACCCCACTGGCTGAGAATCTGG |
| 6 | IL21R | 0.57 | AAGCCTATACGTTTCTGTGGAGTAA |
| 24 | TCF4 | 0.64 | TCCTTGTGCCTGCTCCTGTACTTGT |

TABLE 75

Ifosfamide biomarkers.

| SEQ ID NO | Gene | Correlation | Medianprobe |
|---|---|---|---|
| 9 | ARHGDIB | 0.36 | TGGACCCCACTGGCTGAGAATCTGG |
| 9 | ZFP36L2 | 0.45 | TGGACCCCACTGGCTGAGAATCTGG |
| 6 | ITM2A | 0.39 | AAGCCTATACGTTTCTGTGGAGTAA |
| 4 | LGALS9 | 0.54 | AAATGTTTCCTTGTGCCTGCTCCTG |
| 1 | INPP5D | 0.53 | TCCTGTACTTGTCCTCAGCTTGGGC |
| 10 | SATB1 | 0.35 | TTGGACATCTCTAGTGTAGCTGCCA |
| 6 | TFDP2 | 0.32 | AAGCCTATACGTTTCTGTGGAGTAA |
| 3 | IL2RG | 0.32 | TGCCTGCTCCTGTACTTGTCCTCAG |
| 7 | CD48 | 0.5 | ACTTGTCCTCAGCTTGGGCTTCTTC |
| 7 | SELL | 0.32 | ACTTGTCCTCAGCTTGGGCTTCTTC |

TABLE 75-continued

Ifosfamide biomarkers.

| SEQ ID NO | Gene | Correlation | Medianprobe |
|---|---|---|---|
| 3 | ADA | 0.32 | TGCCTGCTCCTGTACTTGTCCTCAG |
| 2 | LRMP | 0.34 | GCCCCACTGGACAACACTGATTCCT |
| 6 | RIMS3 | 0.37 | AAGCCTATACGTTTCTGTGGAGTAA |
| 1 | LCK | 0.37 | TCCTGTACTTGTCCTCAGCTTGGGC |
| 11 | CXorf9 | 0.4 | CACCCAGCTGGTCCTGTGGATGGGA |
| 2 | RHOH | 0.3 | GCCCCACTGGACAACACTGATTCCT |
| 10 | ZNFN1A1 | 0.31 | TTGGACATCTCTAGTGTAGCTGCCA |
| 1 | LCP2 | 0.37 | TCCTGTACTTGTCCTCAGCTTGGGC |
| 16 | CD1D | 0.49 | TCCTCCATCACCTGAAACACTGGAC |
| 11 | CD2 | 0.42 | CACCCAGCTGGTCCTGTGGATGGGA |
| 4 | ZNF91 | 0.45 | AAATGTTTCCTTGTGCCTGCTCCTG |
| 24 | MAP4K1 | 0.32 | TCCTTGTGCCTGCTCCTGTACTTGT |
| 10 | CCR7 | 0.44 | TTGGACATCTCTAGTGTAGCTGCCA |
| 3 | IGLL1 | 0.43 | TGCCTGCTCCTGTACTTGTCCTCAG |
| 16 | CD3G | 0.3 | TCCTCCATCACCTGAAACACTGGAC |
| 7 | ZNF430 | 0.31 | ACTTGTCCTCAGCTTGGGCTTCTTC |
| 10 | CCR9 | 0.31 | TTGGACATCTCTAGTGTAGCTGCCA |
| 7 | CXCR4 | 0.37 | ACTTGTCCTCAGCTTGGGCTTCTTC |
| 6 | KIAA0922 | 0.31 | AAGCCTATACGTTTCTGTGGAGTAA |
| 2 | TARP | 0.31 | GCCCCACTGGACAACACTGATTCCT |
| 1 | FYN | 0.35 | TCCTGTACTTGTCCTCAGCTTGGGC |
| 10 | SH2D1A | 0.34 | TTGGACATCTCTAGTGTAGCTGCCA |
| 6 | CD1A | 0.31 | AAGCCTATACGTTTCTGTGGAGTAA |
| 10 | LST1 | 0.33 | TTGGACATCTCTAGTGTAGCTGCCA |
| 7 | LAIR1 | 0.36 | ACTTGTCCTCAGCTTGGGCTTCTTC |
| 9 | TRB@ | 0.34 | TGGACCCCACTGGCTGAGAATCTGG |
| 10 | SEPT6 | 0.39 | TTGGACATCTCTAGTGTAGCTGCCA |
| 16 | CD3D | 0.37 | TCCTCCATCACCTGAAACACTGGAC |
| 4 | CD6 | 0.32 | AAATGTTTCCTTGTGCCTGCTCCTG |
| 3 | AIF1 | 0.34 | TGCCTGCTCCTGTACTTGTCCTCAG |
| 1 | CD1E | 0.31 | TCCTGTACTTGTCCTCAGCTTGGGC |
| 1 | TRIM | 0.32 | TCCTGTACTTGTCCTCAGCTTGGGC |
| 1 | GLTSCR2 | 0.34 | TCCTGTACTTGTCCTCAGCTTGGGC |
| 1 | ARHGAP15 | 0.33 | TCCTGTACTTGTCCTCAGCTTGGGC |
| 3 | BIN2 | 0.33 | TGCCTGCTCCTGTACTTGTCCTCAG |
| 9 | SH3TC1 | 0.32 | TGGACCCCACTGGCTGAGAATCTGG |
| 16 | CECR1 | 0.36 | TCCTCCATCACCTGAAACACTGGAC |

TABLE 75-continued

Ifosfamide biomarkers.

| SEQ ID NO | Gene | Correlation | Medianprobe |
|---|---|---|---|
| 16 | BCL11B | 0.38 | TCCTCCATCACCTGAAACACTGGAC |
| 2 | GIMAP6 | 0.32 | GCCCCACTGGACAACACTGATTCCT |
| 10 | STAG3 | 0.46 | TTGGACATCTCTAGTGTAGCTGCCA |
| 7 | GALNT6 | 0.32 | ACTTGTCCTCAGCTTGGGCTTCTTC |
| 24 | MGC5566 | 0.49 | TCCTTGTGCCTGCTCCTGTACTTGT |
| 1 | PACAP | 0.48 | TCCTGTACTTGTCCTCAGCTTGGGC |
| 3 | LEF1 | 0.4 | TGCCTGCTCCTGTACTTGTCCTCAG |

TABLE 76

Tamoxifen biomarkers.

| SEQ ID NO | Gene | Correlation | Medianprobe |
|---|---|---|---|
| 1 | MLP | 0.33 | TCCTGTACTTGTCCTCAGCTTGGGC |
| 24 | GLUL | 0.33 | TCCTTGTGCCTGCTCCTGTACTTGT |
| 11 | SLC9A3R1 | 0.37 | CACCCAGCTGGTCCTGTGGATGGGA |
| 10 | ZFP36L2 | 0.33 | TTGGACATCTCTAGTGTAGCTGCCA |
| 16 | INSIG1 | 0.31 | TCCTCCATCACCTGAAACACTGGAC |
| 1 | TBL1X | 0.36 | TCCTGTACTTGTCCTCAGCTTGGGC |
| 4 | NDUFAB1 | 0.43 | AAATGTTTCCTTGTGCCTGCTCCTG |
| 9 | EBP | 0.31 | TGGACCCCACTGGCTGAGAATCTGG |
| 10 | TRIM14 | 0.43 | TTGGACATCTCTAGTGTAGCTGCCA |
| 2 | SRPK2 | 0.41 | GCCCCACTGGACAACACTGATTCCT |
| 4 | PMM2 | 0.4 | AAATGTTTCCTTGTGCCTGCTCCTG |
| 6 | CLDN3 | 0.41 | AAGCCTATACGTTTCTGTGGAGTAA |
| 10 | GCH1 | 0.34 | TTGGACATCTCTAGTGTAGCTGCCA |
| 4 | IDI1 | 0.34 | AAATGTTTCCTTGTGCCTGCTCCTG |
| 24 | TTF1 | 0.46 | TCCTTGTGCCTGCTCCTGTACTTGT |
| 11 | MYB | 0.39 | CACCCAGCTGGTCCTGTGGATGGGA |
| 11 | RASGRP1 | 0.32 | CACCCAGCTGGTCCTGTGGATGGGA |
| 9 | HIST1H3H | 0.38 | TGGACCCCACTGGCTGAGAATCTGG |
| 4 | CBFA2T3 | 0.34 | AAATGTTTCCTTGTGCCTGCTCCTG |
| 2 | SRRM2 | 0.43 | GCCCCACTGGACAACACTGATTCCT |
| 1 | ANAPC5 | 0.31 | TCCTGTACTTGTCCTCAGCTTGGGC |
| 1 | MBD4 | 0.5 | TCCTGTACTTGTCCTCAGCTTGGGC |
| 16 | GATA3 | 0.32 | TCCTCCATCACCTGAAACACTGGAC |
| 6 | HIST1H2BG | 0.32 | AAGCCTATACGTTTCTGTGGAGTAA |
| 9 | RAB14 | 0.31 | TGGACCCCACTGGCTGAGAATCTGG |

TABLE 76-continued

Tamoxifen biomarkers.

| SEQ ID NO | Gene | Correlation | Medianprobe |
|---|---|---|---|
| 6 | PIK3R1 | 0.36 | AAGCCTATACGTTTCTGTGGAGTAA |
| 11 | MGC50853 | 0.37 | CACCCAGCTGGTCCTGTGGATGGGA |
| 2 | ELF1 | 0.35 | GCCCCACTGGACAACACTGATTCCT |
| 24 | ZRF1 | 0.32 | TCCTTGTGCCTGCTCCTGTACTTGT |
| 4 | ZNF394 | 0.31 | AAATGTTTCCTTGTGCCTGCTCCTG |
| 4 | S100A14 | 0.39 | AAATGTTTCCTTGTGCCTGCTCCTG |
| 11 | SLC6A14 | 0.31 | CACCCAGCTGGTCCTGTGGATGGGA |
| 16 | GALNT6 | 0.37 | TCCTCCATCACCTGAAACACTGGAC |
| 4 | SPDEF | 0.44 | AAATGTTTCCTTGTGCCTGCTCCTG |
| 6 | TPRT | 0.5 | AAGCCTATACGTTTCTGTGGAGTAA |
| 10 | CALML4 | 0.31 | TTGGACATCTCTAGTGTAGCTGCCA |

TABLE 77

Floxuridine biomarkers.

| SEQ ID NO | Gene | Correlation | Medianprobe |
|---|---|---|---|
| 7 | CSDA | 0.33 | ACTTGTCCTCAGCTTGGGCTTCTTC |
| 9 | F8A1 | 0.31 | TGGACCCCACTGGCTGAGAATCTGG |
| 9 | KYNU | 0.32 | TGGACCCCACTGGCTGAGAATCTGG |
| 6 | PHF14 | 0.31 | AAGCCTATACGTTTCTGTGGAGTAA |
| 16 | SERPINB2 | 0.34 | TCCTCCATCACCTGAAACACTGGAC |
| 2 | OPHN1 | 0.31 | GCCCCACTGGACAACACTGATTCCT |
| 6 | HRMT1L2 | 0.31 | AAGCCTATACGTTTCTGTGGAGTAA |
| 2 | TNFRSF1A | 0.3 | GCCCCACTGGACAACACTGATTCCT |
| 6 | PPP4C | 0.31 | AAGCCTATACGTTTCTGTGGAGTAA |
| 16 | CES1 | 0.3 | TCCTCCATCACCTGAAACACTGGAC |
| 2 | TP53AP1 | 0.3 | GCCCCACTGGACAACACTGATTCCT |
| 2 | TM4SF4 | 0.32 | GCCCCACTGGACAACACTGATTCCT |
| 3 | RPL5 | 0.32 | TGCCTGCTCCTGTACTTGTCCTCAG |
| 9 | BC008967 | 0.32 | TGGACCCCACTGGCTGAGAATCTGG |
| 10 | TLK2 | 0.35 | TTGGACATCTCTAGTGTAGCTGCCA |
| 24 | COL4A6 | 0.31 | TCCTTGTGCCTGCTCCTGTACTTGT |
| 11 | PAK3 | 0.32 | CACCCAGCTGGTCCTGTGGATGGGA |
| 24 | RECK | 0.34 | TCCTTGTGCCTGCTCCTGTACTTGT |
| 6 | LOC51321 | 0.32 | AAGCCTATACGTTTCTGTGGAGTAA |
| 16 | MST4 | 0.36 | TCCTCCATCACCTGAAACACTGGAC |

TABLE 77-continued

Floxuridine biomarkers.

| SEQ ID NO | Gene | Correlation | Medianprobe |
|---|---|---|---|
| 9 | DERP6 | 0.32 | TGGACCCCACTGGCTGAGAATCTGG |
| 24 | SCD4 | 0.33 | TCCTTGTGCCTGCTCCTGTACTTGT |
| 9 | FLJ22800 | 0.31 | TGGACCCCACTGGCTGAGAATCTGG |

TABLE 78

Irinotecan biomarkers.

| SEQ ID NO | Gene | Correlation | Medianprobe |
|---|---|---|---|
| 3 | CSDA | 0.32 | TGCCTGCTCCTGTACTTGTCCTCAG |
| 2 | UBE2L6 | 0.32 | GCCCCACTGGACAACACTGATTCCT |
| 9 | TAP1 | 0.44 | TGGACCCCACTGGCTGAGAATCTGG |
| 3 | RPS19 | 0.32 | TGCCTGCTCCTGTACTTGTCCTCAG |
| 7 | SERPINA1 | 0.32 | ACTTGTCCTCAGCTTGGGCTTCTTC |
| 10 | C1QR1 | 0.31 | TTGGACATCTCTAGTGTAGCTGCCA |
| 11 | SLA | 0.33 | CACCCAGCTGGTCCTGTGGATGGGA |
| 3 | GPSM3 | 0.46 | TGCCTGCTCCTGTACTTGTCCTCAG |
| 3 | PSMB9 | 0.3 | TGCCTGCTCCTGTACTTGTCCTCAG |
| 3 | EDG1 | 0.34 | TGCCTGCTCCTGTACTTGTCCTCAG |
| 2 | FMNL1 | 0.4 | GCCCCACTGGACAACACTGATTCCT |
| 10 | PTPN7 | 0.39 | TTGGACATCTCTAGTGTAGCTGCCA |
| 6 | ZNFN1A1 | 0.32 | AAGCCTATACGTTTCTGTGGAGTAA |
| 10 | CENTB1 | 0.33 | TTGGACATCTCTAGTGTAGCTGCCA |
| 7 | BATF | 0.41 | ACTTGTCCTCAGCTTGGGCTTCTTC |
| 4 | MAP4K1 | 0.39 | AAATGTTTCCTTGTGCCTGCTCCTG |
| 6 | PDE4C | 0.31 | AAGCCTATACGTTTCTGTGGAGTAA |
| 24 | SP110 | 0.35 | TCCTTGTGCCTGCTCCTGTACTTGT |
| 9 | HLA-DRA | 0.31 | TGGACCCCACTGGCTGAGAATCTGG |
| 10 | IFI16 | 0.36 | TTGGACATCTCTAGTGTAGCTGCCA |
| 6 | HLA-DRB1 | 0.32 | AAGCCTATACGTTTCTGTGGAGTAA |
| 7 | ARHGEF6 | 0.43 | ACTTGTCCTCAGCTTGGGCTTCTTC |
| 24 | SELPLG | 0.35 | TCCTTGTGCCTGCTCCTGTACTTGT |
| 11 | SEC31L2 | 0.35 | CACCCAGCTGGTCCTGTGGATGGGA |
| 16 | CD3Z | 0.51 | TCCTCCATCACCTGAAACACTGGAC |
| 10 | PRKCQ | 0.39 | TTGGACATCTCTAGTGTAGCTGCCA |
| 6 | SH2D1A | 0.43 | AAGCCTATACGTTTCTGTGGAGTAA |
| 16 | GZMB | 0.49 | TCCTCCATCACCTGAAACACTGGAC |
| 7 | TRB@ | 0.43 | ACTTGTCCTCAGCTTGGGCTTCTTC |

TABLE 78-continued

Irinotecan biomarkers.

| SEQ ID NO | Gene | Correlation | Medianprobe |
|---|---|---|---|
| 7 | HLA-DPA1 | 0.47 | ACTTGTCCTCAGCTTGGGCTTCTTC |
| 24 | AIM1 | 0.36 | TCCTTGTGCCTGCTCCTGTACTTGT |
| 9 | DOCK2 | 0.39 | TGGACCCCACTGGCTGAGAATCTGG |
| 1 | CD3D | 0.31 | TCCTGTACTTGTCCTCAGCTTGGGC |
| 10 | IFITM1 | 0.31 | TTGGACATCTCTAGTGTAGCTGCCA |
| 2 | ZAP70 | 0.31 | GCCCCACTGGACAACACTGATTCCT |
| 11 | PRF1 | 0.47 | CACCCAGCTGGTCCTGTGGATGGGA |
| 2 | C1orf24 | 0.39 | GCCCCACTGGACAACACTGATTCCT |
| 16 | ARHGAP15 | 0.48 | TCCTCCATCACCTGAAACACTGGAC |
| 11 | C13orf18 | 0.33 | CACCCAGCTGGTCCTGTGGATGGGA |
| 24 | TM6SF1 | 0.37 | TCCTTGTGCCTGCTCCTGTACTTGT |

TABLE 79

Satraplatin biomarkers.

| SEQ ID NO | Gene | Correlation | Medianprobe |
|---|---|---|---|
| 1 | STAT1 | 0.32 | TCCTGTACTTGTCCTCAGCTTGGGC |
| 4 | HSBP1 | 0.33 | AAATGTTTCCTTGTGCCTGCTCCTG |
| 6 | IFI30 | 0.35 | AAGCCTATACGTTTCTGTGGAGTAA |
| 16 | RIOK3 | 0.36 | TCCTCCATCACCTGAAACACTGGAC |
| 7 | TNFSF10 | 0.31 | ACTTGTCCTCAGCTTGGGCTTCTTC |
| 24 | ALOX5AP | 0.3 | TCCTTGTGCCTGCTCCTGTACTTGT |
| 9 | ADFP | 0.33 | TGGACCCCACTGGCTGAGAATCTGG |
| 1 | IRS2 | 0.37 | TCCTGTACTTGTCCTCAGCTTGGGC |
| 10 | EFEMP2 | 0.31 | TTGGACATCTCTAGTGTAGCTGCCA |
| 9 | RTPK2 | 0.35 | TGGACCCCACTGGCTGAGAATCTGG |
| 16 | DKFZp564I1922 | 0.33 | TCCTCCATCACCTGAAACACTGGAC |
| 16 | MT1K | 0.34 | TCCTCCATCACCTGAAACACTGGAC |
| 7 | RNASET2 | 0.38 | ACTTGTCCTCAGCTTGGGCTTCTTC |
| 11 | EFHD2 | 0.31 | CACCCAGCTGGTCCTGTGGATGGGA |
| 2 | TRIB3 | 0.33 | GCCCCACTGGACAACACTGATTCCT |
| 4 | ACSL5 | 0.42 | AAATGTTTCCTTGTGCCTGCTCCTG |
| 7 | IFIH1 | 0.37 | ACTTGTCCTCAGCTTGGGCTTCTTC |
| 3 | DNAPTP6 | 0.42 | TGCCTGCTCCTGTACTTGTCCTCAG |

TABLE 80

Vincristine microRNA biomarkers.

| SEQ ID NO | Medianprobe | Corr | Sequence |
|---|---|---|---|
| 2281 | Hcd892 left | 0.3 | GAGGGCTGGAGAGGTTGGGTGCGCTTGTGCGTTTCACTTT |
| 2282 | Hcd678 right | 0.27 | GCCCTGAAGCTCCGGACTACAGCTCCCAGGCCTCTCCAAG |
| 2283 | mir-007-1-prec | 0.28 | TGTTGGCCTAGTTCTGTGTGGAAGACTAGTGATTTTGTTG |
| 2284 | MPR243 left | 0.25 | GTATTTACCTAGTTGTAATGTGGGTTGCCATGGTGTTTTG |
| 2285 | Hcd654 left | 0.25 | AACGAGTAAAAGGCGTACATGGGAGCGCGGGGCGGCAGAG |
| 2286 | mir-487No1 | 0.26 | TTATGACGAATCATACAGGGACATCCAGTTTTTCAGTATC |
| 2287 | Hcd794 right | 0.35 | GGCCACCACAGACACCAACAAGTTCAGTCCGTTTCTGCAG |
| 2288 | Hcd739 right | 0.32 | TATTAGCTGAGGGAGGGCTGGAGGCGGCTGCATTCCGACT |
| 2289 | Hcd562 right | 0.28 | CGCATGTCCTGGCCCTCGTCCTTCCATGGCACTGGCACCG |

TABLE 81

Cisplatin microRNA biomarkers.

| SEQ ID NO | Medianprobe | Corr | Sequence |
|---|---|---|---|
| 2290 | HUMTRF | 0.34 | GATCTAAAGGTCCCTGGTTCGATCCCGGGTTTCGGCACCA |
| 2291 | HPR187 right | 0.25 | TATTTATTACAAGGTCCTTCTTCCCCGTAAAACTTTGTCC |
| 2292 | mir-450-1 | 0.26 | AACGATACTAAACTGTTTTTGCGATGTGTTCCTAATATGC |
| 2293 | mir-155-prec | 0.31 | TTAATGCTAATCGTGATAGGGGTTTTTGCCTCCAACTGAC |
| 2294 | mir-515-15p | 0.25 | GATCTCATGCAGTCATTCTCCAAAAGAAAGCACTTTCTGT |
| 2295 | mir-181b-precNo2 | 0.25 | ACCATCGACCGTTGATTGTACCCTATGGCTAACCATCATC |
| 2296 | mir-124a-1-prec1 | 0.26 | ATACAATTAAGGCACGCGGTGAATGCCAAGAATGGGGCTG |
| 2297 | mir-450-2No1 | 0.3 | GAAAGATGCTAAACTATTTTTGCGATGTGTTCCTAATATG |
| 2298 | Hcd923 right | 0.31 | CTGGAGATAATGATTCTGCATTTCTAATTAACTCCCAGGT |
| 2299 | mir-342No1 | 0.31 | GTCTCACACAGAAATCGCACCCGTCACCTTGGCCTACTTA |
| 2300 | mir-142-prec | 0.27 | CCCATAAAGTAGAAAGCACTACTAACAGCACTGGAGGGTG |
| 2301 | mir-223-prec | 0.26 | GAGTGTCAGTTTGTCAAATACCCCAAGTGCGGCACATGCT |
| 2302 | Hcd754 left | 0.38 | TCCTCCTCCTCCTTTTCGTTCCGGCTCCCTGGCTGGCTCC |
| 2303 | Hcd213_HPR182 left | 0.3 | CTGTTTCATACTTGAGGAGAAATTATCCTTGGTGTGTTCG |

TABLE 82

Azaguanine microRNA biomarkers.

| SEQ ID NO | Medianprobe | Corr | Sequence |
|---|---|---|---|
| 2304 | MPR121 left | 0.3 | CACCTGGCTCTGAGAACTGAATTCCATAGGCTGTGAGCTC |
| 2305 | HUMTRS | 0.26 | TCTAGCGACAGAGTGGTTCAATTCCACCTTTCGGGCGCCA |
| 2306 | mir-213-precNo1 | 0.26 | AACATTCATTGCTGTCGGTGGGTTGAACTGTGTGGACAAG |
| 2293 | mir-155-prec | 0.4 | TTAATGCTAATCGTGATAGGGGTTTTTGCCTCCAACTGAC |

TABLE 82-continued

Azaguanine microRNA biomarkers.

| SEQ ID NO | Medianprobe | Corr | Sequence |
|---|---|---|---|
| 2308 | mir-147-prec | 0.47 | GACTATGGAAGCCAGTGTGTGGAAATGCTTCTGCTAGATT |
| 2309 | mir-100No1 | 0.26 | CCTGTTGCCACAAACCCGTAGATCCGAACTTGTGGTATTA |
| 2310 | mir-138-1-prec | 0.29 | AGCTGGTGTTGTGAATCAGGCCGTTGCCAATCAGAGAACG |
| 2311 | mir-140No2 | 0.38 | TTCTACCACAGGGTAGAACCACGGACAGGATACCGGGGCA |
| 2312 | mir-146-prec | 0.51 | TGAGAACTGAATTCCATGGGTTGTGTCAGTGTCAGACCTC |
| 2313 | mir-509No1 | 0.25 | ATTAAAAATGATTGGTACGTCTGTGGGTAGAGTACTGCAT |
| 2314 | mir-146bNo1 | 0.33 | CACCTGGCACTGAGAACTGAATTCCATAGGCTGTGAGCTC |
| 2315 | Hcd514 right | 0.26 | ATTAGAGACTCGTTAAGAGAAGGTGAGAAGGGCTCAGTAA |
| 2316 | Hcd397 left | 0.34 | GTGTGTATACTTATGTGTGTGTATGTGTGAGTGTGAATAT |
| 2317 | Hcd731 left | 0.27 | AATTGTGACAACTGAGTGGGAGGTTTGTGTGATGATTATC |
| 2318 | mir-034-precNo2 | 0.32 | AGTAAGGAAGCAATCAGCAAGTATACTGCCCTAGAAGTGC |
| 2319 | mir-100-1/2-prec | 0.3 | TGAGGCCTGTTGCCACAAACCCGTAGATCCGAACTTGTGG |

TABLE 83

Etoposide microRNA biomarkers.

| SEQ ID NO | Medianprobe | Corr | Sequence |
|---|---|---|---|
| 2320 | Hcd415 right | 0.28 | GATGTTTGGGAAACAATGGGAGTGAGAGAATGGGAGAGCT |
| 2321 | Hcd768 right | 0.37 | GCCCTGGCGGAACGCTGAGAAGACAGTCGAACTTGACTAT |
| 2290 | HUMTRF | 0.38 | GATCTAAAGGTCCCTGGTTCGATCCCGGGTTTCGGCACCA |
| 2323 | Hcd866 right | 0.26 | GTCATGCTGCCACCAGCAGGCAGAGAAGAAGCAGAAGAAC |
| 2324 | Hcd145 left | 0.33 | AAAAATCCCAGCGGCCACCTTTCCTCCCTGCCCCATTGGG |
| 2325 | HUMTRAB | 0.29 | ATGGTAGAGCGCTCGCTTTGCTTGCGAGAGGTAGCGGGAT |
| 2326 | Hcd913 right | 0.36 | CAAACATCATGTGACGTCTGTGGAGCGGCGGCGGCGGCGG |
| 2327 | HPR163 left | 0.29 | GCTGCCCCCTCCCTTAGCAACGTGGCCCCGGCGTTCCAAA |
| 2328 | Hcd697 right | 0.27 | GGCCTCATGCTGCCAAGGGCTGGCAAGAAGTCCCTGCTTG |
| 2329 | Hcd755 left | 0.26 | GGAAGTGGAGCAAATGGATGGAAAGCAATTTTTGGAAGAT |
| 2330 | Hcd716 right | 0.25 | CAATAAATGTGCCTATAAAGGCGCCGGCTCCGGGGCGCGG |
| 2331 | MPR207 right | 0.33 | AACAACTTTGTGCTGGTGCCGGGGAAGTTTGTGTCTCCTA |
| 2332 | HSTRNL | 0.26 | TCCGGATGGAGCGTGGGTTCGAATCCCACTTCTGACACCA |
| 2333 | HPR206 left | 0.29 | CTATATTGGACCGCAGCGCTGAGAGCTTTTGTGTTTAATG |
| 2284 | MPR243 left | 0.27 | GTATTTACCTAGTTGTAATGTGGGTTGCCATGGTGTTTTG |
| 2285 | Hcd654 left | 0.4 | AACGAGTAAAGGCGTACATGGGAGCGCGGGGCGGCAGAG |
| 2336 | MPR130 left | 0.28 | AGGCCAAGGTGACGGGTGCGATTTCTGTGTGAGACAATTC |
| 2337 | Hcd782 left | 0.26 | GGAGCCCTGTCTGCAAAGAGTGGTGCGTGTGCGTGTGTGA |
| 2287 | Hcd794 right | 0.26 | GGCCACCACAGACACCAACAAGTTCAGTCCGTTTCTGCAG |

TABLE 83-continued

Etoposide microRNA biomarkers.

| SEQ ID NO | Medianprobe | Corr | Sequence |
|---|---|---|---|
| 2288 | Hcd739 right | 0.3 | TATTAGCTGAGGGAGGGCTGGAGGCGGCTGCATTCCGACT |
| 2300 | mir-142-prec | 0.29 | CCCATAAAGTAGAAAGCACTACTAACAGCACTGGAGGGTG |
| 2341 | HSHELA01 | 0.29 | GGCCGCAGCAACCTCGGTTCGTATCCGAGTCACGGCACCA |
| 2342 | HUMTRV1A | 0.29 | ACGCGAAAGGTCCCCGGTTCGAAACCGGGCGGAAACACCA |
| 2302 | Hcd754 left | 0.34 | TCCTCCTCCTCCTTTTCGTTCCGGCTCCCTGGCTGGCTCC |

TABLE 84

Carboplatin microRNA biomarkers.

| SEQ ID NO | Medianprobe | Corr | Sequence |
|---|---|---|---|
| 2344 | Hcd829 right | 0.27 | AAAATGGCGGCGGGAAAAGCGAGCGGCGAGAGCGAGGAGG |
| 2290 | HUMTRF | 0.26 | GATCTAAAGGTCCCTGGTTCGATCCCGGGTTTCGGCACCA |
| 2346 | HPR187 left | 0.29 | TGTGTGTTGCGGGGGTGGGGGCCGGTGAAAGTGATTTGAT |
| 2347 | Hcd210_HPR205 right | 0.32 | CGAAACATTCGCGGTGCACTTCTTTTTCAGTATCCTATTC |
| 2348 | mir-379No1 | 0.26 | TTCCGTGGTTCCTGAAGAGATGGTAGACTATGGAACGTAG |
| 2306 | mir-213-precNo1 | 0.26 | AACATTCATTGCTGTCGGTGGGTTGAACTGTGTGGACAAG |
| 2350 | mir-4325p | 0.29 | CCAGGTCTTGGAGTAGGTCATTGGGTGGATCCTCTATTTC |
| 2292 | mir-450-1 | 0.3 | AACGATACTAAACTGTTTTTGCGATGTGTTCCTAATATGC |
| 2293 | mir-155-prec | 0.25 | TTAATGCTAATCGTGATAGGGGTTTTTGCCTCCAACTGAC |
| 2353 | Hcd28_HPR39right | 0.26 | AAGCTCCCAAATTAGCTTTTTAAATAGAAGCTGAGAGTTA |
| 2354 | MPR244 right | 0.27 | TAAACATAGAGGAAATTTCACGTTTTCAGTGTCAAATGCT |
| 2355 | mir-409-3p | 0.3 | GACGAATGTTGCTCGGTGAACCCCTTTTCGGTATCAAATT |
| 2296 | mir-124a-1-prec1 | 0.28 | ATACAATTAAGGCACGCGGTGAATGCCAAGAATGGGGCTG |
| 2357 | mir-154-prec1No1 | 0.26 | GTGGTACTTGAAGATAGGTTATCCGTGTTGCCTTCGCTTT |
| 2358 | mir-495No1 | 0.32 | GTGACGAAACAAACATGGTGCACTTCTTTTTCGGTATCAA |
| 2359 | mir-515-23p | 0.25 | CAGAGTGCCTTCTTTTGGAGCGTTACTGTTTGAGAAAAAC |
| 2360 | Hcd438 right | 0.27 | GTGTTTATTTGAATCTCACATCGCTCATAAGAATACACGC |
| 2361 | Hcd770 left | 0.3 | CCAGTATACAATCCGTTTTTCAGTTTAGCTTGAGATCAGA |
| 2362 | mir-382 | 0.32 | GGTACTTGAAGAGAAGTTGTTCGTGGTGGATTCGCTTTAC |
| 2301 | mir-223-prec | 0.3 | GAGTGTCAGTTTGTCAAATACCCCAAGTGCGGCACATGCT |
| 2302 | Hcd754 left | 0.48 | TCCTCCTCCTCCTTTTCGTTCCGGCTCCCTGGCTGGCTCC |
| 2303 | Hcd213_HPR182 left | 0.31 | CTGTTTCATACTTGAGGAGAAATTATCCTTGGTGTGTTCG |

TABLE 85

Adriamycin microRNA biomarkers.

| SEQ ID NO | Medianprobe | Corr | Sequence |
|---|---|---|---|
| 2321 | Hcd768 right | 0.25 | GCCCTGGCGGAACGCTGAGAAGACAGTCGAACTTGACTAT |
| 2367 | mir-483No1 | 0.28 | ATCACGCCTCCTCACTCCTCTCCTCCCGTCTTCTCCTCTC |
| 2324 | Hcd145 left | 0.28 | AAAAATCCCAGCGGCCACCTTTCCTCCCTGCCCCATTGGG |
| 2369 | mir-197-prec | 0.25 | TAAGAGCTCTTCACCCTTCACCACCTTCTCCACCCAGCAT |
| 2370 | mir-212-precNo1 | 0.27 | CCTCAGTAACAGTCTCCAGTCACGGCCACCGACGCCTGGC |
| 2327 | HPR163 left | 0.3 | GCTGCCCCCTCCCTTAGCAACGTGGCCCCGGCGTTCCAAA |
| 2285 | Hcd654 left | 0.26 | AACGAGTAAAAGGCGTACATGGGAGCGCGGGGCGGCAGAG |
| 2299 | mir-342No1 | 0.32 | GTCTCACACAGAAATCGCACCCGTCACCTTGGCCTACTTA |
| 2287 | Hcd794 right | 0.32 | GGCCACCACAGACACCAACAAGTTCAGTCCGTTTCTGCAG |
| 2300 | mir-142-prec | 0.38 | CCCATAAAGTAGAAAGCACTACTAACAGCACTGGAGGGTG |
| 2302 | Hcd754 left | 0.28 | TCCTCCTCCTCCTTTTCGTTCCGGCTCCCTGGCTGGCTCC |

TABLE 86

Aclarubicin microRNA biomarkers.

| SEQ ID NO | Medianprobe | Corr | Sequence |
|---|---|---|---|
| 2377 | mir-092-prec-X = 092-2 | 0.32 | GTTCTATATAAAGTATTGCACTTGTCCCGGCCTGTGGAAG |
| 2378 | mir-096-prec-7No2 | 0.29 | TGGCCGATTTTGGCACTAGCACATTTTGCTTGTGTCTCT |
| 2379 | Hcd605 left | 0.26 | ATTACTAGCAGTTAATGATTGGTTTGTTAGTTAATGGCCC |
| 2380 | mir-007-2-precNo2 | 0.34 | GGACCGGCTGGCCCCATCTGGAAGACTAGTGATTTTGTTG |
| 2381 | mir-019b-2-prec | 0.28 | GTGGCTGTGCAAATCCATGCAAAACTGATTGTGATAATGT |
| 2382 | MPR216 left | 0.26 | GATCCTAGTAGTGCCAAAGTGCTCATAGTGCAGGTAGTTT |
| 2383 | mir-019b-1-prec | 0.25 | TTCTGCTGTGCAAATCCATGCAAAACTGACTGTGGTAGTG |
| 2384 | mir-135-2-prec | 0.26 | CACTCTAGTGCTTTATGGCTTTTTATTCCTATGTGATAGT |
| 2332 | HSTRNL | 0.26 | TCCGGATGGAGCGTGGGTTCGAATCCCACTTCTGACACCA |
| 2386 | mir-025-prec | 0.31 | ACGCTGCCCTGGGCATTGCACTTGTCTCGGTCTGACAGTG |
| 2283 | mir-007-1-prec | 0.4 | TGTTGGCCTAGTTCTGTGTGGAAGACTAGTGATTTTGTTG |
| 2388 | mir-019a-prec | 0.26 | TGTAGTTGTGCAAATCTATGCAAAACTGATGGTGGCCTGC |
| 2389 | mir-380-5p | 0.31 | AGGTACCTGAAAAGATGGTTGACCATAGAACATGCGCTAT |
| 2390 | mir-093-prec-7.1 = 093-1 | 0.37 | CCAAAGTGCTGTTCGTGCAGGTAGTGTGATTACCCAACCT |
| 2391 | mir-106-prec-X | 0.37 | CCTTGGCCATGTAAAAGTGCTTACAGTGCAGGTAGCTTTT |
| 2300 | mir-142-prec | 0.32 | CCCATAAAGTAGAAAGCACTACTAACAGCACTGGAGGGTG |
| 2393 | mir-018-prec | 0.31 | TAAGGTGCATCTAGTGCAGATAGTGAAGTAGATTAGCATC |
| 2394 | mir-020-prec | 0.36 | TAAAGTGCTTATAGTGCAGGTAGTGTTTAGTTATCTACTG |

TABLE 87

Mitoxantrone microRNA biomarkers.

| SEQ ID NO | Medianprobe | Corr | Sequence |
|---|---|---|---|
| 2395 | Hcd768 left | 0.26 | GATGGTTTAGTGAGGCCCTCGGATCAGCCCGCTGGGTCAG |
| 2290 | HUMTRF | 0.31 | GATCTAAAGGTCCCTGGTTCGATCCCGGGTTTCGGCACCA |
| 2306 | mir-213-precNo1 | 0.28 | AACATTCATTGCTGTCGGTGGGTTGAACTGTGTGGACAAG |
| 2398 | mir-181b-precNo1 | 0.26 | TGAGGTTGCTTCAGTGAACATTCAACGCTGTCGGTGAGTT |
| 2354 | M2R244 right | 0.27 | TAAACATAGAGGAAATTTCACGTTTTCAGTGTCAAATGCT |
| 2355 | mir-409-3p | 0.29 | GACGAATGTTGCTCGGTGAACCCCTTTTCGGTATCAAATT |
| 2332 | HSTRNL | 0.33 | TCCGGATGGAGCGTGGGTTCGAATCCCACTTCTGACACCA |
| 2362 | mir-382 | 0.34 | GGTACTTGAAGAGAAGTTGTTCGTGGTGGATTCGCTTTAC |
| 2299 | mir-342No1 | 0.3 | GTCTCACACAGAAATCGCACCCGTCACCTTGGCCTACTTA |
| 2300 | mir-142-prec | 0.27 | CCCATAAAGTAGAAAGCACTACTAACAGCACTGGAGGGTG |
| 2405 | Hcd200 right | 0.29 | CAATTAGCCAATTGTGGGTATAATTAGCTGCATGTAGAAT |

TABLE 88

Mitomycin microRNA biomarkers.

| SEQ ID NO | Medianprobe | Corr | Sequence |
|---|---|---|---|
| 2290 | HUMTRF | 0.26 | GATCTAAAGGTCCCTGGTTCGATCCCGGGTTTCGGCACCA |
| 2407 | Hcd148_HPR225left | 0.27 | AATTAATGACCAAAATGTCAGATGTGTCCACAGCTAATTA |
| 2408 | Hcd938 right | 0.26 | ATTCCCTGCATCACTCTCATGAAATGGCTGAGAAAGTGAG |
| 2409 | MPR174 left | 0.32 | GAGCCGGTCTCTTTACATCTCAAATACCAGGTATTTAGGT |
| 2410 | mir-4323p | 0.29 | CCTTACGTGGGCCACTGGATGGCTCCTCCATGTCTTGGAG |

TABLE 89

Paclitaxel (Taxol) microRNA biomarkers.

| SEQ ID NO | Medianprobe | Corr | Sequence |
|---|---|---|---|
| 2377 | mir-092-prec-X = 092-2 | 0.29 | GTTCTATATAAAGTATTGCACTTGTCCCGGCCTGTGGAAG |
| 2412 | mir-096-prec-7No1 | 0.36 | CTCCGCTCTGAGCAATCATGTGCAGTGCCAATATGGGAAA |
| 2413 | mir-101-prec-9 | 0.38 | GCTGTATATCTGAAAGGTACAGTACTGTGATAACTGAAGA |
| 2414 | mir-20bNo1 | 0.28 | AGTACCAAAGTGCTCATAGTGCAGGTAGTTTTGGCATGAC |
| 2381 | mir-019b-2-prec | 0.28 | GTGGCTGTGCAAATCCATGCAAAACTGATTGTGATAATGT |
| 2416 | mir-032-precNo2 | 0.29 | GGAGATATTGCACATTACTAAGTTGCATGTTGTCACGGCC |
| 2417 | MPR156 left | 0.25 | TCCCTCACTTGAACTGACTGCCAGAGTTCACAGACAGCTG |
| 2383 | mir-019b-1-prec | 0.28 | TTCTGCTGTGCAAATCCATGCAAAACTGACTGTGGTAGTG |
| 2384 | mir-135-2-prec | 0.36 | CACTCTAGTGCTTTATGGCTTTTTATTCCTATGTGATAGT |
| 2386 | mir-025-prec | 0.36 | ACGCTGCCCTGGGCATTGCACTTGTCTCGGTCTGACAGTG |

TABLE 89-continued

Paclitaxel (Taxol) microRNA biomarkers.

| SEQ ID NO | Medianprobe | Corr | Sequence |
|---|---|---|---|
| 2283 | mir-007-1-prec | 0.27 | TGTTGGCCTAGTTCTGTGTGGAAGACTAGTGATTTTGTTG |
| 2422 | mir-361No1 | 0.29 | GGATTTGGGAGCTTATCAGAATCTCCAGGGGTACTTTATA |
| 2390 | mir-093-prec-7.1 = 093-1 | 0.37 | CCAAAGTGCTGTTCGTGCAGGTAGTGTGATTACCCAACCT |
| 2391 | mir-106-prec-X | 0.38 | CCTTGGCCATGTAAAAGTGCTTACAGTGCAGGTAGCTTTT |
| 2425 | mir-098-prec-X | 0.29 | TGAGGTAGTAAGTTGTATTGTTGTGGGGTAGGGATATTAG |
| 2300 | mir-142-prec | 0.27 | CCCATAAAGTAGAAAGCACTACTAACAGCACTGGAGGGTG |
| 2427 | HPR169 right | 0.26 | GTTTCTTTCTCACGGTAACTGGCAGCCTCGTTGTGGGCTG |
| 2393 | mir-018-prec | 0.4 | TAAGGTGCATCTAGTGCAGATAGTGAAGTAGATTAGCATC |
| 2394 | mir-020-prec | 0.36 | TAAAGTGCTTATAGTGCAGGTAGTGTTTAGTTATCTACTG |

TABLE 90

Gemcitabine (Gemzar) microRNA biomarkers.

| SEQ ID NO | Medianprobe | Corr | Sequence |
|---|---|---|---|
| 2430 | mir-123-precNo2 | 0.27 | TGTGACACTTCAAACTCGTACCGTGAGTAATAATGCGCCG |
| 2431 | Hcd257 right | 0.29 | CTTGGTTTTTGCAATAATGCTAGCAGAGTACACACAAGAA |
| 2493 | mir-155-prec | 0.35 | TTAATGCTAATCGTGATAGGGGTTTTTGCCTCCAACTGAC |
| 2433 | ath-MIR180aNo2 | 0.26 | TGAGAATCTTGATGATGCTGCATCGGCAATCAACGACTAT |
| 2434 | Hcd448 left | 0.33 | TGTAATTCCATTGAGGGTTTCTGGTGACTCCAGCTTCGTA |
| 2332 | HSTRNL | 0.31 | TCCGGATGGAGCGTGGGTTCGAATCCCACTTCTGACACCA |
| 2436 | MPR174 right | 0.29 | CATTAGGGACACGTGTGAGTGTGCCAGGCTCATTCCTGAG |
| 2405 | Hcd200 right | 0.29 | CAATTAGCCAATTGTGGGTATAATTAGCTGCATGTAGAAT |
| 2410 | mir-4323p | 0.26 | CCTTACGTGGGCCACTGGATGGCTCCTCCATGTCTTGGAG |
| 2439 | HPR244 right | 0.3 | TAGTTCATGGCGTCCAGCAGCAGCTTCTGGCAGACCGGGT |

TABLE 91

Taxotere (docetaxel) microRNA biomarkers.

| SEQ ID NO | Medianprobe | Corr | Sequence |
|---|---|---|---|
| 2412 | mir-096-prec-7No1 | 0.28 | CTCCGCTCTGAGCAATCATGTGCAGTGCCAATATGGGAAA |
| 2441 | mir-095-prec-4 | 0.27 | CGTTACATTCAACGGGTATTTATTGAGCACCCACTCTGTG |
| 2332 | HSTRNL | 0.26 | TCCGGATGGAGCGTGGGTTCGAATCCCACTTCTGACACCA |
| 2283 | mir-007-1-prec | 0.37 | TGTTGGCCTAGTTCTGTGTGGAAGACTAGTGATTTTGTTG |

TABLE 92

Dexamethasone microRNA biomarkers.

| SEQ ID NO | Medianprobe | Corr | Sequence |
|---|---|---|---|
| 2444 | MPR141 left | 0.42 | CTCAGTCGTGCCCTAGCAGCGGGAACAGTACTGCAGTGAG |
| 2445 | mir-424No2 | 0.35 | GTTCAAAACGTGAGGCGCTGCTATACCCCCTCGTGGGGAA |
| 2446 | Hcd690 right | 0.26 | GGACAAGGGAGGAGACACGCAGAGGTGACAGAAAGGTTAG |
| 2447 | Hcd783 left | 0.26 | CAGGCTCACACCTCCCTCCCCCAACTCTCTGGAATGTATA |
| 2448 | mir-150-prec | 0.38 | CTCCCCATGGCCCTGTCTCCCAACCCTTGTACCAGTGCTG |
| 2449 | Hcd266 left | 0.37 | AAGGTCTTTGGTCTTGGAGGAAGGTGTGCTACTGGAAGAG |
| 2450 | mir-503No1 | 0.34 | CTCAGCCGTGCCCTAGCAGCGGGAACAGTTCTGCAGTGAG |
| 2451 | mir-128b-precNo1 | 0.29 | TCACAGTGAACCGGTCTCTTTCCCTACTGTGTCACACTCC |
| 2316 | Hcd397 left | 0.26 | GTGTGTATACTTATGTGTGTGTATGTGTGAGTGTGAATAT |
| 2453 | mir-484 | 0.38 | GTCAGGCTCAGTCCCCTCCCGATAAACCCCTAAATAGGGA |

TABLE 93

Ara-C (Cytarabine hydrochloride) microRNA biomarkers.

| SEQ ID NO | Medianprobe | Corr | Sequence |
|---|---|---|---|
| 2290 | HUMTRF | 0.33 | GATCTAAAGGTCCCTGGTTCGATCCCGGGTTTCGGCACCA |
| 2293 | mir-155-prec | 0.28 | TTAATGCTAATCGTGATAGGGGTTTTTGCCTCCAACTGAC |
| 2294 | mir-515-15p | 0.27 | GATCTCATGCAGTCATTCTCCAAAAGAAAGCACTTTCTGT |
| 2408 | Hcd938 right | 0.26 | ATTCCCTGCATCACTCTCATGAAATGGCTGAGAAAGTGAG |
| 2458 | Hcd642 right | 0.25 | TCAGGGTTTATGAAGTTATCAAAGCCCCTTGATGGAATTA |
| 2459 | Hcd120 left | 0.26 | CTTGGTGTGTTCTCGGTAGCTATGGAAATCCCAGGGTTTC |
| 2389 | mir-380-5p | 0.25 | AGGTACCTGAAAAGATGGTTGACCATAGAACATGCGCTAT |
| 2299 | mir-342No1 | 0.25 | GTCTCACACAGAAATCGCACCCGTCACCTTGGCCTACTTA |
| 2300 | mir-142-prec | 0.27 | CCCATAAAGTAGAAAGCACTACTAACAGCACTGGAGGGTG |
| 2301 | mir-223-prec | 0.31 | GAGTGTCAGTTTGTCAAATACCCCAAGTGCGGCACATGCT |
| 2410 | mir-4323p | 0.28 | CCTTACGTGGGCCACTGGATGGCTCCTCCATGTCTTGGAG |

TABLE 94

Methylprednisolone microRNA biomarkers.

| SEQ ID NO | Medianprobe | Corr | Sequence |
|---|---|---|---|
| 2465 | Hcd544 left | 0.26 | TTCCAGGTGTCCACCAAGGACGTGCCGCTGGCGCTGATGG |
| 2466 | mir-181c-precNo1 | 0.28 | TGCCAAGGGTTTGGGGGAACATTCAACCTGTCGGTGAGTT |
| 2467 | Hcd517 left | 0.25 | TTAAAGCAGGAGAGGTGAGAGGAAGAATTAATGTGTGCTC |
| 2468 | MPR151 left | 0.27 | GGGATTAATGACCAGCTGGGGGAGTTGATAGCCCTCAGTG |

TABLE 94-continued

Methylprednisolone microRNA biomarkers.

| SEQ ID NO | Medianprobe | Corr | Sequence |
|---|---|---|---|
| 2306 | mir-213-precNo1 | 0.34 | AACATTCATTGCTGTCGGTGGGTTGAACTGTGTGGACAAG |
| 2295 | mir-181b-precNo2 | 0.36 | ACCATCGACCGTTGATTGTACCCTATGGCTAACCATCATC |
| 2448 | mir-150-prec | 0.27 | CTCCCCATGGCCCTGTCTCCCAACCCTTGTACCAGTGCTG |
| 2472 | mir-153-1-prec1 | 0.28 | CAGTTGCATAGTCACAAAAGTGATCATTGGCAGGTGTGGC |
| 2451 | mir-128b-precNo1 | 0.48 | TCACAGTGAACCGGTCTCTTTCCCTACTGTGTCACACTCC |
| 2474 | Hcd812 left | 0.25 | CTGTGGGATCTGGTTCTGTAGCTGAGAGCACATCGCTAAA |
| 2475 | mir-195-prec | 0.3 | TCTAGCAGCACAGAAATATTGGCACAGGGAAGCGAGTCTG |
| 2299 | mir-342No1 | 0.38 | GTCTCACACAGAAATCGCACCCGTCACCTTGGCCTACTTA |
| 2477 | mir-370No1 | 0.28 | TTACACAGCTCACGAGTGCCTGCTGGGGTGGAACCTGGTC |
| 2300 | mir-142-prec | 0.32 | CCCATAAAGTAGAAAGCACTACTAACAGCACTGGAGGGTG |
| 2301 | mir-223-prec | 0.36 | GAGTGTCAGTTTGTCAAATACCCCAAGTGCGGCACATGCT |
| 2453 | mir-484 | 0.36 | GTCAGGCTCAGTCCCCTCCCGATAAACCCCTAAATAGGGA |

TABLE 95

Methotrexate microRNA biomarkers.

| SEQ ID NO | Medianprobe | Corr | Sequence |
|---|---|---|---|
| 2377 | mir-092-prec-X = 092-2 | 0.37 | GTTCTATATAAAGTATTGCACTTGTCCCGGCCTGTGGAAG |
| 2412 | mir-096-prec-7No1 | 0.33 | CTCCGCTCTGAGCAATCATGTGCAGTGCCAATATGGGAAA |
| 2483 | mir-123-precNo1 | 0.25 | GACGGGACATTATTACTTTTGGTACGCGCTGTGACACTTC |
| 2484 | Hcd250 left | 0.26 | GTTCTGTTGCTAAGACAACAGGATGCTAGCAGGCATATGC |
| 2485 | mir-518e/526c | 0.3 | TCTCAGGCTGTGACCCTCTAGAGGGAAGCGCTTTCTGTTG |
| 2486 | HPR232 right | 0.3 | TGAATTATTGCACAATAAATTCATGCCCTCTTGTGTCTTA |
| 2487 | Hcd263 left | 0.29 | GAGCATTAAGATTTCCTATTCTTTGAGGCAAATATTGACC |
| 2488 | mir-516-33p | 0.35 | GTGAAAGAAAGTGCTTCCTTTCAGAGGGTTACTCTTTGAG |
| 2379 | Hcd605 left | 0.27 | ATTACTAGCAGTTAATGATTGGTTTGTTAGTTAATGGCCC |
| 2490 | Hcd373 right | 0.25 | CCTGAAAGGTCTGGTGTTAAGCAAATACTCGGTGACCAGA |
| 2491 | MPR254 right | 0.28 | GTTCACAGTGGGAGAAATATGCTTCGTATTACTCTTTCTC |
| 2492 | MPR215 left | 0.3 | CAGCTATGTGGACTCTAGCTGCCAAAGGCGCTTCTCCTTC |
| 2290 | HUMTRF | 0.28 | GATCTAAAGGTCCCTGGTTCGATCCCGGGTTTCGGCACCA |
| 2391 | mir-106aNo1 | 0.27 | CCTTGGCCATGTAAAAGTGCTTACAGTGCAGGTAGCTTTT |
| 2414 | mir-20bNo1 | 0.37 | AGTACCAAAGTGCTCATAGTGCAGGTAGTTTTGGCATGAC |
| 2496 | Hcd361 right | 0.28 | AACTTGGCTACAAGGCTCTTTCCCTCTCTATGAAGGACAG |
| 2497 | Hcd412 left | 0.25 | AGTTGGGGAGAACTTTATGATTATTCTCATGCATCATCTT |
| 2498 | Hcd781 left | 0.26 | GAGTGTGGATCTAATCTTCAGCTGATTAAATGTCCCTCAT |
| 2381 | mir-019b-2-prec | 0.33 | GTGGCTGTGCAAATCCATGCAAAACTGATTGTGATAATGT |

TABLE 95-continued

Methotrexate microRNA biomarkers.

| SEQ ID NO | Medianprobe | Corr | Sequence |
|---|---|---|---|
| 2500 | HPR214 right | 0.29 | AGCAAAAGCTATTATTTGCCCTTGATGAGCCAATCAGATG |
| 2501 | Hcd807 right | 0.26 | GCGCTGACAAATCTTGCCTGATTCTGTATGATCCATGAGA |
| 2502 | Hcd817 left | 0.37 | TAATGAGAATTATGTTTGCACATTGAGGCAGGATAAATCC |
| 2503 | Hcd788 left | 0.25 | GACAAACATGCAGGAAAAATTATCCCCTGGGGATTCTACA |
| 2504 | Hcd970 left | 0.31 | TTGTGGGTCAGCTGCCCAGCTATCGGCTGGATTAGTGAAT |
| 2407 | Hcd148_HPR225left | 0.26 | AATTAATGACCAAAATGTCAGATGTGTCCACAGCTAATTA |
| 2506 | Hcd102 left | 0.27 | ACTGGAATTATGTTTTATCTTAAGTCCACACTGGATCCTC |
| 2507 | Hcd246 right | 0.29 | TAAAGTGAGTTATGGAGGTTACTCTCCTGTGAGAGGAAAT |
| 2508 | HPR199 right | 0.28 | TACACCTAAGGCATGTACTGTATTAATGAACCAATAAAAC |
| 2509 | HPR233 right | 0.27 | CATGATGGGGTGGGGTGAGATGGGGAGCGAAGACTATTAC |
| 2510 | Hcd383 left | 0.28 | GCCCGGGCATGCATTTTATCTAGCACCATGTGTTTCAGCT |
| 2486 | MPR224 right | 0.29 | TGAATTATTGCACAATAAATTCATGCCCTGTTGTGTCTTA |
| 2512 | HPR172 right | 0.26 | GTTTAAACAGCCAGTGCAAACATTTAGATCTGAGTCAAAA |
| 2382 | MPR216 left | 0.34 | GATCCTAGTAGTGCCAAAGTGCTCATAGTGCAGGTAGTTT |
| 2514 | mir-321No2 | 0.25 | CAGGGATTGTGGGTTCGAGTCCCACCCGGGGTAAAGAAAG |
| 2515 | Hcd586 right | 0.28 | GAACTGTTTGCTTTGGATGGGCTTGGTCCTCATTGGCTGA |
| 2516 | Hcd587 right | 0.3 | AAATAATGACTGGCCATAAGATCAAGACAAGTGTCCAAAG |
| 2517 | Hcd249 right | 0.39 | CAGGTACATGTTGATCAGCAGGGGCTGGGAGGCGCCGCTC |
| 2518 | Hcd279 right | 0.27 | CTCACGGCGTTGCCATGGAGACAACTCCGGGGCTGGGGCTC |
| 2519 | HPR159 left | 0.3 | TCCGTCACTTGAACTGGCTGCCAGCGTTCACAGACAGCTG |
| 2520 | Hcd689 right | 0.28 | GTACATCTGGATGTAGTTGTGCTGCAGCTGCTTCTGGTAG |
| 2521 | Hcd691 right | 0.32 | CGGCAAAAACCTCTGTCAGAACAAAATTAGGTGATCTATC |
| 2383 | mir-019b-1-prec | 0.32 | TTCTGCTGTGCAAATCCATGCAAAACTGACTGTGGTAGTG |
| 2523 | Hcd413 right | 0.26 | CACAAAAAGGCATAAGCAGACATCTTGCCCTTTGGTTTCT |
| 2524 | Hcd581 right | 0.26 | AGGAGATATGCCAAGATATATTCACAGCTTTATATACACA |
| 2525 | Hcd536_HPR104 right | 0.28 | GCTGCTCTGCTGAGGGGCTGGACTCTGTCCAGAAGCACCA |
| 2526 | Hcd230 left | 0.28 | CATTCTCTACAAGCATATGGCCTTGGGACATTAAGATGGC |
| 2527 | HPR154 left | 0.28 | AACATCAAGATCTATTGACCTGAGAGGTAAATATTGACCG |
| 2528 | Hcd270 right | 0.31 | AAATGTTGTTATAGTATCCCACCTACCCTGATGTATCTTT |
| 2529 | Hcd649 right | 0.26 | GAACAGGCTTCAAGGTTCTTGGCAGGAATATTCCGTGTAG |
| 2530 | Hcd889 right | 0.27 | ATGCCTTGTGCTCTGTGCTAATTCAGAAGAATAAGCCTGT |
| 2531 | Hcd938 left | 0.36 | CTTGTCGACTAGCCAGTTATGAACAGAGGAGGATGTTCTC |
| 2532 | HPR266 right | 0.32 | GGAGATCCCTTCAAGGTACTTAGTTTTAAATGAGTGCTCT |
| 2386 | mir-025-prec | 0.39 | ACGCTGCCCTGGGCATTGCACTTGTCTCGGTCTGACAGTG |
| 2534 | Hcd355_HPR190 left | 0.25 | TTGTGCACTGCACAACCCTAGTGGCGCCATTCAATTATAG |
| 2535 | MPR162 left | 0.26 | CTCTCTTTTTCCTGCTTGATTTGCCTAATGGAAGCTGACA |
| 2298 | Hcd923 right | 0.34 | CTGGAGATAATGATTCTGCATTTCTAATTAACTCCCAGGT |

TABLE 95-continued

Methotrexate microRNA biomarkers.

| SEQ ID NO | Medianprobe | Corr | Sequence |
|---|---|---|---|
| 2537 | MPR237 left | 0.32 | AGCACATCCCATGATCACAGTAATGTTCTTTGGAGATGTA |
| 2409 | MPR174 left | 0.32 | GAGCCGGTCTCTTTACATCTCAAATACCAGGTATTTAGGT |
| 2388 | mir-019a-prec | 0.31 | TGTAGTTGTGCAAATCTATGCAAAACTGATGGTGGCCTGC |
| 2540 | hsa_mir_490_Hcd20 right | 0.25 | ACCAACCTGGAGGACTCCATGCTGTTGAGCTGTTCACAAG |
| 2389 | mir-380-5p | 0.36 | AGGTACCTGAAAAGATGGTTGACCATAGAACATGCGCTAT |
| 2390 | mir-093-prec-7.1 = 093-1 | 0.38 | CCAAAGTGCTGTTCGTGCAGGTAGTGTGATTACCCAACCT |
| 2391 | mir-106-prec-X | 0.45 | CCTTGGCCATGTAAAAGTGCTTACAGTGCAGGTAGCTTTT |
| 2544 | Hcd627 left | 0.3 | GCATTAGGGAGAATAGTTGATGGATTACAAATCTCTGCAT |
| 2300 | mir-142-prec | 0.27 | CCCATAAAGTAGAAAGCACTACTAACAGCACTGGAGGGTG |
| 2427 | HPR169 right | 0.29 | GTTTCTTTCTCACGGTAACTGGCAGCCTCGTTGTGGGCTG |
| 2547 | mir-001b-2-prec | 0.28 | TAAGCTATGGAATGTAAAGAAGTATGTATCTCAGGCCGGG |
| 2393 | mir-018-prec | 0.4 | TAAGGTGCATCTAGTGCAGATAGTGAAGTAGATTAGCATC |
| 2394 | mir-020-prec | 0.48 | TAAAGTGCTTATAGTGCAGGTAGTGTTTAGTTATCTACTG |
| 2550 | Hcd404 left | 0.29 | TGCTGCTGTTAATGCCATTAGGATGACTATTTATATCACC |
| 2551 | mir-384 | 0.25 | CATAAGTCATTCCTAGAAATTGTTCATAATGCCTGTAACA |
| 2410 | mir-4323p | 0.4 | CCTTACGTGGGCCACTGGATGGCTCCTCCATGTCTTGGAG |

TABLE 96

Bleomycin microRNA biomarkers.

| SEQ ID NO | Medianprobe | Corr | Sequence |
|---|---|---|---|
| 2553 | mir-376aNo1 | 0.27 | AATCATAGAGGAAAATCCACGTTTTCAGTATCAAATGCTG |
| 2293 | mir-155-prec | 0.35 | TTAATGCTAATCGTGATAGGGGTTTTTGCCTCCAACTGAC |
| 2355 | mir-409-3p | 0.28 | GACGAATGTTGCTCGGTGAACCCCTTTTCGGTATCAAATT |
| 2358 | mir-495No1 | 0.29 | GTGACGAAACAAACATGGTGCACTTCTTTTTCGGTATCAA |
| 2557 | Hcd498 right | 0.28 | CACGAAGAAGTTCAGCAACCAGGAGACCAGGTGGGGGCCG |
| 2558 | mir-199a-2-prec | 0.41 | TCGCCCCAGTGTTCAGACTACCTGTTCAGGACAATGCCGT |
| 2362 | mir-382 | 0.3 | GGTACTTGAAGAGAAGTTGTTCGTGGTGGATTCGCTTTAC |
| 2560 | HPR271 right | 0.27 | AATTGAGCAAACAGTGCAATTTTCTGTAATTATGCCAGTG |
| 2561 | mir-145-prec | 0.31 | CCTCACGGTCCAGTTTTCCCAGGAATCCCTTAGATGCTAA |
| 2562 | mir-199a-1-prec | 0.35 | GCCAACCCAGTGTTCAGACTACCTGTTCAGGAGGCTCTCA |

TABLE 97

Methyl-GAG (methyl glyoxal bis amidinohydrazone dihydrochloride) microRNA biomarkers.

| SEQ ID NO | Medianprobe | Corr | Sequence |
|---|---|---|---|
| 2377 | mir-092-prec-X = 092-2 | 0.32 | GTTCTATATAAAGTATTGCACTTGTCCCGGCCTGTGGAAG |
| 2413 | mir-101-prec-9 | 0.3 | GCTGTATATCTGAAAGGTACAGTACTGTGATAACTGAAGA |
| 2565 | mir-144-precNo2 | 0.29 | CCCTGGCTGGGATATCATCATATACTGTAAGTTTGCGATG |
| 2566 | mir-519a-1/526c | 0.29 | TCAGGCTGTGACACTCTAGAGGGAAGCGCTTTCTGTTGTC |
| 2567 | mir-519b | 0.33 | GAAAAGAAAGTGCATCCTTTTAGAGGTTTACTGTTTGAGG |
| 2568 | mir-015b-precNo2 | 0.26 | TGCTACAGTCAAGATGCGAATCATTATTTGCTGCTCTAGA |
| 2391 | mir-106aNo1 | 0.27 | CCTTGGCCATGTAAAAGTGCTTACAGTGCAGGTAGCTTTT |
| 2570 | mir-16-1No1 | 0.26 | GTCAGCAGTGCCTTAGCAGCACGTAAATATTGGCGTTAAG |
| 2571 | mir-181dNo1 | 0.27 | GAGGTCACAATCAACATTCATTGTTGTCGGTGGGTTGTGA |
| 2572 | mir-017-precNo2 | 0.31 | GTCAGAATAATGTCAAAGTGCTTACAGTGCAGGTAGTGAT |
| 2381 | mir-019b-2-prec | 0.32 | GTGGCTGTGCAAATCCATGCAAAACTGATTGTGATAATGT |
| 2574 | mir-192No2 | 0.26 | TGCCAATTCCATAGGTCACAGGTATGTTCGCCTCAATGCC |
| 2306 | mir-213-precNo1 | 0.25 | AACATTCATTGCTGTCGGTGGGTTGAACTGTGTGGACAAG |
| 2576 | mir-215-precNo2 | 0.3 | CATTTCTTTAGGCCAATATTCTGTATGACTGTGCTACTTC |
| 2577 | mir-107No1 | 0.28 | GGCATGGAGTTCAAGCAGCATTGTACAGGGCTATCAAAGC |
| 2578 | mir-200bNo1 | 0.28 | GTCTCTAATACTGCCTGGTAATGATGACGGCGGAGCCCTG |
| 2579 | mir-103-prec-5 = 103-1 | 0.3 | TATGGATCAAGCAGCATTGTACAGGGCTATGAAGGCATTG |
| 2566 | mir-519a-1/526c | 0.37 | TCAGGCTGTGACACTCTAGAGGGAAGCGCTTTCTGTTGTC |
| 2382 | MPR216 left | 0.28 | GATCCAGTAGTGCCAAAGTGCTCATAGTGCAGGTAGTTT |
| 2383 | mir-019b-1-prec | 0.31 | TTCTGCTGTGCAAATCCATGCAAAACTGACTGTGGTAGTG |
| 2577 | mir-107-prec-10 | 0.29 | GGCATGGAGTTCAAGCAGCATTGTACAGGGCTATCAAAGC |
| 2384 | mir-135-2-prec | 0.39 | CACTCTAGTGCTTTATGGCTTTTTATTCCTATGTGATAGT |
| 2585 | mir-103-2-prec | 0.29 | GTAGCATTCAGGTCAAGCAACATTGTACAGGGCTATGAAA |
| 2586 | mir-519a-2No2 | 0.29 | TCTCAGGCTGTGTCCCTCTACAGGGAAGCGCTTTCTGTTG |
| 2386 | mir-025-prec | 0.33 | ACGCTGCCCTGGGCATTGCACTTGTCTCGGTCTGACAGTG |
| 2588 | mir-16-2No1 | 0.33 | GTTCCACTCTAGCAGCACGTAAATATTGGCGTAGTGAAAT |
| 2589 | MPR95 left | 0.28 | TTGTTGGACACTCTTTCCCTGTTGCACTACTGTGGGCCTC |
| 2588 | mir-016b-chr3 | 0.29 | GTTCCACTCTAGCAGCACGTAAATATTGGCGTAGTGAAAT |
| 2591 | Hcd948 right | 0.27 | TGATATAAATAGTCATCCTAATGGCATTAACAGCAGCACT |
| 2475 | mir-195-prec | 0.35 | TCTAGCAGCACAGAAATATTGGCACAGGGAAGCGAGTCTG |
| 2390 | mir-093-prec-7.1 = 093 - 1 | 0.38 | CCAAAGTGCTGTTCGTGCAGGTAGTGTGATTACCCAACCT |
| 2391 | mir-106-prec-X | 0.42 | CCTTGGCCATGTAAAAGTGCTTACAGTGCAGGTAGCTTTT |
| 2300 | mir-142-prec | 0.37 | CCCATAAAGTAGAAAGCACTACTAACAGCACTGGAGGGTG |
| 2596 | mir-519c/526c | 0.27 | TCTCAGCCTGTGACCCTCTAGAGGGAAGCGCTTTCTGTTG |
| 2578 | mir-200a-prec | 0.29 | GTCTCTAATACTGCCTGGTAATGATGACGGCGGAGCCCTG |
| 2598 | mir-016a-chr13 | 0.29 | CAATGTCAGCAGTGCCTTAGCAGCACGTAAATATTGGCGT |

TABLE 97-continued

Methyl-GAG (methyl glyoxal bis amidinohydrazone dihydrochloride) microRNA biomarkers.

| SEQ ID NO | Medianprobe | Corr | Sequence |
|---|---|---|---|
| 2393 | mir-018-prec | 0.41 | TAAGGTGCATCTAGTGCAGATAGTGAAGTAGATTAGCATC |
| 2394 | mir-020-prec | 0.39 | TAAAGTGCTTATAGTGCAGGTAGTGTTTAGTTATCTACTG |

TABLE 98 pXD101 HDAC inhibitors microRNA biomarkers.

| SEQ ID NO | Medianprobe | Corr | Sequence |
|---|---|---|---|
| 2377 | mir-092-prec-X = 092-2 | 0.42 | GTTCTATATAAAGTATTGCACTTGTCCCGGCCTGTGGAAG |
| 2430 | mir-123-precNo2 | 0.31 | TGTGACACTTCAAACTCGTACCGTGAGTAATAATGCGCCG |
| 2391 | mir-106aNo1 | 0.36 | CCTTGGCCATGTAAAAGTGCTTACAGTGCAGGTAGCTTTT |
| 2414 | mir-20bNo1 | 0.36 | AGTACCAAAGTGCTCATAGTGCAGGTAGTTTTGGCATGAC |
| 2572 | mir-017-precNo2 | 0.32 | GTCAGAATAATGTCAAAGTGCTTACAGTGCAGGTAGTGAT |
| 2381 | mir-019b-2-prec | 0.42 | GTGGCTGTGCAAATCCATGCAAAACTGATTGTGATAATGT |
| 2607 | mir-033-prec | 0.3 | GTGGTGCATTGTAGTTGCATTGCATGTTCTGGTGGTACCC |
| 2608 | mir-092-prec-13 = 092-1No2 | 0.31 | TCTGTATGGTATTGCACTTGTCCCGGCCTGTTGAGTTTGG |
| 2609 | mir-122a-prec | 0.29 | CCTTAGCAGAGCTGTGGAGTGTGACAATGGTGTTTGTGTC |
| 2447 | Hcd783 left | 0.27 | CAGGCTCACACCTCCCTCCCCCAACTCTCTGGAATGTATA |
| 2382 | MPR216 left | 0.29 | GATCCTAGTAGTGCCAAAGTGCTCATAGTGCAGGTAGTTT |
| 2383 | mir-019b-1-prec | 0.41 | TTCTGCTGTGCAAATCCATGCAAAACTGACTGTGGTAGTG |
| 2384 | mir-135-2-prec | 0.46 | CACTCTAGTGCTTTATGGCTTTTTATTCCTATGTGATAGT |
| 2451 | mir-128b-precNo1 | 0.39 | TCACAGTGAACCGGTCTCTTTCCCTACTGTGTCACACTCC |
| 2386 | mir-025-prec | 0.45 | ACGCTGCCCTGGGCATTGCACTTGTCTCGGTCTGACAGTG |
| 2616 | Hcd511 right | 0.26 | TACCTCAGAAGCCTCACTCAACCCTCTCCCGCTGAGTCTC |
| 2390 | mir-093-prec-7.1 = 093-1 | 0.45 | CCAAAGTGCTGTTCGTGCAGGTAGTGTGATTACCCAACCT |
| 2391 | mir-106-prec-X | 0.5 | CCTTGGCCATGTAAAAGTGCTTACAGTGCAGGTAGCTTTT |
| 2300 | mir-142-prec | 0.5 | CCCATAAAGTAGAAAGCACTACTAACAGCACTGGAGGGTG |
| 2427 | HPR169 right | 0.26 | GTTTCTTTCTCACGGTAACTGGCAGCCTCGTTGTGGGCTG |
| 2301 | mir-223-prec | 0.26 | GAGTGTCAGTTTGTCAAATACCCCAAGTGCGGCACATGCT |
| 2393 | mir-018-prec | 0.48 | TAAGGTGCATCTAGTGCAGATAGTGAAGTAGATTAGCATC |
| 2394 | mir-020-prec | 0.52 | TAAAGTGCTTATAGTGCAGGTAGTGTTTAGTTATCTACTG |

TABLE 99

5-Fluorouracil microRNA biomarkers.

| SEQ ID NO | Medianprobe | Corr | Sequence |
|---|---|---|---|
| 2378 | mir-096-prec-7No2 | 0.27 | TGGCCGATTTTGGCACTAGCACATTTTGCTTGTGTCTCT |

TABLE 99-continued

5-Fluorouracil microRNA biomarkers.

| SEQ ID NO | Medianprobe | Corr | Sequence |
|---|---|---|---|
| 2625 | mir-429No1 | 0.25 | CTAATACTGTCTGGTAAAACCGTCCATCCGCTGCCTGATC |
| 2626 | Hcd693 right | 0.25 | AGGCTTTGTGCGCGCATTAAAGCTCGCCGGACCCCCGACC |
| 2500 | HPR214 right | 0.27 | AGCAAAAGCTATTATTTGCCCTTGATGAGCCAATCAGATG |
| 2628 | Hcd586 left | 0.26 | GTCCTGTCTAAAGGAAGAAGTTTGTTCTACTGTAAACAGT |
| 2517 | Hcd249 right | 0.26 | CAGGTACATGTTGATCAGCAGGGGCTGGGAGGCGCCGCTC |
| 2520 | Hcd689 right | 0.27 | GTACATCTGGATGTAGTTGTGCTGCAGCTGCTTCTGGTAG |
| 2631 | mir-194-2No1 | 0.25 | TGGTTCCCGCCCCCTGTAACAGCAACTCCATGTGGAAGTG |
| 2524 | Hcd581 right | 0.26 | AGGAGATATGCCAAGATATATTCACAGCTTTATATACACA |
| 2528 | Hcd270 right | 0.3 | AAATGTTGTTATAGTATCCCACCTACCCTGATGTATCTTT |
| 2386 | mir-025-prec | 0.27 | ACGCTGCCCTGGGCATTGCACTTGTCTCGGTCTGACAGTG |
| 2635 | Hcd340 left | 0.27 | GGACAATTCAACAGTGGTGAGTCACTTCGCCACTTTTCAG |
| 2283 | mir-007-1-prec | 0.27 | TGTTGGCCTAGTTCTGTGTGGAAGACTAGTGATTTTGTTG |
| 2390 | mir-093-prec-7.1 = 093-1 | 0.25 | CCAAAGTGCTGTTCGTGCAGGTAGTGTGATTACCCAACCT |
| 2391 | mir-106-prec-X | 0.26 | CCTTGGCCATGTAAAAGTGCTTACAGTGCAGGTAGCTTTT |
| 2287 | Hcd794 right | 0.27 | GGCCACCACAGACACCAACAAGTTCAGTCCGTTTCTGCAG |
| 2394 | mir-020-prec | 0.26 | TAAAGTGCTTATAGTGCAGGTAGTGTTTAGTTATCTACTG |
| 2410 | mir-4323p | 0.26 | CCTTACGTGGGCCACTGGATGGCTCCTCCATGTCTTGGAG |

TABLE 100

Radiation microRNA biomarkers.

| SEQ ID NO | Medianprobe | Corr | Sequence |
|---|---|---|---|
| 2642 | mir-136-precNo2 | 0.3 | TGAGCCCTCGGAGGACTCCATTTGTTTTGATGATGGATTC |
| 2643 | Hcd570 right | 0.26 | GCCCAACAGAACAACTTGTTTCTCCAGAGCCTGAGGTTTA |
| 2644 | Hcd873 left | 0.26 | TCTTCTGACAATGAAGGTAGGCGGACAACGAGGAGATTGC |
| 2645 | Hcd282P0 right | 0.26 | GAAGACGGACTTGGTTCCGTTTGACCAGCCAGAGCAGGGG |
| 2646 | Hcd799 left | 0.25 | GTCCGGCGCGAGTGGAGCTGTTGTAAAATGGCGGCCGAAG |
| 2344 | Hcd829 right | 0.39 | AAAATGGCGGCGGGAAAAGCGAGCGGCGAGAGCGAGGAGG |
| 2347 | Hcd210_HPR205 right | 0.32 | CGAAACATTCGCGGTGCACTTCTTTTTCAGTATCCTATTC |
| 2649 | mir-219-prec | 0.26 | ATTGTCCAAACGCAATTCTCGAGTCTATGGCTCCGGCCGA |
| 2650 | mir-202* | 0.31 | CCGCCCGCCGTTCCTTTTTCCTATGCATATACTTCTTTGA |
| 2651 | mir-429No2 | 0.42 | CACCGCCGGCCGATGGGCGTCTTACCAGACATGGTTAGAC |
| 2626 | Hcd693 right | 0.32 | AGGCTTTGTGCGCGCATTAAAGCTCGCCGGACCCCCGACC |
| 2653 | mir-022-prec | 0.34 | TGTCCTGACCCAGCTAAAGCTGCCAGTTGAAGAACTGTTG |
| 2654 | NPR88 right | 0.32 | CTTACCCTGGTGCGTGGGCCGCAGGGCTAACACCAAAAA |
| 2655 | mir-198-prec | 0.39 | TCATTGGTCCAGAGGGGAGATAGGTTCCTGTGATTTTTCC |

TABLE 100-continued

Radiation microRNA biomarkers.

| SEQ ID NO | Medianprobe | Corr | Sequence |
|---|---|---|---|
| 2656 | mir-199b-precNo1 | 0.29 | GTCTGCACATTGGTTAGGCTGGGCTGGGTTAGACCCTCGG |
| 2324 | Hcd145 left | 0.26 | AAAAATCCCAGCGGCCACCTTTCCTCCCTGCCCCATTGGG |
| 2658 | mir-124a-2-prec | 0.34 | TTAAGGCACGCGGTGAATGCCAAGAGCGGAGCCTACGGCT |
| 2659 | mir-138-2-prec | 0.39 | AGCTGGTGTTGTGAATCAGGCCGACGAGCAGCGCATCCTC |
| 2660 | Hcd960 left | 0.29 | CTCAGTCTGCGGGCCCCGAGGAGGGTTGTGGGCCCTTTTT |
| 2661 | Hcd869 left | 0.31 | CGAGAGGCACTTTGTACTTCTGCCAGGAGACCATATGATA |
| 2662 | Hcd384 left | 0.41 | TTACCCAGCCGGGCCGCCAACACCAGATCCTTCTCCTTCT |
| 2663 | mir-027b-prec | 0.31 | CCGCTTTGTTCACAGTGGCTAAGTTCTGCACCTGAAGAGA |
| 2664 | Hcd444 right | 0.31 | GTATATGTGTGTGTGTGTGTGTGTGTGTGTGTGTGTGTGT |
| 2631 | mir-194-2No1 | 0.3 | TGGTTCCCGCCCCCTGTAACAGCAACTCCATGTGGAAGTG |
| 2369 | mir-197-prec | 0.44 | TAAGAGCTCTTCACCCTTCACCACCTTCTCCACCCAGCAT |
| 2326 | Hcd913 right | 0.39 | CAAACATCATGTGACGTCTGTGGAGCGGCGGCGGCGGCGG |
| 2327 | HPR163 left | 0.39 | GCTGCCCCCTCCCTTAGCAACGTGGCCCCGGCGTTCCAAA |
| 2310 | mir-138-1-prec | 0.25 | AGCTGGTGTTGTGAATCAGGCCGTTGCCAATCAGAGAACG |
| 2670 | mir-010a-precNo1 | 0.25 | GTCTGTCTTCTGTATATACCCTGTAGATCCGAATTTGTGT |
| 2671 | mir-023b-prec | 0.34 | AATCACATTGCCAGGGATTACCACGCAACCACGACCTTGG |
| 2672 | mir-193bNo2 | 0.35 | CTGTGGTCTCAGAATCGGGGTTTTGAGGGCGAGATGAGTT |
| 2285 | Hcd654 left | 0.43 | AACGAGTAAAAGGCGTACATGGGAGCGCGGGGCGGCAGAG |
| 2674 | Hcd542 left | 0.26 | ATCTCAGTAGCCAATATTTTTCTCTGCTGGTATCAAATGA |
| 2558 | mir-199a-2-prec | 0.28 | TCGCCCCAGTGTTCAGACTACCTGTTCAGGACAATGCCGT |
| 2676 | mir-214-prec | 0.43 | TGTACAGCAGGCACAGACAGGCAGTCACATGACAACCCAG |
| 2677 | Hcd608 right | 0.31 | CTTGTGTTTTCACAGCAGCCACAGGCCCTACATCCTTCCT |
| 2678 | Hcd684 right | 0.28 | AGAAGGCGCTCCCTGCTAGCCCGGCTCTGTTCTAATTATA |
| 2561 | mir-145-prec | 0.4 | CCTCACGGTCCAGTTTTCCCAGGAATCCCTTAGATGCTAA |
| 2680 | mir-023a-prec | 0.37 | TCCTGTCACAAATCACATTGCCAGGGATTTCCAACCGACC |
| 2681 | mir-024-2-prec | 0.32 | AGTTGGTTTGTGTACACTGGCTCAGTTCAGCAGGAACAGG |
| 2562 | mir-199a-1-prec | 0.29 | GCCAACCCAGTGTTCAGACTACCTGTTCAGGAGGCTCTCA |

TABLE 101

5-Aza-2'-deoxycytidine (decitabine) microRNA biomarkers.

| SEQ ID NO | Medianprobe | Corr | Sequence |
|---|---|---|---|
| 2412 | mir-096-prec-7No1 | 0.36 | CTCCGCTCTGAGCAATCATGTGCAGTGCCAATATGGGAAA |
| 2684 | Hcd605 right | 0.25 | GGTTAAGACTCTAACAAACGAGTTGTGAATTGTAGCAATG |
| 2414 | mir-20bNo1 | 0.3 | AGTACCAAAGTGCTCATAGTGCAGGTAGTTTTGGCATGAC |
| 2686 | miR-373*No1 | 0.26 | GGGATACTCAAAATGGGGGCGCTTTCCTTTTTGTCTGTAC |
| 2325 | HUMTRAB | 0.3 | ATGGTAGAGCGCTCGCTTTGCTTGCGAGAGGTAGCGGGAT |

TABLE 101-continued

5-Aza-2'-deoxycytidine (decitabine) microRNA biomarkers.

| SEQ ID NO | Medianprobe | Corr | Sequence |
|---|---|---|---|
| 2383 | mir-019b-1-prec | 0.25 | TTCTGCTGTGCAAATCCATGCAAAACTGACTGTGGTAGTG |
| 2327 | HPR163 left | 0.31 | GCTGCCCCTCCCTTAGCAACGTGGCCCCGGCGTTCCAAA |
| 2690 | mir-371No1 | 0.25 | ACTTTCTGCTCTCTGGTGAAAGTGCCGCCATCTTTTGAGT |
| 2386 | mir-025-prec | 0.29 | ACGCTGCCCTGGGCATTGCACTTGTCTCGGTCTGACAGTG |
| 2692 | mir-18bNo2 | 0.27 | AGCAGCTTAGAATCTACTGCCCTAAATGCCCCTTCTGGCA |
| 2390 | mir-093-prec-7.1 = 093-1 | 0.28 | CCAAAGTGCTGTTCGTGCAGGTAGTGTGATTACCCAACCT |
| 2391 | mir-106-prec-X | 0.29 | CCTTGGCCATGTAAAAGTGCTTACAGTGCAGGTAGCTTTT |
| 2300 | mir-142-prec | 0.29 | CCCATAAAGTAGAAAGCACTACTAACAGCACTGGAGGGTG |
| 2394 | mir-020-prec | 0.29 | TAAAGTGCTTATAGTGCAGGTAGTGTTTAGTTATCTACTG |

TABLE 102

Idarubicin microRNA biomarkers.

| SEQ ID NO | Medianprobe | Corr | Sequence |
|---|---|---|---|
| 2290 | HUMTRF | 0.33 | GATCTAAAGGTCCCTGGTTCGATCCCGGGTTTCGGCACCA |
| 2367 | mir-483No1 | 0.3 | ATCACGCCTCCTCACTCCTCTCCTCCCGTCTTCTCCTCTC |
| 2699 | MPR74 left | 0.27 | CAAAGGTCACAATTAACATTCATTGTTGTCGGTGGGTTGT |
| 2609 | mir-122a-prec | 0.27 | CCTTAGCAGAGCTGTGGAGTGTGACAATGGTGTTTGTGTC |
| 2433 | ath-MIR180aNo2 | 0.29 | TGAGAATCTTGATGATGCTGCATCGGCAATCAACGACTAT |
| 2451 | mir-128b-precNo1 | 0.26 | TCACAGTGAACCGGTCTCTTTCCCTACTGTGTCACACTCC |
| 2703 | Hcd923 left | 0.25 | TGGGAACCTTGTTAAAATGCAGATTCTGATTCTCAGGTCT |
| 2391 | mir-106-prec-X | 0.25 | CCTTGGCCATGTAAAAGTGCTTACAGTGCAGGTAGCTTTT |
| 2299 | mir-342No1 | 0.36 | GTCTCACACAGAAATCGCACCCGTCACCTTGGCCTACTTA |
| 2300 | mir-142-prec | 0.34 | CCCATAAAGTAGAAAGCACTACTAACAGCACTGGAGGGTG |
| 2427 | HPR169 right | 0.25 | GTTTCTTTCTCACGGTAACTGGCAGCCTCGTTGTGGGCTG |
| 2301 | mir-223-prec | 0.36 | GAGTGTCAGTTTGTCAAATACCCCAAGTGCGGCACATGCT |
| 2302 | Hcd754 left | 0.26 | TCCTCCTCCTCCTTTTCGTTCCGGCTCCCTGGCTGGCTCC |
| 2394 | mir-020-prec | 0.29 | TAAAGTGCTTATAGTGCAGGTAGTGTTTAGTTATCTACTG |

TABLE 103

Melphalan microRNA biomarkers.

| SEQ ID NO | Medianprobe | Corr | Sequence |
|---|---|---|---|
| 2711 | mir-124a-3-prec | 0.32 | TTAAGGCACGCGGTGAATGCCAAGAGAGGCGCCTCCGCCG |
| 2712 | mir-181a-precNo1 | 0.28 | TCAGAGGACTCCAAGGAACATTCAACGCTGTCGGTGAGTT |
| 2713 | Hcd773 left | 0.26 | CTTCCTCCCTGGGCATCTCTAGCACAGGGGATCCCCAAAC |

TABLE 103-continued

Melphalan microRNA biomarkers.

| SEQ ID NO | Medianprobe | Corr | Sequence |
|---|---|---|---|
| 2714 | Hcd683 left | 0.25 | CTATGACAGAAGGTACTCTGTGGGAGGGAGGAGATAATAG |
| 2715 | Hcd796 left | 0.29 | GGTGGGATTACCCGGCTGCCGCTGTCGCCTGGATGGTCTC |
| 2290 | HUMTRF | 0.44 | GATCTAAAGGTCCCTGGTTCGATCCCGGGTTTCGGCACCA |
| 2305 | HUMTRS | 0.27 | TCTAGCGACAGAGTGGTTCAATTCCACCTTTCGGGCGCCA |
| 2718 | mir-181b-2No1 | 0.25 | CTGATGGCTGCACTCAACATTCATTGCTGTCGGTGGGTTT |
| 2719 | Hcd294 left | 0.26 | TTATCATAAAATAATCACAGCCCTCAGGTGCTGTGAGGCA |
| 2414 | mir-20bNo1 | 0.27 | AGTACCAAAGTGCTCATAGTGCAGGTAGTTTTGGCATGAC |
| 2571 | mir-181dNo1 | 0.27 | GAGGTCACAATCAACATTCATTGTTGTCGGTGGGTTGTGA |
| 2306 | mir-213-precNo1 | 0.4 | AACATTCATTGCTGTCGGTGGGTTGAACTGTGTGGACAAG |
| 2407 | Hcd148_HPR225left | 0.29 | AATTAATGACCAAAATGTCAGATGTGTCCACAGCTAATTA |
| 2294 | mir-515-15p | 0.34 | GATCTCATGCAGTCATTCTCCAAAAGAAAGCACTTTCTGT |
| 2398 | mir-181b-precNo1 | 0.43 | TGAGGTTGCTTCAGTGAACATTCAACGCTGTCGGTGAGTT |
| 2447 | Hcd783 left | 0.26 | CAGGCTCACACCTCCCTCCCCCAACTCTCTGGAATGTATA |
| 2325 | HUMTRAB | 0.29 | ATGGTAGAGCGCTCGCTTTGCTTGCGAGAGGTAGCGGGAT |
| 2728 | HUMTRN | 0.27 | CAATCGGTTAGCGCGTTCGGCTGTTAACCGAAAGGTTGGT |
| 2729 | mir-181b-1No1 | 0.31 | TTTAAAAGGTCACAATCAACATTCATTGCTGTCGGTGGGT |
| 2296 | mir-124a-1-prec1 | 0.31 | ATACAATTAAGGCACGCGGTGAATGCCAAGAATGGGGCTG |
| 2731 | mir-367No1 | 0.26 | TCTGTTGAATATAAATTGGAATTGCACTTTAGCAATGGTG |
| 2451 | mir-128b-precNo1 | 0.38 | TCACAGTGAACCGGTCTCTTTCCCTACTGTGTCACACTCC |
| 2360 | Hcd43 8right | 0.25 | GTGTTTATTTGAATCTCACATCGCTCATAAGAATACACGC |
| 2386 | mir-025-prec | 0.3 | ACGCTGCCCTGGGCATTGCACTTGTCTCGGTCTGACAGTG |
| 2735 | mir-216-precNo1 | 0.35 | CTGGGATTATGCTAAACAGAGCAATTTCCTAGCCCTCACG |
| 2317 | Hcd731 left | 0.26 | AATTGTGACAACTGAGTGGGAGGTTTGTGTGATGATTATC |
| 2390 | mir-093-prec-7.1 = 093-1 | 0.25 | CCAAAGTGCTGTTCGTGCAGGTAGTGTGATTACCCAACCT |
| 2391 | mir-106-prec-X | 0.27 | CCTTGGCCATGTAAAAGTGCTTACAGTGCAGGTAGCTTTT |
| 2299 | mir-342No1 | 0.36 | GTCTCACACAGAAATCGCACCCGTCACCTTGGCCTACTTA |
| 2300 | mir-142-prec | 0.53 | CCCATAAAGTAGAAAGCACTACTAACAGCACTGGAGGGTG |
| 2341 | HSHELA01 | 0.32 | GGCCGCAGCAACCTCGGTTCGTATCCGAGTCACGGCACCA |
| 2342 | HUMTRV1A | 0.25 | ACGCGAAAGGTCCCCGGTTCGAAACCGGGCGGAAACACCA |
| 2301 | mir-223-prec | 0.46 | GAGTGTCAGTTTGTCAAATACCCCAAGTGCGGCACATGCT |
| 2302 | Hcd754 left | 0.45 | TCCTCCTCCTCCTTTTCGTTCCGGCTCCCTGGCTGGCTCC |
| 2394 | mir-020-prec | 0.3 | TAAAGTGCTTATAGTGCAGGTAGTGTTTAGTTATCTACTG |

TABLE 104

IL4-PR3B fusion protein microRNA biomarkers.

| SEQ ID NO | Medianprobe | Corr | Sequence |
|---|---|---|---|
| 2344 | Hcd829 right | 0.28 | AAAATGGCGGCGGGAAAAGCGAGCGGCGAGAGCGAGGAGG |
| 2369 | mir-197-prec | 0.28 | TAAGAGCTCTTCACCCTTCACCACCTTCTCCACCCAGCAT |
| 2327 | HPR163 left | 0.28 | GCTGCCCCCTCCCTTAGCAACGTGGCCCCGGCGTTCCAAA |
| 2448 | mir-150-prec | 0.47 | CTCCCCATGGCCCTGTCTCCCAACCCTTGTACCAGTGCTG |

TABLE 105

Valproic acid (VPA) microRNA biomarkers.

| SEQ ID NO | Medianprobe | Corr | Sequence |
|---|---|---|---|
| 2750 | mir-034precNo1 | 0.26 | GAGTGTTTCTTTGGCAGTGTCTTAGCTGGTTGTTGTGAGC |
| 2751 | Hcd255 left | 0.28 | CTAGCTCCGTTCGTGATCCGGGAGCCTGGTGCCAGCGAGA |
| 2752 | Hcd712 right | 0.27 | GAAGATCGGTTGTCATCTGGTCTGGTCAGCCCGGCCCCGA |
| 2753 | Hcd965 left | 0.26 | TGTTAAGTGGAAAAGCCTCCAGGAACGTGGCAGAAAAAGG |
| 2754 | Hcd891 right | 0.29 | GCAACGGCCTGATTCACAACACCAGCTGCCCCACCACACC |
| 2347 | Hcd210_HPR205 right | 0.31 | CGAAACATTCGCGGTGCACTTCTTTTTCAGTATCCTATTC |
| 2651 | mir-429No2 | 0.33 | CACCGCCGGCCGATGGGCGTCTTACCAGACATGGTTAGAC |
| 2757 | Hcd753 left | 0.27 | GACCTGATTCCCATCTTTGTATTTGGCGACCACCCGACTG |
| 2626 | Hcd693 right | 0.38 | AGGCTTTGTGCGCGCATTAAAGCTCGCCGGACCCCCGACC |
| 2333 | MPR203 left | 0.25 | CTATATTGGACCGCAGCGCTGAGAGCTTTTGTGTTTAATG |
| 2760 | Hcd704 left | 0.4 | TCTGTATTTAATTTGGCTCAGCCGGGAAGATTTTTGGCTC |
| 2761 | Hcd863PO right | 0.3 | TTGCAGAGCCTAAGACACAGGCCCAGAGAGGCAGTGATCG |
| 2609 | mir-122a-prec | 0.29 | CCTTAGCAGAGCTGTGGAGTGTGACAATGGTGTTTGTGTC |
| 2763 | Hcd760 left | 0.35 | TGTGGTCACGTTTCTCCCTCTCTGCTGGCCCCCATCTGTC |
| 2764 | Hcd338 left | 0.35 | CTTCTCCTCCTGTTCGCCGCAGGCGCCCGTCCCAGTAGTC |
| 2765 | HPR213 right | 0.33 | AACAACTTTGTGCTGGTGCCGGGGAAGTTTGTGTCTCCAA |
| 2766 | Hcd852 right | 0.26 | AAAAGTAAACAACAATTTGCCGCTGCCAGCCTCCCATTAG |
| 2767 | Hcd366 left | 0.28 | ATACTAGATTAAATTTCAGCCCCGGGCCAATCTGTCAAAG |
| 2768 | MPR103 right | 0.27 | GAGGTGTTTGTGCTCCACTCGGCTCCCTTGGTTACATAAC |
| 2769 | Hcd669 right | 0.27 | ATGTTTAACAGTCCAGGTTTTGTAGAATATGTGGTGGACC |
| 2770 | mir-188-prec | 0.27 | TCACATCCCTTGCATGGTGGAGGGTGAGCTTTCTGAAAAC |

TABLE 106

All-trans retinoic acid (ATRA) microRNA biomarkers.

| SEQ ID NO | Medianprobe | Corr | Sequence |
|---|---|---|---|
| 2771 | Hcd257 left | 0.42 | CTTCTTGTATAAGCACTGTGCTAAAATTGCAGACACTAGG |
| 2772 | mir-148-prec | 0.45 | TGAGTATGATAGAAGTCAGTGCACTACAGAACTTTGTCTC |

TABLE 106-continued

All-trans retinoic acid (ATRA) microRNA biomarkers.

| SEQ ID NO | Medianprobe | Corr | Sequence |
|---|---|---|---|
| 2773 | Hcd512 left | 0.28 | CTGCGCTCTCGGAAATGACTCGCTCCAATCCCGCTTCGCG |
| 2774 | HPR227 right | 0.25 | CAGTGCAATGATATTGTCAAAGCATCTGGGACCAGCCTTG |
| 2775 | Hcd421 right | 0.37 | AGTAAACAATGTCGGCTTTCCGCCTCCTCCCCTGCCATCC |
| 2333 | MPR203 left | 0.39 | CTATATTGGACCGCAGCGCTGAGAGCTTTTGTGTTTAATG |
| 2777 | mir-017-precNo1 | 0.26 | GCATCTACTGCAGTGAAGGCACTTGTAGCATTATGGTGAC |
| 2778 | mir-219-2No1 | 0.26 | CTCAGGGGCTTCGCCACTGATTGTCCAAACGCAATTCTTG |
| 2779 | mir-328No1 | 0.3 | GAAAGTGCATACAGCCCCTGGCCCTCTCTGCCCTTCCGTC |
| 2447 | Hcd783 left | 0.31 | CAGGCTCACACCTCCCTCCCCCAACTCTCTGGAATGTATA |
| 2781 | Hcd181 left | 0.32 | TTGGCGTCCTTGTCTCTCTCCCCTGCCCAGTGGCCTCC |
| 2765 | HPR213 right | 0.3 | AACAACTTTGTGCTGGTGCCGGGGAAGTTTGTGTCTCCAA |
| 2783 | mir-191-prec | 0.31 | CAACGGAATCCCAAAAGCAGCTGTTGTCTCCAGAGCATTC |
| 2784 | mir-375 | 0.31 | TTTTGTTCGTTCGGCTCGCGTGAGGCAGGGGCGGCCTCTC |
| 2785 | mir-212-precNo2 | 0.26 | CGGACAGCGCGCCGGCACCTTGGCTCTAGACTGCTTACTG |
| 2326 | Hcd913 right | 0.34 | CAAACATCATGTGACGTCTGTGGAGCGGCGGCGGCGGCGG |
| 2330 | Hcd716 right | 0.48 | CAATAAATGTGCCTATAAAGGCGCCGGCTCCGGGGCGCGG |
| 2331 | MPR207 right | 0.3 | AACAACTTTGTGCTGGTGCCGGGGAAGTTTGTGTCTCCTA |
| 2333 | HPR206 left | 0.26 | CTATATTGGACCGCAGCGCTGAGAGCTTTTGTGTTTAATG |
| 2588 | mir-016b-chr3 | 0.29 | GTTCCACTCTAGCAGCACGTAAATATTGGCGTAGTGAAAT |
| 2285 | Hcd654 left | 0.34 | AACGAGTAAAAGGCGTACATGGGAGCGCGGGGCGGCAGAG |
| 2475 | mir-195-prec | 0.3 | TCTAGCAGCACAGAAATATTGGCACAGGGAAGCGAGTCTG |
| 2793 | Hcd425 left | 0.25 | GGTTCTACTCTCTTACCCCTCCCCCACGTGGTTGTTGCTG |
| 2772 | mir-148aNo1 | 0.35 | TGAGTATGATAGAAGTCAGTGCACTACAGAACTTTGTCTC |
| 2300 | mir-142-prec | 0.36 | CCCATAAAGTAGAAAGCACTACTAACAGCACTGGAGGGTG |
| 2598 | mir-016a-chr13 | 0.25 | CAATGTCAGCAGTGCCTTAGCAGCACGTAAATATTGGCGT |

TABLE 107

Cytoxan microRNA biomarkers.

| SEQ ID NO | Medianprobe | Corr | Sequence |
|---|---|---|---|
| 2797 | Hcd99 right | 0.25 | CAATCCTGGCTGCAGGCATATTTGCATATTGGATGCTGTG |
| 2798 | mir-520c/526a | 0.32 | TCTCAGGCTGTCGTCCTCTAGAGGGAAGCACTTTCTGTTG |
| 2783 | mir-191-prec | 0.32 | CAACGGAATCCCAAAAGCAGCTGTTGTCTCCAGAGCATTC |
| 2800 | mir-205-prec | 0.35 | TCCTTCATTCCACCGGAGTCTGTCTCATACCCAACCAGAT |
| 2784 | mir-375 | 0.33 | TTTTGTTCGTTCGGCTCGCGTGAGGCAGGGGCGGCCTCTC |
| 2802 | mir-423No1 | 0.29 | CAAAAGCTCGGTCTGAGGCCCCTCAGTCTTGCTTCCTAAC |

TABLE 107-continued

Cytoxan microRNA biomarkers.

| SEQ ID NO | Medianprobe | Corr | Sequence |
|---|---|---|---|
| 2803 | mir-449No1 | 0.39 | TGTGATGAGCTGGCAGTGTATTGTTAGCTGGTTGAATATG |
| 2804 | mir-196-2-precNo2 | 0.26 | GCTGATCTGTGGCTTAGGTAGTTTCATGTTGTTGGGATTG |

TABLE 108

Topotecan (Hycamtin) microRNA biomarkers.

| SEQ ID NO | Medianprobe | Corr | Sequence |
|---|---|---|---|
| 2290 | HUMTRF | 0.26 | GATCTAAAGGTCCCTGGTTCGATCCCGGGTTTCGGCACCA |
| 2699 | MPR74 left | 0.29 | CAAAGGTCACAATTAACATTCATTGTTGTCGGTGGGTTGT |
| 2306 | mir-213-precNo1 | 0.28 | AACATTCATTGCTGTCGGTGGGTTGAACTGTGTGGACAAG |
| 2293 | mir-155-prec | 0.31 | TTAATGCTAATCGTGATAGGGGTTTTTGCCTCCAACTGAC |
| 2398 | mir-181b-precNo1 | 0.31 | TGAGGTTGCTTCAGTGAACATTCAACGCTGTCGGTGAGTT |
| 2299 | mir-342No1 | 0.33 | GTCTCACACAGAAATCGCACCCGTCACCTTGGCCTACTTA |
| 2410 | mir-4323p | 0.28 | CCTTACGTGGGCCACTGGATGGCTCCTCCATGTCTTGGAG |

TABLE 109

Suberoylanilide hydroxamic acid (SAHA, vorinostat, Zolinza) microRNA biomarkers.

| SEQ ID NO | Medianprobe | Corr | Sequence |
|---|---|---|---|
| 2377 | mir-092-prec-X = 092-2 | 0.38 | GTTCTATATAAAGTATTGCACTTGTCCCGGCCTGTGGAAG |
| 2483 | mir-123-precNo1 | 0.31 | GACGGGACATTATTACTTTTGGTACGCGCTGTGACACTTC |
| 2814 | mir-514-1No2 | 0.29 | TGTCTGTGGTACCCTACTCTGGAGAGTGACAATCATGTAT |
| 2413 | mir-101-prec-9 | 0.25 | GCTGTATATCTGAAAGGTACAGTACTGTGATAACTGAAGA |
| 2772 | mir-148-prec | 0.36 | TGAGTATGATAGAAGTCAGTGCACTACAGAACTTTGTCTC |
| 2391 | mir-106aNo1 | 0.34 | CCTTGGCCATGTAAAAGTGCTTACAGTGCAGGTAGCTTTT |
| 2414 | mir-20bNo1 | 0.41 | AGTACCAAAGTGCTCATAGTGCAGGTAGTTTTGGCATGAC |
| 2819 | Hcd781 right | 0.32 | AGTTTCTTTAATTAATGAAGTTTTTGGGTCTGCTCCACTT |
| 2572 | mir-017-precNo2 | 0.29 | GTCAGAATAATGTCAAAGTGCTTACAGTGCAGGTAGTGAT |
| 2381 | mir-019b-2-prec | 0.42 | GTGGCTGTGCAAATCCATGCAAAACTGATTGTGATAATGT |
| 2607 | mir-033-prec | 0.27 | GTGGTGCATTGTAGTTGCATTGCATGTTCTGGTGGTACCC |
| 2608 | mir-092prec-13 = 092-1No2 | 0.28 | TCTGTATGGTATTGCACTTGTCCCGGCCTGTTGAGTTTGG |
| 2577 | mir-107No1 | 0.29 | GGCATGGAGTTCAAGCAGCATTGTACAGGGCTATCAAAGC |
| 2579 | mir-103-prec-5 = 103-1 | 0.32 | TATGGATCAAGCAGCATTGTACAGGGCTATGAAGGCATTG |
| 2382 | MPR216 left | 0.29 | GATCCTAGTAGTGCCAAAGTGCTCATAGTGCAGGTAGTTT |
| 2827 | mir-29b-2 = 102prec7.1 = 7.2 | 0.27 | AGTGATTGTCTAGCACCATTTGAAATCAGTGTTCTTGGGG |
| 2383 | mir-019b-1-prec | 0.4 | TTCTGCTGTGCAAATCCATGCAAAACTGACTGTGGTAGTG |

TABLE 109-continued

Suberoylanilide hydroxamic acid (SAHA, vorinostat, Zolinza) microRNA biomarkers.

| SEQ ID NO | Medianprobe | Corr | Sequence |
|---|---|---|---|
| 2577 | mir-107-prec-10 | 0.3 | GGCATGGAGTTCAAGCAGCATTGTACAGGGCTATCAAAGC |
| 2384 | mir-135-2-prec | 0.37 | CACTCTAGTGCTTTATGGCTTTTTATTCCTATGTGATAGT |
| 2524 | Hcd581 right | 0.28 | AGGAGATATGCCAAGATATATTCACAGCTTTATATACACA |
| 2585 | mir-103-2-prec | 0.29 | GTAGCATTCAGGTCAAGCAACATTGTACAGGGCTATGAAA |
| 2526 | Hcd230 left | 0.27 | CATTCTCTACAAGCATATGGCCTTGGGACATTAAGATGGC |
| 2386 | mir-025-prec | 0.4 | ACGCTGCCCTGGGCATTGCACTTGTCTCGGTCTGACAGTG |
| 2835 | mir-208-prec | 0.31 | ACCTGATGCTCACGTATAAGACGAGCAAAAAGCTTGTTGG |
| 2692 | mir-18bNo2 | 0.31 | AGCAGCTTAGAATCTACTGCCCTAAATGCCCCTTCTGGCA |
| 2390 | mir-093-prec-7.1 = 093-1 | 0.39 | CCAAAGTGCTGTTCGTGCAGGTAGTGTGATTACCCAACCT |
| 2391 | mir-106-prec-X | 0.48 | CCTTGGCCATGTAAAAGTGCTTACAGTGCAGGTAGCTTTT |
| 2300 | mir-142-prec | 0.37 | CCCATAAAGTAGAAAGCACTACTAACAGCACTGGAGGGTG |
| 2427 | HPR169 right | 0.28 | GTTTCTTTCTCACGGTAACTGGCAGCCTCGTTGTGGGCTG |
| 2393 | mir-018-prec | 0.44 | TAAGGTGCATCTAGTGCAGATAGTGAAGTAGATTAGCATC |
| 2394 | mir-020-prec | 0.48 | TAAAGTGCTTATAGTGCAGGTAGTGTTTAGTTATCTACTG |

TABLE 110

Depsipeptide (FR901228) microRNA biomarkers.

| SEQ ID NO | Medianprobe | Corr | Sequence |
|---|---|---|---|
| 2320 | Hcd415 right | 0.27 | GATGTTTGGGAAACAATGGGAGTGAGAGAATGGGAGAGCT |
| 2308 | mir-147-prec | 0.27 | GACTATGGAAGCCAGTGTGTGGAAATGCTTCTGCTAGATT |
| 2845 | mir-033b-prec | 0.34 | GTGCATTGCTGTTGCATTGCACGTGTGTGAGGCGGGTGCA |
| 2846 | Hcd778 right | 0.34 | CAGAGGGGAGGCCCAGAGGAGAGGGAAGCTTGGGCAAAGG |
| 2847 | mir-127-prec | 0.25 | TCGGATCCGTCTGAGCTTGGCTGGTCGGAAGTCTCATCAT |
| 2848 | mir-324No1 | 0.28 | TGGAGACCCACTGCCCCAGGTGCTGCTGGGGGTTGTAGTC |
| 2287 | Hcd794 right | 0.35 | GGCCACCACAGACACCAACAAGTTCAGTCCGTTTCTGCAG |
| 2850 | Hcd634 left | 0.27 | CTGCTCCGCTCAGAGCCTTTTCCTCTCCACTTCCTGTTCA |

TABLE 111

Bortezomib microRNA biomarkers.

| SEQ ID NO | Medianprobe | Corr | Sequence |
|---|---|---|---|
| 2304 | MPR121 left | 0.31 | CACCTGGCTCTGAGAACTGAATTCCATAGGCTGTGAGCTC |
| 2852 | Hcd115 left | 0.27 | CTCTGTGGCCATTTCGGTTTTTCCAGTCCGATGCCCTGA |

TABLE 111-continued

Bortezomib microRNA biomarkers.

| SEQ ID NO | Medianprobe | Corr | Sequence |
|---|---|---|---|
| 2626 | Hcd693 right | 0.28 | AGGCTTTGTGCGCGCATTAAAGCTCGCCGGACCCCCGACC |
| 2760 | Hcd704 left | 0.25 | TCTGTATTTAATTTGGCTCAGCCGGGAAGATTTTTGGCTC |
| 2855 | HPR100 right | 0.28 | GGTGTTTGTGCTCCACTCAGCTCCCTTGGTTACATAACAG |
| 2763 | Hcd760 left | 0.26 | TGTGGTCACGTTTCTCCCTCTCTGCTGGCCCCCATCTGTC |
| 2308 | mir-147-prec | 0.3 | GACTATGGAAGCCAGTGTGTGGAAATGCTTCTGCTAGATT |
| 2845 | mir-033b-prec | 0.29 | GTGCATTGCTGTTGCATTGCACGTGTGTGAGGCGGGTGCA |
| 2312 | mir-146-prec | 0.33 | TGAGAACTGAATTCCATGGGTTGTGTCAGTGTCAGACCTC |
| 2860 | Hcd142 right | 0.3 | TAAATGTGTAATTTCTCCCTTGACGGCCCCCGGCCGCTGG |
| 2861 | mir-501No2 | 0.33 | ATGCAATGCACCCGGGCAAGGATTCTGAGAGGGTGAGCCC |
| 2330 | Hcd716 right | 0.26 | CAATAAATGTGCCTATAAAGGCGCCGGCTCCGGGGCGCGG |
| 2331 | MPR207 right | 0.27 | AACAACTTTGTGCTGGTGCCGGGGAAGTTTGTGTCTCCTA |
| 2864 | Hcd777 left | 0.26 | CAGGTGGGTGCTGAGGCCGCGTTGTTGCTTGAAGCTAGCC |
| 2865 | mir-204-precNo2 | 0.27 | AGGCTGGGAAGGCAAAGGGACGTTCAATTGTCATCACTGG |
| 2314 | mir-146bNo1 | 0.26 | CACCTGGCACTGAGAACTGAATTCCATAGGCTGTGAGCTC |
| 2616 | Hcd511 right | 0.29 | TACCTCAGAAGCCTCACTCAACCCTCTCCCGCTGAGTCTC |
| 2316 | Hcd397 left | 0.28 | GTGTGTATACTTATGTGTGTGTATGTGTGAGTGTGAATAT |
| 2869 | MPR130 right | 0.33 | CAATCACAGATAGCACCCCTCACCTTGAGCCCATTTTCAC |
| 2337 | Hcd782 left | 0.28 | GGAGCCCTGTCTGCAAAGAGTGGTGCGTGTGCGTGTGTGA |
| 2871 | mir-324No2 | 0.28 | CTGACTATGCCTCCCCGCATCCCCTAGGGCATTGGTGTAA |
| 2287 | Hcd794 right | 0.34 | GGCCACCACAGACACCAACAAGTTCAGTCCGTTTCTGCAG |
| 2288 | Hcd739 right | 0.29 | TATTAGCTGAGGGAGGGCTGGAGGCGGCTGCATTCCGACT |

TABLE 112

Leukeran microRNA biomarkers.

| SEQ ID NO | Medianprobe | Corr | Sequence |
|---|---|---|---|
| 2377 | mir-092prec-X = 092-2 | 0.39 | GTTCTATATAAAGTATTGCACTTGTCCCGGCCTGTGGAAG |
| 2412 | mir-096-prec-7No1 | 0.26 | CTCCGCTCTGAGCAATCATGTGCAGTGCCAATATGGGAAA |
| 2430 | mir-123-precNo2 | 0.32 | TGTGACACTTCAAACTCGTACCGTGAGTAATAATGCGCCG |
| 2877 | MPR249 left | 0.26 | TCGGTTTGGTTCAGCTGGTATGCTTTCCAGTATCTCATTC |
| 2486 | HPR232 right | 0.28 | TGAATTATTGCACAATAAATTCATGCCCTGTTGTGTCTTA |
| 2413 | mir-101-prec-9 | 0.4 | GCTGTATATCTGAAAGGTACAGTACTGTGATAACTGAAGA |
| 2391 | mir-106aNo1 | 0.31 | CCTTGGCCATGTAAAAGTGCTTACAGTGCAGGTAGCTTTT |
| 2414 | mir-20bNo1 | 0.38 | AGTACCAAAGTGCTCATAGTGCAGGTAGTTTTGGCATGAC |
| 2882 | Hcd861 right | 0.25 | AAGGTCTGGATTGATCGTACTGCTTTCTGAAAGGTAAAAA |
| 2572 | mir-017-precNo2 | 0.26 | GTCAGAATAATGTCAAAGTGCTTACAGTGCAGGTAGTGAT |

TABLE 112-continued

Leukeran microRNA biomarkers.

| SEQ ID NO | Medianprobe | Corr | Sequence |
|---|---|---|---|
| 2381 | mir-019b-2-prec | 0.33 | GTGGCTGTGCAAATCCATGCAAAACTGATTGTGATAATGT |
| 2607 | mir-033-prec | 0.3 | GTGGTGCATTGTAGTTGCATTGCATGTTCTGGTGGTACCC |
| 2506 | Hcd102 left | 0.26 | ACTGGAATTATGTTTTATCTTAAGTCCACACTGGATCCTC |
| 2382 | MFR216 left | 0.32 | GATCCTAGTAGTGCCAAAGTGCTCATAGTGCAGGTAGTTT |
| 2888 | Hcd975 left | 0.25 | GGTTTTGTGTTTTTGTAAACAGCAGAAGGTATTAGTCCAT |
| 2383 | mir-019b-1-prec | 0.3 | TTCTGCTGTGCAAATCCATGCAAAACTGACTGTGGTAGTG |
| 2384 | mir-135-2-prec | 0.38 | CACTCTAGTGCTTTATGGCTTTTTATTCCTATGTGATAGT |
| 2524 | Hcd581 right | 0.26 | AGGAGATATGCCAAGATATATTCACAGCTTTATATACACA |
| 2525 | Hcd536_HPR104 right | 0.25 | GCTGCTCTGCTGAGGGGCTGGACTCTGTCCAGAAGCACCA |
| 2893 | mir-128b-precNo2 | 0.25 | GGGGGCCGATACACTGTACGAGAGTGAGTAGCAGGTCTCA |
| 2332 | HSTRNL | 0.37 | TCCGGATGGAGCGTGGGTTCGAATCCCACTTCTGACACCA |
| 2386 | mir-025-prec | 0.47 | ACGCTGCCCTGGGCATTGCACTTCTCTCGGTCTGACAGTG |
| 2692 | mir-18bNo2 | 0.27 | AGCAGCTTAGAATCTACTGCCCTAAATGCCCCTTCTGGCA |
| 2897 | HPR262 left | 0.26 | TCAGTTTGGTTCAGCTGGTATGCTTTCCAGTATCTCATTC |
| 2298 | Hcd923 right | 0.33 | CTGGAGATAATGATTCTGCATTTCTAATTAACTCCCAGGT |
| 2899 | Hcd434 right | 0.3 | CACTTTTTCCTTTGTGGAAATCCTGGGTGACATCACCTCC |
| 2900 | Hcd658 right | 0.28 | GACTGCAGAGCAAAAGACACGATGGGTGTCTATTGTTTTC |
| 2901 | HPR129 left | 0.29 | TTTTCCTGCTTGATTTGCTTAATGGAAGCTGACAGTGAAG |
| 2389 | mir-380-5p | 0.32 | AGGTACCTGAAAAGATGGTTGACCATAGAACATGCCCTAT |
| 2390 | mir-093-prec-7.1 = 093-1 | 0.45 | CCAAAGTGCTGTTCGTGCAGGTAGTGTGATTACCCAACCT |
| 2391 | mir-106-prec-X | 0.5 | CCTTGGCCATGTAAAAGTGCTTACAGTGCAGGTAGCTTTT |
| 2544 | Hcd627 left | 0.31 | GCATTAGGGAGAATAGTTGATGGATTACAAATCTCTGCAT |
| 2300 | mir-142-prec | 0.33 | CCCATAAAGTAGAAAGCACTACTAACAGCACTGGAGGGTG |
| 2393 | mir-018-prec | 0.46 | TAAGGTGCATCTAGTGCAGATAGTGAAGTAGATTAGCATC |
| 2394 | mir-020-prec | 0.5 | TAAAGTGCTTATAGTGCAGGTAGTGTTTAGTTATCTACTG |

TABLE 113

Fludarabine microRNA biomarkers.

| SEQ ID NO | Medianprobe | Corr | Sequence |
|---|---|---|---|
| 2713 | Hcd773 left | 0.26 | CTTCCTCCCTGGGCATCTCTAGCACAGGGGATCCCCAAAC |
| 2910 | Hcd248 right | 0.33 | CATTATGCAAATGGTATGAGAGGAAAATTAGGCAATAAGG |
| 2571 | mir-181dNo1 | 0.34 | GAGGTCACAATCAACATTCATTGTTGTCGGTGGGTTGTGA |
| 2699 | MPR74 left | 0.3 | CAAAGGTCACAATTAACATTCATTGTTGTCGGTGGGTTGT |
| 2306 | mir-213-precNo1 | 0.37 | AACATTCATTGCTGTCGGTGGGTTGAACTGTGTGGACAAG |
| 2293 | mir-155-prec | 0.32 | TTAATGCTAATCGTGATAGGGGTTTTTGCCTCCAACTGAC |
| 2291 | MPR197 right | 0.29 | TATTTATTACAAGGTCCTTCTTCCCCGTAAAACTTTGTCC |

TABLE 113-continued

Fludarabine microRNA biomarkers.

| SEQ ID NO | Medianprobe | Corr | Sequence |
|---|---|---|---|
| 2398 | mir-181b-precNo1 | 0.26 | TGAGGTTGCTTCAGTGAACATTCAACGCTGTCGGTGAGTT |
| 2827 | mir-29b-2 = 102prec7.1 = 7.2 | 0.32 | AGTGATTGTCTAGCACCATTTGAAATCAGTGTTCTTGGGG |
| 2918 | mir-029c-prec | 0.33 | TTTTGTCTAGCACCATTTGAAATCGGTTATGATGTAGGGG |
| 2919 | Hcd318 right | 0.32 | CAAGTGGTTAATTGAGCCCACAAGTGACCTACTCAATCAG |
| 2451 | mir-128b-precNo1 | 0.25 | TCACAGTGAACCGGTCTCTTTCCCTACTGTGTCACACTCC |
| 2921 | mir-130a-precNo2 | 0.27 | TGTCTGCACCTGTCACTAGCAGTGCAATGTTAAAAGGGCA |
| 2311 | mir-140No2 | 0.26 | TTCTACCACAGGGTAGAACCACGGACAGGATACCGGGGCA |
| 2588 | mir-16-2No1 | 0.31 | GTTCCACTCTAGCAGCACGTAAATATTGGCGTAGTGAAAT |
| 2924 | mir-526a-2No1 | 0.26 | GATCTCGTGCTGTGACCCTCTAGAGGGAAGCACTTTCTGT |
| 2588 | mir-016b-chr3 | 0.3 | GTTCCACTCTAGCAGCACGTAAATATTGGCGTAGTGAAAT |
| 2475 | mir-195-prec | 0.34 | TCTAGCAGCACAGAAATATTGGCACAGGGAAGCGAGTCTG |
| 2735 | mir-216-precNo1 | 0.25 | CTGGGATTATGCTAAACAGAGCAATTTCCTAGCCCTCACG |
| 2299 | mir-342No1 | 0.26 | GTCTCACACAGAAATCGCACCCGTCACCTTGGCCTACTTA |
| 2827 | mir-29b-1No1 | 0.34 | AGTGATTGTCTAGCACCATTTGAAATCAGTGTTCTTGGGG |
| 2544 | Hcd627 left | 0.33 | GCATTAGGGAGAATAGTTGATGGATTACAAATCTCTGCAT |
| 2931 | mir-102-prec-1 | 0.33 | TCTTTGTATCTAGCACCATTTGAAATCAGTGTTTTAGGAG |
| 2300 | mir-142-prec | 0.32 | CCCATAAAGTAGAAAGCACTACTAACAGCACTGGAGGGTG |
| 2301 | mir-223-prec | 0.34 | GAGTGTCAGTTTGTCAAATACCCCAAGTGCGGCACATGCT |
| 2934 | let-7f-2-prec2 | 0.26 | TGAGGTAGTAGATTGTATAGTTTTAGGGTCATACCCCATC |
| 2598 | mir-016a-chr13 | 0.36 | CAATGTCAGCAGTGCCTTAGCAGCACGTAAATATTGGCGT |

TABLE 114

Vinblastine microRNA biomarkers.

| SEQ ID NO | Medianprobe | Corr | Sequence |
|---|---|---|---|
| 2287 | Hcd794 right | 0.33 | GGCCACCACAGACACCAACAAGTTCAGTCCGTTTCTGCAG |
| 2302 | Hcd754 left | 0.25 | TCCTCCTCCTCCTTTTCGTTCCGGCTCCCTGGCTGGCTCC |

TABLE 115

Busulfan microRNA biomarkers.

| SEQ ID NO | Medianprobe | Corr | Sequence |
|---|---|---|---|
| 2378 | mir-096-prec-7No2 | 0.27 | TGGCCGATTTTGGCACTAGCACATTTTTGCTTGTGTCTCT |
| 2711 | mir-124a-3-prec | 0.25 | TTAAGGCACGCGGTGAATGCCAAGAGAGGCGCCTCCGCCG |

TABLE 115-continued

Busulfan microRNA biomarkers.

| SEQ ID NO | Medianprobe | Corr | Sequence |
|---|---|---|---|
| 2413 | mir-101-prec-9 | 0.25 | GCTGTATATCTGAAAGGTACAGTACTGTGATAACTGAAGA |
| 2752 | Hcd712 right | 0.27 | GAAGATCGGTTGTCATCTGGTCTGGTCAGCCCGGCCCCGA |
| 2626 | Hcd693 right | 0.26 | AGGCTTTGTGCGCGCATTAAAGCTCGCCGGACCCCCGACC |
| 2778 | mir-219-2No1 | 0.25 | CTCAGGGGCTTCGCCACTGATTGTCCAAACGCAATTCTTG |
| 2324 | Hcd145 left | 0.29 | AAAAATCCCAGCGGCCACCTTTCCTCCCTGCCCCATTGGG |
| 2293 | mir-155-prec | 0.29 | TTAATGCTAATCGTGATAGGGGTTTTTGCCTCCAACTGAC |
| 2765 | HPR213 right | 0.3 | AACAACTTTGTGCTGGTGCCGGGGAAGTTTGTGTCTCCAA |
| 2785 | mir-212-precNo2 | 0.34 | CGGACAGCGCGCCGGCACCTTGGCTCTAGACTGCTTACTG |
| 2326 | Hcd913 right | 0.33 | CAAACATCATGTGACGTCTGTGGAGCGGCGGCGGCGGCGG |
| 2330 | Hcd716 right | 0.51 | CAATAAATGTGCCTATAAAGGCGCCGGCTCCGGGGCGCGG |
| 2331 | MFR207 right | 0.26 | AACAACTTTGTGCTGGTGCCGGGGAAGTTTGTGTCTCCTA |
| 2951 | Hcd559 right | 0.33 | TTCTTTGTCTATACATTTCCTAGATTTCTATGCAGTTGGG |
| 2285 | Hcd654 left | 0.28 | AACGAGTAAAAGGCGTACATGGGAGCGCGGGGCGGCAGAG |
| 2288 | Hcd739 right | 0.27 | TATTAGCTGAGGGAGGGCTGGAGGCGGCTGCATTCCGACT |
| 2300 | mir-142-prec | 0.4 | CCCATAAAGTAGAAAGCACTACTAACAGCACTGGAGGGTG |

TABLE 116

Dacarbazine microRNA biomarkers.

| SEQ ID NO | Medianprobe | Corr | Sequence |
|---|---|---|---|
| 2377 | mir-092-prec-X = 092-2 | 0.25 | GTTCTATATAAAGTATTGCACTTGTCCCGGCCTGTGGAAG |
| 2430 | mir-123-precNo2 | 0.28 | TGTGACACTTCAAACTCGTACCGTGAGTAATAATGCGCCG |
| 2413 | mir-101-prec-9 | 0.29 | GCTGTATATCTGAAAGGTACAGTACTGTGATAACTGAAGA |
| 2958 | Hcd517 right | 0.3 | GAGGGATTACAGATTAACTCCCACTTCTCCAGACTCAGAA |
| 2715 | Hcd796 left | 0.37 | GGTGGGATTACCCGGCTGCCGCTGTCGCCTGGATGGTCTC |
| 2960 | Hcd749 right | 0.28 | CGAGGAGGAGGTGACTGCTGTGGATGGTTATGAGACAGAC |
| 2961 | Hcd674 left | 0.25 | CTCCAGTGTGGTGTGCCTGCCCCCTTCCGTCATTGCTGTG |
| 2381 | mir-019b-2-prec | 0.27 | GTGGCTGTGCAAATCCATGCAAAACTGATTGTGATAATGT |
| 2607 | mir-033-prec | 0.29 | GTGGTGCATTGTAGTTGCATTGCATGTTCTGGTGGTACCC |
| 2608 | mir092-prec-13 = 092-1No2 | 0.33 | TCTGTATGGTATTGCACTTGTCCCGGCCTGTTGAGTTTGG |
| 2658 | mir-124a-2-prec | 0.29 | TTAAGGCACGCGGTGAATGCCAAGAGCGGAGCCTACGGCT |
| 2966 | mir-143-prec | 0.36 | CTGGTCAGTTGGGAGTCTGAGATGAAGCACTGTAGCTCAG |
| 2967 | mir-516-43p | 0.28 | AAAGAAAGAAAGTGCTTCCTTTCAGAGGGTTACTCTTTG |
| 2735 | mir-216-precNo1 | 0.31 | CTGGGATTATGCTAAACAGAGCAATTTCCTAGCCCTCACG |
| 2317 | Hcd731 left | 0.26 | AATTGTGACAACTGAGTGGGAGGTTTGTGTGATGATTATC |
| 2391 | mir-106-prec-X | 0.26 | CCTTGGCCATGTAAAAGTGCTTACAGTGCAGGTAGCTTTT |

TABLE 116-continued

Dacarbazine microRNA biomarkers.

| SEQ ID NO | Medianprobe | Corr | Sequence |
|---|---|---|---|
| 2300 | mir-142-prec | 0.48 | CCCATAAAGTAGAAAGCACTACTAACAGCACTGGAGGGTG |
| 2301 | mir-223-prec | 0.48 | CAGTGTCAGTTTGTCAAATACCCCAAGTGCGGCACATGCT |
| 2302 | Hcd754 left | 0.32 | TCCTCCTCCTCCTTTTCGTTCCGGCTCCCTGGCTGGCTCC |
| 2393 | mir-018-prec | 0.27 | TAAGGTGCATCTAGTGCAGATAGTGAAGTAGATTAGCATC |

TABLE 117

Oxaliplatin microRNA biomarkers.

| SEQ ID NO | Medianprobe | Corr | Sequence |
|---|---|---|---|
| 2377 | mir-092-prec-X = 092-2 | 0.36 | GTTCTATATAAAGTATTGCACTTGTCCCGGCCTGTGGAAG |
| 2772 | mir-148-prec | 0.27 | TGAGTATGATAGAAGTCAGTGCACTACAGAACTTTGTCTC |
| 2414 | mir-20bNo1 | 0.27 | AGTACCAAAGTGCTCATAGTGCAGGTAGTTTTGGCATGAC |
| 2380 | mir-007-2-precNo2 | 0.28 | GGACCGGCTGGCCCCATCTGGAAGACTAGTGATTTTGTTG |
| 2572 | mir-017-precNo2 | 0.28 | GTCAGAATAATGTCAAAGTGCTTACAGTGCAGGTAGTGAT |
| 2381 | mir-019b-2-prec | 0.32 | GTGGCTGTGCAAATCCATGCAAAACTGATTGTGATAATGT |
| 2763 | Hcd760 left | 0.27 | TGTGGTCACGTTTCTCCCTCTCTGCTGGCCCCATCTGTC |
| 2447 | Hcd783 left | 0.36 | CAGGCTCACACCTCCCTCCCCCAACTCTCTGGAATGTATA |
| 2382 | MPR216 left | 0.26 | GATCCTAGTAGTGCCAAAGTGCTCATAGTGCAGGTAGTTT |
| 278 | mir-375 | 0.33 | TTTTGTTCGTTCGGCTCGCGTGAGGCAGGGGCGGCCTCTC |
| 2383 | mir-019b-1-prec | 0.36 | TTCTGCTGTGCAAATCCATGCAAAACTGACTGTGGTAGTG |
| 2384 | mir-135-2-prec | 0.32 | CACTCTAGTGCTTTATGGCTTTTTATTCCTATGTGATAGT |
| 2448 | mir-150-prec | 0.25 | CTCCCCATGGCCCTGTCTCCCAACCCTTGTACCAGTGCTG |
| 2451 | mir-128b-precNo1 | 0.33 | TCACAGTGAACCGGTCTCTTTCCCTACTGTGTCACACTCC |
| 2989 | mir-499No2 | 0.26 | GTGAACATCACAGCAAGTCTGTGCTGCTTCCCGTCCCTAC |
| 2386 | mir-025-prec | 0.38 | ACGCTGCCCTGGGCATTGCACTTGTCTCGGTCTGACAGTG |
| 2283 | mir-007-1-prec | 0.32 | TGTTGGCCTAGTTCTGTGTGGAAGACTAGTGATTTTGTTG |
| 2388 | mir-019a-prec | 0.33 | TGTAGTTGTGCAAATCTATGCAAAACTGATGGTGGCCTGC |
| 2390 | mir-093-prec-7.1 = 093-1 | 0.46 | CCAAAGTGCTGTTCGTGCAGGTAGTGTGATTACCCAACCT |
| 2391 | mir-106-prec-X | 0.45 | CCTTGGCCATGTAAAAGTGCTTACAGTGCAGGTAGCTTTT |
| 2300 | mir-142-prec | 0.41 | CCCATAAAGTAGAAAGCACTACTAACAGCACTGGAGGGTG |
| 2427 | HPR169 right | 0.34 | GTTTCTTTCTCACGGTAACTGGCAGCCTCGTTGTGGGCTG |
| 2393 | mir-018-prec | 0.4 | TAAGGTGCATCTAGTGCAGATAGTGAAGTAGATTAGCATC |
| 2394 | mir-020-prec | 0.44 | TAAAGTGCTTATAGTGCAGGTAGTGTTTAGTTATCTACTG |
| 2453 | mir-484 | 0.33 | GTCAGGCTCAGTCCCCTCCCGATAAACCCCTAAATAGGGA |

TABLE 118

Hydroxyurea microRNA biomarkers.

| SEQ ID NO | Medianprobe | Corr | Sequence |
|---|---|---|---|
| 2771 | Hcd257 left | 0.34 | CTTCTTGTATAAGCACTGTGCTAAAATTGCAGACACTAGG |
| 2321 | Hcd768 right | 0.26 | GCCCTGGCGGAACGCTGAGAAGACAGTCGAACTTGACTAT |
| 2715 | Hcd796 left | 0.25 | GGTGGGATTACCCGGCTGCCGCTGTCGCCTGGATGGTCTC |
| 2290 | HUMTRF | 0.48 | GATCTAAAGGTCCCTGGTTCGATCCCGGGTTTCGGCACCA |
| 2305 | HUMTRS | 0.3 | TCTAGCGACAGAGTGGTTCAATTCCACCTTTCGGGCGCCA |
| 2699 | MPR74 left | 0.28 | CAAAGGTCACAATTAACATTCATTGTTGTCGGTGGGTTGT |
| 2306 | mir-213-precNo1 | 0.29 | AACATTCATTGCTGTCGGTGGGTTGAACTGTCTGGACAAG |
| 2293 | mir-155-prec | 0.35 | TTAATGCTAATCGTGATAGGGGTTTTTGCCTCCAACTGAC |
| 3008 | Hcd763 right | 0.25 | GGTGCACTCTAAATTCCTGTCCCTGCGGAAGGCTGACTAA |
| 2398 | mir-181b-precNo1 | 0.28 | TGAGGTTGCTTCAGTGAACATTCAACGCTGTCGGTGAGTT |
| 2433 | ath-MIR180aNo2 | 0.26 | TGAGAATCTTGATGATGCTGCATCGGCAATCAACGACTAT |
| 2735 | mir-216-precNo1 | 0.37 | CTGGGATTATGCTAAACAGAGCAATTTCCTAGCCCTCACG |
| 2299 | mir-342No1 | 0.31 | GTCTCACACAGAAATCGCACCCGTCACCTTGGCCTACTTA |
| 2300 | mir-142-prec | 0.49 | CCCATAAAGTAGAAAGCACTACTAACAGCACTGGAGGGTG |
| 2341 | HSHELA01 | 0.31 | GGCCGCAGCAACCTCGGTTCGTATCCGAGTCACGGCACCA |
| 2342 | HUMTRV1A | 0.26 | ACGCGAAAGGTCCCCGGTTCGAAACCGGGCGGAAACACCA |
| 2301 | mir-223-prec | 0.59 | CAGTGTCAGTTTGTCAAATACCCCAAGTGCGGCACATGCT |
| 2302 | Hcd754 left | 0.46 | TCCTCCTCCTCCTTTTCGTTCCGGCTCCCTGGCTGGCTCC |
| 2394 | mir-020-prec | 0.26 | TAAAGTGCTTATAGTGCAGGTAGTGTTTAGTTATCTACTG |

TABLE 119

Tegafur microRNA biomarkers.

| SEQ ID NO | Medianprobe | Corr | Sequence |
|---|---|---|---|
| 2431 | Hcd257 right | 0.26 | CTTGGTTTTTGCAATAATGCTAGCAGAGTACACACAAGAA |
| 3020 | Hcd946 left | 0.26 | CACAGGATTTCAGGGGAGAAACGGTGGATTTTCACAAGAG |
| 3021 | Hcd503 left | 0.3 | GAGATGAGGTAGCTGCCAGGTGCCATGGGGGTATAGGTGA |
| 2625 | mir-429No1 | 0.25 | CTAATACTGTCTGGTAAAACCGTCCATCCGCTGCCTGATC |
| 2626 | Hcd693 right | 0.32 | AGGCTTTGTGCGCGCATTAAAGCTCGCCGGACCCCCGACC |
| 3024 | miR-373*No1 | 0.33 | GGGATACTCAAAATGGGGGCGCTTTCCTTTTTGTCTGTAC |
| 3025 | Hcd738 left | 0.28 | GAAAACTTAAGATTCCCTCTCGGCCCTCATTTTTAGCTG |
| 2779 | mir-328No1 | 0.33 | GAAAGTGCATACAGCCCCTGGCCCTCTCTGCCCTTCCGTC |
| 2447 | Hcd783 left | 0.36 | CAGGCTCACACCTCCCTCCCCCAACTCTCTGGAATGTATA |
| 3028 | Hcd181 right | 0.34 | GCTCACTGGGCAGGAGCCCTAATCGGATTCGACAGCTGAG |
| 3029 | Hcd631 left | 0.38 | CAGATATTTTCTCAGGCAATCCTCAGCCACAGCCTTCTTG |
| 3030 | Hcd279 left | 0.25 | CGGACTAACACTCCGCGGGTGTTTCCATGGAGACCGAGGC |
| 2631 | mir-194-2No1 | 0.3 | TGGTTCCCGCCCCCTGTAACAGCAACTCCATGTGGAAGTG |

TABLE 119-continued

Tegafur microRNA biomarkers.

| SEQ ID NO | Medianprobe | Corr | Sequence |
|---|---|---|---|
| 2369 | mir-197-prec | 0.38 | TAAGAGCTCTTCACCCTTCACCACCTTCTCCACCCAGCAT |
| 2327 | HPR163 left | 0.39 | GCTGCCCCCTCCCTTAGCAACGTGGCCCCGGCGTTCCAAA |
| 2448 | mir-150-prec | 0.32 | CTCCCCATGGCCCTGTCTCCCAACCCTTGTACCAGTGCTG |
| 3035 | Hcd323 left | 0.26 | GTTGTAGCATGTGGTTGTATTAATGAACGTTACAGGAGAG |
| 2585 | mir-103-2-prec | 0.28 | GTAGCATTCAGGTCAAGCAACATTGTACAGGGCTATGAAA |
| 3037 | Hcd243 right | 0.27 | TATTATACATCATTTCCCATCAATCGACGAACTAAAGCCT |
| 2408 | Hcd938 right | 0.27 | ATTCCCTGCATCACTCTCATGAAATGGCTGAGAAAGTGAG |
| 2386 | mir-025-prec | 0.29 | ACGCTGCCCTGGGCATTGCACTTGTCTCGGTCTGACAGTG |
| 2283 | mir-007-1-prec | 0.36 | TGTTGGCCTAGTTCTGTGTGGAAGACTAGTGATTTTGTTG |
| 2284 | MPR243 left | 0.26 | GTATTTACCTAGTTGTAATGTGGGTTGCCATGGTGTTTTG |
| 2616 | Hcd511 right | 0.27 | TACCTCAGAAGCCTCACTCAACCCTCTCCCGCTGAGTCTC |
| 2285 | Hcd654 left | 0.26 | AACGAGTAAAAGGCGTACATGGGAGCGCGGGGCGGCAGAG |
| 2558 | mir-199a-2-prec | 0.3 | TCGCCCCAGTGTTCAGACTACCTGTTCAGGACAATGCCGT |
| 3045 | mir-214-prec | 0.27 | TGTACAGCAGGCACAGACAGGCAGTCACATGACAACCCAG |
| 2390 | mir-093-prec-7.1 = 093-1 | 0.33 | CCAAAGTGCTGTTCGTGCAGGTAGTGTGATTACCCAACCT |
| 2391 | mir-106-prec-X | 0.27 | CCTTGGCCATGTAAAAGTGCTTACAGTGCAGGTAGCTTTT |
| 2287 | Hcd794 right | 0.41 | GGCCACCACAGACACCAACAAGTTCAGTCCGTTTCTGCAG |
| 3049 | Hcd530 right | 0.26 | AAGGAAAATCAAACCCACAATGCTGAACACAACAATGACC |
| 2341 | HSHELA01 | 0.34 | GGCCGCAGCAACCTCGGTTCGTATCCGAGTCACGGCACCA |
| 2302 | Hcd754 left | 0.29 | TCCTCCTCCTCCTTTTCGTTCCGGCTCCCTGGCTGGCTCC |
| 2394 | mir-020-prec | 0.29 | TAAAGTGCTTATAGTGCAGGTAGTGTTTAGTTATCTACTG |

TABLE 120

Daunorubicin microRNA biomarkers.

| SEQ ID NO | Medianprobe | Corr | Sequence |
|---|---|---|---|
| 2321 | Hcd768 right | 0.25 | GCCCTGGCGGAACGCTGAGAAGACAGTCGAACTTGACTAT |
| 2290 | HUMTRF | 0.34 | GATCTAAAGGTCCCTGGTTCGATCCCGGGTTTCGGCACCA |
| 2324 | Hcd145 left | 0.28 | AAAATCCCAGCGGCCACCTTTCCTCCCTGCCCCATTGGG |
| 2298 | Hcd923 right | 0.27 | CTGGAGATAATGATTCTGCATTTCTAATTAACTCCCAGGT |
| 2735 | mir-216-precNo1 | 0.27 | CTGGGATTATGCTAAACAGAGCAATTTCCTAGCCCTCACG |
| 2390 | mir-093-prec-7.1 = 093-1 | 0.25 | CCAAAGTGCTGTTCGTGCAGGTAGTGTGATTACCCAACCT |
| 2299 | mir-342No1 | 0.33 | GTCTCACACAGAAATCGCACCCGTCACCTTGGCCTACTTA |
| 2287 | Hcd794 right | 0.28 | GGCCACCACAGACACCAACAAGTTCAGTCCGTTTCTGCAG |
| 2300 | mir-142-prec | 0.48 | CCCATAAAGTAGAAAGCACTACTAACAGCACTGGAGGGTG |
| 2341 | HSHELA01 | 0.3 | GGCCGCAGCAACCTCGGTTCGTATCCGAGTCACGGCACCA |

TABLE 120-continued

Daunorubicin microRNA biomarkers.

| SEQ ID NO | Medianprobe | Corr | Sequence |
|---|---|---|---|
| 2301 | mir-223-prec | 0.33 | GAGTGTCAGTTTGTCAAATACCCCAAGTGCGGCACATGCT |
| 2302 | Hcd754 left | 0.32 | TCCTCCTCCTCCTTTTCGTTCCGGCTCCCTGGCTGGCTCC |

TABLE 121

Bleomycin microRNA biomarkers.

| SEQ ID NO | Medianprobe | Corr | Sequence |
|---|---|---|---|
| 3065 | mir-125b-2-precNo2 | 0.29 | ACCAGACTTTTCCTAGTCCCTGAGACCCTAACTTGTGAGG |
| 2653 | mir-022-prec | 0.26 | TGTCCTGACCCAGCTAAAGCTGCCAGTTGAAGAACTGTTG |
| 3067 | mir-125b-1 | 0.29 | TCCCTGAGACCCTAACTTGTGATGTTTACCGTTTAAATCC |
| 2293 | mir-155-prec | 0.38 | TTAATGCTAATCGTGATAGGGGTTTTTGCCTCCAACTGAC |
| 2309 | mir-100No1 | 0.25 | CCTGTTGCCACAAACCCGTAGATCCGAACTTGTGGTATTA |
| 2355 | mir-409-3p | 0.27 | GACGAATGTTGCTCGGTGAACCCCTTTTCGGTATCAAATT |
| 2358 | mir-495No1 | 0.31 | GTGACGAAACAAACATGGTGCACTTCTTTTTCGGTATCAA |
| 2558 | mir-199a-2-prec | 0.29 | TCGCCCCAGTGTTCAGACTACCTGTTCAGGACAATGCCGT |
| 2362 | mir-382 | 0.28 | GGTACTTGAAGAGAAGTTGTTCGTGGTGGATTCGCTTTAC |
| 2319 | mir-100-1/2-prec | 0.26 | TGAGGCCTGTTGCCACAAACCCGTAGATCCGAACTTGTGG |

TABLE 122

Estramustine microRNA biomarkers.

| SEQ ID NO | Medianprobe | Corr | Sequence |
|---|---|---|---|
| 2764 | Hcd338 left | 0.32 | CTTCTCCTCCTGTTCGCCGCAGGCGCCCGTCCCAGTAGTC |
| 3076 | mir-099b-prec-19No1 | 0.25 | GCCTTCGCCGCACACAAGCTCGTGTCTGTGGGTCCGTGTC |
| 3077 | mir-149-prec | 0.34 | CGAGCTCTGGCTCCGTGTCTTCACTCCCGTGCTTGTCCGA |

TABLE 123

Chlorambucil microRNA biomarkers.

| SEQ ID NO | Medianprobe | Corr | Sequence |
|---|---|---|---|
| 2712 | mir-181a-precNo1 | 0.26 | TCAGAGGACTCCAAGGAACATTCAACGCTGTCGGTGAGTT |
| 2466 | mir-181c-precNo1 | 0.25 | TGCCAAGGGTTTGGGGGAACATTCAACCTGTCGGTGAGTT |
| 2290 | HUMTRF | 0.35 | GATCTAAAGGTCCCTGGTTCGATCCCGGGTTTCGGCACCA |

TABLE 123-continued

Chlorambucil microRNA biomarkers.

| SEQ ID NO | Medianprobe | Corr | Sequence |
|---|---|---|---|
| 2571 | mir-181dNo1 | 0.26 | GAGGTCACAATCAACATTCATTGTTGTCGGTGGGTTGTGA |
| 2699 | MPR74 left | 0.28 | CAAAGGTCACAATTAACATTCATTGTTGTCGGTGGGTTGT |
| 2502 | Hcd817 left | 0.28 | TAATGAGAATTATGTTTGCACATTGAGGCAGGATAAATCC |
| 2306 | mir-213-precNo1 | 0.42 | AACATTCATTGCTGTCGGTGGGTTGAACTGTGTGGACAAG |
| 2293 | mir-155-prec | 0.33 | TTAATGCTAATCGTGATAGGGGTTTTTGCCTCCAACTGAC |
| 2407 | Hcd148_HPR225left | 0.29 | AATTAATGACCAAAATGTCAGATGTGTCCACAGCTAATTA |
| 2294 | mir-515-15p | 0.27 | GATCTCATGCAGTCATTCTCCAAAAGAAAGCACTTTCTGT |
| 2398 | mir-181b-precNo1 | 0.41 | TGAGGTTGCTTCAGTGAACATTCAACGCTGTCGGTGAGTT |
| 2728 | HUMTRN | 0.27 | CAATCGGTTAGCGCGTTCGGCTGTTAACCGAAAGGTTGGT |
| 2451 | mir-128b-precNo1 | 0.37 | TCACAGTGAACCGGTCTCTTTCCCTACTGTGTCACACTCC |
| 2297 | mir-450-2No1 | 0.29 | GAAAGATGCTAAACTATTTTGCGATGTGTTCCTAATATG |
| 2735 | mir-216-precNo1 | 0.29 | CTGGGATTATGCTAAACAGAGCAATTTCCTAGCCCTCACG |
| 2299 | mir-342No1 | 0.35 | GTCTCACACAGAAATCGCACCCGTCACCTTGGCCTACTTA |
| 2300 | mir-142-prec | 0.45 | CCCATAAAGTAGAAAGCACTACTAACAGCACTGGAGGGTG |
| 2301 | mir-223-prec | 0.39 | GAGTGTCAGTTTGTCAAATACCCCAAGTGCGGCACATGCT |
| 2302 | Hcd754 left | 0.37 | TCCTCCTCCTCCTTTTCGTTCCGGCTCCCTGGCTGGCTCC |
| 2394 | mir-020-prec | 0.28 | TAAAGTGCTTATAGTGCAGGTAGTGTTTAGTTATCTACTG |

TABLE 124

Mechlorethamine microRNA biomarkers.

| SEQ ID NO | Medianprobe | Corr | Sequence |
|---|---|---|---|
| 2711 | mir-124a-3-prec | 0.33 | TTAAGGCACGCGGTGAATGCCAAGAGAGGCGCCTCCGCCG |
| 3020 | Hcd946 left | 0.3 | CACAGGATTTCAGGGGAGAAACGGTGGATTTTCACAAGAG |
| 2714 | Hcd683 left | 0.29 | CTATGACAGAAGGTACTCTGTGGGAGGGAGGAGATAATAG |
| 3101 | HPR264 right | 0.25 | CAAATGGCGCATCAATGACTATCGCTCTTACAAAGCTCTT |
| 3102 | MPR185 right | 0.3 | CAGAACATGCAATGCAACTACAATGCACCACAGCTGCCCG |
| 2290 | HUMTRF | 0.37 | GATCTAAAGGTCCCTGGTTCGATCCCGGGTTTCGGCACCA |
| 3104 | Hcd294 left | 0.25 | TTATCATAAAATAATCACAGCCCTCAGGTGCTGTGAGGCA |
| 3021 | Hcd503 left | 0.27 | GAGATGAGGTAGCTGCCAGGTGCCATGGGGGTATAGGTGA |
| 2414 | mir-20bNo1 | 0.27 | AGTACCAAAGTGCTCATAGTGCAGGTAGTTTTGGCATGAC |
| 2699 | MPR74 left | 0.25 | CAAAGGTCACAATTAACATTCATTGTTGTCGGTGGGTTGT |
| 3108 | MPR234 right | 0.28 | GCTGACGTCACGGGCAGAATTGTCCCATTTAGGGATCCCG |
| 3109 | Hcd447 right | 0.26 | CTCAGGCCATTAACCTCAGTTGGTCACTAATCCCTAGGAA |
| 3110 | Hcd817 right | 0.3 | GAATCTTGCCCTTGGATGCATACTGTAATTTCCATTAAAG |
| 2407 | Hcd148_HPR225left | 0.32 | AATTAATGACCAAAATGTCAGATGTGTCCACAGCTAATTA |
| 2294 | mir-515-15p | 0.29 | GATCTCATGCAGTCATTCTCCAAAAGAAAGCACTTTCTGT |

TABLE 124-continued

Mechlorethamine microRNA biomarkers.

| SEQ ID NO | Medianprobe | Corr | Sequence |
|---|---|---|---|
| 3113 | Hcd383 right | 0.25 | CTGATAGTACACGGGGCCAAAATAGATGTATGCTTCTAAG |
| 2295 | mir-181b-precNo2 | 0.31 | ACCATCGACCGTTGATTGTACCCTATGGCTAACCATCATC |
| 2447 | Hcd783 left | 0.33 | CAGGCTCACACCTCCCTCCCCCAACTCTCTGGAATGTATA |
| 3116 | MPR224 left | 0.34 | TGAGGCCCTCTAGGCCGTGAATTAATGTGTCATAACTCAC |
| 2512 | HPR172 right | 0.28 | GTTTAAACAGCCAGTGCAAACATTTAGATCTGAGTCAAAA |
| 2382 | MPR216 left | 0.32 | GATCCTAGTAGTGCCAAAGTGCTCATAGTGCAGGTAGTTT |
| 2728 | HUMTRN | 0.28 | CAATCGGTTAGCGCGTTCGGCTGTTAACCGAAAGGTTGGT |
| 3120 | mir-321No1 | 0.3 | TTGGCCTCCTAAGCCAGGGATTGTGGGTTCGAGTCCCACC |
| 2519 | HFR159 left | 0.25 | TCCGTCACTTGAACTGGCTGCCAGCGTTCACAGACAGCTG |
| 3122 | MPR228 left | 0.29 | TTTTTGCTCCCAGTCAGTAGGAAGATTGTTTCAAATCTGT |
| 2433 | ath-MIR180aNo2 | 0.31 | TGAGAATCTTGATGATGCTGCATCGGCAATCAACGACTAT |
| 2369 | mir-197-prec | 0.28 | TAAGAGCTCTTCACCCTTCACCACCTTCTCCACCCAGCAT |
| 2296 | mir-124a-1-prec1 | 0.26 | ATACAATTAAGGCACGCGGTGAATGCCAAGAATGGGGCTG |
| 2451 | mir-128b-precNo1 | 0.31 | TCACAGTGAACCGGTCTCTTTCCCTACTGTGTCACACTCC |
| 3127 | Hcd28_HPR39left | 0.28 | CTGACTTTCAGTTCCTATTTAAAATGTCTGAATTGGGAGC |
| 2530 | Hcd889 right | 0.25 | ATGCCTTGTGCTCTGTGCTAATTCAGAAGAATAAGCCTGT |
| 3129 | Hcd350 right | 0.26 | TAGCACTTAGCAGGTTGTATTATCATTGTCCGTGTCTATG |
| 2386 | mir-025-prec | 0.31 | ACGCTGCCCTGGGCATTGCACTTGTCTCGGTCTGACAGTG |
| 2835 | mir-208-prec | 0.27 | ACCTGATGCTCACGTATAAGACGAGCAAAAAGCTTGTTGG |
| 2297 | mir-450-2No1 | 0.25 | GAAAGATGCTAAACTATTTTTGCGATGTGTTCCTAATATG |
| 2298 | Hcd923 right | 0.29 | CTGGAGATAATGATTCTGCATTTCTAATTAACTCCCAGGT |
| 2899 | Hcd434 right | 0.28 | CACTTTTTCCTTTGTGGAAATCCTGGGTGACATCACCTCC |
| 2901 | HPR129 left | 0.27 | TTTTCCTGCTTGATTTGCTTAATGGAAGCTGACAGTGAAG |
| 3136 | HPR220 left | 0.27 | GGAGACACTGTAACAACATTTACTCCTGACTGATTACAT |
| 2389 | mir-380-5p | 0.3 | AGGTACCTGAAAAGATGGTTGACCATAGAACATGCGCTAT |
| 2390 | mir-093-prec-7.1 = 093-1 | 0.29 | CCAAAGTGCTGTTCGTGCAGGTAGTGTGATTACCCAACCT |
| 2391 | mir-106-prec-X | 0.3 | CCTTGGCCATGTAAAAGTGCTTACAGTGCAGGTAGCTTTT |
| 2299 | mir-342No1 | 0.28 | GTCTCACACAGAAATCGCACCCGTCACCTTGGCCTACTTA |
| 2300 | mir-142-prec | 0.45 | CCCATAAAGTAGAAAGCACTACTAACAGCACTGGAGGGTG |
| 2341 | HSHELA01 | 0.29 | GGCCGCAGCAACCTCGGTTCGTATCCGAGTCACGGCACCA |
| 2301 | mir-223-prec | 0.32 | GAGTGTCAGTTTGTCAAATACCCCAAGTGCGGCACATGCT |
| 2302 | Hcd754 left | 0.32 | TCCTCCTCCTCCTTTTCGTTCCGGCTCCCTGGCTGGCTCC |
| 2394 | mir-020-prec | 0.37 | TAAAGTGCTTATAGTGCAGGTAGTGTTTAGTTATCTACTG |
| 2410 | mir-4323p | 0.26 | CCTTACGTGGGCCACTGGATGGCTCCTCCATGTCTTGGAG |

TABLE 125

Streptozocin microRNA biomarkers.

| SEQ ID NO | Medianprobe | Corr | Sequence |
|---|---|---|---|
| 2367 | mir-483No1 | 0.2 | ATCACGCCTCCTCACTCCTCTCCTCCCGTCTTCTCCTCTC |
| 3148 | Hcd631 right | 0.21 | AAAACCAAATGGCTGGCTACTCATGTACTGTTGAATGTCT |
| 2370 | mir-212-precNo1 | 0.24 | CCTCAGTAACAGTCTCCAGTCACGGCCACCGACGCCTGGC |
| 2408 | Hcd938 right | 0.21 | ATTCCCTGCATCACTCTCATGAAATGGCTGAGAAAGTGAG |
| 3151 | MPR133 right | 0.2 | CTGTAGATACTTTCTCCCTGAGCCCCTCCTGCCCCCCTGC |
| 2287 | Hcd794 right | 0.21 | GGCCACCACAGACACCAACAAGTTCAGTCCGTTTCTGCAG |
| 3153 | Hcd438 left | 0.24 | GTTTATTTGAATGTGTGATGGGGAGGTCATCAAAATGAAC |
| 3154 | Hcd886 right | 0.23 | CTCCAGTTGGGGGTGGGGAGTTGGGAACAGTGTGAATGGG |

TABLE 126

Carmustine microRNA biomarkers.

| SEQ ID NO | Medianprobe | Corr | Sequence |
|---|---|---|---|
| 2377 | mir-092-prec-X = 092-2 | 0.33 | GTTCTATATAAAGTATTGCACTTGTCCCGGCCTGTGGAAG |
| 2958 | Hcd517 right | 0.33 | GAGGGATTACAGATTAACTCCCACTTCTCCAGACTCAGAA |
| 2715 | Hcd796 left | 0.28 | GGTGGGATTACCCGGCTGCCGCTGTCGCCTGGATGGTCTC |
| 2290 | HUMTRF | 0.33 | GATCTAAAGGTCCCTGGTTCGATCCCGGGTTTCGGCACCA |
| 2414 | mir-20bNo1 | 0.29 | AGTACCAAAGTGCTCATAGTGCAGGTAGTTTTGGCATGAC |
| 2381 | mir-019b-2-prec | 0.25 | GTGGCTGTGCAAATCCATGCAAAACTGATTGTGATAATGT |
| 2607 | mir-033-prec | 0.27 | GTGGTGCATTGTAGTTGCATTGCATGTTCTGGTGGTACCC |
| 2608 | mir-092-prec-13 = 092-1No2 | 0.33 | TCTGTATGGTATTGCACTTGTCCCGGCCTGTTGAGTTTGG |
| 2407 | Hcd148_HPR225left | 0.27 | AATTAATGACCAAAATGTCAGATGTGTCCACAGCTAATTA |
| 2325 | HUMTRAB | 0.3 | ATGGTAGAGCGCTCGCTTTGCTTGCGAGAGGTAGCGGGAT |
| 2888 | Hcd975 left | 0.26 | GGTTTTGTGTTTTTGTAAACAGCAGAAGGTATTAGTCCAT |
| 2384 | mir-135-2-prec | 0.28 | CACTCTAGTGCTTTATGGCTTTTTATTCCTATGTGATAGT |
| 2451 | mir-128b-precNo1 | 0.27 | TCACAGTGAACCGGTCTCTTTCCCTACTGTGTCACACTCC |
| 2966 | mir-143-prec | 0.32 | CTGGTCAGTTGGGAGTCTGAGATGAAGCACTGTAGCTCAG |
| 2386 | mir-025-prec | 0.33 | ACGCTGCCCTGGGCATTGCACTTGTCTCGGTCTGACAGTG |
| 2735 | mir-216-precNo1 | 0.34 | CTGGGATTATGCTAAACAGAGCAATTTCCTAGCCCTCACG |
| 2390 | mir-093-prec-7.1 = 093-1 | 0.3 | CCAAAGTGCTGTTCGTGCAGGTAGTGTGATTACCCAACCT |
| 2391 | mir-106-prec-X | 0.33 | CCTTGGCCATGTAAAAGTGCTTACAGTGCAGGTAGCTTTT |
| 2300 | mir-142-prec | 0.61 | CCCATAAAGTAGAAAGCACTACTAACAGCACTGGAGGGTG |
| 2341 | HSHELA01 | 0.26 | GGCCGCAGCAACCTCGGTTCGTATCCGAGTCACGGCACCA |
| 2342 | HUMTRV1A | 0.26 | ACGCGAAAGGTCCCCGGTTCGAAACCGGGCGGAAACACCA |
| 2301 | mir-223-prec | 0.52 | GAGTGTCAGTTTGTCAAATACCCCAAGTGCGGCACATGCT |
| 2302 | Hcd754 left | 0.46 | TCCTCCTCCTCCTTTTCGTTCCGGCTCCCTGGCTGGCTCC |

TABLE 126-continued

Carmustine microRNA biomarkers.

| SEQ ID NO | Medianprobe | | Corr Sequence |
|---|---|---|---|
| 2393 | mir-018-prec | 0.34 | TAAGGTGCATCTAGTGCAGATAGTGAAGTAGATTAGCATC |
| 2394 | mir-020-prec | 0.35 | TAAAGTGCTTATAGTGCAGGTAGTGTTTAGTTATCTACTG |

TABLE 127

Lornustine microRNA biomarkers.

| SEQ ID NO | Medianprobe | | Corr Sequence |
|---|---|---|---|
| 2413 | mir-101-prec-9 | 0.27 | GCTGTATATCTGAAAGGTACAGTACTGTGATAACTGAAGA |
| 2715 | Hcd796 left | 0.26 | GGTGGGATTACCCGGCTGCCGCTGTCGCCTGGATGGTCTC |
| 2414 | mir-20bNo1 | 0.28 | AGTACCAAAGTGCTCATAGTGCAGGTAGTTTTGGCATGAC |
| 2325 | HUMTRAB | 0.35 | ATGGTAGAGCGCTCGCTTTGCTTGCGAGAGGTAGCGGGAT |
| 2384 | mir-135-2-prec | 0.27 | CACTCTAGTGCTTTATGGCTTTTTATTCCTATGTGATAGT |
| 2472 | mir-153-1-prec1 | 0.32 | CAGTTGCATAGTCACAAAAGTGATCATTGGCAGGTGTGGC |
| 2386 | mir-025-prec | 0.29 | ACGCTGCCCTGGGCATTGCACTTGTCTCGGTCTGACAGTG |
| 2390 | mir-093-prec-7.1 = 093-1 | 0.26 | CCAAAGTGCTGTTCGTGCAGGTAGTGTGATTACCCAACCT |
| 2391 | mir-106-prec-X | 0.31 | CCTTGGCCATGTAAAAGTGCTTACAGTGCAGGTAGCTTTT |
| 2300 | mir-142-prec | 0.41 | CCCATAAAGTAGAAAGCACTACTAACAGCACTGGAGGGTG |
| 2342 | HUMTRV1A | 0.28 | ACGCGAAAGGTCCCCGGTTCGAAACCGGGCGGAAACACCA |
| 2302 | Hcd754 left | 0.35 | TCCTCCTCCTCCTTTTCGTTCCGGCTCCCTGGCTGGCTCC |
| 2393 | mir-018-prec | 0.27 | TAAGGTGCATCTAGTGCAGATAGTGAAGTAGATTAGCATC |
| 2394 | mir-020-prec | 0.28 | TAAAGTGCTTATAGTGCAGGTAGTGTTTAGTTATCTACTG |

TABLE 128

Mercaptopurine microRNA biomarkers.

| SEQ ID NO | Medianprobe | | Corr Sequence |
|---|---|---|---|
| 2377 | mir-092-prec-X = 092-2 | 0.39 | GTTCTATATAAAGTATTGCACTTGTCCCGGCCTGTGGAAG |
| 2412 | mir-096-prec-7No1 | 0.26 | CTCCGCTCTGAGCAATCATGTGCAGTGCCAATATGGGAAA |
| 2430 | mir-123-precNo2 | 0.32 | TGTGACACTTCAAACTCGTACCGTGAGTAATAATGCGCCG |
| 2877 | MPR249 left | 0.26 | TCGGTTTGGTTCAGCTGGTATGCTTTCCAGTATCTCATTC |
| 2486 | HPR232 right | 0.28 | TGAATTATTGCACAATAAATTCATGCCCTGTTGTGTCTTA |
| 2413 | mir-101-prec-9 | 0.4 | GCTGTATATCTGAAAGGTACAGTACTGTGATAACTGAAGA |
| 2391 | mir-106aNo1 | 0.31 | CCTTGGCCATGTAAAAGTGCTTACAGTGCAGGTAGCTTTT |
| 2414 | mir-20bNo1 | 0.38 | AGTACCAAAGTGCTCATAGTGCAGGTAGTTTTGGCATGAC |
| 2882 | Hcd861 right | 0.25 | AAGGTCTGGATTGATCGTACTGCTTTCTGAAAGGTAAAAA |

TABLE 128-continued

Mercaptopurine microRNA biomarkers.

| SEQ ID NO | Medianprobe | Corr | Sequence |
|---|---|---|---|
| 2572 | mir-017-precNo2 | 0.26 | GTCAGAATAATGTCAAAGTGCTTACAGTGCAGGTAGTGAT |
| 2381 | mir-019b-2-prec | 0.33 | GTGGCTGTGCAAATCCATGCAAAACTGATTGTGATAATGT |
| 2607 | mir-033-prec | 0.3 | GTGGTGCATTGTAGTTGCATTGCATGTTCTGGTGGTACCC |
| 2506 | Hcd102 left | 0.26 | ACTGGAATTATGTTTTATCTTAAGTCCACACTGGATCCTC |
| 2386 | MPR216 left | 0.32 | GATCCTAGTAGTGCCAAAGTGCTCATAGTGCAGGTAGTTT |
| 2888 | Hcd975 left | 0.25 | GGTTTTGTGTTTTTGTAAACAGCAGAAGGTATTAGTCCAT |
| 2383 | mir-019b-1-prec | 0.3 | TTCTGCTGTGCAAATCCATGCAAAACTGACTGTGGTAGTG |
| 2384 | mir-135-2-prec | 0.38 | CACTCTAGTGCTTTATGGCTTTTTATTCCTATGTGATAGT |
| 2524 | Hcd581 right | 0.26 | AGGAGATATGCCAAGATATATTCACAGCTTTATATACACA |
| 2525 | Hcd536_HPR104 right | 0.25 | GCTGCTCTGCTGAGGGGCTGGACTCTGTCCAGAAGCACCA |
| 2893 | mir-128b-precNo2 | 0.25 | GGGGGCCGATACACTGTACGAGAGTGAGTAGCAGGTCTCA |
| 2332 | HSTRNL | 0.37 | TCCGGATGGAGCGTGGGTTCGAATCCCACTTCTGACACCA |
| 2386 | mir-025-prec | 0.47 | ACGCTGCCCTGGGCATTGCACTTGTCTCGGTCTGACAGTG |
| 2692 | mir-18bNo2 | 0.27 | AGCAGCTTAGAATCTACTGCCCTAAATGCCCCTTCTGGCA |
| 2897 | HPR262 left | 0.26 | TCAGTTTGGTTCAGCTGGTATGCTTTCCAGTATCTCATTC |
| 2298 | Hcd923 right | 0.33 | CTGGAGATAATGATTCTGCATTTCTAATTAACTCCCAGGT |
| 2899 | Hcd434 right | 0.3 | CACTTTTTCCTTTGTGGAAATCCTGGGTGACATCACCTCC |
| 2900 | Hcd658 right | 0.28 | GACTGCAGAGCAAAAGACACGATGGGTGTCTATTGTTTTC |
| 2901 | HPR129 left | 0.29 | TTTTCCTGCTTGATTTGCTTAATGGAAGCTGACAGTGAAG |
| 2389 | mir-380-5p | 0.32 | AGGTACCTGAAAAGATGGTTGACCATAGAACATGCGCTAT |
| 2390 | mir-093-prec-7.1 = 093-1 | 0.45 | CCAAAGTGCTGTTCGTGCAGGTAGTGTGATTACCCAACCT |
| 2391 | mir-106-prec-X | 0.5 | CCTTGGCCATGTAAAAGTGCTTACAGTGCAGGTAGCTTTT |
| 2544 | Hcd627 left | 0.31 | GCATTAGGGAGAATAGTTGATGGATTACAAATCTCTGCAT |
| 2300 | mir-142-prec | 0.33 | CCCATAAAGTAGAAAGCACTACTAACAGCACTGGAGGGTG |
| 2393 | mir-018-prec | 0.46 | TAAGGTGCATCTAGTGCAGATAGTGAAGTAGATTAGCATC |
| 2394 | mir-020-prec | 0.5 | TAAAGTGCTTATAGTGCAGGTAGTGTTTAGTTATCTACTG |

TABLE 129

Teniposide microRNA biomarkers.

| SEQ ID NO | Medianprobe | Corr | Sequence |
|---|---|---|---|
| 2711 | mir-124a-3-prec | 0.25 | TTAAGGCACGCGGTGAATGCCAAGAGAGGCGCCTCCGCCG |
| 2321 | Hcd768 right | 0.28 | GCCCTGGCGGAACGCTGAGAAGACAGTCGAACTTGACTAT |
| 2290 | HUMTRF | 0.28 | GATCTAAAGGTCCCTGGTTCGATCCCGGGTTTCGGCACCA |
| 2306 | mir-213-precNo1 | 0.25 | AACATTCATTGCTGTCGGTGGGTTGAACTGTGTGGACAAG |
| 2295 | mir-181b-precNo2 | 0.28 | ACCATCGACCGTTGATTGTACCCTATGGCTAACCATCATC |

TABLE 129-continued

Teniposide microRNA biomarkers.

| SEQ ID NO | Medianprobe | Corr | Sequence |
|---|---|---|---|
| 2447 | Hcd783 left | 0.28 | CAGGCTCACACCTCCCTCCCCCAACTCTCTGGAATGTATA |
| 2785 | mir-212-precNo2 | 0.32 | CGGACAGCGCGCCGGCACCTTGGCTCTAGACTGCTTACTG |
| 2296 | mir-124a-1-prec1 | 0.25 | ATACAATTAAGGCACGCGGTGAATGCCAAGAATGGGGCTG |
| 2299 | mir-342No1 | 0.29 | GTCTCACACAGAAATCGCACCCGTCACCTTGGCCTACTTA |
| 2300 | mir-142-prec | 0.49 | CCCATAAAGTAGAAAGCACTACTAACAGCACTGGAGGGTG |
| 2341 | HSHELA01 | 0.3 | GGCCGCAGCAACCTCGGTTCGTATCCGAGTCACGGCACCA |
| 2301 | mir-223-prec | 0.27 | GAGTGTCAGTTTGTCAAATACCCCAAGTGCGGCACATGCT |
| 2302 | Hcd754 left | 0.29 | TCCTCCTCCTCCTTTTCGTTCCGGCTCCCTGGCTGGCTCC |

TABLE 130

Dactinomycin microRNA biomarkers.

| SEQ ID NO | Medianprobe | Corr | Sequence |
|---|---|---|---|
| 2386 | mir-025-prec | 0.27 | ACGCTGCCCTGGGCATTGCACTTGTCTCGGTCTGACAGTG |
| 2283 | mir-007-1-prec | 0.28 | TGTTGGCCTAGTTCTGTGTGGAAGACTAGTGATTTTGTTG |
| 2390 | mir-093-prec-7.1 = 093-1 | 0.3 | CCAAAGTGCTGTTCGTGCAGGTAGTGTGATTACCCAACCT |
| 2287 | Hcd794 right | 0.33 | GGCCACCACAGACACCAACAAGTTCAGTCCGTTTCTGCAG |
| 2300 | mir-142-prec | 0.34 | CCCATAAAGTAGAAAGCACTACTAACAGCACTGGAGGGTG |

TABLE 131

Tretinoin microRNA biomarkers.

| SEQ ID NO | Medianprobe | Corr | Sequence |
|---|---|---|---|
| 2771 | Hcd257 left | 0.42 | CTTCTTGTATAAGCACTGTGCTAAAATTGCAGACACTAGG |
| 2772 | mir-148-prec | 0.45 | TGAGTATGATAGAAGTCAGTGCACTACAGAACTTTGTCTC |
| 2773 | Hcd512 left | 0.28 | CTGCGCTCTCGGAAATGACTCGCTCCAATCCCGCTTCGCG |
| 2774 | HPR227 right | 0.25 | CAGTGCAATGATATTGTCAAAGCATCTGGGACCAGCCTTG |
| 2775 | Hcd421 right | 0.37 | AGTAAACAATGTCGGCTTTCCGCCTCCTCCCCTGCCATCC |
| 2333 | MPR203 left | 0.39 | CTATATTGGACCGCAGCGCTGAGAGCTTTTGTGTTTAATG |
| 2777 | mir-017-precNo1 | 0.26 | GCATCTACTGCAGTGAAGGCACTTGTAGCATTATGGTGAC |
| 2778 | mir-219-2No1 | 0.26 | CTCAGGGGCTTCGCCACTGATTGTCAAACGCAATTCTTG |
| 2779 | mir-328No1 | 0.3 | GAAAGTGCATACAGCCCCTGGCCCTCTCTGCCCTTCCGTC |
| 2447 | Hcd783 left | 0.31 | CAGGCTCACACCTCCCTCCCCCAACTCTCTGGAATGTATA |
| 2781 | Hcd181 left | 0.32 | TTGGCGTCCTTGTCTCTCTCTCCCCTGCCCAGTGGCCTCC |
| 2765 | HPR213 right | 0.3 | AACAACTTTGTGCTGGTGCCGGGGAAGTTTGTGTCTCCAA |
| 2783 | mir-191-prec | 0.31 | CAACGGAATCCCAAAAGCAGCTGTTGTCTCCAGAGCATTC |

TABLE 131-continued

Tretinoin microRNA biomarkers.

| SEQ ID NO | Medianprobe | Corr | Sequence |
|---|---|---|---|
| 278 | mir-375 | 0.31 | TTTTGTTCGTTCGGCTCGCGTGAGGCAGGGGCGGCCTCTC |
| 2785 | mir-212-precNo2 | 0.26 | CGGACAGCGCGCCGGCACCTTGGCTCTAGACTGCTTACTG |
| 2326 | Hcd913 right | 0.34 | CAAACATCATGTGACGTCTGTGGAGCGGCGGCGGCGGCGG |
| 2330 | Hcd716 right | 0.48 | CAATAAATGTGCCTATAAAGGCGCCGGCTCCGGGGCGCGG |
| 2331 | MPR207 right | 0.3 | AACAACTTTGTGCTGGTGCCGGGGAAGTTTGTGTCTCCTA |
| 2333 | HPR206 left | 0.26 | CTATATTGGACCGCAGCGCTGAGAGCTTTTGTGTTTAATG |
| 2588 | mir-016b-chr3 | 0.29 | GTTCCACTCTAGCAGCACGTAAATATTGGCGTAGTGAAAT |
| 2285 | Hcd654 left | 0.34 | AACGAGTAAAAGGCGTACATGGGAGCGCGGGGCGGCAGAG |
| 2475 | mir-195-prec | 0.3 | TCTAGCAGCACAGAAATATTGGCACAGGGAAGCGAGTCTG |
| 2793 | Hcd425 left | 0.25 | GGTTCTACTCTCTTACCCCTCCCCCACGTGGTTGTTGCTG |
| 2772 | mir-148aNo1 | 0.35 | TGAGTATGATAGAAGTCAGTGCACTACAGAACTTTGTCTC |
| 2300 | mir-142-prec | 0.36 | CCCATAAAGTAGAAAGCACTACTAACAGCACTGGAGGGTG |
| 2598 | mir-016a-chr13 | 0.25 | CAATGTCAGCAGTGCCTTAGCAGCACGTAAATATTGGCGT |

TABLE 132

Ifosfamide microRNA biomarkers.

| SEQ ID NO | Medianprobe | Corr | Sequence |
|---|---|---|---|
| 2377 | mir-092-prec-X = 092-2 | 0.28 | GTTCTATATAAAGTATTGCACTTGTCCCGGCCTGTGGAAG |
| 2718 | mir-181b-2No1 | 0.28 | CTGATGGCTGCACTCAACATTCATTGCTGTCGGTGGGTTT |
| 3275 | Hcd417 right | 0.28 | GGATTTAATGAGAAATATTGAGCCCTTTGGTTCAGGAACT |
| 3276 | Hcd440_HPR257 right | 0.28 | GCTCTGTTGTGATAAATTGGCTGTGTGCTTCATTTGGACT |
| 2381 | mir-019b-2-prec | 0.25 | GTGGCTGTGCAAATCCATGCAAAACTGATTGTGATAATGT |
| 2306 | mir-213-precNo1 | 0.39 | AACATTCATTGCTGTCGGTGGGTTGAACTGTGTGGACAAG |
| 2607 | mir-033-prec | 0.29 | GTGGTGCATTGTAGTTGCATTGCATGTTCTGGTGGTACCC |
| 2608 | mir-092-prec-13 = 092-1No2 | 0.3 | TCTGTATGGTATTGCACTTGTCCCGGCCTGTTGAGTTTGG |
| 2398 | mir-181b-precNo1 | 0.36 | TGAGGTTGCTTCAGTGAACATTCAACGCTGTCGGTGAGTT |
| 2451 | mir-128b-precNo1 | 0.46 | TCACAGTGAACCGGTCTCTTTCCCTACTGTGTCACACTCC |
| 3283 | mir-526a-2No2 | 0.29 | GAAAGAACATGCATCCTTTCAGAGGGTTACTCTTTGAGA |
| 2589 | MPR95 left | 0.25 | TTGTTGGACACTCTTTCCCTGTTGCACTACTGTGGGCCTC |
| 3285 | HPR220 right | 0.27 | GAGCATCAGTATGTAGTGCAATCAGTCAGGAGAAAATGAG |
| 3286 | mir-133a-1 | 0.35 | CCTCTTCAATGGATTTGGTCCCCTTCAACCAGCTGTAGCT |
| 2772 | mir-148aNo1 | 0.3 | TGAGTATGATAGAAGTCAGTGCACTACAGAACTTTGTCTC |
| 2300 | mir-142-prec | 0.4 | CCCATAAAGTAGAAAGCACTACTAACAGCACTGGAGGGTG |
| 2427 | HPR169 right | 0.26 | GTTTCTTTCTCACGGTAACTGGCAGCCTCGTTGTGGGCTG |
| 2301 | mir-223-prec | 0.38 | GAGTGTCAGTTTGTCAAATACCCCAAGTGCGGCACATGCT |

TABLE 132-continued

Ifosfamide microRNA biomarkers.

| SEQ ID NO | Medianprobe | Corr | Sequence |
|---|---|---|---|
| 2393 | mir-018-prec | 0.27 | TAAGGTGCATCTAGTGCAGATAGTGAAGTAGATTAGCATC |
| 2394 | mir-020-prec | 0.25 | TAAAGTGCTTATAGTGCAGGTAGTGTTTAGTTATCTACTG |
| 2453 | mir-484 | 0.27 | GTCAGGCTCAGTCCCCTCCCGATAAACCCCTAAATAGGGA |

TABLE 133

Tamoxifen microRNA biomarkers.

| SEQ ID NO | Medianprobe | Corr | Sequence |
|---|---|---|---|
| 2377 | mir-092-prec-X = 092-2 | 0.31 | GTTCTATATAAAGTATTGCACTTGTCCCGGCCTGTGGAAG |
| 3295 | Hcd547 left | 0.27 | AAAATCAGCTTTAATTAATTTGAGTGCCAGCTCTGTGTAT |
| 2771 | Hcd257 left | 0.27 | CTTCTTGTATAAGCACTGTGCTAAAATTGCAGACACTAGG |
| 2772 | mir-148-prec | 0.27 | TGAGTATGATAGAAGTCAGTGCACTACAGAACTTTGTCTC |
| 2305 | HUMTRS | 0.25 | TCTAGCGACAGAGTGGTTCAATTCCACCTTTCGGGCGCCA |
| 2607 | mir-033-prec | 0.27 | GTGGTGCATTGTAGTTGCATTGCATGTTCTGGTGGTACCC |
| 2608 | mir-092-prec-13 = 092-1No2 | 0.25 | TCTGTATGGTATTGCACTTGTCCCGGCCTGTTGAGTTTGG |
| 278 | mir-375 | 0.46 | TTTTGTTCGTTCGGCTCGCGTGAGGCAGGGGCGGCCTCTC |
| 2441 | mir-095-prec-4 | 0.28 | CGTTACATTCAACGGGTATTTATTGAGCACCCACTCTGTG |
| 2386 | mir-025-prec | 0.35 | ACGCTGCCCTGGGCATTGCACTTGTCTCGGTCTGACAGTG |
| 3304 | mir-202-prec | 0.34 | GATCTGGCCTAAAGAGGTATAGGGCATGGGAAGATGGAGC |
| 2283 | mir-007-1-prec | 0.26 | TGTTGGCCTAGTTCTGTGTGGAAGACTAGTGATTTTGTTG |
| 2390 | mir-093-prec-7.1 = 093-1 | 0.44 | CCAAAGTGCTGTTCGTGCAGGTAGTGTGATTACCCAACCT |
| 2391 | mir-106-prec-X | 0.31 | CCTTGGCCATGTAAAAGTGCTTACAGTGCAGGTAGCTTTT |
| 2300 | mir-142-prec | 0.25 | CCCATAAAGTAGAAAGCACTACTAACAGCACTGGAGGGTG |
| 2301 | mir-223-prec | 0.25 | GAGTGTCAGTTTGTCAAATACCCCAAGTGCGGCACATGCT |
| 2393 | mir-018-prec | 0.26 | TAAGGTGCATCTAGTGCAGATAGTGAAGTAGATTAGCATC |

TABLE 134

Floxuridine microRNA biomarkers.

| SEQ ID NO | Medianprobe | Corr | Sequence |
|---|---|---|---|
| 2290 | HUMTRF | 0.27 | GATCTAAAGGTCCCTGGTTCGATCCCGGGTTTCGGCACCA |
| 2728 | HUMTRN | 0.27 | CAATCGGTTAGCGCGTTCGGCTGTTAACCGAAAGGTTGGT |
| 2296 | mir-124a-1-prec1 | 0.31 | ATACAATTAAGGCACGCGGTGAATGCCAAGAATGGGGCTG |
| 2448 | mir-150-prec | 0.33 | CTCCCCATGGCCCTGTCTCCCAACCCTTGTACCAGTGCTG |

TABLE 134-continued

Floxuridine microRNA biomarkers.

| SEQ ID NO | Medianprobe | Corr | Sequence |
|---|---|---|---|
| 2703 | Hcd923 left | 0.26 | TGGGAACCTTGTTAAAATGCAGATTCTGATTCTCAGGTCT |
| 3316 | HPR181 left | 0.28 | GAAGAAACATCTCAAATCATGCTGACAGCATTTTCACTAT |
| 3317 | Hcd569 right | 0.26 | TTATTGCTTGAATGAGTTTCAGGGTATTGGCCTTCATAAA |
| 2558 | mir-199a-2-prec | 0.25 | TCGCCCCAGTGTTCAGACTACCTGTTCAGGACAATGCCGT |
| 2308 | Hcd754 left | 0.28 | TCCTCCTCCTCCTTTTCGTTCCGGCTCCCTGGCTGGCTCC |
| 2410 | mir-432-3p | 0.3 | CCTTACGTGGGCCACTGGATGGCTCCTCCATGTCTTGGAG |

TABLE 135

Irinotecan microRNA biomarkers.

| SEQ ID NO | Medianprobe | Corr | Sequence |
|---|---|---|---|
| 2290 | HUMTRF | 0.27 | GATCTAAAGGTCCCTGGTTCGATCCCGGGTTTCGGCACCA |
| 2389 | mir-380-5p | 0.27 | AGGTACCTGAAAAGATGGTTGACCATAGAACATGCGCTAT |
| 2299 | mir-342No1 | 0.25 | GTCTCACACAGAAATCGCACCCGTCACCTTGGCCTACTTA |
| 2300 | mir-142-prec | 0.35 | CCCATAAAGTAGAAAGCACTACTAACAGCACTGGAGGGTG |
| 2405 | Hcd200 right | 0.25 | CAATTAGCCAATTGTGGGTATAATTAGCTGCATGTAGAAT |

TABLE 136

Satraplatin microRNA biomarkers.

| SEQ ID NO | Medianprobe | Corr | Sequence |
|---|---|---|---|
| 3326 | Hcd289 left | 0.31 | TTCCTCTCAGAGCATGTTGTCATAGAAGTAAATGAAAAGG |
| 3327 | Hcd939 right | 0.25 | CTCTCCTGCACATAATGAGGTCTGATTTACTGTGATCATT |
| 3328 | Hcd330 right | 0.28 | ATTAATGGTAATTATGTGCGTAAATCCCCATGCTCTCAAT |
| 3329 | HPR76 right | 0.25 | GAGCCGTTTAAATTTAGCGCTTTGGGCTGCCTGGAGCGAG |
| 3330 | Hcd111 left | 0.29 | GCAGGGGATTTGAGGGGTGGTTGTGTGATTTGTACAGCTG |
| 3331 | Hcd976 right | 0.36 | CTTCTCAGAGTTGGAGATGAAAGAAAGAGAAGGTGGCCAC |
| 3332 | mir-15aNo1 | 0.29 | CCTTGGAGTAAAGTAGCAGCACATAATGGTTTGTGGATTT |
| 3333 | mir-001b-1-prec1 | 0.26 | AATGCTATGGAATGTAAAGAAGTATGTATTTTTGGTAGGC |
| 2292 | mir-450-1 | 0.36 | AACGATACTAAACTGTTTTTGCGATGTGTTCCTAATATGC |
| 3335 | mir-200bNo2 | 0.3 | CCAGCTCGGGCAGCCGTGGCCATCTTACTGGGCAGCATTG |
| 3336 | Hcd578 right | 0.3 | AATGATTGTAGAGGGGCGGGGCATGAAGAGTGCCGTTCTG |
| 2578 | mir-200a-prec | 0.28 | GTCTCTAATACTGCCTGGTAATGATGACGGCGGAGCCCTG |

What is claimed is:

1. A method of determining sensitivity of a cancer patient to a treatment for cancer comprising contacting a sample comprising one or more nucleic acid molecules from said patient to a device comprising single-stranded oligonucleotides, wherein at least one of said oligonucleotides comprises a sequence that is substantially complementary to or substantially identical to at least 15 consecutive nucleotides of a first microRNA selected from mir-142-prec or a product of a first gene selected from ZNFN1A1, and measuring hybridization between said nucleic acid molecules from said patient and said single-stranded oligonucleotides of said device to determine a level of expression of at least said first microRNA or said first gene in a cell of said patient, wherein an increase or decrease in the level of expression of said first microRNA or said first gene in said cell of said patient, relative to the level of expression of said first microRNA or said first gene in a control cell sensitive to said treatment, indicates said cell is sensitive to said treatment.

2. The method of claim 1, wherein said measuring further comprises determining a level of expression of:
   i) a second gene selected from at least one of RPS4X, S100A4, NDUFS6, C14orf139, SLC25A5, RPL10, RPL12, EIF5A, RPL36A, BLMH, CTBP1, TBCA, MDH2, and DX59879E, and, optionally, a third gene selected from at least one of UBB, B2M, MAN1A1, and SUI1, or
   ii) a second additional microRNA selected from at least one of Hcd892, Hcd678, hsa-mir-007-1-prec, MPR243, Hcd654, hsa-mir-487, Hcd794, Hcd739, and Hcd562,
   wherein an increase or decrease in said level of expression of said second gene and, optionally, said third gene or said second microRNA indicates that said cell is sensitive to Vincristine.

3. The method of claim 1, wherein said measuring further comprises determining a level of expression of:
i) a second gene selected from at least one of C1QR1, SLA, PTPN7, ZNFNIA1, CENTB1, IFI16, ARHGEF6, SEC31L2, CD3Z, GZMB, CD3D, MAP4K1, GPR65, PRF1, ARHGAP15, TM6SF1, and TCF4, and, optionally, a third gene selected from at least one of HCLS1, CD53, PTPRCAP, and PTPRC, or
ii) a second microRNA selected from at least one of HUMTRF, HPR187, hsa-mir-450-1, hsa-mir-155-prec, hsa-mir-515-15p, hsa-mir-181b-prec, hsa-mir-124a-1-prec1, hsa-mir-450-2, Hcd923, hsa-mir-342, hsa-mir-142-prec, hsa-mir-223-prec, Hcd754, and Hcd213_HPR182,
wherein an increase or decrease in said level of expression of said second gene and, optionally, said third gene or said second microRNA indicates that said cell is sensitive to Cisplatin.

4. The method of claim 1, wherein said measuring further comprises determining a level of expression of:
i) a second gene selected from at least one of SRM, SCARB1, SIAT1, CUGBP2, ICAM1, WASPIP, ITM2A, PALM2-AKAP2, PTPNS1, MPP1, LNK, FCGR2A, RUNX3, EVI2A, BTN3A3, LCP2, BCHE, LY96, LCP1, IFI16, MCAM, MEF2C, SLC1A4, FYN, C1orf38, CHS1, FCGR2C, TNIK, AMPD2, SEPT6, RAFTLIN, SLC43A3, RAC2, LPXN, CKIP-1, FLJ10539, FLJ35036, DOCK10, TRPV2, IFRG28, LEF1, and ADAMTS1, and, optionally, a third gene selected from at least one of MSN, SPARC, VIM, GAS7, ANPEP, EMP3, BTN3A2, FN1, and CAPN3, or
ii) a second microRNA selected from at least one of MPR121, HUMTRS, hsa-mir-213-prec, hsa-mir-155-prec, hsa-mir-147-prec, hsa-mir-100, hsa-mir-138-1-prec, hsa-mir-140, hsa-mir-146-prec, hsa-mir-509, hsa-mir-146b, Hcd514, Hcd397, Hcd731, hsa-mir-034-prec, and hsa-mir-100-1/2-prec,
wherein an increase or decrease in said level of expression of said second gene and, optionally, said third gene or said second microRNA indicates that said cell is sensitive to Azaguanine.

5. The method of claim 1, wherein said measuring further comprises determining a level of expression of:
i) a second gene selected from at least one of CD99, INSIG1, PRG1, MUF1, SLA, SSBP2, GNB5, MFNG, PSMB9, EVI2A, PTPN7, PTGER4, CXorf17, ZNFN1A1, CENTB1, NAP1L1, HLA-DRA, IFI16, ARHGEF6, PSCDBP, SELPLG, LAT, SEC31L2, CD3Z, SH2DIA, GZMB, SCN3A, RAFTLIN, DOCK2, CD3D, RAC2, ZAP70, GPR65, PRF1, ARHGAP15, NOTCH1, and UBASH3A, and, optionally, a third gene selected from at least one of LAPTM5, HCLS1, CD53, GMFG, PTPRCAP, PTPRC, CORO1A, and ITK, or
ii) a second microRNA selected from at least one of Hcd415, Hcd768, HUMTRF, Hcd866, Hcd145, HUMTRAB, Hcd913, HPR163, Hcd697, Hcd755, Hcd716, MPR207, HSTRNL, HPR206, MPR243, Hcd654, MPR130, Hcd782, Hcd794, Hcd739, hsa-mir-142-prec, HSHELA01, HUMTRVIA, and Hcd754,
wherein an increase or decrease in said level of expression of said second gene and, optionally, said third gene or said second microRNA indicates that said cell is sensitive to Etoposide.

6. The method of claim 1, wherein said measuring further comprises determining a level of expression of:
i) a second gene selected from at least one of CD99, ALDOC, SLA, SSBP2, IL2RG, CXorf9, RHOH, ZNFN1A1, CENTB1, CD1C, MAP4K1, CD3G, CCR9, CXCR4, ARHGEF6, SELPLG, LAT, SEC31L2, CD3Z, SH2D1A, CD1A, LAIR1, TRB@, CD3D, WBSCR20C, ZAP70, IFI44, GPR65, A1F1, ARHGAP15, NARF, and PACAP, and, optionally, a third gene selected from at least one the group consisting of LAPTM5, HCLS1, CD53, GMFG, PTPRCAP, TCF7, CD1B, PTPRC, CORO1A, HEM1, and ITK, or
ii) a second microRNA selected from at least one of Hcd768, hsa-mir-483, Hcd145, hsa-mir-197-prec, hsa-mir-212-prec, HPR163, Hcd654, hsa-mir-342, Hcd794, hsa-mir-142-prec, and Hcd754,
wherein an increase or decrease in said level of expression of said second gene and, optionally, said third gene or said second microRNA indicates that said cell is sensitive to Adriamycin.

7. The method of claim 1, wherein said measuring further comprises determining a level of expression of:
i) a second gene selected from at least one of RPL12, RPLP2, MYB, ZNFN1A1, SCAP1, STAT4, SP140, AMPD3, TNFAIP8, DDX18, TAF5, RPS2, DOCK2, GPR65, HOXA9, FLJ12270, and HNRPD, and, optionally, a third gene selected from at least one of RPL32, FBL, and PTPRC, or
ii) a second microRNA selected from at least one of hsa-mir-092-prec-X=092-2, hsa-mir-096-prec-7, Hcd605, hsa-mir-007-2-prec, hsa-mir-019b-2-prec, MPR216, hsa-mir-019b-1-prec, hsa-mir-135-2-prec, HSTRNL, hsa-mir-025-prec, hsa-mir-007-1-prec, hsa-mir-019a-prec, hsa-mir-380-5p, hsa-mir-093-prec-7.1=093-1, hsa-mir-106-prec-X, hsa-mir-142-prec, hsa-mir-018-prec, and hsa-mir-020-prec,
wherein an increase or decrease in said level of expression of said second gene and, optionally, said third gene or said second microRNA indicates that said cell is sensitive to Aclarubicin.

8. The method of claim 1, wherein said measuring further comprises determining a level of expression of:
i) a second gene selected from at least one of PGAM1, DPYSL3, INSIG1, GJA1, BNIP3, PRG1, G6PD, PLOD2, LOXL2, SSBP2, C1orf29, TOX, STC1, TNFRSF1A, NCOR2, NAP1L1, LOC94105, ARHGEF6, GATA3, TFPI, LAT, CD3Z, AF1Q, MAP1B, TRIM22, CD3D, BCAT1, IFI44, CUTC, NAP1L2, NME7, FLJ21159, and COL5A2, and, optionally, a third gene selected from at least one of BASP1, COL6A2, PTPRC, PRKCA, CCL2, and RAB31, or
ii) a second microRNA selected from at least one of Hcd768, HUMTRF, hsa-mir-213-prec, hsa-mir-181b-prec, MPR244, hsa-mir-409-3p, HSTRNL, hsa-mir-382, hsa-mir-342, hsa-mir-142-prec, and Hcd200,
wherein an increase or decrease in said level of expression of said second gene and, optionally, said third gene or said second microRNA indicates that said cell is sensitive to Mitoxantrone.

9. The method of claim 1, wherein said measuring further comprises determining a level of expression of:
i) a second gene selected from at least one of STC1, GPR65, DOCK10, COL5A2, FAM46A, and LOC54103, or
ii) a second microRNA selected from at least one of HUMTRF, Hcd148_HPR225 left, Hcd938, MPR174, and hsa-mir-4323p,
wherein an increase or decrease in said level of expression of said second gene or said second microRNA indicates that said cell is sensitive to Mitomycin.

10. The method of claim 1, wherein said measuring further comprises determining a level of expression of:
  i) a second gene selected from at least one of RPL10, RPS4X, NUDC, DKC1, DKFZP564C186, PRP19, RAB9P40, HSA9761, GMDS, CEP1, IL13RA2, MAGEB2, HMGN2, ALMS1, GPR65, FLJ10774, NOL8, DAZAP1, SLC25A15, PAF53, DXS9879E, PITPNC1, SPANXC, and KIAA1393, and, optionally, RALY, or
  ii) a second microRNA selected from at least one of hsa-mir-092-prec-X=092-2, hsa-mir-096-prec-7, hsa-mir-101-prec-9, hsa-mir-20b, hsa-mir-019b-2-prec, hsa-mir-032-prec, MPR156, hsa-mir-019b-1-prec, hsa-mir-135-2-prec, hsa-mir-025-prec, hsa-mir-007-1-prec, hsa-mir-361, hsa-mir-093-prec-7.1=093-1, hsa-mir-106-prec-X, hsa-mir-098-prec-X, hsa-mir-142-prec, HPR169, hsa-mir-018-prec, and hsa-mir-020-prec,
  wherein an increase or decrease in said level of expression of said second gene or said second microRNA indicates that said cell is sensitive to Paclitaxel.

11. The method of claim 1, wherein said measuring further comprises determining a level of expression of:
  i) a second gene selected from at least one of PFN1, PGAM1, K-ALPHA-1, CSDA, UCHL1, PWP1, PALM2-AKAP2, TNFRSF1A, ATP5G2, AF1Q, NME4, and FHOD1, or
  ii) a second microRNA selected from at least one of hsa-mir-123-prec, Hcd257, hsa-mir-155-prec, ath-MIR180a, Hcd448, HSTRNL, MPR174, Hcd200, hsa-mir-4323p, and HPR244,
  wherein an increase or decrease in said level of expression of said second gene or said second microRNA indicates that said cell is sensitive to Gemcitabine.

12. The method of claim 1, wherein said measuring further comprises determining a level of expression of:
  i) a second gene selected from at least one of ANP32B, GTF3A, RRM2, TRIM14, SKP2, TRIP13, RFC3, CASP7, TXN, MCM5, PTGES2, OBFC1, EPB41L4B, and CALML4, or
  ii) a second microRNA selected from at least one of hsa-mir-096-prec-7, hsa-mir-095-prec-4, HSTRNL, and hsa-mir-007-1-prec,
  wherein an increase or decrease in said level of expression of said second gene or said second additional microRNA indicates that said cell is sensitive to Taxotere.

13. The method of claim 1, wherein said measuring further comprises determining a level of expression of:
  i) a second gene selected from at least one of IFITM2, UBE2L6, USP4, ITM2A, IL2RG, GPRASP1, PTPN7, CXorf9, RHOH, GIT2, ZNFN1A1, CEP1, TNFRSF7, MAP4K1, CCR7, CD3G, ATP2A3, UCP2, GATA3, CDKN2A, TARP, LAIR1, SH2D1A, SEPT6, HA-1, ERCC2, CD3D, LST1, AIF1, ADA, DATF1, ARHGAP15, PLACE, CECR1, LOC81558, and EHD2, and, optionally, a third gene selected from at least one of LAPTM5, ITGB2, ANPEP, CD53, CD37, ADORA2A, GNA15, PTPRC, CORO1A, HEM1, FLII, and CREB3L1, or
  ii) a second microRNA selected from at least one of MPR141, hsa-mir-424, Hcd690, Hcd783, hsa-mir-150-prec, Hcd266, hsa-mir-503, hsa-mir-128b-prec, Hcd397, and hsa-mir-484,
  wherein an increase or decrease in said level of expression of said second gene and, optionally, said third gene or said second microRNA indicates that said cell is sensitive to Dexamethasone.

14. The method of claim 1, wherein said measuring further comprises determining a level of expression of:
  I) a second gene selected from at least one of ITM2A, RHOH, PRIM1, CENTB1, NAP1L1, ATP5G2, GATA3, PRKCQ, SH2DIA, SEPT6, NME4, CD3D, CD1E, ADA, and FHOD1, and, optionally, a third gene selected from at least one of GNA15, PTPRC, and RPL13, or
  ii) a second microRNA selected from at least one of HUMTRF, hsa-mir-155-prec, hsa-mir-515-15p, Hcd938, Hcd642, Hcd120, hsa-mir-380-5p, hsa-mir-342, hsa-mir-142-prec, hsa-mir-223-prec, and hsa-mir-4323p,
  wherein an increase or decrease in said level of expression of said second gene and, optionally, said third gene or said second microRNA indicates that said cell is sensitive to Ara-C.

15. The method of claim 1, wherein said measuring further comprises determining a level of expression of:
  i) a second gene selected from at least one of CD99, ARHGDIB, VWF, ITM2A, LGALS9, INPP5D, SATB1, TFDP2, SLA, IL2RG, MFNG, SELL, CDW52, LRMP, ICAM2, RIMS3, PTPN7, ARHGAP25, LCK, CXorf9, RHOH, GIT2, ZNFN1A1, CENTB1, LCP2, SPI1, GZMA, CEP1, CD8A, SCAP1, CD2, CD1C, TNFRSF7, VAV1, MAP4K1, CCR7, C6orf32, ALOX15B, BRDT, CD3G, LTB, ATP2A3, NVL, RASGRP2, LCP1, CXCR4, PRKD2, GATA3, TRA@, KIAA0922, TARP, SEC31L2, PRKCQ, SH2DIA, CHRNA3, CD1A, LST1, LAIR1, CACNA1G, TRB@, SEPT6, HA-1, DOCK2, CD3D, TRD@, T3JAM, FNBP1, CD6, AIF1, FOLH1, CD1E, LY9, ADA, CDKL5, TRIM, EVL, DATF1, RGC32, PRKCH, ARHGAP15, NOTCH1, BIN2, SEMA4G, DPEP2, CECR1, BCL11B, STAG3, GALNT6, UBASH3A, PHEMX, FLJ13373, LEF1, IL21R, MGC17330, AKAP13, ZNF335, and GIMAP5, and, optionally, a third gene selected from at least one of SRRM1, LAPTM5, ITGB2, CD53, CD37, GMFG, PTPRCAP, GNA15, BLM, PTPRC, CORO1A, PRKCB1, HEM1, and UGT2B17, or
  ii) a second microRNA selected from at least one of Hcd544, hsa-mir-181c-prec, Hcd517, MPR151, hsa-mir-213-prec, hsa-mir-181b-prec, hsa-mir-150-prec, hsa-mir-153-1-prec1, hsa-mir-128b-prec, Hcd812, hsa-mir-195-prec, hsa-mir-342, hsa-mir-370, hsa-mir-142-prec, hsa-mir-223-prec, and hsa-mir-484,
  wherein an increase or decrease in said level of expression of said second gene and, optionally, said third gene or said second microRNA indicates that said cell is sensitive to Methylprednisolone.

16. The method of claim 1, wherein said measuring further comprises determining a level of expression of:
  i) a second gene selected from at least one of PRPF8, RPL18, GOT2, RPL13A, RPS15, RPLP2, CSDA, KHDRBS1, SNRPA, IMPDH2, RPS19, NUP88, ATP5D, PCBP2, ZNF593, HSU79274, PRIM1, PFDN5, OXA1L, H3F3A, ATIC, CIAPIN1, RPS2, PCCB, SHMT2, RPLP0, HNRPA1, STOML2, SKB1, GLTSCR2, CCNB1IP1, MRPS2, FLJ20859, and FLJ12270, and, optionally, a third gene selected from at least one of RNPS1, RPL32, EEF1G, PTMA, RPL13, FBL, RBMX, and RPS9, or
  ii) a second microRNA selected from at least one of hsa-mir-092-prec-X=092-2, hsa-mir-096-prec-7, hsa-mir-123-prec, Hcd250, hsa-mir-518e, HPR232, Hcd263, hsa-mir-516-33p, Hcd605, Hcd373, MPR254, MPR215, HUMTRF, hsa-mir-106a, hsa-mir-20b, Hcd361, Hcd412, Hcd781, hsa-mir-019b-2-prec, HPR214, Hcd807, Hcd817, Hcd788, Hcd970, Hcd148_HPR225 left, Hcd102, Hcd246, HPR199, HPR233, Hcd383, MPR224, HPR172, MPR216, hsa-mir-321, Hcd586, Hcd587, Hcd249, Hcd279, HPR159, Hcd689, Hcd691, hsa-mir-019b-1-prec, Hcd413, Hcd581, Hcd536_HPR104, Hcd230, HPR154, Hcd270, Hcd649, Hcd889, Hcd938, HPR266, hsa-mir-025-prec, Hcd355_HPR190, MPR162, Hcd923, MPR237, MPR174, hsa-mir-019a-prec, hsa_mir_490_Hcd20, hsa-mir-380-5p, hsa-mir-093-prec-7.1=093-1, hsa-mir-106-prec-X, Hcd627, hsa-mir-142-prec, HPR169, hsa-mir-001b-2-prec, hsa-mir-018-prec, hsa-mir-020-prec, Hcd404, hsa-mir-384, and hsa-mir-4323p, wherein an increase or decrease in said level of expression of said second gene and, optionally, said third gene or said second microRNA indicates that said cell is sensitive to Methotrexate.

17. The method of claim 1, wherein said measuring further comprises determining a level of expression of:
  i) a second gene selected from at least one of PFN1, HK1, MCL1, ZYX, RAP1B, GNB2, EPAS1, PGAM1, CKAP4, DUSP1, MYL9, K-ALPHA-1, LGALS1, CSDA, IFITM2, ITGA5, DPYSL3, JUNB, NFKBIA, LAMB1, FHL1, INSIG1, TIMP1, GJA1, PSME2, PRG1, EXT1, DKFZP434J154, MVP, VASP, ARL7, NNMT, TAP1, PLOD2, ATF3, PALM2-AKAP2, IL8, LOXL2, IL4R, DGKA, STC2, SEC61G, RGS3, F2R, TPM2, PSMB9, LOX, STC1, PTGER4, IL6, SMAD3, WNT5A, BDNF, TNFRSFIA, FLNC, OKFZP564K0822, FLOT1, PTRF, HLA-B, MGC4083, TNFRSF108, PLAGL1, PNMA2, TFPI, LAT, GZMB, CYR61, PLAUR, FSCN1, ERP70, AF1Q, HIC, COL6A1, IFITM3, MAPIB, FLJ46603, RAFTLIN, RRAS, FTL, KIAA0877, MT1E, CDC10, DOCK2, TRIM22, RIS1, BCAT1, PRF1, DBN1, MT1K, TMSB10, FLJ10350, C1orf24, NME7, TMEM22, TPK1, COL5A2, ELK3, CYLD, ADAMTS1, EHD2, and ACTB, and, optionally, a third gene selected from at least one of MSN, ACTR2, AKR1B1, VIM, ITGA3, OPTN, M6PRBP1, COL1A1, BASP1, ANPEP, TGFB1, NFIL3, NK4, CSPG2, PLAU, COL6A2, UBC, FGFR1, BAX, COL4A2, and RAB31, or
  ii) a second microRNA selected from at least one of hsa-mir-376a, hsa-mir-155-prec, hsa-mir-409-3p, hsa-mir-495, Hcd498, hsa-mir-199a-2-prec, hsa-mir-382, HPR271, hsa-mir-145-prec, and hsa-mir-199a-1-prec,
  wherein an increase or decrease in said level of expression of said second gene and, optionally, said third gene or said second microRNA indicates that said cell is sensitive to Bleomycin.

18. The method of claim 1, wherein said measuring further comprises determining a level of expression of:
  i) a second gene selected from at least one of SSRP1, NUDC, CTSC, AP1G2, PSME2, LBR, EFNB2, SERPINA1, SSSCA1, EZH2, MYB, PRIM1, H2AFX, HMGA1, HMMR, TK2, WHSC1, DIAPH1, LAMB3, DPAGT1, UCK2, SERPINB1, MDN1, BRRN1, GOS2, RAC2, MGC21654, GTSE1, TACC3, PLEK2, PLACE, HNRPD, and PNAS-4, and, optionally, PTMA, or
  ii) a second microRNA selected from at least one of hsa-mir-092-prec-X=092-2, hsa-mir-101-prec-9, hsa-mir-144-prec, hsa-mir-519a-1, hsa-mir-519b, hsa-mir-015b-prec, hsa-mir-106a, hsa-mir-16-1, hsa-mir-181d, hsa-mir-017-prec, hsa-mir-019b-2-prec, hsa-mir-192, hsa-mir-213-prec, hsa-mir-215-prec, hsa-mir-107, hsa-mir-200b, hsa-mir-103-prec-5=103-1, hsa-mir-519a-1/526c, MPR216, hsa-mir-019b-1-prec, hsa-mir-107-prec-10, hsa-mir-135-2-prec, hsa-mir-103-2-prec, hsa-mir-519a-2, hsa-mir-025-prec, hsa-mir-16-2, MPR95, hsa-mir-016b-chr3, Hcd948, hsa-mir-195-prec, hsa-mir-093-prec-7.1=093-1, hsa-mir-106-prec-X, hsa-mir-142-prec, hsa-mir-519c/526c, hsa-mir-200a-prec, hsa-mir-016a-chr13, hsa-mir-018-prec, and hsa-mir-020-prec,
  wherein an increase or decrease in said level of expression of said second gene or said second microRNA indicates that said cell is sensitive to Methyl-GAG.

19. The method of claim 1, wherein said measuring further comprises determining a level of expression of:
  i) a second gene selected from at least one of ITGA5, TNFAIP3, WNT5A, FOXF2, LOC94105, IFI16, LRRN3, DOCK10, LEPRE1, COL5A2, and ADAMTS1, and, optionally, a third gene selected from at least one of MSN, VIM, CSPG2, and FGFR1, or
  ii) a second microRNA selected from at least one of Hcd829, HUMTRF, HPR187, Hcd210_, HPR205, hsa-mir-379, hsa-mir-213-prec, hsa-mir-4325p, hsa-mir-450-1, hsa-mir-155-prec, Hcd28_HPR39 right, MPR244, hsa-mir-409-3p, hsa-mir-124a-1-prec1, hsa-mir-154-prec1, hsa-mir-495, hsa-mir-515-23p, Hcd438 right, Hcd770, hsa-mir-382, hsa-mir-223-prec, Hcd754, and Hcd213_HPR182,
  wherein an increase or decrease in said level of expression of said second gene and, optionally, said third gene or said second microRNA indicates that said cell is sensitive to Carboplatin.

20. The method of claim 1, wherein said measuring further comprises determining a level of expression of:
  i) a second gene selected from at least one of RPL18, RPL10A, ANAPC5, EEFIB2, RPL13A, RPS15, AKAP1, NDUFAB1, APRT, ZNF593, MRP63, IL6R, SART3, UCK2, RPL17, RPS2, PCCB, TOMM20, SHMT2, RPLP0, GTF3A, STOML2, DKFZp564J157, MRPS2, ALG5, and CALML4, and, optionally, a third gene selected from at least one of RNPS1, RPL13, RPS6, and RPL3, or
  ii) a second microRNA selected from at least one of hsa-mir-096-prec-7, hsa-mir-429, Hcd693, HPR214, Hcd586, Hcd249, Hcd689, hsa-mir-194-2, Hcd581, Hcd270, hsa-mir-025-prec, Hcd340, hsa-mir-007-1-prec, hsa-mir-093-prec-7.1=093-1, hsa-mir-106-prec-X, Hcd794, hsa-mir-020-prec, and hsa-mir-4323p,
  wherein an increase or decrease in said level of expression of said second gene and, optionally, said third gene or said second microRNA indicates that said cell is sensitive to 5-FU (5-Fluorouracil).

21. The method of claim 1, wherein said measuring further comprises determining a level of expression of:
  i) a second gene selected from at least one of KIFC1, VLDLR, RUNX1, PAFAH1B3, H1FX, RNF144, TMSNB, CRY1, MAZ, SLA, SRF, UMPS, CD3Z, PRKCQ, HNRPM, ZAP70, ADD1, RFC5, TM4SF2, PFN2, BMI1, TUBGCP3, ATP6VIB2, CD1D, ADA, CD99, CD2, CNP, ERG, CD3E, CD1A, PSMC3, RPS4Y1, AKT1, TAL1, UBE2A, TCF12, UBE2S, CCND3, PAX6, RAG2, GSTM2, SATB1, NASP, IGFBP2, CDH2, CRABP1, DBN1, AKR1C1, CACNB3, CASP2, CASP2, LCP2, CASP6, MYB, SFRS6, GLRB, NDN, GNAQ, TUSC3, GNAQ, JARID2, OCRL, FHL1, EZH2, SMOX, SLC4A2, UFD1L, ZNF32, HTATSF1, SHD1, PTOV1, NXF1, FYB, TRIM28, BC008967, TRB@, H1F0, CD3D, CD3G, CENPB, ALDH2, ANXA1, H2AFX, CD1E, DDX5, CCNA2, ENO2, SNRPB, GATA3, RRM2, GLUL, SOX4, MAL, UNG, ARHGDIB, RUNX1, MPHOSPH6, DCTN1, SH3GL3, PLEKHC1, CD47, POLR2F, RHOH, and ADD1, and, optionally, a third gene selected from at least one of ITK, RALY, PSMC5, MYL6, CD1B, STMN1, GNA15, MDK, CAPG, ACTN1, CTNNA1, FARSLA, E2F4, CPSF1, SEPW1, TFRC, ABL1, TCF7, FGFR1, NUCB2, SMA3, FAT, VIM, and ATP2A3, wherein an increase or decrease in said level of expression of said second gene and, optionally, said third gene indicates that said cell is sensitive to Rituximab.

22. The method of claim 1, wherein said measuring further comprises determining a level of expression of:
   i) a second gene selected from at least one of TRA1, ACTN4, CALM1, CD63, FKBP1A, CALU, IQGAP1, MGC8721, STAT1, TACC1, TM4SF8, CD59, CKAP4, DUSP1, RCN1, MGC8902, LGALS1, BHLHB2, RRBP1, PRNP, IER3, MARCKS, LUM, FERIL3, SLC20A1, HEXB, EXT1, TJP1, CTSL, SLC39A6, RIOK3, CRK, NNMT, TRAM2, ADAMS, DNAJC7, PLSCR1, PRSS23, PLOD2, NPC1, TOB1, GFPT1, IL8, PYGL, LOXL2, KIAA0355, UGDH, PURA, ULK2, CENTG2, NID2, CAP350, CXCL1, BTN3A3, IL6, WNT5A, FOXF2, LPHN2, CDH11, P4HA1, GRP58, DSIPI, MAP1LC3B, GALIG, IGSF4, IRS2, ATP2A2, OGT, TNFRSF10B, KIAA1128, TM4SF1, RBPMS, RIPK2, CBLB, NR1D2, SLC7A11, MPZL1, SSA2, NQO1, ASPH, ASAH1, MGLL, SERPINB6, HSPA5, ZFP36L1, COL4A1, CD44, SLC39A14, NIPA2, FKBP9, IL6ST, DKFZP564G2022, PPAP2B, MAP1B, MAPK1, MYO1B, CAST, RRAS2, QKI, LHFPL2, 38970, ARHE, KIAA1078, FTL, KIAA0877, PLCB1, KIAA0802, RAB3GAP, SERPINB1, TIMMI7A, SOD2, HLA-A, NOMO2, L0055831, PHLDAI, TMEM2, MLPH, FAD104, LRRC5, RAB7L1, FLJ35036, DOCK10, LRP12, TXNDC5, CDCl4B, HRMT1L1, CORO1C, DNAJC10, TNP01, LONP, AMIGO2, DNAPTP6, and ADAMTS1, and, optionally, a third gene selected from at least one of WARS, CD81, CTSB, PKM2, PPP2CB, CNN3, ANXA2, JAK1, EIF4G3, COL1A1, DYRK2, NFIL3, ACTN1, CAPN2, BTN3A2, IGFBP3, FN1, COL4A2, and KPNB1, or
   ii) a second microRNA selected from at least one of hsa-mir-136-prec, Hcd570, Hcd873, Hcd282PO, Hcd799, Hcd829, Hcd210_HPR205, hsa-mir-219-prec, hsa-mir-202, hsa-mir-429, Hcd693, hsa-mir-022-prec, MPR88, hsa-mir-198-prec, hsa-mir-199b-prec, Hcd145, hsa-mir-124a-2-prec, hsa-mir-138-2-prec, Hcd960, Hcd869, Hcd384, hsa-mir-027b-prec, Hcd444, hsa-mir-194-2, hsa-mir-197-prec, Hcd913, HPR163, hsa-mir-138-1-prec, hsa-mir-010a-prec, hsa-mir-023b-prec, hsa-mir-193b, Hcd654, Hcd542, hsa-mir-199a-2-prec, hsa-mir-214-prec, Hcd608, Hcd684, hsa-mir-145-prec, hsa-mir-023a-prec, hsa-mir-024-2-prec, and hsa-mir-199a-1-prec,
   wherein an increase or decrease in said level of expression of said second gene and, optionally, said third gene or said second microRNA indicates that said cell is sensitive to radiation therapy.

23. The method of claim 1, wherein said measuring further comprises determining a level of expression of:
   i) a second gene selected from at least one of FAU, NOL5A, ANP32A, ARHGDIB, LBR, FABP5, ITM2A, SFRS5, IQGAP2, SLC7A6, SLA, IL2RG, MFNG, GPSM3, PIM2, EVER1, LRMP, ICAM2, RIMS3, FMNL1, MYB, PTPN7, LCK, CXorf9, RHOH, ZNFN1A1, CENTB1, LCP2, DBT, CEP1, IL6R, VAV1, MAP4K1, CD28, PTP4A3, CD3G, LTB, USP34, NVL, CD8B1, SFRS6, LCP1, CXCR4, PSCDBP, SELPLG, CD3Z, PRKCQ, CD1A, GATA2, P2RX5, LAIR1, C1orf38, SH2DIA, TRB@, SEPT6, HA-1, DOCK2, WBSCR20C, CD3D, RNASE6, SFRS7, WBSCR20A, NUP210, CD6, HNRPA1, A1F1, CYFIP2, GLTSCR2, C11orf2, ARHGAP15, BIN2, SH3TC1, STAG3, TM6SF1, C15orf25, FLJ22457, PACAP, and MGC2744, or
   ii) a second microRNA selected from at least one of hsa-mir-092-prec-X=092-2, hsa-mir-123-prec, hsa-mir-106a, hsa-mir-20b, hsa-mir-017-prec, hsa-mir-019b-2-prec, hsa-mir-033-prec, hsa-mir-092-prec-13=092-1, hsa-mir-122a-prec, Hcd783, MPR216, hsa-mir-019b-1-prec, hsa-mir-135-2-prec, hsa-mir-128b-prec, hsa-mir-025-prec, Hcd511, hsa-mir-093-prec-7.1=093-1, hsa-mir-106-prec-X, hsa-mir-142-prec, HPR169, hsa-mir-223-prec, hsa-mir-018-prec, and hsa-mir-020-prec,
   wherein an increase or decrease in said level of expression of said second gene or said second microRNA indicates that said cell is sensitive to PXD101 (belinostat).

24. The method of claim 1, wherein said measuring further comprises determining a level of expression of:
   i) a second gene selected from at least one of CD99, SNRPA, CUGBP2, STAT5A, SLA, IL2RG, GTSE1, MYB, PTPN7, CXorf9, RHOH, ZNFNIA1, CENTB1, LCP2, HIST1H4C, CCR7, APOBEC3B, MCM7, LCP1, SELPLG, CD3Z, PRKCQ, GZMB, SCN3A, LAIR1, SH2D1A, SEPT6, CG018, CD3D, C18orf10, PRF1, AIF1, MCM5, LPXN, C22orf18, ARHGAP15, and LEF1, or
   ii) a second microRNA selected from at least one of hsa-mir-096-prec-7, Hcd605, hsa-mir-20b, hsa-miR-373*, HUMTRAB, hsa-mir-019b-1-prec, HPR163, hsa-mir-371, hsa-mir-025-prec, hsa-mir-18b, hsa-mir-093-prec-7.1=093-1, hsa-mir-106-prec-X, hsa-mir-142-prec, and hsa-mir-020-prec,
   wherein an increase or decrease in said level of expression of said second gene or said second microRNA indicates that said cell is sensitive to 5-Aza-2'-deoxycytidine (Decitabine).

25. The method of claim 1, wherein said measuring further comprises determining a level of expression of:
   i) a second gene selected from at least one of SLC9A3R1, RPS19, ITM2A, SSBP2, CXorf9, RHOH, ZNFN1A1, FXYD2, CCR9, NAP1L1, CXCR4, SH2D1A, CD1A, TRB@, SEPT6, RPS2, DOCK2, CD3D, CD6, ZAP70, A1F1, CD1E, CYFIP2, ADA, TRIM, GLTSCR2, FLJ10858, BCL11B, GIMAP6, STAG3, UBASH3A, and, optionally, a third gene selected from at least one of MRPS24, TRIM22, TRIM41, LAT, CD1C, MRPS22, ADAM11, RPL13, RPS27, RPL13, RPS25, RPL18A, CORO1A, PTPRCAP, GMFG, ITK, CD1B, GMFG, PTPRCAP, CORO1A, ITGB2, HCLS1, and ATP2A3, or
   ii) a second microRNA selected from at least one of HUMTRF, hsa-mir-483, MPR74, hsa-mir-122a-prec, ath-MIR180a, hsa-mir-128b-prec, Hcd923, hsa-mir-106-prec-X, hsa-mir-342, hsa-mir-142-prec, HPR169, hsa-mir-223-prec, Hcd754, and hsa-mir-020-prec,
   wherein an increase or decrease in said level of expression of said second gene and, optionally, said third gene or said second microRNA indicates that said cell is sensitive to Idarubicin.

26. The method of claim 1, wherein said measuring further comprises determining a level of expression of:
i) a second gene selected from at least one of CD99, HLA-DPB1, ARHGDIB, IFITM1, UBE2L6, ITM2A, SERPINA1, STAT5A, INPP5D, DGKA, SATB1, SEMA4D, TFDP2, SLA, IL2RG, CD48, MFNG, ALOX5AP, GPSM3, PSMB9, KIAA0711, SELL, ADA, EDG1, RIMS3, FMNL1, MYB, PTPN7, LCK, CXorf9, RHOH, ZNFN1A1, CENTB1, LCP2, FXYD2, CD1D, BATF, STAT4, VAV1, MAP4K1, CCR7, PDE4C, CD3G, CCR9, SP110, LCP1, IFI16, CXCR4, ARHGEF6, GATA3, SELPLG, SEC31L2, CD3Z, PRKCQ, SH2D1A, GZMB, CD1A, SCN3A, LAIR1, FYB, TRB@, SEPT6, HA-1, DOCK2, CG018, CD3D, T3JAM, FNBP1, CD6, ZAP70, LST1, GPR65, PRF1, A1F1, FLJ20331, RAG2, WDR45, CD1E, CYFIP2, TARP, TRIM, RPL10L, GLTSCR2, GIMAP5, ARHGAP15, NOTCH1, BIN2, C13 orf18, CECR1, BCL11B, GIMAP6, STAG3, TM6SF1, HSD17B7, UBASH3A, MGC5566, FLJ22457, TPK1, PHF11, and DKFZP434B0335, and, optionally, a third gene selected from at least one of FLJ10534, PTPRC, TRIM22, C18orf1, EVL, TRIM41, PSME2, LAT, CD1C, MYBBP1A, ICAM3, ADAM11, CD53, FARSLA, RPL13, RAC2, RPL13, GNA15, PGF, LAPTM5, RPL18A, CD53, CORO1A, PTPRCAP, PTPRC, HEM1, GMFG, GNA15, ITK, CD1B, GMFG, PTPRCAP, PTPRC, CD53, CORO1A, HEM1, GNA15, TCF7, ITGB2, PTPRC, HCLS1, ATP2A3, MYBL1, and FARSLA, or
ii) a second microRNA selected from at least one of hsa-mir-124a-3-prec, hsa-mir-181a-prec, Hcd773, Hcd683, Hcd796, HUMTRF, HUMTRS, hsa-mir-181b-2, Hcd294, hsa-mir-20b, hsa-mir-181d, hsa-mir-213-prec, Hcd148_HPR225 left, hsa-mir-515-15p, hsa-mir-181b-prec, Hcd783, HUMTRAB, HUMTRN, hsa-mir-181b-1, hsa-mir-124a-1-prec1, hsa-mir-367, hsa-mir-128b-prec, Hcd438 right, hsa-mir-025-prec, hsa-mir-216-prec, Hcd731, hsa-mir-093-prec-7A=093-1, hsa-mir-106-prec-X, hsa-mir-342, hsa-mir-142-prec, HSHELA01, HUMTRV1A, hsa-mir-223-prec, Hcd754, and hsa-mir-020-prec,
wherein an increase or decrease in said level of expression of said second cone and, optionally, said third gene or said second microRNA indicates that said cell is sensitive to Melphalan.

27. The method of claim 1, wherein said measuring further comprises determining a level of expression of:
i) a second gene selected from at least one of MCL1, DDX23, JUNB, ZFP36, IFITM1, CKS1B, SERPINA1, IL4R, CLDN3, ARL4A, HMMR, FLJ12671, ANKHDI, KIF2C, RPA3, MCCC2, CDH17, LSM5, PRF1, ROD1, FLJ12666, SUV420H1, MUC13, C13orf18, and CDCA8, and, optionally, a third gene selected from at least one of ETS2, ARID1A, ID1, DDC, NID2, CCT3, ID2, NFIL3, and AREG, or
ii) a second microRNA selected from at least one of Hcd829, hsa-mir-197-prec, HPR163, and hsa-mir-150-prec,
wherein an increase or decrease in said level of expression of said second gene and, optionally, said third gene or said second microRNA indicates that said cell is sensitive to IL4-PE38 fusion protein.

28. The method of claim 1, wherein said measuring further comprises determining a level of expression of:
i) a second gene selected from at least one of MCL1, DDX23, JUNB, ZFP36, IFITM1, CKS1B, SERPINA1, IL13R, CLDN3, ARL4A, HMMR, FLJ12671, ANKHD1, KIF2C, RPA3, MCCC2, CDH17, LSM5, PRF1, ROD1, FLJ12666, SUV420H1, MUC13, C13orf18, and CDCA8, and, optionally, a third gene selected from at least one of ETS2, ARID1A, 1D1, DDC, NID2, CCT3, ID2, NFIL3, and AREG, or
ii) a second microRNA selected from at least one of Hcd829, hsa-mir-197-prec, HPR163, and hsa-mir-150-prec,
wherein an increase or decrease in said level of expression of said second gene and, optionally, said third gene or said second microRNA indicates that said cell is sensitive to IL13-PE38QQR fusion protein (cintredekin besudotox).

29. The method of claim 1, wherein said measuring further comprises determining a level of expression of:
i) a second gene selected from at least one of STOM, TNFAIP3, ASNS, GARS, CXCR4, EGLN3, LBH, and GDF15, and, optionally, at least one a third gene selected from at least one of STOML1 and KIAA0746, or
ii) a second microRNA selected from at least one of hsa-mir-034prec, Hcd255, Hcd712, Hcd965, Hcd891, Hcd210_HPR205, hsa-mir-429, Hcd753, Hcd693, MPR203, Hcd704, Hcd863PO, hsa-mir-122a-prec, Hcd760, Hcd338, HPR213, Hcd852, Hcd366, MPR103, Hcd669, and hsa-mir-188-prec,
wherein an increase or decrease in said level of expression of said second gene and, optionally, said third gene or said second microRNA indicates that said cell is sensitive to Valproic acid (VPA).

30. The method of claim 1, wherein said measuring further comprises determining a level of expression of:
i) a second gene selected from at least one of PPIB, ZFP36L2, 1F130, USP7, SRM, SH3BP5, ALDOC, FADS2, GUSB, PSCD1, IQGAP2, STS, MFNG, FLI1, PIM2, INPP4A, LRMP, ICAM2, EVI2A, MAL, BTN3A3, PTPN7, IL10RA, SPI1, TRAF1, ITGB7, ARHGAP6, MAP4K1, CD28, PTP4A3, LTB, C1orf38, WBSCR22, CD8B1, LCP1, FLJ13052, MEF2C, PSCDBP, IL16, SELPLG, MAGEA9, LAIR1, TNFRSF25, EVI2B, IGJ, PDCD4, RASA4, HA-1, PLCL2, RNASE6, WBSCR20C, NUP210, RPL10L, C11orf2, CABC1, ARHGEF3, TAPBPL, CHST12, FKBP11, FLJ35036, MYLIP, TXNDC5, PACAP, TOSO, PNAS-4, IL21R, and TCF4, and, optionally, a third gene selected from at least one of CLTB, BTN3A2, BCL2, SETBP1, ICAM3, BCL2, BCL2, BCL2, CD53, CCND2, CLTB, CLTB, BCL2L11, BTN3A2, CD37, MYCL2, CTSS, LAPTM5, CD53, CORO1A, HEM1, CD53, CORO1A, HEM1, HCLS1, BCL2L11, MYCL1, MYC, and MAN1A1, or
ii) a second microRNA selected from at least one of Hcd257, hsa-mir-148-prec, Hcd512, HPR227, Hcd421, MPR203, hsa-mir-017-prec, hsa-mir-219-2, hsa-mir-328, Hcd783, Hcd181, HPR213, hsa-mir-191-prec, hsa-mir-375, hsa-mir-212-prec, Hcd913, Hcd716, MPR207, HPR206, hsa-mir-016b-chr3, Hcd654, hsa-mir-195-prec, Hcd425, hsa-mir-148a, hsa-mir-142-prec, and hsa-mir-016a-chr13,
wherein an increase or decrease in said level of expression of said second gene and, optionally, said third gene or said second microRNA indicates that said cell is sensitive to All-trans retinoic acid (ATRA).

31. The method of claim 1, wherein said measuring further comprises determining a level of expression of:
i) a second gene selected from at least one of C6orf29, TRIM31, CD69, LRRN3, GPR35, and CDW52, or ii) a second microRNA selected from at least one of Hcd99, hsa-mir-520c/526a, hsa-mir-191-prec, hsa-mir-205-prec, hsa-mir-375, hsa-mir-423, hsa-mir-449, and hsa-mir-196-2-prec, wherein an increase or decrease in said level of expression of said second gene or said second microRNA indicates that said cell is sensitive to Cytoxan.

32. The method of claim 1, wherein said measuring further comprises comprising determining a level of expression of:
i) at least one a second gene selected from at least one the group consisting of K-ALPHA-1, CSDA, UCHL1, NAP1L1, ATP5G2, HDGFRP3, and IFI44, or
ii) a second microRNA selected from at least one of HUMTRF, MPR74, hsa-mir-213-prec, hsa-mir-155-prec, hsa-mir-181b-prec, hsa-mir-342, and hsa-mir-4323p, wherein an increase or decrease in said level of expression of said second gene or said second additional microRNA indicates that said cell is sensitive to Topotecan (Hycamtin).

33. The method of claim 1, wherein said measuring further comprises determining a level of expression of:
i) a second gene selected from at least one of NOL5A, STOM, SIAT1, CUGBP2, GUSB, ITM2A, JARID2, RUNX3, ICAM2, PTPN7, VAV1, PTP4A3, MCAM, MEF2C, IDH3B, RFP, SEPT6, SLC43A3, WBSCR20C, SHMT2, GLTSCR2, CABC1, FLJ20859, FLJ20010, MGC10993, and FKBP11, and, optionally, a third gene selected from at least one of STOML1, EIF4A1, PDE3B, BCL11A, INPP4B, HLA-DMA, TRFP, EIF4A1, GAS7, MYCL2, HCLS1, MYCL1, and MYC, or
ii) a second microRNA selected from at least one of hsa-mir-092-prec-X=092-2, hsa-mir-123-prec, hsa-mir-514-1, hsa-mir-101-prec-9, hsa-mir-148-prec, hsa-mir-106a, hsa-mir-20b, Hcd781, hsa-mir-017-prec, hsa-mir-019b-2-prec, hsa-mir-033-prec, hsa-mir-092-prec-13=092-1, hsa-mir-107, hsa-mir-103-prec-5=103-1, MPR216, hsa-mir-29b-2=102prec7.1=7.2, hsa-mir-019b-1-prec, hsa-mir-107-prec-10, hsa-mir-135-2-prec, Hcd581, hsa-mir-103-2-prec, Hcd230, hsa-mir-025-prec, hsa-mir-208-prec, hsa-mir-18b, hsa-mir-093-prec-7.1=093-1, hsa-mir-106-prec-X, hsa-mir-142-prec, HPR169, hsa-mir-018-prec, and hsa-mir-020-prec, wherein an increase or decrease in said level of expression of said second gene and, optionally, said third gene or said second microRNA indicates that said cell is sensitive to Suberoylanilide hydroxamic acid (SAHA, vorinostat, Zolinza).

34. The method of claim 1, wherein said measuring further comprises determining a level of expression of:
i) a second gene selected from at least one of ZFP36L2, TRIB2, LCP2, C6orf32, IL16, CACNA1G, SPDEF, HAB1, TOSO, and ARHGAP25, and, optionally, a third gene selected from at least one of SGCD and CAPN3, or
ii) a second microRNA selected from at least one of Hcd415, hsa-mir-147-prec, hsa-mir-033b-prec, Hcd778, hsa-mir-127-prec, hsa-mir-324, Hcd794, and Hcd634, wherein an increase or decrease in said level of expression of said second gene and, optionally, said third gene or said second microRNA indicates that said cell is sensitive to Depsipeptide (FR901228).

35. The method of claim 1, wherein said measuring further comprises determining a level of expression of:
i) a second gene selected from at least one of PLEKHB2, ARPC1B, MX1, CUGBP2, IFI16, TNFRSF14, SP110, ELF1, LPXN, IFRG28, LEF1, and PYCARD, and, optionally, HMX1, or
ii) a second microRNA selected from at least one of MPR121, Hcd115, Hcd693, Hcd704, HPR100, Hcd760, hsa-mir-147-prec, hsa-mir-033b-prec, hsa-mir-146-prec, Hcd142, hsa-mir-501, Hcd716, MPR207, Hcd777, hsa-mir-204-prec, hsa-mir-146b, Hcd511, Hcd397, MPR130, Hcd782, hsa-mir-324, Hcd794, and Hcd739, wherein an increase or decrease in said level of expression of said second gene or said second microRNA indicates that said cell is sensitive to Bortezomib.

36. The method of claim 1, wherein said measuring further comprises determining a level of expression of:
i) a second gene selected from at least one of SSRP1, ALDOC, C1QR1, TTF1, PRIM1, USP34, TK2, GOLGIN-67, NPD014, KIAA0220, SLC43A3, WBSCR20C, ICAM2, TEX10, CHD7, SAMSN1, and TPRT, and, optionally, a third gene selected from at least one of PTPRC, CD53, RNPS1, H3F3A, NUDC, SMARCA4, RPL32, PTMA, CD53, PTPRCAP, PTPRC, RPL32, PTPRCAP, PTPRC, CD53, PTPRC, HCLS1, and SLC19A1, or
ii) a second microRNA selected from at least one of hsa-mir-092-prec-X=092-2, hsa-mir-096-prec-7, hsa-mir-123-prec, MPR249, HPR232, hsa-mir-101-prec-9, hsa-mir-106a, hsa-mir-20b, Hcd861, hsa-mir-017-prec, hsa-mir-019b-2-prec, hsa-mir-033-prec, Hcd102, MPR216, Hcd975, hsa-mir-019b-1-prec, hsa-mir-135-2-prec, Hcd581, Hcd536_HPR104, hsa-mir-128b-prec, HSTRNL, hsa-mir-025-prec, hsa-mir-18b, HPR262, Hcd923, Hcd434, Hcd658, HPR129, hsa-mir-380-5p, hsa-mir-093-prec-7.1=093-1, hsa-mir-106-prec-X, Hcd627, hsa-mir-142-prec, hsa-mir-018-prec, and hsa-mir-020-prec, wherein an increase or decrease in said level of expression of said second gene and, optionally, said third gene or said second microRNA indicates that said cell is sensitive to Leukeran.

37. The method of claim 1, wherein said measuring further comprises determining a level of expression of:
i) a second gene selected from at least one of HLA-E, BAT3, ENO2, UBE2L6, CUGBP2, ITM2A, PALM2-AKAP2, JARID2, DGKA, SLC7A6, TFDP2, ADA, EDG1, ICAM2, PTPN7, CXorf9, RHOH, MX2, ZNFN1A1, COCH, LCP2, CLGN, BNC1, FLNC, HLA-DRB3, UCP2, HLA-DRB1, GATA3, PRKCQ, SH2DIA, NFATC3, TRB@, FNBP1, SEPT6, NME4, DKFZP434C171, ZC3HAV1, SLC43A3, CD3D, AIF1, SPTAN1, CD1E, TRIM, DATF1, FHOD1, ARHGAP15, STAG3, SAP130, and CYLD, and, optionally, a third gene selected from at least one of PTPRC, MX2004PA11424, TRIM22, TRIM41, CD1C, CHD8, ADAM11, ANPEP, RBMX2, RAC2, GNA15, LAPTM5, PTPRCAP, PTPRC, GNA15, CD1B, PTPRCAP, PTPRC, GNA15, PTPRC, and ATP2A3, or
ii) a second microRNA selected from at least one of Hcd773, Hcd248, hsa-mir-181d, MPR74, hsa-mir-213-prec, hsa-mir-155-prec, MPR197, hsa-mir-181b-prec, hsa-mir-29b-2=102prec7.1=7.2, hsa-mir-029c-prec, Hcd318, hsa-mir-128b-prec, hsa-mir-130a-prec, hsa-mir-140, hsa-mir-16-2, hsa-mir-526a-2, hsa-mir-016b-chr3, hsa-mir-195-prec, hsa-mir-216-prec, hsa-mir-342, hsa-mir-29b-1, Hcd627, hsa-mir-102-prec-1, hsa-mir-142-prec, hsa-mir-223-prec, hsa-let-7f-2-prec2, and hsa-mir-016a-chr13, wherein an increase or decrease in said level of expression of said second gene and, optionally, said third gene or said second microRNA indicates that said cell is sensitive to Fludarabine.

38. The method of claim 1, wherein said measuring further comprises determining a level of expression of CD99 or at least a second microRNA selected from at least one of Hcd794 and Hcd754,
wherein an increase or decrease in said level of expression of said CD99 or said second microRNA indicates that said cell is sensitive to Vinblastine.

39. The method of claim 1, wherein said measuring further comprises determining a level of expression of:
i) a second gene selected from at least one of RPLP2, BTG1, CSDA, ARHGDIB, INSIG1, ALDOC, WASPIP, C1QR1, EDEM1, SLA, MFNG, GPSM3, ADA, LRMP, EVI2A, FMNL1, PTPN7, RHOH, ZNFN1A1, CENTB1, MAP4K1, CD28, SP110, NAP1L1, IFI16, ARHGEF6, SELPLG, CD3Z, SH2DIA, LAIR1, RAFTLIN, HA-1, DOCK2, CD3D, T3JAM, ZAP70, GPR65, CYFIP2, LPXN, RPL10L, GLTSCR2, ARHGAP15, BCL11B, TM6SF1, PACAP, and TCF4, and, optionally, a third gene selected from at least one of PTPRC, BCL2, LAT, ICAM3, BCL2, BCL2, BCL2, ADAM11, CD53, FARSLA, BCL2L11, RPL13, RAC2, RPL13, MYCL2, LAPTM5, RPL18A, CD53, CORO1A, PTPRCAP, PTPRC, HEM1, GMFG, GMFG, PTPRCAP, PTPRC, CD53, CORO1A, HEM1, PTPRC, HCLS1, BCL2L11, MYCL1, FARSLA, and MYC, or
ii) a second microRNA selected from at least one of hsa-mir-096-prec-7, hsa-mir-124a-3-prec, hsa-mir-101-prec-9, Hcd712, Hcd693, hsa-mir-219-2, Hcd145, hsa-mir-155-prec, HPR213, hsa-mir-212-prec, Hcd913, Hcd716, MPR207, Hcd559, Hcd654, Hcd739, and hsa-mir-142-prec,
wherein an increase or decrease in said level of expression of said second gene and, optionally, said third gene or said second microRNA indicates that said cell is sensitive to Busulfan.

40. The method of claim 1, wherein said measuring further comprises determining a level of expression of:
i) a second gene selected from at least one ARHGDIB, ITM2A, SSBP2, PIM2, SELL, ICAM2, EVI2A, MAL, PTPN7, ZNFN1A1, LCP2, ARHGAP6, CD28, CD8B1, LCP1, NPD014, CD69, NFATC3, TRB@, IGJ, SLC43A3, DOCK2, FHOD1, and PACAP, and, optionally, a third gene selected from at least one of ICAM3, CD53, SMARCA4, CD37, LAPTM5, CD53, CORO1A, HEM1, GMFG, GMFG, CD53, CORO1A, HEM1, and HCLS1, or
ii) a second microRNA selected from at least one of hsa-mir-092-prec-X=092-2, hsa-mir-123-prec, hsa-mir-101-prec-9, Hcd517, Hcd796, Hcd749, Hcd674, hsa-mir-019b-2-prec, hsa-mir-033-prec, hsa-mir-092-prec-13=092-1, hsa-mir-124a-2-prec, hsa-mir-143-prec, hsa-mir-516-43p, hsa-mir-216-prec, Hcd731, hsa-mir-106-prec-X, hsa-mir-142-prec, hsa-mir-223-prec, Hcd754, and hsa-mir-018-prec,
wherein an increase or decrease in said level of expression of said second gene and, optionally, said third gene or said second microRNA indicates that said cell is sensitive to Dacarbazine.

41. The method of claim 1, wherein said measuring further comprises determining a level of expression of:
i) a second gene selected from at least one of RPL18, RPL10A, RPS3A, EEF1B2, GOT2, RPL13A, RPS15, NOL5A, RPLP2, SLC9A3R1, EIF3S3, MTHFD2, IMPDH2, ALDOC, FABP5, ITM2A, PCK2, MFNG, GCH1, PIM2, ADA, ICAM2, TTF1, MYB, PTPN7, RHOH, ZNFN1A1, PRIM1, FH1T, ASS, SYK, OXA1L, LCP1, DDX18, NOLA2, KIAA0922, PRKCQ, NFATC3, ANAPC5, TRB@, CXCR4, FNBP4, SEPT6, RPS2, MDN1, PCCB, RASA4, WBSCR20C, SFRS7, WBSCR20A, NUP210, SHMT2, RPLP0, MAP4K1, HNRPA1, CYFIP2, RPL10L, GLTSCR2, MRPL16, MRPS2, FLJ12270, CDK5RAP3, ARHGAP15, CUTC, FKBP11, ADPGK, FLJ22457, PUS3, PACAP, and CALML4, and, optionally, a third gene selected from at least one of MRPS24, DUSP2, EIF4A1, BRD2, BCL11A, RASSF2, MRPL37, MRPL30, RASSF1, MYBBPIA, LASS2, MRPS22, ADAM11, CD53, RPS6 KB1, RNPS1, BRD2, EIF4A1, FBL, BRD2, RPL36A, RPL13, RPL38, H3F3A, KIAA0182, RPS27, RPS6, EEF1G, RPL13, MYCL2, FBLN1, RPS25, RPL32, PTMA, RPL18A, RPL3, CD53, CORO1A, HEM1, GMFG, RPL32, GMFG, CD53, CORO1A, HEM1, HCLS1, ATP2A3, RASSF7, MYCL1, MYBL1, MYC, RPS15A, RASSF2, and LASS6, or
ii) a second microRNA selected from at least one of hsa-mir-092-prec-X=092-2, hsa-mir-148-prec, hsa-mir-20b, hsa-mir-007-2-prec, hsa-mir-017-prec, hsa-mir-019b-2-prec, Hcd760, Hcd783, MPR216, hsa-mir-375, hsa-mir-019b-1-prec, hsa-mir-135-2-prec, hsa-mir-150-prec, hsa-mir-128b-prec, hsa-mir-499, hsa-mir-025-prec, hsa-mir-007-1-prec, hsa-mir-019a-prec, hsa-mir-093-prec-7.1=093-1, hsa-mir-106-prec-X, hsa-mir-142-prec, HPR169, hsa-mir-018-prec, hsa-mir-020-prec, and hsa-mir-484,
wherein an increase or decrease in said level of expression of said second gene and, optionally, said third gene or said second microRNA indicates that said cell is sensitive to Oxaliplatin.

42. The method of claim 1, wherein said measuring further comprises determining a level of expression of:
i) a second gene selected from at least one of CSDA, INSIG1, UBE2L6, PRG1, ITM2A, DGKA, SLA, PCBP2, IL2RG, ALOX5AP, PSMB9, LRMP, ICAM2, PTPN7, CXorf9, RHOH, ZNFN1A1, CENTBI, LCP2, STAT5, CCR7, CD3G, SP110, TNFAIP8, IFI16, CXCR4, ARHGEF6, SELPLG, CD3Z, PRKCQ, SH2DIA, CDIA, NFATC3, LAIR1, TRB@, SEPT6, RAFTLIN, DOCK2, CD3D, CD6, AIF1, CD1E, CYFIP2, TARP, ADA, ARHGAP15, GIMAP6, STAG3, FLJ22457, PACAP, and TCF4, and, optionally, a third gene selected from at least one of PTPRC, TRIM22, PSME2, LAT, CD1C, ICAM3, ADAM11, CD53, FARSLA, RPL13, RAC2, RPL13, NK4, LAPTM5, CD53, CORO1A, PTPRCAP, PTPRC, HEM1, GMFG, GMFG, PTPRCAP, PTPRC, CD53, CORO1A, HEM1, ITGB2, PTPRC, HCLS1, ATP2A3, and FARSLA, or
ii) a second microRNA selected from at least one of Hcd257, Hcd768, Hcd796, HUMTRF, HUMTRS, MPR74, hsa-mir-213-prec, hsa-mir-155-prec, Hcd763, hsa-mir-181b-prec, ath-MIR180a, hsa-mir-216-prec, hsa-mir-342, hsa-mir-142-prec, HSHELA01, HUMTRV1A, hsa-mir-223-prec, Hcd7.54, and hsa-mir-020-prec,
wherein an increase or decrease in said level of expression of said second gene and, optionally, said third gene or said second microRNA indicates that said cell is sensitive to Hydroxyurea.

43. The method of claim 1, wherein said measuring further comprises determining a level of expression of:
   i) a second gene selected from at least one of RPL11, RPL17, ANAPC5, RPL13A, STOM, TUFM, SCARB1, FABP5, KIAA0711, IL6R, WBSCR22, UCK2, GZMB, C1orf38, PCBP2, GPR65, GLTSCR2, and FKBP11, and, optionally, a third gene selected from at least one of STOML1, MRPL37, MRPL30, RPL36A, RPL38, HSPD1, MIF, RPL32, RPL3, and RPL32, or
   ii) a second microRNA selected from at least one of Hcd257, Hcd946, Hcd503, hsa-mir-429, Hcd693, hsa-miR-373*, Hcd738, hsa-mir-328, Hcd783, Hcd181, Hcd631, Hcd279, hsa-mir-194-2, hsa-mir-197-prec, HPR163, hsa-mir-150-prec, Hcd323, hsa-mir-103-2-prec, Hcd243, Hcd938, hsa-mir-025-prec, hsa-mir-007-1-prec, MPR243, Hcd511, Hcd654, hsa-mir-199a-2-prec, hsa-mir-214-prec, hsa-mir-093-prec-7.1=093-1, hsa-mir-106-prec-X, Hcd794, Hcd530, HSHELA01, Hcd754, and hsa-mir-020-prec,
   wherein an increase or decrease in said level of expression of said second gene and, optionally, said third gene or said second microRNA indicates that said cell is sensitive to Tegafur.

44. The method of claim 1, wherein said measuring further comprises determining a level of expression of:
   i) a second gene selected from at least one of ALDOC, ITM2A, SLA, SSBP2, IL2RG, MFNG, SELL, STC1, LRMP, MYB, PTPN7, CXorf9, RHOH, ZNFN1A1, CENTB1, MAP4K1, CCR7, CD3G, CCR9, CBFA2T3, CXCR4, ARHGEF6, SELPLG, SEC31L2, CD3Z, SH2D1A, CDIA, SCN3A, LAIR1, TRB@, DOCK2, WBSCR20C, CD3D, T3JAM, CD6, ZAP70, GPR65, A1F1, WDR45, CD1E, CYFIP2, TARP, TRIM, ARHGAP15, NOTCH1, STAG3, UBASH3A, MGC5566, and PACAP, and, optionally, a third gene selected from at least one of PTPRC, TRIM22, TRIM41, LAT, CD1C, MYBBP1A, CD53, FARSLA, PPP2CA, LAPTM5, CD53, CORO1A, PTPRCAP, PTPRC, HEM1, GMFG, ITK, CDIB, GMFG, PTPRCAP, PTPRC, CD53, CORO1A, HEM1, TCF7, PTPRC, HCLS1, ATP2A3, MYBL1, and FARSLA, or
   ii) a second microRNA selected from at least one of Hcd768, HUMTRF, Hcd145, Hcd923, hsa-mir-216-prec, hsa-mir-093-prec-7.1=093-1, hsa-mir-342, Hcd794, hsa-mir-142-prec, HSHELA01, hsa-mir-223-prec, and Hcd754,
   wherein an increase or decrease in said level of expression of said second gene and, optionally, said third gene or said second microRNA indicates that said cell is sensitive to Daunorubicin.

45. The method of claim 1, wherein said measuring further comprises determining a level of expression of:
   i) a second gene selected from at least one of PFN1, CALU, ZYX, PSMD2, RAPIB, EPAS1, PGAM1, STAT1, CKAP4, DUSP1, RCN1, UCHL1, ITGA5, NFKBIA, LAMB1, TGFBI, FHL1, GJA1, PRG1, EXT1, MVP, NNMT, TAP1, CRIM1, PLOD2, RPS19, AXL, PALM2-AKAP2, IL8, LOXL2, PAPSS2, CAV1, F2R, PSMB9, LOX, C1orf29, STC1, LIF, KCNJ8, SMAD3, HPCAL1, WNT5A, BDNF, TNFRSF1A, NCOR2, FLNC, HMGA2, HLA-B, FLOT1, PTRF, IFI16, MGC4083, TNFRSF10B, PNMA2, TFPI, CLECSF2, SP110, PLAUR, ASPH, FSCN1, HIC, HLA-C, COL6A1, IL6ST, IFITM3, MAP1B, FLJ46603, RAFTLIN, FTL, KIAA0877, MT1E, CDC10, ZNF258, BCAT1, IFI44, SOD2, TMSB10, FLJ10350, C1orf24, EFHD2, RPS27L, TNFRSF12A, FAD104, RAB7L1, NME7, TMEM22, TPK1, ELKS, CYLD, AMIGO2, ADAMTS1, and ACTB, and, optionally, a third gene selected from at least one of ACLY, MPZL1, STC2, BAX, RAB31, RAB31, (UBC12, LOXL1, EMP3, FGFR1OP, IL6, TRIM22, OPTN, CYR61, METAP1, SHC1, FN1, EMP3, RAB31, LOXL1, BAX, BAX, RAB31, FN1, CD44, ANXA1, COL5A2, LGALS1, FGFR1, PLAU, TFPI2, TFPI2, VCAM1, SHC1, CSF2RA, EMP3, COL1A1, TGFB1, COL6A2, FGFR1, ITGA3, AKR1B1, MSN, EMP3, VIM, EMP3, COL6A2, MSN, PSMC5, UBC, FGFR1, BASP1, ANXA11, CSPG2, M6PRBP1, PRKCA, OPTN, OPTN, SPARC, CCL2, and ITGA3, or
   ii) a second microRNA selected from at least one of hsa-mir-125b-2-prec, hsa-mir-022-prec, hsa-mir-125b-1, hsa-mir-155-prec, hsa-mir-100, hsa-mir-409-3p, hsa-mir-495, hsa-mir-199a-2-prec, hsa-mir-382, and hsa-mir-100-1/2-prec,
   wherein an increase or decrease in said level of expression of said second gene and, optionally, said third gene or said second microRNA indicates that said cell is sensitive to Bleomycin.

46. The method of claim 1, wherein said measuring further comprises determining a level of expression of:
   i) a second gene selected from at least one of HSPCB, LDHA, and TM4SF7, and, optionally, LY6E, or
   ii) a second microRNA selected from at least one of Hcd338, hsa-mir-099b-prec-19, and hsa-mir-149-prec,
   wherein an increase or decrease in said level of expression of said second gene or said second microRNA indicates that said cell is sensitive to Estramustine.

47. The method of claim 1, wherein said measuring further comprises determining a level of expression of:
   i) a second gene selected from at least one of CSDA, INSIG1, UBE2L6, PRG1, ITM2A, DGKA, TFDP2, SLA, IL2RG, ALOX5AP, GPSM3, PSMB9, SELL, ADA, EDG1, FMNL1, PTPN7, CXorf9, RHOH, ZNFN1A1, CENTB1, LCP2, CD1D, STAT4, VAV1, MAP4K1, CCR7, PDE4C, CD3G, CCR9, SP110, TNFAIP8, LCP1, IFI16, CXCR4, ARHGEF6, SEL-PLG, SEC31L2, CD3Z, PRKCQ, SH2D1A, GZMB, CD1A, LAIR1, AFIQ, TRB@, SEPT6, DOCK2, RPS19, CD3D, T3JAM, FNBP1, CD6, ZAP70, LST1, BCAT1, PRF1, A1F1, RAG2, CDIE, CYFIP2, TARP, TRIM, GLTSCR2, GIMAP5, ARHGAP15, NOTCH1, BCL11B, GIMAP6, STAG3, TM6SF1, UBASH3A, MGC5566, FLJ22457, and TPK1, and, optionally, a third gene selected from at least one of PTPRC, TRIM22, EVL, TRIM41, PSME2, LAT, CD1C, ADAM11, CD53, FARSLA, RPL13, RAC2, RPL13, GNA15, LAPTM5, RPL18A, CD53, CORO1A, PTPR-CAP, PTPRC, HEM1, GMFG, GNA15, ITK, CD1B, GMFG, PTPRCAP, PTPRC, CD53, CORO1A, HEM1, GNA15, ITGB2, PTPRC, HCLS1, ATP2A3, and FARSLA, or
   ii) a second microRNA selected from at least one of hsa-mir-181a-prec, hsa-mir-181c-prec, HUMTRF, hsa-mir-181d, MPR74, Hcd817, hsa-mir-213-prec, hsa-mir-155-prec, Hcd148_HPR225 left, hsa-mir-515-15p, hsa-mir-181b-prec, HUMTRN, hsa-mir-128b-prec, hsa-mir-450-2, hsa-mir-216-prec, hsa-mir-342, hsa-mir-142-prec, hsa-mir-223-prec, Hcd754, and hsa-mir-020-prec,
   wherein an increase or decrease in said level of expression of said second gene and, optionally, said third gene or said second microRNA indicates that said cell is sensitive to Chlorambucil.

48. The method of claim 1, wherein said measuring further comprises determining a level of expression of:
  i) a second gene selected from at least one of PRG1, SLC2A3, RPS19, PSMB10, ITM2A, DGKA, SEMA4D, SLA, IL2RG, MFNG, ALOX5AP, GPSM3, PSMB9, SELL, ADA, FMNL1, MYB, PTPN7, CXorf9, RHOH, ZNFN1A1, CENTB1, FXYD2, CD1D, STAT4, MAP4K1, CCR7, PDE4C, CD3G, CCR9, SP110, TK2, TNFAIP8, NAP1L1, SELPLG, SEC31L2, CD3Z, PRKCQ, SH2DIA, GZMB, CD1A, LAIR1, TRB@, SEPT6, DOCK2, CG018, WBSCR20C, CD3D, CD6, LST1, GPR65, PRF1, ALMS1, A1F1, CDIE, CYFIP2, TARP, GLTSCR2, FLJ12270, ARHGAP15, NAP1L2, CECR1, GIMAP6, STAG3, TM6SF1, C15orf25, MGC5566, FLJ22457, ET, TPK1, and PHF11, and, optionally, a third gene selected from at least one of ETS2, PTPRC, PETER, SETBP1, LAT, MYBBP1A, ETV5, METAP1, ETS1, ADAM11, CD53, FARSLA, RPL13, ARMET, TETRAN, BET1, RPL13, MET, LAPTM5, CD53, CORO1A, PTPRCAP, PTPRC, HEM1, GMFG, CD1B, GMFG, PTPRCAP, PTPRC, CD53, CORO1A, HEM1, ETV4, ITGB2, PTPRC, HCLS1, MYBL1, FARSLA, and METAP2, or
  ii) a second microRNA selected from at least one of hsa-mir-124a-3-prec, Hcd946, Hcd683, HPR264, MPR185, HUMTRF, Hcd294, Hcd503, hsa-mir-20b, MPR74, MPR234, Hcd447, Hcd817, Hcd148_HPR225 left, hsa-mir-515-15p, Hcd383, hsa-mir-181b-prec, Hcd783, MPR224, HPR172, MPR216, HUMTRN, hsa-mir-321, HPR159, MPR228, ath-MIR180a, hsa-mir-197-prec, hsa-mir-124a-1-prec1, hsa-mir-128b-prec, Hcd28_HPR39 left, Hcd889, Hcd350, hsa-mir-025-prec, hsa-mir-208-prec, hsa-mir-450-2, Hcd923, Hcd434, HPR129, HPR220, hsa-mir-380-5p, hsa-mir-093-prec-7.1=093-1, hsa-mir-106-prec-X, hsa-mir-342, hsa-mir-142-prec, HSHELA01, hsa-mir-223-prec, Hcd754, hsa-mir-020-prec, and hsa-mir-4323p,
  wherein an increase or decrease in said level of expression of said second gene and, optionally, said third gene or said second microRNA indicates that said cell is sensitive to Mechlorethamine.

49. The method of claim 1, wherein said measuring further comprises determining a level of expression of:
  i) a second gene selected from at least one of PGK1, SCD, INSIG1, IGBP1, TNFAIP3, TNFSF10, ABCA1, AGA, ABCA8, DBC1, PTGER2, UGTIA3, C10 orfl0, TM4SF13, CGI-90, LXN, DNAJC12, HIPK2, and C9orf95, and, optionally, a third gene selected from at least one of FGFR10P, PLXNA1, PSCD2L, TUBB, FGFR1, TUBB2, PAGA, TUBB2, UBB, TUBB2, FGFR1, FGFR1, and TUBB-PARALOG, or
  ii) a second microRNA selected from at least one of hsa-mir-483, Hcd631, hsa-mir-212-prec, Hcd938, MPR133, Hcd794, Hcd438, and Hcd886,
  wherein an increase or decrease in said level of expression of said second gene and, optionally, said third gene or said second microRNA indicates that said cell is sensitive to Streptozocin.

50. The method of claim 1, wherein said measuring further comprises determining a level of expression of:
  i) a second gene selected from at least one of RPLP2, CD99, IFITM1, INSIG1, ALDOC, ITM2A, SERPINA1, C1QR1, STAT5A, INPP5D, SATB1, VPS16, SLA, IL2RG, MFNG, SELL, LRMP, ICAM2, MYB, PTPN7, ARHGAP25, LCK, CXorf9, RHOH, ZNFN1A1, CENTB1, ADD2, LCP2, SPI1, DBT, GZMA, CD2, BATF, HIST1H4C, ARHGAP6, VAV1, MAP4K1, CCR7, PDE4C, CD3G, CCR9, SP140, TK2, LCP1, IFI16, CXCR4, ARHGEF6, PSCDBP, SELPLG, SEC31L2, CD3Z, PRKCQ, SH2D1A, GZMB, CD1A, GATA2, LY9, LAIR1, TRB@, SEPT6, HA-1, SLC43A3, DOCK2, CG018, MLC1, CD3D, T3JAM, CD6, ZAP70, DOK2, LST1, GPR65, PRF1, ALMS1, AIF1, PRDX2, FLJ12151, FBXW12, CD1E, CYFIP2, TARP, TRIM, RPL10L, GLTSCR2, CKIP-1, NRN1, ARHGAP15, NOTCH1, PSCD4, C13orf18, BCL11B, GIMAP6, STAG3, NARF, TM6SF1, C15orf25, FLJ11795, SAMSN1, UBASH3A, PACAP, LEF1, IL21R, TCF4, and DKFZP434B0335, and, optionally, a third gene selected from at least one of FLJ10534, PTPRC, CD27BP, TRIM22, TRIM41, PSCD2L, CD1C, MYBBP1A, ICAM3, CD53, FARSLA, GAS7, ABCD2, CD24, CD29, RAC2, CD37, GNA15, PGF, LAPTM5, RPL18A, CD53, CORO1A, PTPRCAP, PTPRC, HEM1, GMFG, GNA15, ITK, GMFG, PTPRCAP, PTPRC, CD53, CORO1A, HEM1, GNA15, TCF7, ITGB2, PTPRC, HCLS1, PRKCB1, ATP2A3, PRKCBI, MYBL1, and FARSLA, or
  ii) a second microRNA selected from at least one of hsa-mir-092-prec-X=092-2, Hcd517, Hcd796, HUMTRF, hsa-mir-20b, hsa-mir-019b-2-prec, hsa-mir-033-prec, hsa-mir-092-prec-13=092-1, Hcd148_HPR225 left, HUMTRAB, Hcd975, hsa-mir-135-2-prec, hsa-mir-128b-prec, hsa-mir-143-prec, hsa-mir-025-prec, hsa-mir-216-prec, hsa-mir-093-prec-7.1=093-1, hsa-mir-106-prec-X, hsa-mir-142-prec, HSHELA01, HUMTRV1A, hsa-mir-223-prec, Hcd754, hsa-mir-018-prec, and hsa-mir-020-prec,
  wherein an increase or decrease in said level of expression of said second gene and, optionally, said third gene or said second microRNA indicates that said cell is sensitive to Carmustine.

51. The method of claim 1, wherein said measuring further comprises determining a level of expression of:
  i) a second gene selected from at least one of RPS15, INSIG1, ALDOC, ITM2A, C1QR1, STAT5A, INPP5D, VPS16, SLA, USP20, IL2RG, MFNG, LRMP, EVI2A, PTPN7, ARHGAP25, RHOH, ZNFN1A1, CENTBI, LCP2, SPIT, ARHGAP6, MAP4K1, CCR7, LY96, C6orf32, MAGEA1, SP140, LCP1, IFI16, ARHGEF6, PSCDBP, SELPLG, CD3Z, PRKCQ, GZMB, LAIR1, SH2DIA, TRB@, RFP, SEPT6, HA-1, SLC43A3, CD3D, T3JAM, GPR65, PRF1, AIF1, LPXN, RPL10L, SITPEC, ARHGAP15, C13orf18, NARF, TM6SF1, PACAP, and TCF4, and, optionally, a third gene selected from at least one of PTPRC, ICAM3, TRFP, CD53, FARSLA, RAC2, MAGEA11, LAPTM5, CD53, CORO1A, PTPRCAP, PTPRC, HEM1, GMFG, GMFG, PTPRCAP, PTPRC, CD53, CORO1A, HEM1, PTPRC, HCLS1, SLC19A1, FARSLA, and RPS15A, or
  ii) a second microRNA selected from at least one of hsa-mir-101-prec-9, Hcd796, hsa-mir-20b, HUMTRAB, hsa-mir-135-2-prec, hsa-mir-153-1-prec1, hsa-mir-025-prec, hsa-mir-093-prec-7.1=093-1, hsa-mir-106-prec-X, hsa-mir-142-prec, HUMTRV1A, Hcd754, hsa-mir-018-prec, and hsa-mir-020-prec,
  wherein an increase or decrease in said level of expression of said second gene and, optionally, said third gene or said second microRNA indicates that said cell is sensitive to Lomustine.

52. The method of claim 1, wherein said measuring further comprises determining a level of expression of:
  i) a second gene selected from at least one of SSRP1, ALDOC, C1QR1, TTF1, PRIM1, USP34, TK2, GOL- GIN-67, NPD014, KIAA0220, SLC43A3, WBSCR20C, ICAM2, TEX10, CHD7, SAMSN1, and TPRT, and, optionally, a third gene selected from at least one of PTPRC, CD53, RNPS1, H3F3A, NUDC, SMARCA4, RPL32, PTMA, CD53, PTPRCAP, PTPRC, RPL32, PTPRCAP, PTPRC, CD53, PTPRC, HCLS1, and SLC19A1, or ii) a second microRNA selected from at least one of hsa-mir-092-prec-X=092-2, hsa-mir-096-prec-7, hsa-mir-123-prec, MPR249, HPR232, hsa-mir-101-prec-9, hsa-mir-106a, hsa-mir-20b, Hcd861, hsa-mir-017-prec, hsa-mir-019b-2-prec, hsa-mir-033-prec, Hcd102, MPR216, Hcd975, hsa-mir-019b-1-prec, hsa-mir-135-2-prec, Hcd581, Hcd536_HPR104, hsa-mir-128b-prec, HSTRNL, hsa-mir-025-prec, hsa-mir-18b, HPR262, Hcd923, Hcd434, Hcd658, HPR129, hsa-mir-380-5p, hsa-mir-093-prec-7.1=093-1, hsa-mir-106-prec-X, Hcd627, hsa-mir-142-prec, hsa-mir-018-prec, and hsa-mir-020-prec, wherein an increase or decrease in said level of expression of said second gene and, optionally, said third gene or said second microRNA indicates that said cell is sensitive to Mercaptopurine.

53. The method of claim 1, wherein said measuring further comprises determining a level of expression of:
i) a second gene selected from at least one of CD99, INSIG1, PRG1, ALDOC, ITM2A, SLA, SSBP2, IL2RG, MFNG, ALOX5AP, C1 orf29, SELL, STC1, LRMP, MYB, PTPN7, CXorf9, RHOH, ZNFN1A1, CENTBI, ADD2, CD1D, BATF, MAP4K1, CCR7, PDE4C, CD3G, CCR9, SP110, TNFAIP8, NAP1L1, CXCR4, ARHGEF6, GATA3, SELPLG, SEC31L2, CD3Z, SH2D1A, GZMB, CDIA, SCN3A, LAIR1, AF1Q, TRB@, DOCK2, MLC1, CD3D, T3JAM, CD6, ZAP70, IFI44, GPR65, PRF1, A1F1, WDR45, CD1E, CYFIP2, TARP, TRIM, ARHGAP15, NOTCH1, STAG3, NARF, TM6SF1, UBASH3A, and MGC5566, and, optionally, a third gene selected from at least one of FLJ10534, PTPRC, TRIM22, C18orf1, TRIM41, LAT, CDIC, MYBBP1A, CD53, FARSLA, PPP2CA, COL5A2, LAPTM5, CD53, CORO1A, PTPRCAP, PTPRC, HEM1, GMFG, ITK, CDIB, GMFG, PTPR-CAP, PTPRC, CD53, CORO1A, HEM1, TCF7, PTPRC, HCLS1, ATP2A3, MYBL1, and FARSLA, or
ii) a second microRNA selected from at least one of hsa-mir-124a-3-prec, Hcd768, HUMTRF, hsa-mir-213-prec, hsa-mir-181b-prec, Hcd783, hsa-mir-212-prec, hsa-mir-124a-1-prec1, hsa-mir-342, hsa-mir-142-prec, HSHELA01, hsa-mir-223-prec, and Hcd754, wherein an increase or decrease in said level of expression of said second gene and, optionally, said third gene or said second microRNA indicates that said cell is sensitive to Teniposide.

54. The method of claim 1, wherein said measuring further comprises determining a level of expression of:
i) a second gene selected from at least one of ALDOC, C1QR1, SLA, WBSCR20A, MFNG, SELL, MYB, RHOH, ZNFN1A1, LCP2, MAP4K1, CBFA2T3, LCP1, SELPLG, CD3Z, LAIR1, WBSCR20C, CD3D, GPR65, ARHGAP15, FLJ10178, NARF, and PUS3, and, optionally, a third gene selected from at least one of PTPRC, MYBBP1A, ICAM3, CD53, FARSLA, CD53, PTPR-CAP, PTPRC, HEM1, GMFG, GMFG, PTPRCAP, PTPRC, CD53, HEM1, PTPRC, HCLS1, PRKCB1, PRKCB1, MYBL1, and FARSLA, or ii) a second microRNA selected from at least one of hsa-mir-025-prec, hsa-mir-007-1-prec, hsa-mir-093-prec-7.1=093-1, Hcd794, and hsa-mir-142-prec,
wherein an increase or decrease in said level of expression of said second gene and, optionally, said third gene or said second microRNA indicates that said cell is sensitive to Dactinomycin.

55. The method of claim 1, wherein said measuring further comprises determining a level of expression of:
i) a second gene selected from at least one of PPIB, ZFP36L2, IFI30, USP7, SRM, SH3BP5, ALDOC, FADS2, GUSB, PSCD1, IQGAP2, STS, MFNG, FLI1, PIM2, INPP4A, LRMP, ICAM2, EVI2A, MAL, BTN3A3, PTPN7, IL10RA, SPI1, TRAF1, ITGB7, ARHGAP6, MAP4K1, CD28, PTP4A3, LTB, C1orf38, WBSCR22, CD8B1, LCP1, FLJ3052, MEF2C, PSCDBP, IL16, SELPLG, MAGEA9, LAIR1, TNFRSF25, EVI2B, IGJ, PDCD4, RASA4, HA-1, PLCL2, RNASE6, WBSCR20C, NUP210, RPL10L, C11orf2, CABC1, ARHGEF3, TAPBPL, CHST12, FKBP11, FLJ35036, MYL1P, TXNDC5, PACAP, TOSO, PNAS-4, IL21R, and TCF4, and, optionally, a third gene selected from at least one of CLTB, BTN3A2, BCL2, SETBP1, ICAM3, BCL2, BCL2, BCL2, CD53, CCND2, CLTB, CLTB, BCL2L11, BTN3A2, CD37, MYCL2, CTSS, LAPTM5, CD53, CORO1A, HEM1, CD53, CORO1A, HEM1, HCLS1, BCL2L11, MYCL1, MYC, and MAN1A1, or
ii) a second microRNA selected from at least one of Hcd257, hsa-mir-148-prec, Hcd512, HPR227, Hcd421, MPR203, hsa-mir-017-prec, hsa-mir-219-2, hsa-mir-328, Hcd783, Hcd181, HPR213, hsa-mir-191-prec, hsa-mir-375, hsa-mir-212-prec, Hcd913, Hcd716, MPR207, HPR206, hsa-mir-016b-chr3, Hcd654, hsa-mir-195-prec, Hcd425, hsa-mir-148a, hsa-mir-142-prec, and hsa-mir-016a-chr13, wherein an increase or decrease in said level of expression of said second gene and, optionally, said third gene or said second microRNA indicates that said cell is sensitive to Tretinoin.

56. The method of claim 1, wherein said measuring further comprises determining a level of expression of a second gene selected from at least one of PDGFRB, KDR, KIT, and FLT3, and, optionally, a third gene selected from at least one of FLT1, FLT4, PDGFRA, and CSF1R,
wherein an increase or decrease in said level of expression of said second gene and, optionally, said third gene indicates that said cell is sensitive to sunitinib.

57. The method of claim 1, wherein said measuring further comprises determining a level of expression of BCL2,
wherein an increase or decrease in said level of expression of said BCL2 indicates that said cell is sensitive to SPC2996.

58. The method of claim 1, wherein said measuring further comprises determining a level of expression of:
i) a second gene selected from at least one of ARHGDIB, ZFP36L2, ITM2A, LGALS9, INPP5D, SATB1, TFDP2, IL2RG, CD48, SELL, ADA, LRMP, RIMS3, LCK, CXorf9, RHOH, ZNFN1A1, LCP2, CD1D, CD2, ZNF91, MAP4K1, CCR7, IGLL1, CD3G, ZNF430, CCR9, CXCR4, KIAA0922, TARP, FYN, SH2D1A, CDIA, LST1, LA1R1, TRB@, SEPT6, CD3D, CD6, AIF1, CD1E, TRIM, GLTSCR2, ARHGAP15, BIN2, SH3TC1, CECR1, BCL11B, GIMAP6, STAG3, GALNT6, MGC5566, PACAP, and LEF1, and, optionally, a third gene selected from at least one of CD27BP, TRIM22, TRA@, C18 orf1, EVL, PRKCH, TRIM41, PSCD2L, CD1C, ADAM11, ABCD2, CD24, CD29, CD37, GNA15, LAPTM5, CORO1A, HEM1, GMFG, GNA15, CD1B, GMFG, CORO1A, HEM1, GNA15, ITGB2, PRKCB1, ATP2A3, and PRKCB1, or ii) a second microRNA selected from at least one of hsa-mir-092-prec-X=092-2, hsa-mir-181b-2, Hcd417, Hcd440_HPR257, hsa-mir-019b-2-prec, hsa-mir-213-prec, hsa-mir-033-prec, hsa-mir-092-prec-13=092-1, hsa-mir-181b-prec, hsa-mir-128b-prec, hsa-mir-526a-2, MPR95, HPR220, hsa-mir-133a-1, hsa-mir-148a, hsa-mir-142-prec, HPR169, hsa-mir-223-prec, hsa-mir-018-prec, hsa-mir-020-prec, and hsa-mir-484, wherein an increase or decrease in said level of expression of said second gene and, optionally, said third gene or said second microRNA indicates that said cell is sensitive to Ifosfamide.

59. The method of claim 1, wherein said measuring further comprises determining a level of expression of:

i) a second gene selected from at least one of MLP, GLUL, SLC9A3R1, ZFP36L2, INSIG1, TBL1X, NDUFAB1, ESP, TRIM14, SRPK2, PMM2, CLDN3, GCH1, IDI1, TTF1, MYB, RASGRP1, HIST1H3H, CBFA2T3, SRRM2, ANAPC5, MBD4, GATA3, HIST1H2BG, RAB14, PIK3R1, MGC50853, ELF1, ZRF1, ZNF394, S100A14, SLC6A14, GALNT6, SPDEF, TPRT, and CALML4, and, optionally, a third gene selected from at least one of EIF4A1, TFF1, TFF1, MYBBP1A, AKAP1, DGKZ, EIF4A1, KIAA0182, SLC19A1, ATP2A3, MYBL1, EIF4EBP2, GIP2, and MANIA1, or ii) a second microRNA selected from at least one of hsa-mir-092-prec-X=092-2, Hcd547, Hcd257, hsa-mir-148-prec, HUMTRS, hsa-mir-033-prec, hsa-mir-092-prec-13=092-1, hsa-mir-375, hsa-mir-095-prec-4, hsa-mir-025-prec, hsa-mir-202-prec, hsa-mir-007-1-prec, hsa-mir-093-prec-7.1=093-1, hsa-mir-106-prec-X, hsa-mir-142-prec, hsa-mir-223-prec, and hsa-mir-018-prec, wherein an increase or decrease in said level of expression of said second gene and, optionally, said third gene or said second microRNA indicates that said cell is sensitive to Tamoxifen.

60. The method of claim 1, wherein said measuring further comprises determining a level of expression of:

i) a second gene selected from at least one of CSDA, F8A1, KYNU, PHF14, SERPINB2, OPHN1, HRMT1L2, TNFRSF1A, PPP4C, CES1, TP53AP1, TM4SF4, RPL5, BC008967, TLK2, COL4A6, PAK3, RECK, LOC51321, MST4, DERP6, SCD4, and FLJ22800, and, optionally, a third gene selected from at least one of STC2, BAX, CDKN1A, DDB2, RGS2, BAX, BAX, RPL13, RPL13, CDKN1A, and GABPB2, or ii) a second microRNA selected from at least one of HUMTRF, HUMTRN, hsa-mir-124a-1-prec1, hsa-mir-150-prec, Hcd923, HPR181, Hcd569, hsa-mir-199a-2-prec, Hcd754, and hsa-mir-4323p, wherein an increase or decrease in said level of expression of said second gene and, optionally, said third gene or said second microRNA indicates that said cell is sensitive to Floxuridine.

61. The method of claim 1, wherein said measuring further comprises determining a level of expression of:

i) a second gene selected from at least one of CSDA, UBE2L6, TAP1, RPS19, SERPINA1, C1QR1, SLA, GPSM3, PSMB9, EDG1, FMNL1, PTPN7, ZNFN1A1, CENTB1, BATE, MAP4K1, PDE4C, SP110, HLA-DRA, IFI16, HLA-DRB1, ARHGEF6, SELPLG, SEC31L2, CD3Z, PRKCQ, SH2DIA, GZMB, TRB@, HLA-DPA1, AIM1, DOCK2, CD3D, IFITM1, ZAP70, PRF1, C1orf24, ARHGAP15, C13orf18, and TM6SF1, and, optionally, a third gene selected from at least one of PTPRC, TRIM22, PSME2, LAT, METAP1, CD53, FARSLA, RPL13, RAC2, RPL13, PTMA, CD53, CORO1A, PTPRCAP, PTPRC, GMFG, ITK, GMFG, PTPRCAP, PTPRC, CD53, CORO1A, ITGB2, PTPRC, HCLS1, and FARSLA, or ii) a second microRNA selected from at least one of HUMTRF, hsa-mir-380-5p, hsa-mir-342, hsa-mir-142-prec, and Hcd200, wherein an increase or decrease in said level of expression of said second gene and, optionally, said third gene or said second microRNA indicates that said cell is sensitive to Irinotecan.

62. The method of claim 1, wherein said measuring further comprises determining a level of expression of:

i) a second gene selected from at least one of STAT1, HSBP1, IF130, RIOK3, TNFSF10, ALOX5AP, ADFP, IRS2, EFEMP2, RIPK2, DKFZp56411922, MT1K, RNASET2, EFHD2, TRIB3, ACSL5, IFIH1, and DNAPTP6, and, optionally, a third gene selected from at least one of IFI27, OPTN, C20orf18, FN1, LOC0051123, FN1, OPTN, and OPTN, or ii) a second microRNA selected from at least one of Hcd289, Hcd939, Hcd330, HPR76, Hcd111, Hcd976, hsa-mir-15a, hsa-mir-001b-1-prec1, hsa-mir-450-1, hsa-mir-200b, Hcd578, and hsa-mir-200a-prec, wherein an increase or decrease in said level of expression of said second gene and, optionally, said third gene or said second microRNA indicates that said cell is sensitive to Satraplatin.

63. The method of claim 1, wherein said level of expression of said gene is determined by detecting the level of mRNA transcribed from said gene.

64. The method of claim 1, wherein said level of expression of said gene is determined by detecting the level of a protein product of said gene.

65. The method of claim 1, wherein said level of expression of said gene is determined by detecting the level of the biological activity of a protein product of said gene.

66. The method of claim 1, wherein an increase in the level of expression of said gene or microRNA indicates increased sensitivity of said cell to said treatment.

67. The method of claim 1, wherein said cell is a cancer cell.

68. The method of claim 1, wherein a decrease in the level of expression of said gene or microRNA indicates increased sensitivity of said cell to said treatment.

69. The method of claim 1, wherein said level of expression of said gene or microRNA is measured using a quantitative reverse transcription-polymerase chain reaction (qRT-PCR).

70. The method of claim 1, wherein said measuring further comprises further determining a level of expression of:

i) a second gene selected from at least one of ACTB, ACTN4, ADA, ADAM9, ADAMTS1, ADD1, AF1Q, A1F1, AKAP1, AKAP13, AKR1C1, AKT1, ALDH2, ALDOC, ALG5, ALMS1, ALOX15B, AMIGO2, AMPD2, AMPD3, ANAPC5, ANP32A, ANP32B, ANXA1, AP1G2, APOBEC3B, APRT, ARHE, ARHGAP15, ARHGAP25, ARHGDIB, ARHGEF6, ARL7, ASAH1, ASPH, ATF3, ATIC, ATP2A2, ATP2A3, ATP5D, ATP5G2, ATP6V1B2, BC008967, BCAT1, BCHE, BCL11B, BDNF, BHLHB2, BIN2, BLMH, BMI1, BNIP3, BRDT, BRRN1, BTN3A3, C11orf2, C14orf139, C15orf25, C18orf10, C1orf24, C1orf29, C1orf38, C1QR1, C22orf18, C6orf32, CACNA1G, CACNB3, CALM1, CALML4, CALU, CAP350, CASP2, CASP6, CASP7, CAST, CBLB, CCNA2, CCNB11P1, CCND3, CCR7, CCR9, CD1A, CD1C, CD1D, CD1E, CD2, CD28, CD3D, CD3E, CD3G, CD3Z, CD44, CD47, CD59, CD6, CD63, CD8A, CD8B1, CD99, CDC10, CDC14B, CDH11, CDH2, CDKL5, CDKN2A, CDW52, CECR1, CENPB, CENTB1, CENTG2, CEP1, CG018, CHRNA3, CHS1, CIAPIN1, CKAP4, CKIP-1, CNP, COL4A1, COL5A2, COL6A1, CORO1C, CRABP1, CRK, CRY1, CSDA, CTBP1, CTSC, CTSL, CUGBP2, CUTC, CXCL1, CXCR4, CXorf9, CYFIP2, CYLD, CYR61, DATF1, DAZAP1, DBN1, DBT, DCTN1, DDX18, DDX5, DGKA, DIAPH1, DKC1, DKFZP434J154, DKFZP564C186, DKFZP564G2022, DKFZp564J157, DKFZP564K0822, DNAJC10, DNAJC7, DNAPTP6, DOCK10, DOCK2, DPAGT1, DPEP2, DPYSL3, DSIPI, DUSP1, DXS9879E, EEF1B2, EFNB2, EHD2, EIF5A, ELK3, ENO2, EPAS1, EPB41L4B, ERCC2, ERG, ERP70, EVER1, EVI2A, EVL, EXT1, EZH2, F2R, FABP5, FAD104, FAM46A, FAU, FCGR2A, FCGR2C, FER1L3, FHL1, FHOD1, FKBP1A, FKBP9, FLJ10350, FLJ10539, FLJ10774, FLJ12270, FLJ13373, FLJ20859, FLJ21159, FLJ22457, FLJ35036, FLJ46603, FLNC, FLOT1, FMNL1, FNBP1, FOLH1, FOXF2, FSCN1, FTL, FYB, FYN, GOS2, G6PD, GALIG, GALNT6, GATA2, GATA3, GFPT1, GIMAP5, GIT2, GJA1, GLRB, GLTSCR2, GLUL, GMDS, GNAQ, GNB2, GNB5, GOT2, GPR65, GPRASP1, GPSM3, GRP58, GSTM2, GTF3A, GTSE1, GZMA, GZMB, H1F0, H1FX, H2AFX, H3F3A, HA-1, HEXB, HIC, HIST1H4C, HK1, HLA-A, HLA-B, HLA-DRA, HMGA1, HMGN2, HMMR, HNRPA1, HNRPD, HNRPM, HOXA9, HRMT1L1, HSA9761, HSPA5, HSU79274, HTATSF1, ICAM1, ICAM2, IER3, IFI16, IFI44, IFITM2, IFITM3, IFRG28, IGFBP2, IGSF4, IL13RA2, IL21R, IL2RG, IL4R, IL6, IL6R, IL6ST, IL8, IMPDH2, INPP5D, INSIG1, IQGAP1, IQGAP2, IRS2, ITGA5, ITM2A, JARID2, JUNB, K-ALPHA-1, KHDRBS1, KIAA0355, KIAA0802, KIAA0877, KIAA0922, KIAA1078, KIAA1128, KIAA1393, KIFC1, LAIR1, LAMB1, LAMB3, LAT, LBR, LCK, LCP1, LCP2, LEF1, LEPRE1, LGALS1, LGALS9, LHFPL2, LNK, LOC54103, LOC55831, LOC81558, LOC94105, LONP, LOX, LOXL2, LPHN2, LPXN, LRMP, LRP12, LRRC5, LRRN3, LST1, LTB, LUM, LY9, LY96, MAGEB2, MAL, MAP1B, MAP1 LC3B, MAP4K1, MAPK1, MARCKS, MAZ, MCAM, MCL1, MCM5, MCM7, MDH2, MDN1, MEF2C, MFNG, MGC17330, MGC21654, MGC2744, MGC4083, MGC8721, MGC8902, MGLL, MLPH, MPHOSPH6, MPP1, MPZL1, MRP63, MRPS2, MT1E, MT1K, MUF1, MVP, MYB, MYL9, MYO1B, NAP1L1, NAP1L2, NARF, NASP, NCOR2, NON, NDUFAB1, NDUFS6, NFKB1A, NID2, NIPA2, NME4, NME7, NNMT, NOL5A, NOL8, NOMO2, NOTCH1, NPC1, NQO1, NRID2, NUDC, NUP210, NUP88, NVL, NXF1, OBFC1, OCRL, OGT, OXA1L, P2RX5, P4HA1, PACAP, PAF53, PAFAH1B3, PALM2-AKAP2, PAX6, PCBP2, PCCB, PFDN5, PFN1, PFN2, PGAM1, PHEMX, PHLDA1, PIM2, PITPNC1, PLAC8, PLAGL1, PLAUR, PLCB1, PLEK2, PLEKHC1, PLOD2, PLSCR1, PNAS-4, PNMA2, POLR2F, PPAP2B, PRF1, PRG1, PRIM1, PRKCH, PRKCQ, PRKD2, PRNP, PRP19, PRPF8, PRSS23, PSCDBP, PSMB9, PSMC3, PSME2, PTGER4, PTGES2, PTOV1, PTP4A3, PTPN7, PTPNS1, PTRF, PURA, PWP1, PYGL, QKI, RAB3GAP, RAB7L1, RAB9P40, RAC2, RAFTLIN, RAG2, RAP1B, RASGRP2, RBPMS, RCN1, RFC3, RFC5, RGC32, RGS3, RHOH, RIMS3, RIOK3, RIPK2, RIS1, RNASE6, RNF144, RPL10, RPL10A, RPL12, RPL13A, RPL17, RPL18, RPL36A, RPLP0, RPLP2, RPS15, RPS19, RPS2, RPS4X, RPS4Y1, RRAS, RRAS2, RRBP1, RRM2, RUNX1, RUNX3, S100A4, SART3, SATB1, SCAP1, SCARB1, SCN3A, SEC31L2, SEC61G, SELL, SELPLG, SEMA4G, SEPT10, SEPT6, SERPINA1, SERPINB1, SERPINB6, SFRS5, SFRS6, SFRS7, SH2D1A, SH3GL3, SH3TC1, SHD1, SHMT2, SIAT1, SKBI, SKP2, SLA, SLC1A4, SLC20A1, SLC25A15, SLC25A5, SLC39A14, SLC39A6, SLC43A3, SLC4A2, SLC7A11, SLC7A6, SMAD3, SMOX, SNRPA, SNRPB, SOD2, SOX4, SP140, SPANXC, SPI1, SRF, SRM, SSA2, SSBP2, SSRP1, SSSCA1, STAGS, STAT1, STAT4, STAT5A, STC1, STC2, STOML2, T3JAM, TACC1, TACC3, TAF5, TAL1, TAP1, TARP, TBCA, TCF12, TCF4, TFDP2, TFPI, TIMM17A, TIMP1, TJP1, TK2, TM4SF1, TM4SF2, TM4SF8, TM6SF1, TMEM2, TMEM22, TMSB10, TMSNB, TNFAIP3, TNFAIP8, TNFRSF10B, TNFRSF1A, TNFRSF7, TNIK, TNPO1, TOB1, TOMM20, TOX, TPK1, TPM2, TRA@, TRA1, TRAM2, TRB@, TRD@, TRIM, TRIM14, TRIM22, TRIM28, TRIP13, TRPV2, TUBGCP3, TUSC3, TXN, TXNDC5, UBASH3A, UBE2A, UBE2L6, UBE2S, UCHL1, UCK2, UCP2, UFD1L, UGDH, ULK2, UMPS, UNG, USP34, USP4, VASP, VAV1, VLDLR, VWF, WASPIP, WBSCR20A, WBSCR20C, WHSC1, WNT5A, ZAP70, ZFP36L1, ZNF32, ZNF335, ZNF593, ZNFN1A1, and ZYX; or ii) a second microRNA selected from at least one of ath-MIR180aNo2, Hcd102 left, Hcd111 left, Hcd115 left, Hcd120 left, Hcd142 right, Hcd145 left, Hcd148_HPR225 left, Hcd181 left, Hcd181 right, Hcd210_HPR205 right, Hcd213_HPR182 left, Hcd230 left, Hcd243 right, Hcd246 right, Hcd248 right, Hcd249 right, Hcd250 left, Hcd255 left, Hcd257 left, Hcd257 right, Hcd263 left, Hcd266 left, Hcd270 right, Hcd279 left, Hcd279 right, Hcd28_HPR39 left, Hcd28_HPR39 right, Hcd282PO right, Hcd289 left, Hcd294 left, Hcd318 right, Hcd323 left, Hcd330 right, Hcd338 left, Hcd340 left, Hcd350 right, Hcd355_HPR190 left, Hcd361 right, Hcd366 left, Hcd373 right, Hcd383 left, Hcd383 right, Hcd384 left, Hcd397 left, Hcd404 left, Hcd412 left, Hcd413 right, Hcd415 right, Hcd417 right, Hcd421 right, Hcd425 left, Hcd438 right, Hcd434 right, Hcd438 left, Hcd440_HPR257 right, Hcd444 right, Hcd447 right, Hcd448 left, Hcd498 right, Hcd503 left, Hcd511 right, Hcd512 left, Hcd514 right, Hcd517 left, Hcd517 right, Hcd530 right, Hcd536_HPR104 right, Hcd542 left, Hcd544 left, Hcd547 left, Hcd559 right, Hcd562 right, Hcd569 right, Hcd570 right, Hcd578 right, Hcd581 right, Hcd586 left, Hcd586 right, Hcd587 right, Hcd605 left, Hcd605 left, Hcd605 right, Hcd608 right, Hcd627 left, Hcd631 left, Hcd631 right, Hcd634 left, Hcd642 right, Hcd649 right, Hcd654 left, Hcd658 right, Hcd669 right, Hcd674 left, Hcd678 right, Hcd683 left, Hcd684 right, Hcd689 right, Hcd690 right, Hcd691 right, Hcd693 right, Hcd697 right, Hcd704 left, Hcd704 left, Hcd712 right, Hcd716 right, Hcd731 left, Hcd738 left, Hcd739 right, Hcd739 right, Hcd749 right, Hcd753 left, Hcd754 left, Hcd755 left, Hcd760 left, Hcd763 right, Hcd768 left, Hcd768 right, Hcd770 left, Hcd773 left, Hcd777 left, Hcd778 right, Hcd781 left, Hcd781 right, Hcd782 left, Hcd783 left, Hcd788 left, Hcd794 right, Hcd796 left, Hcd799 left, Hcd807 right, Hcd812 left, Hcd817 left, Hcd817 right, Hcd829 right, Hcd852 right, Hcd861 right, Hcd863PO right, Hcd866 right, Hcd869 left, Hcd873 left, Hcd886 right, Hcd889 right, Hcd891 right, Hcd892 left, Hcd913 right, Hcd923 left, Hcd923 right, Hcd938 left, Hcd938 right, Hcd939 right, Hcd946 left, Hcd948 right, Hcd960 left, Hcd965 left, Hcd970 left, Hcd975 left, Hcd976 right, Hcd99 right, HPR100 right, HPR129 left, HPR154 left, HPR159 left, HPR163 left, HPR169 right, HPR172 right, HPR181 left, HPR187 left, HPR199 right, HPR206 left, HPR213 right, HPR214 right, HPR220 left, HPR220 right, HPR227 right, HPR232 right, HPR233 right, HPR244 right, HPR262 left, HPR264 right, HPR266 right, HPR271 right, HPR76 right, hsa_mir_490_Hcd20 right, HSHELA01, HSTRNL, HUMTRAB, HUMTRF, HUMTRN, HUMTRS, HUMTRVIA, let-7f-2-prec2, mir-001b-1-prec1, mir-001b-2-prec, mir-007-1-prec, mir-007-2-precNo2, mir-010a-precNo1, mir-015b-precNo2, mir-016a-chr13, mir-016b-chr3, mir-017-precNo1, mir-017-precNo2, mir-018-prec, mir-019a-prec, mir-019b-1-prec, mir-019b-2-prec, mir-020-prec, mir-022-prec, mir-023a-prec, mir-023b-prec, mir-024-2-prec, mir-025-prec, mir-027b-prec, mir-029c-prec, mir-032-precNo2, mir-033b-prec, mir-033-prec, mir-034-precNo1, mir-034-precNo2, mir-092-prec-13=092-1No2, mir-092-prec-X=092-2, mir-093-prec-7.1=093-1, mir-095-prec-4, mir-096-prec-7No1, mir-096-prec-7No2, mir-098-prec-X, mir-099b-prec-19No1, mir-100-1/2-prec, mir-100No1, mir-101-prec-9, mir-102-prec-1, mir-103-2-prec, mir-103-prec-5=103-1, mir-106aNo1, mir-106-prec-X, mir-107No1, mir-107-prec-10, mir-122a-prec, mir-123-precNo1, mir-123-precNo2, mir-124a-1-prec1, mir-124a-2-prec, mir-124a-3-prec, mir-125b-1, mir-125b-2-precNo2, mir-127-prec, mir-128b-precNo1, mir-128b-precNo2, mir-133a-1, mir-135-2-prec, mir-136-precNo2, mir-138-1-prec, mir-140No2, mir-143-prec, mir-144-precNo2, mir-145-prec, mir-146bNo1, mir-146-prec, mir-147-prec, mir-148aNo1, mir-148-prec, mir-149-prec, mir-150-prec, mir-153-1-prec1, mir-154-prec1No1, mir-155-prec, mir-15aNo1, mir-16-1No1, mir-16-2No1, mir-181a-precNo1, mir-181b-1No1, mir-181b-2No1, mir-181b-precNo1, mir-181b-precNo2, mir-181c-precNo1, mir-181dNo1, mir-188-prec, mir-18bNo2, mir-191-prec, mir-192No2, mir-193bNo2, mir-194-2No1, mir-195-prec, mir-196-2-precNo2, mir-197-prec, mir-198-prec, mir-199a-1-prec, mir-199a-2-prec, mir-199b-precNo1, mir-200a-prec, mir-200bNo1, mir-200bNo2, mir-202*, mir-202-prec, mir-204-precNo2, mir-205-prec, mir-208-prec, mir-20bNo1, mir-212-precNo1, mir-212-precNo2, mir-213-precNo1, mir-214-prec, mir-215-precNo2, mir-216-precNo1, mir-219-2No1, mir-219-prec, mir-223-prec, mir-29b-1No1, mir-29b-2=102prec7.1=7.2, mir-321No1, mir-321No2, mir-324No1, mir-324No2, mir-328No1, mir-342No1, mir-361No1, mir-367No1, mir-370No1, mir-371No1, miR-373*No1, mir-375, mir-376aNo1, mir-379No1, mir-380-5p, mir-382, mir-384, mir-409-3p, mir-423No1, mir-424No2, mir-429No1, mir-429No2, mir-4323p, mir-4325p, mir-449No1, mir-450-1, mir-450-2No1, mir-483No1, mir-484, mir-487No1, mir-495No1, mir-499No2, mir-501No2, mir-503No1, mir-509No1, mir-514-1No2, mir-515-15p, mir-515-23p, mir-516-33P, mir-516-43p, mir-518e/526c, mir-519a-1/52, mir-519a-2No2, mir-519b, mir-519c152, mir-520c/52, mir-526a-2No1, mir-526a-2No2, MPR103 right, MPR121 left, MPR121 left, MPR130 left, MPR130 right, MPR133 right, MPR141 left, MPR151 left, MPR156 left, MPR162 left, MPR174 left, MPR174 right, MPR185 right, MPR197 right, MPR203 left, MPR207 right, MPR215 left, MPR216 left, MPR224 left, MPR224 right, MPR228 left, MPR234 right, MPR237 left, MPR243 left, MPR244 right, MPR249 left, MPR254 right, MPR74 left, MPR88 right, and MPR95 left, wherein an increase or decrease in said level of expression of said second gene or said second microRNA indicates said cell is sensitive to said treatment.

71. The method of claim 1, wherein said at least one single-stranded oligonucleotide is substantially complementary to or substantially identical to at least 20 consecutive nucleotides of said first microRNA selected from mir-142-prec or said product of said first gene selected from ZNFN1A1.

72. The method of claim 71, wherein said at least one single-stranded oligonucleotide is substantially complementary to or substantially identical to at least 25 consecutive nucleotides of said first microRNA selected from mir-142-prec or said product of said first gene selected from ZNFN1A1.

73. The method of claim 1, wherein said at least one single-stranded oligonucleotide is substantially complementary to or substantially identical to at least 15 consecutive nucleotides of SEQ ID NO: 2300.

74. The method of claim 1, wherein said device further comprises at least one single-stranded oligonucleotide that is substantially complementary to or substantially identical to at least 15 consecutive nucleotides of SEQ ID NO: 1, 2, 4, 6, 7, 10, 11, 16, or 24.

75. A method for determining the development of resistance of cells in a patient to a treatment to which said cells have previously been sensitive, said method comprising contacting a sample comprising one or more nucleic acid molecules from said patient to a device comprising single-stranded oligonucleotides, wherein at least one of said oligonucleotides comprises a sequence that is substantially complementary to or substantially identical to at least 15 consecutive nucleotides of a first microRNA selected from mir-142-prec or a product of a first gene selected from ZNFN1A1, and measuring hybridization between said nucleic acid molecules from said patient and said single-stranded oligonucleotides of said device to determine a level of expression of said first microRNA or said first gene in at least one of said cells, wherein a decrease in said level of expression of said first microRNA or said first gene in at least one of said cells, relative to the level of expression of said first microRNA or said first gene in a control cell sensitive to said treatment, indicates resistance or a propensity to develop resistance to the treatment by said patient and, optionally, wherein said method further comprises measuring a level of expression of at least one second gene in at least one of said cells selected from:

ACTB, ACTN4, ADA, ADAM9, ADAMTS1, ADD1, AF1Q, AIF1, AKAP1, AKAP13, AKR1C1, AKT1, ALDH2, ALDOC, ALG5, ALMS1, ALOX15B, AMIGO2, AMPD2, AMPD3, ANAPC5, ANP32A, ANP32B, ANXA1, APIG2, APOBEC3B, APRT, ARHE, ARHGAP15, ARHGAP25, ARHGD1B, ARHGEF6, ARL7, ASAH1, ASPH, ATF3, ATIC, ATP2A2, ATP2A3, ATP5D, ATP5G2, ATP6V1B2, BC008967, BCAT1, BCHE, BCL11B, BDNF, BHLHB2, BIN2, BLMH, BMI1, BNIP3, BRDT, BRRN1, BTN3A3, C11orf2, C14orf139, C15orf25, C18orf10, C1orf24, C1orf29, C1orf38, C1QR1, C22orf18, C6orf32, CACNA1G, CACNB3, CALM1, CALML4, CALU, CAP350, CASP2, CASP6, CASP7, CAST, CBLB, CCNA2, CCNB1IP1, CCND3, CCR7, CCR9, CDIA, CD1C, CD1D, CD1E, CD2, CD28, CD3D, CD3E, CD3G, CD3Z, CD44, CD47, CD59, CD6, CD63, CD8A, CD8B1, CD99, CDC10, CDC14B, CDH11, CDH2, CDKL5, CDKN2A, CDW52, CECR1, CENPB, CENTB1, CENTG2, CEP1, CG018, CHRNA3, CHS1, CIAPIN1, CKAP4, CKIP-1, CNP, COL4A1, COL5A2, COL6A1, CORO1C, CRABP1, CRK, CRY1, CSDA, CTBP1, CTSC, CTSL, CUGBP2, CUTC, CXCL1, CXCR4, CXorf9, CYFIP2, CYLD, CYR61, DATF1, DAZAP1, DBN1, DBT, DCTN1, DDX18, DDX5, DGKA, DIAPH1, DKC1, DKFZP434J154, DKFZP564C186, DKFZP564G2022, DKFZp564J157, DKFZP564K0822, DNAJC10, DNAJC7, DNAPTP6, DOCK10, DOCK2, DPAGT1, DPEP2, DPYSL3, DSIPI, DUSP1, DXS9879E, EEF1B2, EFNB2, EHD2, EIF5A, ELK3, ENO2, EPAS1, EPB41L4B, ERCC2, ERG, ERP70, EVER1, EVI2A, EVL, EXT1, EZH2, F2R, FABP5, FAD104, FAM46A, FAU, FCGR2A, FCGR2C, FER1L3, FHL1, FHOD1, FKBPIA, FKBP9, FLJ10350, FLJ10539, FLJ10774, FLJ12270, FLJ13373, FLJ20859, FLJ21159, FLJ22457, FLJ35036, FLJ46603, FLNC, FLOT1, FMNL1, FNBP1, FOLH1, FOXF2, FSCN1, FTL, FYB, FYN, GOS2, G6PD, GALIG, GALNT6, GATA2, GATA3, GFPT1, GIMAP5, GIT2, GJA1, GLRB, GLTSCR2, GLUL, GMDS, GNAQ, GNB2, GNB5, GOT2, GPR65, GPRASP1, GPSM3, GRP58, GSTM2, GTF3A, GTSE1, GZMA, GZMB, H1F0, H1FX, H2AFX, H3F3A, HA-1, HEXB, HIC, HIST1H4C, HK1, HLA-A, HLA-B, HLA-DRA, HMGA1, HMGN2, HMMR, HNRPA1, HNRPD, HNRPM, HOXA9, HRMTIL1, HSA9761, HSPA5, HSU79274, HTATSF1, ICAM1, ICAM2, IER3, IFI16, IFI44, IFITM2, IFITM3, IFRG28, IGFBP2, IGSF4, IL13RA2, IL21R, IL2RG, IL4R, IL6, IL6R, IL6ST, IL8, IMPDH2, INPP5D, INSIG1, IQGAP1, IQGAP2, IRS2, ITGA5, ITM2A, JARID2, JUNB, K-ALPHA-1, KHDRBS1, KIAA0355, KIAA0802, KIAA0877, KIAA0922, KIAA1078, KIAA1128, KIAA1393, KIFC1, LA1R1, LAMB1, LAMB3, LAT, LBR, LCK, LCP1, LCP2, LEF1, LEPRE1, LGALS1, LGALS9, LHFPL2, LNK, LOC54103, LOC55831, LOC81558, LOC94105, LONP, LOX, LOXL2, LPHN2, LPXN, LRMP, LRP12, LRRC5, LRRN3, LST1, LTB, LUM, LY9, LY96, MAGEB2, MAL, MAP1B, MAP1LC3B, MAP4K1, MAPK1, MARCKS, MAZ, MCAM, MCL1, MCM5, MCM7, MDH2, MDN1, MEF2C, MFNG, MGC17330, MGC21654, MGC2744, MGC4083, MGC8721, MGC8902, MGLL, MLPH, MPHOSPH6, MPP1, MPZL1, MRP63, MRPS2, MT1E, MT1K, MUF1, MVP, MYB, MYL9, MYO1B, NAPIL1, NAP1L2, NARF, NASP, NCOR2, NDN, NDUFAB1, NDUFS6, NFKB1A, NID2, NIPA2, NME4, NME7, NNMT, NOL5A, NOL8, NOMO2, NOTCH1, NPC1, NQO1, NRID2, NUDC, NUP210, NUP88, NVL, NXF1, OBFC1, OCRL, OGT, OXA1L, P2RX5, P4HA1, PACAP, PAF53, PAFAH1B3, PALM2-AKAP2, PAX6, PCBP2, PCCB, PFDN5, PFN1, PFN2, PGAM1, PHEMX, PHLDA1, PIM2, PITPNC1, PLACE, PLAGL1, PLAUR, PLCB1, PLEK2, PLEKHC1, PLOD2, PLSCR1, PNAS-4, PNMA2, POLR2F, PPAP2B, PRF1, PRG1, PRIM1, PRKCH, PRKCQ, PRKD2, PRNP, PRP19, PRPF8, PRSS23, PSCDBP, PSMB9, PSMC3, PSME2, PTGER4, PTGES2, PTOV1, PTP4A3, PTPN7, PTPNS1, PTRF, PURA, PWP1, PYGL, QKI, RAB3GAP, RAB7L1, RAB9P40, RAC2, RAFTLIN, RAG2, RAP1B, RASGRP2, RBPMS, RCN1, RFC3, RFC5, RGC32, RGS3, RHOH, RIMS3, RIOK3, RIPK2, RIS1, RNASE6, RNF144, RPL10, RPL10A, RPL12, RPL13A, RPL17, RPL18, RPL36A, RPLP0, RPLP2, RPS15, RPS19, RPS2, RPS4X, RPS4Y1, RRAS, RRAS2, RRBP1, RRM2, RUNX1, RUNX3, S100A4, SART3, SATB1, SCAP1, SCARB1, SCN3A, SEC31L2, SEC61G, SELL, SELPLG, SEMA4G, SEPT10, SEPT6, SERPINA1, SERPINB1, SERPINB6, SFRS5, SFRS6, SFRS7, SH2DIA, SH3GL3, SH3TC1, SHD1, SHMT2, SIAT1, SKB1, SKP2, SLA, SLC1A4, SLC20A1, SLC25A15, SLC25A5, SLC39A14, SLC39A6, SLC43A3, SLC4A2, SLC7A11, SLC7A6, SMAD3, SMOX, SNRPA, SNRPB, SOD2, SOX4, SP140, SPANXC, SPI1, SRF, SRM, SSA2, SSBP2, SSRP1, SSSCA1, STAG3, STAT1, STAT4, STAT5A, STC1, STC2, STOML2, T3JAM, TACC1, TACC3, TAF5, TAL1, TAP1, TARP, TBCA, TCF12, TCF4, TFDP2, TFPI, TIMM17A, TIMP1, TJP1, TK2, TM4SF1, TM4SF2, TM4SF8, TM6SF1, TMEM2, TMEM22, TMSB10, TMSNB, TNFAIP3, TNFAIP8, TNFRSF10B, TNFRSF1A, TNFRSF7, TNIK, TNPO1, TOB1, TOMM20, TOX, TPK1, TPM2, TRA@, TRA1, TRAM2, TRB@, TRD@, TRIM, TRIM14, TRIM22, TRIM28, TRIP13, TRPV2, TUBGCP3, TUSC3, TXN, TXNDC5, UBASH3A, UBE2A, UBE2L6, UBE2S, UCHL1, UCK2, UCP2, UFD1L, UGDH, ULK2, UMPS, UNG, USP34, USP4, VASP, VAV1, VLDLR, VWF, WASPIP, WBSCR20A, WBSCR20C, WHSC1, WNT5A, ZAP70, ZFP36L1, ZNF32, ZNF335, ZNF593, ZNFN1A1, and ZYX; or at least one second microRNA in at least one of said cells selected from:

ath-MIR180aNo2, Hcd102 left, Hcd111 left, Hcd115 left, Hcd120 left, Hcd1 42 right, Hcd145 left, Hcd148_HPR225 left, Hcd181 left, Hcd181 right, Hcd210_HPR205 right, Hcd213_HPR182 left, Hcd230 left, Hcd243 right, Hcd246 right, Hcd248 right, Hcd249 right, Hcd250 left, Hcd255 left, Hcd257 left, Hcd257 right, Hcd263 left, Hcd266 left, Hcd270 right, Hcd279 left, Hcd279 right, Hcd28_HPR39 left, Hcd28_HPR39 right, Hcd282PO right, Hcd289 left, Hcd294 left, Hcd318 right, Hcd323 left, Hcd330 right, Hcd338 left, Hcd340 left, Hcd350 right, Hcd355_HPR190 left, Hcd361 right, Hcd366 left, Hcd373 right, Hcd383 left, Hcd383 right, Hcd384 left, Hcd397 left, Hcd404 left, Hcd412 left, Hcd413 right, Hcd415 right, Hcd417 right, Hcd421 right, Hcd425 left, Hcd438 right, Hcd434 right, Hcd438 left, Hcd440_HPR257 right, Hcd444 right, Hcd447 right, Hcd448 left, Hcd498 right, Hcd503 left, Hcd511 right, Hcd512 left, Hcd514 right, Hcd517 left, Hcd517 right, Hcd530 right, Hcd536_HPR104 right, Hcd542 left, Hcd544 left, Hcd547 left, Hcd559 right, Hcd562 right, Hcd569 right, Hcd570 right, Hcd578 right, Hcd581 right, Hcd586 left, Hcd586 right, Hcd587 right, Hcd605 left, Hcd605 left, Hcd605 right, Hcd608 right, Hcd627 left, Hcd631 left, Hcd631 right, Hcd634 left, Hcd642 right, Hcd649 right, Hcd654 left, Hcd658 right, Hcd669 right, Hcd674 left, Hcd678 right, Hcd683 left, Hcd684 right, Hcd689 right, Hcd690 right, Hcd691 right, Hcd693 right, Hcd697 right, Hcd704 left, Hcd704 left, Hcd712 left, Hcd716 right, Hcd731 left, Hcd738 left, Hcd739 right, Hcd739 left, Hcd749 right, Hcd753 left, Hcd754 left, Hcd755 left, Hcd760 left, Hcd763 right, Hcd768 left, Hcd768 right, Hcd770 left, Hcd773 left, Hcd777 left, Hcd778 right, Hcd781 left, Hcd781 right, Hcd782 left, Hcd783 left, Hcd788 left, Hcd794 right, Hcd796 left, Hcd799 left, Hcd807 right, Hcd812 left, Hcd817 left, Hcd817 right, Hcd829 right, Hcd852 right, Hcd861 right, Hcd863PO right, Hcd866 right, Hcd869 left, Hcd873 left, Hcd886 right, Hcd889 right, Hcd891 right, Hcd892 left, Hcd913 right, Hcd923 left, Hcd923 right, Hcd938 left, Hcd938 right, Hcd939 right, Hcd946 left, Hcd948 right, Hcd960 left, Hcd965 left, Hcd970 left, Hcd975 left, Hcd976 right, Hcd99 right, HPR100 right, HPR129 left, HPR154 left, HPR159 left, HPR163 left, HPR169 right, HPR172 right, HPR181 left, HPR187 left, HPR199 right, HPR206 left, HPR213 right, HPR214 right, HPR220 left, HPR220 right, HPR227 right, HPR232 right, HPR233 right, HPR244 right, HPR262 left, HPR264 right, HPR266 right, HPR271 right, HPR76 right, hsa_mir_490_Hcd20 right, HSHELA01, HSTRNL, HUMTRAB, HUMTRF, HUMTRN, HUMTRS, HUMTRVIA, let-7f-2-prec2, mir-001b-1-prec1, mir-001b-2-prec, mir-007-1-prec, mir-007-2-precNo2, mir-010a-precNo1, mir-015b-precNo2, mir-016a-chr13, mir-016b-chr3, mir-017-precNo1, mir-017-precNo2, mir-018-prec, mir-019a-prec, mir-019b-1-prec, mir-019b-2-prec, mir-020-prec, mir-022-prec, mir-023a-prec, mir-023b-prec, mir-024-2-prec, mir-025-prec, mir-027b-prec, mir-029c-prec, mir-032-precNo2, mir-033b-prec, mir-033-prec, mir-034-precNo1, mir-034-precNo2, mir-092-prec-13=092-1No2, mir-092-prec-X=092-2, mir-093-prec-7.1=093-1, mir-095-prec-4, mir-096-prec-7No1, mir-096-prec-7No2, mir-098-prec-X, mir-099b-prec-19No1, mir-100-1/2-prec, mir-100No1, mir-101-prec-9, mir-102-prec-1, mir-103-2-prec, mir-103-prec-5=103-1, mir-106aNo1, mir-106-prec-X, mir-107No1, mir-107-prec-10, mir-122a-prec, mir-123-precNo1, mir-123-precNo2, mir-124a-1-prec1, mir-124a-2-prec, mir-124a-3-prec, mir-125b-1, mir-125b-2-precNo2, mir-127-prec, mir-128b-precNo1, mir-128b-precNo2, mir-133a-1, mir-135-2-prec, mir-136-precNo2, mir-138-1-prec, mir-140No2, mir-143-prec, mir-144-precNo2, mir-145-prec, mir-146bNo1, mir-146-prec, mir-147-prec, mir-148aNo1, mir-148-prec, mir-149-prec, mir-150-prec, mir-153-1-prec1, mir-154-prec1No1, mir-155-prec, mir-15aNo1, mir-16-1No1, mir-16-2No1, mir-181a-precNo1, mir-181b-1No1, mir-181b-2No1, mir-181b-precNo1, mir-181b-precNo2, mir-181c-precNo1, mir-181dNo1, mir-188-prec, mir-18bNo2, mir-191-prec, mir-192No2, mir-193bNo2, mir-194-2No1, mir-195-prec, mir-196-2-precNo2, mir-197-prec, mir-198-prec, mir-199a-1-prec, mir-199a-2-prec, mir-199b-precNo1, mir-200a-prec, mir-200bNo1, mir-200bNo2, mir-202*, mir-202-prec, mir-204-precNo2, mir-205-prec, mir-208-prec, mir-20bNo1, mir-212-precNo1, mir-212-precNo2, mir-213-precNo1, mir-214-prec, mir-215-precNo2, mir-216-precNo1, mir-219-2No1, mir-219-prec, mir-223-prec, mir-29b-1No1, mir-29b-2=102prec7.1=7.2, mir-321No1, mir-321No2, mir-324No1, mir-324No2, mir-328No1, mir-342No1, mir-361No1, mir-367No1, mir-370No1, mir-371No1, miR-373*No1, mir-375, mir-376aNo1, mir-379No1, mir-380-5p, mir-382, mir-384, mir-409-3p, mir-423No1, mir-424No2, mir-429No1, mir-429No2, mir-4323p, mir-4325p, mir-449No1, mir-450-1, mir-450-2No1, mir-483No1, mir-484, mir-487No1, mir-495No1, mir-499No2, mir-501No1, mir-503No1, mir-509No1, mir-514-1No2, mir-515-15p, mir-515-23p, mir-516-33p, mir-516-43p, mir-518e/526c, mir-519a-1/52, mir-519a-2No2, mir-519b, mir-519c/52, mir-520c/52, mir-526a-2No1, mir-526a-2No2, MPR103 right, MPR121 left, MPR121 left, MPR130 left, MPR130 right, MPR133 right, MPR141 left, MPR151 left, MPR156 left, MPR162 left, MPR174 left, MPR174 right, MPR185 right, MPR197 right, MPR203 left, MPR207 right, MPR215 left, MPR216 left, MPR224 left, MPR224 right, MPR228 left, MPR234 right, MPR237 left, MPR243 left, MPR244 right, MPR249 left, MPR254 right, MPR74 left, MPR88 right, and MPR95 left, wherein a decrease in the level of expression of said second gene or said second microRNA in at least one of said cells, relative to the level of expression of said second gene or said second microRNA in a control cell sensitive to said treatment, indicates resistance or a propensity to develop resistance to the treatment by said patient.

76. A method for determining the development of resistance of cells in a patient to a treatment to which said cells have previously been sensitive, said method comprising contacting a sample comprising one or more nucleic acid molecules from said patient to a device comprising single-stranded oligonucleotides, wherein at least one of said oligonucleotides comprises a sequence that is substantially complementary to or substantially identical to at least 15 consecutive nucleotides of a first microRNA selected from mir-142-prec or a product of a first gene selected from ZNFN1A1, and measuring hybridization between said nucleic acid molecules from said patient and said single-stranded oligonucleotides of said device to determine a level of expression of said first microRNA or said first gene in at least one of said cells, wherein an increase in said level of expression of said first microRNA or said first gene in at least one of said cells, relative to the level of expression of said first microRNA or said first gene in a control cell sensitive to said treatment, indicates resistance or a propensity to develop resistance to the treatment by said patient and, optionally, wherein said method further comprises measuring a level of expression of at least one second gene in at least one of said cell selected from:

ACTB, ACTN4, ADA, ADAM9, ADAMTS1, ADD1, AF1Q, A1F1, AKAP1, AKAP13, AKR1C1, AKT1, ALDH2, ALDOC, ALG5, ALMS1, ALOX15B, AMIGO2, AMPD2, AMPD3, ANAPC5, ANP32A, ANP32B, ANXA1, AP1G2, APOBEC3B, APRT, ARHE, ARHGAP15, ARHGAP25, ARHGDIB, ARHGEF6, ARL7, ASAH1, ASPH, ATF3, ATIC, ATP2A2, ATP2A3, ATP5D, ATP5G2, ATP6V1B2, BC008967, BCAT1, BCHE, BCL11B, BDNF, BHLHB2, BIN2, BLMH, BMI1, BNIP3, BRDT, BRRN1, BTN3A3, C11orf2, C14orf139, C15 orf25, C18orf10, C1orf24, C1orf29, C1orf38, C1QR1, C22orf18, C6orf32, CACNA1G, CACNB3, CALM1, CALML4, CALU, CAP350, CASP2, CASP6, CASP7, CAST, CBLB, CCNA2, CCNB1IP1, CCND3, CCR7, CCR9, CD1A, CD1C, CD1D, CD1E, CD2, CD28, CD3D, CD3E, CD3G, CD3Z, CD44, CD47, CD59, CD6, CD63, CD8A, CD8B1, CD99, CDC10, CDCl$_4$B, CDH11, CDH2, CDKL5, CDKN2A, CDW52, CECR1, CENPB, CENTB1, CENTG2, CEP1, CG018, CHRNA3, CHS1, CIAPIN1, CKAP4, CKIP-1, CNP, COL4A1, COL5A2, COL6A1, CORO1C, CRABP1, CRK, CRY1, CSDA, CTBP1, CTSC, CTSL, CUGBP2, CUTC, CXCL1, CXCR4, CXorf9, CYFIP2, CYLD, CYR61, DATF1, DAZAP1, DBN1, DBT, DCTN1, DDX18, DDX5, DGKA, DIAPH1, DKC1, DKFZP434J154, DKFZP564C186, DKFZP564G2022, DKFZp564J157, DKFZP564K0822, DNAJC10, DNAJC7, DNAPTP6, DOCK10, DOCK2, DPAGT1, DPEP2, DPYSL3, DSIPI, DUSP1, DXS9879E, EEFIB2, EFNB2, EHD2, EIF5A, ELK3, ENO2, EPAS1, EPB41L4B, ERCC1, ERG, ERP70, EVER1, EVI2A, EVL, EXT1, EZH2, F2R, FABP5, FAD104, FAM46A, FAU, FCGR2A, FCGR2C, FER1L3, FHL1, FHOD1, FKBP1A, FKBP9, FLJ10350, FLJ10539, FLJ10774, FLJ12270, FLJ13373, FLJ20859, FLJ21159, FLJ22457, FLJ35036, FLJ46603, FLNC, FLOT1, FMNL1, FNBP1, FOLH1, FOXF2, FSCN1, FTL, FYB, FYN, GOS2, G6PD, GALIG, GALNT6, GATA2, GATA3, GFPT1, GIMAP5, GIT2, GJA1, GLRB, GLTSCR2, GLUL, GMDS, GNAQ, GNB2, GNB5, GOT2, GPR65, GPRASP1, GPSM3, GRP58, GSTM2, GTF3A, GTSE1, GZMA, GZMB, H1F0, H1FX, H2AFX, H3F3A, HA-1, HEXB, HIC, HIST1H4C, HK1, HLA-A, HLA-B, HLA-DRA, HMGA1, HMGN2, HMMR, HNRPA1, HNRPD, HNRPM, HOXA9, HRMT1L1, HSA9761, HSPA5, HSU79274, HTATSF1, ICAM1, ICAM2, IER3, IFI16, IFI44, IFITM2, IFITM3, IFRG28, IGFBP2, IGSF4, IL13RA2, IL21R, IL2RG, IL4R, IL6, IL6R, LOST, IL8, IMPDH2, INPP5D, INSIG1, IQGAP1, IQGAP2, IRS2, ITGA5; ITM2A, JAR102, JUNB, K-ALPHA-1, KHDRBS1, KIAA0355, KIAA0802, KIAA0877, KIAA0922, KIAA1078, KIAA1128, KIAA1393, KIFC1, LA1R1, LAMB1, LAMB5, LAT, LBR, LCK, LCP1, LCP2, LEF1, LEPRE1, LGALS1, LGALS9, LHFPL2, LNK, LOC54103, LOC55831, LOC81558, LOC94105, LONP, LOX, LOXL2, LPHN2, LPXN, LRMP, LRP12, LRRC5, LRRN3, LST1, LTB, LUM, LY9, LY96, MAGEB2, MAL, MAP1B, MAP1LC3B, MAP4K1, MAPK1, MARCKS, MAZ, MCAM, MCL1, MCM5, MCM7, MDH2, MDN1, MEF2C, MFNG, MGC17330, MGC21654, MGC2744, MGC4083, MGC8721, MGC8902, MGLL, MLPH, MPHOSPH6, MPP1, MPZL1, MRP63, MRPS2, MT1E, MT1K, MUF1, MVP, MYB, MYL9, MYO1B, NAP1L1, NAP1L2, NARF, NASP, NCOR2, NDN, NDUFAB1, NDUFS6, NFKB1A, NID2, NIPA2, NME4, NME7, NNMT, NOL5A, NOL8, NOMO2, NOTCH1, NPC1, NQO1, NRID2, NUDC, NUP210, NUP88, NVL, NXF1, OBFC1, OCRL, OGT, OXA1 L, P2RX5, P4HA1, PACAP, PAF53, PAFAH1B3, PALM2-AKAP2, PAX6, PCBP2, PCCB, PFDN5, PFN1, PFN2, PGAM1, PHEMX, PHLDA1, PIM2, PITPNC1, PLAC8, PLAGL1, PLAUR, PLCB1, PLEK2, PLEKHC1, PLOD2, PLSCR1, PNAS-4, PNMA2, POLR2F, PPAP2B, PRF1, PRG1, PRIM1, PRKCH, PRKCQ, PRKD2, PRNP, PRP19, PRPF8, PRSS23, PSCDBP, PSMB9, PSMC3, PSME2, PTGER4, PTGES2, PTOV1, PTP4A3, PTPN7, PTPNS1, PTRF, PURA, PWP1, PYGL, QKI, RAB3GAP, RAB7L1, RAB9P40, RAC2, RAFTLIN, RAG2, RAP1B, RASGRP2, RBPMS, RCN1, RFC3, RFC5, RGC32, RGS3, RHOH, RIMS3, RIOK3, RIPK2, RIS1, RNASE6, RNF144, RPL10, RPL10A, RPL12, RPL13A, RPL17, RPL18, RPL36A, RPLP0, RPLP2, RPS15, RPS19, RPS2, RPS4X, RPS4Y1, RRAS, RRAS2, RRBP1, RRM2, RUNX1, RUNX3, S100A4, SART3, SATB1, SCAP1, SCARB1, SCN3A, SEC31L2, SEC61G, SELL, SELPLG, SEMA4G, SEPT10, SEPT6, SERPINA1, SERPINB1, SERPINB6, SFRS5, SFRS6, SFRS7, SH2DIA, SH3GL3, SH3TC1, SHD1, SHMT2, SIAT1, SKB1, SKP2, SLA, SLC1A4, SLC20A1, SLC25A15, SLC25A5, SLC39A14, SLC39A6, SLC43A3, SLC4A2, SLC7A11, SLC7A6, SMAD3, SMOX, SNRPA, SNRPB, SOD2, SOX4, SP140, SPANXC, SPI1, SRF, SRM, SSA2, SSBP2, SSRP1, SSSCA1, STAG3, STAT1, STAT4, STAT5A, STC1, STC2, STOML2, T3JAM, TACC1, TACC3, TAF5, TAL1, TAP1, TARP, TBCA, TCF12, TCF4, TFDP2, TFPI, TIMM17A, TIMP1, TJP1, TK2, TM4SF1, TM4SF2, TM4SF8, TM6SF1, TMEM2, TMEM22, TMSB10, TMSNB, TNFAIP3, TNFAIP8, TNFRSF10B, TNFRSF1A, TNFRSF7, TNIK, TNPO1, TOB1, TOMM20, TOX, TPK1, TPM2, TRA@, TRA1, TRAM2, TRB@, TRD@, TRIM, TRIM14, TRIM22, TRIM28, TRIP13, TRPV2, TUBGCP3, TUSC3, TXN, TXNDC5, UBASH3A, UBE2A, UBE2L6, UBE2S, UCHL1, UCK2, UCP2, UFD1L, UGDH, ULK2, UMPS, UNG, USP34, USP4, VASP, VAV1, VLDLR, VWF, WASPIP, WBSCR20A, WBSCR20C, WHSC1, WNT5A, ZAP70, ZFP36L1, ZNF32, ZNF335, ZNF593, ZNFN1A1, and ZYX; or at least one second microRNA in at least one of said cells selected from:

ath-MIR180aNo2, Hcd102 left, Hcd111 left, Hcd115 left, Hcd120 left, Hcd142 right, Hcd145 left, Hcd148_HPR225 left, Hcd181 left, Hcd181 right, Hcd210_HPR205 right, Hcd213_HPR182 left, Hcd230 left, Hcd243 right, Hcd246 right, Hcd248 right, Hcd249 right, Hcd250 left, Hcd255 left, Hcd257 left, Hcd257 right, Hcd263 left, Hcd266 left, Hcd270 right, Hcd279 left, Hcd279 right, Hcd28_HPR39 left, Hcd28_HPR39 right, Hcd282PO right, Hcd289 left, Hcd294 left, Hcd318 right, Hcd323 left, Hcd330 right, Hcd338 left, Hcd340 left, Hcd350 right, Hcd355_HPR190 left, Hcd361 right, Hcd366 left, Hcd373 right, Hcd383 left, Hcd383 right, Hcd384 left, Hcd397 left, Hcd404 left, Hcd412 left, Hcd413 right, Hcd415 right, Hcd417 right, Hcd421 right, Hcd425 left, Hcd438 right, Hcd434 right, Hcd438 left, Hcd440_HPR257 right, Hcd444 right, Hcd447 right, Hcd448 left, Hcd498 right, Hcd503 left, Hcd511 right, Hcd512 left, Hcd514 right, Hcd517 left, Hcd517 right, Hcd530 right, Hcd536_HPR104 right, Hcd542 left, Hcd544 left, Hcd547 left, Hcd559 right, Hcd562 right, Hcd569 right, Hcd570 right, Hcd578 right, Hcd581 right, Hcd586 left, Hcd586 right, Hcd587 right, Hcd605 left, Hcd605 left, Hcd605 right, Hcd608 right, Hcd627 left, Hcd631 left, Hcd631 right, Hcd634 left, Hcd642 right, Hcd649 right, Hcd654 left, Hcd658 right, Hcd669 right, Hcd674 left, Hcd678 right, Hcd683 left, Hcd684 right, Hcd689 right, Hcd690 right, Hcd691 right, Hcd693 right, Hcd697 right, Hcd704 left, Hcd704 left, Hcd712 right, Hcd716 right, Hcd731 left, Hcd738 left, Hcd739 right, Hcd739 right, Hcd749 right, Hcd753 left, Hcd754 left, Hcd755 left, Hcd760 left, Hcd763 right, Hcd768 left, Hcd768 right, Hcd770 left, Hcd773 left, Hcd777 left, Hcd778 right, Hcd781 left, Hcd781 right, Hcd782 left, Hcd783 left, Hcd788 left, Hcd794 right, Hcd796 left, Hcd799 left, Hcd807 right, Hcd812 left, Hcd817 left, Hcd817 right, Hcd829 right, Hcd852 right, Hcd861 right, Hcd863PO right, Hcd866 right, Hcd869 left, Hcd873 left, Hcd886 right, Hcd889 right, Hcd891 right, Hcd892 left, Hcd913 right, Hcd923 left, Hcd923 right, Hcd938 left, Hcd938 right, Hcd939 right, Hcd946 left, Hcd948 right, Hcd960 left, Hcd965 left, Hcd970 left, Hcd975 left, Hcd976 right, Hcd99 right, HPR100 right, HPR129 left, HPR154 left, HPR159 left, HPR163 left, HPR169 right, HPR172 right, HPR181 left, HPR187 left, HPR199 right, HPR206 left, HPR213 right, HPR214 right, HPR220 left, HPR220 right, HPR227 right, HPR232 right, HPR233 right, HPR244 right, HPR262 left, HPR264 right, HPR266 right, HPR271 right, HPR76 right, hsa_mir_490_Hcd20 right, HSHELA01, HSTRNL, HUMTRAB, HUMTRF, HUMTRN, HUMTRS, HUMTRV1A, let-7f-2-prec2, mir-001b-1-prec1, mir-001b-2-prec, mir-007-1-prec, mir-007-2-precNo2, mir-010a-precNo1, mir-015b-precNo2, mir-016a-chr13, mir-016b-chr3, mir-017-precNo1, mir-017-precNo2, mir-018-prec, mir-019a-prec, mir-019b-1-prec, mir-019b-2-prec, mir-020-prec, mir-022-prec, mir-023a-prec, mir-023b-prec, mir-024-2-prec, mir-025-prec, mir-027b-prec, mir-029c-prec, mir-032-precNo2, mir-033b-prec, mir-033-prec, mir-034-precNo1, mir-034-precNo2, mir-092-prec-13=092-1No2, mir-092-prec-X=092-2, mir-093-prec-7.1=093-1, mir-095-prec-4, mir-096-prec-7No1, mir-096-prec-7No2, mir-098-prec-X, mir-099b-prec-19No1, mir-100-1/2-prec, mir-100No1, mir-101-prec-9, mir-102-prec-1, mir-103-2-prec, mir-103-prec-5=103-1, mir-106aNo1, mir-106-prec-X, mir-107No1, mir-107-prec-10, mir-122a-prec, mir-123-precNo1, mir-123-precNo2, mir-124a-1-prec1, mir-124a-2-prec, mir-124a-3-prec, mir-125b-1, mir-125b-2-precNo2, mir-127-prec, mir-128b-precNo1, mir-128b-precNo2, mir-133a-1, mir-135-2-prec, mir-136-precNo2, mir-138-1-prec, mir-140No2, mir-143-prec, mir-144-precNo2, mir-145-prec, mir-146bNo1, mir-146-prec, mir-147-prec, mir-148aNo1, mir-148-prec, mir-149-prec, mir-150-prec, mir-153-1-prec1, mir-154-prec1 No1, mir-155-prec, mir-15aNo1, mir-16-1No1, mir-16-2No1, mir-181a-precNo1, mir-181b-1No1, mir-181b-2No1, mir-181b-precNo1, mir-181b-precNo2, mir-181c-precNo1, mir-181dNo1, mir-188-prec, mir-18bNo2, mir-191-prec, mir-192No2, mir-193bNo2, mir-194-2No1, mir-195-prec, mir-196-2-precNo2, mir-197-prec, mir-198-prec, mir-199a-1-prec, mir-199a-2-prec, mir-199b-precNo1, mir-200a-prec, mir-200bNo1, mir-200bNo2, mir-202*, mir-202-prec, mir-204-precNo2, mir-205-prec, mir-208-prec, mir-20bNo1, mir-212-precNo1, mir-212-precNo2, mir-213-precNo1, mir-214-prec, mir-215-precNo2, mir-216-precNo1, mir-219-2No1, mir-219-prec, mir-223-prec, mir-29b-1No1, mir-29b-2=102prec7.1=7.2, mir-321No1, mir-321No2, mir-324No1, mir-324No2, mir-328No1, mir-342No1, mir-361No1, mir-367No1, mir-370No1, mir-371No1, miR-373*No1, mir-375, mir-376aNo1, mir-379No1, mir-380-5p, mir-382, mir-384, mir-409-3p, mir-423No1, mir-424No2, mir-429No1, mir-429No2, mir-4323p, mir-4325p, mir-449No1, mir-450-1, mir-450-2No1, mir-483No1, mir-484, mir-487No1, mir-495No1, mir-499No2, mir-501No2, mir-503No1, mir-509No1, mir-514-1No2, mir-515-15p, mir-515-23p, mir-516-33p, mir-516-43p, mir-518e/526c, mir-519a-1/52, mir-519a-2No2, mir-519b, mir-519c/52, mir-520c/52, mir-526a-2No1, mir-526a-2No2, MPR103 right, MPR121 left, MPR121 left, MPR130 left, MPR130 right, MPR133 right, MPR141 left, MPR151 left, MPR156 left, MPR162 left, MPR174 left, MPR174 right, MPR185 right, MPR197 right, MPR203 left, MPR207 right, MPR215 left, MPR216 left, MPR224 left, MPR224 right, MPR228 left, MPR234 right, MPR237 left, MPR243 left, MPR244 right, MPR249 left, MPR254 right, MPR74 left, MPR88 right, and MPR95 left, wherein an increase in the level of expression of said second gene or said second microRNA in at least one of said cells, relative to the level of expression of said second gene or said second microRNA in a control cell sensitive to said treatment, indicates resistance or a propensity to develop resistance to the treatment by said patient.

77. The method of claim 75, wherein said at least one single-stranded oligonucleotide is substantially complementary to or substantially identical to at least 20 consecutive nucleotides of said first microRNA selected from mir-142-prec or said product of said first gene selected from ZNFN1A1.

78. The method of claim 77, wherein said at least one single-stranded oligonucleotide is substantially complementary to or substantially identical to at least 25 consecutive nucleotides of said first microRNA selected from mir-142-prec or said product of said first gene selected from ZNFN1A1.

79. The method of claim 75, wherein said at least one single-stranded oligonucleotide is substantially complementary to or substantially identical to at least 15 consecutive nucleotides of SEQ ID NO: 2300.

80. The method of claim 75, wherein said at least one single-stranded oligonucleotide is substantially complementary to or substantially identical to at least 15 consecutive nucleotides of SEQ ID NO: 1, 2, 4, 6, 7, 10, 11, 16, or 24.

81. The method of claim 76, wherein said at least one single-stranded oligonucleotide is substantially complementary to or substantially identical to at least 20 consecutive nucleotides of said first microRNA selected from mir-142-prec or said product of said first gene selected from ZNFN1A1.

82. The method of claim 81, wherein said at least one single-stranded oligonucleotide is substantially complementary to or substantially identical to at least 25 consecutive nucleotides of said first microRNA selected from mir-142-prec or said product of said first gene selected from ZNFNIA1.

83. The method of claim 76, wherein said at least one single-stranded oligonucleotide is substantially complementary to or substantially identical to at least 15 consecutive nucleotides of SEQ ID NO: 2300.

84. The method of claim 76, wherein said at least one single-stranded oligonucleotide is substantially complementary to or substantially identical to at least 15 consecutive nucleotides of SEQ ID NO: 1, 2, 4, 6, 7, 10, 11, 16, or 24.

* * * * *